US009770502B2

(12) United States Patent
Bublot et al.

(10) Patent No.: US 9,770,502 B2
(45) Date of Patent: *Sep. 26, 2017

(54) RECOMBINANT GALLID HERPESVIRUS 3 (MDV SEROTYPE 2) VECTORS EXPRESSING ANTIGENS OF AVIAN PATHOGENS AND USES THEREOF

(71) Applicant: Merial, Inc., Duluth, GA (US)

(72) Inventors: Michel Bublot, Chaponost (FR); Teshome Mebatsion, Watkinsville, GA (US); Joyce Pritchard, Gainesville, GA (US); Perry Linz, Jefferson, GA (US)

(73) Assignee: MERIAL, INC., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/682,798

(22) Filed: Apr. 9, 2015

(65) Prior Publication Data

US 2016/0015801 A1  Jan. 21, 2016

Related U.S. Application Data

(63) Continuation of application No. 13/689,572, filed on Nov. 29, 2012, now Pat. No. 9,101,598.

(60) Provisional application No. 61/564,877, filed on Nov. 30, 2011, provisional application No. 61/694,957, filed on Aug. 30, 2012.

(51) Int. Cl.
| | |
|---|---|
| *A61K 39/17* | (2006.01) |
| *C12N 7/00* | (2006.01) |
| *A61K 39/12* | (2006.01) |
| *A61K 39/245* | (2006.01) |
| *A61K 39/00* | (2006.01) |
| *A61K 39/295* | (2006.01) |

(52) U.S. Cl.
CPC .......... *A61K 39/17* (2013.01); *A61K 39/12* (2013.01); *A61K 39/295* (2013.01); *C12N 7/00* (2013.01); *A61K 2039/5256* (2013.01); *A61K 2039/53* (2013.01); *A61K 2039/545* (2013.01); *A61K 2039/55* (2013.01); *A61K 2039/552* (2013.01); *A61K 2039/70* (2013.01); *C12N 2710/16043* (2013.01); *C12N 2710/16334* (2013.01); *C12N 2710/16343* (2013.01); *C12N 2710/20034* (2013.01); *C12N 2720/10034* (2013.01); *C12N 2720/10071* (2013.01); *C12N 2760/18134* (2013.01); *C12N 2760/18171* (2013.01)

(58) Field of Classification Search
CPC .. A61K 39/12; A61K 39/295; A61K 2039/53; C12N 2710/16334; C12N 2710/20034; C12N 2760/18134
See application file for complete search history.

(56) References Cited

U.S. PATENT DOCUMENTS

| | | | |
|---|---|---|---|
| 5,187,087 A | 2/1993 | Sondermeijer et al. | |
| 5,853,733 A | 12/1998 | Cochran et al. | |
| 5,980,906 A | 11/1999 | Audonnet et al. | |
| 6,183,753 B1 | 2/2001 | Cochran et al. | |
| 2002/0081316 A1* | 6/2002 | Cochran | C07K 14/005 424/199.1 |
| 2005/0019348 A1* | 1/2005 | Reddy | A61K 39/255 424/199.1 |

FOREIGN PATENT DOCUMENTS

| | | |
|---|---|---|
| EP | 1 298 139 | 4/2003 |
| WO | WO-A-87/04463 | 7/1987 |

OTHER PUBLICATIONS

Jarosinski KW, et. al. PLoS One. 2012;7(5):e37428. Epub May 21, 2012.*
Senne et. al.Dev Biol (Basel). 2004;119:165-70.*
Sharma JM, et. al. Avian Dis. Jul.-Sep. 2002;46(3):613-22.*
Bublot M, et. al. Acta Virol. Apr.-Jun. 1999;43(2-3):181-5.*
Yao Y, et. al. J Virol. Jul. 2007;81(13):7164-70. Epub Apr. 25, 2007.*
Liu HL, Chen PY, Wang YK. Newcastle disease virus fusion glycoprotein precursor gene, complete cds. GenBank: AY337464.1. Dep. Jul. 29, 2003.*
Liu HL, Chen PY, Wang YK. Newcastle disease virus fusion glycoprotein precursor. GenBank: AAP97877.1. Dep. Jul. 29, 2003.*
U.S. Appl. No. 13/689,625, filed May 29, 2014, Michel Bublot, et al.
Bublot et al J.Comp. Path.2007,vol. 137, S81-S84, "Use of a Vectored Vaccine against Infectious Bursal Disease of Chickens in the Face of High-Titred maternally Derived Antibody".
Petherbridge, et al., J. Virol. Methods 158, Nov. 17, 2009, "Cloning of Gallid herpesvirus 3 (Marek's disease virus serotype-2) genome as infectious bacterial artificial chromosomes for analysis of viral gene functions".
Jarosinski, et al., J. of Virology 81, 10575-10587, 2007, "Horizontal Transmission of Marek's Disease Virus Requires $U_S2$, the $U_L13$ protein Kinase, and gC".
Jarosinski, et al., J. of Virology 84, 7911-7916, 2010, "Further analysis of Marek's disease virus horizontal transmission confirms that $U_L44$ (gC) and $U_L13$ protein kinase activity are essential, while $U_S2$ is nonessential".

(Continued)

*Primary Examiner* — Rachel B Gill
(74) *Attorney, Agent, or Firm* — Judy Jarecki-Black; Ruoying Chen; Merial Inc.

(57) ABSTRACT

The present invention provides recombinant Gallid herpesvirus 3 (MDV-2) vectors that contain and express antigens of avian pathogens, recombinant Gallid herpesvirus 3 (MDV-2) vectors that contain a mutated gC gene, compositions comprising the recombinant Gallid herpesvirus 3 (MDV-2) vectors, polyvalent vaccines comprising the recombinant Gallid herpesvirus 3 (MDV-2) vectors and one or more wild type viruses or recombinant vectors. The present invention further provides methods of vaccination against a variety of avian pathogens and method of producing the recombinant Gallid herpesvirus 3 (MDV-2) vectors.

25 Claims, 37 Drawing Sheets

(56) References Cited

OTHER PUBLICATIONS

Johnson et al, 2010 Avian Dis 54, 1251-1259, "Protection Against Infectious Laryngotracheitis by In Ovo Vaccination with Commercially Available Viral Vector Recombinant Vaccines".
Morgan et al 1992, Avian dis. 36, 858-70, "Protection of Chickens from Newcastle and Marek's Diseases with a Recombinant Herpesvirus of Turkeys Vaccine Expressing the Newcastle Disease Virus Fusion Protein".
Rudolf Heine 2011; Issues of the Poultry Recombinant Viral Vector Vaccines which May Cause an Effect on the Economic Benefits of those Vaccines; paper presented at the XVII World Veterinary Poultry Association (WVPA) Congress in Cancún, Mexico, Aug. 14-18, 2011.
Singh et al., Research in Veterinary Science 89, 140-145, 2010, "Comparative efficacy of BAC-derived recombinant SB-1 vaccine and the parent wild type strain in preventing replication, shedding and disease induced by virulent Marek's disease virus".
Slacum et al, 2009, The compatibility of HVT recombinants with other Marek's disease vaccines, 58th Western Poultry Disease Conference, Sacramento, CA, USA, Mar. 23-25, p. 84.
Spatz et al, Virus Gene 42, 331-338, 2011, "Comparative genomic sequence analysis of the Marek's disease vaccine strain SB-1".
Witter et al, 1984, Avian Pathology 13, 75-92, "Polyvalent Marek's disease vaccines: safety, efficacy and protective synergism in chickens with maternal antibodies".

\* cited by examiner

Figure 1

| SEQ ID NO: | Type | Gene Description |
|---|---|---|
| 1 | DNA | NDV F codon-optimized gene from modified wt VIId |
| 2 | Protein | NDV F protein of codon-optimized NDV-F gene of modified wt VIId |
| 3 | DNA | NDV-F DNA wt VIId in SB-1 construct |
| 4 | DNA | NDV-F DNA with GenBank accession No. AY337464.1 |
| 5 | Protein | NDV-F protein with GenBank accession No. AAP97877.1 |
| 6 | DNA | NDV-F DNA wildtype V (CA02 strain) with GenBank accession No. EF520718 |
| 7 | Protein | NDV-F protein wildtype V (CA02 strain) with GenBank accession No. ABS84266 |
| 8 | DNA | NDV-F codon-optimized gene from modified wildtype V (CA02 strain) |
| 9 | Protein | NDV-F protein of codon-optimized NDV-F gene of modified wildtype V (CA02 strain) in vSB1-008 and vSB1-009 |
| 10 | DNA | MCMV IE promoter |
| 11 | DNA | SV40 PolyA |
| 12 | DNA | SV40 promoter |
| 13 | DNA | Synthetic PolyA |
| 14 | DNA | SB-1 genome HQ840738.1 |
| 15 | Oligo | MB080 primer: CGA ACA AAC TTC ATC GCT ATG C |
| 16 | Oligo | MB081 primer: TAA CTC AAA TGC GAA GCG TTG C |
| 17 | Oligo | SB-1 US10 primer: TCA ACG TGC GAC AAT CGT CTG |
| 18 | Oligo | SB-1 SORF4 primer: ATG TGG AGG AAC GAT CCT ATA |
| 19 | Oligo | ALLNDVFprimer: ATG GCT TGG GAA TAA TAC |
| 20 | Oligo | mCMVF primer: AAC TCC GCC CGT TTT ATG |
| 21 | Oligo | SV40tailR primer: TCG ACT CTA GAG GAT CCG |
| 22 | Oligo | newSB-1 UL55R primer: ATGGCTATAGAGGGACTGTGT |
| 23 | Oligo | New SB-1 ORF5F primer: GATCTCAACGCTATACCGGCG |
| 24 | Oligo | OptF primer: ACT GAC AAC ACC CTA CAT GGC |
| 25 | Oligo | VIIoptF RP primer: GCC AGC ACC AGG CTC AGG G |
| 26 | Oligo | SV40promoterF primer: AGC TTG GCT GTG AAT GT |
| 27 | Oligo | SB1 43.F primer: GCT CTC GGA GAC GCG GCT CGC |
| 28 | Oligo | SB1 45.R primer: GCT CTT GTA ACA TCG CGG ACG |
| 29 | Oligo | SV40 promoter F primer: AGC TTG GCT GTG AAT GT |
| 30 | Oligo | HVTUS10 FP primer: CCG GCA ACA TAC ATA ATG TG |
| 31 | Oligo | HVTUS10 RP primer: GGC ACT ATC CAC AGT ACG |
| 32 | Oligo | CaoptF RP primer: GCC AGC ACC AGG CTC ATC A |
| 33 | Oligo | SynTailR primer: ATG TTC TGG CAC CTG CAC |
| 34 | DNA | Gene coding for glycoprotein C of SB-1 strain GenBank accession No.HQ840738 |
| 35 | Protein | Glycoprotein C of SB-1 strain GenBank accession No. AEI00252 |

Figure 1 (continued)

| SEQ ID NO: | Type | Gene Description |
|---|---|---|
| 36 | DNA | Plasmid pSB1 44cds (for gC deletion) |
| 37 | DNA | Partial plasmid pSB1 44 cds SV FCAopt (for vSB1-009) |
| 38 | DNA | Partial plasmid pHM103+Fopt DNA sequence (for vHVT114) |
| 39 | DNA | IBDV DNA encoding VP2 protein |
| 40 | Protein | IBDV VP2 protein |
| 41 | DNA | Partial plasmid sequence of SB-1 US10mFwt SbfI (for vSB1-004) |
| 42 | DNA | Partial plasmid sequence of SB1 UL55 SVFopt syn tail SbfI (for vSB1-006) |
| 43 | DNA | Partial plasmid sequence of pSB1 44 cds SVOptF (for vSB1-007) |
| 44 | DNA | Partial plasmid sequence of SB-1 UL55 CaFopt syn tail SbfI (for vSB1-008) |
| 45 | DNA | Partial plasmid sequence of pHVT US2 SV- Fopt-synPA (for vHVT306) |
| 46 | DNA | Partial plasmid pCD046+NDV-F VII YZCQ sequence (vHVT112) |
| 47 | DNA | Partial plasmid pCD046+NDV Texas F sequence (for vHVT113) |
| 48 | DNA | Partial plasmid pHM119 sequence (for vHVT039) |
| 49 | DNA | NDV-F Wtnm-Texas wildtype DNA sequence |
| 50 | protein | NDV-F protein from Wtnm-Texas wildtype |
| 51 | DNA | NDV-F YZCQ wildtype DNA sequence |
| 52 | protein | NDV-F protein from wildtype YZCQ strain |
| 53 | DNA | NDV-F Texas wildtype DNA sequence |
| 54 | protein | NDV-F protein from wildtype Texas strain |
| 55 | DNA | MDV gB promoter |
| 56 | DNA | Partial plasmid HVT SORF3-US2 gpVar-Ewtsyn sequence (vHVT202) |
| 57 | DNA | Partial plasmid SB1US2 gpVIIdwtsyn sequence (vSB1-010) |
| 58 | DNA | IBDV DNA encoding VP2 protein of IBDV E strain |
| 59 | protein | IBDV VP2 protein of IBDV E strain |
| 60 | DNA | Guinea pig CMV promoter |
| 61 | oligo | primer HM101 |
| 62 | oligo | Primer HM102 |
| 63 | oligo | primer F-ATG |
| 64 | oligo | Primer F-STOP |

Schematic diagram of SB-1 genome organization

The UL44 (gC), UL55/LORF5 and US10/SORF4 insertion sites are shown

Figure 3

Immunofluorescent staining of recombinant vSB1-004 virus
expressing NDV-F protein Schematic representation of primer binding sites vSB1-004 Identity PCR Lane 1: no template
Lane 2: HVT FC126
Lane 3: SB-1 parental virus
Lane 4: vSB1-004

Figure 6

Immunofluorescent staining of recombinant vSB1-006 virus
expressing NDV-F protein Schematic representation of primer binding sites Figure 8
vSB1-006 Identity PCR Results
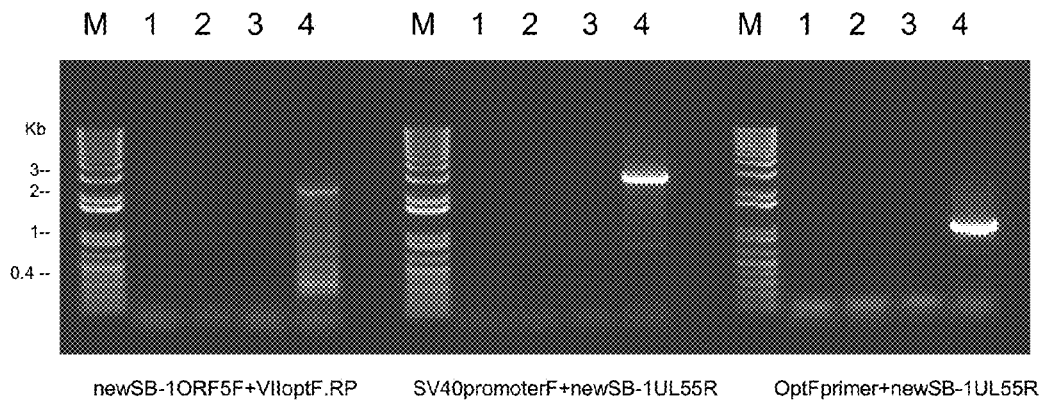
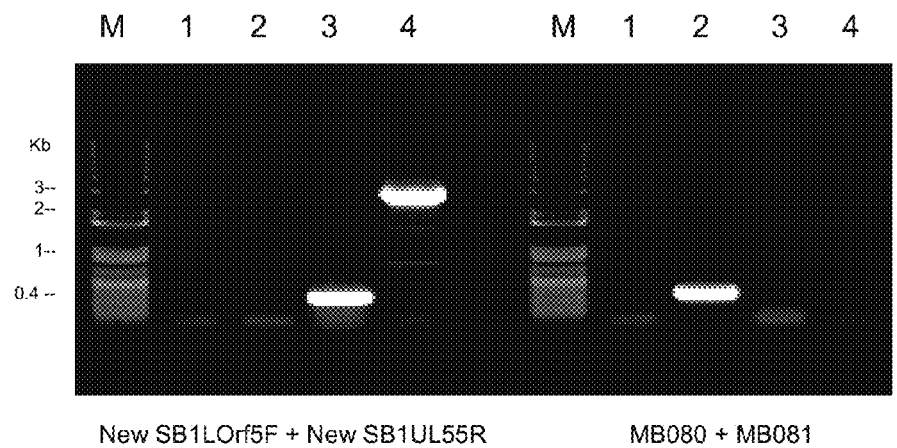
Lane 1: no template
Lane 2: HVT FC126
Lane 3: parent SB-

Figure 9

Immunofluorescent staining of recombinant SB1-007 virus
expressing NDV-F protein Schematic diagram of primer location on pSB1 44 cds SVOptF donor plasmid vSB1-007 Identity PCR

Figure 12

Immunofluorescent staining of recombinant SB1-008 virus
expressing NDV-F protein Schematic representation of primer binding sites SB-1 UL55 SVCaFsyn tail SbfI rc
6867 bp Figure 14
vSB1-008 Identity PCR Results
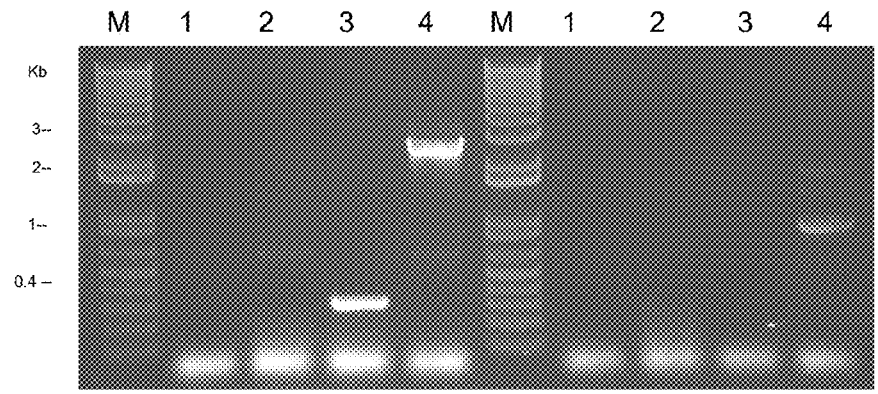
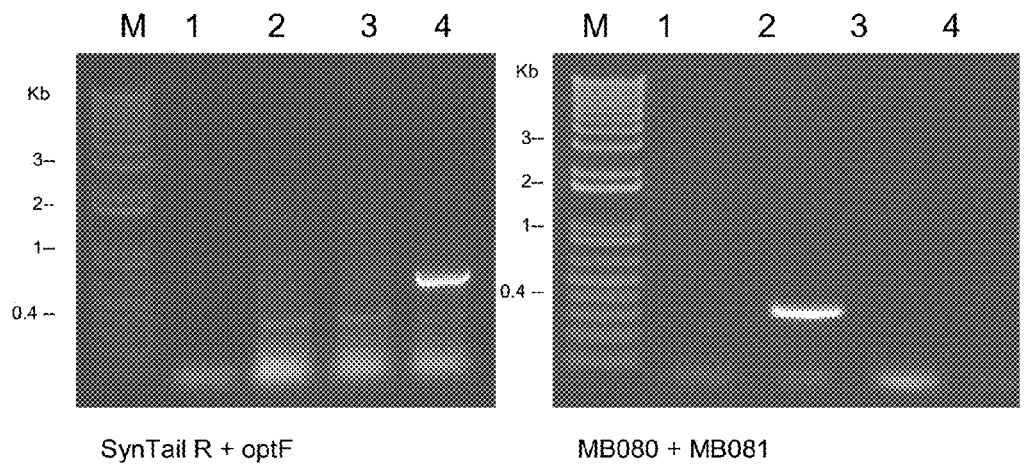
Lane 1: no template
Lane 2: HVT FC126
Lane 3: parent SB-1
Lane 4: vSB1-008

Figure 15

Western blot analysis of immunoprecipitated sample
from vSB1-009 infected cells

|  | M | 1 | 2 |

(kDa)

64 —

51 —

39 —

28 —

19 —

14 —

Lane M: pre-stained protein standard (Invitrogen, SeeBlue)
Lane 1: uninfected CEF
Lane 2: vSB1-009 pre-MSV stock Immunoprecipitation and Western Blot of vHVT114

Lane M: Pre-Stained Standard (SeeBlue, Invitrogen)
Lane 1: CEF
Lane 2: vHVT114

FIG. 17A

Shedding (% positive birds) after CA/02 challenge

- Oral_2dpch
- Cloacal_2dpch
- Oral_4dpch
- Cloacal_4dpch (Bar chart with categories: Ctrl, vHVT114, vHVT116, vSB1-007, vSB1-008, vSB1-008+vHVT13, vHVT304)

FIG. 17B

Shedding (% positive birds) after ZJ1 challenge

- Oral_2dpch
- Cloacal_2dpch
- Oral_4dpch
- Cloacal_4dpch (Bar chart with categories: Ctrl, vHVT114, vHVT116, vSB1-007, vSB1-008, vSB1-008+vHVT13, vHVT304)

Figure 19A

DNA sequence alignment of NDV-F genes

```
                        1                                                  50
SEQ ID NO:1    (1)   ------------------------------------ATGGGCAGCAAGCCCAGC
SEQ ID NO:3    (1)   ------------------------------------ATGGGCTCCAAAGCTTCT
SEQ ID NO:4    (1)   CTGGATCCCGGTTGGCTCATTCAGGACGCAATATGGGCTCCAAACTTCT
SEQ ID NO:8    (1)   ------------------------------------ATGGGCAGCAAGCCCAGC
SEQ ID NO:49   (1)   ------------------------------------ATGGGCTCCAGATCTTCT
SEQ ID NO:51   (1)   ------------------------------------ATGGGCTCCAGATCTTCT
SEQ ID NO:53   (1)   ------------------------------------ATGGGCTCTAAAGCTTCT 51                                                 100
SEQ ID NO:1    (19)  ACAAGAATCCAGGCCGCCCTGATGCTGATCAGCCGCAGCATGCTGATCCT
SEQ ID NO:3    (19)  ACCAGGATCCCAGCCACCCTGATGCTGATCACCGGATTATGCTGATATT
SEQ ID NO:4    (51)  ACCAGGATCCCAGCCACCCTGATGCTGATCACCGGATTATGCTGATATT
SEQ ID NO:8    (19)  ACTTGATCAGCGTGACCCTGATGCTGATCACCAGAACCATGCTGATCCT
SEQ ID NO:49   (19)  ACCAGGATCCCGGTACCTCTAATGCTGATCATCGGAACCGCGCTGACACT
SEQ ID NO:51   (19)  ACCAGGATCCCGGTACCTCTAATGCTGATCATCGGAACCGCGCTGACACT
SEQ ID NO:53   (19)  ACCAGGATCCCAGCCACCCTGATGCTGATCACCGGATTATGCTGATATT 101                                                150
SEQ ID NO:1    (69)  GGCTGCATCAGACCCACAAGCTCCCTGCATGGACGCCCCCTGGCCGCTG
SEQ ID NO:3    (69)  GGCTGTATCCGTCGACAAGCTCTCTTGACGGCAGGCCTCTTGCAGCTG
SEQ ID NO:4    (101) GGCTGTATCCGTCGACAAGCTCTCTTGACGGCAGGCCTCTTGCAGCTG
SEQ ID NO:8    (69)  GAGCTGCATCTGCCGCACAAGCAGCCTGGAGGGCAGACCCTGGCCGCTG
SEQ ID NO:49   (69)  GAGCTGTATCCGTCTGACAAGCTCTCTTGATGGCAGGCCTCTTGCGGCTG
SEQ ID NO:51   (69)  GAGCTGTATCCGTCTGACAAGCTCTCTTGATGGCAGGCCTCTTGCGGCTG
SEQ ID NO:53   (69)  GGACTGTATCCGTCGACAAGCTCTCTTGACGGCAGGCCTCTTGCAGCTG 151                                                200
SEQ ID NO:1    (119) CCGGCATGGTGGTGACCGGCGACAAGGCCGTGAAGGTGTACACCAGCAGG
SEQ ID NO:3    (119) CAGGAATTGTAGTAACAGGAGATAAGGCAGTCAATGTATACACTTCGTCT
SEQ ID NO:4    (151) CAGGAATTGTAGTAACAGGAGATAAGGCAGTCAATGTATACACTTCGTCT
SEQ ID NO:8    (119) CCGGCATGGTGGTGACCGGCGACAAGGCCGTGAAGATCTACACCAGCAGG
SEQ ID NO:49   (119) CAGGGATCGTGGTAACAGGAGATAAAGCAGTCAACATAGACCCTCATCC
SEQ ID NO:51   (119) CAGGGATCGTGGTAACAGGAGATAAAGCAGTCAACATAGACCCTCATCC
SEQ ID NO:53   (119) CAGGAATTGTAGTAACAGGAGATAAGGCAGTCAATGTATATACCTCGTCT 201                                                250
SEQ ID NO:1    (169) CAGACCGGCAGCATCATCGTGAAGCTGCTGCCCAACATGCCCAGAGACAA
SEQ ID NO:3    (169) CAGACAGGGTCAATCATAGTCAAGTTGCTCCCGAATATGCCCAGGGATAA
SEQ ID NO:4    (201) CAGACAGGGTCAATCATAGTCAAGTTGCTCCCGAATATGCCCAGGGATAA
SEQ ID NO:8    (169) CAGACCGGCAGCATCATCATCAAGCTGCTGCCCAACATGCCCAGGACAA
SEQ ID NO:49   (169) CAGACAGGGTCAATCATAGTTAAGTTACTCCCGAATATGCCCAAGGACAA
SEQ ID NO:51   (169) CAGACAGGGTCAATCATAGTTAAGTTACTCCCGAATATGCCCAAGGACAA
SEQ ID NO:53   (169) CAGACAGGGTCAATCATAGTCAAGTTGCTCCCGAATATGCCCAAGGATAA
```

Figure 19B

```
              251                                                300
SEQ ID NO:1   (219) AGAGGCCTGCGCCAAGGCCCCCTGAAGCCTACAACAGAACCCTGACCA
SEQ ID NO:3   (219) GGAGGCGTGTGCAAAAGCCCATTAGAGGCATATAACAGAACACTGACTA
SEQ ID NO:4   (251) GGAGGCGTGTGCAAAAGCCCATTAGAGGCATATAACAGAACACTGACTA
SEQ ID NO:8   (219) AGAGGCCTGCGCCAAGGCCCCCTGAAGCCTACAACAGAACCCTGACCA
SEQ ID NO:49  (219) AGAGGTGTGTGCAAAAGCCCATTGGAGGCATACAACAGGACACTGACTA
SEQ ID NO:51  (219) AGAGGTGTGTGCAAAAGCCCATTGGAGGCATACAACAGGACACTGACTA
SEQ ID NO:53  (219) GGAGGCGTGTGCGAAAGACCCATTAGAGGCATATAACAGAACACTGACTA 301                                                350
SEQ ID NO:1   (269) CCCTGCTGACCCCGCTGGGCGACAGCATCAGAAAGATCCAGGGCTGCCTG
SEQ ID NO:3   (269) CTTTGCTGACTCCTCTTGGCGACTGCATCCGCAAGATCCAAGGGTCTGTG
SEQ ID NO:4   (269) CTTTGCTGACTCCTCTTGGCGACTGCATCCGCAAGATCCAAGGGTCTGTG
SEQ ID NO:8   (269) CCCTGCTGACCCCGCTGGGCGACAGCATCAGAAGAATCCAGGGCAGCGCC
SEQ ID NO:49  (269) CTTTACTCACCCCGCTGGTGATTCTATCCGCAGGATACAAGAGTCTGTG
SEQ ID NO:51  (269) CTTTACTCACCCCGCTGGTGATTCTATCCGCAGGATACAAGAGTCTGTG
SEQ ID NO:53  (269) CTTTGCTGACTCCTCTTGGCGAATCCATCCGCAAGATCCAAGGGTCTGTG 351                                                400
SEQ ID NO:1   (319) AGCACAAGCCGCAGCAAAGCAGGGCAGACTGATCGGCGCCGTGATCGG
SEQ ID NO:3   (319) TCCACATCTGGAGGAGGCAAGCAAGCGCCGCTGATAGCTGCTGTTATTGG
SEQ ID NO:4   (351) TCCACATCTGGAGGAGACAAAAACGCTTTATAGCTGCTGTTATTGG
SEQ ID NO:8   (319) AGCACAAGCCGCAGCAAAGCAGGGCAGACTGGTGGGCGCTATCATTGG
SEQ ID NO:49  (319) ACTACTTCGGAGGAAGGAGACAGAGACGCTTTATAGCTGCCATTATGG
SEQ ID NO:51  (319) ACTACTTCGGAGGAGGCAAGCAAGCGCCGCTGATAGCTGCCATTATGG
SEQ ID NO:53  (319) TCCACGTCTGGAGGAGGCAAGCAAGCGCCGCTGATAGCTGCTGTTATTGG 401                                                450
SEQ ID NO:1   (369) GAGCGTGGCCCTGGGCAGTGGCTACAGCTGCCCAGATTACCGCTGCAGCCG
SEQ ID NO:3   (369) CAGTGTAGCTCTTGGGGTTGCAACAGCGGCACAGATAACAGCAGCTGCGG
SEQ ID NO:4   (401) CAGTGTAGCTCTTGGGGTTGCAACAGCGGCACAGATAACAGCAGCTGCGG
SEQ ID NO:8   (369) GAGCGTGGCCCTGGGCCGTTGGCTACAGCTGCCCAGATTACCGCTGCAGCCG
SEQ ID NO:49  (369) CAGTGTAGCTCTTGGGGTTGCGACAGCTGCACAGATAACAGCAGCTTCGG
SEQ ID NO:51  (369) CAGTGTAGCTCTTGGGGTTGCGACAGCTGCACAGATAACAGCAGCTTCGG
SEQ ID NO:53  (369) TAGTGTAGCTCTTGGGGTTGCAACAGCGGCACAAATAACAGCAGCTGCGG 451                                                500
SEQ ID NO:1   (419) CCCTGATCCAGGCCAAGCAGAACGCCGCCAACATCCTGAGACTGAAAGAG
SEQ ID NO:3   (419) CCCTAATACAAGCCAAGCAGAATGCCGCCAACATCCTGCGGCTTAAGGAG
SEQ ID NO:4   (451) CCCTAATACAAGCCAAGCAGAATGCCGCCAACATCCTGCGGCTTAAGGAG
SEQ ID NO:8   (419) CCCTGATTCAGGCCAATCAGAACGCCGCCAACATCCTGAGACTGAAAGAG
SEQ ID NO:49  (419) CCCTGATACAAGCCAAGCAGAATGCTGCCAACATCCTGCGGCTTAAAGAG
SEQ ID NO:51  (419) CCCTGATACAAGCCAAGCAGAATGCTGCCAACATCCTGCGGCTTAAAGAG
SEQ ID NO:53  (419) CCCTAATACAAGCCAAGCAGAATGCTGCCAACATCCTTCGGCTTAAGGAG 501                                                550
SEQ ID NO:1   (469) AGCATTGCCGCCACCAACGAGGCCGTGCACGAAGTGACCGACGGCCTGAG
SEQ ID NO:3   (469) AGCATTGCTGCAACCAATGAAGCTGTGCATGAAGTCACCGACGGATTATC
SEQ ID NO:4   (501) AGCATTGCTGCAACCAATGAAGCTGTGCATGAAGTCACCGACGGATTATC
SEQ ID NO:8   (469) AGCATTGCCGCCACCAACGACGCCGTGCACGAAGTGACAAACGGACTGTC
SEQ ID NO:49  (469) AGCATTGCTGCAACCAATGAAGCTGTGCACCAGGTCACTGACGGATTATC
SEQ ID NO:51  (469) AGCATTGCTGCAACCAATGAAGCTGTGCACCAGGTCACTGACGGATTATC
SEQ ID NO:53  (469) AGCATTGCTGCAACCAATGAAGCTGTGCATGAAGTCACCGACGGATTATC
```

Figure 19C

```
              551                                                      600
SEQ ID NO:1   (519) CCAGCTGTCCCTGGCCTGGGCAAGATGCAGCAGTTCGTGAACGACCAGT
SEQ ID NO:3   (519) ACAACTATCAGTGGCAGTTGGAAGATGCAGCAGTTTGTCAATGACCAGT
SEQ ID NO:4   (551) ACAACTATCAGTGGCAGTTGGAAGATGCAGCAGTTTGTCAATGACCAGT
SEQ ID NO:8   (519) CCAGCTGGCTGTCGCTGTCGGCAAGATGCAGCAGTTCGTGAACAACCAGT
SEQ ID NO:49  (519) ACAACTAGCAGTGGCAGTAGGGAAGATGCAACAGTTTGTCAATGACCAGT
SEQ ID NO:51  (519) ACAACTAGCAGTGGCAGTAGGGAAGATGCAACAGTTTGTCAATGACCAGT
SEQ ID NO:53  (519) ACAACTATCAGTGGCAGTTGGAAGATGCAGCAGTTTGTCAATGACCAGT 601                                                      650
SEQ ID NO:1   (569) TGAACAACACCGCCAGACAGCTGGACTGCATCAAGATCGCCCAGCAGGTG
SEQ ID NO:3   (569) TTAATAATACGGCGGAGAATTGGACTGTATAAAATCACACAACAGGTT
SEQ ID NO:4   (601) TTAATAATACGGCGGAGAATTGGACTGTATAAAATCACACAACAGGTT
SEQ ID NO:8   (569) TGAACAACACCGCCAGACAGCTGGACTGCATCAAGATCGCCCAGCAGGTG
SEQ ID NO:49  (569) TGAATAATACAGCGGAACAATTGGACTGTATAAAATGCACAGCAGGTC
SEQ ID NO:51  (569) TGAATAATACAGCGGAACAATTGGACTGTATAAAATGCACAGCAGGTC
SEQ ID NO:53  (569) TTAATAATACAGCGGCGAGAATTGGACTGTATAAAATCACACAACAGGTT 651                                                      700
SEQ ID NO:1   (619) GGCGTGGAGCTGAACCTGTACCTGACCGAGCTGACCACAGTGTTCGGCCC
SEQ ID NO:3   (619) GGTGTAGAACTCAACCTATACCTAACTGAATTGACTACAGTATTCGGGCC
SEQ ID NO:4   (651) GGTGTAGAACTCAACCTATACCTAACTGAATTGACTACAGTATTCGGGCC
SEQ ID NO:8   (619) GGCGTGGAGCTGAACCTGTACCTGACCGAGCTGACCACAGTGTTCGGCCC
SEQ ID NO:49  (619) GGTGTAGAACTCAACTTGTACCTAACTGAATTGACTACAGTATTTGGGCC
SEQ ID NO:51  (619) GGTGTAGAACTCAACTTGTACCTAACTGAATTGACTACAGTATTTGGGCC
SEQ ID NO:53  (619) GGTGTAGAACTCAACCTATACCTAACTGAATTGACTACAGTATTCGGGCC 701                                                      750
SEQ ID NO:1   (669) CCAGATCACAAGCCCAGCCCTGACACAGCTGACCATCCAGGCCCTGTACA
SEQ ID NO:3   (669) ACAGATCACCTCCCCTGCATTAACTCAGCTGACCATCCAGGCACTTTATA
SEQ ID NO:4   (701) ACAGATCACCTCCCCTGCATTAACTCAGCTGACCATCCAGGCACTTTATA
SEQ ID NO:8   (669) CCAGATCACAAGCCCCGCTCTGACCCAGCTGACAATCCAGGCCCTGTACA
SEQ ID NO:49  (669) ACAAATCACTTCCCCTGCCTTAACTCAGCTGACTATCCAAGCGCTTTACA
SEQ ID NO:51  (669) ACAAATCACTTCCCCTGCCTTAACTCAGCTGACTATCCAAGCGCTTTACA
SEQ ID NO:53  (669) ACAGATCACCTCCCCTGCATTAACTCAGCTGACCATCCAGGCACTTTATA 751                                                      800
SEQ ID NO:1   (719) ACCTGGCTGGCGGGAACATGGACTATCTGGTGACAAAGCTGGGAATCGCC
SEQ ID NO:3   (719) ATTAGCTGGTGGCAATATGGATTACTTATTAACTAAGTTAGGTATAGCG
SEQ ID NO:4   (751) ATTAGCTGGTGGCAATATGGATTACTTATTAACTAAGTTAGGTATAGCG
SEQ ID NO:8   (719) ACCTGGCTGGCGGGAACATGGACTATCTGGTGACAAGCTGGAGTGGGC
SEQ ID NO:49  (719) ATCTAGCTGGTGGTAATATGGATTACTTGCTGACTAAGTTAGGTGTAGGG
SEQ ID NO:51  (719) ATCTAGCTGGTGGTAATATGGATTACTTGCTGACTAAGTTAGGTGTAGGG
SEQ ID NO:53  (719) ATTAGCTGGTGGCAATATGGATTACTTATTAACTAAGTTAGGTATAGGG 801                                                      850
SEQ ID NO:1   (769) AACAAGCAGCTGTCCAGCCTGATCGGAAGCGGCGTGATCACCGCTACCC
SEQ ID NO:3   (769) AACAATCAACTCAGCTGGTAATTGGTAGCGGCGTGATCACTGGTTACCC
SEQ ID NO:4   (801) AACAATCAACTCAGCTGGTAATTGGTAGCGGCGTGATCACTGGTTACCC
SEQ ID NO:8   (769) AACAGCAGCTGTCCAGCCTGATCGGGTCGGGCTGATCACAGGCAACCC
SEQ ID NO:49  (769) AACAGCAACTCAGCTCATTAATTGGTAGCGGCTTGATCACCGGCAACCC
SEQ ID NO:51  (769) AACAATCAACTCAGCTCATTAATTGGTAGCGGCTTGATCACCGGCAACCC
SEQ ID NO:53  (769) AACAATCAACTCAGCTCATTAATTGGCAGCGGCGTGATCACTGGTTACCC
```

Figure 19D

```
                    851                                               900
SEQ ID NO:1   (819) CATCCTGTACGACAGCCAGACACAGGTGCTGGGCATCCAGGTGAACCTGC
SEQ ID NO:3   (819) TATACTGTATGACTCACAGACTCAACTCTTGGGCATACAAGTGAATTTAC
SEQ ID NO:4   (851) TATACTGTATGACTCACAGACTCAACTCTTGGGCATACAAGTGAATTTAC
SEQ ID NO:8   (819) CATCCTGTACGACAGCCAGACACAGGTGCTGGGCATCCAGATCAACCTGC
SEQ ID NO:49  (819) TATTCTGTACGACTCACAGACTCAGATCTTGGGTATACAGGTACTTTGC
SEQ ID NO:51  (819) TATTCTGTACGACTCACAGACTCAGATCTTGGGTATACAGGTACTTTGC
SEQ ID NO:53  (819) TATATTGTATGACTCACAGACTCAACTCTTGGGCATACAAGTGAATTTGC 901                                               950
SEQ ID NO:1   (869) CCAGCGTGGGCAACCTGAACAACATGCGCGCCACCTACCTGAAACCCTG
SEQ ID NO:3   (869) CCTCAGTCGGGAACTTAAATAATATGCGTGCCACCTATTGGAGACCTTA
SEQ ID NO:4   (901) CCTCAGTCGGGAACTTAAATAATATGCGTGCCACCTATTGGAGACCTTA
SEQ ID NO:8   (869) CATCCGTGGGAAGCCTGAACAACATGAGAGCCACCTACCTGAAACCCTG
SEQ ID NO:49  (869) CTTCAGTTGGGAACCTGAATAATATGCGTGCCACCTACCTGGAGACCTTA
SEQ ID NO:51  (869) CTTCAGTTGGGAACCTGAATAATATGCGTGCCACCTACCTGGAGACCTTA
SEQ ID NO:53  (869) CCTCAGTCGGGAACTTAAATAATATGCGTGCCACCTATTAGAGACCTTA 951                                              1000
SEQ ID NO:1   (919) AGCGTGTCCACCACCAAGGGCTACGCCAGCGCCCTGGTGCCCAAGGTGGT
SEQ ID NO:3   (919) TCTGTAAGTACAACCAAAGGATATGCCTCAGCACTTGTCCCGAAAGTAGT
SEQ ID NO:4   (951) TCTGTAAGTACAACCAAAGGATATGCCTCAGCACTTGTCCCGAAAGTAGT
SEQ ID NO:8   (919) AGCGTGTCCACCACCAAGGGCTTCGCCAGCGCCCTGGTGCCCAAGGTGGT
SEQ ID NO:49  (919) TCTGTAAGCACAACCAAGGGATTTGCCTCAGCACTTGTCCCAAAAGTGGT
SEQ ID NO:51  (919) TCTGTAAGCACAACCAAGGGATTTGCCTCAGCACTTGTCCCAAAAGTGGT
SEQ ID NO:53  (919) TCTGTAAGTACAGCCAAAGGATATGCCTCAGCACTTGTTCAAAAGTAGT 1001                                             1050
SEQ ID NO:1   (969)  GACACAGGTGGGCAGGGTGATCGAGGAACTGGACACCAGCTACTGCATCG
SEQ ID NO:3   (969)  GACACAAGTGGTTCCGTGATAGAAGAGCTTGACACCTCATACTGTATAG
SEQ ID NO:4   (1001) GACACAAGTGGTTCCGTGATAGAAGAGCTTGACACCTCATACTGTATAG
SEQ ID NO:8   (969)  GACACAGGTGGGCAGGGTGATCGAGGAACTGGACACCAGCTACTGCATCG
SEQ ID NO:49  (969)  GACACAGGTGGTTCCGTGATAGAAGAACTTGACACCTCATACTGTATAG
SEQ ID NO:51  (969)  GACACAGGTGGTTCCGTGATAGAAGAACTTGACACCTCATACTGTATAG
SEQ ID NO:53  (969)  GACACAAGTGGTTCCTGTGATAGAAGAGCTTGACACCTCATACTGTATAG 1051                                             1100
SEQ ID NO:1   (1019) ACAGCGACCTGGACCTGTACTGCACCAGAATCGTGACCTTCCCAATGAGC
SEQ ID NO:3   (1019) AGTCCGATCTGGATTTATATTGTACTAGAATAGTGACATTCCCCATGTCC
SEQ ID NO:4   (1051) AGTCCGATCTGGATTTATATTGTACTAGAATAGTGACATTCCCCATGTCC
SEQ ID NO:8   (1019) ACAGCGACATCGACCTGTACTGCACCAGAGTGGACCTTCCCAATGAGC
SEQ ID NO:49  (1019) GGACCGACTTGGATTTATACTGTACAAGAATAGTGACATTCCCTATGTCT
SEQ ID NO:51  (1019) GGACCGACTTGGATTTATACTGTACAAGAATAGTGACATTCCCTATGTCT
SEQ ID NO:53  (1019) AGTCCGATCTGGATTTATATTGTACTAGAATAGTGACATTCCCCATGTCC 1101                                             1150
SEQ ID NO:1   (1069) CCCGGCATCTACAGCTGCCTGAGCGGCAATACCAGCGCCTGCATGTACAG
SEQ ID NO:3   (1069) CCAGGTATTTATTCCTGTTTGAGCGGCAACACATCAGCTTGCATGTATTC
SEQ ID NO:4   (1101) CCAGGTATTTATTCCTGTTTGAGCGGCAACACATCAGCTTGCATGTATTC
SEQ ID NO:8   (1069) CCCGGCATCTACAGCTGCCTGAGCGGCAACACCAGCGCCTGCATGTACAG
SEQ ID NO:49  (1069) CCTGGTATTTATTCTTGTCTGAGCGGTAATACATCGGCTTGCATGTATTC
SEQ ID NO:51  (1069) CCTGGTATTTATTCTTGTCTGAGCGGTAATACATCGGCTTGCATGTATTC
SEQ ID NO:53  (1069) CCAGGTATTTATTCCTGTTTAAGCGGCAACACATCAGCTTGCATGTATTC
```

Figure 19E

```
                    1151                                              1200
SEQ ID NO:1   (1119) CAAGACCGAAGGCGCACTGACAACACCCTACATGGCGCTGAAGGGAAGCG
SEQ ID NO:3   (1119) AAAGACTGAAGGCGCACTCACTACGCCGTATATGGCGCTTAAAGGCTCAG
SEQ ID NO:4   (1151) AAAGACTGAAGGCGCACTCACTACGCCGTATATGGCGCTTAAAGGCTCAG
SEQ ID NO:8   (1119) CAAGACCGAAGGAGCACTGACAACACCCTACATGGCGCTGAAGGGAAGCG
SEQ ID NO:49  (1119) AAAGACTGAAGGCGCACTTACTACGCATATATGGCTCTCAAAGGCTCAG
SEQ ID NO:51  (1119) AAAGACTGAAGGCGCACTTACTACGCATATATGGCTCTCAAAGGCTCAG
SEQ ID NO:53  (1119) AAAGACTGAAGGCGCACTCACTACGCCGTATATGGCGCTTAAAGGCTCAG 1201                                              1250
SEQ ID NO:1   (1169) TGATCGCCAACTGCAAGATCACCACCTGCAGATGCACCGAGCGCCAGGC
SEQ ID NO:3   (1169) TTATTGCCAATTGTAAAATAACAACATGTAGATGTACAGACCCTCCTGCT
SEQ ID NO:4   (1201) TTATTGCCAATTGTAGGATAACAACATGTAGATGTACAGACCCTCCTGGT
SEQ ID NO:8   (1169) TGATCGCCAACTGCAAGATGACCACCTGTAGATGCGCCAGCCGCCAGGC
SEQ ID NO:49  (1169) TTATTGCCAATTGCAAGCTGACAACATGTAGATGTGCAGATCCGCAGGT
SEQ ID NO:51  (1169) TTATTGCCAATTGCAAGCTGACAACATGTAGATGTGCAGATCCGCAGGT
SEQ ID NO:53  (1169) TTATTGCCAATTGTAAGATAACAACATGTAGATGTACAGACCCTCCTGGT 1251                                              1300
SEQ ID NO:1   (1219) ATCATCAGCCAGAACTACGGCGAGGCCGTGAGCCTGATCGATCGCCAGTTC
SEQ ID NO:3   (1219) ATCATATCGCAAAATTATGGAGAAGCTGTATCCCTGATAGATAGACATTC
SEQ ID NO:4   (1251) ATCATATCGCAAAATTATGGAGAAGCTGTATCCCTGATAGATAGACATTC
SEQ ID NO:8   (1219) ATCATCAGCCAGAACTACGGCGAGGCCGTGAGCCTGATCGACAAACATTC
SEQ ID NO:49  (1219) ATCATATCGCAAAATTATGGAGAAGCTGTGTCCTTAATAGATAGGCACTC
SEQ ID NO:51  (1219) ATCATATCGCAAAATTATGGAGAAGCTGTGTCCTTAATAGATAGGCACTC
SEQ ID NO:53  (1219) ATCATATCGCAAAATTATGGAGAAGCTGTATCCCTGATAGATAGACATTC 1301                                              1350
SEQ ID NO:1   (1269) CTGTAAGCTGCTGTCGCTGGACGGCATCACACTGAGACTGAGCGGCAGT
SEQ ID NO:3   (1269) GTGCAATGTCTTATCATTAGACGGGATAACTCTAAGGCTCACTGGGCAAT
SEQ ID NO:4   (1301) GTGCAATGTCTTATCATTAGACGGGATAACTCTAAGGCTCAGTGGGCAAT
SEQ ID NO:8   (1269) CTGTAGCGTGCTGTCGCTGGATGGCATCACACTGAGACTGAGCGGCAGT
SEQ ID NO:49  (1269) ATGCAAGGTCTTATCGTTAGACGGGATAACTCTGAGGCTCAGTGGACAAT
SEQ ID NO:51  (1269) ATGCAAGGTCTTATCGTTAGACGGGATAACTCTGAGGCTCAGTGGACAAT
SEQ ID NO:53  (1269) GTGCAATGTCTTATCATTAGACGGGATAACTCTGAGGCTCAGTGGACAAT 1351                                              1400
SEQ ID NO:1   (1319) TCGATGCCACGTACCAGAAGAACATCAGCATCCTGGACAGCCAGCTGATC
SEQ ID NO:3   (1319) TTGATGCAACTTATCAAAAGAACATCGAATACAGATTCTCAAGTCATC
SEQ ID NO:4   (1351) TTGATGCAACTTATCAAAAGAACATCGAATACAGATTCTCAAGTCATC
SEQ ID NO:8   (1319) TCGACGCCACCTACCAGAAGAACATCAGCATCCTGGACAGCCAGCTGATC
SEQ ID NO:49  (1319) TTGATGCAACCTATCAAAAGAATATCTCTATACAGATTCTCAAGTTATA
SEQ ID NO:51  (1319) TTGATGCAACCTATCAAAAGAATATCTCTATACAGATTCTCAAGTTATA
SEQ ID NO:53  (1319) TTGATGCAACTTATCAAAAGAACATCGAATACAGATTCTCAAGTCATC 1401                                              1450
SEQ ID NO:1   (1369) GTGACCGGCAACCTGGACATCAGCACCGAGCTGGGCAACGTGAATAACAG
SEQ ID NO:3   (1369) GTGACAGGCAATCTTGATATATCAACTGAACTTGGAAACGTCAACAATTC
SEQ ID NO:4   (1401) GTGACAGGCAATCTTGATATATCAACTGAACTTGGAAACGTCAACAATTC
SEQ ID NO:8   (1369) GTGACCGGCAACCTGGACATCAGCACCGAGCTGGGCAACGTGAACAACAG
SEQ ID NO:49  (1369) GTGACAGGCAATCTTGATATATCAACTGAGCTTGGGAATGTCAACAACTC
SEQ ID NO:51  (1369) GTGACAGGCAATCTTGATATATCAACTGAGCTTGGGAATGTCAACAACTC
SEQ ID NO:53  (1369) GTGACAGGCAATCTTGATATATCAACTGAACTTGGAAACGTCAACAATTC
```

Figure 19F

```
                    1451                                          1500
SEQ ID NO:1   (1419) CATCAGCAACGCCCTGGACAGACTGGCCGAGAGCAACAGCAAGCTGAAA
SEQ ID NO:3   (1419) AATCAGCAATGCCTTGGATAGGTTGCCAGAAAGCAACAGCAAGCTAGAAA
SEQ ID NO:4   (1451) AATCAGCAATGCCTTGGATAGGTTGCCAGAAAGCAACAGCAAGCTAGAAA
SEQ ID NO:8   (1419) CATCAGCAGCACCCTGGACAAGCTGGCCGAGTCCAACAACAAGCTGAACA
SEQ ID NO:49  (1419) AATAAGTAATGCCCTGAATAAGTTAGAGAAAGCAACAGCAAACTAGACA
SEQ ID NO:51  (1419) AATAAGTAATGCCCTGAATAAGTTAGAGAAAGCAACAGCAAACTAGACA
SEQ ID NO:53  (1419) AATCAGCAATGCCTTGGATAAGTTGCCAAAAAGCAACAGCAAGCTAGAAA 1501                                          1550
SEQ ID NO:1   (1469) AAGTGAACGTGCGCCTGACATCCACTTCCGCTCTGATCACCTACATCGTG
SEQ ID NO:3   (1469) AAGTCAATGTCAGACTAACCAGCACATCGCTCTCATTACCTATATTGTT
SEQ ID NO:4   (1501) AAGTCAATGTCAGACTAACCAGCACATCGCTCTCATTACCTATATTGTT
SEQ ID NO:8   (1469) AAGTGAACGTGAACCTGACCAGCACAAGCGCCCTGATCACCTACATCGTG
SEQ ID NO:49  (1469) AAGTCAATCTCAAACTGACCAGCACATCGCTCTCATTACCTATATGTT
SEQ ID NO:51  (1469) AAGTCAATCTCAAACTGACCAGCACATCGCTCTCATTACCTATATGTT
SEQ ID NO:53  (1469) AAGTCAATCTCAGACTAACCAGCACATCGCTCTCATTACCTATATTGTT 1551                                          1600
SEQ ID NO:1   (1519) CTGACCGTGATCAGCCTGCTGTTCGGCGGCCTGAGCCTGGTGCTGGCCTG
SEQ ID NO:3   (1519) CTAACTGTCATTTCTCTAGTTTTCGGTGCACTTAGTCTGGTGTTAGCGTG
SEQ ID NO:4   (1551) CTAACTGTCATTTCTCTAGTTTTCGGTGCACTTAGTCTGGTGTTAGCGTG
SEQ ID NO:8   (1519) CTGGCCATCGTGTCCTGGCCTTCGGCCTGATCAGCCTGGTGCTGGCCTG
SEQ ID NO:49  (1519) TTAACTGTCATATCCCTTGTTTTTGGTGTACTTAGCCTGGTTCTAGCATG
SEQ ID NO:51  (1519) TTAACTGTCATATCCCTTGTTTTTGGTGTACTTAGCCTCGTTCTAGCATG
SEQ ID NO:53  (1519) CTGACTGTCATTTCTCTAGTTTTCGGTGCACTAAGTCTGGGTTAACATG 1601                                          1650
SEQ ID NO:1   (1569) CTACCTGATGTACAAGCAGAAGGCCCAGCAGAAAACCCTGCTGTGGCTGG
SEQ ID NO:3   (1569) TTACCTGATGTACAAACAGAAGGCACAACAAAGACCTTGCTATGGCTTG
SEQ ID NO:4   (1601) TTACCTGATGTACAAACAGAAGGCACAACAAAGACCTTGCTATGGCTTG
SEQ ID NO:8   (1569) CTACCTGATGTACAAGCAGAGAGCCCAGCAGAAAACCCTGCTGTGGCTGG
SEQ ID NO:49  (1569) CTACCTGATGTACAAGCAAAAGGCACAACAAAGACCTTGTTATGGCTTG
SEQ ID NO:51  (1569) CTACCTGATGTACAAGCAAAAGGCACAACAAAGACCTTGTTATGGCTTG
SEQ ID NO:53  (1569) TTACCTGATGTACAAACAAAAGGCACAACAAAGACCTTGCTATGGCTTG 1651                                     1697
SEQ ID NO:1   (1619) GCAACAACACCCTGGACCAGATGAGAGCCACCACCAGAGCCTGATGA
SEQ ID NO:3   (1619) GGAATAATACCCTCGATCAGATGAGAGCCTACAAGAGCATGA---
SEQ ID NO:4   (1651) GGAATAATACCCTCGATCAGATGAGAGCCTACAAGAGCATGA--
SEQ ID NO:8   (1619) GCAACAACACCCTGGACCAGATGAGGGCCACCACCAGAAGCTGATGA
SEQ ID NO:49  (1619) GGAATAATACCCTTGATCAGATGAGAGCCACTACAAAAATATGA---
SEQ ID NO:51  (1619) GGAATAATACCCTTGATCAGATGAGAGCCACTACAAAAATATGA---
SEQ ID NO:53  (1619) GGAATAATACCCTCGATCAGATGAGAGCCACTACAAGAGCATGA---
```

Figure 19G

|        | SEQ:1 | SEQ:3 | SEQ:4 | SEQ:8 | SEQ:49 | SEQ:51 | SEQ:53 |
|--------|-------|-------|-------|-------|--------|--------|--------|
| SEQ:1  | 100%  | 72%   | 72%   | 92%   | 71%    | 71%    | 71%    |
| SEQ:3  |       | 100%  | 99%   | 69%   | 88%    | 89%    | 98%    |
| SEQ:4  |       |       | 100%  | 69%   | 88%    | 88%    | 97%    |
| SEQ:8  |       |       |       | 100%  | 70%    | 71%    | 69%    |
| SEQ:49 |       |       |       |       | 100%   | 99%    | 88%    |
| SEQ:51 |       |       |       |       |        | 100%   | 88%    |
| SEQ:53 |       |       |       |       |        |        | 100%   |

Figure 20A

The DNA sequence alignment between SEQ ID NO:3 and SEQ ID NO:4 (AY337464.1) to highlight the differences at nucleotide level:

```
SEQ ID NO:3    1     ATGGGCTCCAAACCTTCTACCAGGATCCCAGCACCTCTGATGCTGATCACCCGGATTATG   60
SEQ ID NO:4   33     ............................................................   92

SEQ ID NO:3   61     CTGATATTGGGCTGTATCCGTCCGACAAGCTCTCTTGACGGCAGGCCTCTTGCAGCTGCA   120
SEQ ID NO:4   93     ............................................................   152

SEQ ID NO:3  121     GGAATTGTAGTAACAGGAGATAAGGCAGTCAATGTATACACTTCGTCTCAGACAGGGTCA   180
SEQ ID NO:4  153     ............................................................   212

SEQ ID NO:3  181     ATCATAGTCAAGTTGCTCCCGAATATGCCCAGGGATAAGGAGGCGTGTGCAAAAGCCCCA   240
SEQ ID NO:4  213     ............................................................   272

SEQ ID NO:3  241     TTAGAGGCATATAACAGAACACTGACTACTTTGCTCACTCCTCTTGGCGACTCCATCCGC   300
SEQ ID NO:4  273     ............................................................   332

SEQ ID NO:3  301     AAGATCCAAGGGTCTGTGTCCACATCTGGAGGAGGCAAGCAAGGCCGCCTGATAGGTGCT   360
SEQ ID NO:4  333     ...........................A.G.GA...AAA...T.T..........   392

SEQ ID NO:3  361     GTTATTGGCAGTGTAGCTCTTGGGGTTGCAACAGCGGCACAGATAACAGCAGCTGCGGCC   420
SEQ ID NO:4  393     ............................................................   452

SEQ ID NO:3  421     CTAATACAAGCCAACCAGAATGCCGCCAACATCCTCCGGCTTAAGGAGAGCATTGCTGCA   480
SEQ ID NO:4  453     ............................................................   512

SEQ ID NO:3  481     ACCAATGAAGCTGTGCATGAAGTCACCGACGGATTATCACAACTATCAGTGGCAGTTGGG   540
SEQ ID NO:4  513     ............................................................   572

SEQ ID NO:3  541     AAGATGCAGCAGTTTGTCAATGACCAGTTTAATAATACGGCGCGAGAATTGGACTGTATA   600
SEQ ID NO:4  573     ............................................................   632

SEQ ID NO:3  601     AAAATCACACAACAGGTTGGTGTAGAACTCAACCTATACCTAACTGAATTGACTACAGTA   660
SEQ ID NO:4  633     ............................................................   692

SEQ ID NO:3  661     TTCGGGCCACAGATCACCTCCCCTGCATTAACTCAGCTGACCATCCAGGCACTTTATAAT   720
SEQ ID NO:4  693     ............................................................   752

SEQ ID NO:3  721     TTAGCTGGTGGCAATATGGATTACTTATTAACTAAGTTAGGTATAGGGAACAATCAACTC   780
SEQ ID NO:5  753     ............................................................   812

SEQ ID NO:3  781     AGCTCGTTAATTGGTAGCGGCCTGATCACTGGTTACCCTATACTGTATGACTCACAGACT   840
SEQ ID NO:4  813     ............................................................   872

SEQ ID NO:3  841     CAACTCTTGGGCATACAAGTCAATTTACCCTCAGTCGGGAACTTAAATAATATGCGTGCC   900
SEQ ID NO:4  873     ............................................................   932

SEQ ID NO:3  901     ACCTATTTGGAGACCTTATCTGTAAGTACAACCAAAGGATATGCCTCAGCACTTGTCCCG   960
SEQ ID NO:4  933     ............................................................   992

SEQ ID NO:3  961     AAAGTAGTGACACAAGTCGGTTCCGTGATAGAAGAGCTTGACACCTCATACTGTATAGAG   1020
SEQ ID NO:4  993     ............................................................   1052

SEQ ID NO:3 1021     TCCGATCTGGATTTATATTGTACTAGAATAGTGACATTCCCCATGTCCCCAGGTATTTAT   1080
SEQ ID NO:4 1053     ............................................................   1112

SEQ ID NO:3 1081     TCCTGTTTGAGCGGCAACACATCAGCTTGCATGTATTCAAAGACTGAAGGCGCACTCACT   1140
SEQ ID NO:4 1113     ............................................................   1172

SEQ ID NO:3 1141     ACGCCGTATATGGCCCTTAAAGGCTCAGTTATTGCCAATTGTAAAATAACAACATGTAGA   1200
SEQ ID NO:4 1173     ..................................................GG..............   1232

SEQ ID NO:3 1201     TGTACAGACCCTCCTGGTATCATATCGCAAAATTATGGAGAAGCTGTATCCCTGATACAT   1260
SEQ ID NO:4 1233     ............................................................   1292
```

Figure 20B

```
SEQ ID NO:3   1261  AGACATTCGTGCAATGTCTTATCATTAGACGGGATAACTCTAAGGCTCAGTGGGGAATTT  1320
SEQ ID NO:4   1293  ............................................................  1352

SEQ ID NO:3   1321  GATGCAACTTATCAAAAGAACATCTCAATACTAGATTCTCAAGTCATCGTGACAGGCAAT  1380
SEQ ID NO:4   1353  ............................................................  1412

SEQ ID NO:3   1381  CTTGATATATCAACTGAACTTGGAAACGTCAACAATTCAATCAGCAATGCCTTGGATAGG  1440
SEQ ID NO:4   1413  ............................................................  1472

SEQ ID NO:3   1441  TTGGCAGAAAGCAACAGCAAGCTAGAAAAAGTCAATGTCAGACTAACCAGCACATCTGCT  1500
SEQ ID NO:4   1473  ............................................................  1532

SEQ ID NO:3   1501  CTCATTACCTATATTGTTCTAACTGTCATTTCTCTAGTTTTCGGTGCACTTAGTCTGGTG  1560
SEQ ID NO:4   1533  ........................................................GT  1592

SEQ ID NO:3   1561  TTAGCGTGTTACCTGATGTACAAACAGAAGGCACAACAAAAGACCTTGCTATGGCTTGGG  1620
SEQ ID NO:4   1593  ............................................................  1652

SEQ ID NO:3   1621  AATAATACCCTCGATCAGATGAGAGCCACTACAAGAGCATGA  1662
SEQ ID NO:4   1653  ..........................................  1694
```

Figure 21A

Protein sequence alignment of NDV-F

```
                     1                                                  50
SEQ ID NO:2    (1)   MGSKPSTRIPAPLMLITRIMLILGCIRPTSSLDGRPLAAAGIVVTGDKAV
SEQ ID NO:5    (1)   MGSKPSTRIPAPLMLITRIMLILGCIRPTSSLDGRPLAAAGIVVTGDKAV
SEQ ID NO:50   (1)   MGSASSTRIPVPLMLIIRPALTLSCIRLTSSLDGRPLAAAGIVVTGDKAV
SEQ ID NO:52   (1)   MGSASSTRIPVPLMLIIRPALTLSCIRLTSSLDGRPLAAAGIVVTGDKAV
SEQ ID NO:54   (1)   MGSKPSTRIPAPLMLITRIMLILDCIRPTSSLDGRPLAAAGIVVTGDKAV
SEQ ID NO:7    (1)   MGSKPSTWISVTLMLITRIMLILSCICPTSSLDGRPLAAAGIVVTGDKAV
SEQ ID NO:9    (1)   MGSKPSTWISVTLMLITRIMLILSCICPTSSLDGRPLAAAGIVVTGDKAV 51                                                 100
SEQ ID NO:2    (51)  NVYTSSQTGSIIVKLLPNMPRDKEACAKAPLEAYNRTLTTLLTPLGDSIR
SEQ ID NO:5    (51)  NVYTSSQTGSIIVKLLPNMPRDKEACAKAPLEAYNRTLTTLLTPLGDSIR
SEQ ID NO:50   (51)  NIYTSSQTGSIIVKLLPNMPKDKEVCAKAPLEAYNRTLTTLLTPLGDSIR
SEQ ID NO:52   (51)  NIYTSSQTGSIIVKLLPNMPKDKEVCAKAPLEAYNRTLTTLLTPLGDSIR
SEQ ID NO:54   (51)  NVYTSSQTGSIIVKLLPNMPKDKEACAKDPLEAYNRTLTTLLTPLGESIR
SEQ ID NO:7    (51)  NIYTSSQTGSIIIKLLPNMPKDKEACAKAPLEAYNRTLTTLLTPLGDSIR
SEQ ID NO:9    (51)  NIYTSSQTGSIIIKLLPNMPKDKEACAKAPLEAYNRTLTTLLTPLGDSIR 101                                                150
SEQ ID NO:2   (101)  RIQGSVSTSGGKQGRLIGAVIGSVALGVATAAQITAAAALIQANQNAAN
SEQ ID NO:5   (101)  RIQGSVSTSGGRRQKRFIGAVIGSVALGVATAAQITAAAALIQANQNAAN
SEQ ID NO:50  (101)  AIQESVTTSGGRRQRRFIGAIIGSVALGVATAAQITAASALIQANQNAAN
SEQ ID NO:52  (101)  RIQESVTTSGGKQGRLIGAIIGSVALGVATAAQITAASALIQANQNAAN
SEQ ID NO:54  (101)  RIQGSVSTSGGKQGRLIGAVIGSVALGVATAAQITAAAALIQANQNAAN
SEQ ID NO:7   (101)  RIQGSATTSGGRRQKRFVGAIIGSVALGVATAAQITAAAALIQANQNAAN
SEQ ID NO:9   (101)  RIQGSATTSGGRQGRLVGAIIGSVALGVATAAQITAAAALIQANQNAAN 151                                                200
SEQ ID NO:2   (151)  ILRLKESIAATNEAVHEVTDGLSQLSVAVGKMQQFVNDQFNNTARELDCI
SEQ ID NO:5   (151)  ILRLKESIAATNEAVHEVTDGLSQLSVAVGKMQQFVNDQFNNTARELDCI
SEQ ID NO:50  (151)  ILRLKESIAATNEAVHEVTDGLSQLAVAVGKMQQFVNDQFNNTAQELDCI
SEQ ID NO:52  (151)  ILRLKESIAATNEAVHEVTDGLSQLAVAVGKMQQFVNDQFNNTAQELDCI
SEQ ID NO:54  (151)  ILRLKESIAATNEAVHEVTDGLSQLSVAVGKMQQFVNDQFNNTARELDCI
SEQ ID NO:7   (151)  ILRLKESIAATNDAVHEVTNGLSQLAVAVGKMQQFVNNQFNNTARELDCI
SEQ ID NO:9   (151)  ILRLKESIAATNDAVHEVTNGLSQLAVAVGKMQQFVNNQFNNTARELDCI 201                                                250
SEQ ID NO:2   (201)  KITQQVGVELNLYLTELTTVFGPQITSPALTQLTIQALYNLAGGNMDYLL
SEQ ID NO:5   (201)  KITQQVGVELNLYLTELTTVFGPQITSPALTQLTIQALYNLAGGNMDYLL
SEQ ID NO:50  (201)  KIAQQVGVELNLYLTELTTVFGPQITSPALTQLTIQALYNLAGGNMDYLL
SEQ ID NO:52  (201)  KIAQQVGVELNLYLTELTTVFGPQITSPALTQLTIQALYNLAGGNMDYLL
SEQ ID NO:54  (201)  KITQQVGVELNLYLTELTTVFGPQITSPALTQLTIQALYNLAGGNMDYLL
SEQ ID NO:7   (201)  KIAQQVGVELNLYLTELTTVFGPQITSPALTQLTIQALYNLAGGNMDYLL
SEQ ID NO:9   (201)  KIAQQVGVELNLYLTELTTVFGPQITSPALTQLTIQALYNLAGGNMDYLL
```

Figure 21B

```
                    251                                                300
SEQ ID NO:2   (251) TKLGIGNNQLSSLIGSGLITGYPILYDSQTQLLGIQVNLPSVGNLNNMRA
SEQ ID NO:5   (251) TKLGIGNNQLSSLIGSGLITGYPILYDSQTQLLGIQVNLPSVGNLNNMRA
SEQ ID NO:50  (251) TKLGVGNNQLSSLIGSGLITGNPILYDSQTQILGIQVTLPSVGNLNNMRA
SEQ ID NO:52  (251) TKLGVGNNQLSSLIGSGLITGNPILYDSQTQILGIQVTLPSVGNLNNMRA
SEQ ID NO:54  (251) TKLGIGNNQLSSLIGSGLITGYPILYDSQTQLLGIQVNLPSVGNLNNMRA
SEQ ID NO:7   (251) TKLGVGNNQLSSLIGSGLITGNPILYDSQTQLLGIQINLPSVGSLNNMRA
SEQ ID NO:9   (251) TKLGVGNNQLSSLIGSGLITGNPILYDSQTQLLGIQINLPSVGSLNNMRA 301                                                350
SEQ ID NO:2   (301) TYLETLSVSTTKGFASALVPKVVTQVGSVIEELDTSYCIESDLDLYCTRI
SEQ ID NO:5   (301) TYLETLSVSTTKGFASALVPKVVTQVGSVIEELDTSYCIESDLDLYCTRI
SEQ ID NO:50  (301) TYLETLSVSTTKGFASALVPKVVTQVGSVIEELDTSYCIGSDLDLYCTRI
SEQ ID NO:52  (301) TYLETLSVSTTKGFASALVPKVVTQVGSVIEELDTSYCIGSDLDLYCTRI
SEQ ID NO:54  (301) TYLETLSVSTAKGFASALVPKVVTQVGSVIEELDTSYCIESDLDLYCTRI
SEQ ID NO:7   (301) TYLETLSVSTTKGFASALVPKVVTQVGSVIEELDTSYCIESDLDLYCTRV
SEQ ID NO:9   (301) TYLETLSVSTTKGFASALVPKVVTQVGSVIEELDTSYCIESDLDLYCTRV 351                                                400
SEQ ID NO:2   (351) VTFPMSPGIYSCLSGNTSACMYSKTEGALTPPYMALKGSVIANCRITTCR
SEQ ID NO:5   (351) VTFPMSPGIYSCLSGNTSACMYSKTEGALTPPYMALKGSVIANCRITTCR
SEQ ID NO:50  (351) VTFPMSPGIYSCLSGNTSACMYSKTEGALTPPYMALKGSVIANCRITTCR
SEQ ID NO:52  (351) VTFPMSPGIYSCLSGNTSACMYSKTEGALTPPYMALKGSVIANCRITTCR
SEQ ID NO:54  (351) VTFPMSPGIYSCLSGNTSACMYSKTEGALTPPYMALKGSVIANCRITTCR
SEQ ID NO:7   (351) VTFPMSPGIYSCLSGNTSACMYSKTEGALTPPYMALKGSVIANCKMTTCR
SEQ ID NO:9   (351) VTFPMSPGIYSCLSGNTSACMYSKTEGALTPPYMALKGSVIANCKMTTCR 401                                                450
SEQ ID NO:2   (401) CTDPPGIISQNYGEAVSLIDRHSCNVLSLDGITLRLSGEFDATYQKNISI
SEQ ID NO:5   (401) CTDPPGIISQNYGEAVSLIDRHSCNVLSLDGITLRLSGEFDATYQKNISI
SEQ ID NO:50  (401) CADPPGIISQNYGEAVSLIDRHSCNVLSLDGITLRLSGEFDATYQKNISI
SEQ ID NO:52  (401) CADPPGIISQNYGEAVSLIDRHSCNVLSLDGITLRLSGEFDATYQKNISI
SEQ ID NO:54  (401) CTDPPGIISQNYGEAVSLIDRHSCNVLSLDGITLRLSGEFDATYQKNISI
SEQ ID NO:7   (401) CADPPGIISQNYGEAVSLIDRHSCSVLSLDGITLRLSGEFDATYQKNISI
SEQ ID NO:9   (401) CADPPGIISQNYGEAVSLIDRHSCSVLSLDGITLRLSGEFDATYQKNISI 451                                                500
SEQ ID NO:2   (451) LDSQVIVTGNLDISTELGNVNNSISNALDRLAESNSKLEKVNVRLTSTSA
SEQ ID NO:5   (451) LDSQVIVTGNLDISTELGNVNNSISNALDRLAESNSKLEKVNVRLTSTSA
SEQ ID NO:50  (451) LDSQVIVTGNLDISTELGNVNNSISNALNRLERSNSKLDKVNVKLTSTSA
SEQ ID NO:52  (451) LDSQVIVTGNLDISTELGNVNNSISNALNRLERSNSKLDKVNVKLTSTSA
SEQ ID NO:54  (451) LDSQVIVTGNLDISTELGNVNNSISNALDRLAKSNSKLEKVNVRLTSTSA
SEQ ID NO:7   (451) LDSQVIVTGNLDISTELGNVNRSISSTLDRLAESNNELNKVNVNLTSTSA
SEQ ID NO:9   (451) LDSQVIVTGNLDISTELGNVNRSISSTLDRLAESNNELNKVNVNLTSTSA 501                                                550
SEQ ID NO:2   (501) LITYIVLTVISLVPGALSIVLACYLMYKQKAQQKTLLWLGNNTLDQMRAT
SEQ ID NO:5   (501) LITYIVLTVISLVPGALSIGLACYLMYKQKAQQKTLLWLGNNTLDQMRAT
SEQ ID NO:50  (501) LITYIVLTVISLVPGVLSIVLACYLMYKQKAQQKTLLWLGNNTLDQMRAT
SEQ ID NO:52  (501) LITYIVLTVISLVPGVLSIVLACYLMYKQKAQQKTLLWLGNNTLDQMRAT
SEQ ID NO:54  (501) LITYIVLTVISLVPGALSIGLTCYLMYKQKAQQKTLLWLGNNTLDQMRAT
SEQ ID NO:7   (501) LITYIVLAVVSLAPGVISLVLACYLMYKQKAQQKTLLWLGNNTLDQMRAT
SEQ ID NO:9   (501) LITYIVLAVVSLAPGVISLVLACYLMYKQKAQQKTLLWLGNNTLDQMRAT
```

Figure 21C

```
                        551
SEQ ID NO:2   (551)  ░░A-
SEQ ID NO:5   (551)  ░░A-
SEQ ID NO:50  (551)  ░░I-
SEQ ID NO:52  (551)  ░░I-
SEQ ID NO:54  (551)  ░░A-
SEQ ID NO:7   (551)  ░░T-
SEQ ID NO:9   (551)  ░░T-
```

|        | SEQ:2 | SEQ:5 | SEQ:50 | SEQ:52 | SEQ:54 | SEQ:7 | SEQ:9 |
|--------|-------|-------|--------|--------|--------|-------|-------|
| SEQ:2  | 100%  | 99%   | 92%    | 93%    | 98%    | 91%   | 92%   |
| SEQ:5  |       | 100%  | 93%    | 92%    | 98%    | 92%   | 91%   |
| SEQ:50 |       |       | 100%   | 99%    | 92%    | 92%   | 91%   |
| SEQ:52 |       |       |        | 100%   | 92%    | 91%   | 92%   |
| SEQ:54 |       |       |        |        | 100%   | 90%   | 91%   |
| SEQ:7  |       |       |        |        |        | 100%  | 99%   |
| SEQ:9  |       |       |        |        |        |       | 100%  |

Figure 22

Protein sequence alignment of IBDV VP2

```
                     1                                                  50
SEQ ID NO:40   (1)   MTNLQDQTQQIVPFIRSLLMPTTGPASIPDDTLEKHTLRSETSTYNLTVG
SEQ ID NO:59   (1)   MTNLQDQTQQIVPFIRSLLMPTTGPASIPDDTLEKHTLRSETSTYNLTVG 51                                                100
SEQ ID NO:40  (51)   DTGSGLIVFFPGFPGSIVGAHYTLQSNGNYKFDQMLLTAQNLPASYNYCR
SEQ ID NO:59  (51)   DTGSGLIVFFPGFPGSIVGAHYTLQSNGNYKFDQMLLTAQNLPASYNYCR 101                                               150
SEQ ID NO:40 (101)   LVSRSLTVRSSTLPGGVYALNGTINAVTFQGSLSELTDVSYNGLMSATAN
SEQ ID NO:59 (101)   LVSRSLTVRSSTLPGGVYALNGTINAVTFQGSLSELTDVSYNGLMSATAN 151                                               200
SEQ ID NO:40 (151)   INDKIGNVLVGEGVTVLSLPTSYDLGYVRLGDPIPAIGLDPKMVATCDSS
SEQ ID NO:59 (151)   INDKIGNVLVGEGVTVLSLPTSYDLGYVRLGDPIPAIGLDPKMVATCDSS 201                                               250
SEQ ID NO:40 (201)   DRPRVYTITAADDYQFSSQYQPGGVTITLFSANIDAITSLSIGGELVFQT
SEQ ID NO:59 (201)   DRPRVYTITAADNYQFSSQYQTGGVTITLFSANIDAITSLSVGGELVFKT 251                                               300
SEQ ID NO:40 (251)   SVQGLVLGATIYLIGFDGTAVITRAVAADNGLTAGTDNLMPFNLVIPTNE
SEQ ID NO:59 (251)   SVQSLVLGATIYLIGFDGTAVITRAVAANNGLTAGIDNLMPFNLVIPTNE 301                                               350
SEQ ID NO:40 (301)   ITQPITSIKLEIVTSKSGSQAGRQMSWSASGSLAVTIHGGNYPGALRPVT
SEQ ID NO:59 (301)   ITQPITSIKLEIVTSKSDGQAGRQMSWSASGSLAVTIHGGNYPGALRPVT 351                                               400
SEQ ID NO:40 (351)   LVAYERVATGSVVTVAGVSNFELIPNPELAKNLVTEYGRFDPGAMNYTKL
SEQ ID NO:59 (351)   LVAYERVATGSVVTVAGVSNFELIPNPELAKNLVTEYGRFDPGAMNYTKL 401                                               450
SEQ ID NO:40 (401)   ILSERDRLGIKTVWPTREYTDFREYFMEVADLNSPLKIAGAFGFKDIIRA
SEQ ID NO:59 (401)   ILSERDRLGIKTVWPTREYTDFREYFMEVADLNSPLKIAGAFGFKDIIRA

451
SEQ ID NO:40 (451)   IRK-
SEQ ID NO:59 (451)   IRK-
```

SEQ ID NO:40 is 98% identical to SEQ ID NO:59

Figure 23A

DNA sequence alignment of IBDV VP2 genes

```
                      1                                                  50
SEQ ID NO:39    (1)   ATGACAAACCTGCAAGATCAAACCCAACAGATTGTTCCGTTCATACGGAG
SEQ ID NO:58    (1)   ATGACAAACCTGCAAGATCAAACCCAACAGATTGTTCCGTTCATACGGAG 51                                                 100
SEQ ID NO:39   (51)   CCTTCTGATGCCAACAACCGGACCGGCGTCCATTCCGGACGACACCCTGG
SEQ ID NO:58   (51)   CCTTCTGATGCCAACAACCGGACCGGCGTCCATTCCGGACGACACCCTGG 101                                                150
SEQ ID NO:39  (101)   AGAAGCACACTCTCAGGTCAGAGACCTCGACCTACAATTTGACTGTGGGG
SEQ ID NO:58  (101)   AGAAGCACACTCTCAGGTCAGAGACCTCGACCTACAATTTGACTGTGGGG 151                                                200
SEQ ID NO:39  (151)   GACACAGGGTCAGGGCTAATTGTCTTTTTCCCTGGATTCCCTGGCTCAAT
SEQ ID NO:58  (151)   GACACAGGGTCAGGGCTAATTGTCTTTTTCCCTGGATTCCCTGGCTCAAT 201                                                250
SEQ ID NO:39  (201)   TGTGGGTGCTCACTACACACTGCAGAGCAATGGGAACTACAAGTTCGATC
SEQ ID NO:58  (201)   TGTGGGTGCTCACTACACACTGCAGAGCAATGGGAACTACAAGTTCGATC 251                                                300
SEQ ID NO:39  (251)   AGATGCTCCTGACTGCCCAGAACCTACCGGCCAGCTACAACTACTGCAGA
SEQ ID NO:58  (251)   AGATGCTCCTGACTGCCCAGAACCTACCGGCCAGCTACAACTACTGCAGG 301                                                350
SEQ ID NO:39  (301)   CTAGTGAGTCGGAGTCTCACAGTGAGGTCAAGCACACTCCCTGGTGGCGT
SEQ ID NO:58  (301)   CTAGTGAGTCGGAGTCTCACAGTAAGGTCAAGCACACTCCCTGGTGGCGT 351                                                400
SEQ ID NO:39  (351)   TTATGCACTAAACGGCACCATAAACGCCGTGACCTTCCAAGGAAGCCTGA
SEQ ID NO:58  (351)   TTATGCACTAAACGGCACCATAAACGCCGTGACCTTCCAAGGAAGCCTGA 401                                                450
SEQ ID NO:39  (401)   GTGAACTGACAGATGTTAGCTACAATGGGTTGATGTCTGCAACAGCCAAC
SEQ ID NO:58  (401)   GTGAACTGACAGATGTTAGCTACAACGGGTTGATGTCTGCAACAGCCAAC 451                                                500
SEQ ID NO:39  (451)   ATCAACGACAAAATTGGGAATGTCCTGGTAGGGGAAGGGGTCACTGTCCT
SEQ ID NO:58  (451)   ATCAACGACAAAATTGGGAACGTCCTAGTAGGGGAAGGGGTAACCGTCCT 501                                                550
SEQ ID NO:39  (501)   CAGCCTACCCACATCATATGATCTTGGGTATGTGAGGCTTGGTGACCCCA
SEQ ID NO:58  (501)   CAGCCTTACCCACATCATATGATCTTGGGTATGTGAGGCTTGGTGACCCCA 551                                                600
SEQ ID NO:39  (551)   TTCCCGCTATAGGGCTTGACCCAAAAATGGTAGCTACATGCGACAGCAGT
SEQ ID NO:58  (551)   TACCCGCTATAGGGCTTGACCCAAAAATGGTAGCAACATGTGACAGCAGT 601                                                650
SEQ ID NO:39  (601)   GACAGGCCCAGAGTCTACACCATAACTGCAGCCGATGATTACCAATTCTC
SEQ ID NO:58  (601)   GACAGGCCCAGAGTCTACACCATAACTGCAGCCGATAATTACCAATTCTC
```

Figure 23B

```
                    651                                              700
SEQ ID NO:39  (651) ATCACAGTACCAACCAGGTGGGGTAACAATCACACTGTTCTCAGCCAACA
SEQ ID NO:58  (651) ATCACAGTACCAAACAGGTGGGGTAACAATCACACTGTTCTCAGCCAACA 701                                              750
SEQ ID NO:39  (701) TTGATGCTATCACAAGCCTCAGCATTGGGGAGAGCTCGTGTTTCAAACA
SEQ ID NO:58  (701) TTGATGCCATCACAAGTCTCAGCGTTGGGGAGAGCTCGTGTTCAAAACA 751                                              800
SEQ ID NO:39  (751) AGCGTCCAAGGCCTTGTACTGGGCGCCACCATCTACCTTATAGGCTTTGA
SEQ ID NO:58  (751) AGCGTCCAAAGCCTTGTACTGGGCGCCACCATCTACCTTATAGGCTTTGA 801                                              850
SEQ ID NO:39  (801) TGGGACTGCGGTAATCACCAGAGCTGTAGCCGCAGATAATGGGCTGACGG
SEQ ID NO:58  (801) TGGGACTGCGGTAATCACCAGAGCTGTGGCCGCAAACAATGGGCTGACGG 851                                              900
SEQ ID NO:39  (851) CCGGCACCGACAATCTTATGCCATTCAATCTTGTCATTCCAACCAATGAG
SEQ ID NO:58  (851) CCGGCATCGACAATCTTATGCCATTCAATCTTGTGATTCCAACCAATGAG 901                                              950
SEQ ID NO:39  (901) ATAACCCAGCCAATCACATCCATCAAACTGGAGATAGTGACCTCCAAAAG
SEQ ID NO:58  (901) ATAACCCAGCCAATCACATCCATCAAACTGGAGATAGTGACCTCCAAAAG 951                                             1000
SEQ ID NO:39  (951) TGGTGGTCAGGCAGGGGATCAGATGTCATGGTCGGCAAGTGGGAGCCTAG
SEQ ID NO:58  (951) TGATGGTCAGGCAGGGGAACAGATGTCATGGTCGGCAAGTGGGAGCCTAG 1001                                            1050
SEQ ID NO:39 (1001) CAGTGACGATCCATGGTGGCAACTATCCAGGGGCCCTCCGTCCCGTCACA
SEQ ID NO:58 (1001) CAGTGACGATCCATGGTGGCAACTATCCAGGAGCCCTCCGTCCCGTCACA 1051                                            1100
SEQ ID NO:39 (1051) CTAGTAGCCTACGAAAGAGTGGCAACAGGATCCGTCGTTACGGTCGCTGG
SEQ ID NO:58 (1051) CTAGTGGCCTACGAAAGAGTGGCAACAGGATCTGTCGTTACGGTCGCTGG 1101                                            1150
SEQ ID NO:39 (1101) GGTGAGTAACTTCGAGCTGATTCCAAATCCTGAACTAGCAAAGAACCTGG
SEQ ID NO:58 (1101) GGTGAGCAACTTCGAGCTGATCCCAAATCCTGAACTAGCAAAGAACCTGG 1151                                            1200
SEQ ID NO:39 (1151) TTACAGAATACGGCCGATTTGACCCAGGAGCCATGAACTACACAAAATTG
SEQ ID NO:58 (1151) TTACAGAATATGGCCGATTTGACCCAGGAGCCATGAACTACACGAAATTG 1201                                            1250
SEQ ID NO:39 (1201) ATACTGAGTGAGAGGGACCGTCTTGGCATCAAGACCGTCTGGCCAACAAG
SEQ ID NO:58 (1201) ATACTGAGTGAGAGGGACCGCCTTGGCATCAAGACCGTCTGGCCAACAAG 1251                                            1300
SEQ ID NO:39 (1251) GGAGTACACTGATTTTCGTGAGTACTTCATGGAGGTGGCCGACCTCAACT
SEQ ID NO:58 (1251) GGAGTACACTGACTTTCGTGAGTACTTCATGGAGGTGGCCGACCTCAACT
```

Figure 23C

```
                    1301                                                  1350
SEQ ID NO:39 (1301) CTCCCCTGAAGATTGCAGGAGCATTTGGCTTCAAAGACATAATCCGGGCT
SEQ ID NO:58 (1301) CTCCCCTGAAGATTGCAGGAGCATTTGGCTTCAAAGACATAATCCGGGCC 1351    1362
SEQ ID NO:39 (1351) ATAAGGAGGTAA
SEQ ID NO:58 (1351) ATAAGGAGGTGA
```

SEQ ID NO:39 is 97% identical to SEQ ID NO:58

Figure 24

The protein sequence alignment between SEQ ID NO:2 and SEQ ID NO:5 (AAP97877.1) to highlight the differences at amino acid level:

```
SEQ ID NO:2    1   MGSKPSTRIPAPLMLITRIMLILGCIRPTSSLDGRPLAAAGIVVTGDKAVNVYTSSQTGS   60
SEQ ID NO:5    1   ............................................................   60

SEQ ID NO:2   61   IIVKLLPNMPRDKEACAKAPLEAYNRTLTTLLTPLGDSIRKIQGSVSTSGGGKQGRLIGA  120
SEQ ID NO:5   61   .....................................................RR.K.F...  120

SEQ ID NO:2  121   VIGSVALGVATAAQITAAAALIQANQNAANILRLKESIAATNEAVHEVTDGLSQLSVAVG  180
SEQ ID NO:5  121   ............................................................  180

SEQ ID NO:2  181   KMQQFVNDQFNNTARELDCIKITQQVGVELNLYLTELTTVFGPQITSPALTQLTIQALYN  240
SEQ ID NO:5  181   ............................................................  240

SEQ ID NO:2  241   LAGGNMDYLLTKLGIGNNQLSSLIGSGLITGYPILYDSQTQLLGIQVNLPSVGNLNNMRA  300
SEQ ID NO:5  241   ............................................................  300

SEQ ID NO:2  301   TYLETLSVSTTKGYASALVPKVVTQVGSVIEELDTSYCIESDLDLYCTRIVTFPMSPGIY  360
SEQ ID NO:5  301   ............................................................  360

SEQ ID NO:2  361   SCLSGNTSACMYSKTEGALTTPYMALKGSVIANCKITTCRCTDPPGIISQNYGEAVSLID  420
SEQ ID NO:5  361   ...............................R............................  420

SEQ ID NO:2  421   RHSCNVLSLDGITLRLSGEFDATYQKNISILDSQVIVTGNLDISTELGNVNNSISNALDR  480
SEQ ID NO:5  421   ............................................................  480

SEQ ID NO:2  481   LAESNSKLEKVNVRLTSTSALITYIVLTVISLVFGALSLVLACYLMYKQKAQQKTLLWLG  540
SEQ ID NO:5  481   .........................................G..................  540

SEQ ID NO:2  541   NNTLDQMRATTRA   553
SEQ ID NO:5  541   .............   553
```

Note: the changes between amino acid positions 112 to 117 were introduced to change the velogenic F-cleavage site sequence to a lentogenic F-cleavage site sequence. The changes at amino acid positions 395 and 520 were made to keep the amino aacid sequence between the wt VIId NDV-F of the present invention and codon-optimized NDV-F the same. The codon optimized NDV-F VIId was based on a consensus sequence of VIId NDV strains.

Figure 25

The protein sequence alignment between SEQ ID NO:2 and SEQ ID NO:9 to highlight the differences at amino acid level:

```
SEQ ID NO:2    1   MGSKFSTRIPAPLMLITRIMLILGCIRPTSSLDGRPLAAAGIVVTGDKAVNVYTSSQTGS   60
SEQ ID NO:9    1   .......W.SVT......T....S..C.........................I........   60

SEQ ID NO:2   61   IIVKLLPNMPRDKEACAKAPLEAYNRTLTTLLTPLGDSIRKIQGSVSTSGGGKQGRLIGA  120
SEQ ID NO:9   61   ..I.......K.....................R....AT..........V..  120

SEQ ID NO:2  121   VIGSVALGVATAAQITAAAALIQANQNAANILRLKESIAATNEAVHEVTDGLSQLSVAVG  180
SEQ ID NO:9  121   I............................D......N.....A....  180

SEQ ID NO:2  181   KMQQFVNDQFNNTARELDCIKITQQVGVELNLYLTELTTVFGPQITSPALTQLTIQALYN  240
SEQ ID NO:9  181   .......N............A.................................  240

SEQ ID NO:2  241   LAGGNMDYLLTKLGIGNNQLSSLIGSGLITGYPILYDSQTQLLGIQVNLPSVGNLNNMRA  300
SEQ ID NO:9  241   .............V..............N.............I......S......  300

SEQ ID NO:2  301   TYLETLSVSTTKGYASALVPKVVTQVGSVIEELDTSYCIESDLDLYCTRIVTFPMSPGIY  360
SEQ ID NO:9  301   .............F......................I......V..........  360

SEQ ID NO:2  361   SCLSGNTSACMYSKTEGALTTPYMALKGSVIANCKITTCRCTDPPGIISQNYGEAVSLID  420
SEQ ID NO:9  361   ......................................M.....A..........  420

SEQ ID NO:2  421   RHSCNVLSLDGITLRLSGEFDATYQKNISILDSQVIVTGNLDISTELGNVNNSISNALDR  480
SEQ ID NO:9  421   K...S................................................ST..K  480

SEQ ID NO:2  481   LAESNSKLEKVNVRLTSTSALITYIVLTVISLVFCALSLVLACYLMYKQKAQQKTLLWLC  540
SEQ ID NO:9  481   .....N..N....N............AIV..A..VI............R..........  540

SEQ ID NO:2  541   NNTLDQMRATTR  552
SEQ ID NO:9  541   ............  552
```

RECOMBINANT GALLID HERPESVIRUS 3 (MDV SEROTYPE 2) VECTORS EXPRESSING ANTIGENS OF AVIAN PATHOGENS AND USES THEREOF

CROSS-REFERENCE TO RELATED APPLICATIONS

This application is a continuation of U.S. application Ser. No. 13/689,572 filed on Nov. 29, 2012, which claims priority to U.S. provisional application 61/564,877 filed on Nov. 30, 2011 and U.S. provisional application 61/694,957 filed on Aug. 30, 2012.

FIELD OF THE INVENTION

The invention relates to recombinant viral vectors for the insertion and expression of foreign genes for use as safe immunization vehicles to protect against a variety of pathogens. It also relates to multivalent composition or vaccine comprising one or more recombinant viral vectors for protection against a variety of pathogens. The present invention relates to methods of making and using the recombinant viral vectors.

BACKGROUND OF THE INVENTION

Poultry vaccination is widely used to protect poultry flocks against devastating diseases including Newcastle disease (ND), infectious bursal disease (IBD), Marek's disease (MD), infectious bronchitis (IB), infectious laryngotracheitis (ILT) and avian influenza (AI). ND is caused by the avian paramyxovirus 1 (APMV-1) also designated ND virus (NDV) belonging to the Paramyxoviridae family. MD is caused by Gallid herpesvirus 2 (Herpesviridae family) also designated as MD virus serotype 1 (MDV1). IB is caused by IB virus (IBV) belonging to the Coronaviridae family, ILT is caused by Gallid herpesvirus 1 (Herpesviridae family) also designated ILT virus (ILTV) and AI is caused by AI virus (AIV) belonging to the Orthomyxoviridae family.

A number of recombinant avian viral vectors have been proposed with a view to vaccinating birds against these avian pathogens. The viral vectors used comprise avipox viruses, especially fowlpox (EP-A-0,517,292), Marek's virus, such as serotypes 2 and 3 (HVT) (WO-A-87/04463), or alternatively the ITLV, NDV and avian adenovirus. When some of these recombinant avian viral vectors were used for vaccination, they display variable levels of protection.

Several recombinant herpesvirus of turkeys (HVT, also designated Meleagrid herpesvirus 1 or MDV serotype 3) vectors expressing antigens from various pathogens (U.S. Pat. Nos. 5,980,906, 5,853,733, 6,183,753, 5,187,087) including IBDV, NDV, ILTV and AIV have been developed and licensed. Of particular interest is a HVT vector-expressing IBDV VP2 protective gene that has shown clear advantages over classical IBD vaccines (Bublot et al J. Comp. Path. 2007, Vol. 137, S81-S84). Other HVT vectors of interest are those expressing either NDV (Morgan et al 1992, Avian dis. 36, 858-70) or ILTV (Johnson et al, 2010 Avian Dis 54, 1251-1259) protective gene(s). One of the practical problems of using several HVT-based recombinant vaccines together is their interference. Lower protection is induced at least against one of the disease when two HVT recombinants expressing different antigens are mixed (Rudolf Heine 2011; Issues of the Poultry Recombinant Viral Vector Vaccines which May Cause an Effect on the Economic Benefits of those Vaccines; paper presented at the XVII World Veterinary Poultry Association (WVPA) Congress in Cancún, Mexico, Aug. 14-18, 2011; Slacum G, Hein R. and Lynch P., 2009, The compatibility of HVT recombinants with other Marek's disease vaccines, 58$^{th}$ Western Poultry Disease Conference, Sacramento, Calif., USA, March 23$^{th}$-25$^{th}$, p 84).

The combination of HVT and SB-1, a Gallid herpesvirus 3 (MDV serotype 2 or MDV-2) vaccine strain, has shown a synergistic effect on MD protection (Witter and Lee, 1984, Avian Pathology 13, 75-92). To address the interference problem, it is of interest to evaluate the SB-1 virus as a vaccine vector to express protective antigen(s) that could be compatible with HVT vector and improve MD protection.

The SB-1 genome was cloned and characterized in bacterial artificial chromosome (BAC) (Petherbridge, et al., J. Virol. Methods 158, 11-17, 2009; Singh et al., Research in Veterinary Science 89, 140-145, 2010). The MDV2 SB-1 sequence was recently obtained and analyzed (Spatz and Schat, Virus Gene 42, 331-338, 2011). A glycoprotein E deletion of SB-1 virus was described by Petherbridge et al. (J. Virol. Methods 158, 11-17, 2009). However, no research has been reported using SB-1 as a viral vector expressing foreign protective genes.

It has been shown that both $U_L13$ protein kinase and glycoprotein C ($U_L44$) genes individually are essential for horizontal transmission of MDV in chickens (Jarosinski, et al., J. of Virology 81, 10575-10587, 2007; Jarosinski, et al., J. of Virology 84, 7911-7916, 2010).

Considering the potential effect of animal pathogens, such as NDV and IBDV on veterinary public health and the economy, efficient methods of preventing infection and protecting animals are needed. There is a need for a solution of combined effective vector vaccines and a suitable method for making the vaccine that could alleviate the problem of interference observed between 2 HVT-based vector vaccines.

SUMMARY OF THE INVENTION

The present invention demonstrated for the first time a recombinant Gallid Herpesvirus-3 (MDV-2) viral vector protecting against a poultry pathogen beyond Marek's disease virus.

The present invention showed surprising result when multivalent vaccines were used to protect animals against a variety of avian pathogens.

The present invention relates to a recombinant Gallid Herpesvirus-3 (MDV-2) vector comprising one or more heterologous polynucleotides coding for and expressing at least one antigen of an avian pathogen. The present invention further relates to a recombinant Gallid Herpesvirus-3 (MDV-2) vector comprising a mutated glycoprotein C (gC) gene.

The present invention provides a composition or vaccine comprising one or more recombinant Gallid Herpesvirus-3 (MDV-2) vectors comprising one or more heterologous polynucleotides coding for and expressing at least one antigen of an avian pathogen. The present invention further provides a composition for vaccine comprising one or more Gallid Herpesvirus-3 (MDV-2) vectors comprising a mutated glycoprotein C (gC) gene.

The present invention provides a polyvalent composition or vaccine comprising: i) a recombinant Gallid Herpesvirus-3 (MDV-2) vector comprising heterologous polynucleotides coding for and expressing at least one antigen of an avian pathogen, or comprising a mutated glycoprotein C (gC) gene; and ii) at least one of: a recombinant HVT vector (or MDV-3 or Meleagrid herpesvirus-1) comprising heterologous polynucleotides coding for and expressing at least one antigen of an avian pathogen; or wild type HVT (MDV-3); or recombinant MDV serotype 1 vector (i.e., MDV-1, Gallid herpesvirus-2) comprising heterologous polynucleotides coding for and expressing at least one antigen of an avian pathogen; or any wild type MDV-1.

The present invention relates to a method of vaccinating an animal, or inducing an immunogenic or protective response in an animal, comprising at least one administration of the composition or vector of the present invention.

The present invention further provides specific insertion loci for the introduction of one or more isolated polynucleotide into nonessential regions of the SB-1 genome.

BRIEF DESCRIPTION OF THE DRAWINGS

The following detailed description, given by way of example, and which is not intended to limit the invention to specific embodiments described, may be understood in conjunction with the accompanying figures, incorporated herein by reference, in which:

FIG. 1 is a table showing the SEQ ID NO assigned to each DNA and protein sequence.

FIG. 3 depicts the immunofluorescent staining of recombinant vSB1-004 virus expressing NDV-F protein.

FIG. 6 depicts the immunofluorescent staining of recombinant vSB1-006 virus expressing NDV-F protein.

FIG. 8 shows the PCR results of vSB1-006.

FIG. 9 depicts the immunofluorescent staining of recombinant SB1-007 virus expressing NDV-F protein.

FIG. 12 depicts the immunofluorescent staining of recombinant SB1-008 virus expressing NDV-F protein.

FIG. 14 shows the PCR results of vSB1-008.

FIG. 15 depicts the Western blot analysis of immunoprecipitated sample from vSB1-009 infected cells.

FIG. 17 depicts the clinical analysis (percentage of birds shedding challenge virus) of the recombinants against CA02 and ZJ1 NDV challenge.

FIGS. 19A-19F depict the DNA sequence alignment of NDV-F genes. FIG. 19G shows the sequence identity percentage.

FIGS. 20A-20B depict the DNA sequence alignment between SEQ ID NO:3 and SEQ ID NO:4 (AY337464.1) highlighting the differences at nucleotide level.

FIGS. 21A-21C depict protein sequence alignment of NDV-F and the sequence identity percentage.

FIG. 22 depicts the protein sequence alignment of IBDV VP2 and the sequence identity percentage.

FIGS. 23A-23C depict DNA sequence alignment of IBDV VP2 genes and the sequence identity percentage.

FIG. 24 depicts the protein sequence alignment between SEQ ID NO:2 and SEQ ID NO:5 (AAP97877.1) highlighting the differences at amino acid level.

FIG. 25 depicts the protein sequence alignment between SEQ ID NO:2 and SEQ ID NO:9 highlighting the differences at amino acid level.

DETAILED DESCRIPTION OF THE INVENTION

Figure 2:
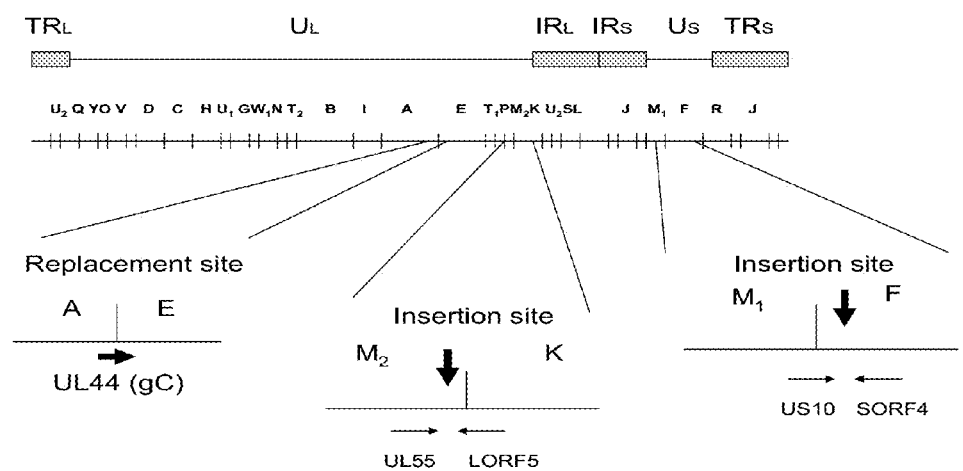
FIG. 2 depicts a schematic diagram of SB-1 genome organization.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Unless otherwise noted, technical terms are used according to conventional usage. Definitions of common terms in molecular biology may be found in Benjamin Lewin, Genes V. published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). The singular terms "a," "an," and "the" include plural referents unless context clearly indicates otherwise. Similarly, the word "or" is intended to include "and" unless the context clearly indicate otherwise. The word "or" means any one member of a particular list and also includes any combination of members of that list.

The term "animal" is used herein to include all mammals, birds and fish. The animal as used herein may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), bovine (e.g., cattle), porcine (e.g., pig), ovine (e.g., sheep, goats, lamas, bisons), avian (e.g., chicken, duck, goose, turkey, quail, pheasant, parrot, finches, hawk, crow, ostrich, emu and cassowary), primate (e.g., prosimian, tarsier, monkey, gibbon, ape), humans, and fish. The term "animal" also includes an individual animal in all stages of development, including embryonic and fetal stages.

The terms "polypeptide" and "protein" are used interchangeably herein to refer to a polymer of consecutive amino acid residues.

The term "nucleic acid", "nucleotide", and "polynucleotide" are used interchangeably and refer to RNA, DNA, cDNA, or cRNA and derivatives thereof, such as those containing modified backbones. It should be appreciated that the invention provides polynucleotides comprising sequences complementary to those described herein. The "polynucleotide" contemplated in the present invention includes both the forward strand (5' to 3') and reverse complementary strand (3' to 5'). Polynucleotides according to the invention can be prepared in different ways (e.g. by chemical synthesis, by gene cloning etc.) and can take various forms (e.g. linear or branched, single or double stranded, or a hybrid thereof, primers, probes etc.).

The term "genomic DNA", or "genome" is used interchangeably and refers to the heritable genetic information of a host organism. The genomic DNA comprises the DNA of the nucleus (also referred to as chromosomal DNA) but also the DNA of the plastids (e.g., chloroplasts) and other cellular organelles (e.g., mitochondria). The genomic DNA or genome contemplated in the present invention also refers to the RNA of a virus. The RNA may be a positive strand or a negative strand RNA. The term "genomic DNA" contemplated in the present invention includes the genomic DNA containing sequences complementary to those described herein. The term "genomic DNA" also refers to messenger RNA (mRNA), complementary DNA (cDNA), and complementary RNA (cRNA).

The term "gene" is used broadly to refer to any segment of polynucleotide associated with a biological function. Thus, genes or polynucleotides include introns and exons as in genomic sequence, or just the coding sequences as in cDNAs, such as an open reading frame (ORF), starting from the start codon (methionine codon) and ending with a termination signal (stop codon). Genes and polynucleotides can also include regions that regulate their expression, such as transcription initiation, translation and transcription termination. Thus, also included are promoters and ribosome binding regions (in general these regulatory elements lie approximately between 60 and 250 nucleotides upstream of the start codon of the coding sequence or gene; Doree S M et al.; Pandher K et al.; Chung J Y et al.), transcription terminators (in general the terminator is located within approximately 50 nucleotides downstream of the stop codon of the coding sequence or gene; Ward C K et al.). Gene or polynucleotide also refers to a nucleic acid fragment that expresses mRNA or functional RNA, or encodes a specific protein, and which includes regulatory sequences.

The term "heterologous DNA" as used herein refers to the DNA derived from a different organism, such as a different cell type or a different species from the recipient. The term also refers to a DNA or fragment thereof on the same genome of the host DNA wherein the heterologous DNA is inserted into a region of the genome which is different from its original location.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The term "immunogenic protein or peptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

The term "immunogenic protein or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The terms "recombinant" and "genetically modified" are used interchangeably and refer to any modification, alteration or engineering of a polynucleotide or protein in its native form or structure, or any modification, alteration or engineering of a polynucleotide or protein in its native environment or surrounding. The modification, alteration or engineering of a polynucleotide or protein may include, but is not limited to, deletion of one or more nucleotides or amino acids, deletion of an entire gene, codon-optimization of a gene, conservative substitution of amino acids, insertion of one or more heterologous polynucleotides.

The terms "polyvalent vaccine or composition", "combination or combo vaccine or composition" and "multivalent vaccine or composition" are used interchangeably to refer to a composition or vaccine containing more than one composition or vaccines. The polyvalent vaccine or composition may contain two, three, four or more compositions or vaccines. The polyvalent vaccine or composition may comprise recombinant viral vectors, active or attenuated or killed wild-type viruses, or a mixture of recombinant viral vectors and wild-type viruses in active or attenuated or killed forms.

One embodiment of the present invention provides a recombinant Gallid herpesvirus 3 (MDV-2) vector that comprises a mutated Glycoprotein C (gC or UL44) gene. The term "mutated gC gene" refers to the gC gene of Gallid herpesvirus 3 (MDV-2) that is altered or engineered which results in a non-functional gC protein upon expression. The alteration or engineering of the gC gene includes mutation or deletion of a segment of the gC gene which is essential for the expression of a functional gC protein. The term "mutated gC gene" also includes deletion of the entire gC gene of Gallid herpesvirus 3 (MDV-2) wherein gC protein is not expressed. Another embodiment of the present invention provides a recombinant Gallid herpesvirus 3 (MDV-2) wherein the Glycoprotein C (gC) gene in the native (wild-type) Gallid herpesvirus 3 (MDV-2) genome encoding the gC protein is deleted. The term "Glycoprotein C (gC) gene" includes any gene or polynucleotide that encodes the Glycoprotein C (gC) of Gallid herpesvirus 3 (MDV-2), and homologs, fragments or variants thereof. The gC gene may encode a gC protein having at least 75%, 80%, 85%, 90%, 95%, 95%, 96%, 97%, 98%, 99%, 99.1%, 99.2%, 99.3%, 99.4%, 99.5%, 99.6%, 99.7%, 99.8% or 99.9% sequence identity to SEQ ID NO: 35, or a variant thereof. The gC gene having at least 75%, 80%, 85%, 90%, 95%, 95%, 96%, 97%, 98%, 99%, 99.1%, 99.2%, 99.3%, 99.4%, 99.5%, 99.6%, 99.7%, 99.8% or 99.9% sequence identity to SEQ ID NO:34 is also encompassed in the present invention.

Another embodiment of the invention provides a recombinant Gallid herpesvirus 3 (MDV-2) viral vector comprising one or more heterologous polynucleotides coding for and expressing at least one antigen or polypeptide of an avian pathogen. The Gallid herpesvirus 3 (MDV-2) strains used for the recombinant viral vector may be any SB-1 strains, including, but not limited to, the commercial Marek's Disease Vaccine (SB-1 vaccine) (Merial Select Inc., Gainesville, Ga. 30503, USA), the SB-1 strain having the genome sequence as defined by GenBank Accession Number HQ840738.1. The Gallid herpesvirus 3 (MDV-2) strains used for the recombinant viral vector may be any other Gallid herpesvirus 3 isolate including the HPRS24 strain having the genome sequence as defined by GenBank Accession Number AB049735.1, or the HPRS24 strain having the genome sequence as defined by GenBank Accession Number NC_002577.1. The genomes of HPRS24 and SB-1 share 98.4% sequence identity (Spatz and Schat, 2011; Virus Gene 42, 331-338). The Gallid herpesvirus 3 (MDV-2) strains used for the recombinant viral vector may be the 301B/1 isolate described by Witter (1987 Avian Dis 31, 752-765) or by Witter et al. (1987 Avian Dis 31, 829-840). The Gallid herpesvirus 3 (MDV-2) strains may be any Gallid herpesvirus 3 (MDV-2) strains comprising the genome sequence having at least 90%, 91%, 92%, 93%, 94%, 95%, 96%, 97%, 98%, or 99% sequence identity to the sequence as defined in GenBank Accession Number HQ840738.1 (SEQ ID NO:14), AB049735.1, or NC 002577.1.

The genes coding for antigen or polypeptide may be those coding for Newcastle Disease Virus fusion protein (NDV-F), Newcastle Disease Virus hemagglutinin neuraminidase (NDV-HN), Marek's Disease Virus glycoprotein C (gC), Marek's Disease Virus glycoprotein B (gB), Marek's Disease Virus glycoprotein E (gE), Marek's Disease Virus glycoprotein I (gI), Marek's Disease Virus glycoprotein H (gH) or Marek's Disease Virus glycoprotein L (gL), IBDV VP2, IBDV VPX, IBDV VP3, IBDV VP4, ILTV glycoprotein B, ILTV glycoprotein I, ILTV UL32, ILTV glycoprotein D, ILTV glycoprotein E, ILTV glycoprotein C, influenza hemaglutinin (HA), influenza neuraminidase (NA), protective genes derived from *Mycoplasma gallisepticum* (MG), or *Mycoplasma synoviae* (MS), or combinations thereof. The antigen or polypeptide may be any antigen from the poultry pathogen selected form the group consisting of avian encephalomyelitis virus, avian reovirus, avian paramyxovirus, avian metapneumovirus, avian influenza virus, avian adenovirus, fowl pox virus, avian coronavirus, avian rotavirus, chick anemia virus, avian astrovirus, avian parvovirus, coccidiosis (*Eimeria* sp.), *Campylobacter* sp., *Salmonella* sp., *Pasteurella* sp., *Avibacterium* sp., *Mycoplasma gallisepticum, Mycoplasma synoviae, Clostridium* sp., and *E. coli*.

Moreover, homologs of aforementioned antigen or polynucleotides are intended to be within the scope of the present invention. As used herein, the term "homologs" includes orthologs, analogs and paralogs. The term "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type polypeptide can differ from the wild-type polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the polynucleotide or polypeptide sequences of antigens described above, and will exhibit a similar function.

In one embodiment, the present invention provides a recombinant Gallid Herpesvirus-3 (MDV-2) viral vector comprising one, two or more heterologous polynucleotides coding for and expressing the NDV-F antigen or polypeptide. In one aspect of the embodiment, the NDV-F antigen or polypeptide has at least 70%, 75%, 80%, 85%, 90%, 95%, 96%, 97%, 98% or 99% sequence identity to a polypeptide having the sequence as set forth in SEQ ID NO:2, 9, 50, 52, or 54, or a conservative variant, an allelic variant, a homolog or an immunogenic fragment comprising at least eight or at east ten consecutive amino acids of one of these polypeptides, or a combination of these polypeptides. In another aspect of the embodiment, the heterologous polynucleotide encoding an NDV-F antigen or polypeptide has at least 70%, 75%, 80%, 85%, 90%, 95%, 96%, 97%, 98% or 99% sequence identity to a polypeptide having the sequence as set forth in SEQ ID NO:2, 9, 50, 52, or 54. In yet another aspect of the embodiment, the heterologous polynucleotide has at least 70%, 75%, 80%, 85%, 90%, 95%, 96%, 97%, 98% or 99% sequence identity to a polynucleotide having the sequence as set forth in SEQ ID NO:1, 8, 49, 51, or 53.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

The term "identity" with respect to sequences can refer to, for example, the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman). The sequence identity or sequence similarity of two amino acid sequences, or the sequence identity between two nucleotide sequences can be determined using Vector NTI software package (Invitrogen, 1600 Faraday Ave., Carlsbad, Calif.). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for NDV-F polypeptides, the DNA sequence of the NDV-F protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of NDV F protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the NDV-F polypeptide encoded by the nucleotide sequence is functionally unchanged.

In another embodiment, the present invention provides a method for producing a recombinant Gallid Herpesvirus-3 or SB-1 viral vector comprising the introduction into the SB-1 genome of one, two or more isolated polynucleotides in a nonessential region of the SB-1 genome. In yet another embodiment, the present invention provides a method for producing a recombinant Gallid Herpesvirus-3 or SB-1 viral vector comprising the steps of altering, engineering, or deleting the gC gene from the SB-1 genome. The term "nonessential region" refers to a region of a virus genome which is not essential for replication and propagation of the virus in tissue culture or in chickens. Any nonessential region or portion thereof can be deleted from the SB-1 genome or a foreign sequence can be inserted in it, and the viability and stability of the recombinant Gallid Herpesvirus-3 or SB-1 vector resulting from the deletion or insertion can be used to ascertain whether a deleted region or portion thereof is indeed nonessential. In one aspect of the embodiment, the non-essential regions are located in the unique long (UL) and unique short (US) regions of the SB-1 genome (see Spatz et al., Virus Genes 42:331-338, 2011). The UL region of SB-1 is about 109,744 bp to about 109,932 bp in length and may extend from positions 12,209 to 121,952 of SEQ ID NO:14 (GenBank accession No, HQ840738.1) or equivalent positions of other SB1-genomes, for example, from 11,826 bp to 121,757 bp of HPRS24 genome. The US region of SB-1 is about 12,109 bp to about 12,910 bp in length and may extend from positions 143,514 to 156,423 of SEQ ID NO:14 (GenBank accession No, HQ840738.1) or equivalent positions of other SB1-genomes, for example from 142,681 bp to 154,789 bp of HPRS24 genome (Spatz et al., 2011). In one aspect of the embodiment, the non-essential region is between ORF of UL55 and ORF of LORF5 in the unique long (UL) region of SB-1. In another aspect, the polynucleotide is inserted into or to replace SB-1 glycoprotein C gene (also designated UL44). The use of the gC locus may allow the generation of recombinant virus unable to produce a functional gC protein and unable to be transmitted horizontally. In yet another embodiment, the nonessential region may be in the intergenic regions between UL7 and UL8, between UL 21 and UL22, between UL40 and UL41, between UL50 and UL51, between UL54 and LORF4, between US10 and SORF4, or within the UL43, US2, US10 or US6 (coding for gD) gene (see GenBank accession No, HQ840738.1). In yet another embodiment, the nonessential regions may be in the region of nucleotide positions 118057-118306 (intergenic UL55-LORF5), 98595-100031 (gC or UL44), 25983-26038 (intergenic UL7-UL8), 49865-50033 (intergenic UL21-UL22), 75880-75948 (intergenic UL35-UL36), 93928-93990 (intergenic UL40-UL41), 109777-109847 (intergenic UL50-UL51), 116466-116571 (intergenic UL54-LORF4), 146548-146697 (intergenic US10-SORF4), 97141-98385 (UL43), 147857-148672 (US2), 145853 . . . 146548 (US10) or 150322-151479 (gD or US6) of SEQ ID NO:14.

Construction of recombinant virus is well known in the art as described in, e.g., U.S. Pat. Nos. 4,769,330, 4,722,848, 4,603, 112, 5,174, 993, and 5,756,103, 6,719,979. Specifically, a recombinant Gallid Herpesvirus-3 (MDV-2) viral vector may be constructed in two steps. First, the Gallid Herpesvirus-3 (MDV-2) or SB-1 genomic regions flanking the locus of insertion are cloned into an *E. coli* plasmid construct; unique(s) restriction site(s) is (are) placed between the two flanking regions (insertion plasmid) in order to allow the insertion of the donor expression cassette DNA. Separately, the cDNA or DNA gene sequence to be inserted is preceded by a promoter region (gene start region) and a terminator (or poly-adenylation, polyA) sequence which is specific for the Gallid Herpesvirus-3 (MDV-2) or SB-1 vector and/or eukaryotic cells. The whole expression cassette (promoter-foreign gene-poly-A) is then cloned into the unique(s) restriction site(s) of the insertion plasmid to construct the “donor plasmid” which contains the expression cassette flanked by Gallid Herpesvirus-3 (MDV-2) or SB-1 “arms” flanking the insertion locus. The resulting donor plasmid construct is then amplified by growth within *E. coli* bacteria and plasmid DNA is extracted. This plasmid is then linearized using a restriction enzyme that cut the plasmid backbone (outside the Gallid Herpesvirus-3 (MDV-2) or SB-1 arms and expression cassette). Chicken embryo fibroblasts are then co-transfected with parental Gallid Herpesvirus-3 (MDV-2) or SB-1 DNA and linearized donor plasmid DNA. The resulting virus population is then cloned by multiple limiting dilution steps where viruses expressing the foreign gene are isolated from the non-expressing viral population. Similarly, another foreign cassette can be inserted in another locus of insertion to create a double Gallid Herpesvirus-3 (MDV-2) or SB-1 recombinant expressing two genes. The second cassette can also be inserted into the same locus. The Gallid Herpesvirus-3 (MDV-2) or SB-1 recombinant is produced in primary chicken embryo fibroblasts similarly to the parental Gallid Herpesvirus-3 (MDV-2) or SB-1 MD vaccine. After incubation, infected cells are harvested, mixed with a freezing medium allowing survival of infected cells, and frozen usually in cryovial or glass ampoules and stored in liquid nitrogen.

Successful expression of the inserted cDNA genetic sequence by the modified infectious virus requires two conditions. First, the insertion must be introduced into a region of the genome of the virus in order that the modified virus remains viable. The second condition for expression of inserted cDNA is the presence of a regulatory sequences allowing expression of the gene in the viral background (for instance: promoter, enhancer, donor and acceptor splicing sites and intron, Kozak translation initiation consensus sequence, polyadenylation signals, untranslated sequence elements).

In general, it is advantageous to employ a strong promoter functional in eukaryotic cells. The promoters include, but are not limited to, an immediate early cytomegalovirus (CMV) promoter, guinea pig CMV promoter, an SV40 promoter, Pseudorabies Virus promoters such as that of glycoprotein X promoter, Herpes Simplex Virus-1 such as the alpha 4 promoter, Marek’s Disease Viruses (including MDV-1, MDV-2 and HVT) promoters such as those driving glycoproteins gC, gB, gE, or gI expression, Infectious Laryngotracheitis Virus promoters such as those of glycoprotein gB, gE, gI, gD genes, or other herpesvirus promoters. When the insertion locus consists of a SB-1 gene (for instance, gC, gD, US2 or US10 genes), the foreign gene can be inserted into the vector with no additional promoter sequence since the promoter of the deleted gene of the vector will drive the transcription of the inserted foreign gene.

In one embodiment, the present invention relates to a pharmaceutical composition or vaccine comprising one or more recombinant Gallid Herpesvirus-3 (MDV-2) rival vectors of the present invention and a pharmaceutically or veterinarily acceptable carrier, excipient, vehicle or adjuvant. The Gallid herpesvirus 3 (MDV-2) strains used for the recombinant Gallid Herpesvirus-3 viral vector may be any SB-1 strains, the HPSR24 strains, or the 301B/1 strains. The Gallid Herpesvirus-3 (MDV-2) strains may also include those described in Witter et al (Avian Diseases 34, 944-957; 1990), Witter (Avian Pathology 21, 601-614, 1992) and Witter (Avian Pathology 24, 665-678, 1995): 280-5/1, 281MI/1, 287C/1, 298B/1, 301A/1, 401/1, 437A/1, 437B/1, 468A/1, 468A/2, 468B/1, 471B/1, or HN-1/1.

In another embodiment, the present invention provides a composition or vaccine comprising: i) a recombinant Gallid Herpesvirus-3 vector (MDV-2) comprising heterologous polynucleotides coding for and expressing at least one antigen of an avian pathogen; and ii) at least one of: a recombinant HVT vector (or MDV-3 or Meleagrid Herpesvirus-1) comprising heterologous polynucleotides coding for and expressing at least one antigen of an avian pathogen; or wild type MDV-3; or recombinant MDV-1 vector (or Gallid herpesvirus-2) comprising heterologous polynucleotides coding for and expressing at least one antigen of an avian pathogen; or wild type MDV-1. The composition or vaccine may further comprise a pharmaceutically or veterinarily acceptable carrier, excipient, vehicle or adjuvant. This composition may further contain a recombinant fowlpox vector comprising heterologous polynucleotides coding for and expressing at least one antigen of an avian pathogen; or wild type fowlpox.

In one aspect of the embodiment, the composition or vaccine comprises one (or more) recombinant Gallid Herpesvirus-3 (MDV-2) vectors and one or more wild type HVT (MDV-3). In another aspect, the composition or vaccine comprises one (or more) recombinant Gallid Herpesvirus-3 (MDV-2) vectors and one or more recombinant HVT (MDV-3). In another aspect, the composition or vaccine comprises one or more recombinant Gallid Herpesvirus-3 (MDV-2) vectors and one or more wild type or genetically modified MDV-1. In another aspect, the composition or vaccine comprises one or more recombinant Gallid Herpesvirus-3 (MDV-2) vectors and one or more recombinant MDV-1. In another aspect, the composition or vaccine comprises one or more recombinant Gallid Herpesvirus-3 (MDV-2) vectors, one or more wild type HVT (MDV-3) and one or more wild type MDV-1. In another aspect, the composition or vaccine comprises one or more recombinant Gallid Herpesvirus-3 (MDV-2) vectors, one or more recombinant HVT (MDV-3) and one or more wild type MDV-1. In another aspect, the composition or vaccine comprises one or more recombinant Gallid Herpesvirus-3 (MDV-2) vectors, one or more wild type HVT (MDV-3) and one or more recombinant MDV-1. In yet another aspect, the composition or vaccine comprises one or more recombinant Gallid Herpesvirus-3 (MDV-2) vectors, one or more recombinant HVT (MDV-3) and one or more recombinant MDV-1. The wild type HVT (MDV-3) or wild type MDV-1 may be live, attenuated or genetically modified. The heterologous polynucleotides in recombinant Gallid Herpesvirus-3 (MDV-2) vectors, recombinant HVT (MDV-3) vectors, and recombinant MDV-1 vectors may encode same or different antigens from the same or different avian pathogens.

The pharmaceutically or veterinarily acceptable carriers or adjuvant or vehicles or excipients are well known to the one skilled in the art. For example, a pharmaceutically or veterinarily acceptable carrier or adjuvant or vehicle or excipient can be Marek’s disease vaccine diluent used for MD vaccines. Other pharmaceutically or veterinarily acceptable carrier or adjuvant or vehicle or excipients that can be used for methods of this invention include, but are not limited to, 0.9% NaCl (e.g., saline) solution or a phosphate buffer, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro), or facilitating transfection or infection and/or improve preservation of the vector (or protein). Doses and dose volumes are herein discussed in the general description and can also be determined by the skilled artisan from this disclosure read in conjunction with the knowledge in the art, without any undue experimentation.

Optionally other compounds may be added as pharmaceutically or veterinarily acceptable carriers or adjuvant or vehicles or excipients, including, but not limited to, alum; CpG oligonucleotides (ODN), in particular ODN 2006, 2007, 2059, or 2135 (Pontarollo R. A. et al., Vet. Immunol. Immunopath, 2002, 84: 43-59; Wernette C. M. et al., Vet. Immunol. Immunopath, 2002, 84: 223-236; Mutwiri G. et al., Vet. Immunol. Immunopath, 2003, 91: 89-103); polyA-polyU, dimethyldioctadecylammonium bromide (DDA) ("Vaccine Design The Subunit and Adjuvant Approach", edited by Michael F. Powell and Mark J. Newman, Pharmaceutical Biotechnology, 6: p. 03, p. 157); N,N-dioctadecyl-N',N'-bis(2-hydroxyethyl) propanediamine (such as AVRIDINE®) (Ibid, p. 148); carbomer, chitosan (see U.S. Pat. No. 5,980,912 for example).

The pharmaceutical compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

Another aspect of the invention relates to a method for inducing an immunological response in an animal against one or more antigens or a protective response in an animal against one or more avian pathogens, which method comprises inoculating the animal at least once with the vaccine or pharmaceutical composition of the present invention. Yet another aspect of the invention relates to a method for inducing an immunological response in an animal to one or more antigens or a protective response in an animal against one or more avian pathogens in a prime-boost administration regimen, which is comprised of at least one primary administration and at least one booster administration using at least one common polypeptide, antigen, epitope or immunogen. The immunological composition or vaccine used in primary administration may be same, may be different in nature from those used as a booster.

The avian pathogens may be Newcastle Disease Virus (NDV), Infectious Bursal Disease Virus (i.e., IBDV or Gumboro Disease virus), Marek's Disease Virus (MDV), Infectious Laryngotracheitis Virus (ILTV), avian encephalomyelitis virus and other picornavirus, avian reovirus, avian paramyxovirus, avian metapneumovirus, avian influenza virus, avian adenovirus, fowl pox virus, avian coronavirus, avian rotavirus, avian parvovirus, avian astrovirus and chick anemia virus, coccidiosis (Eimeria sp.), Campylobacter sp., Salmonella sp., Mycoplasma gallisepticum, Mycoplasma synoviae, Pasteurella sp., Avibacterium sp., E. coli or Clostridium sp.

Usually, one administration of the vaccine is performed either at one day-of-age by the subcutaneous or intramuscular route or in ovo in 17-19 day-old embryo. A second administration can be done within the first 10 days of age. The animals are preferably at least 17-day-embryo or one day old at the time of the first administration.

A variety of administration routes in day-old chicks may be used such as subcutaneously or intramuscularly, intradermally, transdermally. The in ovo vaccination can be performed in the amniotic sac and/or the embryo. Commercially available in ovo and SC administration devices can be used for vaccination.

The invention will now be further described by way of the following non-limiting examples.

EXAMPLES

Construction of DNA inserts, plasmids and recombinant viral vectors was carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989).

Example 1 Construction of Recombinant vSB1-004 Expressing NDV-F

The aim of the work is to construct a recombinant SB-1 virus in which an expression cassette containing mouse cytomegalovirus (mCMV) promoter, Newcastle disease virus fusion protein (NDV-F), and Simian virus 40 (SV40) poly A tail is inserted into the intergenic site between US10 and SORF4 site of SB-1 virus (Table 1 and FIG. 2).

TABLE 1

Characteristics of vSB1-004

| Name | Parental virus | Promoter | gene | Poly-A | Locus |
|---|---|---|---|---|---|
| vSB1-004 | SB-1* | mCMV IE | Wt-NDV-F of VIId | SV40 | SORF4/US10 |

SB-1 *: Merial's commercial Marek's Disease Vaccine SB-1(Merial Select Inc., Gainesville, GA 30503, USA). Vaccine Lot # JV505.

A Newcastle disease virus Fusion Protein (NDV-F) corresponding to genotype VIId sequence (SEQ ID NO:2 encoded by SEQ ID NO:3) was chemically synthesized (GenScript, Piscataway, N.J., USA). The F protein cleavage site of this synthetic gene was altered to match with a lentogenic F cleavage site sequence and the resultant NDV-F gene sequence has 99% nucleotide as well as 99% amino acid sequence identity to NDV-F sequence deposited in GenBank under accession number AY337464 (for DNA) and AAP97877.1 (for protein), respectively.

Donor Plasmid SB-1 US10mFwt SbfI Construction

A fragment containing the synthetic NDV-F gene was excised from pUC57 NDV-F VIId wt plasmid (synthesized by GeneScript) using NotI and inserted into the same site of pCD046 plasmid containing mCMV promoter and SV40 polyA tail. The resultant plasmid, pCD046+NDV-F wt was digested with EcoRI and SalI and blunt ended with Klenow. A 3.3 kb fragment was gel extracted and ligated to a SmaI digested and dephosphorylated (CIPed) vector (SB1 US10-SORF4 SbfI pUC57) containing flanking arms. Ligated material was transformed using Top10 Oneshot kit (Invitrogen, CA, USA). Bacterial colonies were grown in LBamp broth, plasmid extracted by using Qiagens MiniSpin Prep kit, and screened for insert orientation using PstI digestion. The correct donor plasmid was designated SB-1 10mFwt SbfI. Large scale cultures were grown and plasmid extraction was done using Qiagens Maxi Prep kit. Transient expression of the maxi preps was verified using Fugene Transfection Reagent in Chicken Embryo Fibroblast Cells (CEF's) and chicken polyclonal sera against NDV.

Recombinant Generation

A standard homologous recombination procedure was followed by co-electroporation of secondary CEF cells using SB-1 US10mFwt SbfI donor plasmid and viral DNA isolated from vaccine strain of SB-1 virus. Co-electroporation was performed using $1\times10^7$ 2° CEF in 300 μl Opti-MEM and shocked at 150 volts with 950 capacitance in a 2 mm electroporation cuvette. The transfected cells were seeded into 96-well plate and incubated for 5-7 days. The cells grown in the 96-well plate were then treated with trypsin and transferred into two "sisters" 96-well plates and incubated for 5 more days. One set of 96-well plates was used for IFA using chicken polyclonal sera against NDV-F to identify positive wells containing recombinants and another set of 96-well plates was used for recovering the infected cells from the positive wells.

The recombinant viral purification methods were performed first by 96-well plate duplication and IFA selection for the wells containing the most IFA positive plaques with the least amount of IFA negative plaques. Wells matching those criteria were then harvested and adjusted to 1 ml in DMEM+2% FBS. From the 1 ml stock, 5-20 μl (depending on the number of visible plaques) were removed and mixed with $1\times10^7$ CEFs in 10 ml DMEM+2% FBS and aliquoted onto a new 96-well plate to have single SB-1 plaques per well. The 96-well plates were duplicated after 5 days of incubation and wells that contained plaques were tested for the presence of recombinant SB-1 and absence of parental virus by IFA and PCR. Again the wells that appeared to have more recombinant virus, by comparing the PCR banding results, were harvested and adjusted to 1 ml and aliquoted onto new 96-well plates. After three to five rounds of purification of virus infected cells, recombinant SB-1 expressing NDV-F protein was isolated and the purity of the recombinant virus was tested by IFA and PCR to confirm the absence of parental virus. Selected recombinant virus was then passed from one well of a 96-well plate (P0) to 2xT-25 flasks (P1), then 2xT-75 flasks (P2), 2xT-175 flasks (P3), and finally 2×850 cm² roller bottles (pre-MSV stock or P4). Vials with 2 ml aliquot were stored in liquid nitrogen. Titrations were performed in triplicate on CEFs and a titer of $1\times10^5$ pfu/ml was obtained for SB1-004.

Expression Analysis

For immunofluorescence testing, the P3 material was diluted 1:100 in media. Approximately 50 μl of the diluted virus was added to 10 ml of DMEM+2% FBS with $1\times10^7$ CEFs and then aliquoted onto a 96 well plate (100 μl/well). The plates were incubated for 5 days at 37° C.+5% $CO_2$ until viral plaques were visible. The plates were fixed with 95% ice-cold acetone for three minutes and washed three times with PBS. Chicken anti-sera against Newcastle Disease Virus (lot#C0139, Charles Rivers Laboratory) at 1:1000 was added and the plates were incubated at 37° C. for 1 hour. After one hour incubation, the plates were washed three times with PBS and FITC anti-chicken (cat# F8888, Sigma) was added at 1:500. Again the plates were incubated at 37° C. for 1 hour. After one hour incubation the cells were rinsed three times with PBS and visualized with a fluorescent microscope using fluorescein isothiocyanate (FITC) filter. All examined plaques of vSB1-004 were found to express NDV-F protein (FIG. 3).

Analysis of Recombinant by PCR

Figure 4:
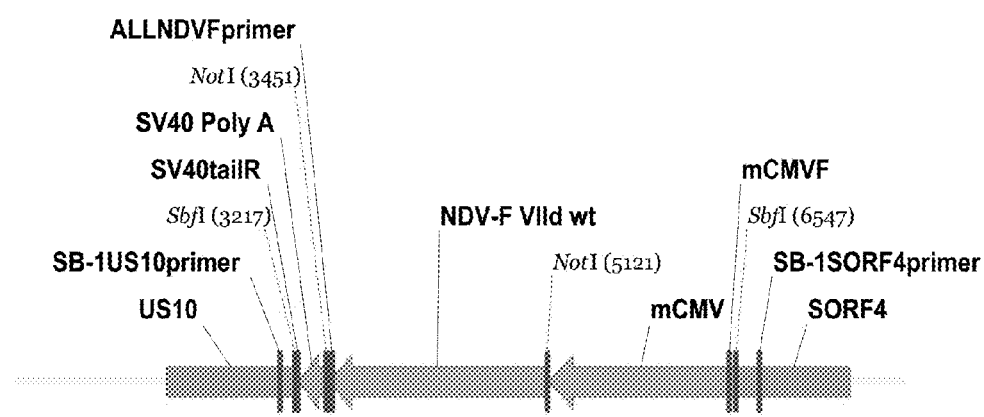
FIG. 4 depicts the schematic representation of primer binding sites.

DNA was extracted from a stock virus by phenol/chloroform extraction, ethanol precipitated, and resuspended in 20 mM HEPES. PCR primers were designed to specifically identify the NDV-F VIId gene, the promoter, the SV40 poly A and the SB-1 flanking arms (see FIG. 4). Primers, specific to HVT (strain FC126), MDV serotype 3 (MB080+MB081) were also included in the analysis to check the purity of the recombinant virus from SB-1 parental virus. PCR was performed using 200 μg of DNA template along with the specified primers pairs.

Figure 5:
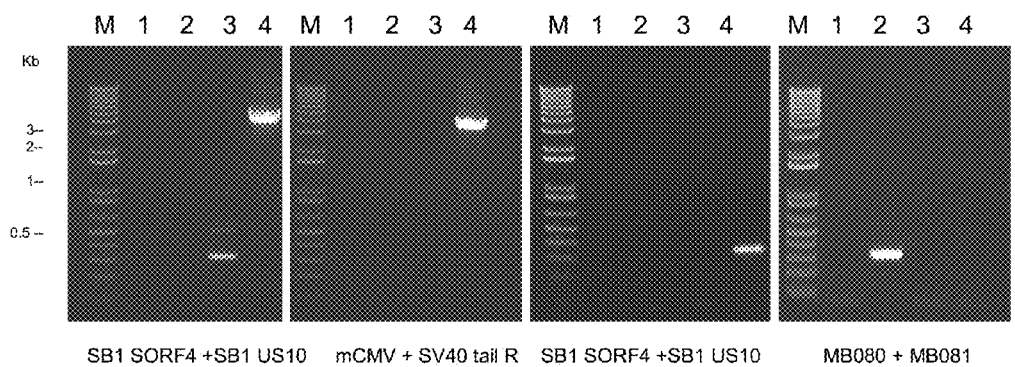
FIG. 5 shows the PCR results of identifying vSB1-004.

The PCR reactions with all primer pairs resulted in the expected PCR products and banding patterns. The PCR results demonstrate that recombinant virus vSB1-004 carries the intended expression cassette and the virus stock is free from detectable amounts of parental SB-1 virus (FIG. 5).

The nucleotide sequence of the donor plasmid SB-1 US10mFwt SbfI (SEQ ID NO:41) is shown in FIG. 20.

Based on PCR testing and immunofluorescence analysis, vSB1-004 is a recombinant SB-1 expressing a NDV-F gene under the control of mCMV promoter. Recombinant vector vSB1-004 is free of any detectable parental SB-1 virus or potential HVT contaminant.

Example 2 Construction of Recombinant vSB1-006 Expressing NDV-F

The aim of the work is to construct a recombinant SB-1 virus in which an expression cassette containing SV40 promoter, Newcastle disease virus fusion protein (NDV-F), and synthetic polyA tail is inserted between the UL55 and LORF5 site of SB-1 virus (Table 2).

TABLE 2

Characteristics of vSB1-006

| Name | Parental virus | Promoter | gene | Poly-A | Locus |
|---|---|---|---|---|---|
| vSB1-006 | SB-1 | SV40 | Opt-NDV-F of VIId | Syn | UL55/LORF5 |

A Newcastle disease virus Fusion Protein (NDV-F) corresponding to a consensus codon-optimized genotype VIId sequence (SEQ ID NO:2 encoded by SEQ ID NO:1) was chemically synthesized (GeneArt).

Donor Plasmid SB-1 UL55 SV Fopt Syn Tail SbfI Construction

A synthetic SB-1 UL55-LOrf5 SbfI plasmid covering approximately 1 kb sequence on each side of the insertion site (GenScript) was digested with SbfI and dephosphorylated. A synthetic SV OptF syn tail pUC57 plasmid (Genscript) was digested with SbfI and a 2239 base pair fragment was gel extracted and ligated to the SbfI digested vector to create the new SB1 UL55 SVFopt syn tail SbfI donor plasmid.

Recombinant Generation, Expression Analysis and PCR Testing

A standard homologous recombination procedure was followed by co-electoporation of secondary CEF cells using donor plasmid SB1 UL55 SV Fopt syn tail SbfI and viral DNA isolated from vaccine strain of SB-1 virus. Essentially the procedure described in example 1 for vSB1-004 was followed to generate, plaque purify and characterize recombinants by immunofluorescence and PCR.

The nucleotide sequence of the donor plasmid SB1 UL55 SVFopt syn tail SbfI (SEQ ID NO:42) is shown in FIG. 20.

Recombinant Generation and Expression Analyses

Genomic DNA of SB-1 virus was co-electroporated with SB-1 UL55 SV Fopt syn tail SbfI donor plasmid to generate recombinant SB-1 using homologous recombination technique. Recombinant virus was separated from parental SB-1 virus by immunofluorescent positive well selection and PCR screening in multiple rounds of plaque purification. A plaque purified recombinant SB-1 virus expressing the NDV-F protein, designated vSB1-006, was scaled up from tissue culture flasks to 2×850 cm$^2$ roller bottles. After about 72 hrs post infection in roller bottles, the infected CEFs were harvested. Aliquots were frozen in liquid nitrogen containing 10% FBS and 10% DMSO. Titrations were performed in triplicate on CEFs and a titer of 8×10$^5$ pfu/ml was obtained for SB1-006.

Immunofluorescence was preformed using chicken antisera (lot# C0139, Charles Rivers Laboratories) followed by a FITC labeled anti-chicken IgG (cat#02-24-06, KPL). All examined plaques of vSB1-006 were found to express NDV-F protein (FIG. 6).

PCR Analysis of vSB1-006

Figure 7:
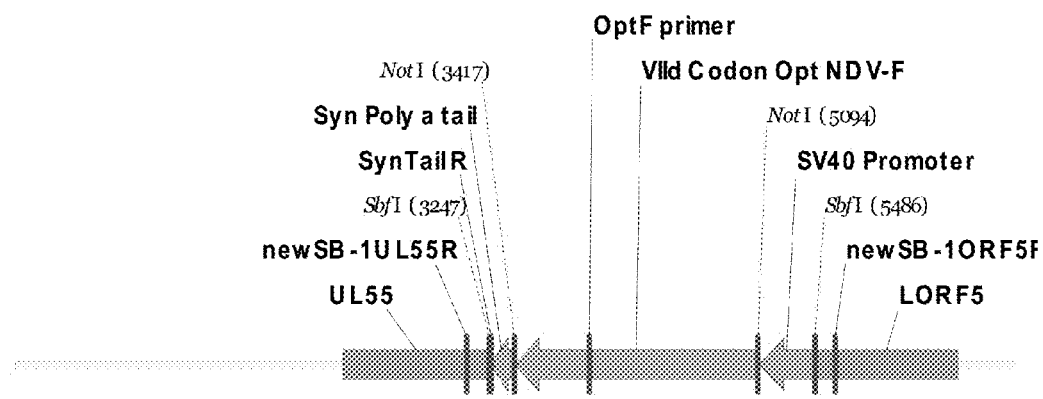
FIG. 7 depicts the schematic representation of primer binding sites on vSB1-006.

Purity of recombinant virus was verified by PCR using primer pairs that are specific to the SB-1 flanking arms, codon-optimized NDV-F VIId, SV40 promoter as well as primer pairs specific to HVT (see FIG. 7). PCR reactions with all primer pairs resulted in the expected PCR products and banding patterns. In addition, there was no evidence of the parental SB-1 virus in vSB1-006 (FIG. 8).

Based on PCR testing and immunofluorescence analysis, it is confirmed that vSB1-006 is a recombinant SB-1 expressing a codon-optimized NDV-F gene under the control of SV40 promoter. Recombinant vector vSB1-006 is free of any detectable amount of parental SB-1 virus and potential HVT contaminant.

Example 3 Construction of Recombinant vSB1-007 Expressing NDV-F

The aim of the work is to construct a recombinant SB-1 virus in which an expression cassette containing SV40 promoter, NDV-F gene corresponding to the F sequence of genotype VIId of NDV is used to replace the coding sequence of glycoprotein C (gC or UL44) of SB-1 virus (Table 3).

TABLE 3

Characteristics of vSB1-007

| Name | Parental virus | Promoter | gene | Poly-A | Locus |
|---|---|---|---|---|---|
| vSB1-007 | SB-1 | SV40 | Opt-NDV-F of VIId | (endogeneous from gC gene) | gC |

A Newcastle disease virus Fusion Protein (NDV-F) corresponding to a consensus codon-optimized genotype VIId sequence (SEQ ID NO:2 encoded by SEQ ID NO:1) was chemically synthesized (GeneArt).

Donor Plasmid pSB1 44 Cds SVOptF Construction

A synthetic pSB1 44 cds plasmid containing flanking arms was generated by gene synthesis (GenScript). The pSB1 44 cds was digested with SbfI, dephosphorylated. Another plasmid named SV-OptF-syn no polyA tail-pUC57 was digested with SbfI and 2.1 kb fragment containing SV40 promoter and NDV-F gene was gel extracted, ligated into the SbfI digested vector and transformed using the Top10 One-shot kit (Invitrogen). Bacterial colonies were grown in LB-ampicillin media (100 ug/ml), and plasmids were extracted by using Qiagen Mini Spin Prep kit, and screened for insertions by EcoRI and NcoI digestion. The resultant donor plasmid was designated pSB1 44 cds SVOptF.

The synthetic plasmid pSB1 44 cds (SEQ ID NO:36 in FIG. 20) can also be used as a donor plasmid without further modification (without inserting NDV-F expression cassette) to generate a recombinant SB-1 lacking the glycoprotein (gC) gene.

Recombinant Generation and Expression Analyses

A standard homologous recombination procedure was followed by co-electroporation of secondary CEF cells using donor plasmid pSB1 44 cds SVOptF and viral DNA isolated from vaccine strain of SB-1 virus. Essentially the procedure described in example 1 for vSB1-004 was followed to generate, plaque purify and characterize recombinants by immunofluorescence. A plaque purified recombinant SB-1 virus expressing the NDV-F protein, designated vSB1-007, was scaled up from T-25 tissue culture flasks to 10xT-150 cm$^2$ flasks. Infected CEF cells were harvested and aliquots were frozen in liquid nitrogen containing 10% FBS and 10% DMSO. Titrations were performed in triplicate on CEFs and a titer of 7.2×10$^4$ pfu/ml was obtained for SB1-007.

Immunofluorescents was performed using chicken antisera (lot# C0139, Charles Rivers Laboratories) followed by a FITC labeled anti-chicken IgG (cat#02-24-06, KPL). All examined plaques of vSB1-007 were found to express NDV-F protein (FIG. 9).

PCR Analysis of vSB1-007

Figure 10:
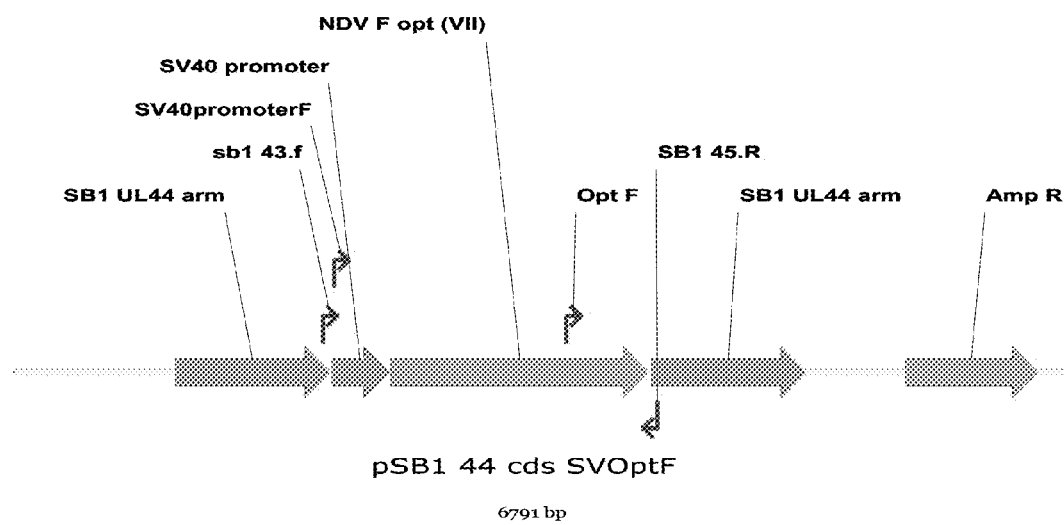
FIG. 10 depicts the schematic diagram of primer location on pSB1 44 cds SVOptF donor plasmid.

Viral DNA was extracted from SB1-007 from P.1 through P.6 by QIA DNeasy Blood & Tissue Kit (Qiagen). PCR primers were designed to specifically identify the presence of NDV F (codon-optimized), the SV40 promoter and the flanking arms of UL44 (see FIG. 10). PCR amplifications were preformed using 200 ng of DNA template along with the specified primer pairs.

Similarly, a standard homologous recombination procedure using synthetic plasmid pSB1 44 cds and viral DNA isolated from vaccine strain of SB-1 virus will generate a recombinant SB-1 in which the coding region of gC gene is deleted. Two PCR primers (SB1 43.F and SB1 45.R, Table 4) will produce a PCR product of 103 nucleotides for a gC-deleted recombinant SB-1 versus a 1540 nucleotides for the parent SB-1 virus.

Figure 11:
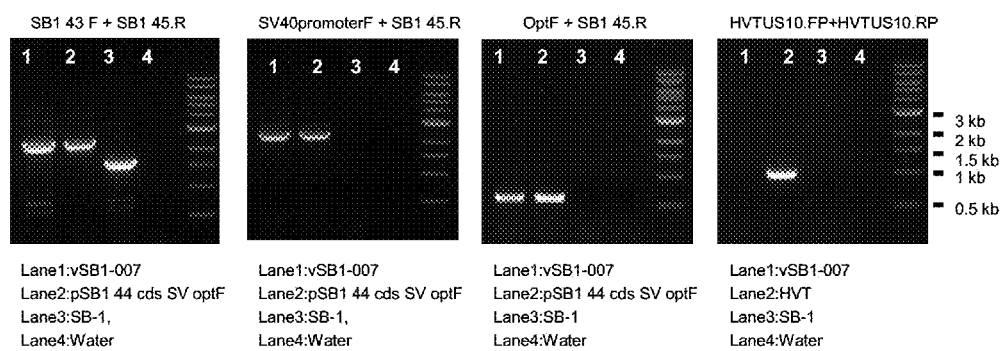
FIG. 11 shows the PCR results of vSB1-007.

Purity of recombinant virus was verified by PCR using primer pairs that are specific to the SB-1 flanking arms, codon-optimized NDV-F VIId, SV40 promoter as well as primer pairs (MB080+MB081) specific to HVT. PCR reactions with all primer pairs resulted in the expected PCR products and banding patterns. In addition, there is no evidence of the parental SB-1 virus in vSB1-007 (Tables 4-5 and FIG. 11).

TABLE 4

PCR primers

| Primer | SEQ ID NO: | Sequence (5' to 3') |
|---|---|---|
| SB1 43.F | 27 | GCTCTCGGAGACGCGGCTCGC |
| SB1 45.R | 28 | GCTCTTGTAACATCGCGGACG |

TABLE 4-continued

PCR primers

| Primer | SEQ ID NO: | Sequence (5' to 3') |
|---|---|---|
| SV40 promoter.F | 29 | AGCTTGGCTGTGGAATGT |
| Opt F | 24 | ACTGACAACACCCTACATGGC |
| HVTUS10.FP | 30 | CCGGCAACATACATAATGTG |
| HVTUS10.RP | 31 | GGCACTATCCACAGTACG |

TABLE 5

Expected amplicon size

| | Expected amplicon size (bp) | |
|---|---|---|
| Primer pairs | SB-1 | vSB1-007/pSB1 44 cds SVOptF |
| SB1 43.F + SB1 45.R | 1540 | 2188 |
| SV40promoterF + SB1 45.R | None | 2113 |
| Opt F + SB1 45.R | None | 611 |
| HVTUS10.FP + HVTUS10.RP | None | None |

Based on PCR testing and immunofluorescence analysis, it is confirmed that vSB1-007 is a recombinant SB-1 expressing a codon-optimized NDV-F gene under the control of SV40 promoter. The NDV-F expression cassette was successfully used to replace the gC gene of SB1, demonstrating that gC is dispensable for in vitro propagation of SB-1 virus. Recombinant vector vSB1-007 is free of any detectable amount of parental SB-1 virus or HVT.

The nucleotide sequence of the donor plasmid pSB1 44 cds SVOptF (SEQ ID NO:43) is shown in FIG. 20.

Example 4 Construction of Recombinant vSB1-008 Expressing NDV-F

The aim of the work is to construct a recombinant SB-1 virus in which an expression cassette containing SV40 promoter, NDV-F gene corresponding to the F sequence of CA02 strain of NDV, and synthetic polyA tail is inserted between the UL55 and LORF5 site of SB-1 virus (Table 6).

TABLE 6

Characteristics of vSB1-008

| Name | Parental virus | Promoter | gene | Poly-A | Locus |
|---|---|---|---|---|---|
| vSB1-008 | SB-1 | SV40 | Opt-NDV-F of CA02 | Syn | UL55/LORF5 |

An NDV-F corresponding to a codon-optimized genotype V (CA02 strain) sequence (SEQ ID NO:9 encoded by SEQ ID NO:8) was chemically synthesized (GeneArt). The F protein cleavage site of this synthetic gene was altered to match a lentogenic F cleavage site sequence and the resultant NDV-F gene sequence has 99% amino acid sequence identity to NDV-F sequence deposited in GenBank (ABS84266).

Donor Plasmid SB1 UL55 SV CaFopt Syn Tail SbfI Construction

A synthetic SB-1 UL55-LOrf5 SbfI plasmid (Genscript) containing approximately 1 kb sequence of each side of the insertion site was digested with SbfI and dephosphorylated. A synthetic SV OptF syn tail pUC57 plasmid (Genscript) was digested with SbfI and a 2239 base pair fragment containing syn tail was gel extracted and ligated to the SbfI digested vector to create the new SB1 UL55 SVFopt syn tail SbfI donor plasmid. This donor plasmid was then digested with NotI, CIPed, and a 5196 base pair fragment was gel extracted. A synthetic NDV-F 0 plasmid (GeneArt) was digested with NotI and a 1677 base pair fragment was gel extracted and ligated to the NotI digested and CIPed UL55 vector resulting in donor plasmid SB1 UL55 SV CaFopt syn tail SbfI.

Recombinant Generation and Expression Analysis

A standard homologous recombination procedure was followed by co-electroporation of secondary CEF cells using donor plasmid SB-1 UL55 SV CaFopt syn tail SbfI and viral DNA isolated from vaccine strain of SB-1 virus. Essentially the procedure described in example 1 was followed to generate and characterize recombinants by immunofluorescence and PCR.

Recombinant virus was separated from parental SB-1 virus by immunofluorescent positive well selection and PCR screening in multiple rounds of plaque purification. A plaque purified recombinant SB-1 virus expressing the NDV-F protein, designated vSB1-008, was scaled up from tissue culture flasks to 2×850 cm$^2$ roller bottles. After about 72 hrs post infection in roller bottles, the infected CEFs were harvested. Aliquots were frozen in liquid nitrogen containing 10% FBS and 10% DMSO.

Immunofluorescence was performed using chicken antisera (Charles Rivers Laboratories) followed by a FITC labeled anti-chicken IgG (KPL) (FIG. 12).

PCR Analysis of vSB1-008

Figure 13:
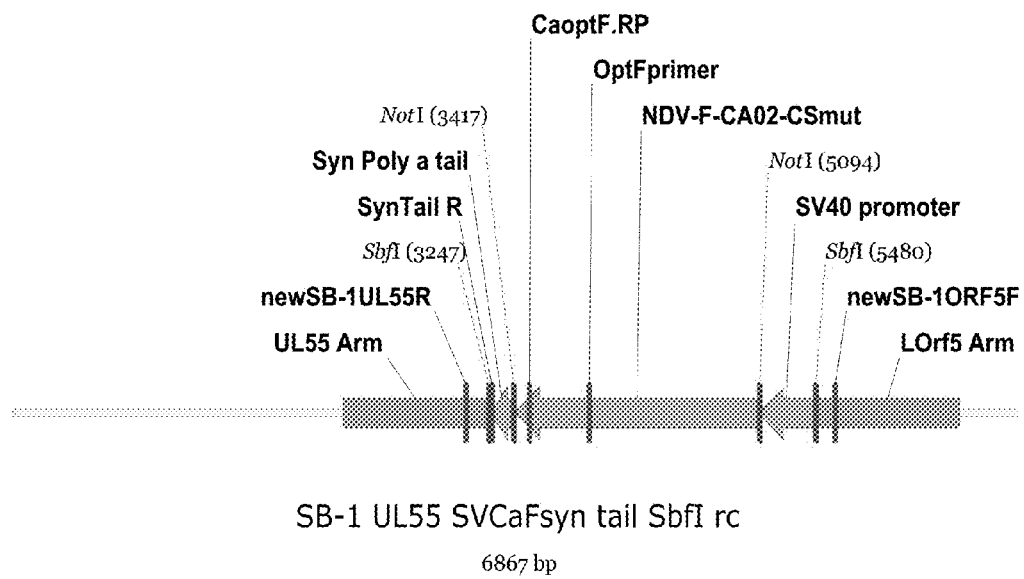
FIG. 13 depicts the schematic representation of primer binding sites.

Purity of recombinant virus was verified by PCR using primer pairs that are specific to the SB-1 flanking arms, codon-optimized NDV-F VIId, SV40 promoter (see FIG. 13) as well as primer pairs (MB080+MB081) specific to HVT, MDV serotype 3. PCR reactions with all primer pairs resulted in the expected PCR products and banding patterns. In addition, there is no evidence of the parental SB-1 virus in vSB1-008 (FIG. 14).

The nucleotide sequence of the donor plasmid SB1 UL55 CaFopt syn tail SbfI (SEQ ID NO:44) is shown in FIG. 20.

Based on PCR testing and immunofluorescence analysis, it is confirmed that vSB1-008 is a recombinant SB-1 expressing a codon-optimized NDV-F gene under the control of SV40 promoter. Recombinant vector vSB1-008 is free of any detectable parental SB-1 virus or HVT.

Example 5 Construction of Recombinant vSB1-009 and vSB1-010 Expressing NDV-F The aim of the study is to construct a recombinant SB-1 viral vector vSB1-009 in which an expression cassette containing SV40 promoter and Newcastle disease virus fusion (NDV-F) gene is inserted to replace UL44 coding (gC) sequence of SB-1 and to construct a recombinant SB-1 viral vector vSB1-010 in which an additional expression cassette containing guinea pig CMV promoter and NDV-F gene is inserted in SORF-US2 locus of SB1-009 vector backbone.

Example 5.1 Construction of vSB1-009

A donor plasmid pSB1 44 cds SV FCAopt was constructed containing UL44 flanking arms of SB1 virus, SV40 promoter and NDV F codon optimized gene sequence (SEQ ID NO:8, coding for SEQ ID NO:9) (Table 7).

TABLE 7

Characteristics of vSB1-009

| Name | Parental virus | Promoter | F gene | Poly-A | Locus |
|---|---|---|---|---|---|
| vSB1-009 | SB1 | SV40 | Opt-NDV-F of CA02 | (endogeneous from gC gene) | UL44 (gC) |

Generation of Recombinant Virus

A standard homologous recombination procedure was followed by co-electroporation of secondary CEF cells using donor plasmid pSB1 44 cds SV FCAopt and viral DNA isolated from SB-1 virus infected CEFs. Essentially the procedure described in example 1 was followed to generate, plaque purify and characterize recombinants by immunofluorescence.

After two rounds of plaque purification, pure recombinant virus (vSB1-009) was isolated and the purity of vSB1-009 was tested by IFA and PCR to validate the appropriate insertion as well as no remnant parental virus.

PCR Analysis

Viral DNA was extracted from vSB1-009 pre-master seed virus (pre-MSV) stock by QIA DNeasy Blood & Tissue Kit (Qiagen). PCR primers were designed to identify the presence of the NDV F optimized, the NDV F wild type, the SV40 promoter, the mCMV promoter, the UL44 flanking arms of SB-1 virus and HVT virus. PCR amplifications were performed using approximately 200 ng of DNA template along with the primer pairs.

PCR amplification with various primers confirmed that the vSB1-009 has the expected amplification patterns and amplicons.

Expression Analysis

Indirect immunofluorescent assay (IFA) was performed on the vSB1-009 pre-MSV stock to examine the expression of NDV F gene and SB-1 virus antigen. The CEFs that were inoculated with vSB1-009 were fixed with ice-cold 95% acetone for three minutes at room temperature and air-dried for 10 min. The plates were washed with PBS, then two primary antibodies, chicken anti-Newcastle Disease Virus sera (Charles Rivers Laboratories cat#10100641, lot#C0117A) at 1:500 dilution and Y5.9 monoclonal antibody against SB-1 virus (Merial Select, Gainesville, Ga.) at 1:3000 dilution were added and the plates were incubated for 45 min at 37° C. After three washes with PBS, two secondary antibodies, goat anti-chicken IgG-fluorescein (KPL) at 1:500 dilution and donkey anti-mouse IgG-Alexa Fluor 568 (Molecular Probe) at 1:250 dilution were added. The plates were incubated at 37° C. for 45 min and followed by three washes with PBS. The wells were screened for IFA positive plaques with a fluorescent microscope using fluorescein isothiocyanate (FITC) and tetramethylrhodamine isothiocyanate (TRITC)-filters of Nikon Eclipse Ti inverted microscope. Similarly, reactivity of vSB1-009 with NDV F Mab was examined by Dual IFA using anti-MDV serum (Charles River Laboratories (1/300 dilution) and anti-NDV F monoclonal antibody (1/300 dilution) as primary antibody. The goat anti-chicken IgG-fluorescein (KPL) (1:500 dilution) and donkey anti-mouse IgG-Alexa Fluor 568 (Molecular Probe) (1:250 dilution) were used as secondary antibodies. The wells were observed to identify the IFA positive plaques with a fluorescent microscope using FITC- and TRITC-filters of Nikon Eclipse Ti inverted microscope.

IFA results indicate that vSB1-009 expresses the NDV F protein in virus-infected CEF. Over 500 vSB1-009 plaques were counted for NDV F protein expression as well as SB-1 virus specific protein expression with dual IFA. The expression of NDV F protein completely matched with SB-1 virus antigen expression in each virus plaque (Table 8).

TABLE 8

| Dual IFA of vSB1-009 | | | | |
|---|---|---|---|---|
| | Dual IFA plate #1 (total 189 plaques) | | Dual IFA plate #2 (total 361 plaques) | |
| Virus | Anti-NDV serum positive plaques | Anti-SB-1 Mab positive plaques | Anti-NDV serum positive plaques | Anti-SB-1 Mab positive plaques |
| vSB1-009 | 189 | 189 | 361 | 361 |

NDV F Mab reactivity was confirmed by Dual IFA. Over 200 vSB1-009 plaques were examined for NDV F Mab reactivity as well as anti-MDV serum reactivity. The reactivity with NDV F Mab completely matched with anti-MDV serum reactivity in each virus plaque (Table 9).

TABLE 9

| Reactivity of vSB1-009 with anti-NDV F Mab | | |
|---|---|---|
| | Dual IFA (total 254 plaques) | |
| Virus | Anti-MDV serum positive plaques | Anti-NDV F Mab positive plaques |
| vSB1-009 | 254 | 254 |

Southern Blot Analysis

Total genomic DNA was extracted from vSB1-009 pre-MSV stock infected CEFs. The genomic DNA of vSB1-009, SB-1 virus (negative control), pSB1 44 cds SV FCA opt donor plasmid were digested at 37° C. with EcoRI, NcoI, and KpnI restriction endonucleases separately. The restriction fragments were separated by a 0.8% agarose gel electrophoresis and transferred onto a positively charged Nylon membrane. After transfer, the membrane was treated with 0.4M NaOH and then neutralized with 2×SSC-HCl buffer. The membrane was then air dried and UV crosslinked.

Following the North2South Chemiluminescent Hybridization and Detection Kit (Thermo Scientific cat#89880) manufacturers' instructions, the membrane was pre-hybridized for 1 hr and then hybridized with the probe at 55° C. for overnight. For hybridization, two probes were used; 1) the SbfI fragment of pSB1 44 cds SV FCA opt as NDV F cassette probe, 2) the SmaI-EcoRI fragment of pUC57 SB1 44 arm (GenScript) as recombination arm probe. After the overnight hybridization, several stringency washes were conducted until the membrane was placed in blocking buffer with the addition of Streptavidin-HRP. After rinsing the membrane of any unbound Streptavidin-HRP, the substrate solution of Luminal and peroxide were added. The membrane was then exposed to X-ray film and the film was developed.

The Southern blot results were as expected based on Vector NTI map analysis. The NDV F cassette (SV40 promoter, NDV-F CA02 codon optimized gene) replaced the UL44 coding sequences of SB-1 virus.

Genomic Analysis

The genomic DNA of vSB1-009 pre-MSV stock was conducted by nucleotide sequence determination of the region of recombination arm as well as inserted gene cassette. Primers were designed and used to amplify the entire NDV-F gene cassette including the recombination arms.

The vSB1-009 sequence (donor plasmid pSB1 44 cds SV FCAopt) containing the recombinant arms, SV40 promoter and NDV F codon-optimized gene was confirmed to be correct as shown in SEQ ID NO:37 (FIG. 20).

Western Blot Analysis

The CEF monolayer was infected with vSB1-009 pre-MSV at MOI~0.1. After a 5-day incubation, the CEFs were pelleted and washed with PBS followed by lysis with IP Lysis/Wash buffer of Pierce Classic IP Kit (Thermo Scientific cat#26146) according to the manufacturers' protocols. The lysate was pre-cleared and incubated with 100 ul of anti-NDV F monoclonal antibody to make the immune complex. The immune complex was captured by Protein A/G Plus Agarose and after removing of the un-bounded immune complex by washing steps, the 50 ul of sample buffer was used to elute under non-reducing conditions. The uninfected CEFs were included as a control. The 20 ul of eluted samples were separated in 10% Bis-Tris gels by electrophoresis. After the electrophoresis, the separated proteins in a gel were transferred onto PVDF membrane. The Protein Detection TMB Western Blot Kit (KPL cat#54-11-50) was used to detect the NDV antigens onto PVDF membrane with chicken anti-N13V serum (Charles River Laboratories Laboratories cat#10100641, lot#C0117A), and goat anti-chicken IgG-peroxidase conjugate (KM, cat#14-24-06) following the manufacturers' protocols.

The NDV F protein expression of vSB1-009 was confirmed by two-step immunodetection. First, the expressed NDV F proteins from vSB1-009 infected CEF lysate were captured by the immunoprecipitation using anti-NDV F monoclonal antibody 001C3. Subsequently Western blot analysis using anti-NDV polyclonal serum (Charles River Laboratories cat#10100641, lot#C0117A) was applied to detect the NDV F protein in the captured samples (NDV F protein-monoclonal antibody complex) (FIG. 15). An approximately 55 kDa protein in vSB1-007 pre-MSV lysates was detected by anti-NDV serum that corresponding the expected size of NDV F1 fusion protein (FIG. 15).

Example 5.2 Construction of vSB1-010

Donor Plasmid SB1US2 gpVIIdwtsvn Construction

Using the plasmid HVT SOrf3-US2 gpVar-Ewt Syn, the gpCMV, Varient E, Syn tail was removed by SbfI digestion. This fragment was ligated into the SB1 US2 donor plasmid. The Varient E gene was cut out by NotI and replaced by NDV-F VIId wt. The synthetic NDV-F VIId wild type gene (SEQ ID NO:3 encoding SEQ ID NO:2) was excised from pUC57 NDV-F VIId wt plasmid (synthesized by GeneScript) using NotI digestion. Ligated material was transformed using Top10 Oneshot kit (cat#C404002, Invitrogen). Bacterial colonies were grown in LBamp broth, plasmid extracted by using Qiagens MiniSpin Prep kit, and screened for insert orientation using NcoI+SalI digestion. The correct donor plasmid was designated pSB1 US2 gpVIIdwt Syn. Table 10.1 shows the features unique to the construct around the expression cassettes, including the respective sequences. Large scale cultures were grown and plasmid extraction was done by using Qiagens Maxi Prep kit. Transient expression of the maxi preps was verified using Fugene Transfection Reagent in Chicken Embryo Fibroblast Cells (CEF's) and chicken polyclonal sera against NDV-F.

Recombinant Generation

A standard homologous recombination procedure was followed by co-electroporation of secondary CEF cells using pSB1 US2 gpVIIdWt Syn donor plasmid and viral DNA isolated from vSB1-009 (vSB1-009 is already a recombinant virus expressing CA02 F gene of NDV). Essentially the procedure described in example 1 for was followed to generate, plaque purify and characterize recombinants by immunofluorescence.

After five rounds of plaque purification, pure recombinant virus (vSB1-010) was isolated and the purity of vSB1-010 was tested by IFA and PCR to validate the appropriate insertion as well as no remnant parental virus.

TABLE 10.1

Characteristics of vSB1-010

| Name | Parental virus | Promoter | F gene | Poly-A | Locus |
|---|---|---|---|---|---|
| vSB1-010 | vSB1-009 | Guinea pig CMV | NDV-F VIId | Synthetic | SORF4-US2 |

Sequencing of the insert region confirmed that vSB1-010 contains the correct sequences of guinea pig CMV promoter and the NDV-F VIId wt gene as shown in the sequence of the donor plasmid SB1US2 gpVIIdwtsyn (SEQ ID NO:57).

Analysis of Recombinant by PCR

DNA was extracted from a stock virus by phenol/chloroform extraction, ethanol precipitated, and resuspended in 20 mM HEPES. PCR primers were designed to specifically identify the NDV-F VIId wt gene, the promoter, the polyA, as well as, the purity of the recombinant virus from SB1 parental virus. PCR was performed using 200 μg of DNA template along with the specified primers pairs indicted in Table 1. PCR cycling conditions are as follows (unless otherwise noted): 94° C. —2 min; 30 cycles of 94° C. —30 sec, 55° C. —30 sec, 68° C. —3 min; 68° C. —5 min.

Purity of recombinant virus was verified by PCR using primer pairs that are specific to the SB1 flanking arms, the gpCMV promoter, the NDV-F VIId wt gene and the syn tail. Primers, specific to HVT, MDV serotype 3 (MB080+MB081) were also included in the analysis. The PCR results demonstrate that recombinant virus vSB1-010 carries the intended expression cassette and the virus stock is free from detectable amounts of parental SB1-009 virus.

Immunofluorescent Staining of Recombinant vSB1-010 Virus Expressing Two NDV-F Proteins For immunofluorescence testing, the P3 material was diluted 1:100 in media. Approximately 50 μl of the diluted virus was added to 10 ml of DMEM+2% FBS with $1\times10^7$ CEFs and then aliquoted onto a 96 well plate (100 μl/well). The plates were incubated for 5 days at 37° C.+5% $CO_2$ until viral plaques were visible. The plates were fixed with 95% ice-cold acetone for three minutes and washed three times with PBS. Chicken anti-sera against Newcastle Disease Virus (lot#C0139, Charles Rivers Laboratory) at 1:1000 was added and the plates were incubated at 37° C. for 1 hour. After one hour incubation, the plates were washed three times with PBS and FITC anti-chicken (cat# F8888, Sigma) was added at 1:500. Again the plates were incubated at 37° C. for 1 hour. After one hour incubation the cells were rinsed three times with PBS and visualized with a fluorescent microscope using fluorescein isothiocyanate (FITC) filter.

The immunofluorescent staining results indicate that vSB1-010 exhibited a very strong expression of the NDV-F protein when the polyclonal sera against both CA02 and VIId F proteins of NDV were used.

Conclusion

Based on PCR testing and immunofluorescence analysis, vSB1-010 is a recombinant SB-1 in which VIId-F gene of NDV under the control of gpCMV promoter was successfully inserted into a vSB1-009, which already expresses the CA02-F gene of NDV. Consequently vSB1-010 carries both VIId and CA02 F genes of NDV genotypes and it is free of any detectable parental vSB1-009.

Example 6 Construction of Recombinant vHVT Vectors Expressing NDV-F

Preparation of Donor Plasmid pHM103+Fopt for vHVT114

The plasmid pHM103 (Merial Limited) containing the Intergenic I arms of HVT FC126, SV40 promoter and SV40 poly A was digested with NotI, dephosphorylated, and the 5.6 kb fragment was gel extracted. A NotI flanked 1.7 kb fragment of a chemically synthesized codon-optimized genotype VIId NDV-F gene (SEQ ID NO:1, coding for SEQ ID NO:2) was also NotI digested and the 1.7 kb fragment was gel extracted. The 5.6 and 1.7 kb fragments were ligated to create pHM103+Fopt (Table 10.2).

TABLE 10.2

Characteristics of vHVT114

| Name | Parental virus | Promoter | F gene | Poly-A | Locus |
|---|---|---|---|---|---|
| vHVT114 | HVT FC126 strain | SV40 | Opt-VIId | SV40 | IG1 |

Generation of Recombinant HVT Viral Vector

A standard homologous recombination procedure was followed by co-electroporation of secondary CEF cells using donor plasmid pHM103+Fopt and viral DNA isolated from the HVT strain FC126 (Igarashi T. et al., J. Gen. Virol. 70, 1789-1804, 1989). Essentially the procedure described in example 1 was followed to generate, plaque purify and characterize recombinants by immunofluorescence.

After five rounds of plaque purification, a recombinant virus designated as vHVT114 was isolated and the purity was tested by IFA and PCR to confirm NDV-F expression and the absence of parental virus.

PCR Analysis of Recombinant vHVT114

DNA was extracted from vHVT114 by phenol/chloroform extraction, ethanol precipitated, and was resuspended in 20 mM HEPES. PCR primers were designed to specifically identify the presence of the codon optimized NDV-F, the SV40 promoter, as well as, the purity of the recombinant virus from FC126 CL2 parental virus.

The PCR results showed that the sizes of PCR products after gel electrophoresis correspond well with the expected sizes and the banding patterns.

Sequence Analysis of the Inserted Region in Recombinant vHVT114

Analysis of vHVT114 genomic DNA region was performed by PCR amplification. Total of 10 primers were used to amplify the entire cassette, as well as, beyond the flanking BamHI-I arms used in the donor plasmid. The 4.727 kb PCR product was gel purified and the entire fragment was sequenced using the sequencing primers. The sequence result confirmed that the vHVT114 contains the correct SV40 promoter, the codon-optimized NDV-F and the SV40 polyA sequences that match exactly the sequence described for the donor plasmid pHM103+Fopt in SEQ ID NO:38 (see FIG. 20).

Western Blot Analysis of Recombinant vHVT114

Approximately $2 \times 10^6$ chicken fibroblast cells were infected at ~0.1 MOI with vHVT114 Pre-MSV. After two days of incubation at 37° C., infected as well as uninfected cells were harvested using a cell scraper after removing the media and rinsing with PBS. The cells were harvested with 1 ml of PBS and centrifuged. The cell pellets were lysed by following the Pierce Classic IP Kit (Thermo Scientific). 100 μl of the anti-NDV-F monoclonal antibody 001C3 (Merial Limited) was used to form the immune complex. The antibody/lysate sample was added to Protein A/G Plus Agarose to capture the immune complex. The immune complex was washed three times to remove non-bound material and then eluted in 50 ul volume using sample buffer elution under non-reducing condition. After boiling for 5 minutes, 10 μl of the samples were loaded into a 10% Acrylamide gel (Invitrogen). The PAGE gel was run in MOPS buffer (Invitrogen) at 200 volts for 1 hour. Then the gel was transferred onto a PVDF membrane.

The Protein Detector Western Blot Kit TMB System (KPL, cat#54-11-50) was used for blotting the PVDF membrane by using the reagents and following manufacturer's directions. After blocking the membrane for 1 hour at room temperature, the membrane was then rinsed three times in 1× Wash Buffer, five minutes each and then soaked in blocking buffer containing 1:1000 dilution of chicken serum raised against NDV virus (Lot # C0139, Charles River Laboratories). After washing three times in a washing buffer, the membrane was incubated with a peroxidase labeled goat anti-chicken IgG (KPL, cat#14-24-06) at a dilution of 1:2000 for 1 hour at room temperature. The membrane was then rinsed three times in 1× Wash Buffer, five minutes each. 5 ml of TMB membrane peroxidase substrate was added to the membrane and gently rocked for about 1 minute. The developing reaction was stopped by placing the membrane into water.

Figure 16:
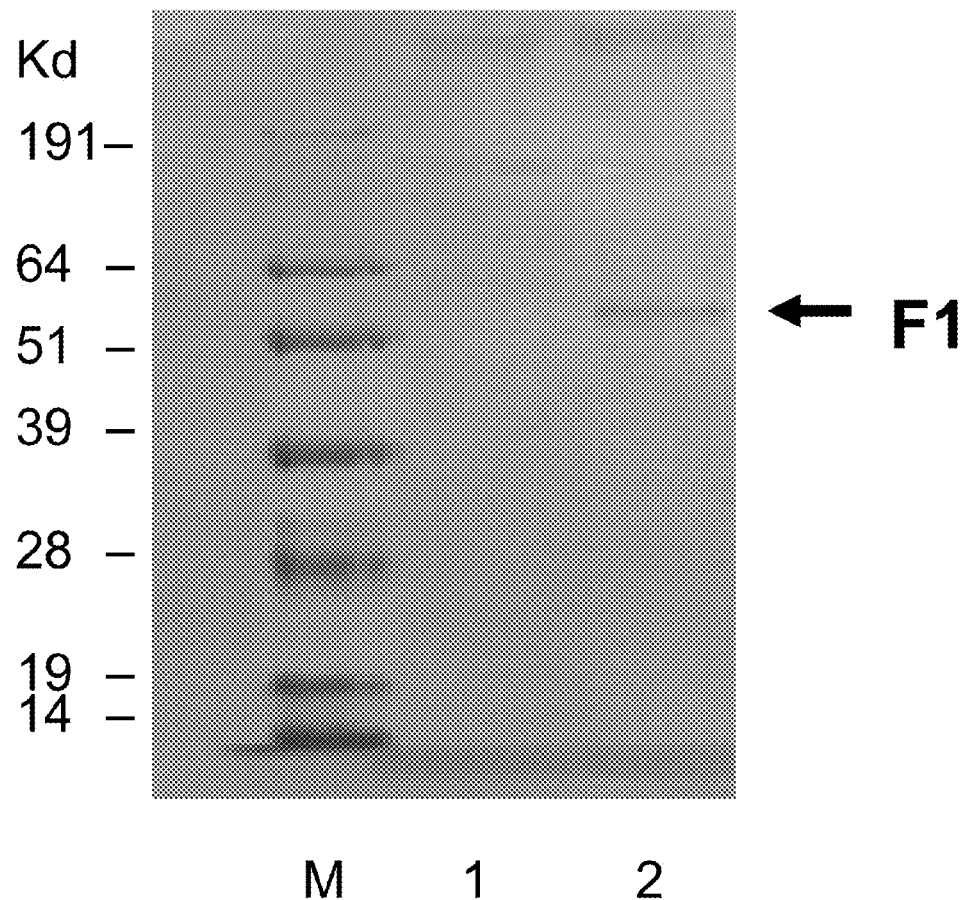
FIG. 16 depicts the Immunoprecipitation and Western Blot of vHVT114.

The immunoprecipitation and Western blot technique detected an approximately 55 kD protein in vHVT114 sample that corresponds to the expected size of F1 component of the NDV-F protein (FIG. 16).

Generation and Characterization of Other HVT Recombinants

Generation of other HVT recombinants, such as vHVT039, vHVT110, vHVT111, vHVT112, vHVT113, and vHVT116 were essentially done in the same way as for vHVT114 described above. The generation and characterization of recombinant HVT viral vectors were also described in U.S. patent application Ser. No. 13/689,625 filed on Nov. 29, 2012 (Merial limited), which is incorporated herein by reference in its entirety. Table 11 shows the features unique to each construct around the expression cassettes, including the respective sequences.

TABLE 11

Characteristics of the expression cassettes of single HVT recombinants

| Name | Parental virus | Promoter | F gene | Poly-A | Locus |
|---|---|---|---|---|---|
| vHVT039 | HVT | MDV gB | Wtnm-Texas | SV40 | IG1 |
| vHVT110 | HVT | mCMV IE | Wt-VIId | SV40 | IG1 |
| vHVT111 | HVT | SV40 | Wt-VIId | SV40 | IG1 |
| vHVT112 | HVT | MCMV IE | Wt-YZCQ | SV40 | IG1 |
| vHVT113 | HVT | MCMV IE | Wt-Texas | SV40 | IG1 |
| vHVT114 | HVT | SV40 | Opt-VIId | SV40 | IG1 |
| vHVT116 | HVT | SV40 | Opt-NDV-F of CA02 | SV40 | IG1 |

Example 7 Construction of Double HVT Vectors Expressing NDV-F and IBDV VP2, and Double HVT Vectors Expressing IBDV VP2 Variants Preparation of Donor Plasmid pHVT US2 SV-Fopt-synPA for vHVT306

The donor plasmid pHVT US2 SV-Fopt-synPA was constructed containing SV40 promoter, synthetic NDV F codon optimized VII gene, synthetic polyA tail flanked by the SORF3 and US2 arm sequences of HVT FC126.

Generation of Recombinant Virus

A standard homologous recombination procedure was followed by co-electroporation of secondary CEF cells using donor plasmid pHVT US2 SV-Fopt-synPA and viral DNA isolated from vHVT13 (an HVT vector expressing the IBDV VP2 gene, Merial Limited). Essentially the procedure described in example 1 was followed to generate, plaque purify and characterize recombinants by immunofluorescence.

After two rounds of plaque purification, pure recombinant virus (vHVT306) was isolated and the purity of vHVT306 was tested and confirmed by IFA and PCR.

PCR Analysis

Viral DNA was extracted from vHVT306 pre-master seed virus (pre-MSV) stock by QIA DNeasy Blood & Tissue Kit (Qiagen). PCR primers were designed to identify the presence of the NDV F optimized, the NDV F wild type, the SV40 promoter, the mCMV promoter, the flanking arms of US2 HVT virus and SB-1 virus.

PCR amplification with various primers confirmed that the vHVT306 had the expected amplification patterns and amplicons.

Genomic Analysis

The genomic DNA of vHVT306 pre-MSV stock was sequenced to verify the sequence of the recombination arm region as well as inserted gene cassette.

Primers were designed to amplify the entire inserted gene cassette including recombination arm used in donor plasmid. Analysis of vHVT306 genomic DNA was performed by PCR amplification and followed by nucleotide sequence determination.

The vHVT306 (donor plasmid pHVT US2 SV-Fopt-synPA) containing the recombinant arms, SV40 promoter and NDV F codon-optimized gene was confirmed to be correct as shown in SEQ ID NO:45 (FIG. 20).

Western Blot Analysis

The NDV F protein expression of vHVT306 was confirmed by two-step immunodetection. First, the expressed NDV F proteins from vHVT306 infected CEF were captured by the immunoprecipitation using anti-NDV F monoclonal antibody 001C3 (Merial Limited). Subsequently Western blot analysis using anti-NDV polyclonal serum (Charles River Laboratories) was applied to detect the NDV F protein in the captured samples (NDV F protein-monoclonal antibody complex). A 55 kDa protein in vHVT306 pre-MSV lysates was detected by anti-NDV serum which corresponds to the expected size of NDV F1 fusion protein.

Generation and Characterization of Other Double HVT Recombinants

Generation and characterization of double HVT recombinants, such as vHVT301, vHVT302, vHVT303, vHVT304, vHVT202, and vHVT307 were essentially done in the same way as for vHVT306 described above. The generation and characterization of recombinant HVT viral vectors were also described in U.S. patent application Ser. No. 13/689,625 filed on Nov. 29, 2012 Merial limited), which is incorporated herein by reference in its entirety. Table 12 shows the features unique to each construct around the expression cassettes, including the respective sequences.

TABLE 12

Characteristics of the expression cassettes of double HVT recombinants

| Name | Parental virus | Promoter | NDV-F gene or IBDV VP2 gene | Poly-A | Locus |
|---|---|---|---|---|---|
| vHVT 301 | vHVT13 | SV40 | Wt-VIId NDV-F | SV40 | IG2 |
| vHVT302 | vHVT13 | US10 | Opt-VIId NDV-F | US10 | US10 |
| vHVT303 | vHVT13 | US10 | Opt-V (CA02) NDV-F | US10 | US10 |
| vHVT304 | vHVT13 | SV40 | Opt-VIId NDV-F | Synthetic | IG2 |
| vHVT306 | vHVT13 | SV40 | Opt-VIId NDV-F | Synthetic | SORF3-US2 |
| vHVT307 | vHVT13 | SV40 | Opt-V (CA02) NDV-F | Synthetic | SORF3-US2 |
| vHVT202 | vHVT306 | Guinea pig CMV | IBDV E VP2 | Synthetic | SORF3-US2 |

Example 8 Lack of Horizontal Transmission of gC-Deleted SB-1 Mutant

The objective of the study was to compare the level of viremia and horizontal transmission induced by the parental SB-1 with that of a recombinant SB-1 virus in which the gC gene was deleted (see example 3).

Two groups (A and B) of thirty one-day-old specific pathogen free (SPF) white Leghorn chicks were randomly constituted. Twenty birds from groups A were vaccinated (D0) by the subcutaneous route (nape of the neck; 0.2 ml/bird) with 2000 PFU of parental SB-1 and twenty from groups B with 2000 PFU of the SB-1 gC-deleted mutant. Ten birds were kept unvaccinated in the same isolator as the vaccinated birds (groups Ac and Bc). At 2-weeks-of-age (D14), the spleen as well as 2 feathers of twenty vaccinated birds of groups A and B were removed after euthanasia. At 4-weeks-of-age (D28) the spleen of the 10 contact birds of groups Ac and Bc were also removed for viral isolation. White blood cells were collected from the buffy coat of ground spleens which had added to lymphocyte separation medium and centrifuged. For each bird, $10^6$ leucocytes were added to a 60 mm tissue culture dish that contained confluent monolayers of primary chicken embryo fibroblasts (CEF) prepared the day before. Five days post-infection, MDV plaques were counted on each dish and the number of positive birds and mean number of plaques was calculated. For feather follicles samples, the feather pulp was added to SPGA medium and sonicated for 10 seconds before placing on confluent monolayers of primary CEF from which the media had been removed. The pulp suspension was allowed to absorb for 45 minutes prior to adding fresh media with 1% calf serum.

Results of virus isolation from spleen and from feather follicles of vaccinated birds at D14 are reported in Table 13. All birds from both groups were positive for virus isolation from spleen with a similar mean number of plaques of 142.5 and 176.0 for groups A and B, respectively. Virus could be isolated from feather follicles of all birds in group A and from 90% of birds in group B.

Results of virus isolation from spleen of unvaccinated contact birds at D28 are reported in Table 14. Seven out of ten birds from group Ac were positive for virus isolation from spleen indicating that the parental SB-1 spread horizontally to contact birds. Virus could not be isolated from birds of group Bc suggesting that the gC-deleted mutant did not spread to contact birds.

TABLE 13

Results of viral isolation from spleen buffy coat (BC) and from feather follicles (FF) of vaccinated birds from groups A and B at D14

| | Group A – SB1 | | Group B – SB-1 gC deleted | |
|---|---|---|---|---|
| Sample No. | Spleen BC* | FF** | Spleen BC* | FF |
| 1 | 46 | + | 179 | + |
| 2 | 92 | + | 129 | + |
| 3 | 80 | + | 108 | + |
| 4 | 135 | + | 111 | + |
| 5 | 18 | + | 38 | + |
| 6 | 55 | + | 109 | – |
| 7 | 187 | + | 83 | – |
| 8 | 233 | + | 383 | + |
| 9 | 51 | + | 31 | + |
| 10 | 213 | + | 251 | + |
| 11 | 100 | + | 345 | + |
| 12 | 50 | + | 44 | + |
| 13 | 271 | + | 331 | + |
| 14 | 128 | + | 106 | + |
| 15 | 155 | + | 80 | + |
| 16 | 226 | + | TNTC (563) | + |
| 17 | 145 | + | 145 | + |
| 18 | 114 | + | 224 | + |
| 19 | 88 | + | 181 | + |
| 20 | TNTC*** (462) | + | 78 | + |
| Mean or positive/total | 142.5 | 20/20 | 176.0 | 18/20 |
| Standard deviation | 103.3 | – | 137.6 | – |

*Average plaque counts from spleen buffy coat (BC)
**positive sample from feather follicles
***TNTC too numerous to count

TABLE 14

Results of viral isolation from spleen buffy coat (BC) of unvaccinated contact birds from groups Ac and Bc at D28

| Sample No. | Group Ac – SB-1 Spleen BCE* | Group Bc – SB-1 gC deleted Spleen BCE* |
|---|---|---|
| 1 | 0 | 0 |
| 2 | 0 | 0 |
| 3 | 0 | 0 |
| 4 | 8 | 0 |
| 5 | 129 | 0 |
| 6 | 3 | 0 |
| 7 | 25 | 0 |
| 8 | 1 | 0 |
| 9 | 108 | 0 |
| 10 | 1 | 0 |

*Average plaque counts

This study indicates that the level of viremia of the gC-deleted SB-1 mutant measured at D14 post-vaccination was similar to that of the parental SB-1 virus suggesting that the gC deletion did not impair the ability of the SB-1 virus to replicate in vaccinated birds. The level of virus at the feather follicle was slightly lower with the gC-deleted mutant since 2/20 birds did not have detectable amount of virus. Horizontal transmission could be detected in 7/10 birds in contact with birds vaccinated with the parental SB-1. In contrast, no virus could be detected from the birds in contacts with birds vaccinated with the gC-deleted mutant indicating that the gC deletion severely impaired horizontal transmission.

Example 9 ND Efficacy Induced by SB-1 Recombinant Alone or in Combination with an HVT-IBD Vector Vaccine in One Day-Old SPF Chickens The objective of the study was to evaluate the efficacy of the vSB1-004 recombinant expressing NDV F gene against an ND challenge performed at 4 week-of-age in SPF chicks vaccinated with vSB1-004 alone or in combination with an HVT-IBD vector vaccine.

Three groups (1, 2 and 3) of fifteen one-day-old specific pathogen free (SPF) white Leghorn chicks were randomly constituted. Two vectored vaccines were used: the vSB1-004 described in example 1 and vHVT13, an herpesvirus of turkey (HVT) vector expressing the VP2 gene of infectious bursal disease virus Faragher 52/70 strain (active ingredient of the Merial licensed VAXXITEK® HVT+IBD vaccine, U.S. Pat. No. 5,980,906 and EP 0 719 864). Birds from groups 1, 2 and 3 received vHVT13 only (control group), vSB1-004 only and a mix of vHVT13 and vSB1-004, respectively (see Table 6). All birds were vaccinated by the subcutaneous route (nape of the neck) with 2000 PFU of vSB1-004 and/or vHVT13 (D0). Twenty seven days after vaccination (D27), birds of each group were challenged with the genotype V Mexican Chimalhuacan (Mex V) velogenic NDV strain. The challenge was performed by the intramuscular (IM) route using $10^5$ Egg Infectious Dose 50 (EID50) diluted in 0.2 ml of physiological sterile water. Birds were observed daily during 14 days after challenge for clinical signs and mortality. Oropharyngeal swabs were also sampled from 10 birds per group 5, 7 and 9 days after challenge. The viral RNA load was evaluated in these swabs after RNA extraction by using a quantitative reverse transcriptase real time polymerase chain reaction (qRT-PCR) based on the M gene and described by Wise et al. (2004; Development of a Real-Time Reverse-Transcription PCR for Detection of Newcastle Disease Virus RNA in Clinical Samples; J. Clin. Microbiol. 42, 328-338). Shedding levels were expressed as log 10 egg infectious dose 50% (EID50) per mL. Blood was also sampled at the time of challenge (D27). The serums were tested with the anti-IBD ELISA (Synbiotics ELISA ProFlok PLUS IBD) to evaluate the impact of vSBA-004 on the vHVT13-induced IBDV antibodies.

Results of protection and serology are summarized in Table 15. All control birds died within 5 days after ND challenge. The vSB1-004 recombinant virus induced full clinical protection either alone or when combined with vHVT13. The number of birds shedding detectable amount of challenge ND virus was very low in both vaccinated groups. The mean IBD ELISA titers in groups 1 and 3 were nearly identical indicating the lack of vSB1-004 interference on vHVT13-induced IBDV antibodies.

TABLE 15

Results of ND protection induced by SB-1 recombinants expressing NDV F gene in SPF day-old chicks (15/group) challenged at D27

| Group | Vaccine (D0) | ND protection | IBD ELISA titer (log10 ± SD*) | Shedding in oropharyngeal swabs** D5*** | D7 | D9 |
|---|---|---|---|---|---|---|
| 1 | vHVT13 | 0% | 4.04 ± 0.15 | —**** | — | — |
| 2 | vSB1-004 | 100% | 0.26 ± 0.50 | 1/10 (2.2) | 0/10 | 0/10 |
| 3 | vSB1-004 + vHVT13 | 100% | 4.02 ± 0.08 | 3/10 (4.1) | 2/10 (2.8) | 1/9 (3.4) |

*Standard deviation
**number of birds shedding/total (mean log10 EID50 equivalent/mL)
***day post-challenge
****all birds of group 1 died before D5 and therefore, shedding was not evaluated in this group The ND challenge model with the genotype V Chimalhuacan velogenic NDV is very severe. In these severe challenge conditions, vSB1-004 induced full clinical protection and excellent protection against shedding of challenge virus by the oropharyngeal route. It is worth noting that the F gene inserted in vSB1-004 is from a genotype VIId NDV strain and the challenge strain used here is a genotype V. It shows therefore that the genotype VIId F gene inserted into the SB-1 vector is cross-protecting birds against a genotype V challenge. The addition of vHVT13 did not impair the ND protection induced by vSB1-004 and the vSB1-004 did not interfere on vHVT13-induced IBD antibody titers, demonstrating compatibility of SB-1 vector with HVT vector.

Example 10 ND Early Efficacy Induced by SB-1 Recombinant in One-Day-Old SPF Chickens The objective of the study was to evaluate the efficacy of the vSB1-004 recombinant expressing NDV F gene against an early (D14) ND challenge in SPF chicks performed with two different NDV challenge strains.

Two groups (1 and 2) of twenty one-day-old specific pathogen free (SPF) white Leghorn chicks were randomly constituted. Birds from group 2 were vaccinated by the subcutaneous route (nape of the neck) with 2000 PFU of vSB1-004. Chicks from group 1 were not vaccinated and were kept as control birds. At 2 week-of-age, half of the birds of each group were challenged with the genotype V Mexican Chimalhuacan (Mex V) velogenic NDV strain and the other half with the genotype VIId Malaysia 04-1 (Mal VIId) velogenic NDV strain. The challenge was performed by the intramuscular (IM) route using $10^5$ Egg Infectious Dose 50 (EID50) diluted in 0.2 ml of physiological sterile water. Birds were observed daily during 14 days after challenge for clinical signs and mortality.

Results of protection are summarized in Table 16. All control birds died within 5 days after ND challenges. The vSB1-004 recombinant virus induced partial protection against mortality (70% and 40% protection after challenge with Mal VIId and Mex V, respectively) and against morbidity (50% and 30% protection after challenge with Mal VIId and Mex V, respectively) in these severe early challenge conditions.

TABLE 16

Results of early ND protection induced by SB-1 recombinants expressing NDV F gene in SPF day-old chicks

| Group | Vaccine | Challenge strain | Protection against mortality | Protection against morbidity |
|---|---|---|---|---|
| 1 | — | Mal VIId | 0/10 | 0/10 |
|   |   | Mex V | 0/9 | 0/9 |
| 2 | vSB1-004 | Mal VIId | 7/10 | 5/10 |
|   |   | Mex V | 4/10 | 3/10 |

The early ND challenge model that was used to evaluate the efficacy of vSB1-004 recombinant was chosen because Marek's disease virus vectors expressing NDV F gene do not generally provide full protection in this model. Indeed, their onset of immunity is delayed compared to live NDV vaccines (Morgan et al. (1993) Avian Dis 37, 1032-40; Heckert et al. (1996) Avian Dis 40, 770-777). It is therefore a good model to evaluate and compare the vaccine candidates. In these severe early challenge conditions, vSB1-004 recombinant induced partial protection that was only slightly higher against the Malaysian genotype VIId challenge than against the Mexican Chimalhuacan genotype V one indicating a broad protection against the 2 most prevalent genotypes circulating in the Americas and Eurasia/Africa, respectively.

Example 11 ND Efficacy Induced by SB-1 Recombinant Alone or in Combination with an HVT-IBD Vector Vaccine in 1 Day-Old Broiler Chickens with Maternal Antibodies The objective of the study was to evaluate the efficacy of the vSB1-004 recombinant expressing NDV F gene against two ND challenges performed at 4 week of age in broiler chicks vaccinated with vSB1-004 alone or in combination with an HVT-IBD vector vaccine.

Six groups (1a, 1b, 2a, 2b, 3a, 3b) of twelve one-day-old broilers (Hubbard JA957 line) were randomly constituted. Two vectored vaccines were used: the vSB1-004 described in example 1 and vHVT13, an herpesvirus of turkey (HVT) vector expressing the VP2 gene of infectious bursal disease virus Faragher 52/70 strain (active ingredient of the Merial licensed VAXXITEK® HVT+IBD vaccine). Birds from groups 1 (1a & 1b) were vaccinated with vHVT13 only (control group); those from groups 2 with vSB1-004 only and those from groups 3 with a mix of vHVT13 and vSB1-004 (see Table 17). All birds were vaccinated by the subcutaneous route (nape of the neck) with 2000 PFU of vSB1-004 and/or vHVT13 (D0). Twenty eight days after vaccination (D28), all birds of each subgroup "a" were challenged with the genotype VIId Malaysia 04-1 (Mal VIId) velogenic NDV strain and all birds of each subgroup "b" with the genotype V Mexican Chimalhuacan (Mex V) velogenic NDV strain. The challenge was performed by the intramuscular (IM) route using $10^5$ Egg Infectious Dose 50 (EID50) diluted in 0.2 ml of physiological sterile water. Birds were observed daily during 14 days after challenge for clinical signs and mortality. Blood was also sampled from 5 birds in each group at the time of challenge (D28). The serums were tested with the anti-IBD ELISA (Synbiotics ELISA ProFlok PLUS IBD) to evaluate the impact of vSB1-004 on the vHVT13-induced IBDV antibodies in broilers.

Results of protection and serology are summarized in Table 17. All control birds died within 5 days after ND challenges. The vSB1-004 recombinant virus induced significant level of clinical protection when combined or not with vHVT13. The number of birds shedding detectable amount of virus was very low in both vaccinated groups. The mean IBD antibody titers in groups 2 was still high (3 log 10) at D27 indicating a high level of maternally-derived IBD antibodies; nevertheless, vHVT13 induced a clear IBD antibody response which was not affected when mixed with vSB1-004.

TABLE 17

Results of ND protection induced by SB-1 recombinants expressing NDV F gene in broiler day-old chicks (12 per group except group 1b: 11) challenged at D28

| Group | Vaccine (D0) | ND challenge | ND protection | IBD ELISA titer (log10 ± SD*) |
|---|---|---|---|---|
| 1a | vHVT13 | Mal VIId | 0% | 3.94 ± 0.24 |
| 1b | vHVT13 | Mex V | 0% | |
| 2a | vSB1-004 | Mal VIId | 83% | 3.03 ± 0.44 |
| 2b | vSB1-004 | Mex V | 75% | |
| 3a | vSB1-004 + vHVT13 | Mal VIId | 75% | 4.02 ± 0.23 |
| 3b | vSB1-004 + vHVT13 | Mex V | 83% | |

*Standard deviation

Results of this study indicated significant levels of protection induced by vSB1-004 in broilers with NDV MDA. The addition of vHVT13 did not have negative impact on vSB1-004-induced ND protection indicating the lack of vHVT13 interference. Furthermore, vSB1-004 did not interfere on vHVT13-induced IBD antibodies, confirming in broilers the compatibility between these two vectors.

Example 12 Lack of Interference of vSB1-004 on IBD Early Efficacy Induced by an HVT-IBD Vector Vaccine in 1 Day-Old SPF Chicks The objective of the study was to evaluate the potential interference of the vSB1-004 recombinant on the IBD efficacy induced by an HVT-IBD vector vaccine (vHVT13) in an early (D14) IBD challenge model in SPF chicks.

Three groups (1 to 3) of ten one-day-old specific pathogen free (SPF) white Leghorn chicks were randomly constituted. Birds from group 1 were vaccinated by the subcutaneous route (nape of the neck) with 2000 PFU of vSB1-004 (control group). Chicks from group 2 were vaccinated with 2000 PFU of vHVT13 and birds from group 3 were vaccinated with 2000 PFU of vHVT13 and 2000 PFU of vSB1-004. At 2 week of age, all birds of each group were challenged by the ocular route with 50 μL containing 2.5 log 10 EID50 of the IBDV classical strain Faragher 52/70. Birds were observed daily during 10 days after challenge for clinical signs and mortality. All birds were euthanized 10 days after challenge and body and bursa of Fabricius weights were recorded in order to evaluate the bursa/body weight ratio. Their bursa was also checked for histological lesions typical of IBD. A score was assigned to each bursa based on the severity of the lesions as shown in Table 18. The number of affected birds (non-protected) in each group was calculated. A bird was considered as affected if it died and/or showed notable sign of disease and/or intermediate or severe lesions of the bursa of Fabricius (i.e., histology score 3).

TABLE 18

Scoring scale of histological lesions of the bursa of Fabricius

| Score | Histology observation/lesions |
|---|---|
| 0 | No lesion, normal bursa |
| 1 | 1% to 25% of the follicles show lymphoid depletion (i.e., less than 50% of depletion in 1 affected follicle), influx of heterophils in lesions |
| 2 | 26% to 50% of the follicles show nearly complete lymphoid depletion (i.e., with more than 75% of depletion in 1 affected follicle), the affected follicles show necrosis lesions and severe influx of heterophils may be detected |
| 3 | 51% to 75% of the follicles show lymphoid depletion; affected follicles show necrosis lesions and a severe influx of heterophils is detected |
| 4 | 76% to 100% of the follicles show nearly complete lymphoid depletion; hyperplasia and cyst structures are detected; affected follicles show necrosis lesions and severe influx of heterophils is detected |
| 5 | 100% of the follicles show nearly complete lymphoid depletion; complete loss of follicular structure; thickened and folded epithelium; fibrosis of bursal tissue |

Results of protection are summarized in Table 19. All control birds became sick and one died after challenge whereas all vaccinated birds remained healthy. The bursal body weight ratios of groups 2 and 3 were similar and significantly higher than that of group 1. All 8 birds that survived challenge from group 1 had bursa lesion scores of 4 or

TABLE 19

Results of early (D14) IBD protection induced by vHVT13 alone or in combination with vSB1-004 recombinant expressing NDV F gene in SPF day-old chicks.

| Group | Vaccine | Mortality | Morbidity | Bursal/Body weight ratio * 100 | Bursa with score ≥3 | Protection |
|---|---|---|---|---|---|---|
| 1 | vSB1-004 | 1/9* | 9/9 | 0.14 ± 0.02 | 8/8 | 0% |
| 2 | vHVT13 | 0/10 | 0/10 | 0.47 ± 0.10 | 0/10 | 100% |
| 3 | vHVT13 + vSB1-004 | 0/9* | 0/9 | 0.46 ± 0.20 | 1/9 | 89% |

*One bird in these groups died before challenge.

The early IBD challenge model that was used to evaluate the lack of interference of vSB1-004 recombinant on vHVT13-induced IBD protection was chosen because it is very sensitive to detect interference on vHVT13 protection. Results obtained with vSB1-004+vHVT13 indicated an excellent level of IBD protection (89%) indicating compatibility between vSB1-004 and vHVT13 even when measured in an early IBD challenge.

Example 13 Efficacy of vHVT114, vHVT116, vSB1-007, vSB1-008 (Alone or with vHVT13) and vHVT 304 Against Challenges with NDV ZJ1 (Genotype VIId) and California/02 (Genotype V) at 21 Days of Age in SPF Chickens The aim of the study was to assess the efficacy of 2 single HVT recombinant constructs (vHVT114 and vHVT116), 2 SB1 recombinant constructs (vSB1-007 & vSB1-008) expressing the NDV F gene and a double HVT recombinant (vHVT304) against Newcastle disease challenge with NDV ZJ1 (genotype VIId) and California/02 (genotype V) performed at 21 days of age in SPF chickens.

The characteristics of these 5 vaccine candidates are described in Table 20 below.

TABLE 20

Characteristics of the vectors used in the challenge study

| Name | Parental virus | Promoter | F gene | Poly-A | Locus |
|---|---|---|---|---|---|
| vHVT114 | HVT | SV40 | Opt-VIId | SV40 | IG1 |
| vHVT116 | HVT | SV40 | Opt-V | SV40 | IG1 |
| vSB1-007 | SB-1 | SV40 | Opt-VIId | gC | gC |
| vSB1-008 | SB-1 | SV40 | Opt-V | SV40 | IG1 |
| vHVT304 | vHVT13* | SV40 | Opt-VIId | Synth | IG2 |

*vHVT13 is the active ingredient of the licensed Vaxxitek HVT-IBD vaccine based on an HVT vector expressing the IBDV VP2 gene (see U.S. Pat. No. 5,980,906 and EP 0 719 864).

On D0, 158 one-day-old SPF chickens were randomly allocated into 6 groups of 24 birds (vaccinated) and 1 group of 12 birds (non-vaccinated controls). The birds were injected by subcutaneous injection in the neck at D0 with 0.2 mL of recombinant vaccines containing a target dose of 1000 pfu as described in Table 21 below. The birds were then separated into two sub-groups, each sub-group being challenged by the intramuscular route on D21 with 5 log 10 EID50 of either NDV ZJ1 (genotype VIId) or California/02 (genotype V) velogenic strain.

TABLE 21

Results of efficacy

| Group | Vaccine at day-old (D0) | % clinical protection CA/02 (genotype V) | ZJ1 (genotype VIId) |
|---|---|---|---|
| G1 | — | 0% | 0% |
| G2 | vHVT114 | 100% | 100% |
| G3 | vHVT116 | 100% | 90% |
| G4 | vSB1-007 | 92% | 100% |
| G5 | vSB1-008 | 100% | 100% |
| G6 | vSB1-008 + vHVT13 | 100% | 83% |
| G7 | vHVT304 | 92% | 75% |

Each group was monitored before and after challenge. Technical problems observed with isolators reduced the number of birds in group 2 (vHVT114: from 24 to 14) and in group 3 (vHVT116: from 24 to 20). NDV clinical signs were recorded after challenge. Serum was collected from blood samples taken from birds of groups 2 and 7 before challenge (D21) for NDV serology by HI test using each challenge strains as antigen.

Percentages of protection against mortality and morbidity are reported in the table above. Full susceptibility was observed in the non-vaccinated challenged control group G1 thus validating the high severity of both challenges. All vaccines induced high levels (≥75%) of protection against both challenges. Full clinical protection against both challenges was induced by vHVT114 and vSB1-008.

The shedding was evaluated after challenge by real time RT-PCR in oral and cloacal swabs taken 2 and 4 days post-challenge. Percentage of positive (Ct<40) birds are shown for both challenges in FIGS. 17A and 17B. Note that all 6 birds were dead at 4 dpch in the control group challenged with the CA/02 isolate and only one bird (out of 6) was still alive at 4 dpch in the control group challenged with ZJ1. Shedding was detected in all control birds. Reduction of the percentage of birds positive for shedding was observed in all vaccinated groups.

In conclusion, the results of this study showed the very good ND protection at 3 weeks of age induced by tested Marek's disease vector vaccines.

Example 14 Efficacy of vHVT114, vSB1-007, vSB1-009, vHVT306 and vHVT307 Vaccines Against Challenges with NDV Texas GB Strain at 28 Days of Age in SPF Chickens The aim of the study was to assess the efficacy of combinations of different Marek's disease vector vaccines expressing the NDV F and/or the IBDV VP2 gene against Newcastle disease challenge (Texas GB strain, genotype II) performed at 28 days of age in SPF chickens.

The characteristics of the 5 recombinant vaccine candidates tested in this study are described in Table 22 below.

TABLE 22

Characteristics of the vectors used in the challenge study

| Name | Parental virus | Promoter | F gene | Poly-A | Locus |
|---|---|---|---|---|---|
| vHVT114 | HVT | SV40 | Opt-VIId | SV40 | IG1 |
| vSB1-007 | SB-1 | SV40 | Opt-VIId | gC | gC |
| vSB1-009 | SB-1 | SV40 | Opt-V (CA02) | gC | gC |

TABLE 22-continued

Characteristics of the vectors used in the challenge study

| Name | Parental virus | Promoter | F gene | Poly-A | Locus |
|---|---|---|---|---|---|
| vHVT306 | vHVT13 | SV40 | Opt-VIId | Synth | SORF3-US2 |
| vHVT307 | vHVT13 | SV40 | Opt-V (CA02) | Synth | SORF3-US2 |

The Marek's disease virus serotype 1 (CVI988 (or Rispens) strain; Gallid herpesvirus 2) and serotype 2 (SB-1 strain; gallid herpesvirus 3) vaccines were used also in combination with recombinant viruses in some of the groups.

On D0, 135 one-day-old SPF chickens were randomly allocated into 9 groups of 15 birds. The birds were injected by subcutaneous injection in the neck at D0 with 0.2 mL containing a target dose of 2000 pfu for recombinant vaccines (vSB1-007, vSB1-009, vHVT13, vHVT306, vHVT307, vHVT114), and 1000 pfu for parental Marek's disease vaccine strains (SB-1 and CVI988). The design of the study is shown in Table 23 below. The birds were challenged by the intramuscular route on D28 with 4.0 log 10 EID50 velogenic ND Texas GB (genotype II) strain.

TABLE 23

Results of efficacy

| Group | Vaccine at day-old (D0) | % ND protection after Newcastle disease challenge at 28 days of age |
|---|---|---|
| G1 | — | 0% |
| G2 | vSB1-007 + vHVT13 | 80% |
| G3 | vSB1-009 | 100% |
| G4 | vSB1-009 + vHVT13 | 86% |
| G5 | vSB1-009 + vHVT13 + CVI988 | 93% |
| G6 | vHVT306 + SB-1 | 100% |
| G7 | vHVT307 | 100% |
| G8 | vHVT307 + SB-1 | 93% |
| G9 | vHVT114 + vHVT13 + SB-1 | 100% |

Each group was monitored before and after challenge. NDV clinical signs after challenge were recorded.

Percentages of protection against mortality and morbidity are reported in the table 23 above. Full susceptibility was observed in the non-vaccinated challenged control group G1 thus validating the high severity of challenge. Excellent levels of protection were observed in all vaccinated groups. Birds from G3, G6, G7 and G9 were fully protected. This study shows that the vSB1-ND candidates can be co-administered with vHVT13 and CVI988 and still provide a very good ND protection. Similarly, double HVT-IBD+ND are compatible with SB-1 and vHVT-ND (vHVT114) is compatible with vHVT13 and SB-1.

In conclusion, the results of this study showed the lack of interference on ND protection induced by the tested Marek's disease parental and vector vaccines.

Example 15 Efficacy of vHVT114, vHVT307, vSB1-007 and vSB1-009 in Combination with vHVT13 Against Challenges with NDV Chimalhuacan Strain (Genotype V) at D28 in SPF Chickens The aim of the study was to assess the efficacy of one HVT recombinant construct (vHVT114) and two SB1 recombinant constructs (vSB1-007 and vSB1-009) expressing the NDV F gene in combination with vHVT-IBD (vHVT13), as well as a double HVT vHVT307 expressing both NDV F and IBDV VP2 against Newcastle disease challenge (Chimalhuacan, genotype V) performed at 28 days of age in SPF chickens.

The characteristics of these 4 vaccine candidates are described in Table 24 below.

TABLE 24

Characteristics of the vectors used in the challenge study

| Name | Parental virus | Promoter | F gene | Poly-A | Locus |
|---|---|---|---|---|---|
| vHVT114 | HVT | SV40 | Opt-VIId | SV40 | IG1 |
| vSB1-007 | SB-1 | SV40 | Opt-VIId | gC | gC |
| vSB1-009 | SB-1 | SV40 | Opt-V (CA02) | gC | gC |
| vHVT307 | vHVT13* | SV40 | Opt-V (CA02) | Synth | SORF3-US2 |

On D0, 45 one-day-old SPF chickens were randomly allocated into 4 groups of 10 birds and 1 group of 5 birds (unvaccinated control group). The birds were injected by subcutaneous injection in the neck at D0 with 0.2 mL of recombinant vaccines containing a target dose of 2000 pfu as described in Table 25 below. The birds were challenged by the intramuscular route on D28 with 5.0 log 10 EID50 velogenic Chimalhuacan (genotype V) strain.

TABLE 25

Study design and results of ND efficacy

| Group | Vaccine at day-old (D0) | % protection against mortality | % protection against morbidity |
|---|---|---|---|
| G1 | — | 0% | 0% |
| G2 | vHVT114 + vHVT13 | 100% | 100% |
| G3 | vHVT307 | 80% | 80% |
| G4 | vSB1-007 + vHVT13 | 90% | 90% |
| G5 | vSB1-009 + vHVT13 | 90% | 90% |

Each group was monitored before and after challenge. NDV clinical signs were recorded after challenge. Oropharyngeal swabs were taken in the vaccinated groups at 5 and 7 days post-challenge to evaluate the viral load by real time RT-PCR.

Figure 18A:
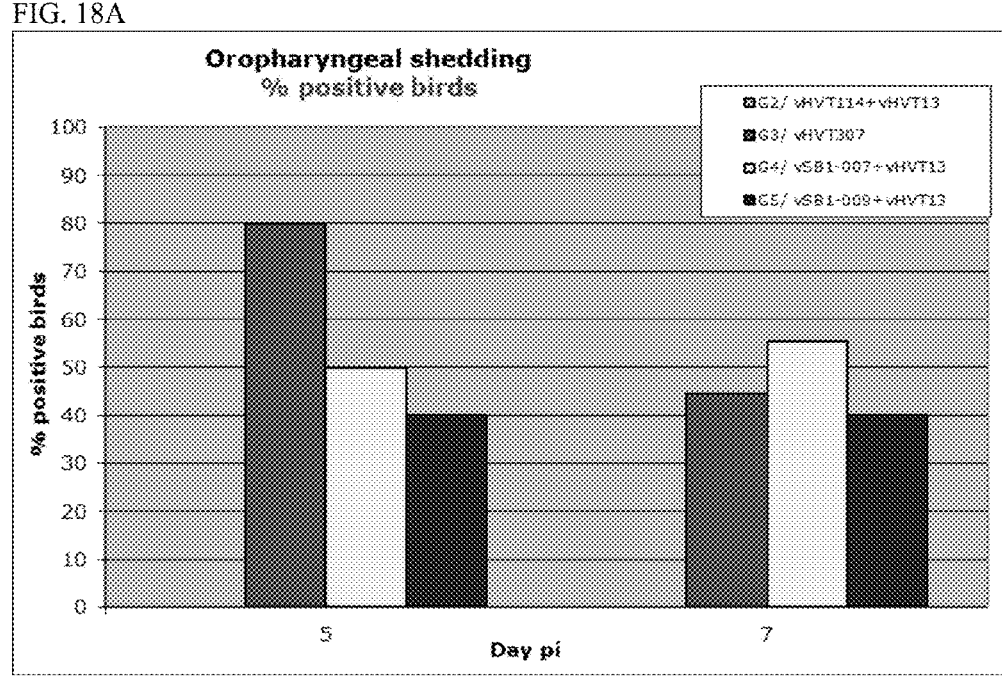
FIG. 18 depicts the clinical analysis (oropharyngeal shedding) of the recombinants against NDV challenge.
Figure 18B:
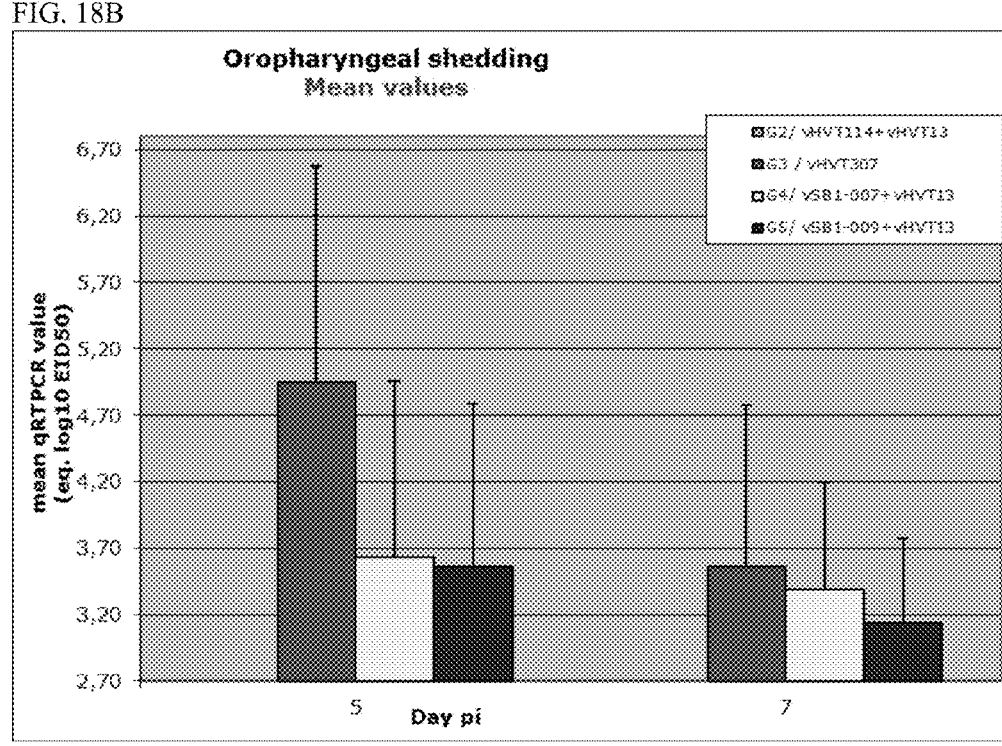

Percentages of protection against mortality and morbidity are reported in the table above. Full susceptibility was observed in the non-vaccinated challenged control group G1 thus validating the high severity of challenge. Very good protection was observed in all 4 vaccinated groups, a full clinical protection being induced by vHVT114+vHVT13. The percentage of positive birds and the mean shedding titer (expressed as log 10 EID50 equivalent per mL) are shown in FIGS. 18A and 18B. Surprisingly, no shedding was detected in G2 indicating a complete (against both clinical signs and shedding) ND protection induced by vHVT114 even if co-administered with vHVT13, in the tested conditions. The shedding levels detected in the other vaccinated groups were low with a slightly higher level detected in G3 (vHVT307) at 5 days post-infection (pi) only.

In conclusion, this example further illustrates the excellent ND protection induced by double HVT-IBD+ND recombinant or a combination of SB1-ND or HVT-ND and HVT-IBD (vHVT13) recombinant viruses. Contrary to the general belief in the field that a second HVT vaccine (regular HVT vaccines or recombinant HVT vaccines) interferes with the immunity to the foreign genes inserted into the first recombinant HVT vaccine, the present invention showed surprising result that vHVT114 in combination with vHVT13 offered excellent protection against NDV and no interference effect was observed.

Example 16 Efficacy of vHVT306, vSB1-008 in Combination with vHVT13 Administered by SC or in Ovo Route Against Challenge with NDV Chimalhuacan Strain (Genotype V) at D28 in SPF Chickens The aim of the study was to assess the efficacy of the vHVT306 double HVT expressing both NDV F and IBDV VP2 genes, and the vSB1-008 SB1 recombinant expressing the NDV F gene in combination with vHVT-IBD (vHVT13), administered by the in ovo or by the subcutaneous route against Newcastle disease challenge (Chimalhuacan, genotype V) performed at 28 days of age in SPF chickens.

The design of the groups is shown on Table 26. Sixty SPF embryonated eggs (after approximately 18 days and 18 hours of incubation; D-3) were used for the in ovo administration (20 per group for G1, G2 and G3). Fifty microliters of vaccine containing 2000 PFU were administered by the in ovo route using the IntelliLab System device from AviTech LLC (Salisbury, Md., USA). Hatchability and survival were recorded after in ovo administration. On D0, 20 one-day-old SPF chickens were randomly allocated into 2 groups of 10 birds (G4 and G5). The birds were injected by subcutaneous (SC) injection in the neck at D0 with 0.2 mL of recombinant vaccines containing a target dose of 2000 pfu as described in Table 26 below. Ten birds per group were challenged by the intramuscular route on D28 with 5.0 log 10 EID50 velogenic Chimalhuacan (genotype V) strain.

TABLE 26

Study design and results of ND efficacy

| Group | Vaccine at day-old (D0) | Admin. route | % protection against mortality | % protection against morbidity |
|---|---|---|---|---|
| G1 | vHVT13 | In ovo | 0% | 0% |
| G2 | vHVT306 | In ovo | 100% | 100% |
| G3 | vSB1-008 + vHVT13 | In ovo | 78% | 68% |
| G4 | vHVT306 | SC | 100% | 100% |
| G5 | vSB1-008 + vHVT13 | SC | 100% | 70% |

Each group was monitored before and after challenge. NDV clinical signs were recorded after challenge. Oropharyngeal swabs were taken in the vaccinated groups at 5 and 7 days post-challenge to evaluate the viral load by real time RT-PCR.

Full hatchability and viability were recorded up to D28 (challenge day) for birds of groups G1 and G2. Hatchability in G3 was 85% and one additional bird died after hatching in this group. The lower hatchability of that group may be due to egg incubator problems. Body weights of males and females in G1, G2 and G3 were similar at D1 and at D28.

Percentages of protection against mortality and morbidity are reported in the table 26. Full susceptibility was observed in the non-vaccinated challenged control group G1 thus validating the high severity of challenge. Very good protection was observed in all 4 vaccinated groups, a full clinical protection being induced by vHVT306 administered by both routes.

The percentage of positive birds and the mean shedding titer (expressed as log 10 EID50 equivalent per mL) are shown in Table 27. Absence of detectable or very low shedding was observed in G2 and G4 vaccinated with vHVT306. The shedding levels detected in the groups vaccinated with vSB1-008+vHVT13 were higher especially at 5 days post-infection (pi).

TABLE 27

Results of protection against shedding (percentage of birds with detectable shedding and mean viral load in log10) evaluated at D5 and D7 after NDV challenge

| Group | Vaccine at day-old (D0) | Admin. Route | Percent of positive birds (D5/D7 pi) | Mean viral load* (D5/D7 pi) |
|---|---|---|---|---|
| G2 | vHVT306 | In ovo | 0/0% | 2.7/2.7 |
| G3 | vSB1-008 + vHVT13 | In ovo | 100/38% | 5.2/3.2 |
| G4 | vHVT306 | SC | 20/10% | 3.2/2.9 |
| G5 | vSB1-008 + vHVT13 | SC | 80/50% | 4.6/3.4 |

*Mean quantitative real time PCR value expressed in equivalent log10 EID50; the threshold is set at 2.7 log10.

In conclusion, this example shows excellent ND protection induced by vHVT306 double HVT recombinant administered either by in ovo or by SC routes. The performance of vSB1-008+vHVT13 was slightly lower especially after in ovo administration, but it may be at least partially due to egg incubator problems. Indeed, the in ovo safety testing of another SB1-ND recombinant (vSB1-009) at 1000 or 4000 PFU associated with 6000 PFU of vHVT13 did not show any difference in hatchability and early survival with a group receiving 6000 PFU of vHVT13 only.

Example 17 Efficacy of vHVT304, vHVT306, vSB1-007 and vSB1-008 in Combination with vHVT13 Against Challenge with NDV Chimalhuacan Strain (Genotype V) at D42 in Commercial Broiler Chickens The aim of the study was to assess the efficacy of two double HVT (vHVT304 and vHVT306) expressing both NDV F and IBDV VP2 genes, and two SB1 recombinants (vSB1-007 and vSB1-008) expressing the NDV F gene in combination with vHVT-IBD (vHVT13) against Newcastle disease challenge (Chimalhuacan, genotype V) performed at 42 days of age in commercial broiler chickens.

The design of the groups is shown on Table 28. On D0, 55 one-day-old commercial broiler chickens were randomly allocated into 5 groups of 11 birds. The birds were injected by subcutaneous (SC) injection in the neck at D0 with 0.2 mL of recombinant vaccines containing a target dose of 2000 pfu as described in Table 28 below. Ten birds per group were challenged by the intramuscular route on D42 with 5.0 log 10 EID50 velogenic Chimalhuacan (genotype V) strain.

TABLE 28

Study design and results of ND efficacy

| Group | Vaccine at day-old (D0) | % protection against mortality | % protection against morbidity |
|---|---|---|---|
| G1 | vHVT13 | 0% | 0% |
| G2 | vHVT304 | 82% | 82% |
| G3 | vHVT306 | 100% | 100% |

TABLE 28-continued

Study design and results of ND efficacy

| Group | Vaccine at day-old (D0) | % protection against mortality | % protection against morbidity |
|---|---|---|---|
| G4 | vSB1-007 + vHVT13 | 100% | 100% |
| G5 | vSB1-008 + vHVT13 | 91% | 91% |

Each group was monitored before and after challenge. NDV clinical signs were recorded during 14 days after challenge. Oropharyngeal swabs were taken in the vaccinated groups at 5 and 7 days post-challenge to evaluate the viral load by real time RT-PCR.

Percentages of protection against mortality and morbidity are reported in the table 28. Full susceptibility was observed in the non-vaccinated challenged control group G1 thus validating the high severity of challenge. Very good protection was observed in all 4 vaccinated groups, a full clinical protection being induced by vHVT306 and by vSB1-007+vHVT13.

The percentage of positive birds and the mean shedding titer (expressed as log 10 EID50 equivalent per mL) are shown in Table 29. The best reduction of shedding was induced by vHVT306 and vSB1-007+vHVT13, which were also the best candidates for clinical protection.

TABLE 29

Results of protection against shedding (percentage of birds with detectable shedding and mean viral load in log10) evaluated at D5 and D7 after NDV challenge (pi)

| Group | Vaccine at day-old (D0) | Percent of positive birds (D5/D7 pi) | Mean viral load* (D5/D7 pi) |
|---|---|---|---|
| G2 | vHVT304 | 100/100% | 5.4/4.6 |
| G3 | vHVT306 | 40/50% | 3.5/3.7 |
| G4 | vSB1-007 + vHVT13 | 80/70% | 3.8/4.8 |
| G5 | vSB1-008 + vHVT13 | 100/100% | 4.8/4.3 |

*Mean quantitative real time PCR value expressed in equivalent log10 EID50; the threshold is set at 2.7 log10.

The vSB1-007+vHVT13 performed better than vSB1-008+vHVT13. The vSB1-007 genomic structure differs from that of vSB1-008 in different aspects: locus of insertion, promoter, poly-adenylation signal and F gene origin. The combination of these foreign sequences and locus of insertion in vSB1-007 were likely responsible for its better ND protection performances.

In summary, this example illustrates the importance of the locus of insertion and other regulatory sequences of the NDV expression cassette in the ND protection induced by HVT and MDV serotype 2 vectors.

Example 18 Efficacy of Double HVT-ND+IBD (vHVT304 and vHVT306) or SB1-ND (vSB1-008) in Combination with vHVT13 Recombinant Vaccines, Against Challenge with a Classical IBDV Isolate on D14 in SPF Chickens The aim of the study was to assess the early IBD efficacy of double HVT recombinants vHVT304 and vHVT306 as well as that of vHVT13 co-administered with a SB1-ND (vSB1-008) recombinant constructs against a virulent infectious bursal disease virus (vIBDV) challenge (Faragher 52/70 strain) performed at 14 days of age in SPF chickens.

On D0, 95 one-day-old SPF chickens were randomly allocated into 9 groups of 10 birds and 1 group of 5 birds (unvaccinated unchallenged control group). The birds were injected by subcutaneous injection in the neck at D0 with 0.2 mL of recombinant vaccines containing a target dose of 300 or 1000 pfu as described in the Table 30 below. On D14, blood sample was collected from 5 birds per group for serological testing with the Kit ProFLOK® plus IBD (Synbiotics Corp). The birds (10 birds per group except for group 7 in which 1 bird died before challenge) were challenged by the eye drop (0.05 mL per bird) with 2.5 log 10 EID50.

TABLE 30

Study design and results of IBD efficacy

| Group | Vaccine at day-old (dose in PFU) | IBD+ ELISA titer at D14[1] | Number Dead/Sick[2] | % protection[3] | Mean bursal/body weight ratio[4] |
|---|---|---|---|---|---|
| G1 | vSB1-008 (1000) | 0.2 | 7/10 | 0% | 0.0013 |
| G2 | vHVT13 (300) | 2.7 | 0/0 | 100% | 0.0051 |
| G3 | vHVT13 (1000) | 2.7 | 0/0 | 90% | 0.0049 |
| G4 | vHVT13 + vSB1-008 (300) | 1.9 | 1/1 | 60% | 0.0041 |
| G5 | vHVT13 + vSB1-008 (1000) | 2.4 | 0/0 | 70% | 0.0041 |
| G6 | vHVT304 (300) | 2.9 | 0/0 | 60% | 0.0037 |
| G7 | vHVT304 (1000) | 2.2 | 0/0 | 67% | 0.0047 |
| G8 | vHVT306 (300) | 2.4 | 0/0 | 80% | 0.0033 |
| G9 | vHVT306 (1000) | 2.7 | 0/0 | 40% | 0.0026 |

[1] Mean IBD+ ELISA titers expressed in log10 in the serum of 5 birds per group sampled at D14 before challenge;
[2] Birds sick for more than 2 days or still sick on D25 were considered as sick.
[3] Protection against clinical signs and severe bursal lesion (bursal score <3)
[4] The bursal/body weight ratio of the unvaccinated/unchallenged group was 0.0047.

Each group was monitored before and after challenge. IBDV clinical signs were recorded for 11 days after challenge (from D15 to D25). At the end of the post-challenge observation period (D25), all the surviving birds were euthanized and necropsied. Body and bursal weights were recorded. Each bursa of Fabricius (BF) was weighted then stored in individual recipients containing 4% formaldehyde for histology. Histological lesions of the bursa were scored according to the scale presented in Table 31.

TABLE 31

Scoring scale of histological lesions of the bursa of Fabricius*

| Score | Histology observation/lesions |
|---|---|
| 0 | No lesion, normal bursa |
| 1 | 1% to 25% of the follicles show lymphoid depletion (i.e. less than 50% of depletion in 1 affected follicle), influx of heterophils in lesions |
| 2 | 26% to 50% of the follicles show nearly complete lymphoid depletion (i.e. more than 75% of depletion in 1 affected follicle), affected follicles show necrosis and severe influx of heterophils may be detected |
| 3 | 51% to 75% of the follicles show lymphoid depletion; affected follicles show necrosis lesions and a severe influx of heterophils is detected |
| 4 | 76% to 100% of the follicles show nearly complete lymphoid depletion; hyperplasia and cyst structures are detected; affected follicles show necrosis and severe influx of heterophils is detected |
| 5 | 100% of the follicles show nearly complete lymphoid depletion; complete loss of follicular structure, thickened and folded epithelium, fibrosis of bursal tissue |

*sourced from Monograph No. 01/2008: 0587 of EU Pharmacopoeia "Avian Infectious Bursal Disease vaccine (live)

A bird was considered as affected if it died and/or showed notable sign of disease and/or severe lesions of the bursa of Fabricius (i.e., histology score 3).

The mean ELISA IBD+ antibody titer expressed in log 10 before challenge is shown in Table 30. Significant titers were detected in all vaccinated groups that were significantly higher than that of the control group G1. The serology titer was not dose-dependent.

Severe clinical signs were observed after challenge in all birds of the control group G1. Seven out of 10 birds of that group died within the 11 days observation period indicating the high severity of challenge. None of the vaccinated birds showed severe clinical signs after challenge except 1 bird of G4 that died. Percentages of protection against severe bursal lesions are shown in the table 30 above. Significant IBD protection was observed in all groups, the best protection being observed in G2 and G3 (vHVT13 alone). The co-administration of vSB1-008+vHVT13 and the double vHVT304 and vHVT306 constructs induced similar levels of IBD protection. The protection was not dose-dependent at the tested doses. The mean bursal/body weight ratios are also shown in Table 30. Ratios in all vaccinated groups were higher than those of the challenged control group.

In conclusion, these data indicate that both the combination of a SB1-ND vector with a single HVT-IBD or double HVT expressing both NDV-F and IBDV-VP2 induce IBD antibodies and early IBD protection in a severe IBDV challenge model.

Example 19 Efficacy of Single HVT-ND (vHVT114) or SB1-ND (vSB1-007 and vSB1-009) in Combination with vHVT13 Recombinant Vaccines, Against Challenge with a Very Virulent IBDV Isolate on D23 in Commercial Broiler Chickens The aim of the study was to assess the IBD efficacy of vHVT13 co-administered with an HVT-ND (vHVT114) or SB1-ND (vSB1-007 and vSB1-009) recombinant constructs against a very virulent infectious bursal disease virus (vvIBDV) challenge (91-168/980702 isolate) performed at 23 days of age in commercial broiler chickens.

On D0, 90 one-day-old broiler chickens were randomly allocated into 7 groups of 12 birds and 1 group of 6 birds (unvaccinated unchallenged control group). The birds were injected by subcutaneous injection in the neck at D0 with 0.2 mL of recombinant vaccines containing a target dose of 3000 pfu as described in the Table 32. On D14, blood sample was collected from 5 birds per group for serological testing with the Kit ProFLOK® plus IBD (Synbiotics Corp). The serum of 10 extra one-day-old broiler chickens was tested at D0 with the same kit to evaluate the level of IBDV maternal antibody. The birds (10 birds per group) were challenged by the eye drop (0.05 mL per bird) on D23 with 4.3 log 10 EID50 of the vvIBDV 91-168 isolate.

Each group was monitored before and after challenge. IBDV clinical signs were recorded for 11 days after challenge (from D23 to D33). At the end of the post-challenge observation period (D33), all the surviving birds were euthanized and necropsied. Body and bursal weights were recorded. Each bursa of Fabricius (BF) was weighted then stored in individual recipients containing 4% formaldehyde for histology. Histological lesions of the bursa were scored according to the scale presented in Table 31.

A bird was considered as affected if it died and/or showed notable signs of disease and/or severe lesions of the bursa of Fabricius (i.e., histology score 3).

TABLE 32

Study design and serology results

| Group | Vaccine at day-old (D0) | IBD+ ELISA titer at D23[1] | Mean bursal/body weight ratio[2] |
|---|---|---|---|
| G1 | — | 3.9 | 0.0007 |
| G2 | vHVT13 | 4.0 | 0.0015 |
| G3 | vHVT114 + vHVT13 | 4.1 | 0.0015 |
| G4 | vSB1-007 + vHVT13 | 3.8 | 0.0018 |
| G5 | vSB1-009 + vHVT13 | 4.0 | 0.0019 |

[1]Mean IBD+ ELISA titers expressed in log10 in the serum of 5 birds per group sampled at D23 before challenge;
[2]The bursal/body weight ratio of the unvaccinated/unchallenged group was 0.0047

The mean ELISA IBD+ serological titer at D0 was 4.36±0.01 log 10 indicating a very high level of IBD maternal antibody at hatch. At D23, the mean ELISA IBD+ titer was still high (3.9) in the control G1. ELISA mean titers in the vaccinated groups were not significantly different from those of the control group.

Neither morbidity nor mortality was observed in any of the groups after challenge. Percentages of protection against severe bursal lesions are shown in Table 32 above. The result showed that co-administration of vHVT114, vSB1-007 or vSB1-009 did not interfere with vHVT13-induced IBD protection indicating a lack of interference. Similarly, the mean bursal/body weight ratios of the vaccinated groups were similar and clearly higher than that of the control group, indicating IBD protection and no difference between the vaccination regimens.

In conclusion, the data indicate the compatibility between vHVT114, vSB1-007 or vSB1-009 and vHVT13 for IBD protection.

Example 20 Efficacy of Double HVT-ND+IBD (vHVT304 and vHVT306) Associated or not with SB-1 and of SB1-ND (vSB1-007 and vSB1-008) in Combination with vHVT13 Recombinant Vaccines, Against Challenge with a Variant E IBDV Isolate on D28 in SPF Chickens The aim of the study was to assess the efficacy of two double HVT (HVT-ND+IBD: vHVT304 and vHVT306) or two vSB-1-NDV in combination with vHVT13 (vSB1-007+ vHVT13, vSB1-008+vHVT13) vectored vaccines administered subcutaneously (SC) to day-old SPF chicks and challenged with IBDV-Variant (VAR-E) 28 days post-vaccination.

On D0, 105 one-day-old SPF chickens were randomly allocated into 7 groups of 15 birds including a group of challenged controls (G6) and unchallenged controls (G7). The birds of groups G1 to G5 were injected by subcutaneous injection in the neck at D0 with 0.2 mL of recombinant and/or SB-1 vaccines containing each a target dose of 2000 pfu. The design of the study is shown in Table 33 below. On D28, all birds from groups G1 to G6 were challenged by the eye drop (0.03 mL containing 3 log 10 EID50 per bird) of the IBDV variant E isolate from University of Delaware (USA). Each group was monitored before and after challenge. Eleven days post-challenge, birds were weighed and necropsied. The bursa were collected and weighed. The bursal/body weight ratio (bursa weight/body weight ratio× 100) was calculated.

TABLE 33

Study design and results of IBD efficacy

| Group | Vaccine at day-old | Mean bursal/body weight ratio (*100) |
|---|---|---|
| G1 | vHVT304 | 0.33 |
| G2 | vHVT304 + SB-1 | 0.33 |
| G3 | vHVT306 | 0.29 |
| G4 | vHVT13 + vSB1-007 | 0.49 |
| G5 | vHVT13 + vSB1-008 | 0.47 |
| G6 | — (challenged) | 0.13 |
| G7 | — (unchallenged) | 0.46 |

The mean bursal/body weight ratios are shown in Table 33. The challenged control birds had a severe bursal atrophy compared to unchallenged ones. The vSB1-007 and vSB1-008 vaccines did not interfere on vHVT13-induced protection (G4 and G5). The bursal/body weight ratios of birds vaccinated with the double HVT (HVT-ND+IBD) were slightly lower than the unchallenged control group but were clearly higher than the challenged control groups. Furthermore, the SB-1 serotype 2 Marek's disease vaccine did not interfere with vHVT304-induced IBD protection.

In conclusion, these data indicate that both the combination of a SB1-ND vector with a single HVT-IBD or double HVT expressing both NDV-F and IBDV-VP2 induce IBD protection in a variant E IBDV challenge model.

Example 21 Lack of Interference of vHVT114, vSB1-009 and/or SB-1 on vHVT13 Induced Variant E IBD Protection in SPF Chickens The aim of the study was to assess the IBD efficacy of vHVT13 when administered by SC or in ovo route concomitantly with vHVT114, vSB1-009 and/or SB-1 in SPF chicks in an IBDV-Variant (VAR-E) at D28 challenge model.

75 one-day-old SPF chickens and 75 SPF 18 to 19 day-old chicken embryo were randomly allocated into 5 groups (G1 to G5 and G6 to G10, respectively) including a group of challenged controls (G4 and G9, respectively) and unchallenged controls (G5 and G10, respectively). The birds of groups G1 to G3 were injected by subcutaneous injection in the neck at D0 with 0.2 mL of vaccines containing each a target dose of 3000 pfu except for SB-1 which had a target dose of 1000 PFU. Birds from G6 to G8 received the same vaccine doses but in 0.05 mL volume by the in ovo route 2-3 days before hatch. The design of the study is shown in Table 34 below. At 28 days of age, all birds from groups G1 to G4 and G6 to G9 were challenged by the eye drop (0.03 mL containing 3 log 10 EID50 per bird) of the IBDV variant E isolate from University of Delaware (USA). Each group was monitored before and after challenge. Eleven days post-challenge, birds were weighed and necropsied. The bursa were collected and weighed. The bursal/body weight ratio (bursa weight/body weight ratio×100) was calculated.

TABLE 34

Study design and results of IBD efficacy

| Group | Vaccine at day-old | Administration route | Mean bursal/body weight ratio (*100) |
|---|---|---|---|
| G1 | vHVT13 + vHVT114 + SB-1 | SC | 0.56 |
| G2 | vHVT13 + vHVT114 + vSB1-009 | SC | 0.58 |
| G3 | vHVT13 + vSB1-009 | SC | 0.52 |
| G4 | — (challenged) | SC | 0.13 |
| G5 | — (unchallenged) | SC | 0.51 |
| G6 | vHVT13 + vHVT114 + SB-1 | In ovo | 0.54 |
| G7 | vHVT13 + vHVT114 + vSB1-009 | In ovo | 0.47 |
| G8 | vHVT13 + vSB1-009 | In ovo | 0.53 |
| G9 | — (challenged) | In ovo | 0.14 |
| G10 | — (unchallenged) | In ovo | 0.58 |

The mean bursal/body weight ratios are shown in Table 34. The challenged control birds (G4 and G9) had a severe bursal atrophy compared to unchallenged ones. The bursal/body weight ratios of the vaccinated groups (G1 to G3 and G6 to G8) were similar to those of the unchallenged control groups (G5 and G10) and well above those of the challenged control groups (G4 and G9). The lack of interference of vHVT114 on vHVT13-induced IBD protection after both SC or in ovo routes was surprising and confirmed data obtained in examples 15 and 19.

In conclusion, these data indicate clearly the compatibility of vHVT114+vSB1-009 or +SB-1 and of vSB1-009 with vHVT13 when administered by SC or in ovo route in a variant E IBDV challenge model.

Example 22 Efficacy of vHVT114 and vHVT13 and SB1 or vSB1-009 Vectors Against Very Virulent Plus Marek's Disease Challenge The aim of this study was to evaluate the Marek's disease efficacy induced by different combinations of vaccines including vHVT114, vHVT13, SB-1 and/or vSB1-009 administered by the SC route to one-day-old SPF chicks and challenged 4 days later with the very virulent plus Marek's disease virus (vv+MDV) T-King isolate.

On D0, 100 one-day-old SPF chickens were randomly allocated into 5 groups of 20 birds. The birds from groups 1 to 3 were injected by subcutaneous injection in the neck at D0 with 0.2 mL of vaccines containing a target dose of 2000 pfu for each vaccine except for SB-1 for which the target dose was 1000 pfu. Birds from groups 4 and 5 were non-vaccinated and were used as sham controls challenged (group 4) or unchallenged (group 5). The study design is shown in the Table 35. On D4, All birds from groups 1 to 4 were challenged with 0.2 mL of the vv+MDV T-King isolate using the intraperitoneal route of administration.

TABLE 35

Study design and MD protection results

| Group | Vaccine at day-old (D0) | Number of MD positive/total | Percentage of protection |
|---|---|---|---|
| G1 | vHVT13 + SB-1 | 7/20 | 65% |
| G2 | vHVT114 + SB-1 | 7/20 | 65% |
| G3 | vHVT13 + vHVT114 + vSB1-009 | 7/20 | 65% |
| G4 | — (challenged) | 20/20 | 0% |
| G5 | — (unchallenged) | 0/20 | 100% |

Each group was monitored daily for any unfavourable reactions before and after challenge. At day 49, all live birds were terminated and necropsied to examine for gross lesions associated with Marek's disease. Chickens were classified as positive for infection with Marek's disease if nervous signs, such as paralysis, locomotive signs attributable to the disease, and severe emaciation or depression are observed, if mortality directly attributable to Marek's Disease occurs, or if gross lesions are observed at necropsy. Lesions might include, but not be limited to, the following: liver, heart, spleen, gonads, kidneys, and muscle lesions Results of protection are shown in the Table 35 above. All vaccinated groups (G1 to G3) performed equally, inducing a partial (65%) MD protection as expected in this very severe and early challenge model. These results indicated that the vector vaccine candidates retain their ability to protect against Marek's disease.

Example 23 Evaluation of Marek's Disease Efficacy of the SB1-ND Vector Combined with HVT-IBD Vector The synergy between parental HVT and SB-1 in inducing a protection against Marek's disease is well known. The SB-1 vector expressing a foreign gene can therefore be mixed with either parental HVT or vectored HVT expressing another foreign gene in order to get a bivalent or a trivalent vaccine solution, respectively. An example of evaluation of Marek's disease efficacy induced by a combination of vSB1-009 with vHVT114 and vHVT13 is shown above (example 22). Marek's disease (MD) efficacy is also demonstrated for Marek's disease vectored recombinants either alone or in combination in other MD challenge models including virulent Marek's disease (vMD) challenge such as GA22, very virulent Marek's disease (vvMD) challenge such as RB1B and/or very virulent plus Marek's disease (vv+MD) challenge such as the T. King virus. One-day-old chickens are inoculated subcutaneously or 18-19-day-old embryonated eggs are inoculated with a 0.2 ml dose or 0.05 ml dose, respectively, of the test viruses. At five days of age the vaccinated chickens and naïve controls are challenged with the relevant Marek's challenge virus (v, vv, or vv+MDV). The challenged birds are observed until seven weeks of age. All birds are terminated and necropsied to observe for grossly visible lesions associated with Marek's disease as described in Example 22.

Example 24 Efficacy of vSB1-004, vSB1-006, vSB1-007, vSB1-008, SB1-Vectored ND Vaccine Alone or in Association with vHVT13 HVT-Vectored IBD Vaccine, and the vHVT302 and vHVT304 Vaccines Against Challenges with NDV Texas GB Strain at 14 and/or 28 Days of Age in SPF Chickens The aim of the study was to assess the efficacy of combinations of different Marek's disease vector vaccines expressing the NDV F and/or the IBDV VP2 gene against Newcastle disease challenge (Texas GB strain, genotype II) performed at 14 and/or 28 days of age in SPF chickens.

The characteristics of the 6 NDV recombinant vaccine candidates tested in this study are described in the Table 36 below.

TABLE 36 characteristics of the 6 NDV recombinant vaccine candidates tested in this study

| Name | Parental virus | Promoter | F gene | Poly-A | Locus |
|---|---|---|---|---|---|
| vSB1-004 | SB-1* | mCMV IE | Wt-VIId | SV40 | SORF4/US10 |
| vSB1-006 | SB-1 | SV40 | Opt-VIId | Synthetic | UL55/LORF5 |
| vSB1-007 | SB-1 | SV40 | Opt-VIId | (endogenous from gC gene) | gC |
| vSB1-008 | SB-1 | SV40 | Opt-CA02 | Synthetic | UL55/LORF5 |
| vHVT302 | vHVT13 | US10 | Opt-VIId | US10 | US10 |
| vHVT304 | vHVT13 | SV40 | Opt-VIId | Synthetic | IG2 |

On D0, 225 one-day-old SPF chickens were randomly allocated into 9 groups of 15 birds (G1a to G9a challenged at D14) and 6 groups of 15 birds (G1b, G3b, G4b, G5b, G8b, G9b challenged at D28). The birds were injected by subcutaneous injection in the neck at D0 with 0.2 mL containing a target dose of 2000 pfu for recombinant vaccines. The design of the study is shown in Table 37 below. The birds were challenged by the intramuscular route on D14 or D28 with 4.3 and 4.2 log 10 EID50 (0.1 mL) velogenic ND Texas GB (genotype II) strain, respectively.

TABLE 37

Results of ND efficacy

| Group | Vaccine at day-old (D0) | % ND protection after ND challenge at 14 days of age | % ND protection after ND challenge at 28 days of age |
|---|---|---|---|
| G1a & 1b | — | 0% | 0% |
| G2a | vSB1-004 | 20% | ND* |
| G3a & 3b | vSB1-006 | 26.6% | 73.3% |
| G4a & 4b | vSB1-007 | 33.3% | 93.3% |
| G5a & 5b | vSB1-008 | 46.6% | 86.6% |
| G6a | vSB1-006 + vHVT13 | 14% | ND |
| G7a | vSB1-008 + vHVT13 | 21.4% | ND |
| G8a & 8b | vHVT302 | 13.3% | 80% |
| G9a & 9b | vHVT304 | 33.3% | 93.3% |

*ND = not done

Each group was monitored before and after challenge. NDV clinical signs after challenge were recorded. One bird died in G6 and G7 before challenge reducing the number of birds from 15 to 14 in these groups.

Percentages of clinical protection (including protection against both mortality and morbidity) are reported in Table 37 above. Full susceptibility was observed in the non-vaccinated challenged control group G1a and G1b thus validating the high severity of challenge. Partial protections ranging from 13.3 to 46.6% were observed after challenge at D14, the highest levels of protection being induced by vSB1-008, vSB1-007 and vHVT304. Protection levels after ND challenge at D28 were much higher for all vaccinated groups and were again slightly higher in the groups vaccinates with vSB1-008, vSB1-007 or vHVT304. These results indicated that ND protection levels were dependent on the date of challenge and on the construct. The vSB1-008 and vSB1-007 constructs performed slightly better than vSB1-004 and vSB1-006, and the vHVT304 performed slightly better than vHVT302, indicating that different characteristics of the constructs are playing a role in the performances of MDV-based vector vaccines.

In conclusion, the results of this study showed that ND protection levels induced by Marek's disease vectors expressing NDV F gene may depend on different parameters including the vector, the locus of insertion, the F gene, the promoter, the poly-adenylation site and the challenge conditions.

Example 25 Efficacy of Double HVT-ND+IBD vHVT304 and vHVT306 Vaccines Against Challenges with NDV Texas GB Strain at 14 and/or 28 Days of Age in SPF Chickens The aim of the study was to assess the efficacy of HVT-vectored vaccine expressing both NDV F and IBDV VP2 genes against Newcastle disease challenge (Texas GB strain, genotype II) performed at 14 and/or 28 days of age in SPF chickens.

The characteristics of the 2 recombinant vaccine candidates tested in this study are described in the Table 38 below.

TABLE 38

Characteristics of the recombinant vaccine candidates used in this study

| Name | Parental virus | Promoter | F gene | Poly-A | Locus |
|---|---|---|---|---|---|
| vHVT304 | vHVT13 | SV40 | Opt-VIId | Synthetic | IG2 |
| vHVT306 | vHVT13 | SV40 | Opt-VIId | Synthetic | SORF3-US2 |

On D0, 90 one-day-old SPF chickens were randomly allocated into 3 groups of 15 birds (G1a to G3a challenged at D14) and 3 groups of 15 birds (G1b to G3b challenged at D28). The birds were injected by subcutaneous injection in the neck at D0 with 0.2 mL containing a target dose of 2000 pfu for recombinant vaccines. The design of the study is shown in Table 39 below. The birds were challenged by the intramuscular route on D14 or D28 with a target dose of 4.0 log 10 EID50 (0.1 mL) velogenic ND Texas GB (genotype II) strain.

TABLE 39

Results of ND efficacy

| Group | Vaccine at day-old (D0) | % ND protection after ND challenge at 14 days of age | % ND protection after ND challenge at 28 days of age |
|---|---|---|---|
| G1a & 1b | — | 0% | 0% |
| G2a & 2b | vHVT304 | 26.7% | 92.9% |
| G3a & 3b | vHVT306 | 33.3% | 86.7% |

Each group was monitored before and after challenge. NDV clinical signs after challenge were recorded. One bird died in G2b before challenge reducing the number of birds from 15 to 14 in this group.

Percentages of clinical protection (including protection against both mortality and morbidity) are reported in Table 39 above. Full susceptibility was observed in the non-vaccinated challenged control group G1a and G1b thus validating the high severity of challenge. Protections levels after challenge at D14 were much lower than those obtained after challenge at D28. These vaccine candidates had the same NDV F expression cassette inserted into 2 different loci of vHVT13 genome. They performed equally in terms of ND protection in the tested conditions, indicating that both insertion loci (IG2 and SORF3-US2) are equally suitable for NDV F cassette insertion.

In conclusion, the results of this study showed that ND protection levels induced by Marek's disease vectors expressing NDV F gene depend on different parameters including the vector, the locus of insertion, the F gene, the promoter, the poly-adenylation site and the challenge conditions.

Example 26 ND Early Efficacy Induced by Double HVT-ND+IBD (vHVT302, vHVT303, and vHVT304) or SB1-Vectors (vSB1-006 and vSB1-007) in One Day-Old SPF Chickens Against a Velogenic Genotype V NDV Challenge The objective of the study was to evaluate the efficacy of three double HVT-ND+IBD (vHVT302, vHVT303, and vHVT304) and two SB1-ND vectors (vSB1-006 and vSB1-007) in one day-old SPF chickens against a velogenic genotype V (Chimalhuacan) NDV challenge performed at D14.

The characteristics of the 5 recombinant vaccine candidates tested in this study are described in the Table 40 below.

TABLE 40

Characteristics of the recombinant vaccine candidates used in this study

| Name | Parental virus | Promoter | F gene | Poly-A | Locus |
|---|---|---|---|---|---|
| vHVT302 | vHVT13 | US10 | Opt-VIId | US10 | US10 |
| vHVT303 | vHVT13 | US10 | Opt-V (CA02) | US10 | US10 |
| vHVT304 | vHVT13 | SV40 | Opt-VIId | Synthetic | IG2 |
| vSB1-006 | SB-1 | SV40 | Opt-VIId | Synthetic | UL55/LORF5 |
| vSB1-007 | SB-1 | SV40 | Opt-VIId | (endogenous from gC gene) | gC |

Six groups (1 and 2) of ten one-day-old specific pathogen free (SPF) white Leghorn chicks were randomly constituted. Birds from groups 2 to 6 were vaccinated by the subcutaneous route (nape of the neck) with a target dose of 2000 PFU as shown in the Table 41 below. Chicks from group 1 were not vaccinated and were kept as control birds. At 2 week-of-age, all birds were challenged with the genotype V Mexican Chimalhuacan (Mex V) velogenic NDV strain. The challenge was performed by the intramuscular (IM) route using $10^5$ Egg Infectious Dose 50 (EID50) diluted in 0.2 ml of physiological sterile water. All birds were monitored until 14 days post-challenge. After challenge, health status of each bird was scored daily as follows: healthy/with specific symptoms (ruffled feathers, prostration, torticollis, tremor)/dead. Any bird that showed specific symptoms for more than 2 days or was noted sick on D28 was taken into account for calculation of morbidity.

TABLE 41

Results of early ND protection induced by different MDV vectored candidates expressing NDV F gene in SPF day-old chicks

| Group | Vaccine | Target dose (PFU) under 0.2 mL (actual dose) | Protection against mortality | Protection against morbidity |
|---|---|---|---|---|
| G1 | — | — | 0% | 0% |
| G2 | vHVT302 | 2000 (4427) | 50% | 10% |
| G3 | vHVT303 | 2000 (ND) | 10% | 0% |
| G4 | vHVT304 | 2000 (1169) | 80% | 60% |

TABLE 41-continued

Results of early ND protection induced by different MDV vectored candidates expressing NDV F gene in SPF day-old chicks

| Group | Vaccine | Target dose (PFU) under 0.2 mL (actual dose) | Protection against mortality | Protection against morbidity |
|---|---|---|---|---|
| G5 | vSB1-006 | 2000 (1720) | 60% | 40% |
| G6 | vSB1-007 | 2000 (1564) | 80% | 50% |

Results of protection are summarized in Table 41. All control birds died after ND challenge. Variable levels of ND protection were induced by the different tested vaccines ranging from 10% to 80% and from 0% and 60% in terms of protection against mortality and morbidity, respectively. The vHVT304 candidate induced a better protection than the vHVT303 and vHVT302 candidates; this may be due to the exogenous SV40 promoter placed in front of the NDV F gene. The vSB1-007 performed slightly better than the vSB1-006. Furthermore, performances obtained with vHVT304 were comparable to those obtained with vSB1-007 indicating that different Marek's disease vectors can reach the same level of ND protection.

In conclusion, this study demonstrates that both double HVT-ND+IBD and SB1-ND vectored vaccines can reach significant levels of ND protection in a very severe and early NDV challenge model.

Example 27 ND Efficacy Induced by the Double HVT-ND+IBD vHVT306 Administered by in Ovo or SC Route to One Day-Old SPF Chickens Against a Velogenic Genotype V NDV Challenge Performed at D28

The objective of the study was to evaluate the efficacy of one double HVT-ND+IBD (vHVT306) administered by the in ovo or SC route to SPF chickens against a velogenic genotype V (Chimalhuacan) NDV challenge performed at 28 days of age.

The characteristics of the vHVT306 recombinant vaccine candidate tested in this study are described in Table 42 below. The single HVT-IBD vector vaccine vHVT13 was used as a control.

TABLE 42

Characteristics of the recombinant vaccine candidate used in this study

| Name | Parental virus | Promoter | F gene | Poly-A | Locus |
| --- | --- | --- | --- | --- | --- |
| vHVT306 | vHVT13 | SV40 | Opt-VIId | Synthetic | SORF3-US2 |

On day −3, 40 SPF embryonated eggs aged around 18 days and 18 hours of incubation were randomly allocated into 2 groups of 20 eggs each. On D0, one group of 12 day-old SPF chicks was added. The definition of groups is given in Table 43 below. The vaccination was performed on D-3 (in ovo route) or on D0 (SC route, in the back of the neck) and the target dose of vHVT306 and vHVT13 was 2000PFU/bird. For the in ovo route, hatchability, viability (until D28) and growth of the birds (between hatching and D28) were monitored.

On D28, 10 birds per group were challenged with virulent ND Chimalhuacan strain. The challenge was performed by the intramuscular (IM) route using $10^5$ Egg Infectious Dose 50 (EID50) diluted in 0.2 ml of physiological sterile water. Birds were monitored until 14 days post-challenge. Specific clinical signs and mortality were recorded. Any bird that showed specific symptoms for more than 2 days or was noted sick on D42 was taken into account for calculation of morbidity. Five and seven days post-challenge (i.e. on D33 and D35), oropharyngeal swab was taken from each surviving bird. All the swabs were analyzed by specific NDV qRT-PCR.

TABLE 43

Results of ND protection induced by vHVT306 MDV vectored candidate expressing both NDV F and IBDV VP2 genes administered by the SC or in ovo route into SPF chicks

| Group | Vaccine/route | Hatch-ability/ viability (%) | Protection against mortality/ morbidity | % birds shed-ding at 5 dpi/ 7 dpi (mean log10 titer*) |
| --- | --- | --- | --- | --- |
| G1 | vHVT13/in ovo | 100%/100% | 0%/0% | (not tested) |
| G2 | vVHT306/in ovo | 100%/100% | 100%/100% | 0% (2.7)/ 0% (2.7) |
| G3 | vHVT306/SC | — | 100%/100% | 20% (3.2)/ 10% (2.9) |

*The threshold titer of the real time RT PCR was set at 2.7 log10 equivalent EID50

Full hatchability was recorded after in ovo vaccination in groups 1 and 2 and all hatched birds survived up to D28. No difference in body weights was detected between the two groups at both D0 and D28 confirming the perfect safety of vHVT306 when administered in ovo. Results of protection are summarized in Table 43. All vHVT13-vaccinated control birds died by 4 days after ND challenge. Full clinical ND protection was induced by vHVT306 administered by both routes. Furthermore, no shedding was detected after in ovo administration whereas only a few birds shed detectable amount of challenge virus after SC administration.

In conclusion, this study demonstrates that the double HVT-ND+IBD vHVT306 induce excellent level of ND protection by SC or in ovo administration routes in a very severe heterologous NDV challenge model.

Example 28 Efficacy of Double HVT-ND+IBD (vHVT302, vHVT303 and vHVT304) Recombinant Vaccines, Against Challenge with a Classical IBDV Isolate on D15 in SPF Chickens The aim of the study was to assess the early IBD efficacy of double HVT recombinants vHVT302, vHVT303 and vHVT304 recombinant constructs against a virulent infectious bursal disease virus (vIBDV) challenge (Faragher 52/70 strain) performed at 15 days of age in SPF chickens.

The characteristics of the 3 double HVT-ND+IBD recombinant vaccine candidates tested in this study are described in the Table 44 below.

TABLE 44

Characteristics of the expression cassettes of double HVT recombinants

| Name | Parental virus | Promoter | F gene | Poly-A | Locus |
| --- | --- | --- | --- | --- | --- |
| vHVT302 | vHVT13 | US10 | Opt-VIId | US10 | US10 |
| vHVT303 | vHVT13 | US10 | Opt-V (CA02) | US10 | US10 |
| vHVT304 | vHVT13 | SV40 | Opt-VIId | Synthetic | IG2 |

On D0, 40 one-day-old SPF chickens were randomly allocated into 4 groups of 10 birds including one control groups (G1) that was vaccinated with vSB1-004, a SB-1 vector expressing NDV F gene. Five other SPF birds were kept unvaccinated and unchallenged for bursal/body weights evaluation. The birds were injected by subcutaneous injection in the neck at D0 with 0.2 mL of recombinant vaccines containing a target dose of 2000 pfu as described in the Table 45 below. On D15, blood sample was collected from all birds per group (10 birds per group except for groups 1 and 3 in which 1 bird died before blood sampling) for serological testing with the Kit ProFLOK® plus IBD (Synbiotics Corp). On D15, birds from all 4 groups were challenged by the eye drop (0.05 mL per bird) with 2.5 log 10 EID50.

TABLE 45

Study design and results of IBD efficacy

| Group | Vaccine at day-old | ELISA IBD+ titer (log10) | Number Dead/Sick (total)[1] | % protection[2] | Mean bursal/ body weight ratio[4] |
|---|---|---|---|---|---|
| G1 | vSB1-004 | 0.25 | 1/9 (9) | 0% | 0.0014 |
| G2 | vHVT302 | 2.6 | 0/1 (10) | 80% | 0.0043 |
| G3 | vHVT303 | 3.0 | 0/0 (9) | 100% | 0.0053 |
| G4 | vHVT304 | 2.4 | 0/0 (10) | 80% | 0.0034 |

[1]Birds sick for more than 2 days or still sick on D25 were considered as sick. The number in brackets is the total number of birds in the group that were challenged.
[2]Protection against clinical signs and severe bursal lesion (bursal score <3)
[4]The bursal/body weight ratio of the unvaccinated/unchallenged group was 0.0043.

Each group was monitored before and after challenge. IBDV clinical signs were recorded for 11 days after challenge (from D15 to D25). At the end of the post-challenge observation period (D25), all the surviving birds were euthanized and necropsied. Body and bursal weights were recorded. Each bursa of Fabricius (BF) was weighted then stored in individual recipients containing 4% formaldehyde for histology. Histological lesions of the bursa were scored according to the scale presented in Table 46.

TABLE 46

Scoring scale of histological lesions of the bursa of Fabricius*

| Score | Histology observation/lesions |
|---|---|
| 0 | No lesion, normal bursa |
| 1 | 1% to 25% of the follicles show lymphoid depletion (i.e. less than 50% of depletion in 1 affected follicle), influx of heterophils in lesions |
| 2 | 26% to 50% of the follicles show nearly complete lymphoid depletion (i.e. more than 75% of depletion in 1 affected follicle), affected follicles show necrosis and severe influx of heterophils may be detected |
| 3 | 51% to 75% of the follicles show lymphoid depletion; affected follicles show necrosis lesions and a severe influx of heterophils is detected |
| 4 | 76% to 100% of the follicles show nearly complete lymphoid depletion; hyperplasia and cyst structures are detected; affected follicles show necrosis and severe influx of heterophils is detected |
| 5 | 100% of the follicles show nearly complete lymphoid depletion; complete loss of follicular structure, thickened and folded epithelium, fibrosis of bursal tissue |

*sourced from Monograph No. 01/2008: 0587 of EU Pharmacopoeia "Avian Infectious Bursal Disease vaccine (live)

A bird was considered as affected if it died and/or showed notable sign of disease and/or severe lesions of the bursa of Fabricius (i.e., histology score 3).

The mean ELISA IBD+ antibody titer expressed in log 10 before challenge is shown in Table 45. Significant titers were detected in all vaccinated groups that were significantly higher than that of the control group G1. The serology titer was slightly higher in G3 (vHVT303).

Severe clinical signs were observed after challenge in all 9 birds of the control group G1, which lead to the death of 1 bird. Only one vaccinated bird in G2 (vHVT302) showed clinical signs after challenge. Percentages of protection against severe bursal lesions are shown in Table 45 above. Significant IBD protection was observed in all vaccinated groups, a full protection being observed in G3 (vHVT303). The mean bursal/body weight ratios are also shown in Table 45. Ratios in all vaccinated groups were higher than those of the challenged control group G1 and not significantly different from the unvaccinated and unchallenged control group.

In conclusion, these data indicate that the three double HVT-IBD+ND tested in this study induced IBD antibodies and early IBD protection in a severe IBDV challenge model.

Example 29 Efficacy of Five Different HVT-ND Vaccine Candidates Against Challenges with Velogenic NDV ZJ1 (Genotype VIId) Isolate at 14 Days of Age in SPF Chickens The aim of the study was to assess the efficacy of 5 single HVT recombinant constructs (vHVT39, vHVT110, vHVT111, vHVT112 and vHVT113) expressing the NDV F gene against Newcastle disease challenge with velogenic NDV ZJ1 (genotype VIId) isolate performed at 14 days of age in SPF chickens.

The characteristics of these 5 vaccine candidates are described in Table 47 below.

TABLE 47

Characteristics of the HVT-ND recombinant viruses used in the challenge study

| Name | Parental virus | Promoter | F gene* | Poly-A | Locus |
|---|---|---|---|---|---|
| vHVT039 | HVT | MDV gB | Wtnm-Texas | SV40 | IG1 |
| vHVT110 | HVT | MCMV IE | Wt-VIId | SV40 | IG1 |
| vHVT111 | HVT | SV40 | Wt-VIId | SV40 | IG1 |
| vHVT112 | HVT | MCMV IE | Wt-YZCQ | SV40 | IG1 |
| vHVT113 | HVT | MCMV IE | Wt-Texas | SV40 | IG1 |

*Wt means that the wild type velogenic F gene sequence was used but the cleavage site was modified to that of a lentogenic virus. Wtnm means that the cleavage site of the wild type sequence was not modified. The Texas velogenic strain belongs to genotype IV and YZCQ to the genotype VIId.

On D0, 72 one-day-old SPF chickens were randomly allocated into 5 groups of 12 birds (vaccinated) and 1 group of 12 birds (non-vaccinated controls). The birds were injected by subcutaneous injection in the neck at D0 with 0.2 mL of recombinant vaccines containing a target dose of 6000 pfu as described in Table 48 below. The birds were challenged by the intramuscular route on D14 with 5 log 10 EID50 of NDV ZJ1/2000 (genotype VIId) velogenic strain.

TABLE 48

Results of ND efficacy

| | | % clinical protection | |
|---|---|---|---|
| Group | Vaccine at day-old (D0) | Protection against mortality/morbidity | Mean shedding titer (log10) at 2/4 dpi |
| G1 | — | 0%/0% | 3.5/— (all dead) |
| G2 | vHVT039 | 25%/8% | 2.5/4.8 |
| G3 | vHVT110 | 100%/83% | 1.8/2.0 |

TABLE 48-continued

Results of ND efficacy

| Group | Vaccine at day-old (D0) | % clinical protection | |
|---|---|---|---|
| | | Protection against mortality/morbidity | Mean shedding titer (log10) at 2/4 dpi |
| G4 | vHVT111 | 100%/67% | 1.8/2.8 |
| G5 | vHVT112 | 75%/42% | 1.7/3.4 |
| G6 | vHVT113 | 83%/25% | 1.4/3.3 |

Each group was monitored before and after challenge. NDV clinical signs and mortality were recorded after challenge. Oropharyngeal swabs were taken at 2 and 4 days post-infection (dpi) for evaluation of viral load by real time RT-PCR using the method described by Wise et al. (2004; Development of a Real-Time Reverse-Transcription PCR for Detection of Newcastle Disease Virus RNA in Clinical Samples. J Clin Microbiol 42, 329-338).

Percentages of protection against mortality and morbidity are reported in Table 48 above. Full susceptibility was observed in the non-vaccinated challenged control group G1 thus validating the high severity of the challenge. Vaccines induced variable levels of protection against mortality (25-100%) or against morbidity (8%-83%). The best protection level was induced by vHVT110 whereas the lowest one was induced by vHVT039, the other candidates giving intermediate results. Results of oropharyngeal shedding at 2 and 4 dpi are also shown in Table 48 above and are in line with those of clinical protection. These vaccine candidates differ in their promoter and F gene sequence. These results show that both of these parameters are important for the design of optimal HVT-ND vaccine candidate.

In conclusion, the results of this study showed the importance of promoter and F gene sequence in the ND efficacy induced by HVT-vectored ND vaccine candidates.

Example 30 Evaluation of the Newcastle Disease Efficacy Induced by Double SB1 Constructs Expressing IBDV VP2 and NDV F The aim of the study is to assess the efficacy of double SB1 constructs expressing IBDV VP2 and NDV F against Newcastle disease challenge.

On D0, one-day-old SPF chickens are randomly allocated into several groups of 10-20 birds, including vaccinated and non-vaccinated groups. The birds of the vaccinated groups are injected by subcutaneous injection in the neck at D0 with 0.2 mL containing a target dose of 1000 to 5000 pfu of recombinant vaccines. Alternatively, the same dose in 0.05 mL may be administered in ovo 2 or 3 days before hatch. The birds (at least one vaccinated and one non vaccinated group) are challenged by the intramuscular route at different time after vaccination: for instance, D14, D28 or D42 with about 4.0 log 10 EID50 (0.1 mL) of a velogenic NDV strain such as Texas GB (genotype II), ZJ1 (genotype VIId), Chimalhuacan (genotype V) strain.

Each group is monitored clinically before and after challenge. NDV clinical signs (morbidity) and mortality are recorded after challenge. Percentages of clinical protection in all groups are calculated. At least 90% of non-vaccinated challenged SPF birds should die or be severely sick after challenge to validate the severity of challenge. Oropharyngeal and cloacal swabs can be samples at different times after challenge such as 3, 5, 7 and 9 days post-challenge and the viral load can be estimated by real-time RT-PCR. The best candidates will be those who induced the highest level of clinical protection and the lowest level of viral load in the swabs. A similar study can be performed in broilers containing NDV maternal antibodies; however, these maternal antibodies may potentially protect the non-vaccinated birds if the challenge is performed early. The double SB1 construct may also be tested in combination with other Marek's disease vaccine or vector vaccines.

Example 31 Evaluation of the Infectious Bursal Disease Efficacy Induced by Double SB1 Constructs Expressing IBDV VP2 and NDV F The aim of the study is to assess the IBD efficacy of double SB1 expressing both the IBDV VP2 and the NDV F.

One-day-old SPF chickens are randomly allocated into several groups of 10 to 20 birds including vaccinated and non-vaccinated controls. Non-vaccinated controls will be separated into 2 subgroups including challenged and unchallenged birds. The birds of vaccinated groups are injected by subcutaneous injection in the neck at D0 with 0.2 mL of vaccines containing each a target dose of 1000 to 5000 pfu. Alternatively, the same dose in 0.05 mL may be administered in ovo 2 or 3 days before hatch. At different times after vaccination such as 14, 21, 28 or 42 days post-vaccination, all birds from vaccinated groups and the challenged controls are challenged by the eye drop (0.03 mL containing 2 to 4 log 10 EID50 per bird) of a virulent IBDV (such as the Faragher or the US standard strain), a very virulent IBDV such as the 91-168 isolate or a variant IBDV isolate such as the US Delaware variant E isolate. Each group is clinically monitored before and after challenge. Birds can be necropsied 4 or 5 days post-challenge for bursal gross lesions evaluation. They can also be necropsied 10 to 11 days post-challenge. Gross and/or histological lesions can be evaluated. Furthermore, birds and bursa are weighed the bursal/body weight ratios (bursa weight/body weight ratio× 100) are calculated compared to those of the non-vaccinated unchallenged group. Control SPF challenged birds must show clinical signs and/or have significant gross and/or histological lesions, and/or should have a bursal/body weight ratio significantly lower than the unvaccinated unchallenged control birds to validate the severity of challenge. The efficacy of the vaccine is evaluated by comparing these parameters with unvaccinated/challenged and unvaccinated/unchallenged groups. Such study may be performed in broiler chickens containing IBDV maternal antibodies; however, these maternal antibodies may potentially protect the non-vaccinated birds if the challenge is performed early. The double SB1 construct may also be tested in combination with other Marek's disease vaccine or vector vaccines.

Example 32 Evaluation of the Marek's Disease Efficacy Induced by Double SB1 Constructs Expressing IBDV VP2 and NDV F The aim of the study is to evaluate Marek's disease efficacy induced by the SB1 vectors expressing both IBDV VP2 and NDVF.

One-day-old SPF chickens are randomly allocated into several groups of 20 to 50 birds including vaccinated and non-vaccinated controls. Non-vaccinated controls may be separated into 2 subgroups including challenged and unchallenged birds. The birds of vaccinated groups are injected by subcutaneous injection in the neck at D0 with 0.2 mL of vaccines containing each a target dose of 1000 to 5000 pfu. Alternatively, the same dose in 0.05 mL may be administered in ovo 2 or 3 days before hatch. At different times after vaccination such as 3 to 10 days post-vaccination, all birds from vaccinated groups and the challenged controls are challenged by the intraperitoneal route with 0.2 mL of a Marek's disease virus (MDV) strain. MDV strain may be of several pathotypes such as virulent MDV (vMDV) including the JM or GA22 isolate, very virulent MDV (vvMDV) such as the RB-1B or Md5 isolate, very virulent plus (vv+MDV) such as the T-King or 648A isolate. MDV challenge strain inoculum are prepared by infecting chickens, harvesting and freezing their blood cells into liquid nitrogen in presence of a cryopreservative such as DMSO. The chicken infectious dose 50 (CID50) is established for each challenge batch before performing vaccination/challenge studies. Each group is clinically monitored before and after challenge. Birds are necropsied after at least 7 weeks post-vaccination and the presence Marek's disease gross lesions is checked in each bird. Lesions might include, but not be limited to, the following: liver, heart, spleen, gonads, kidneys, nerve and muscle lesions. Such study may be performed in broiler chickens containing MDV maternal antibodies. The double SB1 construct may also be tested in combination with other Marek's disease vaccine (for instance HVT and or CVI988 Rispens strains) or MD vector vaccines. MD challenge may also be performed by contact between vaccinated birds and MDV infected non-vaccinated SPF chicks.

Example 33 DNA and Protein Sequences

```
NDV-F codon optimized gene from modified wt VIId
                                                                (SEQ ID NO: 1)
atgggcagcaagcccagcacaagaatcccagcccccctgatgctgatcacccgcatcatgctgatcctgggctgcatcagacc
cacaagctccctggatggacgcccctggccgctgccggcatcgtggtgaccggcgacaaggccgtgaacgtgtacaccag
cagccagaccggcagcatcatcgtgaagctgctgcccaacatgcccagagacaaagaggcctgcgccaaggccccctgga
agcctacaacagaaccctgaccaccctgctgaccccctgggcgacagcatcagaaagatccagggctccgtgagcacaagc
ggcggaggaaagcagggcagactgatcggcgccgtgatcggcgtggccctgggagtggctacagctgcccagattacc
gctgcagccgcctgatccaggccaaccagaacgccgccaacatcctgagactgaaagagagcattgccgccaccaacgag
gccgtgcacgaagtgaccgacggcctgagccagctgtccgtggccgtgggcaagatgcagcagttcgtgaacgaccagttca
acaacaccgccagagagctggactgcatcaagatcacccagcaggtgggcgtggagctgaacctgtacctgaccgagctgac
cacagtgttcggccccagatcacaagcccagccctgacacagctgaccatccaggccctgtacaacctggctggcggcaac
atggactatctgctgacaaagctgggaatcggcaacaaccagctgtccagcctgatcggaagcggcctgatcaccggctaccc
catcctgtacgacagccagacacagctgctgggcatccaggtgaacctgcccagcgtgggcaacctgaacaacatgcgcgcc
acctacctggaaaccctgagcgtgtccaccaccaagggctacgccagcgccctggtgcccaaggtggtgacacaggtgggca
gcgtgatcgaggaactggacaccagctactgcatcgagagcgacctggacctgtactgcaccagaatcgtgaccttcccaatg
agccccggcatctacagctgcctgagcggcaacaccagcgcctgcatgtacagcaagaccgaaggcgcactgacaacaccc
tacatggccctgaaggaagcgtgatcgccaactgcaagatcaccacctgcagatgcaccgaccccccaggcatcatcagcc
agaactacggcgaggccgtgagcctgatcgatcgccattcctgtaacgtgctgtccctggacggcatcacactgagactgagc
ggcgagttcgatgccacctaccagaagaacatcagcatcctggacagccaggtgatcgtgaccggcaacctggacatcagca
ccgagctgggcaacgtgaataacagcatcagcaacgccctggcagactggccgagcaacagcaagctggaaaagtga
acgtgcgcctgacatccacttccgctctgatcacctacatcgtgctgaccgtgatcagcctggtgttcggcgcctgagcctggtg
ctggcctgctacctgatgtacaagcagaaggcccagcagaaaaccctgctgtggctgggcaacaacaccctggaccagatga
gagccaccaccagagcctgatga NDV-F protein encoded by codon-optimized NDV-F gene of wt VIId
                                                                (SEQ ID NO: 2)
mgskpstripaplmlitrimlilgcirptssldgrplaaagivvtgdkavnvytssqtgsiivkllpnmprdkeacakapleay
nrtlttlltplgdsirkiqgsvstsgggkqgrligavigsvalgvataaqitaaaaliqanqnaanilrlkesiaatneavhevtdgl
sqlsvavgkmqqfvndqfnntareldcikitqqvgvelnlyltelttvfgpqitspaltqltiqalynlaggnmdylltklgign
nqlssligsglitgypilydsqtqllgiqvnlpsvgnlnnmratyletlsysttkgyasalvpkvvtqvgsvieeldtsyciesdld
lyctrivtfpmspgiyscsgntsacmysktegalttpymalkgsvianckittcrctdppgiisqnygeavslidrhscnvlsl
dgitlrlsgefdatyqknisildsqvivtgnldistelgnvnnsisnaldrlaesnsklekvnvrltstsalityivltvislvfgalslv
lacylmykqkaqqktllwlgnntldqmrattra NDV-F DNA wt VIId
                                                                (SEQ ID NO: 3)
Atgggctccaaaccttctaccaggatcccagcacctctgatgctgatcacccggattatgctgatattgggctgtatccgtccgac
aagctctcttgacggcaggcctatgcagctgcaggaattgtagtaacaggagataaggcagtcaatgtatacacttcgtctcaga
cagggtcaatcatagtcaagttgctcccgaatatgcccagggataaggaggcgtgtgcaaaagcccccattagaggcatataaca
gaacactgactactttgctcactcctcttggcgactccatccgcaagatccaagggtctgtgtccacatctggaggaggcaagca
aggccgcctgataggtgctgttattggcagtgtagctcttggggagcaacagcggcacagataacagcagctgcggccctaat
acaagccaaccagaatgccgccaacatcctccggcttaaggagagcattgctgcaaccaatgaagctgtgcatgaagtcaccg
acggattatcacaactatcagtggcagttgggaagatgcagcagtttgtcaatgaccagtttaataatacggcgcgagaattggac
tgtataaaaatcacacaacaggttggtgtagaactcaacctatacctaactgaattgactacagtattcgggccacagatcacctcc
cctgcattaactcagctgaccatccaggcactttataatttagctggtggcaatatggattacttattaactaagttaggtataggaa
caatcaactcagctcgttaattggtagccgcctgatcactggttaccctatactgtatgactcacagactcaactatgggcatacaa
gtgaatttaccctcagtcgggaacttaaataatatgcgtgccacctatttggagaccttatctgtaagtacaaccaaaggatatgcct
cagcacttgtcccgaaagtagtgacacaagtcggttccgtgatagaag
agcttgacacctcatactgtatagagtccgatctgatttatattgtactagaatagtgacattcccatgtcccaggtattattcct
gtttgagcggcaacacatcagcttgcatgtattcaaagactgaaggcgcactcactacgccgtatatggcccttaaaggctcagtt
attgccaattgtaaaataacaacatgtagatgtacagaccctcctggtatcatatcgcaaaattatggagaagctgtatccctgatag
atagacattcgtgcaatgtcttatcattagacgggataactctaaggctcagtggggaatttgatgcaacttatcaaaagaacatctc
aatactagattctcaagtcatcgtgacaggcaatcttgatatatccaactgaaactggaaacgtcaacaattcaatcagcaatgccttg
gataggttggcagaaagcaacagcaagctagaaaaagtcaatgtcagactaaccagcacatctgctctcattacctatattgttct
aactgtcatttctctagifttcggtgcacttagtctggtgttagcgtgttacctgatgtacaaacagaaggcacaacaaaagaccttg
ctatggcttgggaataatccctcgatcagatgagagccactacaagagcatga NDV-F gene GenBank Accession No. AY337464.1
                                                                (SEQ ID NO: 4)
CTGGATCCCGGTTGGCTCATTCAGGACGCAATATGGGCTCCAAACCTTCTACCAGGATCCCAGCACCTCT
GATGCTGATCACCCGGATTATGCTGATATTGGGCTGTATCCGTCCGACAAGCTCTCTTGACGGCAGGCCT
CTTGCAGCTGCAGGAATTGTAGTAACAGGAGATAAGGCAGTCAATGTATACACTTCGTCTCAGACAGGGT
```

-continued

CAATCATAGTCAAGTTGCTCCCGAATATGCCCAGGGATAAGGAGGCGTGTGCAAAAGCCCCATTAGAGGC
ATATAACAGAACACTGACTACTTTGCTCACTCCTCTTGGCGACTCCATCCGCAAGATCCAAGGGTCTGTG
TCCACATCTGGAGGAAGGAGACAAAAACGCTTTATAGGTGCTGTTATTGGCAGTGTAGCTCTTGGGGTTG
CAACAGCGGCACAGATAACAGCAGCTGCGGCCCTAATACAAGCCAACCAGAATGCCGCCAACATCCTCCG
GCTTAAGGAGAGCATTGCTGCAACCAATGAAGCTGTGCATGAAGTCACCGACGGATTATCACAACTATCA
GTGGCAGTTGGGAAGATGCAGCAGTTTGTCAATGACCAGTTTAATAATACGGCGCGAGAATTGGACTGTA
TAAAAATCACACAACAGGTTGGTGTAGAACTCAACCTATACCTAACTGAATTGACTACAGTATTCGGGCC
ACAGATCACCTCCCCTGCATTAACTCAGCTGACCATCCAGGCACTTTATAATTTAGCTGGTGGCAATATG
GATTACTTATTAACTAAGTTAGGTATAGGGAACAATCAACTCGTCGTTAATTGGTAGCGGCCTGATCA
CTGGTTACCCTATACTGTATGACTCACAGACTCAACTCTTGGGCATACAAGTGAATTTACCCTCAGTCGG
GAACTTAAATAATATGCGTGCCACCTATTTGGAGACCTTATCTGTAAGTACAACCAAAGGATATGCCTCA
GCACTTGTCCCGAAAGTAGTGACACAAGTCGGTTCCGTGATAGAAGAGCTTGACACCTCATACTGTATAG
AGTCCGATCTGGATTTATATTGTACTAGAATAGTGACATTCCCCATGTCCCCAGGTATTTATTCCTGTTT
GAGCGGCAACACATCAGCTTGCATGTATTCAAAGACTGAAGGCGCACTCACTACGCCGTATATGGCCCTT
AAAGGCTCAGTTATTGCCAATTGTAGGATAACAACATGTAGATGTACAGACCCTCCTGGTATCATATCGC
AAAATTATGGAGAAGCTGTATCCCTGATAGATAGACATTCGTGCAATGTCTTATCATTAGACGGGATAAC
TCTAAGGCTCAGTGGGAATTTGATGCAACTTATCAAAGAACATCTCAATACTAGATTCTCAAGTCATC
GTGACAGGCAATCTTGATATATCAACTGAACTTGGAAACGTCAACAATTCAATCAGCAATGCCTTGATA
GGTTGGCAGAAAGCAACAGCAAGCTAGAAAAAGTCAATGTCAGACTAACCAGCACATCTGCTCTCATTAC
CTATATTGTTCTAACTGTCATTTCTCTAGTTTTCGGTGCACTTAGTCTGGGTTTAGCGTGTTACCTGATG
TACAAACAGAAGGCACAACAAAAGACCTTGCTATGGCTTGGGAATAATACCCTCGATCAGATGAGAGCCA
CTACAAGAGCATGAA

NDV-F protein GenBank Accession No. AAP97877.1

(SEQ ID NO: 5)

MGSKPSTRIPAPLMLITRIMLILGCIRPTSSLDGRPLAAAGIVVTGDKAVNVYTSSQTGSIIVKLLPNMP
RDKEACAKAPLEAYNRTLTTLLTPLGDSIRKIQGSVSTSGGRRQKRFIGAVIGSVALGVATAAQITAAAA
LIQANQNAANILRLKESIAATNEAVHEVTDGLSQLSVAVGKMQQFVNDQFNNTARELDCIKITQQVGVEL
NLYLTELTTVFGPQITSPALTQLTIQALYNLAGGNMDYLLTKLGIGNNQLSSLIGSGLITGYPILYDSQT
QLLGIQVNLPSVGNLNNMRATYLETLSVSTTKGYASALVPKVVTQVGSVIEELDTSYCIESDLDLYCTRI
VTFPMSPGIYSCLSGNTSACMYSKTEGALTTPYMALKGSVIANCRITTCRCTDPPGIISQNYGEAVSLID
RHSCNVLSLDGITLRLSGEFDATYQKNISILDSQVIVTGNLDISTELGNVNNSISNALDRLAESNSKLEK
VNVRLTSTSALITYIVLTVISLVFGALSLGLACYLMYKQKAQQKTLLWLGNNTLDQMRATTRA

NDV-F gene of CA02 strain GenBank Accession No. EF520718.1

(SEQ ID NO: 6)

ATGGGCTCCAAACCTTCTACCTGGATCTCAGTAACTCTGATGCTGATCACTCGGACCATGCTTATACTTA
GCTGTATCTGTCCGACAAGCTCTCTTGACGGTAGACCTCTCGCAGCCGCAGGGATTGTGGTGACGGGAGA
TAAAGCAGTCAATATATACACTTCATCTCAAACAGGGTCAATCATCATCAAGTTACTCCCAAATATGCCC
AAGGATAAAGAAGCGTGCGCAAAAGCCCCATTGGAAGCATACAATAGAACACTGACCACTTTACTCACCC
CTCTTGGTGACTCTATCCGCAGAATACAAGGGTCTGCGACTACATCTGGAGGAAGGAGACAGAAACGCTT
TGTAGGTGCCATTATCGGCAGTGTAGCTCTTGGGGTTGCAACAGCTGCACAGATAACAGCAGCCGCAGCT
CTGATACAAGCCAACCAAAATGCTGCCAACATCCTCCGGCTTAAGGAGAGCATTGCTGCAACCAATGACG
CTGTACACGAGGTCACTAACGGATTATCACAACTAGCGGTGGCGGTCGGGAAGATGCAGCAGTTTGTTAA
TAACCAGTTTAATAATACGGCGCGAGAATTGGACTGCATAAAAATTGCACAACAAGTGGGCGTGGAACTC
AATTTGTATCTAACTGAATTGACCACAGTGTTCGGGCCACAAATCACCTCCCCTGCTTTAACTCAGCTGA
CTATCCAGGCACTTTATAATTTAGCCGGTGGCAATATGGATTACCTGTTGACTAAGTTGGGTGTAGGGAA
TAATCAACTCAGTTCGTTAATTGGTAGTGGCTTGATAACTGGCAACCCTATACTATATGACTCACAGACC
CAACTCTTAGGCATACAGATAAATTTACCCTCAGTCGGGAGCCTAAATAATATGCGTGCCACCTACTTGG
AGACCTTATCCGTAAGCACGACCAAAGGGTTCGCCTCAGCACTTGTCCCGAAAGTTGTGACGCAAGTCGG
CTCTGTGATAGAAGAACTTGACACCTCATATTGTATAGAATCCGATATAGATCTATATTGTACAAGGGTA
GTGACATTCCCCATGTCTCCTGGTATTTACTCCTGTCTGAGCGGCAATACGTCAGCTTGTATGTATTCAA
AGACCGAAGGTGCACTCACTACACCATACATGGCCCTCAAAGGCTCAGTTATTGCCAATTGCAAGATGAC
TACATGCAGATGCGCAGATCCCCCAGGTATCATATCACAGAATTATGGGGAAGCTGTGTCTCTAATAGAT
AAACATTCATGCAGTGTCTTGTCCCTAGACGGGATAACTCTGAGGCTCAGTGGGGAATTTGATGCGACCT
ATCAAAAGAACATCTCAATACTAGATTCTCAAGTCATCGTGACAGGAAATCTCGATATATCAACTGAGCT
TGGGAATGTTAACAACTCGATAAGCAGTACCCTGGACAAATTAGCAGAAAGCAACAACAAGCTAAACAAG
GTCAATGTAAACCTAACCAGCACATCTGCTCTCATCACTTATATTGTCTTAGCTATCGTATCTCTTGCTT
TCGGCGTAATTAGCCTGGTTCTAGCATGCTACCTGATGTATAAACAAAGAGCACAACAAAAGACCTTACT
ATGGCTCGGGAACAACACCCTTGATCAGATGAGAGCCACCACAAGAACCTGA

NDV-F wildtype protein sequence of CA02 strain, GenBank Accession No. ABS84266.1

(SEQ ID NO: 7)

MGSKPSTWISVTLMLITRTMLILSCICPTSSLDGRPLAAAGIVVTGDKAVNIYTSSQTGSIIIKLLPNMP
KDKEACAKAPLEAYNRTLTTLLTPLGDSIRRIQGSATTSGGRRQKRFVGAIIGSVALGVATAAQITAAAA
LIQANQNAANILRLKESIAATNDAVHEVTNGLSQLAVAVGKMQQFVNNQFNNTARELDCIKIAQQVGVEL
NLYLTELTTVFGPQITSPALTQLTIQALYNLAGGNMDYLLTKLGVGNNQLSSLIGSGLITGNPILYDSQT
QLLGIQINLPSVGSLNNMRATYLETLSVSTTKGFASALVPKVVTQVGSVIEELDTSYCIESDIDLYCTRV
VTFPMSPGIYSCLSGNTSACMYSKTEGALTTPYMALKGSVIANCKMTTCRCADPPGIISQNYGEAVSLID
KHSCSVLSLDGITLRLSGEFDATYQKNISILDSQVIVTGNLDISTELGNVNNSISSTLDKLAESNNKLNK
VNVNLTSTSALITYIVLAIVSLAFGVISLVLACYLMYKQRAQQKTLLWLGNNTLDQMRATTRT

NDV-F codon-optimized gene of modified CA02 strain (SEQ ID NO: 8)

Atgggcagcaagcccagcacctggatcagcgtgaccctgatgctgatcaccagaaccat
gctgatcctgagctgcatctgccccacaagcagcctggacggcagaccccttggccgctg
ccggcatcgtggtgaccggcgacaaggccgtgaacatctacaccagcagccagaccggc
agcatcatcatcaagctgctgcccaacatgcccaaggacaaagaggcctgcgccaaggc
ccccctggaagcctacaacagaaccctgaccaccctgctgacccccctgggcgacagca
tcagaagaatccagggcagcgccaccacaagcggcggaggaaagcagggcagactggtg
ggcgctatcatcggagcgtggccctgggcgtggccacagctgcccagattaccgctgc -continued

```
agccgccctgattcaggccaatcagaacgccgccaacatcctgagactgaaagagagca
ttgccgccaccaacgacgccgtgcacgaagtgacaaacggactgtcccagctggctgtc
gctgtcggcaagatgcagcagttcgtgaacaaccagttcaacaacaccgccagagagct
ggactgcatcaagatcgcccagcaggtgggcgtggagctgaacctgtacctgaccgagc
tgaccacagtgttcggccccccagatcacaagcccgctctgacccagctgacaatccag
gccctgtacaacctggctggcggcaacatggactatctgctgactaagctgggagtggg
caacaaccagctgtccagcctgatcgggtccgggctgatcacaggcaacccatcctgt
acgacagccagacagctgctgggcatccagatcaacctgccatccgtgggaagcctg
aacaacatgagagccacctacctggaaaccctgagcgtgtccaccaccaagggcttcgc
cagcgccctggtgccaaggtggtgacacaggtgggcagcgtgatcgaggaactggaca
ccagctactgcatcgagagcgacatcgacctgtactgcaccagagtggtgaccttccca
atgagccccggcatctacagctgcctgagcggcaacaccagcgcctgcatgtacagcaa
gaccgaaggagcactgacaacaccctacatggccctgaagggaagcgtgatcgccaact
gcaagatgaccacctgcagatgcgccgaccccccaggcatcatcagccagaactacggc
gaggccgtgagcctgatcgacaaacattcctgtagcgtgctgtccctggatggcatcac
actgagactgagcggcgagttcgacgccacctaccagaagaacatcagcatcctggaca
gccaggtgatcgtgaccggcaacctggacatcagcaccgagctgggcaacgtgaacaac
agcatcagcagcacctggacaagctggccgagtccaacaacaagctgaacaaagtgaa
cgtgaacctgaccagcacaagcgccctgatcacctacatcgtgctggccatcgtgtccc
tggccttcggcgtgatcagcctggtgctggcctgctacctgatgtacaagcagagagcc
cagcagaaaaccctgctgtggctgggcaataacaccctggaccagatgagggccaccac
cagaacctgatga
```

Amino Acid Sequence of the codon optimized genotype V NDV-F gene in vSB1-008

(SEQ ID NO: 9)

```
mgskpstwisvtlmlitrtmlilscicptssldgrplaaagivvtgdkavniytssqtgsiiikllpnmpkdkeacakapleayn
rtlttlltplgdsirriqgsattsgggkqgrlvgaiigsvalgvataaqitaaaaliqanqnaanilrlkesiaatndavhevtnglsq
lavavgkmqqfvnnqfnntareldcikiaqqvgvelnlyltelttvfgpqitspaltqltiqalynlaggnmdyllktklgvgnn
qlsssligsglitgnpilydsqtqllgiqinlpsvgslnnmratyletlsysttkgfasalvpkvvtqvgsvieeldtsyciesdidly
ctrvvtfpmspgiyscslsgntsacmysktegalttpymalkgsvianckmttcrcadppgiisqnygeavslidkhscsvlsl
dgitlrlsgefdatyqknisildsqvivtgnldistelgnvnnsisstldklaesnnklnkvnvnltstsalityivlaivslafgvisl
vlacylmykqraqqktllwlgnnntldqmrattrt*
``` mCMV IE promoter (SEQ ID NO: 10)

```
aattcaatagtggatcccccaactccgcccgttttatgactagaaccaatagttttaa
tgccaaatgcactgaaatcccctaatttgcaaagccaaacgcccccctatgtgagtaata
cggggacttttacccaatttcccacgcggaaagcccccctaatacactcatatggcata
tgaatcagcacggtcatgcactctaatggcggcccataggacttttccacataggggc
gttcaccatttcccagcataggggtggtgactcaatggccttttacccaagtacattggg
tcaatgggaggtaagccaatgggttttttcccattactggcaagcacactgagtcaaatg
ggactttccactgggttttgcccaagtacattgggtcaatgggaggtgagccaatggga
aaaacccattgctgccaagtacactgactcaataggggacttttccaatgggtttttccat
tgttggcaagcatataaggtcaatgtgggtgagtcaataggggactttccattgtattct
gcccagtacataaggtcaataggggggtgaatcaacaggaaagtcccattggagcaagt
acactgcgtcaataggggactttccattgggttttgcccagtacataaggtcaataggggg
atgagtcaatgggaaaaaacccattggagccaagtacactgactcaataggggacttttcca
ttgggttttgcccagtacataaggtcaataggggggtgagtcaacaggaaagttccattg
gagccaagtacattgagtcaataggggactttccaatgggttttgcccagtacataaggt
caatgggaggtaagccaatgggttttttcccattactggcacgtatactgagtcattagg
gactttccaatgggttttgcccagtacataaggtcaataggggggtgaatcaacaggaaag
tcccattggagccaagtacactgagtcaataggggacttttccattgggttttgcccagta
caaaaggtcaataggggggtgagtcaatgggttttttcccattattggcacgtacataagg
tcaataggggtgagtcattgggttttttccagccaatttaattaaaacgccatgtactttt
cccaccattgacgtcaatgggctattgaaactaatgcaacgtgacctttaaacggtact
ttcccatagctgattaatgggaaagtaccgttctcgagccaatacacgtcaatgggaag
tgaaagggcagccaaaacgtaacaccgccccggttttcccctggaaattccatattggc
acgcattctattggctgagctgcgttctacgtgggtataagaggcgcgaccagcgtcgg
taccgtcgcagtcttcggtctgaccaccgtagaacgcagagctcctcgctgcag
```

SV40 PolyA (SEQ ID NO: 11)

```
ggggatccagacatgataagatacattgatgagtttggacaaaccacaactagaatgca
gtgaaaaaaatgctttatttgtgaaatttgtgatgctattgctttatttgtaaccatta
taagctgcaataaacaagttaacaacaacaattgcattcattttatgtttcaggttcag
ggggaggtgtgggaggttttttcggatcctctagagtcga
```

SV40 promoter (SEQ ID NO: 12)

```
caattcgagctcggtacagcttggctgtggaatgtgtgtcagttagggtgtggaaagtccccaggctccccagcaggcagaagt
atgcaaagcatgcatctcaattagtcagcaaccaggtgtggaaagtccccaggctccccagcaggcagaagtatgcaaagcat
gcatctcaattagtcagcaaccatagtcccgcccctaactccgcccatcccgcccctaactccgcccagttccgcccattctccgc
cccatggctgactaattttttttatttatgcagaggccgaggccgcctcggcctctgagctattccagaagtagtgaggaggattttt
ggaggcctaggcttttgcaaaaagct
```

Synthetic PolyA (SEQ ID NO: 13)

```
aataaaatatctttattttcattacatctgtgtgttggttttttgtgtgaatcgatagtactaacatacgctctccatcaaaacaaaacgaa
acaaaacaaactagcaaaataggctgtccccagtgcaagtgcaggtgccagaacattctct
```

-continued

Gene coding for glycoprotein C of SB-1 strain from genome HQ840738 (98595..100031)

(SEQ ID NO: 34)

```
     atgcac gcgtcacgcg cgttgcgagc tttggggtgg acgagactct
tatttgtcgt tttattttcg ggccgcgtcc taagcgctag cattaacccc
gatctagcta caccccccggt cattgctttc aacccgtcaa gtattccggc
cgatgatggg cctttggcca aagttcctgc atccccgccg gcaggggaga
aagaggagag ccacaagaat gcaagcgacg cgcgtaggat gcctagtata
gtttgcgata agaagaagt tttcgttttc ctgaacaaga ccgggcgttt
cgtgtgcact cttaagatcg cccctccctc cgacaacgaa tggtcgaact
ttgctctgga ccttattttc aatccgatcg aataccatgc taatgagaag
aacgtggaag cagcgcgtat tgctggcctc tatggggtgc ccggatcaga
ttacgcctac ccgcgtcctt ctgaattaat ctcttctatt cggcgagacc
cccaagggac cttttggaca agcccatcgg cacatggaga caagtacttc
atatggctaa acaaaacgac gaatacgatg ggcgtggaaa ttaggaacgt
cgactacgca gacaacggtt acatccaagt tgccatgcgg gatcctttca
atcggccttt actagataag cacgtgtaca tccgcgtgtg tcaacgaccc
gcctcggtcg acgttctagc cccccccgtc ctcagtgcga ataagtacaa
ggcttcatgc atcgttaggc attttttatcc accgggctcc gtctatgtgt
tctggaggca agatgggaat atcgttacac cacgtaagga cacggacgga
agttttggt ggtttgaatc agcccgggga gccaccctgg tatctacgat
aacgctgggc aactcggcca tcgaccctcc tcccaagatt tcatgtctgg
tagcctggaa gcagggaaat atgatgagta ctacgaacgc cactgcaatc
ccgaccgtat atcatcatcc ccggatatcc ctggctttca aagatgggta
tgcaatatgt actacgcaat gtgtgccgtt cggaattacc atacgatggt
tagtacacga tgaacccaaa cctaatacaa cttatgatac tgtggttcaa
ggtctttgca ggaccctcaa gcggcataga aatatcatca gccgaatatt
actccaagat gactggcaga aaacaaagta tacatgtcgt ctcatcggct
atcctttcga cgaagacaaa tttcaagctt tcgattactt cgacgcgacg
ccatcgacga ggggtcccc catggttctc gcgatagcgg ctgttgtggg
actagctttg attttgggaa tgggtacact cctgacggct ctgtgtttct
acgcctccgg gaaaaatac atattacttt cgtccgtcta g
```

Glycoprotein C of SB-1 [Gallid herpesvirus 3] with GenBank Accession NO. AEI00252.1

(SEQ ID NO: 35)

MHASRALRALGWTRLLFVVLFSGRVLSASINPDLATPPVIAFNPSSIPADDGPLAKVPASPPAGEKEESH
KNASDARRMPSIVCDKEEVFVFLNKTGRFVCTLKIAPPSDNEWSNFALDLIFNPIEYHANEKNVEAARIA
GLYGVPGSDYAYPRPSELISSIRRDPQGTFWTSPSAHGDKYFIWLNKTTNTMGVEIRNVDYADNGYIQVA
MRDPFNRPLLDKHVYIRVCQRPASVDVLAPPVLSGDKYKASCIVRHFYPPGSVYVFWRQDGNIVTPRKDT
DGSFWWFESARGATLVSTITLGNSAIDPPPKISCLVAWKQGNMMSSTTNATAIPTVYHHPRISLAFKDGYA
ICTTQCVPFGITIRWLVHDEPKPNTTYDTVVTGLCRTLKRHRNIISRILLQDDWQKTKYTCRLIGYPFDE
DKFQAFDYFDATPSTRGSPMVLAIAAVVGLALILGMTLLTALCFYASGKKYILLSSV

Partial plasmid pSB1_44cds_SV_FCAopt sequence for vSB1-009
(6791 bp)
*Italic* = UL44 Recombination Arms
UPPERCASE = SV40 PROMOTER
Bold = NDV-F-CAO2-CSmut sequence (SEQ ID NO: 37)

*Cttttgtcatgctcggagctctgatcgcatcttatcattacgtctgcatagcaacgtct*
*ggagacgtgacgtgtgaagaccgggtttttagttgtggcggcagggacgattgccggcat*
*cacggctccgtatggagacatttctcctctagccggctttctttcggcgtatacggcgt*
*tagctattcacgtggtcagagacgccagtcggtctctaatgaacacgtgctactaccgt*
*gcacgtcgggaaattactgtgaacggtgcatatcgcctcggtcgcgcgcgtctcccgcc*
*cagcacggacgccgaggcgacgcgcgaagaagacgtatccagttacgatacgctgggggg*
*ggaatattcctacgataattctgagcctcatagcggtcatctcgattccagcatagcc*
*agctttcaaaagtacatgtcgaacgcaactaagcaccagtcaacattgactgacacgtt*
*acgcagtatatgcggtttcttggtgggtacaagtgtcgcgatattccttccgtcgcgct*
*accacgaggttctgttccgtccaattcttgtattactgttaatattcggggcaatggct*
*actaccttagccggcttcggtttacttctcgggccgacattgttttccgcgacagccgc*
*ggttctgtgctgctacacttgtataaatgtacgcaacgcgaatagcggaataaagcaat*
*tggcggccgccagctggtaaatgcatattaggaactgccatctcgagcatgttggtt*
*tgcgtgttaatacaatattcctgatcgcggagcgattaattttatatcatgtgctcat*
*agcgttctttcgaactgcgaataaaactttcgtggctactaaagggcctatcgtgggt*
*ttatgcgctgtcgaaaacatgaaagggccgatttaaagctaagttgcgcaggcagaggc*
*cactccatatacgctctcggagacgcggctcgcacgccagctgaaatattttcccccct*
*gcaggtcgaccCAATTCGAGCTCGGTACAGCTTGGCTGTGGAATGTGTGTCAGTTAGGG*
TGTGGAAAGTCCCCAGGCTCCCCAGCAGGCAGAAGTATGCAAAGCATGCATCTCCAATTA
GTCAGCAACCAGGTGTGGAAAGTCCCCAGGCTCCCCAGCAGGCAGAAGTATGCAAAGCA
TGCATCTCAATTAGTCAGCAACCATAGTCCCGCCCCTAACTCCGCCCATCCCGCCCCTA
ACTCCGCCCAGTTCCGCCCATTCTCCGCCCCATGGCTGACTAATTTTTTTATTTATGC
AGAGGCCGAGGCCGCCTCGGCCTCTGAGCTATTCCAGAAGTAGTGAGGAGGCTTTTTG
GAGGCCTAGGCTTTTGCAAAAAGCTcccggggcggccgccaccatgggcagcaagccca
gcacctggatcagcgtgacctgatgctgatcaccagaaccatgctgatcctgagctgc
atctgccccacaagcagcctggacggcagaccctggccgctgccggcatcgtggtgac
cggcgacaaggccgtgaacatctacaccagcagccagaccggcagcatcatcatcaagc
tgctgcccaacatgcccaaggacaaagaggcctgcgccaaggcccctggaagcctac
aacagaaccctgaccacctgctgaccccctgggcgacagcatcagaagaatccaggg
cagcgccaccacaagcggcggaggaaagcagggcagactggtgggcgctatcatcggga
gcgtggccctgggcgtggccacagctgcccagattaccgctgcagccgccctgattcag
gccaatcagaacgccgccaacatcctgagactgaaagagagcattgccgccaccaacga

```
cgccgtgcacgaagtgacaaacggactgtcccagctggctgtcgctgtcggcaagatgc
agcagttcgtgaacaaccagttcaacaacaccgccagagagctggactgcatcaagatc
gcccagcaggtgggcgtggagctgaacctgtacctgaccgagctgaccacagtgttcgg
ccccagatcacaagccccgctctgacccagctgacaatccaggccctgtacaacctgg
ctggcggcaacatggactatctgctgactaagctgggagtgggcaacaaccagctgtcc
agcctgatcgggtccgggctgatcacaggcaaccccatcctgtacgacagccagacaca
gctgctgggcatccagatcaacctgccatccgtgggaagcctgaacaacatgagagcca
cctacctggaaaccctgagcgtgtccaccaccaagggcttcgccagcgcctggtgccc
aaggtggtgacacaggtgggcagcgtgatcgaggaactggacaccagctactgcatcga
gagcgacatcgacctgtactgcaccagagtggtgaccttcccaatgagcccggcatct
acagctgcctgagcggcaacaccagcgcctgcatgtacagcaagaccgaaggagcactg
acaacacccatacatggccctgaagggaagcgtgatcgccaactgcaagatgaccacctg
cagatgcgccgaccccccaggcatcatcagccagaactacggcgaggccgtgagcctga
tcgacaaacattcctgtagcgtgctgtccctggatggcatcacactgagctgagcggc
gagttcgacgccacctaccagaagaacatcagcatcctggacagccaggtgatcgtgac
cggcaacctggacatcagcaccgagctgggcaacgtgaacaacagcatcagcagcaccc
tggacaagctggccgagtccaacaacaagctgaacaaagtgaacgtgaacctgaccagc
acaagcgccctgatcacctacatcgtgctggccatcgtgtccctggccttcggcgtgat
cagcctggtgctggcctgctacctgatgtacaagcagagagcccagcagaaaaccctgc
tgtggctgggcaataacacccctggaccagatgagggccaccaccagaacctgatgagcg
gccgcgatacctgcaggtttgcggtgacattgatctggctcattatatgccccgagctc
ttgtaacatcgcggacgcgatttccgtagtaggcacatctcaaatgcaaaagcggcatg
tcaaccgtataggtacatccggccctgcttacagtcggtagggcatatatccaccggaa
aacttcagctttagactcctcaggtgatgaggaatagtatgtaaccctctagcagtacg
gtatttctaaaaaaggtagatcctttttccacacggcacagactaaataacgtacacta
cacaggttctctcgaacttcgtttggaccggaattattccctcggcagcgcctaaaaag
caaacctctagagtagataagtgtcagtgaacctaggccttctttgttccacggctgga
aagctaagggacgaggtacacgcgaccccagccacgcacgaacagagtttaacggaagc
gtcgtttgcgggataaggttgtcggaccccgcgggtccgttgaaaagtggctgcgcgcc
taccgacgaatacgtcggtaacaattttagaaatcgaatatgactgcgagtaccgtaca
atcgcgaaatacggtctctatatagctactcggtccttaaatatgtaagtatgatgtcc
cctactcccgaagacgaccgcgacttggtcgcagtacgtgggctgctccggatgatgga
cgagaccacatctgagcgcacaaacgttcgcgttcaggatgcccccggttgttatgcg
gttgtacgatcgggatcgctcttactgtgttcgtcatcacagctacggtcgtgctagct
tcgctgtttgcattctcttacatgtccctggagtccggtacatgtcctcacgaatggat
cggtttaggctatagttgtatgcgcgcgatggggagcaacgctaccgagctagaagcc
tagatacgtgctcccgacataacagcaagcttgtcgactttactcatgcgaaaattcta
atcgaagctatcgc Partial plasmid pHM103 + Fopt DNA sequence for vHVT114
Italic = Arms
bold = NDV Fop -continued

```
gaccgacggcctgagccagctgtccgtggccgtgggcaagatgcagcagttcgtgaacg
accagttcaacaacaccgccagagagctggactgcatcaagatcacccagcaggtgggc
gtggagctgaacctgtacctgaccgagctgaccacagtgttcggcccccagatcacaag
cccagccctgacacagctgaccatccaggccctgtacaacctggctggcggcaacatgg
actatctgctgacaaagctgggaatcggcaacaaccagctgtccagcctgatcggaagc
ggcctgatcaccggctaccccatcctgtacgacagccagacacagctgctgggcatcca
ggtgaacctgcccagcgtgggcaacctgaacaacatgcgcgccacctacctggaaaccc
tgagcgtgtccaccaccaagggctacgccagcgccctggtgcccaaggtggtgacacag
gtgggcagcgtgatcgaggaactggacaccagctactgcatcgagagcgacctggacct
gtactgcaccagaatcgtgaccttcccaatgagcccggcatctacagctgcctgagcg
gcaacaccagcgcctgcatgtacagcaagaccgaaggcgcactgacaacaccctacatg
gccctgaagggaagcgtgatcgccaactgcaagatcaccgctgcagatgcaccgaccc
ccaggcatcatcagccagaactacggcgaggccgtgagcctgatcgatcgccattcct
gtaacgtgctgtccctggacggcatcacactgagactgagcggcgagttcgatgccacc
taccagaagaacatcagcatcctggacagccaggtgatcgtgaccggcaacctggacat
cagcaccgagctgggcaacgtgaataacagcatcagcaacgccctggacagactggccg
agagcaacagcaagctggaaaaagtgaacgtgcgcctgacatccacttccgctctgatc
acctacatcgtgctgaccgtgatcagcctggtgttcggcgccctgagcctggtgctggc
ctgctacctgatgtacaagcagaaggcccagcagaaaaaccctgctgtggctgggcaaca
cacccctggaccagatgagagccaccaccagagcctgatgagcggccgcggggatccag
acatgataagatacattgatgagtttggacaaaccacaactagaatgcagtgaaaaaaa
tgctttatttgtgaaatttgtgatgctattgcttatttgtaaccattataagctgcaa
taaacaagttaacaacaacaattgcattgattttatgtttcaggttcagggggaggtgt
gggaggttttttcggatcctctagagtcgacaattatttttatttaataacatatagccc
aaagacctctatgaacatttagtttcccgtatactcaacggcgcgtgtacacacgcatc
tctttgcatagcgatgaagtttgttcggcagcagaaaatgcagatatccaacaatctgg
agaaaacttatcatcacagtggcagtggaaacatacccccctctatattcatggtataat
tatcgtctacagcgtccaggatagtggcgtgagaaaatggagatctgcagccctcctt
ccatggcatgccgctttattgttcattaaacgcacaatggtctcaacgccagatatggg
catagattctgaagaacccgttgacaatccgaagaagaaggcgtgcaggtctttggaag
actcgcacgttggtcttataatgtatgatcgagatgtcaccctaatgccacatggtaca
ggcttatcgcggtcatggcgatcggacttgtaatttgcaacgatgggcaaaggatcgac
gacatgccaaacattctgaacccgtagagatgttaacgatgacgaggatgaatatccca
tgctcgctgccatagtatcaagtacaccgcgaataaggacgcgtccaacatcgttatat
gcacacaatgggctacacgtgactaacaccccgaatattagtcatatgtgagtttcag
tctggctcccatatagcctgtagactatttgtggtttaagtgtgaacgaggcgctgtga
acgagactcgggccgattgtaagaacaagcaaatgcactttccatttaacaagaagtgt
agagagaatactcaacctctttggatgtatcctcgag
```

DNA coding for IBDV VP2 protein                                      (SEQ ID NO: 39)

```
ATGACAAACCTGCAAGATCAAACCCAACAGATTGTTCCGTTCATACGGAGCCTTCTGAT
GCCAACAACCGGACCGGCGTCCATTCCGGACGACACCCTGGAGAAGCACACTCTCAGGT
CAGAGACCTCGACCTACAATTTGACTGTGGGGGACACAGGGTCAGGGCTAATTGTCTTT
TTCCCTGGATTCCCTGGCTCAATTGTGGGTGCTCACTACACACTGCAGAGCAATGGGAA
CTACAAGTTCGATCAGATGCTCCTGACTGCCCAGAACCTACCGGCCAGCTACAACTACT
GCAGACTAGTGAGTCGGAGTCTCACAGTGAGGTCAAGCACACTCCCTGGTGGCGTTTAT
GCACTAAACGGCACCATAAACGCCGTGACCTTCCAAGGAAGCCTGAGTGAACTGACAGA
TGTTAGCTACAATGGGTTGATGTCTGCAACAGCCAACATCAACGACAAAATTGGGAATG
TCCTGGTAGGGGAAGGGGTCACTGTCCTCAGCCTACCCACATCATATGATCTTGGGTAT
GTGAGGCTTGGTGACCCCATTCCCGCTATAGGGCTTGACCCAAAAATGGTAGCTACATG
CGACAGCAGTGACAGGCCCAGAGTCTACACCATAACTGCAGCCGATGATTACCAATTCT
CATCACAGTACCAACCAGGTGGGGTAACAATCACACTGTTCTCAGCCAACATTGATGCT
ATCACAAGCCTCAGCATTGGGGGAGAGCTCGTGTTTCAAACAAGCGTCCAAGGCCTTGT
ACTGGGCGCCACCATCTACCTTATAGGCTTTGATGGGACTGCGGTAATCACCAGAGCTG
TAGCCGCAGATAATGGGCTGACGGCCGGCACCGACAATCTTATGCCATTCAATCTTGTC
ATTCCAACCAATGAGATAACCCAGCCAATCACATCCATCAAACTGGAGATAGTGACCTC
CAAAAGTGGTGGTCAGGCAGGGGATCAGATGTCATGGTCGGCAAGTGGGAGCCTAGCAG
TGACGATCCATGGTGGCAACTATCCAGGGGCCCTCCGTCCCGTCACACTAGTAGCCTAC
GAAAGAGTGGCAACAGGATCCGTCGTTACGGTCGCTGGGGTGAGTAACTTCGAGCTGAT
TCCAAATCCTGAACTAGCAAAGAACCTGGTTACAGAATACGGCCGATTTGACCCAGGAG
CCATGAACTACACAAAATTGATACTGAGTGAGAGGGACCGTCTTGGCATCAAGACCGTC
TGGCCAACAAGGGAGTACACTGATTTTCGTGAGTACTTCATGGAGGTGGCCGACCTCAA
CTCTCCCCTGAAGATTGCAGGAGCATTTGGCTTCAAAGACATAATCCGGGCTATAAGGA
GGTAA
```

IBDV VP2 protein                                                     (SEQ ID NO: 40)

```
MTNLQDQTQQIVPFIRSLLMPTTGPASIPDDTLEKHTLRSETSTYNLTVGDTGSGLIVF
FPGFPGSIVGAHYTLQSNGNYKFDQMLLTAQNLPASYNYCRLVSRSLTVRSSTLPGGVY
ALNGTINAVTFQGSLSELTDVSYNGLMSATANINDKIGNVLVGEGVTVLSLPTSYDLGY
VRLGDPIPAIGLDPKMVATCDSSDRPRVYTITAADDYQFSSQYQPGGVTITLFSANIDA
ITSLSIGGELVFQTSVQGLVLGATIYLIGFDGTAVITRAVAADNGLTAGTDNLMPFNLV
IPTNEITQPITSIKLEIVTSKSGGQAGDQMSWSASGSLAVTIHGGNYPGALRPVTLVAY
ERVATGSVVTVAGVSNFELIPNPELAKNLVTEYGRFDPGAMNYTKLILSERDRLGIKTV
WPTREYTDFREYFMEVADLNSPLKIAGAFGFKDIIRAIRR
```

-continued

Partial plasmid pCD046 + NDV-F VII YZCQ for vHVT112
*Italic* = Flanking Arms
UPPERCASE = mCMV IE
Bold = NDV-F VIId wt YZCQ
<u>underlined</u> = SV40 Poly A (SEQ ID NO: 46)

*gagctcagggtatgatactcagctgttattgtggccgaccaggaggactccaatgctta*
*gcattcataagaacgctagagatgctatttaacgatgtgctgtcgtctaaagaatttgt*
*gcatttagcctttaaatgtaaaaccaatgacgcattcactacgctcgtgcgtgcaattt*
*ctgggccagggtatgcatattccataacagaaatcgacacttgagaagaggatctgact*
*gtttgggataaaggtcgtttgggtctgtcctagcgatataatttatatgacgatataca*
*ttaaacatctgtgtgcagtacttaggtatttaatcatgtcgatgaaatgttatgtgtaa*
*atatcggacaatatagataacgggcacgctgctattgtaacgtgcgcccgcgcgctagt*
*gctgactaatagtgtggatgatgtatacagtatattacaaacggaaatgatacgtaata*
*aattatgtactcttattgatttataaaaacatacatgcagtgttgctatgtcacataat*
*tagcctcgcccgtctacgctccactgaagataatgggctcccgctgttcaaaaaaatca*
*gcgtgcgtcgataagactttggtgcagtctcttcggggtcgcaatttagatttgccgca*
*tggagggtatctggggattttttgccaatgctggagcgacgactgtacgattcgtcccat*
*cgggatctagcagaccaatgatgttgacacacatcggccatgcatgtacggacggtcta*
*ttgcgcgagtttgttattttcgaaggcaagatggaagtgtatatggaaccgacaataa*
*tgttagtttgcatttcttagggcggaatctacatgatatcttatccaagcggggtatga*
*gccagagagatgtgatggtcataaagggtaaatttttttagatctgaaataacgcagttg*
*cccaaacaacgatcgcgattaaaagaaaaatcggatggttcaattaggacatgcatgga*
*ttctgtgcgcataaaccataaccgcagcactgttgggcacttcggtaactcaaatgcga*
*agcgttgcacgtctgcgataactacgcctactatgcacattgttactcctgcatcttaa*
*aaatatatcctgtagtaattttcacagcaatgtcataacatcatctcgctaaagaatga*
*cctgggattggagaagtaatgaatatttgcaaccaatgcattgaataaactaacattaa*
*ac*GAATTCAATAGTGGATCCCCCAACTCCGCCCGTTTTATGACTAGAACCAATAGTTTT
TAATGCCAAATGCACTGAAATCCCCTAATTTGCAAAGCCAAACGCCCCCTATGTGAGTA
ATACGGGGACTTTTTACCCAATTTCCCACGCGGAAAGCCCCCTAATACACTCATATGGC
ATATGAATCAGCACGGTCATGCACTCTAATGGCGGCCCATAGGGACTTTCCACATAGGG
GGCGTTCACCATTTCCCAGCATAGGGGTGGTGACTCAATGGCCTTTACCCAAGTACATT
GGGTCAATGGGAGGTAAGCCAATGGGTTTTTCCCATTACTGGCAAGCACACTGAGTCAA
ATGGGACTTTCCACTGGGTTTTGCCCAAGTACATTGGGTCAATGGGAGGTGAGCCAATG
GGAAAAACCCATTGCTGCCAAGTACACTGACTCAATAGGGACTTTCCAATGGGTTTTTC
CATTGTTGGCAAGCATATAAGGTCAATGTGGGTGAGTCAATAGGGACTTTCCATTGTAT
TCTGCCCAGTACATAAGGTCAATAGGGGGTGAATCAACAGGAAAGTCCCATTGGAGCCA
AGTACACTGCGTCAATAGGGACTTTCCATTGGGTTTTGCCCAGTACATAAGGTCAATAG
GGGATGAGTCAATGGGAAAAACCCATTGGAGCCAAGTACACTGACTCAATAGGGACTTT
CCATTGGGTTTTGCCCAGTACATAAGGTCAATAGGGGGTGAGTCAACAGGAAAGTTCCA
TTGGAGCCAAGTACATTGAGTCAATAGGGACTTTCCAATGGGTTTTGCCCAGTACATAA
GGTCAATGGGAGGTAAGCCAATGGGTTTTTCCCATTACTGGCACGTATACTGAGTCATT
AGGGACTTTCCAATGGGTTTTGCCCAGTACATAAGGTCAATAGGGGTGAATCAACAGGA
AAGTCCCATTGGAGCCAAGTACACTGAGTCAATAGGGACTTTCCATTGGGTTTTGCCCA
GTACAAAAGGTCAATAGGGGGTGAGTCAATGGGTTTTTCCCATTATTGGCACGTACATA
AGGTCAATAGGGGTGAGTCATTGGGTTTTTCCAGCCAATTTAATTAAAACGCCATGTAC
TTTCCCACCATTGACGTCAATGGGCTATTGAAACTAATGCAACGTGACCTTTAAACGGT
ACTTTCCCATAGCTGATTAATGGGAAAGTACCGTTCTCGAGCCAATACACGTCAATGGG
AAGTGAAAGGGCAGCCAAAACGTAACACCGCCCCGGTTTTCCCCTGGAAATTCCATATT
GGCACGCATTCTATTGGCTGAGCTGCGTTCTACGTGGGTATAAGGAGGCGCGACCAGCGT
CGGTACCGTCGCAGTCTTCGGTCTGACCACCGTAGAACGCAGAGCTCCTCGCTGCAG*gc*
*ggccgc*atgggctctaaaccttctaccaggatcccagcacctctgatgctgatcacccg
gattatgctgatattggactgtatccgtccgacaagctctcttgacggcaggcctcttg
cagctgcaggaattgtagtaacaggagataaggcagtcaatgtatatacctcgtctcag
acagggtcaatcatagtcaagttgctcccgaatatgcccaaggataaggaggcgtgtgc
gaaagacccattagaggcatataacagaacactgactactttgctcactcctcttggcg
aatccatccgcaagatccaagggtctgtgtccacgtctggaggaggcaagcaaggccgc
ctgataggtgctgttattggtagtgtagctcttggggttgcaacagcggcacaaataac
agcagctgcggccctaatacaagccaaccagaatgctgccaacatccttcggcttaagg
agagcattgctgcaaccaatgaagctgtgcatgaagtcaccgacggattatcacaacta
tcagtggcagttgggaagatgcagcagtttgtcaatgaccagtttaataatacagcgcg
agaattggactgtataaaaatcacacaacaggttggtgtagaactcaacctatacctaa
ctgaattgactacagtattcgggccacagatcacctcccctgcattaactcagctgacc
atccaggcacttttataatttagctggtggcaatatggattacttattaactaagttagg
tatagggaacaatcaactcagctcattaattggcagcggcctgatcactggttaccccta
tattgtatgactcacagactcaactcttgggcatacaagtgaatttgccctcagtcggg
aacttaaataatatgcgtgccacctatttagagaccttatctgtagatacagccaaagg
atatgcctcagcacttgttccaaaagtagtgacacaagtcggttctgtgatagaagagc
ttgacacctcatactgtatagagtccgatctggatttatattgtactagaatagtgaca
ttccccatgtccccaggtatttattcctgtttaagcggcaacacatcagcttgcatgta
ttcaaagactgaaggcgcactcactacgccgtatatggccctaaaggctcagttattg
ccaattgtaagataacaacatgtagatgtacagaccctcctggtatcatatcgcaaaat
tatgagaagctgtatcctgatagatagacattcgtgcaatgtcttatcattagacgg
gataactctgaggctcagtggagaatttgatgcaacttatcaaaagaacatctcaatac
tagattctcaagtcatcgtgacaggcaatcttgatatatcaactgaacttggaaacgtc
aacaattcaatcagcaatgccttggataagttggcaaaaagcaacagcaagctagaaaa
agtcaatgtcagactaaccagcacatccgctctcattacctatattgttctgactgtca
tttctctagttttcggtgcactaagtctgggtttaacatgttacctgatgtacaaacaa
aaggcacaacaaaagaccttgctatggcttgggaataatacctcgatcagatgagagc
cactacaagagcatga*gcggccgc*<u>gggggatccagacatgataagatacattgatgagtt</u>

-continued

<u>tggacaaaccacaactagaatgcagtgaaaaaaatgctttatttgtgaaatttgtgatg
ctattgctttatttgtaaccattataagctgcaataaacaagttaacaacaacaattgc
attgattttatgtttcaggttcaggggggaggtgtgggaggttttttcggatcctctaga
gtcgac</u> *aattatttatttaataacatatagcccaaagacctctatgaacatttagttt
cccgtatactcaacggcgcgtgtacacacgcatctctttgcatagcgatgaagtttgtt
cggcagcagaaaatgcagatatccaacaatctggagaaaacttatcatcacagtggcag
tggaaacataccccctctatattcatggtataattatcgtctacagcgtccaggatagt
ggcgtgagaaaatggagatctgcagcccctttccatggcatgccgctttattgttca
ttaaacgcacaatggtctcaacgccagatatgggcatagattctgaagaacccgttgac
aatccgaagaagaaggcgtgcaggtctttggaagactcgcacgttggtcttataatgta
tgatcgagatgtcaccctaatgccacatggtacaggcttatcgcggtcatgcgatcgg
acttgtaatttgcaacgatgggcaaaggatcgacgacatgccaaacattctgaaccgt
agagatgttaacgatgacgaggatgaatatcccatgctcgctgccatagtatcaagtac
accgcgaataaggacgcgtccaacatcgttatatgcacacaatgggctacaCgtgacta
acaccccgaatattagtcatatgtgagtttcagtctggctcccatatagcctgtagac
tatttgtggtttaagtgtgaacgaggcgctgtgaacgagactcgggccgattgtaagaa
caagcaaatgcactttccatttaacaagaagtgtagagagaatactcaacctctttgga
tgtatcctcgag*

Partial plasmid pCD046 + NDV Texas F

-continued

```
ctgaattgactacagtattttgggccacaaatcacttccctgccttaactcagctgact
atccaagcgctttacaatctagctggtggtaatatggattacttgctgactaagttagg
tgtagggaacaaccaactcagctcattaattggtagcggcttgatcaccggcaaccccta
ttctgtacgactcacagactcagatcttgggtatacaggtaactttgccttcagttggg
aacctgaataatatgcgtgccacctacctggagaccttatctgtaagcacaaccaaggg
atttgcctcagcacttgtcccaaaagtggtgacacaggtcggttccgtgatagaagaac
ttgacacctcatactgtatagggaccgacttggatttatactgtacaagaatagtgaca
ttccctatgtctcctggtatttattcttgtctgagcggtaatacatcggcttgcatgta
ttcaaagactgaaggcgcacttactacgccatatatggctctcaaaggctcagttattg
ccaattgcaagctgacaacatgtagatgtgcagatccccccaggtatcatatcgcaaaat
tatgagaagctgtgtccttaatagataggcactcatgcaacgtcttatccttagacgg
gataactctgaggctcagtggggaatttgatgcaacctatcaaaagaatatctctatac
tagattctcaagttatagtgacaggcaatcttgatatatcaactgagcttgggaatgtc
aacaactcaataagtaatgccctgaataagttagaggaaagcaacagcaaactagacaa
agtcaatgtcaaactgaccagcacatctgctctcattacctacatcgtttttaactgtca
tatctcttgttttggtgtacttagcctggttctagcatgctacctgatgtacaagcaa
aaggcacaacaaaagaccttgttatggcttgggaataataccccttgatcagatgagagc
cactacaaaaatgagcggccgcgggatccagacatgataagatacattgatgagtt
tggacaaaccacaactagaatgcagtgaaaaaaatgctttatttgtgaaatttgtgatg
ctattgctttatttgtaaccattataagctgcaataaacaagttaacaacaacaattgc
attgatttatgtttcaggttcaggggaggtgtgggaggtttttttcggatcctctaga
gtcgacaattatttatttaataacatatagcccaaagacctctatgaacatttagttt
cccgtatactcaacggcgcgtgtacacacgcatctctttgcatagcgatgaagtttgtt
cggcagcagaaaatgcagatatccaacaatctggagaaaacttatcatcacagtggcag
tggaaacatacccctctatattcatggtataattatcgtctacagcgtccaggatagt
ggcgtgagaaaatggagatctgcagccctcctttccatggcatgccgctttattgttca
ttaaacgcacaatggtctcaacgccagatatgggcatagattctgaagaacccgttgac
aatccgaagaagaaggcgtgcaggtctttggaagactcgcacgttggtcttataatgta
tgatcgagatgtcaccctaatgccacatggtacaggcttatcgcggtcatggcgatcgg
acttgtaatttgcaacgatgggcaaaggatcgacgacatgccaaacattctgaacccgt
agagatgttaacgatgacgaggatgaatatcccatgctcgctgccatagtatcaagtac
accgcgaataaggacgcgtccaacatcgttatatgcacacaatgggctacacgtgacta
acaccccgaatattagtcatatgtgagtttcagtctggctcccatatagcctgtagac
tatttgtggtttaagtgtgaacgaggcgctgtgaacgagactcgggccgattgtaagaa
caagcaaatgcactttccatttaacaagaagtgtagagagaatactcaacctctttgga
tgtatcctcgag
```

Partial plasmid pHM119 sequence for vHVT039  
Italic = BamHI fragment I intergenic Recombination Arms  
UPPERCASE = MDV gB PROMOTER  
Bold = NDV-F wild type unmodified Texas strain sequence  
*Italic and Underlined* = SV40 Poly A tail (SEQ ID NO: 48)

*gagctcagggtatgatactcagctgttattgtggccgaccaggaggactccaatgctta*  
*gcattcataagaacgctagagatgttatttaacgatgtgctgtcgtctaaagaatttgt*  
*gcatttagcctttaaatgtaaaaccaatgacgcattcactacgctcgtgcgtgcaattt*  
*ctgggccagggtatgcatattccataacagaaatcgacacttgagaggaggatctgact*  
*gtttgggataaaggtcgtttgggtctgtcctagcgatataatttatatgacgatataca*  
*ttaaacatctgtgtgcagtacttaggtatttaatcatgtcgatgaaatgttatgtgtaa*  
*atatcggacaatatagataacgggcacgctgctattgtaacgtgcgcccgcgcgctagt*  
*gctgactaatagtgtggatgatgtatacagtatattacaaacggaaatgatacgtaata*  
*aattatgtactcttattgatttataaaaacatacatgcagtgttgctatgtcacataat*  
*tagcctcgcccgtctacgctccactgaagataatgggctcccgctgttcaaaaaaatca*  
*gcgtgcgtcgataagactttggtgcagtctcttcggggtcgcaatttagatttgccgca*  
*tggagggtatctggggattttttgcaatgctggagcgacgactgtacgattcgtcccat*  
*cgggatctagcagaccaatgatgttgacacacatcggccatgcatgtacggacggtcta*  
*ttgcgcgagtttgttattttcgaaggacaagatggaagtgtatatggaaccgacaataa*  
*tgttagtttgcatttcttagggcgaatctacatgatatcttatccaagcggggtatga*  
*gccagagagatgtgatggtcataaagggtaaattttttagatctgaaataacgcagttg*  
*cccaaacaacgatcgcgattaaaagaaaaatcggatggttcaattaggacatgcatgga*  
*ttctgtgcgcataaaccataaccgcagcactgttgggcacttcggtaactcaaatgcga*  
*agcgttgcacgtctgcgataactacgctactatgcacattgttactcctgcatcttaa*  
*aaatatatcctgtagtaattttcacagcaatgtcataacatcatctcgctaaagaatga*  
*cctgggattggagaagtaatgaatatttgcaaccaatgcattgaataaactaacattaa*  
acgaattcCGATGTTTAGTCACGATAGACATCGGTTCGCCCAGCCGTCGAATACAGCAT  
TATATTTTAGTGTTGAAAATGTAGGGCTGCTTCCTCACTTAAAGGAGGAAATGGCTCGA  
TTCATGTTTCATAGCAGTAGAAAAACAGATTGGACCGTCAGTAAGTTTAGAGGGTTTTA  
TGACTTTAGCACTATAGATAATGTAACTGCGGCCCATCGCATGGCTTGGAAATATATCA  
AAGAACTGATTTTTGCAACAGCTTATTTTCTTCTGTATTTAAATGTGGCGAATTGCAC  
ATCTGTCGTGCCGACAGTTTGCAGATCAACAGCAATGGAGACTATGTATGGAAAAATGG  
AATATATATAACATATGAAACCGAATATCCACTTATAATGATTCTGGGGTCAGAATCAA  
GCACTTCAGAAACGCAAAATATGACTGCAATTATTGATACAGATGTTTTTTCGTTGCTT  
TATTCTATTTTGCAGTATATGGCCCCCGTTACGGCAGATCAGGTGCGAGTAGAACAGAT  
TACCAACAGCCACGCCCCCATCTGACCCGTCCAATATTCTTGTGTCCCTGCATTTTATC  
TCACACAATTTATGAACAGCATCATTAAGATCATCTCACTgcggccgcaagatgggctc  
cagatcttctaccaggatcccggtacctctaatgctgatcatccgaaccgcgctgacac  
tgagctgtatccgtctgacaagctctcttgatgcaggcctcttgcggctgcagggatc  
gtggtaacaggagataaagcagtcaacatatacacctcatcccagacagggtcaatcat  
agttaagttactccgaatatgcccaaggacaaagaggtgtgtgcaaaagcccattgg  
aggcatacaacaggacactgactactttactcaccccccttggtgattctatccgcagg  
atacaagagtctgtgactacttccggaggaaggagacagagacgctttataggtgccat

-continued

```
tatcggcagtgtagctcttggggttgcgacagctgcacagataacagcagcttcggccc
tgatacaagccaaccagaatgctgccaacatcctccggcttaaagagagcattgctgca
accaatgaagctgtgcacgaggtcactgacggattatcacaactagcagtggcagtagg
gaagatgcaacagtttgtcaatgaccagttcaataatacagcgcaagaattggactgta
taaaaattgcacagcaggtcggtgtagaactcaacttgtactaactgaattgactaca
gtatttgggccacaaatcacttccctgccttaactcagctgactatccaagcgcttta
caatctagctggtggtaatatggattacttgctgactaagttaggtgtagggaacaacc
aactcagctcattaattggtagcggcttgatcaccggcaaccctattctgtacgactca
cagactcagatcttgggtatacaggtaactttgccttcagttgggaacctgaataatat
gcgtgccacctacctggagacctatctgtaagcacaaccaaggggattttgcctcagcac
ttgtcccaaaagtggtgacacaggtcggttccgtgatagaagaacttgacacctcatac
tgtatagggaccgacttggatttatactgtacaagaatagtgacattccctatgtctcc
tggtatttattcttgtctgagcggtaatacatcggcttgcatgtattcaaagactgaag
gcgcacttactacgccatatatggctctcaaaggctcagttattgccaattgcaagctg
acaacatgtagatgtgcagatcccccaggtatcatatcgcaaaattatggagaagctgt
gtccttaatagataggcactcatgcaacgtcttatccttagacgggataactctgaggc
tcagtggggaatttgatgcaacctatcaaaagaatatctctatactagattctcaagtt
atagtgacaggcaatcttgatatatcaactgagcttgggaatgtcaacaactcaataag
taatgccctgaataagttagaggaaagcaacagcaaactagacaaagtcaatgtcaaac
tgaccagcacatctgctctcattacctacatcgtttaactgtcatatctcttgttttt
ggtgtacttagcctggttctagcatgctacctgatgtacaagcaaaaggcacaacaaaa
gaccttgttatggcttgggaataataccccttgatcagatgagagccactacaaaaatat
ga```gcggccgc*ggggatccagacatgataagatacattgatgagtttggacaaaccacaa*
*ctagaatgcagtgaaaaaaatgctttatttgtgaaatttgtgatgctattgctttattt*
*gtaaccattataagctgcaataaacaagttaacaacaacaattgcattcattttatgtt*
*tcaggttcaggggaggtgtgggaggttttttcggatcctctagag*tcgacaattattt
tatttaataacatatagcccaaagacctctatgaacatttagtttcccgtatactcaac
ggcgcgtgtacacacgcatctctttgcatagcgatgaagtttgttcggcagcagaaaat
gcagatatccaacaatctggagaaaacttatcatcacagtggcagtggaaacatacccc
ctctatattcatggtataattatcgtctacagcgtccaggatagtggcgtgagaaaatg
gagatctgcagccctcctttccatggcatgccgctttattgttcattaaacgcacaatg
gtctcaacgccagatatgggcatagattctgaagaacccgttgacaatccgaagaagaa
ggcgtgcaggtcttggaagactcgcacgttggtcttataatgtatgatcgagatgtca
ccctaatgccacatggtacaggcttatcgcggtcatggcgatcggacttgtaatttgca
acgatgggcaaaggatcgacgacatgccaaacattctgaacccgtagagatgttaacga
tgacgaggatgaatatcccatgctcgctgccatagtatcaagtacaccgcgaataagga
cgcgtccaacatcgttatatgcacacaatgggctacacgtgactaacaccccgaatat
tagtcatatgtgagtttcagtctggctcccatatagcctgtagactatttgtggtttaa
gtgtgaacgaggcgctgtgaacgagactcgggccgattgtaagaacaagcaaatgcact
ttccatttaacaagaagtgtagagagaatactcaacctctttggatgtatcctcgag
```

Partial plasmid SORF3-US2 gpVar-Ewtsyn sequence (for vHVT202)
*Italic* = Flanking Arms
UPPERCASE = GPCMV
Bold = Varient E wt
*Italic and Underlined* = Syn Poly A (SEQ ID NO: 56)

```
taaaatgggatctatcattacattcgttaagagtctggataattttactgtttgccagc
ttcgatcttggaacgtactgtggatagtgccttacttggaatcgtgaaaatttgaaacg
tccattatttggatatcttccggttgtcccatatcccgccctggtaccgctcggatacc
ttgcccgtatggattcgtattgacagtcgcgcaatcgggaccaacaacgcgtgggtcc
acactcattcggaaatttttccgatgattctgaatatttattgccgctcgttacgagtcg
ttggacatatctgtaatacatttcttcttctgaaggatcgctgcacatttgatctatac
attggccaggatgttcaagtctcagatgttgcattctggcacagcacaactttatggca
tttccgatgtaatcgtccggcagccctggggagttctatattcgcatattgggatggt
aaggacaatagcagatctcgcaacctccagggaggctataataacgttttttaaaggatg
gatttctcataaaaatctgtcgcaaattacactgagaatatcctttactagcgccgatt
gagagcatcgtcgtccaatttttctaaatgaaagaaaacaaggcgggcaagagtgttcc
aaacattttcattttcggcgaatctctcaaatcccatggcgtgcaattgattgcaaaat
tggcacttccgttcacgtttgtatcttccaaactctaagacacttttaattgaaaaacta
cgttctagtgtggaaagaaacctataggcagaccatagaactatttgacaccacatatc
ttttgtatgtcaaactgaccatgatcgtatgttgctgaatgcactagggcaattcgct
cgcgcgactccatacattgaataattccacacgtcagctcatcggttagcaaggtccag
tagttgaagtcatttattttttccccgggctggccaaatctacctctgggaatatccaa
gttgtcgaatatgatcgcaccggctctggtcatggtgaaggaacttgtagcataaagac
gcaggtatcataggggtaatattttttttattcactcacatactaaaagtaacgcatatt
agcaccatgtatgggctatcaattgacatttgcgtagcactacatcacgattatgtaca
acataatgggacaacatatgcctgcagg**TTAGTCATATGTTACTTGGCAGAGGCCGCAT
GGAAAGTCCCTGGACGTGGGACATCTGATTAATACGTGAGGAGGTCAGCCATGTTCTTT
TTGGCAAAGGACTACGGTCATTGGACGTTTGATTGGCATGGGATAGGGTCAGCCAGAGT
TAACAGTGTTCTTTTGGCAAAGGGATACGTGGAAAGTCCCGGCCATTTACAGTAAACT
GATACGGGACAAAGCACAGCCATATTTAGTCATGTATTGCTTGGCAGAGGGTCTATGG
AAAGTCCCTGGACGTGGGACGTCTGATTAATATGAAAGAAGGTCAGCCAGAGGTAGCTG
TGTCCTTTTTGGCAAAGGGATACGGTTATGGGACGTTTGATTGGACTGGGATAGGGTCA
GCCAGAGTTAACAGTGTTCTTTTGGCAAAGGAAACGTGGAAAGTCCCGGGCCATTTACA
GTAAACTGATACTGGGACAAAGTACACCCATATTTAGTCATGTTCTTTTGGCAAAGAG
CATCTGGAAAGTCCCGGGCAGCATTATAGTCACTTGGCAGAGGGAAAGGGTCACTCAGA
GTTAAGTACATCTTTCCAGGGCCAATATTCCAGTAAATTACACTTAGTTTTATGCAAAT
CAGCCACAAAGGGGATTTTCCCGGTCAATTATGACTTTTTCCTTAGTCATGCGGTATCC
AATTACTGCCAAATTGGCAGTACATACTAGGTGATTCACTGACATTTGGCCGTCCTCTG
GAAAGTCCCTGGAAACCGCTCAAGTACTGTATCATGGTGACTTTGCATTTTTGGAGAGC**
```

-continued

ACGCCCCACTCCACCATTGGTCCACGTACCCTATGGGGGAGTGGTTTATGAGTATATAA
GGGGCTCCGGTTTAGAAGCCGGGCAGAgcggccgcatgacaaacctgcaagatcaaacc
caacagattgttccgttcatacggagccttctgatgccaacaaccggaccggcgtccat
tccggacgacacccctggagaagcacactctcaggtcagagacctcgacctacaatttga
ctgtgggggacacagggtcagggctaattgtcttttttccctggattccctggctcaatt
gtgggtgctcactacacactgcagagcaatgggaactacaagttcgatcagatgctcct
gactgcccagaacctaccggccagctacaactactgcaggctagtgagtcggagtctca
cagtaaggtcaagcacactccctggtggcgtttatgcactaaacggcaccataaacgcc
gtgaccttccaaggaagcctgagtgaactgacagatgttagctacaacgggttgatgtc
tgcaacagccaacatcaacgacaaaattgggaacgtcctagtaggggaaggggtaaccg
tcctcagcttacccacatcatatgatcttgggtatgtgaggcttggtgacccccataccc
gctagggcttgacccaaaaatggtagcaacatgtgacagcagtgacaggcccagagt
ctacaccataactgcagccgataattaccaattctcatcacagtaccaaacaggtgggg
taacaatcacactgttctcagccaacattgatgccatcacaagtctcagcgttggggga
gagctcgtgttcaaaacaagcgtccaaagccttgtactgggcgccaccatctaccttat
aggctttgatgggactgcggtaatcaccagagctgtggccgaaacaatgggctgacgg
ccggcatcgacaatcttatgccattcaatcttgtgattccaaccaatgagataacccag
ccaatcacatccatcaaactggagatagtgacctccaaaagtgatggtcaggcagggga
acagatgtcatggtcggcaagtgggagcctagcagtgacgatccatggtggcaactatc
caggagccctccgtcccgtcacactagtggcctacgaaagagtggcaacaggatctgtc
gttacggtcgctggggtgagcaacttcgagctgatcccaaatcctgaactagcaaagaa
cctggttacagaatatggccgatttgacccaggagccatgaactacacgaaattgatac
tgagtgagagggaccgccttggcatcaagaccgtctggccaacaagggagtacactgac
tttcgtgagtacttcatggaggtggccgacctcaactctccctgaagattgcaggagc
atttggcttcaaagacataatccgggccataaggaggtgagcggccgcgatatcaataa
aatatctttattttcattacatctgtgtgttggttttttgtgtgaatcgatagtactaa
catacgctctccatcaaaacaaaacgaaacaaaacaaactagcaaaataggctgtcccc
agtgcaagtgcaggtgccagaacatttctcttctagacctgcaggcccggggcaagtag
atgcaatttcctcacactagttgggtttatctactattgaattttcccctatctgtgat
acacttgggagcctctacaagcatattgccatcatgtacgttttatctactgtcttaa
cgcccatgggaacggaggcgtcgtcgtcatgtattggacggcaacataggcagcaacac
aaattgcgtttaggtggggtgcatgtggactcgataccaagcccctgcagctggggaac
gtctggtggagagccgataatttgatatacgcacgccatattactgtcgttgaagtacg
ccttatcttctatgttttcaaatttaggttcccaagtggacgtgagaagtgtttgtatc
tcacatggaatggcccaaggcattccagcccaggtgcctgactttaatggcaaacaa
acgttttggtagaggtattgattctattgcagttctgcagatatctgcagccccgagta
tccacaggctatacgatacgttatcggaggcctccgattctagcattacatagccggtc
agtagatcctgccattcggtagcgcaaccggctacatcttcaaacagtctcacaataaa
tgcatctctcgttcctgccaatccggaaccgggcataccactcccgcctgccgatttaa
ttctcacaattgggcgatgccggcggggcaaaacgaatgtggatttggcaaaccgacac
aggtctgctgtacggactaatatgggcacacccacatcattcttcagatgctccatgca
ttgttctatgagaaagatccataggggtggaggcagcgtcacgagatcgcccaggcaatc
gatcgcattcgtctagtaaagtgacgagagttatcatgcacacacccatgcccacgcct
tccgaataactggagctgtggaagatcggaaacgtctttttgactgccggtctcgtact
actttcgcacaggtgtatacccggacgcgtactatatattttatatcatccaacgtccc
gaaattacatcgtggcggcgatggaagtagatgttgagtcttcgaaagtaagtgcctc
gaatatgggtattgtctgtgaaaatatcgaaagcggtacgacggttcagaaccgtcga
tgtcgccagatactagtaacaatagcttcgataacgaagacttccgtgggcctgaatac
gatgtggagata Partial plasmid SB1US2 gpVIIdwtsyn sequence (for vSB1-010)
*Italic* = Fl -continued

```
TGGACTGGGATAGGGTCAGCCAGAGTTAACAGTGTTCTTTTGGCAAAGGAAACGTGGAA
AGTCCCGGGCCATTTACAGTAAACTGATACTGGGACAAAGTACACCCATATTTAGTCAT
GTTCTTTTTGGCAAAGAGCATCTGGAAAGTCCCGGGCAGCATTATAGTCACTTGGCAGA
GGGAAAGGGTCACTCAGAGTTAAGTACATCTTTCCAGGGCCAATATTCCAGTAAATTAC
ACTTAGTTTTATGCAAATCAGCCACAAAGGGATTTTCCCGGTCAATTATGACTTTTTC
CTTAGTCATGCGGTATCCAATTACTGCCAAATTGGCAGTACATACTAGGTGATTCACTG
ACATTTGGCCGTCCTCTGGAAAGTCCCTGGAAACCGCTCAAGTACTGTATCATGGTGAC
TTTGCATTTTTGGAGAGCACGCCCCACTCCACCATTGGTCCACGTACCCTATGGGGAG
TGGTTTATGAGTATATAAGGGGCTCCGGTTTAGAAGCCGGGCAGAgcggccgcatgggc
tccaaaccttctaccaggatcccagcacctctgatgctgatcacccggattatgctgat
attgggctgtatccgtccgacaagctctcttgacggcaggcctcttgcagctgcaggaa
ttgtagtaacaggagataaggcagtcaatgtatacacttcgtctcagacagggtcaatc
atagtcaagttgctcccgaatatgcccagggataaggaggcgtgtgcaaaagcccatt
agaggcatataacagaacactgactactttgctcactcctcttggcgactccatccgca
agatccaagggtctgtgtccacatctggaggaggcaagcaaggccgcctgataggtgct
gttattggcagtgtagctcttggggttgcaacagcgggcacagataacagcagctgcgg
cctaatacaagccaaccagaatgccgccaacatcctccggcttaaggagagcattgctg
caaccaatgaagctgtgcatgaagtcaccgacggattatcaacctatcagtggcagtt
gggaagatgcagcagtttgtcaatgaccagtttaataatacggcgcgagaattggactg
tataaaaatcacacaacaggttggtgtagaactcaacctatacctaactgaattgacta
cagtattcgggccacagatcacctcccctgcattaactcagctgaccatccaggcactt
tataatttagctggtggcaatatggattacttattaactaagttaggtataggaacaa
tcaactcagctcgttaattggtagcggcctgatcactggttaccctatactgtatgact
cacagactcaactcttgggcatacaagtgaatttaccctcagtcgggaacttaaataat
atgcgtgccacctatttggagaccttatctgtaagtacaaccaaaggatatgcctcagc
acttgtcccgaaagtagtgacacaagtcggttccgtgatagaagagcttgacacctcat
actgtatagagtccgatctggatttatattgctagaatagtgacattccccatgtcc
ccaggtatttattcctgtttgagcggcaaacacatcagcttgcatgtattcaaagactga
aggcgcactcactacgccgtatatggcccttaaaggctcagttattgccaattgtaaaa
taacaacatgtagatgtacagaccctcctggtatcatatcgcaaaattatggagaagct
gtatccctgatagatagacattcgtgcaatgtcttatcattagacgggataactctaag
gctcagtggggaatttgatgcaacttatcaaaagaacatctcaatactagattctcaag
tcatcgtgacaggcaatcttgatatatcaactgaacttggaaacgtcaacaattcaatc
agcaatgccttggataggttggcagaaagcaacagcaagctagaaaaagtcaatgtcag
actaaccagcacatctgctctcattacctatattgttctaactgtcatttctctagttt
tcggtgcacttagtctggtgttagcgtgttacctgatgtacaaacagaaggcacaacaa
aagaccttgctatggcttgggaataatacctcgatcagatgagagccactacaagagc
atgagcggccgcgatatcaataaaatatcttttattttcattacatctgtgtgttggttt
tttgtgtgaatcgatagtactaacatacgctctccatcaaaacaaaacgaaacaaaaca
aactagcaaaataggctgtccccagtgcaagtgcaggtgccagaacatttctcttctag
acctgcaggggagtctgtgcaaggttaatgaccctcgcagttcattcggaagttataac
tgccgccttcgcacatttctttttgtcctgttttgtattgccataacagataggaattg
aaacctgatcctcctgtttttttgcagcatggccagcaacagaatactttgtcggatcga
ctacttgcgcgagatggttccgttcttggaggtttcggcgggtcgggtggagaacctat
tatttatacacacacgtcataccgttgtcgcgaaaatgttcttttgtcttctgccgtct
cgaacgtcggttcccacgtagacgttaggagcgttggaatggtatcaggaagagcccac
ggcatgccggaccaagtacccgctactttgaccgcgcaagtcagtctcttcggtaatgggat
gtattccagagcagcgcggcagagatcagcggcccccactatccacagactgtatgaag
tgtttttctgaaacatcggactccaacatcaaatatccagacataacatcttgccattcg
gaagcacatccgccgacatcttcaaatagcctaactataaacgagtctctagttcctgc
taacccagtacctcgaatgccagtcccatccggtgggttcgtcctgataatcggtctct
gacgccgaggaagaactaaaagggtctggaaaagcggaacagatctgcagaccgaacg
actacagacacgcccacatcatcatgtatctgttccatgcattgctttatgagaaaat
ccataaggccgaggcggcatctctagatctcccggggagtctctcgcactcatctagga
gagtgacgacagttatcatagacacgcccatttgtgcaccaaaacgaaaagttcctgtac
tggtgggagcgtcggcgcgggaatcggtccgtgctctgaaaccagtgtctagacagaaga
ccatccggtaaattctggtgtatgaactgacggtctccagacgaacgtcgaagacatta
acgatggaaactaacgagctttcttcaaaagtgtctgattacaacgctaatagacctta
cgaaactatacgcagcgataccagtgacacagatccgtcggtgtcg
```

The nucleotide sequence of the cloned NDV Texas F gene (wild type non-modified)

(SEQ ID NO: 49)

```
ATGGGCTCCAGATCTTCTACCAGGATCCCGGTACCTCTAATGCTGATCATCCGAACCGC
GCTGACACTGAGCTGTATCCGTCTGACAAGCTCTCTTGATGGCAGGCCTCTTGCGGCTG
CAGGGATCGTGGTAACAGGAGATAAAGCAGTCAACATATACACCTCATCCCAGACAGGG
TCAATCATAGTTAAGTTACTCCCGAATATGCCCAAGGACAAAGAGGTGTGTGCAAAAGC
CCCATTGGAGGCATACAACAGGACACTGACTACTTTACTCACCCCCCTTGGTGATTCTA
TCCGCAGGATCAAGAGTCTGTGACTACTTCCGGAGGAAGGAGACAGGAGACGCTTTATA
GGTGCCATTATCGGCAGTGTAGCTCTTGGGGTTGCGACAGCTGCACAGATAACAGCAGC
TTCGGCCCTGATACAAGCCAACCAGAATGCTGCCAACATCCTCCGGCTTAAAGAGACA
TTGCTGCAACCAATGAAGCTGTGCACGAGGTCACTGACGGATTATCACAACTAGCAGTG
GCAGTAGGGAAGATGCAACAGTTTGTCAATGACCAGTTCAATAATACAGCGCAAGAATT
GGACTGTATAAAAATTGCACAGCAGGTCGGTGTAGAACTCAACTTGTACCTAACTGAAT
TGACTACAGTATTTGGGCCACAAATCACTTCCCCTGCCTTAACTCAGCTGACTATCCAA
GCGCTTTACAATCTAGCTGGTGGTAATATGGATTACTTGCTGACTAAGTTAGGTGTAGG
GAACAACCAACTCAGCTCATTAATTGGTAGCGGCTTGATCACCGGCAACCCTATTCTGT
ACGACTCACAGACTCAGATCTTGGGTATACAGGTAACTTTGCCTTCAGTGGGAACCTG
AATAATATGCGTGCCACCTACCTGGAGACCTTATCTGTAAGCACAACCAAGGGATTTGC
CTCAGCACTTGTCCCAAAAGTGGTGACACAGGTCGGTTCCGTGATAGAAGAACTTGACA
CCTCATACTGTATAGGGACCGACTTGGATTTATACTGTACAAGAATAGTGACATTCCCT
ATGTCTCCTGGTATTTATTCTTGTCTGAGCGGTAATACATCGGCTTGCATGTATTCAAA
```

```
GACTGAAGGCGCACTTACTACGCCATATATGGCTCTCAAAGGCTCAGTTATTGCCAATT
GCAAGCTGACAACATGTAGATGTGCAGATCCCCCAGGTATCATATCGCAAAATTATGGA
GAAGCTGTGTCCTTAATAGATAGGCACTCATGCAACGTCTTATCCTTAGACGGGATAAC
TCTGAGGCTCAGTGGGAATTTGATGCAACCTATCAAAGAATATCTCTATACTAGATT
CTCAAGTTATAGTGACAGGCAATCTTGATATATCAACTGAGCTTGGGAATGTCAACAAC
TCAATAAGTAATGCCCTGAATAAGTTAGAGGAAAGCAACAGCAAACTAGACAAAGTCAA
TGTCAAACTGACCAGCACATCTGCTCTCATTACCTACATCGTTTTAACTGTCATATCTC
TTGTTTTTGGTGTACTTAGCCTGGTTCTAGCATGCTACCTGATGTACAAGCAAAAGGCA
CAACAAAAGACCTTGTTATGGCTTGGGAATAATACCCTTGATCAGATGAGAGCCACTAC
AAAAATATGA

The amino acid sequence of the cloned NDV Texas F gene (wild
type non-modified; cleavage site underlined)
                                                                (SEQ ID NO: 50)
MGSRSSTRIPVPLMLIIRTALTLSCIRLTSSLDGRPLAAAGIVVTGDKAVNIYTSSQTG
SIIVKLLPNMPKDKEVCAKAPLEAYNRTLTTLLTPLGDSIRRIQESVTTSGGRRQRRFI
GAIIGSVALGVATAAQITAASALIQANQNAANILRLKESIAATNEAVHEVTDGLSQLAV
AVGKMQQFVNDQFNNTAQELDCIKIAQQVGVELNLYLTELTTVFGPQITSPALTQLTIQ
ALYNLAGGNMDYLLTKLGVGNNQLSSLIGSGLITGNPILYDSQTQILGIQVTLPSVGNL
NNMRATYLETLSVSTTKGFASALVPKVVTQVGSVIEELDTSYCIGTDLDLYCTRIVTFP
MSPGIYSCLSGNTSACMYSKTEGALTTPYMALKGSVIANCKLTTCRCADPPGIISQNYG
EAVSLIDRHSCNVLSLDGITLRLSGEFDATYQKNISILDSQVIVTGNLDISTELGNVNN
SISNALNKLEESNSKLDKVNVKLTSTSALITYIVLTVISLVFGVLSLVLACYLMYKQKA
QQKTLLWLGNNTLDQMRATTKI NDV-F YZCQ wildtype DNA sequence
                                                                (SEQ ID NO: 51)
atgggctccagatcttctaccaggatcccggtacctctaatgctgatcatccgaaccgc
gctgacactgagctgtatccgtctgacaagctctcttgatggcaggcctcttgcggctg
cagggatcgtggtaacaggagataaagcagtcaacatatacacctcatcccagacaggg
tcaatcatagttaagttactcccgaatatgcccaaggacaaagaggtgtgtgcaaaagc
cccattggaggcatacaacaggacactgactactttactcaccccccttggtgattcta
tccgcaggatacaagagtctgtgactacttccggaggaggcaagcaaggccgcctgata
ggtgccattatcggcagtgtagctcttgggggttgcgacagctgcacagataacagcagc
ttcgggccctgatacaagccaaccagaatgctgccaacatcctccggcttaagagagca
ttgctgcaaccaatgaagctgtgcacgaggtcactgacggattatcacaactagcagtg
gcagtagggaagatgcaacagtttgtcaatgaccagttcaataatacagcgcaagaatt
ggactgtataaaattgcacagcaggtcggtagaactcaacttgtacctaactgaat
tgactacagtatttgggccacaaatcacttcccctgccttaactcagtgactatccaa
gcgctttacaatctagctggtggtaatatggattacttgctgactaagttaggtgtagg
gaacaaccaactcagctcattaattggtagcggcttgatcaccggcaacccctattctgt
acgactcacagactcagatcttgggtatacaggtaactttgccttcagttggggaacctg
aataatatgcgtgccacctacctggagaccttatctgtaagcacaaccaagggatttgc
ctcagcacttgtcccaaaagtggtgacacaggtcggttccgtgataagaacttgaca
cctcatactgtataggccgacttggatttatactgtacaagaatagtgacattccct
atgtctcctggtatttattcttgtctgagcggtaatacatcggcttgcatgtattcaaa
gactgaaggcgcacttactacgccatatatggctctcaaaggctcagttattgccaatt
gcaagctgacaacatgtagatgtgcagatccccagggtatcatatcgcaaaattatgga
gaagctgtgtccttaatagataggcactcatgcaacgtcttatccttagacgggataac
tctgaggctcagtgggaatttgatgcaacctatcaaagaatatctctatactagatt
ctcaagttatagtgacaggcaatcttgatatatcaactgagcttgggaatgtcaacaac
tcaataagtaatgccctgaataagttagaggaaagcaacagcaaactagacaaagtcaa
tgtcaaactgaccagcacatctgctctcattacctacatcgttttaactgtcatatctc
ttgttttggtgtacttagcctggttctagcatgctacctgatgtacaagcaaaaggca
caacaaaagaccttgttatggcttgggaataatacccttgatcagatgagagccactac
aaaaatatga NDV-F protein from wildtype YZCQ strain (Amino Acid Sequence
of NDV-F of Texas strain with lentogenic cleavage site sequence)
                                                                (SEQ ID NO: 52)
mgsrsstripvplmliirtaltlscirltssldgrplaaagivvtgdkavniytssqtg
siivkllpnmpkdkevcakapleaynrtltltlltplgdsirriqesvttsgggkqgrli
gaiigsvalgvataaqitaasaliqanqnaanilrlkesiaatneavhevtdglsqlav
avgkmqqfvndqfnntaqeldcikiaqqvgvelnlyltelttvfgpqitspaltqltiq
alynlaggnmdyllltklgvgnnqlssligsglitgnpilydsqtqilgiqvtlpsvgnl
nnmratyletlsvsttkgfasalvpkvvtqvgsvieeldtsycigtdldlyctrivtfp
mspgiysclsgntsacmysktegalttpymalkgsvianckltttcrcadppgiisqnyg
eavslidrhscnvlsldgitlrlsgefdatyqknisildsqvivtgnldistelgnvnn
sisnalnkleesnskldkvnvkltstsalityivltvislvfgvlslvlacylmykqka
qqktllwlgnntldqmrattki*

NDV-F Texas wildtype DNA sequence
                                                                (SEQ ID NO: 53)
atgggctctaaaccttctaccaggatcccagcacctctgatgctgatcacccggattat
gctgatattggactgtatccgtccgacaagctctcttgacggcaggcctcttgcagctg
caggaattgtagtaacaggagataaggcagtcaatgtatataccctcgtctcagacaggg
tcaatcatagtcaagttgctcccgaatatgcccaaggataagaggcgtgtgcgaaaga
cccattagaggcatataacagaacactgactactttgctcactcctcttggcgaatcca
tccgcaggatccaagggtctgtgtccacgtctggaggaggcaagcaaggccgcctgata
ggtgctgttattggtagtgtagctcttgggggttgcaacagcggcacaaataacagcagc
tgcggccctaatacaagccaaccagaatgctgccaacatccttcggcttaaggagagca
```

-continued ttgctgcaaccaatgaagctgtgcatgaagtcaccgacggattatcacaactatcagtg
gcagttgggaagatgcagcagtttgtcaatgaccagtttaataatacagcgcgagaatt
ggactgtataaaaatcacacaacaggttggtgtagaactcaacctatacctaactgaat
tgactacagtattcgggccacagatcacctcccctgcattaactcagctgaccatccag
gcactttataatttagctggtggcaatatggattacttattaactaagttaggtatagg
gaacaatcaactcagctcattaattggcagcggcctgatcactggttaccctatattgt
atgactcacagactcaactcttgggcatacaagtgaatttgccctcagtcgggaactta
aataatatgcgtgccacctatttagagaccttatctgtaagtacagccaaaggatatgc
ctcagcacttgttccaaaagtagtgacacaagtcggtctgtgatagaagagcttgaca
cctcatactgtatagagtccgatctggatttatattgtactagaatagtgacattcccc
atgtccccaggtatttattcctgtttaagcggcaacacatcagcttgcatgtattcaaa
gactgaaggcgcactcactacgccgtatatggcccttaaaggctcagttattgccaatt
gtaagataacaacatgtagatgtacagaccctcctggtatcatatcgcaaaattatgga
gaagctgtatccctgatagatagacattcgtgcaatgtcttatcattagacgggataac
tctgaggctcagtgagaatttgatgcaacttatcaaaagaacatctcaatactagatt
ctcaagtcatcgtgacaggcaatcttgatatatcaactgaacttggaaacgtcaacaat
tcaatcagcaatgccttggataagttggcaaaaagcaacagcaagctagaaaaagtcaa
tgtcagactaaccagcacatccgctctcattacctatattgttctgactgtcatttctc
tagttttcggtgcactaagtctgggtttaacatgttacctgatgtacaaacaaaaggca
caacaaaagaccttgctatggcttgggaataataccctcgatcagatgagagccactac
aagagcatga NDV-F protein from wildtype Texas strain (Amino Acid Sequence
of NDV-F VIId wt YZCQ with lentogenic cleavage site sequence)

(SEQ ID NO: 54)

mgskpstripaplmlitrimlildcirptssldgrplaaagivvtgdkavnvytssqtg
siivkllpnmpkdkeacakdpleaynrtltttltplgesirkiqgsystsgggkqgrli
gavigsvalgvataaqitaaaaliqanqnaanilrlkesiaatneavhevtdglsqlsv
avgkmqqfvndqfnntareldcikitqqvgvelnlylteltttvfgpqitspaltqltiq
alynlaggnmdyllltklgignnqlssligsglitgypilydsqtqllgiqvnlpsvgnl
nnmratyletlsvstakgyasalvpkvvtqvgsvieeldtsyciesdldlyctrivtfp
mspgiysclsgntsacmysktegalttpymalkgsvianckittcrctdppgiisqnyg
eavslidrhscnvlsldgitlrlsgefdatyqknisildsqvivtgnldistelgnvnn
sisnaldklaksnsklekvnvrltstsalityivltvislvfgalslgltcylmykqka
qqktlllwlgnntldqmrattra*

MDV gB promoter (SEQ ID NO: 55)

CGATGTTTAGTCACGATAGACATCGGTTCGCCCAGCCGTCGAATACAGCATTATATTTT
AGTGTTGAAAATGTAGGGCTGCTTCCTCACTTAAAGGAGGAAATGGCTCGATTCATGTT
TCATAGCAGTAGAAAAACAGATTGGACCGTCAGTAAGTTTAGAGGGTTTTATGACTTTA
GCACTATAGATAATGTAACTGCGGCCCATCGCATGGCTTGGAAATATATCAAAGAACTG
ATTTTTTGCAACAGCTTTATTTTCTTCTGTATTTAAATGTGGCGAATTGCACATCTGTCG
TGCCGACAGTTTGCAGATCAACAGCAATGGAGACTATGTATGGAAAAATGGAATATATA
TAACATATGAAACCGAATATCCACTTATAATGATTCTGGGGTCAGAATCAAGCACTTCA
GAAACGCAAAATATGACTGCAATTATTGATACAGATGTTTTTTCGTTGCTTTATTCTAT
TTTGCAGTATATGGCCCCCGTTACGGCAGATCAGGTGCGAGTAGAACAGATTACCAACA
GCCACGCCCCATCTGACCCGTCCAATATTCTTGTGTCCCTGCATTTTATCTCACACAA
TTTATGAACAGCATCATTAAGATCATCTCACT

IBDV DNA encoding VP2 protein of IBDV E strain (SEQ ID NO: 58)

Atgacaaaacctgcaagatcaaaccccaacagattgttccgttcatacggagccttctgat
gccaacaaccggaccggcgtccattccggacgacaccctgggagaagcacactctcaggt
cagagacctcgacctacaatttgactgtggggacacagggtcagggctaattgtcttt
ttccctggattccctggctcaattgtgggtgctcactacacactgcagagcaatgggaa
ctacaagttcgatcagatgctcctgactgcccagaacctaccggccagctacaactact
gcaggctagtgagtcggagtctcacagtaaggtcaagcacactccctggtggcgtttat
gcactaaacggcaccataaacgccgtgaccttccaaggaagcctgagtgaactgacaga
tgttagctacaacgggttgatgtctgcaacagccaacatcaacgacaaaattgggaacg
tcctagtaggggaagggtaaccgtcctcagcttacccacatcatatgatcttgggtat
gtgaggcttggtgacccccataccgctataggcttgacccaaaaatggtagcaacatg
tgacagcagtgacaggcccagagtctacaccataactgcagccgataattaccaattct
catcacagtaccaaacaggtggggtaacaatcacactgttctcagccaacattgatgcc
atcacaagtctcagcgttgggggagagctcgtgttcaaaacaagcgtccaaagccttgt
actgggcgccaccatctacctataggctttgatgggactgcggtaatcaccagagctg
tggccgcaaacaatgggctgacggccggcatcgacaatcttatgccattcaatcttgtg
attccaaccaatgagataacccagccaatcacatccatcaaactggagatagtgacctc
caaaagtgatggtcaggcagggggaacagatgtcatggtcggcaagtgggagcctagcag
tgacgatccatggtggcaactatccaggagccctccgtcccgtcacactagtggcctac
gaaagagtggcaacaggatctgtcgttacggtcgctggggtgagcaacttcgagctgat
cccaaatcctgaactagcaaagaacctggttacagaatatgccgatttgacccaggag
ccatgaactacacgaaattgatactgagtgagagggaccgccttggcatcaagaccgtc
tggccaacaaggggagtacactgactttcgtgagtacttcatggaggtggccgacctcaa
ctctcccctgaagattgcaggagcatttggcttcaaagacataatccggccataagga
ggtga IBDV VP2 protein of IBDV E strain (SEQ ID NO: 59)

mtnlqdqtqqivpfirsllmpttgpasipddtlekhtlrsetstynltvgdtgsglivf
fpgfpgsivgahytlqsngnykfdqmlltaqnlpasynycrlvsrsltvrsstlpggvy
alngtinavtfqgslseltdvsynglmsataninindkignvlvgegvtvlslptsydlgy
vrlgdpipaigldpkmvatcdssdrprvytitaadnyqfssqyqtggvtitlfsanida
itslsvggelvfktsvqslvlgatiyligfdgtavitravaanngltagidnlmpfnlv
iptneitqpitsikleivtsksdgqageqmswsasgslavtihggnypgalrpvtivay
ervatgsvvtvagvsnfelipnpelaknlvteygrfdpgamnytklilserdrlgiktv
wptreytdfreyfmevadlnsplkiagafgfkdiirairr*

Guinea pig CMV promoter (SEQ ID NO: 60)

ttagtcatatgttacttggcagaggccgcatggaaagtccctggacgtgggacatctga
ttaatacgtgaggaggtcagccatgttcttttggcaaaggactacggtcattggacgt
tgattggcatgggatagggtcagccagagttaacagtgttcttttggcaaagggatac
gtggaaagtcccgggccatttacagtaaactgatacggggacaaagcacagccatattt
agtcatgtattgcttggcagagggtctatggaaagtccctggacgtgggacgtctgatt
aatatgaaagaaggtcagccagaggtagctgtgtccttttttggcaaagggatacggtta
tgggacgtttgattggactgggatagggtcagccagagttaacagtgttcttttggcaa
aggaaacgtggaaagtcccgggccatttacagtaaactgatactgggacaaagtacacc
catatttagtcatgttcttttggcaaagagcatctggaaagtcccgggcagcattata
gtcacttggcagagggaaagggtcactcagagttaagtacatctttccagggccaatat
tccagtaaattacacttagttttatgcaaatcagccacaaaggggattttcccggtcaa
ttatgacttttccttagtcatgcggtatccaattactgccaaattggcagtacatact
aggtgattcactgacatttggccgtcctctggaaagtccctggaaaccgctcaagtact
gtatcatggtgactttgcattttttggagagcacgccccactccaccattggtccacgta
ccctatggggagtggtttatgagtatataaggggctccggtttagaagccgggcaga Locus positions of SEQ ID NO: 14 (GenBank Accession No. HQ840738.1,
Gallid herpesvirus 3 strain SB-1, complete genome)

117554..118057 UL55 gene, product = "UL55 protein"; protein id = "AEI00266.1"

Complement(118306..120927) LORF5 gene; product = "ORF996 protein"; protein id = "AEI00267.1"

98595..100031 UL44 gene; product = "glycoprotein C"; protein id = "AEI00252.1"

25078..25983 UL7 gene; product = "UL-7 like protein"; protein id = "AEI00208.1"

Complement(26038..28332) UL8 gene; product = "UL-8 like protein"; protein id = "AEI00209.1"

48267..49865 UL21 gene; product = "UL-21 like protein"; protein id = "AEI00223.1"

Complement(50033..52549) UL22 gene; product = "UL-22 like protein"; protein id = "AEI00225.1"

75497..75880 UL35 gene; product = "UL-35 protein"; protein id = "AEI00241.1"

Complement(75498..85154) UL36 gene; product = "UL-36 protein"; protein id = "AEI00242.1"

92867..93928 UL40 gene; product = "UL-40 protein"; protein id = "AEI00248.1"

Complement(93990..95261) UL41 gene; product = "UL-41 protein"; protein id = "AEI00249.1"

108470..109777 UL50 gene; product = "UL-50 protein"; protein id = "AEI00260.1"

Complement(109847..110593) UL51 gene; product = "UL-51 protein"; protein id = "AEI00261.1"

115036..116466 UL54 gene; product = "UL-54 protein"; protein id = "AEI00264.1"

Complement(116571..117377) LORF4 gene; product = "LORF4 protein"; protein id = "AEI00265.1"

145853..146548 US10 gene; product = "US10 protein"; protein id = "AEI00292.1"

Complement(146697..147665) SORF4 gene; product = "SORF4 protein"; protein id = "AEI00294.1"

97141..98385 UL43 gene; product = "UL43 protein"; protein id = "AEI00251.1"

Complement(147857..148672) US2 gene; product = "US2 protein"; protein id = "AEI00297.1"

150322..151479 US6 gene; product = "glycoprotein D"; protein id = "AEI00299.1"

Having thus described in detail preferred embodiments of the present invention, it is to be understood that the invention defined by the above examples is not to be limited to particular details set forth in the above description as many apparent variations thereof are possible without departing from the spirit or scope of the present invention.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

SEQUENCE LISTING

```
<160> NUMBER OF SEQ ID NOS: 64

<210> SEQ ID NO 1
<211> LENGTH: 1665
<212> TYPE: DNA
<213> ORGANISM: artificial sequence
<220> FEATURE:
<223> OTHER INFORMATION: NDV-F codon-optimized gene from modified wt
      VIId

<400> SEQUENCE: 1
atgggcagca agcccagcac aagaatccca gcccccctga tgctgatcac ccgcatcatg      60
ctgatcctgg gctgcatcag acccacaagc tccctggatg gacgccccct ggccgctgcc     120
ggcatcgtgg tgaccggcga caaggccgtg aacgtgtaca ccagcagcca gaccggcagc     180
atcatcgtga agctgctgcc caacatgccc agagacaaag aggcctgcgc caaggccccc     240
ctggaagcct acaacagaac cctgaccacc tgctgaccc cctgggcga cagcatcaga      300 aagatccagg gctccgtgag cacaagcggc ggaggaaagc agggcagact gatcggcgcc     360
gtgatcggca gcgtggccct gggagtggct acagctgccc agattaccgc tgcagccgcc     420
ctgatccagg ccaaccagaa cgccgccaac atcctgagac tgaaagagag cattgccgcc     480
accaacgagg ccgtgcacga agtgaccgac ggcctgagcc agctgtccgt ggccgtgggc     540
aagatgcagc agttcgtgaa cgaccagttc aacaacaccg ccagagagct ggactgcatc     600
aagatcaccc agcaggtggg cgtggagctg aacctgtacc tgaccgagct gaccacagtg     660 ttcggcccc agatcacaag cccagccctg acacagctga ccatccaggc cctgtacaac     720
ctggctggcg gcaacatgga ctatctgctg acaaagctgg aatcggcaa caaccagctg     780 tccagcctga tcggaagcgg cctgatcacc ggctacccca tcctgtacga cagccagaca     840
cagctgctgg gcatccaggt gaacctgccc agcgtgggca acctgaacaa catgcgcgcc     900
acctacctgg aaaccctgag cgtgtccacc accaagggct acgccagcgc cctggtgccc     960
aaggtggtga cacaggtggg cagcgtgatc gaggaactgg acaccagcta ctgcatcgag    1020
agcgacctgg acctgtactg caccagaatc gtgaccttcc aatgagccc cggcatctac    1080 agctgcctga gcggcaacac cagcgcctgc atgtacagca agaccgaagg cgcactgaca    1140
acaccctaca tggccctgaa gggaagcgtg atcgccaact gcaagatcac cacctgcaga    1200
tgcaccgacc ccccaggcat catcagccag aactacggcg aggccgtgag cctgatcgat    1260
cgccattcct gtaacgtgct gtccctggac ggcatcacac tgagactgag cggcgagttc    1320
gatgccacct accagaagaa catcagcatc ctggacagcc aggtgatcgt gaccggcaac    1380
ctggacatca gcaccgagct gggcaacgtg aataacagca tcagcaacgc cctggacaga    1440
ctggccgaga gcaacagcaa gctggaaaaa gtgaacgtgc gcctgacatc cacttccgct    1500
ctgatcacct acatcgtgct gaccgtgatc agcctggtgt tcggcgccct gagcctggtg    1560
ctggcctgct acctgatgta caagcagaag gcccagcaga aaccctgct gtggctgggc    1620 aacaacaccc tggaccagat gagagccacc accagagcct gatga                   1665
```

<210> SEQ ID NO 2
<211> LENGTH: 553
<212> TYPE: PRT
<213> ORGANISM: artificial sequence
<220> FEATURE:
<223> OTHER INFORMATION: NDV-F protein of modified wt VIId of codon-
      optimized gene

<400> SEQUENCE: 2

```
Met Gly Ser Lys Pro Ser Thr Arg Ile Pro Ala Pro Leu Met Leu Ile
1               5                   10                  15

Thr Arg Ile Met Leu Ile Leu Gly Cys Ile Arg Pro Thr Ser Ser Leu
            20                  25                  30

Asp Gly Arg Pro Leu Ala Ala Ala Gly Ile Val Val Thr Gly Asp Lys
        35                  40                  45

Ala Val Asn Val Tyr Thr Ser Ser Gln Thr Gly Ser Ile Ile Val Lys
    50                  55                  60

Leu Leu Pro Asn Met Pro Arg Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Lys Ile Gln Gly Ser Val Ser Thr Ser Gly Gly Gly
            100                 105                 110

Lys Gln Gly Arg Leu Ile Gly Ala Val Ile Gly Ser Val Ala Leu Gly
        115                 120                 125

Val Ala Thr Ala Ala Gln Ile Thr Ala Ala Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ser
                165                 170                 175

Val Ala Val Gly Lys Met Gln Gln Phe Val Asn Asp Gln Phe Asn Asn
            180                 185                 190

Thr Ala Arg Glu Leu Asp Cys Ile Lys Ile Thr Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Tyr
            260                 265                 270

Pro Ile Leu Tyr Asp Ser Gln Thr Gln Leu Leu Gly Ile Gln Val Asn
        275                 280                 285

Leu Pro Ser Val Gly Asn Leu Asn Asn Met Arg Ala Thr Tyr Leu Glu
    290                 295                 300

Thr Leu Ser Val Ser Thr Thr Lys Gly Tyr Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Ser Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
```

```
              355                 360                 365
Ala Cys Met Tyr Ser Lys Thr Glu Gly Ala Leu Thr Thr Pro Tyr Met
370                 375                 380

Ala Leu Lys Gly Ser Val Ile Ala Asn Cys Lys Ile Thr Thr Cys Arg
385                 390                 395                 400

Cys Thr Asp Pro Pro Gly Ile Ile Ser Gln Asn Tyr Gly Glu Ala Val
                405                 410                 415

Ser Leu Ile Asp Arg His Ser Cys Asn Val Leu Ser Leu Asp Gly Ile
                420                 425                 430

Thr Leu Arg Leu Ser Gly Glu Phe Asp Ala Thr Tyr Gln Lys Asn Ile
                435                 440                 445

Ser Ile Leu Asp Ser Gln Val Ile Val Thr Gly Asn Leu Asp Ile Ser
                450                 455                 460

Thr Glu Leu Gly Asn Val Asn Asn Ser Ile Ser Asn Ala Leu Asp Arg
465                 470                 475                 480

Leu Ala Glu Ser Asn Ser Lys Leu Glu Lys Val Asn Val Arg Leu Thr
                485                 490                 495

Ser Thr Ser Ala Leu Ile Thr Tyr Ile Val Leu Thr Val Ile Ser Leu
                500                 505                 510

Val Phe Gly Ala Leu Ser Leu Val Leu Ala Cys Tyr Leu Met Tyr Lys
                515                 520                 525

Gln Lys Ala Gln Gln Lys Thr Leu Leu Trp Leu Gly Asn Asn Thr Leu
                530                 535                 540

Asp Gln Met Arg Ala Thr Thr Arg Ala
545                 550

<210> SEQ ID NO 3
<211> LENGTH: 1662
<212> TYPE: DNA
<213> ORGANISM: artificial sequence
<220> FEATURE:
<223> OTHER INFORMATION: NDV-F DAN wt VIId

<400> SEQUENCE: 3
atgggctcca aaccttctac caggatccca gcacctctga tgctgatcac ccggattatg      60
ctgatattgg gctgtatccg tccgacaagc tctcttgacg gcaggcctct tgcagctgca     120
ggaattgtag taacaggaga taaggcagtc aatgtataca cttcgtctca gacagggtca     180
atcatagtca agttgctccc gaatatgccc agggataagg aggcgtgtgc aaaagcccca     240
ttagaggcat ataacagaac actgactact tgctcactc ctcttggcga ctccatccgc      300
aagatccaag ggtctgtgtc cacatctgga ggaggcaagc aaggccgcct gataggtgct     360
gttattggca gtgtagctct ggggttgcaa cagcggcac agataacagc agctgcggcc     420
ctaatacaag ccaaccagaa tgccgccaac atcctccggc ttaaggagag cattgctgca     480
accaatgaag ctgtgcatga agtcaccgac ggattatcac aactatcagt ggcagttggg     540
aagatgcagc agtttgtcaa tgaccagttt aataatacgg cgcgagaatt ggactgtata     600
aaaatcacac aacaggttgg tgtagaactc aacctatacc taactgaatt gactacagta     660
ttcgggccac agatcaccta ccctgcatta actcagctga ccatccaggc actttataat     720
ttagctggtg gcaatatgga ttacttatta actaagttag gtatagggaa caatcaactc     780
agctcgttaa ttggtagcgg cctgatcact ggttacccta tactgtatga ctcacagact     840
caactcttgg gcatacaagt gaatttaccc tcagtcggga acttaaataa tatgcgtgcc     900
acctatttgg agaccttatc tgtaagtaca accaaaggat atgcctcagc acttgtcccg     960
```

```
aaagtagtga cacaagtcgg ttccgtgata gaagagcttg acacctcata ctgtatagag   1020
tccgatctgg atttatattg tactagaata gtgacattcc ccatgtcccc aggtatttat   1080
tcctgtttga gcggcaacac atcagcttgc atgtattcaa agactgaagg cgcactcact   1140
acgccgtata tggcccttaa aggctcagtt attgccaatt gtaaaataac aacatgtaga   1200
tgtacagacc ctcctggtat catatcgcaa aattatggag aagctgtatc cctgatagat   1260
agacattcgt gcaatgtctt atcattagac gggataactc taaggctcag tggggaattt   1320
gatgcaactt atcaaaagaa catctcaata ctagattctc aagtcatcgt gacaggcaat   1380
cttgatatat caactgaact tggaaacgtc aacaattcaa tcagcaatgc cttggatagg   1440
ttggcagaaa gcaacagcaa gctagaaaaa gtcaatgtca gactaaccag cacatctgct   1500
ctcattacct atattgttct aactgtcatt tctctagttt tcggtgcact tagtctggtg   1560
ttagcgtgtt acctgatgta caaacagaag gcacaacaaa agaccttgct atggcttggg   1620
aataataccc tcgatcagat gagagccact acaagagcat ga                       1662
```

<210> SEQ ID NO 4
<211> LENGTH: 1695
<212> TYPE: DNA
<213> ORGANISM: artificial sequence
<220> FEATURE:
<223> OTHER INFORMATION: NDV-F DNA with GenBank accession No. AY337464.1

<400> SEQUENCE: 4

```
ctggatcccg gttggctcat tcaggacgca atatgggctc caaaccttct accaggatcc     60
cagcacctct gatgctgatc acccggatta tgctgatatt gggctgtatc cgtccgacaa    120
gctctcttga cggcaggcct cttgcagctg caggaattgt agtaacagga gataaggcag    180
tcaatgtata cacttcgtct cagacagggt caatcatagt caagttgctc ccgaatatgc    240
ccagggataa ggaggcgtgt gcaaaagccc cattagaggc atataacaga acactgacta    300
ctttgctcac tcctcttggc gactccatcc gcaagatcca agggtctgtg tccacatctg    360
gaggaaggag acaaaaacgc tttataggtg ctgttattgg cagtgtagct cttggggttg    420
caacagcggc acagataaca gcagctgcgg ccctaataca agccaaccag aatgccgcca    480
acatcctccg gcttaaggag agcattgctg caaccaatga agctgtgcat gaagtcaccg    540
acggattatc acaactatca gtggcagttg ggaagatgca gcagtttgtc aatgaccagt    600
ttaataatac ggcgcgagaa ttggactgta taaaaatcac acaacaggtt ggtgtagaac    660
tcaacctata cctaactgaa ttgactacag tattcgggcc acagatcacc tcccctgcat    720
taactcagct gaccatccag gcactttata atttagctgg tggcaatatg gattacttat    780
taactaagtt aggtataggg aacaatcaac tcagctcgtt aattggtagc ggcctgatca    840
ctggttaccc tatactgtat gactcacaga ctcaactctt gggcatacaa gtgaatttac    900
cctcagtcgg gaacttaaat aatatgcgtg ccacctattt ggagacctta tctgtaagta    960
caaccaaagg atatgcctca gcacttgtcc cgaaagtagt gacacaagtc ggttccgtga   1020
tagaagagct tgacacctca tactgtatag agtccgatct ggatttatat tgtactagaa   1080
tagtgacatt ccccatgtcc ccaggtattt attcctgttt gagcggcaac acatcagctt   1140
gcatgtattc aaagactgaa ggcgcactca ctacgccgta tatggccctt aaaggctcag   1200
ttattgccaa ttgtaggata acaacatgta gatgtacaga ccctcctggt atcatatcgc   1260
aaaattatgg agaagctgta tccctgatag atagacattc gtgcaatgtc ttatcattag   1320
```

```
acgggataac tctaaggctc agtggggaat tgatgcaac ttatcaaaag aacatctcaa    1380
tactagattc tcaagtcatc gtgacaggca atcttgatat atcaactgaa cttggaaacg    1440
tcaacaattc aatcagcaat gccttggata ggttggcaga aagcaacagc aagctagaaa    1500
aagtcaatgt cagactaacc agcacatctg ctctcattac ctatattgtt ctaactgtca    1560
tttctctagt tttcggtgca cttagtctgg gtttagcgtg ttacctgatg tacaaacaga    1620
aggcacaaca aaagaccttg ctatggcttg ggaataatac cctcgatcag atgagagcca    1680
ctacaagagc atgaa                                                     1695
```

<210> SEQ ID NO 5
<211> LENGTH: 553
<212> TYPE: PRT
<213> ORGANISM: artificial sequence
<220> FEATURE:
<223> OTHER INFORMATION: NDV-F protein with GenBank accession No. AAP97877.1

<400> SEQUENCE: 5

```
Met Gly Ser Lys Pro Ser Thr Arg Ile Pro Ala Pro Leu Met Leu Ile
1               5                   10                  15

Thr Arg Ile Met Leu Ile Leu Gly Cys Ile Arg Pro Thr Ser Ser Leu
                20                  25                  30

Asp Gly Arg Pro Leu Ala Ala Ala Gly Ile Val Val Thr Gly Asp Lys
            35                  40                  45

Ala Val Asn Val Tyr Thr Ser Ser Gln Thr Gly Ser Ile Ile Val Lys
        50                  55                  60

Leu Leu Pro Asn Met Pro Arg Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Lys Ile Gln Gly Ser Val Ser Thr Ser Gly Gly Arg
            100                 105                 110

Arg Gln Lys Arg Phe Ile Gly Ala Val Ile Gly Ser Val Ala Leu Gly
        115                 120                 125

Val Ala Thr Ala Ala Gln Ile Thr Ala Ala Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ser
                165                 170                 175

Val Ala Val Gly Lys Met Gln Gln Phe Val Asn Asp Gln Phe Asn Asn
            180                 185                 190

Thr Ala Arg Glu Leu Asp Cys Ile Lys Ile Thr Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Tyr
            260                 265                 270

Pro Ile Leu Tyr Asp Ser Gln Thr Gln Leu Leu Gly Ile Gln Val Asn
        275                 280                 285
```

Leu Pro Ser Val Gly Asn Leu Asn Asn Met Arg Ala Thr Tyr Leu Glu
290                 295                 300

Thr Leu Ser Val Ser Thr Thr Lys Gly Tyr Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Ser Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
370                 375                 380

Ala Leu Lys Gly Ser Val Ile Ala Asn Cys Arg Ile Thr Thr Cys Arg
385                 390                 395                 400

Cys Thr Asp Pro Pro Gly Ile Ile Ser Gln Asn Tyr Gly Glu Ala Val
                405                 410                 415

Ser Leu Ile Asp Arg His Ser Cys Asn Val Leu Ser Leu Asp Gly Ile
            420                 425                 430

Thr Leu Arg Leu Ser Gly Glu Phe Asp Ala Thr Tyr Gln Lys Asn Ile
        435                 440                 445

Ser Ile Leu Asp Ser Gln Val Ile Val Thr Gly Asn Leu Asp Ile Ser
450                 455                 460

Thr Glu Leu Gly Asn Val Asn Asn Ser Ile Ser Asn Ala Leu Asp Arg
465                 470                 475                 480

Leu Ala Glu Ser Asn Ser Lys Leu Glu Lys Val Asn Val Arg Leu Thr
                485                 490                 495

Ser Thr Ser Ala Leu Ile Thr Tyr Ile Val Leu Thr Val Ile Ser Leu
            500                 505                 510

Val Phe Gly Ala Leu Ser Leu Gly Leu Ala Cys Tyr Leu Met Tyr Lys
        515                 520                 525

Gln Lys Ala Gln Gln Lys Thr Leu Leu Trp Leu Gly Asn Asn Thr Leu
530                 535                 540

Asp Gln Met Arg Ala Thr Thr Arg Ala
545                 550

<210> SEQ ID NO 6
<211> LENGTH: 1662
<212> TYPE: DNA
<213> ORGANISM: artificial sequence
<220> FEATURE:
<223> OTHER INFORMATION: NDV-F DNA wildtype V (CA02 strain) with GenBank
      accession No. EF520718

<400> SEQUENCE: 6
atgggctcca aaccttctac ctggatctca gtaactctga tgctgatcac tcggaccatg      60
cttatactta gctgtatctg tccgacaagc tctcttgacg gtagacctct cgcagccgca     120
gggattgtgg tgacgggaga taaagcagtc aatatataca cttcatctca aacagggtca     180
atcatcatca agttactccc aaatatgccc aaggataaag aagcgtgcgc aaaagcccca     240
ttggaagcat acaatagaac actgaccact ttactcaccc ctcttggtga ctctatccgc     300
agaatacaag ggtctgcgac tacatctgga ggaaggagac agaaacgctt tgtaggtgcc     360
attatcggca gtagctct tggggttgca acagctgcac agataacagc agccgcagct     420
ctgatacaag ccaaccaaaa tgctgccaac atcctccggc ttaaggagag cattgctgca     480
accaatgacg ctgtacacga ggtcactaac ggattatcac aactagcggt ggcggtcggg     540

```
aagatgcagc agtttgttaa taaccagttt aataatacgg cgcgagaatt ggactgcata    600
aaaattgcac aacaagtggg cgtcgaactc aatttgtatc taactgaatt gaccacagtg    660
ttcgggccac aaatcacctc ccctgcttta actcagctga ctatccaggc actttataat    720
ttagccggtg gcaatatgga ttacctgttg actaagttgg gtgtagggaa taatcaactc    780
agttcgttaa ttggtagtgg cttgataact ggcaacccta tactatatga ctcacagacc    840
caactcttag gcatacagat aaatttaccc tcagtcggga gcctaaataa tatgcgtgcc    900
acctacttgg agaccttatc cgtaagcacg accaaagggt cgcctcagc acttgtcccg     960 aaagttgtga cgcaagtcgg ctctgtgata aagaacttg acacctcata ttgtatagaa    1020
tccgatatag atctatattg tacaagggta gtgacattcc ccatgtctcc tggtatttac    1080
tcctgtctga gcggcaatac gtcagcttgt atgtattcaa agaccgaagg tgcactcact    1140
acaccataca tggccctcaa aggctcagtt attgccaatt gcaagatgac tacatgcaga    1200
tgcgcagatc ccccaggtat catatcacag aattatgggg aagctgtgtc tctaatagat    1260
aaacattcat gcagtgtctt gtccctagac gggataactc tgaggctcag tggggaattt    1320
gatgcgacct atcaaaagaa catctcaata ctagattctc aagtcatcgt gacaggaaat    1380
ctcgatatat caactgagct tgggaatgtt aacaactcga taagcagtac cctggacaaa    1440
ttagcagaaa gcaacaacaa gctaaacaag gtcaatgtaa acctaaccag cacatctgct    1500
ctcatcactt atattgtctt agctatcgta tctcttgctt tcggcgtaat tagcctggtt    1560
ctagcatgct acctgatgta taaacaaaga gcacaacaaa agaccttact atggctcggg    1620
aacaacaccc ttgatcagat gagagccacc acaagaacct ga                       1662
```

<210> SEQ ID NO 7
<211> LENGTH: 553
<212> TYPE: PRT
<213> ORGANISM: artificial sequence
<220> FEATURE:
<223> OTHER INFORMATION: NDV-F protein wildtype V (CA02 strain) with
      GenBank accession No. ABS84266

<400> SEQUENCE: 7

```
Met Gly Ser Lys Pro Ser Thr Trp Ile Ser Val Thr Leu Met Leu Ile
1               5                   10                  15

Thr Arg Thr Met Leu Ile Leu Ser Cys Ile Cys Pro Thr Ser Ser Leu
            20                  25                  30

Asp Gly Arg Pro Leu Ala Ala Ala Gly Ile Val Val Thr Gly Asp Lys
        35                  40                  45

Ala Val Asn Ile Tyr Thr Ser Ser Gln Thr Gly Ser Ile Ile Ile Lys
    50                  55                  60

Leu Leu Pro Asn Met Pro Lys Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Gly Ser Ala Thr Thr Ser Gly Gly Arg
            100                 105                 110

Arg Gln Lys Arg Phe Val Gly Ala Ile Ile Gly Ser Val Ala Leu Gly
        115                 120                 125

Val Ala Thr Ala Ala Gln Ile Thr Ala Ala Ala Ala Leu Ile Gln Ala
    130                 135                 140

Asn Gln Asn Ala Ala Asn Ile Leu Arg Leu Lys Glu Ser Ile Ala Ala
145                 150                 155                 160
```

-continued

Thr Asn Asp Ala Val His Glu Val Thr Asn Gly Leu Ser Gln Leu Ala
                165                 170                 175

Val Ala Val Gly Lys Met Gln Gln Phe Val Asn Gln Phe Asn Asn
        180                 185                 190

Thr Ala Arg Glu Leu Asp Cys Ile Lys Ile Ala Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Leu Leu Gly Ile Gln Ile Asn
        275                 280                 285

Leu Pro Ser Val Gly Ser Leu Asn Asn Met Arg Ala Thr Tyr Leu Glu
    290                 295                 300

Thr Leu Ser Val Ser Thr Thr Lys Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Ser Asp Ile Asp Leu Tyr Cys Thr Arg Val Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Ala Leu Lys Gly Ser Val Ile Ala Asn Cys Lys Met Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Lys His Ser Cys Ser Val Leu Ser Leu Asp Gly Ile
            420                 425                 430

Thr Leu Arg Leu Ser Gly Glu Phe Asp Ala Thr Tyr Gln Lys Asn Ile
        435                 440                 445

Ser Ile Leu Asp Ser Gln Val Ile Val Thr Gly Asn Leu Asp Ile Ser
    450                 455                 460

Thr Glu Leu Gly Asn Val Asn Asn Ser Ile Ser Ser Thr Leu Asp Lys
465                 470                 475                 480

Leu Ala Glu Ser Asn Asn Lys Leu Asn Lys Val Asn Val Asn Leu Thr
                485                 490                 495

Ser Thr Ser Ala Leu Ile Thr Tyr Ile Val Leu Ala Ile Val Ser Leu
            500                 505                 510

Ala Phe Gly Val Ile Ser Leu Val Leu Ala Cys Tyr Leu Met Tyr Lys
        515                 520                 525

Gln Arg Ala Gln Gln Lys Thr Leu Leu Trp Leu Gly Asn Asn Thr Leu
    530                 535                 540

Asp Gln Met Arg Ala Thr Thr Arg Thr
545                 550

<210> SEQ ID NO 8
<211> LENGTH: 1665

<212> TYPE: DNA
<213> ORGANISM: artificial sequence
<220> FEATURE:
<223> OTHER INFORMATION: NDV-F codon-optimized gene from modified wildtype V (CA02 strain)

<400> SEQUENCE: 8

```
atgggcagca agcccagcac ctggatcagc gtgaccctga tgctgatcac cagaaccatg      60
ctgatcctga gctgcatctg ccccacaagc agcctggacg cagacccct ggccgctgcc     120
ggcatcgtgg tgaccggcga caaggccgtg aacatctaca ccagcagcca gaccggcagc    180
atcatcatca gctgctgcc caacatgccc aaggacaaag aggcctgcgc caaggccccc     240
ctggaagcct acaacagaac cctgaccacc ctgctgaccc ccctgggcga cagcatcaga    300
agaatccagg gcagcgccac cacaagcggc ggaggaaagc agggcagact ggtgggcgct    360
atcatcggga gcgtggccct gggcgtggcc acagctgccc agattaccgc tgcagccgcc    420
ctgattcagg ccaatcagaa cgccgccaac atcctgagac tgaaagagag cattgccgcc    480
accaacgacg ccgtgcacga gtgacaaac ggactgtccc agctggctgt cgctgtcggc    540
aagatgcagc agttcgtgaa caaccagtta acaacaccg ccagagagct ggactgcatc     600
aagatcgccc agcaggtggg cgtggagctg aacctgtacc tgaccgagct gaccacagtg    660
ttcggccccc agatcacaag cccccgctctg acccagctga caatccaggc cctgtacaac    720
ctggctggcg gcaacatgga ctatctgctg actaagctgg gagtgggcaa caaccagctg    780
tccagcctga tcgggtccgg gctgatcaca ggcaacccca tcctgtacga cagccagaca    840
cagctgctgg gcatccagat caacctgcca tccgtgggaa gctgaacaa catgagagcc    900
acctacctgg aaaccctgag cgtgtccacc accaagggct cgccagcgc cctggtgccc     960
aaggtggtga cacaggtggg cagcgtgatc gaggaactgg acaccagcta ctgcatcgag   1020
agcgacatcg acctgtactg caccagagtg gtgaccttcc caatgagccc cggcatctac   1080
agctgcctga gcggcaacac cagcgcctgc atgtacagca gaccgaagg agcactgaca   1140
acaccctaca tggccctgaa gggaagcgtg atcgccaact gcaagatgac cacctgcaga   1200
tgcgccgacc cccaggcat catcagccag aactacggcg aggccgtgag cctgatcgac   1260
aaacattcct gtagcgtgct gtccctggat ggcatcacac tgagactgag cggcgagttc   1320
gacgccacct accagaagaa catcagcatc ctggacagcc aggtgatcgt gaccggcaac   1380
ctggacatca gcaccgagct gggcaacgtg aacaacagca tcagcagcac cctggacaag   1440
ctggccgagt ccaacaacaa gctgaacaaa gtgaacgtga acctgaccag cacaagcgcc   1500
ctgatcacct acatcgtgct ggccatcgtg tccctggcct tcggcgtgat cagcctggtg   1560
ctggcctgct acctgatgta caagcagaga gcccagcaga aaaccctgct gtggctgggc   1620
aataacaccc tggaccagat gagggccacc accagaacct gatga                   1665
```

<210> SEQ ID NO 9
<211> LENGTH: 553
<212> TYPE: PRT
<213> ORGANISM: artificial sequence
<220> FEATURE:
<223> OTHER INFORMATION: NDV-F protein of codon-optimized NDV-F gene of modified wildtype V (CA02 strain)

<400> SEQUENCE: 9

```
Met Gly Ser Lys Pro Ser Thr Trp Ile Ser Val Thr Leu Met Leu Ile
1               5                   10                  15

Thr Arg Thr Met Leu Ile Leu Ser Cys Ile Cys Pro Thr Ser Ser Leu
```

```
                    20                  25                  30
Asp Gly Arg Pro Leu Ala Ala Gly Ile Val Val Thr Gly Asp Lys
                35                  40                  45

Ala Val Asn Ile Tyr Thr Ser Ser Gln Thr Gly Ser Ile Ile Lys
 50                  55                  60

Leu Leu Pro Asn Met Pro Lys Asp Lys Glu Ala Cys Ala Lys Ala Pro
 65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Gly Ser Ala Thr Thr Ser Gly Gly Gly
                100                 105                 110

Lys Gln Gly Arg Leu Val Gly Ala Ile Ile Gly Ser Val Ala Leu Gly
                115                 120                 125

Val Ala Thr Ala Ala Gln Ile Thr Ala Ala Ala Ala Leu Ile Gln Ala
                130                 135                 140

Asn Gln Asn Ala Ala Asn Ile Leu Arg Leu Lys Glu Ser Ile Ala Ala
145                 150                 155                 160

Thr Asn Asp Ala Val His Glu Val Thr Asn Gly Leu Ser Gln Leu Ala
                165                 170                 175

Val Ala Val Gly Lys Met Gln Gln Phe Val Asn Asn Gln Phe Asn Asn
                180                 185                 190

Thr Ala Arg Glu Leu Asp Cys Ile Lys Ile Ala Gln Gln Val Gly Val
                195                 200                 205

Glu Leu Asn Leu Tyr Leu Thr Glu Leu Thr Thr Val Phe Gly Pro Gln
                210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Gly Ser Gly Leu Ile Thr Gly Asn
                260                 265                 270

Pro Ile Leu Tyr Asp Ser Gln Thr Gln Leu Leu Gly Ile Gln Ile Asn
                275                 280                 285

Leu Pro Ser Val Gly Ser Leu Asn Asn Met Arg Ala Thr Tyr Leu Glu
                290                 295                 300

Thr Leu Ser Val Ser Thr Thr Lys Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Ser Asp Ile Asp Leu Tyr Cys Thr Arg Val Val Thr
                340                 345                 350

Phe Pro Met Ser Pro Gly Ile Tyr Ser Cys Leu Ser Gly Asn Thr Ser
                355                 360                 365

Ala Cys Met Tyr Ser Lys Thr Glu Gly Ala Leu Thr Thr Pro Tyr Met
                370                 375                 380

Ala Leu Lys Gly Ser Val Ile Ala Asn Cys Lys Met Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Lys His Ser Cys Ser Val Leu Ser Leu Asp Gly Ile
                420                 425                 430

Thr Leu Arg Leu Ser Gly Glu Phe Asp Ala Thr Tyr Gln Lys Asn Ile
                435                 440                 445
```

```
Ser Ile Leu Asp Ser Gln Val Ile Val Thr Gly Asn Leu Asp Ile Ser
    450                 455                 460

Thr Glu Leu Gly Asn Val Asn Asn Ser Ile Ser Ser Thr Leu Asp Lys
465                 470                 475                 480

Leu Ala Glu Ser Asn Asn Lys Leu Asn Lys Val Asn Val Asn Leu Thr
                485                 490                 495

Ser Thr Ser Ala Leu Ile Thr Tyr Ile Val Leu Ala Ile Val Ser Leu
                500                 505                 510

Ala Phe Gly Val Ile Ser Leu Val Leu Ala Cys Tyr Leu Met Tyr Lys
                515                 520                 525

Gln Arg Ala Gln Gln Lys Thr Leu Leu Trp Leu Gly Asn Asn Thr Leu
    530                 535                 540

Asp Gln Met Arg Ala Thr Thr Arg Thr
545                 550
```

<210> SEQ ID NO 10
<211> LENGTH: 1411
<212> TYPE: DNA
<213> ORGANISM: artificial sequence
<220> FEATURE:
<223> OTHER INFORMATION: MCMV IE promoter

<400> SEQUENCE: 10

```
aattcaatag tggatccccc aactccgccc gttttatgac tagaaccaat agttttaat       60 gccaaatgca ctgaaatccc ctaatttgca aagccaaacg cccctatgt gagtaatacg      120 gggactttt acccaatttc ccacgcggaa agccccctaa tacactcata tggcatatga     180
atcagcacgg tcatgcactc taatggcggc ccataggggac tttccacata gggggcgttc   240
accatttccc agcatagggg tggtgactca atggccttta cccaagtaca ttgggtcaat   300
gggaggtaag ccaatgggtt tttcccatta ctggcaagca cactgagtca aatgggactt   360
tccactgggt tttgcccaag tacattgggt caatgggagg tgagccaatg gaaaaaccc    420 attgctgcca agtacactga ctcaataggg actttccaat gggttttcc attgttggca    480 agcatataag gtcaatgtgg gtgagtcaat agggactttc cattgtattc tgcccagtac   540
ataaggtcaa taggggtga atcaacagga aagtcccatt ggagccaagt acactgcgtc    600
aatagggact ttccattggg ttttgcccag tacataaggt caataggga tgagtcaatg   660 ggaaaaaccc attggagcca agtacactga ctcaataggg actttccatt gggttttgcc   720
cagtacataa ggtcaatagg gggtgagtca acaggaaagt tccattggag ccaagtacat   780
tgagtcaata gggactttcc aatgggtttt gcccagtaca aaggtcaat gggaggtaag    840 ccaatgggtt tttcccatta ctggcacgta tactgagtca ttagggactt tccaatgggt   900
tttgcccagt acataaggtc aatagggtg aatcaacagg aaagtcccat ggagccaag    960 tacactgagt caatagggac tttccattgg gttttgccca gtacaaaagg tcaatagggg   1020
gtgagtcaat gggttttcc cattattggc acgtacataa ggtcaatagg ggtgagtcat   1080
tgggtttttc cagccaattt aattaaaacg ccatgtactt tcccaccatt gacgtcaatg   1140
ggctattgaa actaatgcaa cgtgaccttt aaacggtact ttcccatagc tgattaatgg  1200
gaaagtaccg ttctcgagcc aatacacgtc aatgggaagt gaaagggcag ccaaaacgta  1260
acaccgcccc ggttttcccc tgaaattcc atattggcac gcattctatt ggctgagctg   1320
cgttctacgt gggtataaga ggcgcgacca gcgtcggtac cgtcgcagtc ttcggtctga  1380
ccaccgtaga acgcagagct cctcgctgca g                                  1411
```

<210> SEQ ID NO 11
<211> LENGTH: 217
<212> TYPE: DNA
<213> ORGANISM: artificial sequence
<220> FEATURE:
<223> OTHER INFORMATION: SV40 PolyA

<400> SEQUENCE: 11

```
ggggatccag acatgataag atacattgat gagtttggac aaaccacaac tagaatgcag      60
tgaaaaaaat gctttatttg tgaaatttgt gatgctattg ctttatttgt aaccattata     120
agctgcaata aacaagttaa caacaacaat tgcattgatt ttatgtttca ggttcagggg     180
gaggtgtggg aggttttttc ggatcctcta gagtcga                              217
```

<210> SEQ ID NO 12
<211> LENGTH: 368
<212> TYPE: DNA
<213> ORGANISM: artificial sequence
<220> FEATURE:
<223> OTHER INFORMATION: SV40 promoter

<400> SEQUENCE: 12

```
caattcgagc tcggtacagc ttggctgtgg aatgtgtgtc agttagggtg tggaaagtcc      60
ccaggctccc cagcaggcag aagtatgcaa agcatgcatc tcaattagtc agcaaccagg     120
tgtggaaagt ccccaggctc cccagcaggc agaagtatgc aaagcatgca tctcaattag     180
tcagcaacca tagtcccgcc ctaactccg cccatcccgc ccctaactcc gcccagttcc     240
gcccattctc cgccccatgg ctgactaatt ttttttattt atgcagaggc cgaggccgcc     300
tcggcctctg agctattcca gaagtagtga ggaggctttt ttggaggcct aggcttttgc     360
aaaaagct                                                             368
```

<210> SEQ ID NO 13
<211> LENGTH: 154
<212> TYPE: DNA
<213> ORGANISM: artificial sequence
<220> FEATURE:
<223> OTHER INFORMATION: Synthetic PolyA

<400> SEQUENCE: 13

```
aataaaatat ctttattttc attacatctg tgtgttggtt ttttgtgtga atcgatagta      60
ctaacatacg ctctccatca aaacaaaacg aaacaaaaca aactagcaaa ataggctgtc     120
cccagtgcaa gtgcaggtgc cagaacattt ctct                                 154
```

<210> SEQ ID NO 14
<211> LENGTH: 165994
<212> TYPE: DNA
<213> ORGANISM: artificial sequence
<220> FEATURE:
<223> OTHER INFORMATION: SB-1 genome HQ840738.1

<400> SEQUENCE: 14

```
ataccaaaac tctcgcggcg gcgaactgaa taaaaaaat tcaccctaac cctaacccta      60
aaggcctaac cctaacccta aaggcctaac cctaacccta acggcctaac cctaacccta     120
accctaaccc taaccctaac cctaacccta accctaaccc taaccctaac cctaacccta     180
accctaaccc taaccaactt aatatccccc cctgcatttc accccccccc caaaaaagga     240
acatagcaca acaattaacg cggctgggcc gcagcctccc gccgccacag gtgcactcag     300
```

```
cccgcgggct gccgcacccc gcgaactgtc ggctacaggc agaatgaacg cgcagcattg      360
cgcggacaca gtgggtgacc gaagcacacc accacagact ctgaccctgc catagccccg      420
accgtgaaat gaggcccggc gaggcctaac agtcaccccg accgtgatac atgacaccaa      480
cgctgcccgt tacattaaaa ggtcctagcc ctacatgccg taaccgccaa agccgctacc      540
cttaatatgt cctgaccccg actatggact attaccctaa ccctgaaagg ccataacagt      600
gaccctaaca gtcctgacgc cgaccccgag aggccctaac cgccaccgta aacgccctg       660 gcccaagccc ttaatgtggc cctaacaggc actaaaacga ataagacagg ccctaacccc      720
gaccgtgatg acaggccgaa cccccgaccc taacagaccc tatcgcgggg tccaataatc      780
cgctttccca ccccgtcctt caacggaaga gtgcgtgctt cagacccgcg acccgggca       840 acttgtaccc ggccccgagc gtctctgtgc aacgcactac attgaaagta aacaacaggt      900
aggcggtgtc gactcaggtc tgtgcgaacg ccaaccgctt tcaagaacgg aggctacgcg      960
cagtcacgaa tgaggaagtg gttttgtgag gccgatcccc tttcctgttt ttttgagact     1020
cgcagccgat tccgagagga ccgggagcgc acgacgatgg gctcccgcct tacagttttc     1080
tccgcgaaca ccgtactcct gctgggaagg taagccgcgg tccactgttt acttcccgtg     1140
caagcacttc cgcgtacgcg attgtccggc acgtccggac gcgcttaatt tccgtgtcct     1200
gactgcatcc ggcgactaca gcgccgcatc ccccctcaa cccccccccc gtagattcca      1260
tggccgagtc cgccacaccg gcttttggaa atttcgcggg gggctggcgg agaccgcctc     1320
tgtcccggcg ctcgggaagt gcgtacagga tgttttctt tttccggcag cggtgcagca      1380
atggcgggga cgcaggacgc ttgggaaccg cggaccgcag cctttgcgtc gccgccggga     1440
gacggcggct tcatcgcgca cgcgggcgct cctagccccg acccgggctg aagccgtcgg     1500
ccagtacgaa taaaaacgcc catggaatgc tgctacgaga cgcgtccgtc cgtccgtccg     1560
tctggctcgc gcgcgagcgc atgcgcgcac atccgccgtt tccgtaaaca ccggaacgac     1620
accctcgccg gccccgaccc tcaatccgcg gcacgccctg accctataac cattacacgc     1680
cccgccctaa ttccgagaga ccttaacccc taacctaacc ctgttaccct acccctaaca     1740
ggccctaacc ctgacgggga gggggaacgc ctccttaaca gactaacaat aatgggggg      1800 gggaggaggg tcgctcctag ccctaacggg cccaaccttc gcgcctaccc taccctgcc      1860 aggccctaac cctactcggg gggggaggg gggatgggaa cctaagcgtg gcaggtcgaa      1920
ccgtgtgggg ggggccctgc ccgtaacaga ccccagcccc tacccttacg ggcccaacc      1980 cttacaagac cctaacctta gtactcggtg ggagcctaac ccgaataggg cctgacatta     2040
ataggcccta ataaccctta cacctgtgac cacgaactct gataggccat aaccctgacc     2100
ttgacaggtc ctaaccccgg gcccctaagc caaacgccgc ccttgagacc ctaaccccga     2160
ggccttaacc ctgacccaga gaacctaaca ctgataggcc ttcgcgctct tagtctctga     2220
tcataatcac cccgacccta agacccgat ccagaagcct aacccgacc ctaaagaccc       2280 gatccagaag cctaaccccg accctgaccc taaccctgcc cctaaaggcc taaccccgac     2340
cctgcacctg agcttgcccc taaaggccta accccgaccc cgacactacc cctaaaggcc     2400
taaccccgac aacgcactac cccctacagg cctaaccccg acaacgacac tacccctaaa     2460
ggcctaaccc taaacccgac actacccta aaggtctaac cccgaactcg acccgacccc     2520
taaacgccta accacgaccc cgagactgcc cctaaaggcc taaccctaaa ccagacacaa     2580
cccctaaagg cctaaccccg aacccgaccc gaccctaaa cgcctaactt tggacccaa      2640 ccctaacctt aacggcatat ccctgtccat gaccctgaca cccgaccctg gcactaaccc     2700
```

```
ttaccccgag ccctgcccc taagggccca accatcaccc taaaggcccg accctgcccc    2760
taaagaccta agcatgacct taaaggccta accctgacca tgaccctaag ggcccgaccc    2820
taaccctaac ctagtaccct ccttccacac ccccccccg aaaaccgagc atagcccaac     2880
aatgaactcg gccggtttaa agatttattt cgatgcgatg cgcggtcacg cccaccacaa    2940
aaatagaccc tgcaatattg atgccggaac cagcccatcg cagagcgggc gaccgctaca    3000
cgggacgcgt attcgtcggg accgcctttc tccggcaggt agcctacacg tacctcacta    3060
tggccataaa gatgcagcca tagagaggta cgtgaagaag cccgtcgga atcagaagca     3120 acatttcagg acgtacgact cgagccgac atgataccag acaccggagt ccacagcgac     3180
cgcgatttcc tctgcgccta ccctcggccg acgaacaacg ccgagggtag gcgtcgagaa    3240
aatcgcgacc gagggtgcgc cctcgttcca cgcgatcccg cagaacgctt cgcgcccagt    3300
ctccgtccat cgacgtggtg cttgatgaca ggatccacct ctaacaccac gcgatgcgct    3360
ccgcagcgcc ttcgtcccgg agtagagcgc catctccttc ctccagcacg gtgctcgacg    3420
cggcaataca aaagtctcac gcctcgaaca ccggacgaag gagggaactg cgcgcgtctg    3480
gactttaccg gggcggcttc gtcccgcggc gttccggatg acgtttcgag ggcccactcc    3540
atccttcggt gcggtgcccg agaagggatg acgacctctc acacacagca caaggacgg    3600 cgctgggctc cgtccgatgc tctcgatctc aggcagcacg gcaccgatcc ggagagcgcg    3660
tcgcacgtcg cgtcctaccc ccggagtagt gcatgacggt tactccccgg caagcactcg    3720
tccgaaggag gacacgccac gcgacccgat tcccagccgc ttcgcgcccg gctacttctt    3780
cgcctgcagt ccgccggcag ggctcgagca aacaaactcc catctttccc tgacggcatc    3840
taaccgttaa aatacgacgt caggcaccgt aagggaaaaa atggaagcag ttcggagtac    3900
agacgcctaa ccacgggccc tctctcgccc ctccgcgtcc gatatgcaga tcggtgagag    3960
tactgatcgt ctcatatccg caacgaagac ttcgggatcg atagacgtta tccttcccgc    4020
cccccccccc ccacatagga acctctgttc catcgccatc tgttacaaaa aagggcgagc    4080
ctatccactg gcaacgagcg agaacacagc taggcctccc aggtcgtaac aagccactta    4140
cgtcgtcgcg ggggaaggtc ggtccatttc gctcctattc cgcaccttcg tttggaacag    4200
aagcattaca cacaccgcca tttcccgcg ggcagaattc tagtcttttt gtggttatgc      4260
tcccacctac ccgcacagac acgtactcac ctctcacgat ccagcatatc gccgtaagat    4320
ttacagacat tcctccctcc ccacccaacc gaacactgca cagcggcagc ctaaaagtcg    4380
ctctgcggtc gcatatcccc cccacccccc ttcgatggtc cggtgtacgg agacctctca    4440
cacaacacag gacaccgtac cacggaccat ccgaacggcg ggcgaacagt cacgcaggac    4500
gtggacacga gtcctgcgct cgcacaggca gctgggcggc ggtgctgtct tcctccgacg    4560
gacagcctac aagcaagcca ctaggactac cgatacgacc agagtgacgt gcgtgtaaga    4620
cggcccagga cgaagtcccg cgccccgccg aaaataacag caccgacctg aaagagacca    4680
cgtcttaccc aacagccgac ccccgaacga tgcacgctcc caagagtcgg ccgtaggaga    4740
gcacgcgccc cccatactc ggcgcgcgta cccgcggcca tccctgcagc gcggcccggc      4800
ctcgttgcga ttcagtgaac gtaccgcgcg ccatctccgt ccatcggcgt ggtgctcgat    4860
cccgtcattc ggtgatctca agcaccccgc gaaggaggaa gcggagcgtg taacgatttc    4920
cgcggcgcgc gacgacgccg cgccgtcccg tccgacgttt ggaacgccgc ctcggtcctt    4980
gcgcgcagta cttgagacga tacgtgttaa aatctcaggc accacgctaa ggacggagca    5040
```

```
gagctcggtt cgcttcgctc gcgcgccgac gcatctctgc ttcgcagaac ctgttttgaa    5100
aagaccgcag cgaccaccgc gtgctaccct cggaggggggg catgaggacg gcgcccgata    5160
ctcccgtgca caccgccgag gggggacacg gcgcgcgcgc cgatgctcag ccggttcttc    5220
gcccagagcc ctcccaacct tgtcccacac gacggggagc ggcacgggga atcaattcgt    5280
cttctctcc gcaggcattg cacaacggca atgacacgtg caatgccagc ctgagagaaa      5340
acatacgaac agtcccgagt tccgagtagt aactctcgct ttcgcgccct tccccgactc    5400
gttccgagca tatcaggcga tacgaggcat ttcgcgcgcg tcgccctgtc cgtcccggtt    5460
gtcctagaac gtgacacctc tagggggaccc gggaaggact ggacgacgcg ccgtcgtgcg    5520
gtccgaccgc aatacggcgt cgttacccct tcctcacaac acctgatctc gtggcctaaa    5580
tacccgctca tcgccccgca tccgacgcct ctacctcccc tttgtcccca accgagaaac    5640
ctatccgggg cccgctaagg tcgaaccgcc gagactccgt cgtccggcta ttacccgcca    5700
taacaagtcg ctagtcgaag gatggaatcg cagcggtccg agcggctctc ctctgatatc    5760
ccggcacggc ctattgggat taaggtccgg gcctattcag attacggtta gagtcctcga    5820
gaaacatttc agtctctctg gcatctgaca acggctacgc gccactcaga tgccaaaaca    5880
gactggatgc gtttccaaag gccatcgtgt ctaacaaagg ccagtccctg taactaggcc    5940
aaacatctca tcaccgtcca agtcacaggt acttcaggtt tacggtcgtc tgctatctac    6000
aacgaagaat tcagagccga tctcgccagg gccccttctc cccccctccct tcttccccccc    6060
tcccttctcc cccctccct tctccccct ccttcttcc ccctccctt cttccccct         6120
cccttcttcc ccctccctt cttccccct ccttcttcc ccctccctt cttccccct         6180
cccttcttcc ccctccctt cttccccct ccttcttcc tcccttcccc cccctcccc        6240
tcttcctccc ttccccctcc cttcccccc tcccttcccc cctccttc cccccctccc       6300
ttccccccct cccttcccccc ctccttccc ccttcccc cttccccctct tccccccc        6360
ccctccccac tccctccctt cttccccctt ctcccacctc cgttcagcct tccccctccc    6420
ccctcccttc tccccctcc gttcagcctt ccccctcccc cctcccttct ccccctccg      6480
ttcagacttc ctcctcccca atcgccccc ttcgcaactt gcgaaatcta gtctaacacg      6540
ggtttactta cgcggtttac attcacacag cgggtgcatg ttttccgctg acatttccca    6600
agccggccac aagaaacgaa gcaaaaaaaa aaaagatagg ggtattaatg cgcgccaccc    6660
gtcgctacgc agcccgactc caaatttcga ataatgccct tctaggcatt ggaccgccgc    6720
cccactcccc gcgcaatatc taggcttaat cgccaagatt gaccacgtat cccttatcgc    6780
gccggccgtt caggccctcc ccccccccc acgcctctcg actctttttt ttttccatgg     6840
gccgtccaga ctgagacgac acgtagattc gcggtcgtcc cagaataaag gatgaccccg    6900
cgatgcccat tcccactcgc ccgacgtctc cctccgattc aaaagtactg cggcacgacc    6960
tgcgatggaa gggaaaaaca caccaaacgg ccttaagttt tccggtttgc ctttcccttc    7020
catcgcaaat agcccgcaaa agaaggatcg catttccggc cccgtccggc catcgcgact    7080
catccaccgg ccaaacgggg atatcggacc gcgagacttt aacggctatg tatttcccca    7140
cccgctcttc tcagaggaat ccccgatgca atctagaagc ttatcgttca gagcgtttcg    7200
ggcacggaac ttcctgagaa tatagatcat ctctcagggt gcaccgtacc acacaacgtt    7260
tctgtgggaa aacggaaggc cagtcacttt cacgtagacc cctcaggata cccataacag    7320
aaaaactcag cccccccctcc cctcacgacc attttcctac gtggaatgca ctacaagtac    7380
ctgacatttt gcaaacaggg cgccgagacg tccgatgggg ttccagcttc cgtggcggac    7440
```

```
gaaccaacac cagtgtgggc gttcgcatct cccccccct ccccccccc catacatgaa    7500 agacctacga ttactgcata ggaccccgct cctgggacaa atactccgga aacctccagg    7560
gatcggaaat ttatttagaa gggggtggg gtacagggca tgcttgctta ggatctgctc    7620
gaaacttgac tataaaaggc aatctgacta gaatcgccaa aggcgatagg tctcagaaga    7680
aaagtaggac gcgcgggga gggataattg tttacgcggg ggggaagata aatggcccac    7740
ggcggaaacg agaaagcgcg gggggggtt aggccttgga aggggaaag acgcattcgc    7800 gcatgtcaga attaagatgg cttccctata agacgaacgc acggtttaac agaaaagcgg    7860
acatcacgcc ggggtcgaac gcgggaaaat aaaaccgttg cgggggggg ggggagtccg    7920 aaccgtgcgg cgggaaggct ccgagtccga ccggaaacgg aaaaaggcgg cacggcacgg    7980
ggcgctcaac gcacagggga taggaagaat ttccctcgg cccgcggatt cggatcgcgc    8040
tcgcgatcca ccttttctcc gccgactcgc cgaccgcccg gaacgccggt acttacgcgc    8100
tggagaagcc ccgtattact cttcttcccg gattcggccc cggcgcttct gcgtctgcgc    8160
ggcggacata cgcagttgcg cttccgtcga cgtattcaat gtaaacaagg aagtcggccc    8220
tgcgacttcc gcgatcgcga tcgcgaaccg gtaaacaacg caggggagc gcggagcgcg    8280 ggcgcgggca gggagttaac ctcgcgatcc gaccgcgcat tcggatgtgc gggtcggggg    8340
cgtagagata acgcggcgtt tccgctccgg gccggagagg ctggcgggcg gtctctccg    8400 tacattcttt ttttttgcaa acgcgccgct gcgcgcctaa acgccgcagc ggcgcgaaac    8460
gcccgcgctc tctaagcgtc cgaaggccgt acggacaccg gtgcgtccgg gcgctcggcc    8520
gggcgaacgg cggagctttt ctttctcttt tcagtctcgg agaaacggc ccggtgcaca    8580 cctcctctcg ggagcgtcgc aggaaagtaa gttcgtgtca ctcaccaccc ccccccccc    8640 gccatcgaca cggagtctga gcatgagggc tttaataaac cgatttgaac gtgctacgac    8700
gagagtccgt gcaagtgttc gcgctcgcgc ctatacgtac tacgacagcc gctctgtagc    8760
cgcggtgtgt gtgggggtgt gtggggtgt gtgtggggt gtgtgggt gtgcgcgcgg    8820 ccgggacggg attcctgatt ccgtagcact tcatctcgaa tgtggaattc ggttccgacg    8880
ggggccgtta acacatatac gcgacactgg tcggaactcg cgacttccac ggtcgccgcg    8940
taagtcagtg gtgcttatac gtgggaacga agcgaggcta agtagcaggt cgcgaacaag    9000
gaggtggacc gcggggctgt ttatatcgca tctgcgtctc ccgcggggcc ggtgagctaa    9060
cggctcctcc ccgtcgcgaa actgtatccc ccgcacaaac acctggacga tccgcgagcg    9120
acttatgatg cgcgtgcccc tcccccaact aaccccttcgc gcgcaccgcg ggcctcggcg    9180
cggtacgttc tccacaacac taatcgcacg cattccggt cgcccgtcgc ccccccctc    9240 gcacatcccg cctcgggga gaggagagga caaagtacgt tccccgactt acgcgacgga    9300
ctcccccgcc cgcgccatcg ccagacaccg aaacgggacc gaagcgagaa agactttta    9360 ataaacacgt tcatacgcac tacgacgaga ccgctcgcac gcggtctcgt acacgcacgt    9420
acaccttaac gatcgacgca ctgtacgcga gggctaagag cgggcgagcg atccacccg    9480 tttcgcaaga aacgacgcgt cccgggcgcg gctccgctaa gcattcgttt acacggcagt    9540
ttcggcgtct ccctcctccg gtcgtccgta ggagccctct gcgttccccc gcacggccct    9600
cgaaaccaaa ctccacagac tcttccagac gtttgcgacg ctaggctggc ccggggcgcg    9660
gacgcggtct gagggcttga gccggtggct gcagctcgtg agagcgtgtt cgaactctga    9720
aacgtaaaac ggtccggctc gattccggat aacgcaaacg tcttttcccc tcccccccga    9780
```

```
tccggcaggc gagaccttcc cactcaacct cggtcccgca cgggcttggg ggggggggggg    9840 ggagggaaat agccggccga accctactcg ggcccggacc caaacgacat cgctccaaaa    9900
gagagcgttc cgtttgacgg agcccgcggt gcgtacctgc acgggattcc ggatcccgat    9960
cccatagcga ccaatctcga atactgaact ccgttgttcc gtcggaggcc gttaacacat   10020 atagggcaa ttggtctggg ctcacgattt tcattgtcgc cgcaaaagtg agtgtgcttg    10080
tgtgtgcaac aaagcgagac cctctaccct gttcgtgagg agagggtcgc ggggttgcat   10140
atatgtggca tatgcgttga tcacgggacc ggtgagctga caactcctcc ccgtcaggga   10200
actctattcc ccgcattacc acatggacgg gccgcggcgt cgcggcgttt cccacacccc   10260
tccaccgacc atgccccacc cccgctctcg ttcgagaggc cgtcccctcc cccatttcgt   10320
tccgcctcgt ccagagccag cgcgggactt cactttttcc ccatccctct actcctatct   10380
cgttgcccag cccacgatcg ctatgtacgc gttctctccg aggccggctc gcgccgagcc   10440
ggccagacaa agtcacttcg gaactgacgc cgaagtgagt gctgaacggt tgaggggggcg   10500 gcgtatcgcg gataagctat tctcctcgga gtcttttttgc ggcaggccgc aagcttcctc   10560
gtacccccct ttcggggttc gctagaactc gatcgaaacc cgagacgagt tactactgag   10620
ccgatcccta cagctcggga ccgctcccga acagaacgcg gcctcatcgg gttctttcgt   10680
agagcgccgc aagggcagaa acggaccgac gcgcgtccga gactcatccc gagctcacgc   10740
cgaacggctt tattgctccg cttccgaacg agagagcggt cctatctcga ccggcccgtt   10800
ttcaatcgat tcccgaggtt ccgacctcgc cgcgggtgcg gggccggggg gaaagtcggg   10860
gggcgacccg cgaccgtgtt ccgcgagcgg cgttcggccg cgtcgccgac gcggggtcgg   10920
atctcgttct cgtgcgaggg atcgggacga tccgcggacg agaacgatgg ggcgtcctcc   10980
ctcgacgtcc gacggttccg gacgccgcga gggtcgcggc ccgaaggcgg agatgccgag   11040
ctcggccagt tcgatgccct cggtacccat ccccttcca cccgtcggcg acccccgcga    11100
acgcgagccg tagacgacgt tctcgggacg gcgcgcgatc gcttcccggc cgcctgcgat    11160
cccaacggga cgggttcgtt cgccgcgcgg ttcgcccggc ggtaaaagaa cgaccagaaa   11220
atccgatccg cgacggcggg cgctttatta ccgcggtccc gcgctttcgg acggcgggcc   11280
ggccagcgga acgacggtcc ccgccggacc tccgctcgcg tatttgtagg ccggaggtcc   11340
ccgaatccgc ccccgtggga ggggggcggc gtttctagcc cccggcgcgg gccgcggccg    11400
gacacgaaca cgtggcatag gatcccgctt cccgattggc ccggacgggc gttcgcacct   11460
tgcgccaata atatattata tatataatct tatattggtt cgcggtgcga acgctgacgc    11520
gttcgccccg ctcgtttgca ttgcatcacg tgatcgttac gccctcacga ccggcccggt    11580
cataagaagc ggaggcgccg gatctccgct tagagcgccg gtccggcgct tcccgcgaac   11640
ggacgcaagg tggcggcaga ggataagcga tcgccgaacg agagcccgt cgggagcgat    11700 cccggatcgg acgccgcggc gaacgcgtag gtttcggccg tctccccctt ccttccccc    11760 acacatcctc ccgccccca aacctcctc cccggcggcc tcggacggcg cctccccgc     11820 tcttcccgaa ctgcaggccg gccggctacc ctccctcccc cctctcctcc ttccccccct   11880
cccccttctt ctcccgtccg accggcccgg cggaacgcga tgcggcgggg gaaaaggcgc   11940
cgatccgacg gacgcgatcg cgacccgacc gctgatccgc gcgcccctcc ggacgccgag   12000
agggatgcgg agcgcgagag cggagccggg gacggagggg gcgacccgga cgccggagag   12060
aacgacgccg gagggcgcgg accgggcgcg gacccgggcg acgacccggg cgacgacccg   12120
ggcgacgacc cgggcgacga cccgggcgcg gacgcgggcg cggacgcgga cgaggcgcac   12180
```

```
gcgcgcctgc tccggcgcgc cgagcgcgaa aacaagaaac tccgaagggg atgtaattta   12240
gtgtttacta taagcaacaa aaccctagta gtcggaacat gttttatgct tgcggcaggt   12300
gtactagtcg gtgcaagtgg tgctgaccac gagactgcat gcaacaaaac taatttgctg   12360
ttggtatttg ttactgccct cttgacacga tttatttgaa acggtaacga atgctcgtgt   12420
actttataat tgcatgcccg attacaatct gttctgtaag aatagttata cgtagcgtgt   12480
tttacatagt cttcgatgta tagaagagac gcagtcaact tgccggtgcc gtgaaattgt   12540
ctccacacta tgatgttttt actgttacaa ggtaattaaa gaccttcgag ttttcactc    12600 cacttgtgtg acgctccttc gattatgaga gtacaatgtc gtctaagggg gatgtggatc   12660
accacgcggg ttatggggtg gcactcgcaa ttattgctct attgctcgta catgctactg   12720
cactgattat ggtgagtgtc ttttaccctc tgtcccatca gtaattgcta acaatgatt    12780 gttttaatgc caaaaatctt ttttagatc ttttctgatg tcaaattcag accagtttca    12840
caggatctta gtacgcagta cccatctcat aagcattatg atgatgcgta ctcgccacat   12900
atgtctgggg tagaccacgg ccattcggat gtatggacta acactgtaaa tgacccatcc   12960
ggcggaataa actcaaattt gcctggtgcg aagagcgtgg agaagatcta tcctagcgta   13020
gaaccaagta cgtcgcatga caaagtgtcg tatggaaatg catggggagg ggacataaac   13080
accggcagtg tttcaccttc tgatgacaaa gcattgcccg ccactgtcga accatcgacg   13140
gacatcgttt ccatcgcgat cacggggagc agtttaaacg gagaaagtag ttggcggatt   13200
tctaaggatg gcccgcgtcg ggtttataca ccacaccaga ctaaaagaag tcctcctcag   13260
atcgatggca cgcgtttatc tactagaacg gcatacttga gtgtgtggga tgaacaggag   13320
gggattttta aaacgttccc ggccaatgct gctgcattca atttattgga cgctaatcag   13380
ttagagaaag cgcgccgtga agttttttc gttgtgtcgg tgtggcatgg aaatacgaac    13440
gaaacccgta tatttttatc cgccacgagg ctactgacgc gaatgatgtc cacatcgctc   13500
gtcgtttatc tttcctggga ctctcgaggg gccctgggga cgacaactga tgcggctttt   13560
ctggcacgga gcgtaaatat atcccagttc ctgaccgctg taccaccaca ttcgcaagtt   13620
cgttgtatgg gccattcatt aggaatgtat acttgcggtt ccatctgtag acaatataat   13680
agtgtaggta cgaccagatg caaaagcatt ttaagtattg atccttacgg cgcctcatca   13740
cccgagtctc atgtatcctc ggcagacagc tcaaatacaa tacgctttga tgccgactat   13800
gttgcgattt tcgcaacaag taagtggcac ttgaacacgt ccgattcaaa cgcagacgaa   13860
tatataatag tagatggctt gaatgcaaat gctgtgtgtg tcgatcccta cgagtggagt   13920
gtcttattgt gtgttagcaa tcgccaacga aatgccgttt gtgagcgatt cggtgctaac   13980
aacgtaacga ctaccggcga ccctgcgaaa gacggttcgg aaacatgcat gcgaatactc   14040
cctatactat cggtgctgca gtcgctcgat aagaattctg cgtatccgct gttacgtatg   14100
gatccgccgg gagcttctgc agcggtacca tccttaccgt ccacatggaa tatctacgtg   14160
atgggaaagg attacagata ttctacttat ggaaaaaatg agagcctgtg gtattctagc   14220
gccgtgcata tgggaggacc gggattcttt cctgcgtcgg tatttactgt gtttcttccc   14280
tcgggtatac ccgctgtggt atccaatgtc gtgcaacaca gtagcatcag ttacggagat   14340
gtagcggttc attccgcttt cttaactgat aggtccctct actaccccg agtgatggtc    14400 caaacatccg ggcctatttt atctgcctat tcttggagag cgcgactgca taatgacagc   14460
ctctatttat taccacttcc agaacaggag ataatgcaat acaaatgcgc agttgcacag   14520
```

```
ggaagctatg catgtagtcc cacaggcccg atcttgacaa ctgttatgtg gcgttcactg   14580
ttattcgcgg gcagatcttc gccggtgccc ccaaacggta gttgtttgac ttatatcccc   14640
gctaacacaa tcatccggag ccggtccccc attgaaatag gccctcgaag tattataact   14700
gcatcgtttc agctaagcag acaattaatg gctatgacgc tcgaaaatca tttcacgtcc   14760
acgaaccgga ctctattgac atttcatgat gtgtgccacg acactgctat ggagtcggat   14820
atatacttcg agtataactg gttaggcgca tcgatgaaca ttaccatact gaaccccggc   14880
ctctatacgt ttagatggtt tttcccattt gaggttttcg taatgccggt ggtagttacg   14940
cctcccaagt ccagagcgga taccgtcacg atcgctcccg taggactata accctgttgg   15000
acaaataaag tatacagact gttcaaactg tgtagtgagt ccatcttagt cgtactggat   15060
gcaaacgagc ccaataaagt gtaacagttg gaaaactttt aactgtcgtg ggataaccct   15120
tataatgtta tagtgcagtg actgacttgt aagcaaacat tgactggaag ttagcttata   15180
ctgtacttcg tcgagactgc cgttgccgac tgtacgatgg agcggcctct cgatcgtgac   15240
tatcaaagtg cgataacgtg cttgacgtgc gagagagtac ttttttgtcg cctctgacat   15300
gggcaggttc gtggcgataa ctccaactac atcaatgcca agaggtttaa gcgttaggtc   15360
gccggtttaa atactcattc ggaagccgtg ggtggcgcct cgcgtacccc agaccgttgt   15420
gttataaaac ccagactcgt cgccacacat gtaggcaaaa aaatgactag cgaaagagct   15480
cttgcgctag cacccggtcg ggcggccacg gcagatttct acgaagtgga tccggtatat   15540
cggcgagact tcgcacgccg gcttttacaa cgtaagttcc agcttgtcgt gttgtagagg   15600
tatttactac tctgatcttc acctaattag caccatgccg tttgtattta ggtttattcc   15660
ccaagacgct tgccgccgtc agggaatcgg agggaggccg aaacacgcgc ccgcccaaaa   15720
cagatctgtg tacgcttttg cgcataatcg cgcatcatga gaccccgcac attttcaccc   15780
caggtcccag actcccgaaa tcctcagcaa ttgtcgacgg gctatgggta gcgtgtcgag   15840
gacttgcgga agagtgcatg ttcgatggcc gggcgacaat agagttagca gaacgcctcg   15900
caacttcatg gttgacggcc ataagattaa ttctagtttg gcatcccgtg tatgccctcg   15960
gccagcaaca cgaaccactc gagcggatat gtcgccaagg tcgagaatat attgctatgc   16020
tctcgggaac gattcaaaca tcgtatgcga catggccgtt ttggcaaatg atgcaacgat   16080
gcttagattg gtgctgctca tttcacatcc ccgatgaccg ttcttgtgag cacggatctc   16140
cacgtctggg gatccaacta gagggcgaaa accagatatt cgcgccaagt ttggggctct   16200
actccgctgt aatggcatgg accccaattc catgtcacgt acaggttcct gtatttccga   16260
gacctggcga atcggacgat gtctcgaccc cgcctagtgg ggcacagata ggacgggtgc   16320
gacctcacag tcttcaaagg ctggcactaa aacacagacc tattgatgcc gatgtacata   16380
gacccatgcc gttaggccgg ccactccctt caatgcatat ggacgatcca gacgatccgc   16440
aacctggacc ctccggacaa ggccgggcgc ccagaactcc aactctggaa ggagtccggg   16500
tcgcagaaca accggtaagt cttcgccgcg caagaacacc accgccgccg ctcaatgtcg   16560
acgaagacga caacgatctt cctcccggcc aaccccccg ccctcatctt cgaactcccc   16620
catcatcacc atcgtcctcc gagactgaaa tcgatgagga acttaacgcg caacccgatc   16680
cttggggtac aaaccgtagc tctaccccta cagataactc ctctgccagt gaggatgaag   16740
ccagagggag cgggttgccc cgaccattgc gcagcgcgac tactgaaccg cgcgtaacgc   16800
gtagaagccg ccgtgaggct cgcagccgga gccgaagtcg gtctgagac cggaggtggg   16860 gaccgtcccg attaaggtca atgcctggac gcaggagagc ttctcgacaa gatacagtac   16920
```

```
ttgtagacag ttctgaagag gaaccgtagc cgtttgtagt cagggttcta gttaagtagg   16980
cgccgcgcga tttacgaatt agtacatttg ggccctgccg cgcagcgagc gtctcacgac   17040
tgcgatagtc atgcacgttt cgctggtatg ggtgctgtgt ttgcttttcg gaactagtgg   17100
gggtgtttta aagtggtctg acgttgactt gtcgcgggga ttcatttcgg tcccaaatgt   17160
aagttcgctt atgcttttag actgcgctcc aaattcgata ctctcaactg ccagattcgc   17220
cgatctgaca acagatgatg tccctaccgg tatatttatt aagatcaatt gcagcgttcc   17280
ggaattcatt ttatggtatg ggtctaaaag cgtggcggcg cggctcaacc caattattgc   17340
aagcgcttta atgatggacg atgttttaaa gagcggattg gacgattccg tgaaggcgga   17400
acttcgcgtg tttttaaaaa gaatatccga acggctacct tggagctctc tccggaaaag   17460
acacggttgt ctgaacctgg acgcaccttta tgacttctcc tgttatggct cggcacggct   17520
cgacagattt gaacgagaca tcgaggacga tggccgcgga atgtcatgcc gagctaaatc   17580
aacccgagct aaagcggccc gcaccaacgc catcgaggga tagttcggcc gcgattaaaa   17640
agcgtcgccg gccgatcgga cctccgcccg gtttcgcgcc actgggcgat aatgcgccat   17700
ccccacaggg tgaaactgac gcgtacggac atcaactgtc gatgaccgaa aacgtccgcg   17760
ctgaattgtg gcctgttata gccgagtctt acaacataga ctggagttgg aaagattggc   17820
tgctccccga attatgctgt cctaacggct ccaagttgtt ggcggaatac gaacgccgtg   17880
ctgcggtaga agacgtcttt cctccgcgag cagatatttt cgcgtggact aagtactgcg   17940
ctccgcccga cgtcaaagtt gtgatcgtcg ggcaagaccc gtacgttcat ccgggacaag   18000
ctcacggctt ggcatttagc gtcaagcgcg gcattacaat tcctcctagt ctgcagaata   18060
tattttcggc agtcaaggcg tgctatccct cgatcgaact cggagcccac ggatgtctag   18120
aagactgggc taaacgcgga gtcctgttac taaattccgt tttgacagta aagaaggggg   18180
agcccggatc tcatcactct ctaggatggc aaactctggt gcgaaacgtg cttcgaagac   18240
tgtcgttgtc gactcgaggc atagtcttca tgttatgggg agcgcgggca cagactatat   18300
attttcaaac ggatcgcgac gatcgacatt tggtgctgaa atacagtcac ccgtctcctt   18360
tatcccggag accgtttgcg tcctgcacgc actttaaaga cgccaacgag ttcctctgta   18420
aaagcggtaa aggggcata gactggagca ttggcgcgta agtgacggaa gggttaatca   18480
tcacatgcgt acaaaagtcg cagcgctcta ggacttgtcg ctttctgcgc gcgcaatgaa   18540
cgataccgca ccttctgttt tggcagtatt atccaactgg ggttggaaga gcacaccctt   18600
gggcaccgta ggccccgtcc cgattcgcga cgagactgag tgcgcgcgcg aagaccttcc   18660
ggcacatgat tgcgaccact ggtgtaaaac cgccaatgca gaaaacggac ctatggcacc   18720
ctccccgggg aatcgagatt ttgcgggaaa ccaagaatac acacatttcg acactctgtt   18780
tatggtctcg tctctcgacg aattgggaag acgtcaactg acagatacta tacggagaga   18840
tctaaggcat tctctggcca agtttacaat agcttgtact aaaacctcct cgttttcttc   18900
ctcgcacgcc acgaaaaagg ttcgcgcgaa aatgtttcaa agagggcgtc agagcaacaa   18960
gagcttgcag atgttttattt tatgccgcag ggcacacgct aaacatatcc gggcccaact   19020
gcaagcggta attcaagctc gaaaaccccg caagtattac acccgcgccg tggacggaac   19080
tacgcatccg gtggtgcccg tctttgtata cgagtttgcc gccatagacg ttgtcagttt   19140
gcatcgagac aacgtgatag aggtagacac tcccggctcg tgagcttctc gccgctcatc   19200
atgttcgtcg tttcggcagc tttagcatcc gcatcagact acgccgcgtt tttgcgggac   19260
```

```
aacaagcaag ctgctcgcaa gctgcagttt ccgttgtccc cgatgccgag ccaacggatc   19320
ccgcatctgt ctaaggatgg caggactgca gtcgcccggg aaacggggtc gagcgaggtt   19380
atgtcagcga gcggacagaa cgcgtcgacc cgaccggtcg acgctcgttt cgccaaccta   19440
gacaccgaga aatgacaaga agcatctaaa acgcgcttga ttgtcgagtg gctgaataaa   19500
atctttattg atcgactcgc tttcctattt ctgatttaat aaccatagat ggggcgggga   19560
atctataaaa taggcaaggt ccgcgcggat tcgagcacat cgaccgcgtc cgcgacacag   19620
catgcaagtg gcgacgaacg gtcctcaggc atgcacgact ggtctatctg tatatctgcc   19680
tcgcggatcg cttccgtgag aaggtcttcc tcgtacccgg ttgagaaagc gtccactttc   19740
gagggtccgt acccgtgcac agcgccaatt tcgtgcgctt cgatgcactt actaatctcg   19800
ggcgcgtttt cggcagaga tcttatcgga tcgcagctct gtcgatgcgc atctttatta   19860
gggtctgcga tcgcttggca atacaatcgc gcgctggatt cgtgaccgac ccgcattgca   19920
ttggctgttt gtgtcaaaga gccgggctta ccgtagatgg tgatcgttat gtacagtgac   19980
gttcccatcc acataacggt taaaattcct ccggaactgc tgtataagta ggcatccggc   20040
cccgtcacgg tacacgtagc aaatggtatg acgcacaggg attcgggcag aaaggagagc   20100
ggcgcggcat ggtattcggc gccgcactcg ccgacgcgta aagataaga gcaaatgtcc   20160
gcgccgctgt cgacaatgat cagggtacct accggtcctc gctgtatgat aaagttcgac   20220
gatgggatat gatcgcatct ggtcatctta ccaacggcaa tcgagcgcgt accgcctgca   20280
catgagcaaa ccatctgctc ataaggaggc attgtccacg cgggctgagc agtgacgttc   20340
tcaagcgtat acgcgatgaa cgtggacccc atcatatcca cgtctcatgt gacggcccta   20400
tgcttcatgg ccctagttag tatacaatgt ggactttcgg atcccggagg gcggctaata   20460
agtgcgcgct gatattgtta tcatccctag tatgcgtttc ccgaagtggg ttaatgttca   20520
tcctcagaaa cttagaggag gtcactcgag acatggccac gtagacgctg ctgagtttga   20580
tgcccgattg ggcaaaacat atagcaaccc tctcaaggct aagcccttgc gatctggcga   20640
tagtcatcgc cagtttggag cttattccgt agtcggcggt tacggccatc cggagttcct   20700
gatcgtctac cgtttcgaca aaatcattga cgttggtgtt aattgctgcc atgaaaccgt   20760
gttgatcttt caaaaccagg gtcggcatgt gaagttcccc gagcgcttcc gcgacctggg   20820
gatgtatctt acgtctaata ggctcgtctg caaatgtgtt aattctagcg tatgtgtaac   20880
ccatgagagt gtagctgtcc gtctgcaaag cgagcgatag cattcctccg cgcatgctat   20940
ttataaatat ttcgcaccct ttaaagctca cgttgtcgac ataactatcg aatctggacg   21000
ctgcaaactt ttgcccgaat agctccgtca ggatagaata cctgcccata acatgctct   21060
taagcatgct gaactgggta tatatctccg cagaagtttc tgcgcgtcca aattcgtaat   21120
tgcaataaag catgtctatc atctggtcgt cgaaatccat aaatagggca tcgtctgtat   21180
cctccacatg actgatttgg tcattagcta tacaatctaa ttccttctca ctgccatagc   21240
ggtgtcctgg aatcgcgaac gactccctct gctccgctct atccggaggt tgccgtcccg   21300
gatagagcag cgcagaggta agcatcgcca atctatcgta cgcgctttta acagaattgt   21360
ctggaagacc ctgccgttgc agatagttgt agaactgtat catgccgttg aaaagcagtt   21420
gagataagaa acggtacacg tattctacag acccatctcc gtgcgtcttt atgaaggaat   21480
cgtcttttcaa tacggataga aatgtctcga acgtcccgca aaagccgaaa acccacttcc   21540
gaagtcgggt agtaacagcc acttggctgt ttaagacata ggcaatatct acacacgata   21600
ccgcgagccc ctgttggctg cgaatttcac atttggcctg tgtggcatct tggtcgcgac   21660
```

```
tttgcgacca gttgctcaag cgtcccgcat tggcagcaag ccattttcc  aacgtaacgt  21720
gcggttggtt ggcagcagta cgatatcgtt cgaaactatc caaactgacg aaggtataag  21780
ccggcagggt aaacactaca aatttcgtat ttccggacgt tttcaggtag tcgtgtaatc  21840
tgctcatgta cgcgctgact tctttatggg acgaatacag acgcgtccat cccggaaggt  21900
tcgcgggatt gttgatgtat gcttctggga cgacgaaact atctacgatc cgagcgtgct  21960
cctcggttat gggaagacca tactctaagg tcttgaggag gtccccgaac tcgggttcgg  22020
tgcaccgttt gttattaatg aatatcgccc agttcttgga cagttctaag tacgagcgca  22080
acgtctggtt gcatataata tacgtaagaa tattttcgct cgtacgcaca ttacacttca  22140
gcttgctatg ctcaaatgtg gactccaaag aattcgtttg cgtgggcgac ccgacgcata  22200
tcaataccgg cctccttctt ctacagtact gcggcgtgcg gtaaacggcg tttgtgagcc  22260
accaactgta tacgatagcc gtaagcaaat actttcccag aagtccagcc tcgtctatga  22320
cgattatgtt actgcgagtg aacgagggca tcgaaccatg tatgccgaag attgtccacg  22380
ccatactacc gcgaggcttg cttagcagat cctctaacgc gcgaatcatt tcaaaccgcc  22440
ctggcccgac ctcgttagac accgccttca aggcgcattt tgtaatgtcg gataaaacgt  22500
cccaataata cactatatcc ttttctgca  attctttcat cgtcggtggg ctggtcggac  22560
atacgtactg atattttccc aaattcgctt gaatgtgatt acctttaaac ccgaattcct  22620
gaaatatcgt gtttatgtgc tgcgatgtgt atgaattgct aagcttgcaa taaatattct  22680
gcgctgcgac ctttgtcgtg ccggtgataa tacagtccaa gatttcggat agcatctgta  22740
tgcacgtgct ttttcctgag cccgcatttc cgcttattaa gtaaacggcg aaaggtagct  22800
cgcggagttc tagatccaac gggctttcta gttttgacgc gttcataaaa tacgatagcg  22860
gggggactat atcatcgctc accgatgcgt ccgccaggct ccttacacgc gcaatgatag  22920
tctgtatccc gtgcatcgca gtgaaattta gatacgttgc ctcactgaag aaatcgttct  22980
cccgcgacat cgtcggtctt ggggaagacg ggagtgacga atctacgtat cttttagggt  23040
cggggctggc gtgttgttta tttccgatgg agagctcaga cgttcgggcc gcacgcagtc  23100
ccgccctaaa acaaattcga cggccgcagt tgcaatctgt cacgcgccaa tggaaacttt  23160
caagcgacgg cgattcgcaa cagtccctgg aacaggactg gataataatt caccctactc  23220
gccaaacacg tatgttcaaa gaggtcctca ccgggcaatt gggatataca gatggacagg  23280
gcatatataa ctcggtacga tctacagaag ccgcgattcg gcagattcaa agtaccattc  23340
tcacccttc  tttagatgcg gtcagatatg acgacttgaa agaggattgg tcgaagcata  23400
tggataggcg tgggatgtcg gccaaggaaa tcgcaaaaaa gtatggcgtt catagtgaag  23460
ccgaagctgt tagaatggca aaggggggtgt tttcaacttg gcgtaaaact cttcaaatga  23520
ccttaataga attggttcgg cacgcaacag attgcttcgc cgcggccgag aaaaccacgt  23580
cctgcttctc taaatacata gactggatct gctgtttagg tatcgttccg gtcgtcagaa  23640
gcgagcgctc tatgcaggcg tcgcggccgg atagcaactg cagagatcgc gctaccattc  23700
gcccgaattg ggtattcagc gatgccaccg ctaagctact agttgcggat agcgttatgg  23760
cccgcgcaca acaaatcgcg gattacttaa ctgcatccat gcaagcactg actgtgatag  23820
aatacgatag ggcccagata gaatataatt tcttaaaacg tgaacttcgc gttaaggacg  23880
tgttgagcgg cgaacgtggc gagtgtatcg ttatttggag accggtaatg aacgacggag  23940
gggtaatttt tgattcgccc atgcagagaa tctacaagga gatgattgaa tgtcacgatt  24000
```

```
tgcggatgca tgcggcgctg tgtcggctag taaacacggc ccctataaag gtcctcatcg   24060
ggaaacgcga tgaggatagt aaaagcatgg ccggggctca agagcaatc gataaagttc     24120 tgggagacca aactgaaacg gcggcgagct ctgccgcctc taggttggtc aagcttataa   24180
ttggcctcaa aggtatgcgt catgtcgcg atatcacaga tagagtgcgg gattacttgg    24240
aggaaaccgg cggacattta ttggatgcct cgcccgtgga tacatctcag cctggcttcg   24300
ggcgcgctaa tcgaccacag agttctacga tatccgatgg aacttgctcc aataccgcta   24360
gactacgtga tgcgttccac gcgtccgtcg tgacgagtat aaacgaaatg ttagagggct   24420
atataaataa acttttccat accgtggaag ggttaaaggc ggccaataaa gacttatctg   24480
caaaattaag ctctaaagaa atagagctcg acagaatacg cacggaagcc ctgatctcag   24540
aacgggcgcg agctgacgcc tcgtgcgatc ctcactgcaa tccaaccatg gaaactttgg   24600
tgcgcgagct aaaacatgac gtaattgacg taaccaatgc aatggaggat gagtcctata   24660
tcgcgaatag cttccagtct caatacatac catcatacga tggcgatttg aaacggctct   24720
ctaacatttg ggaacaggaa atgttgaggt gctttaagat gactcgtatc accagtaatc   24780
aaggtcgaga ggtttcgatc tcctactcaa atagcgctat aactttatta ctcgcccccct  24840 atttcttctc cgtgttgcag atctatgata ttggtgcgat ggtcacgagc caagacgttt   24900
acaagtcgga ggaggagtta tgtaattccg tgcttgaaaa acccgactt tgtacatatc     24960 tggatgattt ggctctcgtc tttgaggccg atgtgaaaag agctgtcgcg aagtattcgc   25020
tccgtgcggg taacgccgaa atagacttag cgcccgagga gttttcgtac ggctctcatg   25080
gaagcaaatg cgagacacgg ttttcatccg ctagacacga gcgacacgtt ggacgctcta   25140
gttttaagca cgctaaatgg agaagtcggc caaaacgaga ccgtagaaga actaatttgg   25200
caaccgacgg cgcggatgat gatggagatc cgagagattc aaggcggtcc tactcaattc   25260
acgggcgtct ccgtgagtaa acttcgcgtg gcaagatgtg atacgcgctt tcatctgact   25320
ttaaccggag ccgacttgga tgatgaaatg gcaagtgacg tataccacag tcagtgcata   25380
gttaattcgg cgttcaaagg tttcgtcttt atggttctca cggttacgga agatatagtg   25440
cggacgatag gggttccacc ccctctgcta aaatacaggc tcgtgttcta taccccatct   25500
gaacatttgg acttcgcatt atgtttgctc gtagcctatt tggagaatct ccatgcaagc   25560
gcctgcgacg taacttttttt cgtacaggtt caatcttttc tgagatacgc atggacacgg   25620
gtgacgccaa tgaccaaaat gcgcagattt ttatgcgcca cgaacgtttg gttactaaac   25680
actttgatgt cgatgggtc ctgtagccca ttcgacggag atcgagtact ccccattat    25740 gcgatataca gacatttgtg ttctaccagt ggcgtctgcg acgtgttact aaccttgttt   25800
gaacccgata cacggcaggt acgtgaccgc acgcacggca agggacttgt catgctcaac   25860
agaggaatta tgaataaggc ttttcggcag acatggatta gtgatacggt ctacgattgg   25920
tggaccggcg aacgcgagaa gttgatcgga gaagaatctc tgttcaacac gtataatata   25980
tgaataaagt atgacaggca ctgctataaa tagaccgtgg tttcttagcg ttttcattta   26040
tttattgcgg acgaacagaa acctgtacgg ctctacgtcg aatgtgaatt tgctgagatc   26100
gacgttaggc catttcgatg ttagagcacc gatcagtaat ctcgaaaaaa tggacattat   26160
tggtttcata tgatcgatgc acgcgatggc agggagaatt acttgtcccc cttcgaaaag   26220
tgaacacgtg agaggtgcta tgctgccgtc cacagtcacg gtgtggacgg cgtcgttact   26280
gaaggcgctc gtatcgaatc tagctgccgc ccgtagtccc aaagccgtga tatagtgagt   26340
gtggtcgcgc gattctgcgg gacagctcca aaagcaggcg tctccgcggg cttcgaaagc   26400
```

```
cgcggtcacg agctcttcga acactgcacg cgatcgttct tggattgtcc gtagggactc    26460
gtcggaatcg ttgcatgcgg aaatttcttc taaaagggca gacaaggctt tcttaacttg    26520
gcccgcaaac gcaggtcggg ccggaaaccc cacgaaatct gtttcccgct tagtttcgtt    26580
ccacagccag taacaattgg cattccacga tactgcatga gtgtataccc cttccattcg    26640
aaactctaat ctgatatctt cgggaaaccg tagcccgact gacgtggcta atttgttagc    26700
gctcttaccg caagcgactc gtagtgtttc taaagcggtt tctgttcctt tagaggaatg    26760
cagaacgttg ttggccccgt ccgtgaatgt cccccacagt ccatctttga cgtaggtaca    26820
cggggcgaat ccgagagccg acgcggtagc ttctacctcg agactaatat gattcccgat    26880
acagataata gctctataaa catcttcacg cactcttttc aataggcctc cgaactctat    26940
gatgggctgc ttcaaccagt ttttctcgcg ctgcagtcga gcttttaccg cggcgcgcaa    27000
ccgggaatga tcgggaaaca gtcctagata tagagtcgca aaaaggcgc taaaatcaaa    27060 ctttgcgata tacgcttgct ctatgaaagt cggttcccgg aaaatacaag ttatccgccc    27120
agccgtccag tcgtcggcta cctgacgccg cgtactgctt gtgcgccctt ttaaattttc    27180
gagtacgtct ataccagggg tcggatgggt ttccggatgc caaggagcaa gcaggtggaa    27240
ggttctcggt ccggccagtg gccacaggcc atcggtctcc gaatagctgc cgacggcctt    27300
tctgatggcc gaggggccg ccgtagatgt tttcaagagc ggccaagggg gaaatccgat    27360
agtgcaggca tagtcaacgt cctcgccgcg cggactggtt tcggggccaa tatatacaaa    27420
tataggggcc agcctttttt ccgagtcatc ggctagagag tatatttttt tgtgccactg    27480
cgcatagatg gccaataatg ccgtgagaga aaattcggcg ggtgtcgtaa ccaagcagtc    27540
aaaagacgtc ggaaccggag ccgcggtttt tatgggtgcc tgtgagtcgg gtaatgatag    27600
aacgcgttcg acgatagtga atattctatt cgtatttccc catttgattt tcttggacct    27660
gcgacccact gttttatatt cgcggatgaa ccggtcttcc tttgtgtaaa tttcgatacg    27720
ggagtcgaat tccgggatcg tgtcgtcgtg tttaagagcc gacaatttaa tgtgggctag    27780
gtgcgcgccc tcagtatact ccatagccgt ggatacgagg cgtgattctt ctacgtgcac    27840
ggcaccgtcc gttttagta gccccggacg gggagcacat cgatcgcccg gcagaggttc    27900
gcacgatata actaatcccg ttgttgtgtc tacgtacata tcgacgggtg cgaagtatgc    27960
atgataaccg agcttaattc tcaattttgc cagcgtcacg gcgagcagcg ctttccatag    28020
agcgtgctgg tccggcctgc aagacggcca aactcccgtc acagatccgg cactggccat    28080
aatcgccagt gccgcgtcgg ttactgaatc cggattcaat ccccaagctc tcgcgataga    28140
ccgtcccgat acgtttaccg tagagtaatg tgcagaatac gtaccgcact catttctaaa    28200
aagcaagtaa cacagtgcgg taagaccatc ggtgcggtct ctactagtcc atactctata    28260
caaagtggta tagcaaatac acccccggat tttctgtacc gccacagtat tagcctcagc    28320
cattgttgac ataactaggt tcgctgcgta cgccttacaa actgtgaaaa tctatagcgc    28380
cctctacacg aggccagcac gccgggggaa cttctgccaa aaccgtctcc aggtccaaaa    28440
tgtcgtggta tatgcccaat tccgcgtcca agcgagattt cactagcgcg taccacttag    28500
ggcgtcgaat ctcgtagcgc gttttgcgga acgacgcttt gttttcata aggagtgtgt    28560 aaagcgcgcg gtgcgttttg atcgacgttc tatctatccc cgccccatcc aacaaagctt    28620
ctatctccgc ctttcggaga ttcttaactt tggtgccacc cggaaacgtc gtcgcgctct    28680
ttacaaggcg taacccatac agtatttccc atgtgacttt aaaaacagaa aaggcgtggt    28740
```

```
tctcctccgt ctgccggccc aagggatacc tcgcgagacc acttaacgcg cttttcgttg   28800
ttttgactga tcgtttagag gcagtacggg catccagcag ataacatcgc gtgacttcca   28860
ataccgaacg aataaaagta tcgtactcat tttgcatcac acgcagcatc gataatggat   28920
ctaaattttt agctgttccc tctaaagggt taatacccaa cgaggtcgcc catctgcagc   28980
ataaccgata taagtgccac cttccagaca cgttgaaatc ggccgttatt gcgacggtac   29040
ccagccctcc atcgggcccg attattggta agctgcctga tgcgtaatac tgataaatac   29100
gacagaacac ctcttcacta taaagagcgg ccggcgttgc gcgacacgct tccaacatcg   29160
taatatttat aaattgttct ctagtaagcg gttctgccag tttagttaat aattgcgcaa   29220
gatcgctcgg cgatccgtca tgtcttagat atttatgaat aaacggctcc accatctcat   29280
tgtcgatcag atcagcctgg atttgaccgc aggcaatttt acggaggtgt ttcaaatctc   29340
gttgagcgat aagggcgtct gccgttaaat ccgctaagaa ggcgcagaag gtttcagcgt   29400
ccaattgaga gtcagatccg tcaaatctga cgcttattag attcgcgtca agtaaggcgt   29460
ggagaatatt gatgctgtcg ctaagattgt tgagggtgca ccgttcaaac aaatgcttgt   29520
acttaaatcg tgggaaaatg tataacgcgt cggcggactt gaaagtcgga acgcaatctc   29580
ttctgaaatt gttacacaac atattggtcg cgcatacgaa ttgcgccggc catcctcccc   29640
cactggcgat gacgtggttt agtagcatgg gtgtgaaaac tggctccgaa cgagctcccg   29700
atgcatctat gtaaaccaag acttcgttac ggcgtaacga tcggattcta cctaaagatt   29760
gatagaccga aaccatatcg ggcccgtttc gcgtcggctt aatatacgcg aacatgctgt   29820
ggaagtggga gctgataaaa cttaggccta ctgttactac ggtagtgtag atgacaactc   29880
ggtaacgagt ccatgaattt atatcaattg gtatatcacg ggtggaattt aagaccagga   29940
cagaatcggt aaatatgagg cagaagcgtg ccgccgcttc cgagaatgaa attgtcgagg   30000
aaaataagca aatgttcaac ccgcccgcga gtcttctgct gagttcagaa aaaacgtcg    30060 tctcagtcac gcttctatgc cgagagtggg taccgtcagc cccgtgttta ggtgtgggtc   30120
gtacatgaaa acaatctgat tggtcgctat tcatgacgga gagaagtgta tctgttccca   30180
gattgcggag gatggtacat gatctcttag aaaacccagg ggctgcgtat tcgcccacga   30240
tgacatgtat gttatcttct cctctcatgc ttgccaacat atctaccagt tgtgtattta   30300
ttgtagcgtc cattgctatg atcctcgggc aattacgtaa cagagtcgtt agtatcgaat   30360
cgactctgga cagatgcctc atggttggag agtaaagttg actaatggtc gacatgactt   30420
cgtccagtat gatgatttca taccgtccga gcaagtcagg gtctatgcga tgcaaagatt   30480
cgatttggat caacagtctg taaaactctc tgcctcgtat gctgtagtca ctagccgtca   30540
aatagttgcc gaaccccgac agcccggcat tgctcagttt gtcgaataat gtgttcgtaa   30600
aacttcgcct acaggacaca accaaaacgc tcgtgtccgg attatataaa atacgctgca   30660
accagtctat gagagcagtt gtcttgccgg atcccatagg cgcgcgcact acaagtacat   30720
tgcgcgctct cgaggacagt ggcggcgaa aagtaacggg cccgtcggat tggcgctcgg    30780
tcgttactcc gggtctgttc ttagctatcc aatctatgag accttctccg tataatatcc   30840
tcgacaaaga ggcgctacag acatagtcta tcattttctg tgcggtcgat gctctaacgt   30900
cgccgagacc ggtgctccgg gtgaggatta cgttctgacg accagagaac cgtctacgat   30960
cgtcgctatg tcaaaaggac cgcgatcgga aggagcccgg agaggagcag atcatataga   31020
ctacattcac aaaaagatgt gggttgtcca ggcggcgtgt ttttctgtcg ccgtcttggt   31080
tttcctagga accctgatag ctgcatctat aaacatgacc gaaggtttcc catgcttttt   31140
```

```
tgcggccgtc gtggactacg ggatgacgaa cgtgacgctt gtgcatacgg gcatgaccaa   31200
tccgaggctg ggaggcgtag ttcctgtgct gttttttccaa accaaagccg tggcgtttct   31260
cttctattcg gcgagcgtcg tttttgtatg catcacgtgt tatatcgccg taggcgccat   31320
cataactagc aagaaacgag tgggctgctgc gtataccgga aggggcgcgt tcgtcctttc   31380
acttatggca tcgccctcga caattttgtt gggtactgtg tcgatttggc ttcttcaagc   31440
ggtagttata gtcctagccc acaaacttat tgtactagcc gcggcggttt atttagtgca   31500
cttctcgact ataacgtttt tttatgggta tttctgtgga aggggcgttg acagtaaagt   31560
atatgcggaa gacatcgctg ctgcgaaaaa cgtagacgcc ggtctgcaca gattaattgg   31620
aaacgggcgg gcggtcatga tcaacttggt ttcgatcgta tacagtatgc ttctgataat   31680
ggcgtctcta atgttaggca tgttactagc aaacagcttt accttaaagt tttggcatgt   31740
catcgttacc gtcctcataa cttcctcagt cttaaccta atgtatcttt tagtactcga    31800
gttcctagtg gcgcggtacg tgcacatgat ttttgggtgcg tacataggcc ttctgatcgc   31860
ctatgggatg ctctggacca cctcatgtga ttatgtcaac cggttctact tcgcgatggg   31920
cgtaggagcc ggcaacttac gcactgcctg tcacagcgtg ctggcgtttt tcaccgtact   31980
gattgtagcg ggcatgattg ttcgcctaat ccgggccggg ttgtatcacc gtaggcgatc   32040
tactcgtgca tacgccaaag ccaggcagtt acaaagaaat gtaaaggaga gattgagacg   32100
aatgagtcgg ggacgcgatc gtcccgatag ccgagctgag gacgagcggg cgcttacgca   32160
aacccaatat agcgaaacat cagacgacga gactatatat gatcgcgttt attcggggtc   32220
tgatagtgaa tgggatgaat aggaacgccc gaaacataat aaaacgctaa atctacaagt   32280
gattgtcgcg cgacttattt atcactataa cgtatcgtta cattgttccc gaccgtcctt   32340
aaatctgaaa agcgtctttc ctctcgcgca agtacttcca gctaagacag tatcggaatg   32400
gataagaggg tcggaggacc taagaccgtc caaatcgacg gtatcgtatt gctcgtcgtc   32460
gagctcaatt acatgtcccg ttttggtcag aacggtgttt cgtttccgac agcgtcggaa   32520
cagttccgtt acggatattg cttggcccat acttgctgca cgagttcacc gaacgcacgg   32580
tatccggcct cttctacttc accgtagaat gtaacgtcca cgaccacggg agtgatgagg   32640
aggagaacgg gaatcgcttg ttcggggtct attttgacgc ttggagtggg ttctccagtg   32700
tttccttcgg agatcgtcag gcgtctacct aattcgccag gtcgtctgcg gcggcctata   32760
aacgtggcga ggtgtgggat gaccgggttg cttttcaaagt aattagaagc tacgtagttc   32820
tgaacgaaaa tctgcttgaa atttggatgt cgtgggttgg caaatatggg cacaaggaca   32880
gattgttctc cggtactcca gcatagcggg tgtatcgcgt tcgtttgcag atcaggttcg   32940
ccaaacagcc atacgcgaga actgcagttc ttattggagg ccaagtgacg cgaatcaaag   33000
tcgttccgtt taatgtttga tgaaatggcg cggaagcgtg atagccccac tttccagtcg   33060
tcgtcacatg tgattagcgc ctcctttgcc ttaggaaaat cgtcaggttt aaaatagtcc   33120
acgcaaggat gattgatggc gtataagaat cttcggagcg ctgcgacggt tcttgtttgt   33180
aataggcgtt cgtaacattg agatagctcg cttcgacatt ccgggtaaaa cgcgtatttg   33240
gccctacact ttatttcgta cgtttctatg gagtggtcgg ggagggcagg cgtaaggatt   33300
ccgcgtgcgc tgcgagggca taccgccata tcgagggatg ctccgagcat cccggttctg   33360
gcgtctatca tcagaccgca cgcgtatttg tcagaggcgg atgagacggt gattgtctcg   33420
tccggtacgc gtgcattttc gagcacccga gaaggttcgc gaggcctgta cctggggttc   33480
```

```
tccagacaat aggtctctat gagcgctctc gcgagcggct cgttacgcgt tccgaagact   33540
acgctttcgg gcattccttg cgccgtgatt tcggcaggtc ttatgccaac ggtgtttatc   33600
cgtccatcgg cggtccactt caatgtcgat gcggtcaaca gccattgtct aagtacgtgc   33660
catagctcgc agtccgcttg cggtctggtg agagtttcta caattttaca ccagaaaagc   33720
gcatgattag acggcgacgt tgcatttgcg cccgattcat acaggagctt gtcttccgcc   33780
tctaggagag aagaatatga agatgccggc caacgtccct ctgaaatgcc tcgtttgata   33840
acgtccgtta tgtacaataa gcggtgatac agcgggtgtg gcgagggccc cgattgcttc   33900
gggtcgacat tccgtaatat atagtcgctg aaggtataat cgaccacaac actgtagcat   33960
acggtatcgt aaggtttgga ctgcactgct tctgcgtgct cggcgcaagc gaagaccttt   34020
ggacacgatt taaattcgga ctcctttttta cgtttccgtg gcccgttctc gccgagacgg   34080
aacattgcgg tggagtctat ttccataaca gccgtgtagc ggccctcgct tctgagttcg   34140
agtgacagta aagtgcaacg agctcgaaaa gattgcttaa atatggcggg actctcaatg   34200
aatcaaatag cttcctgtgc gtcacttcat atccttctaa atatttctca aacgcgaccc   34260
tgtggtgaga gccgtgtagc tgcgaacgaa tcttttcggc tcgttccac gggataccga   34320
ttttggcagt taacggggta gctggaaata agtactggta cagcatacac cgatacgcta   34380
acatgtctaa aagatagtcg gccggcatca ttttatggta ataaaaatgc accgggtttc   34440
cggggatggc aaagtcccgc gtaaaattca tcccggcggc tagaagcact tccatcagtg   34500
attggcccag tgcgtacata tctatagcga caccttcatc actggacagt tgacttgaac   34560
cccgctccaa gcccgtcccg tttaaggctt taaccagcaa ttcgcagggc tgcgtttgcc   34620
catgccccag cactaaatca aatacaggtc taatgtttgc tctagacact tttactgaat   34680
atactcgatc ggagtctaca gttatgtcga atcgggcttt cgtaatggtg gagttttgtgt   34740
taagtaacgc caagctaaaa tcgccgatta cggcctccac tataataggg ttagacccctt   34800
ccctgacgtt gacgaaaatg ttcccgcact taatatccaa atgagtcagt ccgcaggaca   34860
cgttcaagta cacaacggct ctgccgaggc ccatgaacgc tttttctatg gccctccaat   34920
ggcgtgcagt tttatccatc ttcctcagtc gatggcagta cgagtccatg tccatgtcat   34980
acgctggaaa taccagttcc ctggatggta tcgaaaaggc cagtaatgaa atcacgctat   35040
tgagcgctag agttgacctt gcccgacaag cgcattcgcc ggctatcagt gtcataagca   35100
attcggtctt gaaacactcg aacaccttt tgacggctac atttgcaccc ttaaatactt   35160
taacttctcc atagctcccg cttcccgcat atattggcgt ttcttgcagg tcgatggtgc   35220
tgtaatgtaa gcccggggag atatcgaaaa tgagcgatgt tatattcttt atgcgagata   35280
gagtgaaaat atgatccggc aaagatggtc ttgatagcaa aatgtcagat gttttcctag   35340
atatatgttt gcgtctccta tagaattgtt ttaggcatct cctaatgttg acggagatgt   35400
gttgtttgtg gtcctttttt ctacacgaat ctcttcgggg ggcactgaat gttccctgca   35460
gatcgtctgt tgtgcttgag tatcccttag gcccgctgaa gtcttcttgg tcgctgatgt   35520
cggaaagcca tttaacgtga ggacactcgt cgttttcgcg gccgcgcccc ggctttctgg   35580
ctttgaggtc aagatccatt ttgacagcag cgcctcgcac tctgcgtcca attctatgtc   35640
tggaaggcga tcgctgatgt cgtcgctgat ttgcgttaag atgtcttcgt ttgctagaat   35700
gtcctcttcg gcacgatcca actgtgactg gagcctaggg tttaaaaacc ttcggttcgc   35760
atctaagacg atgcggcggt ccacctgttc gtctatgtgg cgttggataa ttctcgactt   35820
tctatgagct tcttcgatcc gcatgttcga gtgcaactgg gttttgtagt cactgtgggc   35880
```

```
gtttctggct gacgttaacg cttcgatgag ttctgggtcg tccgcttcta cccttggga    35940 caaaagtgtc aaggtgcgtt ccttataaat tttctcccgc gttcgacact cggccaatat    36000
ttgacgcctg cgtctgcgta ttgtgttaac ggcgaacatc gctcgacgag attcgtagtc    36060
tggcgattac cgactccgta aagatgttcg gaggcgcgct cggagaatcg gcgaagaagc    36120
actttgaacg cctgctgaga gataggaacg agcgtttagg tgcgagccgt aaaaatgaat    36180
gcctcgcgcg cggcgggagt ttagtcgacg ccccctttct aaattttgcg atttcggtcc    36240
caaggcgaca tcagacagtg atgcccgctg tcggtacatt gcatgactgc tgcgacggta    36300
ctggtattta ctccgcgatc gctacacgcc tgctgtatgc tggtatcgta agcagcgaat    36360
ttggtgaagt gcgacgcgag tcgttatcta acggtcacat atcgaaaagg aatcgggagg    36420
cgttgcttgc gccgactctg acacgcgtcg ccaattccat aacatttcac gagtacgacg    36480
atgcacaatg cgcggcgcat cgcaacgcgt attacagtac gatgaacact ttcgggtcta    36540
tgaggacatc tgacgcgttt caacagctgg cgtcctttat cgatcgattt tcaaaattat    36600
tagctgcctc gtttaaagac gtgaatattt tggacagaaa taacgctccc aaacgagcac    36660
gaataaccgc tccctcgtac gataagcctc atggcacgct ggagctgttt cagaaaatga    36720
tactgatgca cgccacttat ttcttaacgt ccgttttact tgaagaccac gcggaacgtg    36780
ctgaacgttt gctccgtgtc atatttgata tcccagactt ttcggacgcg ccactagac    36840 atttccgaca aagggcgact gttttttctag ttcctaggag acatgggaaa acttggtttt    36900
tggtgccctt gatagcactg gccatgtcgt cttttgaagg tatccgtatt ggatacacgt    36960
cacatattcg gaaagcgata gaacccgttt ttgaagaaat tggggatcgt ctcagacgct    37020
ggtttggtac tcagtgtgtg gatcacgtta aaggagaaac cataacgttt tcgtttccta    37080
gcggatcgag aagtacggta acgtttgcct ccagccataa tacaaacgtg agtattgcat    37140
tcaaaaccgt tgtgtcggat ggtcccccc ctatacacac acccgtgata gtctaataca    37200
cccttgaacc agtatcgaac tccacatctc cggcaggtag accaaatgcc atccgcatga    37260
atttacggga atcttcctac tgtctacctc ggcttcgatt aactcttcga gccgttctgt    37320
aatgcacgcc ttcgtgccgc tattaccgac cactcggacg gcatttaccg tgtccatgaa    37380
taaaacgcaa cagaggcttt ttttcccctt gacttgtata tctgtctgtc gggctttcat    37440
ccacatacac ggacctctgc aaacacaagc ctgcccgagc gatccgcact cccatctcac    37500
gttacaaaca tccacgtgaa ggtcgaaatg cccacggcat tccgcacagc cgctccggtg    37560
gttaagaaat tttgctagag tagcgcccag agaacgttgc tgccaaccgg cgggacatat    37620
agatagcaaa ctctcttcca tcctgaggta ataaaacctg cgtttggaaa gggaccacca    37680
agctccaata gatatcgcta tacagttgtg tggatcgtct ggcggctgcg tgcgttggac    37740
tagggaattt atgtccggtg cgatacaaga gatagttgac aaaggttcta tggcgacgtc    37800
cggaagaccg atacaggtcc tactaggagc gacgtcagaa aagaaaataa gatctgcgga    37860
agatccgtcg cgcagaatgg gggttatgcg taaagcggca gtcacggaat aggcgcgcgt    37920
cccgttgact aagaacaaga gttgaaaagt gtttctgtcc aagtacatct cctttggtcg    37980
cgtaaggtac atgaatatct ccacccattt cgtcttttgc ggccgagcgc ccagcggtac    38040
gtacgtacat aacgtaaagt ctaacgtggt taatgcgacc aacacagcta gacgcgattc    38100
ggcccgaagc gtgcgccata cgcaaatgcg gtcatttaac ttattaacga actcaactgc    38160
cgccgtatcg caagtccgtt ctgaacgacg cggcgatccg ggcgtccttc gtcttcgcgt    38220
```

```
agtcatcgtc ccacatctgt atgacgctac cgctaattga atattcgagt cttggcaggg   38280
cgctcatgga aaagataatg tagtgttgct gctgcagagg cgcgataaaa ccgcgtccgc   38340
ccgcgccaga ggccaattga actcggcgcc ggcatgcgct gctaacatga accccgcggg   38400
caacacgatt gcaacgcgca tacgttcatc ataacctacg caaatatacg cataactttc   38460
tccaggaaga aatctttcac acgttgcgcg cgatacgaac cattcgggga atgcgcaggt   38520
tctaatagat tcgtcgcccg gcccgccggg cgacaaatgc gctgcgtcac gcaaaataac   38580
tgggataggc ctcttattta acatcataca ttctccgccc gcgctataat aatcaaatag   38640
gaaaagattc ggcgtcctag tagcgacggg ttggtagtcg cctcccagga cttcggcatt   38700
gtttccagtc gtatgtatgt aatatgtttt tcctccagtg cgcttaacat gcctggccag   38760
aaacgagatg ctcgcggacc taagagcgcc tactgaaaac ttctcaggcg aagaactcgc   38820
gattgcctgt agaactgcgc gtactgaatg gggtgtgcgg cttgcgattt ctgccacgca   38880
ctgaacgtct cgcgcataca cgtcgtagct gatcagctga tatagattgg gccctgtttt   38940
caacgcttcc ccaactgccc ttatgacaca cgcagagaca tacgacttga aattaatcat   39000
taattcggtt tcggagcccg gagaaaacgc acgcagttgg ttttcctctg cttttaataa   39060
gggagcagcc aaaataggag cttccgttgc gatttcggtc tttcttcttt gtggtagacg   39120
agaggggtga tcgacgcctt cttccataca agcggtagcg agtaaattgc tcaacgaaga   39180
tggaattgtg gcagaatcgg aggaacggcc ccctaaggca atcgaccgct catacgatat   39240
aagataaagt gttttttttgg tcatggagtg ggtacgtgga acgatggata tgcccccgca   39300
cctccaccgg ttcgcaattg tgagcccgtc cgccaaaatg ccgaccgcag aagataggag   39360
gtctttgggg cttaacgaat tttgcgatgg ttcatcgaac atgagaatgt cttccaaatt   39420
caatgcagtc cctgtagatt gctggtcctt attacggccc tccaagcccc tccgagtgtc   39480
gtggtttctg gcaaaccttc cttttgcccac gggctcgaga ccatctatga cggctttctg   39540
tgacacgctg ctactgggtg tgcacaaatt atttttccaaa caagctatcg ccccttggcg   39600
caatccggac actacgctgg cgtgtatatt ctccgccggc cgttttgcgc ttaccggcgc   39660
tcgcctggta atagcctcgg ctgccttctt aatgagattt gcgatctcta tattgtctgt   39720
ctctagtcgc gtgtcgagag taggagtgtc gaagacgttc ggagaatctg ttacttgccg   39780
cataatgtca aactgaccgg gcagttcgac ggcggataaa cacgcctcta atttagcccc   39840
caattctata acagccgacg gtaattcgac ctcgtatctc ttagtatatc gtatgaattg   39900
acggaagagc gtctttaagc ggttcgcatc gatatcgtat cgagtacctg gaggaactaa   39960
ttcctcttga ctaaacagta aatccatgta cgcttcgtac tctccggttt ccctatcctg   40020
tacgttaaag cgaatagcca cggatgtaaa cggatcaaag cggttcttag aatcatattg   40080
tatgggaaga ctcatgaaca atccaccttg atcgtttcga ttgagcgtcg cgaaaagttt   40140
ggcgtggccc gggacatgag gtatcaagag tatgtgtagt gcgccagagg gaacgtaggc   40200
tgccggtgat tcgcgccaac cggaacattt accggtggca ttatagcgca tctgaacact   40260
taccggaatc ggcagcgatt ggtaagcact gctgggtact ctctgtgccg catccttaaa   40320
acgggcgata tctatccccg ctgccgacaa acactcatcc ggtaagagga catgcgtcag   40380
tacgtgccga ttggggccgt gtttgggagt agatagcgaa tacgcggtct cgctctctat   40440
atgcgcctcc atcctgcacc ggaatggcga tcgggtcct gcggtctaga tagcgtcgcg   40500
tcgccgttaa tgcgagggc tatgccttta cggacccctct cgactcagca ttgcttgttt   40560
ttgtttctgc agagcattcg cggccaagat ttcaacttgc tctttgtcga cgaggcgaat   40620
```

```
ttcatacgtc cggatgccgt gcagacaata atagggtttc tgaatcaagc gaattgcaaa   40680
ataattttcg tgtcgtctac gaacagcggt aaggcgagca cgagtttctt atacggtctg   40740
aagggatcgg ccgacgatct cctaaacgtg gtgacgtata tatgcgacga acacatgaaa   40800
catgtgacga attatactaa cgctacgtca tgttcgtgct atgttctgaa caagcccgtg   40860
ttcattacga tggatggggc catgcgtcgc acggctgaaa tgtttctccc cgactctttt   40920
atgaaggaaa taataggggg tatcaccatg gatagaaaca cgtgccaggg agaccggggg   40980 gttttttactg cttctgctgt tgagcggctt cttctatata ggccgtcgac tgtacggaat   41040
caggatatcc tctcgcgaga cttatacgtg tatgtcgatc cggcgtttac tgccaacacc   41100
agagcctccg gaacggggat agccgtaatc ggtaggtatg gagcagatta catcattttc   41160
ggccttgagc acttttctt gcgggccctg acgggagagt ccgcggatgc cataggagag   41220
tgtgccgcgc agtgtatcgc gcaaatctgc gcgatacact gcgagcgttt cggaacgata   41280
agagtggccg tggaagggaa tagcaaccaa gattcagcgg tagcaatagc tactagaatt   41340
tcgatcgacc tggcctcgta cgtgcagtcc ggagtggcac cggcgccaca cgacgtttgt   41400
ttttaccaca gcaagcctgc cggcagcaac gtcgaatatc ccttttcct cttacagcgc   41460 cagaaaactg cggcgtttga ttttttatc gcccgcttca actcgggtcg agtactagct   41520
tctcaagatt tggtttctac cacgattagc ctgtccaccg atccggtcga gtatttgacc   41580
aaacaattga cgaacctctc ggaggtggtc accggcgcga caggcacaag aacgttctct   41640
ggcaaaaaag ggggctacga cgataccgtt gtggccttgg taatggcggt atatatatct   41700
gcccacgcgt cggacgcgac gttcgctcct ataagaggag tcgaggccac gtgtcgcggc   41760
ccaacagaag cgtgaccggc cccgaagcgt gaaatatatc tgccgcgtcg caggaaaagc   41820
taaccaataa gcagactcgc ataagcacaa accgtttatt agaaggctac ccgatgaata   41880
aagttatttt aattccagtt agaaataacg ggacataggt ctccgacttt tatactcgcg   41940
ggcccgtcga acgtgcacac tttcaatagc gggcgcagcg ctagcatgtc ccctagatgc   42000
agagccatgg taatccacga agacagggct tcgtaaatgg gatatctgcg ccacgcgtct   42060
tgcaaaggcg ggggtctcgg aattctgatg agctgaccta ctgctctcgt ggccgtctgg   42120
agacccacca gggcgttgac gtaaccgtca gacgctccca aagtaagcaa cgtcggtatc   42180
agagcatata ggagcatgtt accttcgtcg atagcgaaaa tcatgtttag caataaggtt   42240
ctcactgcag actccgacgc atccagacta tggagcgtcg gactaatggt ataggttttc   42300
ccgttatatg taatggattc cgcttcacgg ctcgtagggg gaggcgctag ccctccgccg   42360
atcgctatcc cttccgtggc tcgagatagc gtcttagcaa taatttcacg tgcgagtctc   42420
gccgaacgtt gatggaaa taaaagttcg gtatcgatcg attccaaccg gatacggag   42480 caaacgttag ggaaaagcgg aggtatcagg catacagcat ccccgttaca taggtcgaac   42540
gggccggtgt tttgaagtgc caggcctgaa ggaatggtcc ccattcccaa aactacagca   42600
ctcattcgac cgggtagcgc gcgggtgacg acggccgcaa atcgtcgttt gtaggtcgat   42660
agcagactca gcgtatcagg ttcggcccca gcgatgtagt atgacttata atctacttct   42720
ttgagcagca ctctggctct gacgacggt aaaaaagaa ctcgcccctc acatcgttga   42780
agtaggttcg cgtcgcacgt agaaagcccg caggggagct cgatctctac tgtcgtacca   42840
ttagaagcgg ccataacggt accgctggcg gtttatttc ggtaccgacg gcggcagcgg   42900
ataagtgtat aggaaccagg ccgagccgct gtcaggtcaa gcacgtagac cgcggaaggt   42960
```

```
tagcgatcgg cgagctggca gttcagcatg caggcaagca tccaccgatc ggcgaagcgt   43020
ctttgattaa gtattgagcc aagtgcgttt ctgggttatc cgcaccccct gcgaaatacg   43080
tgcggagcaa agctttgtcg gtagcgcaaa gtagcggata ggcttcctga aatagggaac   43140
aaggatcttc gattaattcc gtagatccga ctggtcgttt gaactgtact tctccgtccg   43200
acgcgaatgc tgccacggca gaaccggctt cgctgattag tttatccaag caccggcttt   43260
tgcagcacac ttctgccggg gtaaaaaatt tataggtggg actgaagagg ggagacgccc   43320
cgctcaaatt gtaagttccg ttatagagct tgtccgcgta agagaatttt tgcgaagccc   43380
acggattgtt ggttgcgcgg aacggataag cgggatcccc ctgccggtga tcgtacatga   43440
gtttctcgat atcggatact tcctcgtccg aatgtatcgc cccggccgcc ctccctctcg   43500
ggttacacgg ggttcgaaag tactccaggt ctgcggaaac gggtgtaggg atgaactcgc   43560
atatggacat ttggccatgt tccagcccgt cggggagcat gggcatcagt gtacctagaa   43620
aggggacagt tctttgcgga gctgttctct gtccgcgcgt tgctgctttc cgtagaaagt   43680
catcggcttc ggggtttata aggggggcg agccccgtgt caaatgcagg ctttggacag   43740
tgttccccat atccgtcgta gcgtttcgta agagtaaagg ggtacaagtg gccgtatacc   43800
ccacgcccaa atcaacgtta gctcgtggtt gtgtcagaga aaactgcacc cccctgcgt   43860 gcgggcgctt cgagacagac acctgtccga gaaaaaacga ttcggacgcc cgttcggcaa   43920
acaggcccat atctgctagg aacctatctt gtcgtacgac ggtaaatgca attcccggat   43980 ggaacccgt tctcaactga tgatacaggc ctataggagt gagtttgaaa tatcctgcca   44040
tcagcgcgta cgacatttcg ttgggcccgc atctactttc gcatatgtac tgtgccacgg   44100
gctggcggaa cgtagaataa taattggcgc ccaaaaactg tggaacggga ggagctctgc   44160
cgagcagcgt acgcgcgttc ccggccaact ccccgactgc cgttagatgg tcctgacagg   44220
cgaacaaagc gttaactgga acgggataga agtacgtgcc ggcagcgatc gtctcatcat   44280
tgcatgggta ggccatcatt aaaagcccat ggtgtaacgc gccatcgaac gttcgcatat   44340
gccttgtcgc cgatgacgtg ccgcctacat ccggggtggt tccgtagaga atcgccgttg   44400
tccgctccgc catattgttc accgtttcct gcagagttag aagcgcgtcc gcatccacca   44460
atattctggc gttgtgtagc agcacgttaa acgtgttggg gacaagattt ctagcgttca   44520
acgggtgcct cgggtcttct gcgcccaggg gaggctcctc gtcgggttgg atgtcgggaa   44580
tgatcacaga ttgagacgta gcgtagatgt tgtcgaaacg gatgcccatg gtgcaacact   44640 gaccctgga aaatgccggg accatcacgt aataataaat tttcgatagg attgaccatt   44700
catgggtatg atgaggcgcg aacgtttgtc gatcggcgtc tcctacaggc ctgttatgga   44760
ctaaaacgtt gccggtgcgt tcaaaatccg catcctgcaa ttccagccac ggccgcacag   44820
cgtaattttc gtcgcttccc acgttcaaat acaagtttct atcgcgcacg ccgtgcgctt   44880
gatacatcag ggggtcacag tcccacagta ggggggtag gatcgctcta tcgattaagg   44940
cgtggtttaa ttcctcatta ctctgcccgg tcagtgagtc tgtctgaacg gtataatcct   45000
ttacaatcga ccgcagcgcg cgaacgtgcc gcatcagctc tttgtagata ttcgtacagt   45060
cctcagggag ttcaccgctg cataaatagg tatcgtgaa tgcgaccatg tgaaagttat   45120
tgacgaatgc tactcgtttg cagttgtccc agtaactccg tatacattga atgatcagtc   45180
gcatcagtat accgaaatta cgttcgctgc cgtgaattac ggcttcgatt acataaaacg   45240
cagtggggta gctaacgtct gagaacgttg cacatacggc attgattgtg gaagcgctca   45300
ttttgtggcg actggatgcg agctcttggc cgagcgcatc tctaaagtcg ctactgcaga   45360
```

```
gaggtagcgg aatattacag ttgcaaaccc gccaggaggc ggcgatcgac gccatcactt   45420
gcggaacgtt atgcggcccc gggagctcta catctcccgg gaccacaaaa aagtcaaacg   45480
cgggatgcaa ctccatagat agatgtggat ttccggccga taggaattgc tcttgactca   45540
tatggcattc atctacccac cggggcgacc cgcagagcac gtctccgatg ttctcgaaaa   45600
accgacggct agcttcccgt agaggcaagg ccggcgggtt cgtcacatac gccccgaaaa   45660
cacacgttaa atcgcgtctg tcgcgacgta aatgactaac cgtcgcttcg atatccaaaa   45720
aggatgagtg gcacacggtt ccaatagcat ccgataaaca tacgctaatt atctggttgt   45780
ctttgttatg gaaatatagc tcccgtggcg ggaacccgcg cacatctcct tgacatccag   45840
gcccgggcgc atagtcccca atatgccgcg cataacggtc cgcccgtttc tgatatagtc   45900
ccaaaggcat cacgaacgtt aaatctatgt gtccgattaa agggtactgg acttgcgttg   45960
cttgataaac gcgccgttcc atggcttcta gaaaaattaa cttatcccca atggtcacca   46020
attccgcagg cacttctgcc gtttggggga catcgtcgtc tccccgtacg acttcatctg   46080
tacgatcgat gatgtcgttt tcgtcgagat tgagaatata gcgtgcgatg tcgtccatgt   46140
tgcgtatggc tttgcccatc actacggcgg ttactaggtt tgttcccgat attatcattt   46200
ctccatatgt aacgggcacc ctagcagacg tatccgccat gtctagaatt cctgatagca   46260 gttttttgcct caccatgctc gttgttacta gtacgccatc tacgaggcgc cctttcgaat   46320
cggaatgggt cagcctcggc attgcaattg tctgatgagt agagttaacc atcttggcga   46380
ggaatgagac tatactgtct ttgctcgcac cggctttgct catgatgaag gtatcgttac   46440
acactctgcg tttgagctct gataccaaat tcgctcgcat tacctgcccg tttacccttc   46500
cttctgtcgt gctgcgcgaa aggggtatca gtagcggagt cggcggagcc ttttccatca   46560
gtattctaag catctgatcg accgtgcccc gctcaaacga atccaatatc gttctcacgt   46620
ttcgagctaa ttgctgtatg gctctcagtc tcaggtggtt agatattgcc gttccatcta   46680
aagatacttc agataataat gcgagtgctt ccgccgcaac gacaaaggcc gcgcttaacg   46740
atcgcttgca tacgcgcttt accatgtaag tgtaaagcgg ttgatcggca ggatggggcc   46800
cctcgcgcgc aatcatgggt tgctgtattt caaattgcac ggttccttcg cgcatgtata   46860
gcagatcggg agcacgcgtg cagacgcatg cgactgagag ccccgtttcg agaaatctga   46920
tcaaagacaa tgtattgcag taggttccga gaagaatatc gaactgggcc gaatagcgtc   46980
cgttgtcatc ggaactgaat tgtttgaaat agtcgaacat gcatcgatgg gatgtcattt   47040
ctatagcagt caggagtcta cctgtaggcg ctaacgttgc tcctacgttg aatggtgtcg   47100
aaattgcaca cggtgcgatt ggcggacagt cggtcgccgg aggacagcgg catccggcca   47160
tggtcgtcaa cgggccgcgt ccgatgtaag gactaattgc caccgtgact atccgatgct   47220
atgcgtgatc cagggcatct agtaacgttt ggtcgcgtcg aaggtcacgt taccggctgt   47280
tcgaatgcga cgcaaatgat agccgatatt gtaggagaga cgtgacgtgg agaatgcgcg   47340
agttctagca acacgaacga aattgcatat tagactttaa cgatgcaggt ttttatctac   47400
acaatgaagt cgcgagtgcg cgtgccctta tatgtgcaag tttccgcccc taatcagaac   47460
ggaacgcacg tctttatcag tgctcgtgtc cacaaacgag ggaggagaaa tcccagtgcg   47520
tccgacacag ctactgtagc gtaggtgatg gtagctccca ttaacaggta taccacagct   47580
ccgtctgtct tatcgttttc ctctaattgt aaaactttct ccatgaatct cggatcttga   47640
aacaccatgc ggtaagaaaa tactccgaat atcaccgccc ccaacgtaga cagaatacca   47700
```

```
acgaagattt gctggcagtt atccataggc atgacatcat tctttatgtt tctgtacatg   47760
taataagttt cgaggagtaa ggtaccatag aacactgcgg taatggtcgc gcccaggatc   47820
agaaaacgat tgtcgtgccc gtccatcgcg tacaccagaa atataataca acacgagggt   47880
cggagaacaa atgcagatag ccaagagagc acaacatacc gagtaaattt ggggttcatg   47940
tcacagcttt tcgaaatagt gaaaattgaa cctgataagt aagaggacat cgtggcatac   48000
tcggccgcat cttcgcaatc gatatcgtcc gaaacgcgtg taactattga ctccgtgtct   48060
tgcatattcg tctctaactg ttcatcgcca atatagtcga ggagaatatc gcaatcggtc   48120
ggttttgttg tatggtatcc acgcctgtac caaggcatag tgccactcga aaggaccgt    48180 ttctggccac acgtaacgac tttgtcttct actaaagacc acccggactc ggtacagacc   48240
caagctagag ctcgagaccg cggaaaatgg atatcaaata cgaacagaag atcttgtata   48300
gaaacgtcca cttttatatc tcggaatgcg gccgcatagc ttatttcttc tgcggtggtt   48360
gtctcatggc ggtcgggcga ccgcctaccg atgactcgca ggcagagttt gcaaaatttg   48420
ggctggctct tcgaggcgat ggagagtcta aacccttggc agcttatgta cggcgggaat   48480
tgcttcgtag aggaatgaaa tgggcgctgc ctcccggcga cgatgaatta ttcatcgact   48540
gtatggcctt tttgaatcta gacggggcgt gcagtaacg tgagatttgc gatcttgttt    48600
gcctggaaac gtatgatccg gagatcacaa aacacatggt atccacgaac gtcatttctg   48660
gattgttgat ccagacggcg catgagtcgc gcgggactg cgtgatccac ctgcccggg     48720 ccccacaagt tacagacgca cattccaatg ctgtgtacga atgtaattct ggtgcattcg   48780
tgctaacttg cgcaactttg gtggaactgc ccacgtctct gaacgatctc gtcgaagggt   48840
tgtttgacgg tgtccccatc cccagagatg cgctctcgtc gaggtcgctt agtagacgaa   48900
cgaacgtgat tatcacgtct accaaagccg cggaaacgac gactatacag cggatgcatg   48960
tcccgcgaca taaacagagg ggcaacttaa acaccatcgc agctactttg cgaccggtga   49020
aaaaacacgc gcggtttagc ccgttcgtgc aagtaaagta tatacctcgc gtactcaaaa   49080
tatggagttg tgattcagat agccattcgc cgtccctaaa ggagttgcgg gaattgtttt   49140
gtaaagtgga catggtccgt agagaaaaca tgtacgcaga atcgcaattg gaaccagagt   49200
ccgtcacaag tgaactggtt ctgatagtcg atactgtatt tgggagaccg ctcgcaccat   49260
ttattggcgt cgggtcggaa aacatacgcg tctcacattt ccaaaagttc ttactgctcc   49320
agggcgtcct tatattaaat cgtttgccga attgctacgg accgcttcgg gagctgtgca   49380
ttcagcatgc acctgccggt gaagagtcgc ctcctctggt atccgactct gttatcgcag   49440
acatggcgaa ccatatgttt agggtcgccg tatttattgg catggttgtg gaaatagttg   49500
cgggatgtgt atcttttgca tcagaagaac tcgaaacgcg atttcccagt gcgaccgcgt   49560
ttacggatgc tggcattcta ctgaacggca tagaagcctc gccgaagcca aattgcttgt   49620
cggaacttaa aacacgcaaa ctcgctctta tcctggacgg tatttataga gacatggatc   49680
ctatagacgt tgctctacag gaatcggtgg ggctaaatac agcagagtta ttatccgcag   49740
caatagatat ctcggttatg tctgcatttg agcattcggg atggtgtagc ggctacatgg   49800
aacactttgt ttcattgcta gatgcccgtc tgagagaggg agggtgcttg gcaatattcc   49860
ggtagctttg tagcacagcg gcgagacgcg cataggcgtg ccgggcatat acagaacgta   49920
agccaagctg gagtttgtgt aagtatgtgc tctacagcgt gcgggaaggg cggttcgcga   49980
ataaacacaa cagtacaggt tcgacggtta gaaagtttcc agagtttatt aattagattg   50040
gcccctcaag atcgtctttg cgtcttaatt tctcatatcc atggtaccta aagttgctga   50100
```

```
caagcatttt ggcggtgaca atcgctatag ctgcggctat tagtacaccc gctgcagtag   50160
ttgcgatgta ggtcgccgag aggatggcaa tgcgctgcga ctcaaacgct aggatcctca   50220
cgactgtgcc atttggatac agcaatagtg acgtgccata caggttactg gtggtggggt   50280
tgaaatagcg cacggacgaa ttgcctgctg ctagcaattc ccgctgcaaa tcgcgcgatg   50340
agatataaat cgcatgtcga acgtggccgc ttgcggaata tcgcagcagc acgcagccgc   50400
aatacggaca ttcttttccc agaggcctag gtaaaaccgc aggactgatt atacctgatg   50460
tcgacgtgca cggcagcctg gcatatgtta tgtaaagttg gttgtttaca tcaacgccgt   50520
ctacggtata cacgatccct ctgaccccgg cccgccttgt tacaatgtag ctacctatac   50580
cggagatggg taacaccaga agagtgtcgg attctaacct atcagtgccc gaacattcca   50640
aaacctccga cgcgtatgta gcaactgttc tccctattga tgttcgcagc tttgcaatta   50700
ctgattccgc cttggcctgc agatcttctt cgattctgac ccctgagaa gtattctcta    50760 aatactcctc tattactgga cggtaaacca cattggccat cgcgtatacc ctgtgacgcc   50820
gctcggaaat gtcgatcctc aatgatgtca tgcacggcgt atacgcgtcc aaaatatgta   50880
cgggctcagt gctgcgagtg agtctgatat acatgtcttg caccgttaat tcagcggccg   50940
cgatgtgttc ttcagtacac atcgatgatg caaataacag agatttgcgt gcgttatgcg   51000
atgcgcgcca ttccatcggc gaccgctgaa aaacgctgtc gaatgcataa tacagggcgt   51060
gtctcgtgga agcattccac gagatcgcgt ccctgacgga ttcttcgtgg agagacgtga   51120
taaaatttag tgcgaggtcg gaaattcgcg ccccccattc gcccttctcc cgaggtatgt   51180
cgaacgcgta cacggaccgg aataggtaca actgtcgcgc aatacctaaa gaatgcgtcc   51240
ccctcgatac atcgctaatt tttttttca atacgatgt tagtatagca gcttttcat     51300 tccatacatg tgtccgcgat aataagaagc acgtgccggg gtccgtgctc ggggcaaaat   51360
tgcaaagtgc cgcggcgatt actttcagat ctgcctccct tttaattaat tcatcgaggg   51420
agacgtagcc agacttaaaa gcggcgtgta cggacgcaac aagcgccaga acaaacgcg    51480 tcgttacgat cctaaagccg tggatataat tactagtaga tgcgggcata gaggcagaaa   51540
taaaaagccg ggagtgcgct tgagtgatat gaagattata atctaatagg tcatctacac   51600
tcgaaaccat atctgcgtgg gccttttaatt ccatatccga ggcgttctga tatgttccca   51660
gtaggtatgt cgaaaggaga tgtcgagagg atccgttcat cgggtcatac tgcttcatcg   51720
gtggccacag caaagtcatg ttggtagtcc ccgacgataa tattagttcc acaggcgatg   51780
cggcttccat agagatcgta acggaggcga attgcactcc taccttcatt aagacctccg   51840
cggtatttga accgaatatc gtcgtccgca cgtgggcata atctgtcggg actagtgtgt   51900
ccatggggtc cacgaagcat gcacgcttg caaaagctcc cgataattcg ctgttgagaa     51960
taaaacggtt ctccggagtg aagaagtcat tcggctttat attttctaac actgttggcg   52020
ggtttgcgcc agtaggttgt gacttggcac caccgtgagc ttttggaccg ggtttgtccg   52080
gtgtcttttt ttcgtctcgt cgatgggata atacggctgc cgtcaacgag taatcgaggt   52140
ccggcttcgc gttcaaaact ttgatcaggt tattagacgt tagcagccta gatatcggtc   52200
gtttgaagaa aaccatttgc ttcacttcac ttattggtaa atgaaagaga atgccgctcg   52260
ccggcgtaga tgctcctata tatacaaatg tcgcattgtc gcgtacccag gacgtcgggc   52320
tagtagcatt ttcatcggcc gatgaaaagt ccaattttac ggacgcggt ctccggatgt    52380 ctagcagcga ccatacggag gggatattat ccgaggtggg ggctcccggg gaagatgcga   52440
```

```
gcgctagcag taataaggtg cataccgcca ttccgattac gcggcgtcgg tcgttgcctc    52500
tgcgtatcgc tagttcgagc tcgggtttcc gaagcaacgt aacacacata tcctatagtg    52560
tacaatgttt cgatgcaact gaaagcaacg agctaaagcg aagatgtttt gcaggcgaca    52620
agggcatgca ttaatgcaca ctcgtccgaa atgtcgtagt ctcaaatgtc catctcctta    52680
ttgaatgcct gaacgtccgc ctcgatctca aatacatcat tccagctcat atgcgttatt    52740
aatctttccg ccattgaatc cataagatac tctgcacatt tctggaccga catgtcgctg    52800
acatcaagcc gctcgacatt gatgttcctc agtttcatca catcccca caatatccac    52860 ccgtataccg ttaacaggct accatcttca ctgcataatt ctttccgctt aaaaattggc    52920
aaaagcgtgt gctgcaatga cacccggcta ccatggtaac ctgaacgggg accatctata    52980
aatgtagagg ccatcgatgc atcaaaccac gggagctgca tccactctgt ttcccattcg    53040
tctttactgt aaggacaaat gcaattcgca tacgcgacgg tatctgctaa agccgaatat    53100
gccgcattga gcgccctgag catgcgcacg tctgtagttt cccccgctct gttcctggcc    53160
gataggcgct tcaggtgctc ggtttcgtcg ggcaaatgtg ctattaccaa gttgcagccg    53220
ggcggttcgt ggggcaaccg tgtaatcgca ctaatcaaca tttccagaga acaatcgcca    53280
atcagatgtc gggcgatggg aaagcagacg gtagctgaaa caggatggcg atcaactatt    53340
aatataagag atgggttgcc ccgtgttccg gctaattgat gacatttaga tgatattcgt    53400
tcgtgtagta caatgaaggg atcggcaaat ttggcctgca aagccattac gatcatgcta    53460
gactgaaata gagataattc tccccgacgc cggcgttcgg aagcgtcatt cacagctgca    53520
actaaatcgg taaaatagcg acgccaatat ttcagaggct caaaaacttt cagcacgggt    53580
actcccgtcg cagagtggct cggcacttcg tttaacatcg acgttttacc tatagccaat    53640
ggcccgtcga ggtagacgcg gatcagctgc gcggatgtca tctgagaggg cattaccgac    53700
cacggccgca cgtccgacat gtccggcgcg caagaaaact gctcgtagac gatataaccg    53760
gcggagaagc acttctggac gctcaagtta ccgtgcggct gttaacctca agagaactct    53820
agcggccggc gttcgatgtc acgcacgttt ttaccaaaag ctctacgcag aatctatgca    53880
ccttcgaact caggccgatg attggacggg gcgggcccta tctaagattt taggaaaaat    53940
tatgggtttt gatgtatttta aagcggcaac tgatttccga ttggtctttg aagtaaatct    54000
ggggcggcga aaaccggact gcatttgcat gattaggtgc cccgcggtc tatgggaggc    54060 aagttgtgat ggcgcttgcg tcatcattga gttgaagact tgtaggttct ccaataatct    54120
aggaacggcc agcaaaaagg aacagcgcct cactggaaca aaacagctct tggattcaaa    54180
attgctgatt gactatttag cgcccgtagg ttcggagcgt attttcatct gcccgttact    54240
agtattcgtg tccaggagaa aattaaacgt gttgcgtgta acctgcctca gaagaaacgt    54300
cgtaagtacc gatttccatc gtctcgcaac tttaataacg cttgcatcgg aatataagat    54360
taaacaggtc gacaggcgca gaacggctgt tcggaaaccg gctcagtgtg caagaaattt    54420
cgcaagtctt gagaacgcgc ggcgagacga tcgatcggaa gaggtcgaga tacacacttt    54480
tcctaactgt agtattgtcc taccacctcg taccattcta cccggagccg cgaatacgac    54540
aatgcaccgt ttggcaagta ttgttagctg cttggtacgg aagcagtaac cgaaatcaac    54600
ggcaccctac gaccagctat gttacacggt gcaatccgcg gcccttctcc cgttactttc    54660
ttgctccgca gcccttgtcc aacgtcagtt gtccgtaggc actgcagcaa agcatggcga    54720
gctttgcctg ggatgcaaga attttgacag acccgggccc ggaatctcac ccggctgatg    54780
taaagaattt catagcacct ccctggcctc tgcacttctg gagggaacct atatttagcg    54840
```

```
gcaatcttgg ggatgcggaa cggcaactgg caatcgttaa ggcgcgaaac agtgccgcga   54900
ttgcagcgtt aactagtttg gacgaccgta ctgatttaat tgcggtagaa gtggagcgtc   54960
ggcttcgacc actagaagat aaaatggaac agatcgcaac gactttggcg gatttggaac   55020
gagctgcttc tgcggctgaa cttgccgacg ccgcagccga tgaggctcaa aatgtcgtcg   55080
attcgaacga atgccaaaaa aacattggta gcgctgcgag tcgcgaggtc caaatagtca   55140
ggaacgatcc gtcgctaaga tacgactcta acctgtcggt ggatctgctg aatattatct   55200
atgccagcag gggcgctgcg aattcgggag tggcgttcgg tacatggtac cgtactttac   55260
aaaactccct tattgcggaa aatcccagcg ctgcgcggaa gatagattat cgcgatggaa   55320
gaatgtcgcg gaccttcatt gcaacggcga taacgtcctt acagtcatgt gggcgcttat   55380
atgtggggac gcgtaactat tcttctttag aatctgcagt tctatgtctg tatgcgtttt   55440
atacaaaaac gggagctaat gtgtcccatc caagttcttt taagagtgca ttagaatctg   55500
ttcccattta tctggatcac atgtcagcga gcctcgctag cactgatacc aggcaaatct   55560
acgggttcga taccgggaaa ttgccgaagg atagtttcgc cgccccgtcc ggaaaatacg   55620
aacggggcgc gctaagtgat catagcgtat tgagagctct agcaaattct cgcgtgttgc   55680
ctcctagtgc ggggtcgatc ccccgtggag acgtagcccc agagctagat gccgaccaga   55740
gcgttcgtaa cgacgaagtc aacgctgccg ccgcagcgct actgggacga gcccaacccc   55800
tcttccttat ggaggatcag acgttgctga gagccacttt ggacacaatc gtggcattgc   55860
ttttacttcg ccgtctactt tggaatacga atatatattc agctagagtt aaaaaccagt   55920
tccaactggg ggcgttcgtt ccaggcgtgc ctccagattt aaccgtagga gcctcagtag   55980
acacgccggg ggatgtaatt aagagtgacg ggagaaactt aaccttttta tttcagagat   56040
acgtagttcc cgtatatagt gttgtcaaag ggatagagct cacacaactc tttccggggc   56100
tggtagcgtt gtgtttggac gtcccgtttt ccgatcgagg gttatatagc accaggacgc   56160
cgccatcgcg tatcattgac gtttcgctga gtaaatatca ggcctccctc gtgaaattga   56220
tttccttaga gcttcaaaat cgttcccgcg ctaatgttgt atctgtttgc gaggtgatcg   56280
cgactcacga tttggtgact ctgcagtatg agcgaggctt ggaatcgctg atgcaagtcc   56340
agcgtccccg cacccgcttt tttgaaacca agaaggcttt ggcgttcaat gtggaaacgg   56400
attacgatct gctttatttc gtgtgtttag ggtatattcc gaggtccgta tctgcatcgt   56460
gaaatatacg caaatatttg gcacgtgtcc agcttaaaca acagtttagt agaaatgaat   56520
ccgacggaga aatattcctc ggtatatgtc gccggatatt tgttttttgta cggtgcagat   56580 gatggcagcg aactgcacat cgaccgcgag gatattcgag ctgcaattcc gacacctgct   56640
cctttgccca taaacataga tcatatacgg aactgtaccg tcggagccgt tctggcacta   56700
acggacgacg aacacgggct gttcttttta ggaaaaataa attgcccggt gatgatacgc   56760
acgctcgaga cggccgctag tcaggaaata ttcagcgaat tcgataatct caaaacagag   56820
gagagggtat tgtatttgat aacgaactat ctaccatcgg tgtcgttatc ttccaaacgt   56880
cttgaacccg gggaaaaggc cgacaaaagt tttctggcac acgtagcttt tgtgtttattg   56940 gggaaacgaa tcgggactat cgttacatac gatcttactc cggaaaatgc cattgaaccg   57000
ttcaggaagc tttcccctac taccaagacg gccctactat ccgaggggca agaaacagag   57060
cggctcttag gcgataaggt ctggcatcct agtaaagagg cgatgtcaac cgcgttgttg   57120
ggcaccgctc tgaacaatat gttattaaga gatagatggc gcactatttc cagccgaaga   57180
```

```
cgcatggctg gtatatccgg ccagaagtac ttgcaggcgt cagccttgac cgcactggcc   57240
gagtcgatga cgtccaataa cgcatcaacg atccatccaa tcggcgaaac cgcaaactcg   57300
gacggcatac aaaaggatga tcgaattgaa gtgtgcgcca cttcgccgca acgaacaaa    57360 accttagagt ccagagcatt ttcgggaggg agtgggttcg ccgggactca tgcgatctct   57420
ccaccgcccc agatgagcgc acaatcgcca accgagatgt ctatgaatac taaatctcat   57480 ttccccccg cgacgattt catttgggtt cctatgaaaa gctacaacga actggtgtcg    57540
agacaggcca cgcacgcaat taatgccccc gaagctgcag tggggagcca ggcaccgtat   57600
agttcctctc cgttaatgat tccggcgcac ttgggacagc atgctcacat tgggggatat   57660
ggacatgcct ccaacccgca atttgcatcg ggggccataa attacatggg cgggtttcca   57720
tatgctctgc ctatccaccc cgttccaacc ggccaatcgt cttttggaaac caagctgtcg   57780 gctctactgg attgtatgac gagggagaaa aaatcagtcg atgggggatcg cggacgtgac   57840 gacatgttct ctggccaaga agaacgaggc cggcgcgggc gcaagcgccc gtacaactgt   57900
gacaaatctc ccgagcagga accttattat ccaggcgaat ccagcagtc cgagcatcgt    57960 aacttaagat gcgaagacgg catcgaatac gggcgagacg cgactcaaac gaggcccgcc   58020
ctggcgggcc tcgtgaacgc tgttacgtct ttgcagaaag aagttgaacg gttaaacgga   58080
agggcgcaag cccattcgat accggccgta cagcatatgc aaggaatggg aaccggattc   58140
caggcccccg tatactacgc ataccctcct ctcccaatac cacatgtatt ttcgcggccg   58200
ccagaagacg gccgcccaat ttcttccggg gagggaaggg cctcgctagg tagcgccacg   58260
ggcactcctc cgtctggatc ggtacctccg aacgcttctc aagaacgtgt cgatgcagct   58320
cctaaaagcg acaccgttca gtcgcaagat actgtgaacg ccagtacgat cgccaatgta   58380
catcgcgccg acgatgcagg cgcggatatt ttcattaaac aaatgatggc ttaaatgatg   58440
gcaggggatc cgctatgtcg acgtataagt ttatacattt tgcgaccgca atagcaaata   58500
aaagtaaaat aatcgtatgc gcacgtgaga atttatttat cgagaaacag catcgcgcta   58560
aacggcatcg tcctccgaat cagagtacac aggcgataat ctatcgtagt gctggccact   58620 acttttagc ctcagctttg ttaggtgatt agaaagaata gcagtggtgc ctcttgtttt    58680
tttgcgcaaa tcattttcgt ggcgttcctc tgcggacacc aacgccatat atttttatcat  58740 ttctcgagcc ttctgtaatt tttttttatc gattggtgcc ttttccgagt ccggttcttc   58800
tccgtgcaac tcgcgcgttg cctgggactt tagctcttcc gtcgtcactg gatataggc    58860 tttcatcggg ttgcctctaa gcttgtttac gtaccagtaa gctagaaacg cagccacgag   58920
tcctgctata attatcaatc ctaccgctaa agctccgaac gggttagaca taaaagcgga   58980
cactccagat acggtagcca ccacggcacc ggcggcaccc acaacgacct tccctatggc   59040
ctgaccgact tgccccatac cgttgaacaa ttccgccagg ccgttcataa aagcgtaatt   59100
tgtatctact tctattactt tatttatgtc ataaaattt agttcgtgca actggttgcg    59160
gcgagccacc tcggcatagt ccaataccccc gacatctcgc aactcctctt tcgtgtagac   59220
cgacagagga agaatttctc tgtcttctaa cagtgttaag ttcaggtcta caaacgtgct   59280
ggctgtctgt atatcagcaa cctctaccat cttaacaaag ttatagtctt cgaacagagc   59340
gtatgcggat ccaaacagga agtatctccg ctggttagcc gtacacggtt ctacggcctc   59400
cagtgttggg agtagctcgt tattttcgcg gagctggcct tgtatcctcc cctggttctc   59460
gccatacgaa aacaagacca gcgggcggct gtagcacata ttagtagacg tggcgaccct   59520
catggaattc tgcaatgtta ccgattccgc gtcgatccca gtacaagtag acacggcggt   59580
```

```
cacatcccct aacattttag ccgctacgcg tctccctaag gtagcgctcg cgatggcgct   59640
cgggttaatt ttcatcccdt cctgccataa agccagttct ttattttgta attcgcacca   59700
ggccgtggcg attcggctga acatgtcgtt gatatgagtc tgtatatggt cgtagagaaa   59760
ttggagcatg gcgaattgga cggacgaagt agatcttatc gtagcgcctt cgttcagcgc   59820 cagttttcc ttcggcgcat tacggagctc tcgccgcaaa cgggacaagg agacatttgt   59880
tttattggaa agagcatgct tattatgtac taggtctagc agctcgtctg tcctgttgtc   59940
cctcatcagt tctcttagat acatgtgagc cagagatttc gacataacgg gctgatacgc   60000
cacaagaaat ccaccgaggg ccaaaaaata ttggaccttc ccgaccttga cgtggctgtc   60060
gttatatttt tgcgcgaata tgcgcttgat tgttgtttca gcgtcgcgct ttacgcactg   60120
acctagcctg atacgatccg gatcgaattc agtggtattg ctgataaatg ttgacgatag   60180
ctcgcgggcc atgaatctat acttgccgtt aaccgttgcg cgcaacattt cagtaacatc   60240
tttccattta accatcgagc atacacgagc ggtctttgct gcccagtccc acccaaccgt   60300
aaaatgtgga gtgacgagga agttacgctt gacgggtatg ctcgccttct gacgcttgct   60360
cagatccatt gggaaatagc cgtctatctg cctaaattgt tctagcggat agcccatggg   60420
ttcggcggcg gcctcgggcg gggcgacgcc ataaaacggg gacatatttg cgatatctcc   60480
gttcgccatt gcaaaatacg agtatgggaa tgcagccctg gcatccattt cttccactat   60540
gcagttgaca gacgtccccg tccgatatac ccacggagac ccccatacgg tataagtgtc   60600
gttggtcgta tgccacgcct tggactcggg ggtgttgaat tttgacggtt gtagaagtac   60660 ctgttttct ccggcgtcgc cgtcgtatgc ctcgacgtat acattgtttc tcaggtatcg   60720
cgctttggag gaacatctcc cttcgcgtc gattacatcc gtaatttctt cgatggaaac   60780
gggagtccta tctgtaaacc tgttggtgat ttgtctgtac gtcgtcccgg tccaggtcgt   60840
cgtttgtata acgttcttat aataaagcgt gactttgaat ttgtatgggt ttatattctc   60900
tttgaagagt atagcaattc cttctcccca ttcggtggcc tttagcggtt cggggcattt   60960
tcgcggcggt tctaaccgga ccacggtcgt accgaccgcc ggtgggcaga gaaaaaatga   61020
ggactcgtct tcagacagct gtacgctcga gactgcttcc cgcgacgtta cgttttgggc   61080
cctcgcgact cggccgaaga agtagaaaac cacagatatg aaaagtggaa cgcagatccc   61140
actgaaatgg ttcattacgg gttgatctta acgagtctca tcgatagtgt ggaaaggcgc   61200
gccgcggtac gaaagatatc gcactggtca agtgggggtg tggtcatggt ttgttcgttc   61260
cgcacgtatc tgatccgcag ccgcgggagc catgtactgc agaatggaat agagcagcga   61320
gaaaacatcc gcatcaagga ttacggtcac gttgtctgat tccgcaccga ggaccgttat   61380
gagagggcat tctgtttcat atgtgacgta tattccatcc tcccatatgt attccacgtt   61440
aacattgagc ggcaagcaat ctgcacgacg caggtgcaat tcaccgcagc tgaacgcgga   61500
agaaaataaa gttgtcgcca aaatcacctc ttttatatat ttccaagcca ttctatgggc   61560
cgcggttata ctatctatgc cgtcgaagtc gtaaaaccct ctgaatttac tgacgatcca   61620
gtcagacgaa ctgcaactat gaatcataaa tcgcgctatt tcctccttca aatgcggcaa   61680
tagaccaacg ttctctacac tgaaatatag cgctgtattc gaaggttggg cgaacctatg   61740
tacatcgtga ttaaacatcg ggccgtttaa caaccgaaaa aatttgtgag ttaggctggg   61800
gagcatcgcg ggatctattc tgtgcttaag taatgacgtt tgcatgaaac ggtgggcgtc   61860
gaacgcatca gcggtgatgc gattatcgat gatattcgta catcgtttcc taatggcttc   61920
```

```
caataaccta ttcctggagc ggaacccatt gaataatgtc gtgtatgagt ctatcaatat   61980
ttcaccgtat acgttaaccc gcagcatttt ttccagctcc tttctttgct ctgtaataca   62040
tttatccaaa cttgcgaggg atcttttact taggcgctct gcgtacattt tgcgtctccg   62100
agcaacgtca gccgatgccg atcgtaccaa ctctaaccag tcgtagtgct cgcggacatc   62160
gggtaacggg gtaaccccttt cgcgaatccg tagatgctcg gagttactaa aatcgtcctc   62220
gggcgcgccg tcgccgtcct ggcataggggg accatttctc gtgctatgcg aagtcacttg   62280
ttctaaagta gtcttcagcg cgtcttgcgc cgcctcctcc gggtacaata aacgttttag   62340
cagaggagtc gacatatgat gatcgtaaca tgctcttatc agcgcttcta tgatgtcgtc   62400
tggcgctacc gccctacccc ccagaagcaa tctgtcggcc gcattcatat tctcgatttc   62460
ttgtgcaaac acccgttcga aatgatccat gcgccgcccg aataccgtca tttccacgac   62520
ggatgttctc agatcgaaaa gacgctcttt gaatgctaaa tcttcgaggt tgtccgcaaa   62580
cgagtcaatc gtgtttgctc tcggttggtt aggtttgcgt tcggacgagg caatccagaa   62640
ttgcagctcg ctaatggcat acagattccc cgatgccggc aaaaaaacgt tatgcgcgtc   62700
caggacggcg gttgccgcat cggcgacaga cactgtatcg ccgctacctc cgggatcctt   62760
gtctcccctt gtcggtctaa tgagcgaaag tgccgcttgt acaaccgaac gcttttcgtc   62820
ggacagacaa gcggcatgtg ggatgtgcgc taccatgtca tctgggtgga cgcggagaac   62880
gatctgctta gttacatgat tacatatttt tccgattatg cgcttatgtg ccgagtctcc   62940
actgtttgcc gtcacgcata gttcttcaaa acaaacggag catggttgtg acgggtcgca   63000
caactccggc gaaacgaccg atcccgcgcc cagagtttcg attagatatc gatccagggc   63060
caacataaag tttctgcgg ttcccgcttt tacgattagg tgacagtaat tgagttgctt   63120
caatatgttt tctacgtcgt gtaggaattt aatctcggtc cgcaccgaac cgccgtaagt   63180
atccaattcg acgacttcgt gatacggaca gtccccggat atggtcatcg acttaataaa   63240
aaagccgtgt acatctccgg tgtctgtaaa ctcgcacagc gcacgcagca gcacttctcc   63300
gtctagtcga gctctacgca gagctaacca caaaccgtag ctaaggggac taatattcct   63360
ctcgagttgc tccgtcagcc caggagccat taggttttcc aaatagcgta ccatgagcac   63420
atttaatttc agcggcttga tcattcgcac acctactctc ggatcgcatc tcttcagcag   63480
ctctacttga aacaagtacg attgcaactg accccataca gcgagcagtt tctgactagc   63540
gaatatactg tctcgctcaa cgtctagcgc ttgtgcgttt ccgtgaggca tatccaacgt   63600
ctcggttcgc ctcgtctacg ctgaattgga cctgagtcgg agggagagca tgatgatatt   63660
tataggggtt agccgataac gccccatccg gaataagacc cacaaagcga tataagaaag   63720
agtatgctgt atatttcata tttccgtata caggttgaaa agccgacaat gacgtagtat   63780
ctatcttgat aaggctatgc gagcaggccc catccgggat atgagctagg tagttcgata   63840
caaaagtaaa cgcgtttaga cccaaacaca gattttaaaa gcccgcaacc cacgtactgg   63900
gacaacaata cacgcggtta tagcatatcc accgatagtc ctggagcccg cttttcggga   63960
acgggctcca agtcaaaaac gtccgaacac ggacgtttca aagttggctc taatatggac   64020
gggccgtccg cgcgtctttc cgtattctca tcaagagcat cgtaattaaa cgtaggtccg   64080
tccagcggga gagccttcga catatcgacc atctctttcg ctaatatcgc ggcagcatcg   64140
acactccaac cgcccctcgca tccctctacc tgcttgttaa gttcatctat caaagatgag   64200
atgtacgcat cgttagttat ttccatccag tcatccagtt ccatttgccg tacacgatct   64260
ccaaccattt tcaacgcgat catatatacg gcggcatgag gcgctccgca ctcctcagat   64320
```

```
aaaaccgccc gggctctatc cacgagcgtg gtttccttca agcccgagga aaatccagtc   64380
tgttccgata caaagccgac cctaggacat gccatgacga aacggtgggt tctattaaaa   64440
gacattatgg agcagacgtt tctcccaccc attatgttgc cccagttgcc ggattggaat   64500
acttttgtgc taccggccat tccgtgatat ttactgatgc tgacggctat cacaacaaag   64560
ggtttagagg ccatgatagg accgacgaga ttagtagatg aaaaggcagc acaccatgct   64620
tccttatgat cacagatatt ttttagcagt tgctgggcgg ctggtgccac atctgaccct   64680
tgtgtgagga tatgttcgat ccagggcagg accatagccg gatccctagg tcgcttggag   64740
gttgcaacca aagccgaaat cgtgttgata aagaaatgct tatgtgaaca gtacctcagg   64800
atggtattcg ctagataaaa ttgagccagc tccccgaagc atgtaggact gatgttaatg   64860
taattcatat cggcgtagct attggtaaac cttttaatga atgacgtgtt ctcctcggca   64920
tctttggaga gtataccggc cggcaactga ttgcgttgta agaggatcca aaaccagaga   64980
gcattgggag tcgtgccatt aggcatctta acattcggaa aaagttgcgt gtgataccgt   65040
ttgagcgcaa agccgagagg gccattgagc acatgcatcg cttttgccgg ccgttgatac   65100
gcttctatca tgcccgccag ccgggatttt gtagcgtcgg agacggtact ggaaacgcct   65160
ccgacgaaca taactttatt cttcacttta aattcccgga atatctcaaa tgtaactttc   65220
actagatctc cttccatgtg caccgccagc ggatcatgct gagatttgct aggatcggga   65280
acggagattt gttgatcctc taaggtcacc gttatgtttt tagatgtgat gaacccggcg   65340
ttttgcaagt ccagtacgcg ccgcctgagt accgcttgga actgagtcct aaaatttcta   65400
gcctctactt gttgcccgtg cattatcata gagcactggc ttaacgccat atcttgaacg   65460
acggcaatta tcgtgcgcct ggataaaaat gagagcacgg gacatatgcc tgacgaatac   65520
ggctctattg ccagcgaaag ggtatgggtt gcatcaccta gcccttgcgcg tatgttatat   65580 tctctgattt ctgtcaaatt tcgcatcagc tggccagctt cgctctcgat tatattagcc   65640
attgtcgata gagcacgcat aaacgatttg ccatcccgga tgatggcatc tgcgggtgtc   65700
atgtctgctg gtcctcgca tgtcagcaaa ccttcttttt ctaacgcttt cattactctt   65760
tcgaccgtca gcttgtacgt gtcctgcatt acactgcggc tcgtctctcc ctccgatcgt   65820
ttgagagtcg agaatggggc gtagcttccc agcgcgttca cgtcgcagta gttattcgtc   65880
atagatccaa agagccccat agccccacgc atctgatacc cgaatttcgg caatcgatat   65940
tctaagcgct taattgtggt atgggcgcaa taaatacgcg acgctttgtc gcacaaatcg   66000
catggtacgt ccgcgtccat ggcagatgaa acaaatttca cggtatctaa atcgtgatgg   66060
caagcttgag atccgccgtc acacctctcc aggtagaaca agaatcttgc cagcaattgc   66120
ggacaaaacc cacacgccaa aattaggtaa tctaacgagt attccgacgg gctggccgat   66180
gtggctttgg acaaatcttc gcccggaatc ggcttgccgt ctctatcgat taacgggttt   66240
gaggccaaat gcggcgcggc tatttggaaa accgataaa acgaggctgc ggtcgtactt   66300
gtgtcttttc cgtctgcgct actcgcttct cccacctcgg tcatgtatat aaccgaattc   66360
gaactaaaca ccattgcccc gaccagtcct gccacgcggg ccatatacgc agacagcgct   66420
tccactctat ctgtatatcc gatcggactg caatagaggg gccatttctt tacatcgggt   66480
atagactcct cgtagaccga tgtcgcgatt acgttttcta tggacagagt agcgtcggat   66540
gccattagag aagccgtcct acgttcatac ccccgccag atagctccat gccttccttt   66600
ttccccgctt tatactgcga tttcgaagca gattcgatgg gagtgaatgc gttaaaagct   66660
```

```
gtatctgcgg gtaacaatgt ccctcgtga ttttcgtcaa agcttaaatg ggcggcacag    66720
cgcgcaatcg cgtctacatt gcgaacgcga aggcctacgg ccgcggtact gagcacataa    66780
ccgtgtaata gacgacataa ggaatcatta tagaaagcct ttggcataag agctccctcg    66840
cctagtgctc taggcttcgt actaaatgga tcgctggcaa cgcggttgaa gtccgggaaa    66900
accaagtgca ggggatataa cggtattcta cgaacatcga cgccattaat gctcacgact    66960
ccagtaccac cgtaatgtaa atatgagttg cagaggtaca cggcctcttt aaataattcg    67020
gtcactacta agtagagcat agtttcttga ggattcattc cgagattatc gcatatttgc    67080
tcgccggttg tttcgaacga cgtggctacc gggggcgaat aggtgctgta gccgaatctt    67140
cctcgtgcca aatcacatgc tttagtcaga ttcggagcct tcgtgcacgg ttttatacat    67200
tctccgccgt gaaacacaaa cacgcacgga tggtaatgcg tcggaacgag cttgagagta    67260
gttgatccgc tacccagacc cgttgtcttc gttcctgcaa cagctgccac gttccacatg    67320
aaatccgctt caactgtaag acctgaaacg agaggcaata tcgcatcctc gcagtcattg    67380
ctcttggccg cgaagatcga gagatcttca gctggcatgc tgctcgtggg tgcagcatat    67440
acatatccta tcggcccccc ggtgatctta acgcttttcc ctacatccat ggttaaggtg    67500
tcagcgttta tccggtagac tgtacaacgg aatggcaagg ggcgatgtgc cttccaaagc    67560
tgcgaacgcc ggcttcgcca ggagatggca ctttgacttt tcgtgccgg atgttttaaa    67620 gccagaggac ctccaaagga tatgacgcaa cacttcctaa agtgcgccac gaaacacgtc    67680
gcgcatattg tatgttttat aagtcctcga cttcaaactt gccttctctg taagccgata    67740
tgtcagtaga tggggctaga acttttttca acccgtacct cggtgcacga aagaggggac    67800
gggatgaaga tagtaccata ccgccgctaa gtagaccgcg ggacggggag atataccttc    67860
ggcaacatcg caatgcgatt acctatatag cgactataga cgaatttaaa tatatcgccc    67920
ccaaatgctt agacgcggcg gaaataaagc agcgggcac tcatatcggc aaattgaaac    67980
gctcgcctat actgtacaaa aacgagagg aacgtgagtt cttgaatttc gaggctttgg    68040
gggacgcgtg gccacggaga tgttttagct ggaataacgt atcattctta cccacggaat    68100
tcgacccgcg ttttctagg tttcatgtgt acgatatgat tgaaacggta gagttttgcaa    68160 atggggcaac aggcagagat aaaaaccgtt ttctggagct attgcggcct atgggcacga    68220
ttattaccat gatgggaatg actgaatgcg gcaggcgcgt ggctgtgcat gtctacggcg    68280
tcaaaccata cttctatatg cgtaagatcg atgtagacac cgcctgcggg agtcgatcca    68340
cccgcggact cgctgagcag atggcgagcg tggtacgctc gtctgtgaac gaaagcgcaa    68400
gaaaacgatt ttacggctca agcactgtga cggccgactg tttcgaagtg gacgtggtac    68460
gtcgtaagga tatttatttc tacgggacag attgcgaaga gtattaccgg attaggtgtc    68520
agagcggcaa attcgttgcg ctcatatgtg ataactttca cccctccata attaaatacg    68580
aaggcagtgt cgatacaatt actcgaatgg tgctggacaa cgccggattt agtacatttg    68640
gatggtattc cctaaaaatt gggaattgcg gtgagaaagt acaagttcga gcgccccagc    68700
accatgttac ttcatgcgac atcgaaatta attgtacggt ggacaatttg attggtcatc    68760
cagaggacga tcactggccc gattacaagc tcctatgctt tgatatcgaa tgcaaatccg    68820
ggggagcgaa cgaatgcgca tttccggtgg ccacgaacga ggaggatgta gtcattcaga    68880
tctcgtgtct gatgtattcg gttcgacaaa agcaattaga acatgcgctg ttgtttgccc    68940
tcggttcatg tgatcttccc gaaaccttcc aagagacgtt tcgtgatacc tatgcgtttt    69000
tgcccgaagt cctcgaattc gacagtgaat tcgaactgct gttggcgttc atgactttg    69060
```

```
tcaagcagta cgccccggaa ttcgtaacgg ggtataatat agtcaatttc gattgggcgt   69120
tcatagtgaa taagttgacc accgtttacg gtattagatt ggacggatac ggggttatta   69180
accaaagagg gacgttcaaa gtatgggatg ccggggcaaa cgcatttcaa aaaaaaggga   69240
aatttaaggc caccggaata atcgctttag atatgtattg catagccacc gagaagttga   69300
agctgcaaag ttacaagtta gacgtggtgg cggaagccgc gttggggag cggaaaaagg    69360 agctgtcgta taaagaaata ccaacgcact ttgcggcagg tcccagccaa cgtgaattaa   69420
taggagaata ctgttttcag gattcgttgt tggtagggaa attattttc aaatacgttc    69480 ctcatttgga actgtcagcg atagcaaaat tagcccgggat attgctatcg cgagcggtat  69540
tcgatggcca gcaaatacgc gtgtacacgt gcttactacg gttggcgggc tcgcgaaatt   69600
tcattctgcc gaataagccg caggtgcgtg cgggaaccga gttcgaaaac agcatcgcca   69660
gtacggatga atttgaaggc gaaccttccc cttcgaatcc aaaggcatcc tcatcatttc   69720
atggaaatgg cggcagagtc gtcggttacc aaggagcgaa agtgttagat cccatttcgg   69780
gattccacgt cgaccccgtg gtagtctttg attttgccag cttgtatcct agcataattc   69840
aggcacataa cctgtgtttc accaccctaa taaacgacga cagaaaactc gccgatctac   69900
gtccacgcga tgattatatg gaaatcgacg tacaaggaaa atcgctgcat tttgccaaac   69960
cccatattcg agaagtttta ctgggtatcc tattaaagga ctggttggcc atgagaaaag   70020
cgatccgagc taaaatcccc gctagctctg atgatacagc tgttcttttg gataagcagc   70080
aggcagccat caaagtggtc tgcaattccg tgtacgggtt ttgcggtgtg gcaaacgggc   70140
tattaccttg cattgatgtg gccgcgaccg tgaccacaat tggtcgtgac atgttgctta   70200
cagtacgtga ctacgttaag gttaagtggg gaaccagaga tgccctcctc cgcgaatttc   70260
ccgcgctgac gaattatatg ttgggcgacg attactccgt gagcgtgatt tacggtgata   70320
ccgattcggt gttcattaag ttcaaagggg tagcgataca gggcctcgtc gcaaatggag   70380
acgatatggc aaaacgcata tcgtccgatt tatttcccaa acctatcaag ttggagtgtg   70440
aaaagacatt cgacaagctg ttgcttataa cgaaaaagaa atacatgggg acgattcacg   70500
gtgggaggat gttaatgaag ggagtggaca ttgttcgaaa gaataattgc cgcttcatta   70560
acacatacgc aaaaaagtta agtgatttgc tatttcagga cgatgcggtg gcaaaagcag   70620
ccgccctcgt cgcggaaagg ccttcgtcat tttgggcaac ggctccccta ccagaaggct   70680
tgaagccctt cggggacata ttggctgagg catacggtca aatgacggca agcacgttgt   70740
ccgacgtggg agatttcgtc atgtcggccg aactaagtcg gccaccgcag gcctacgcta   70800 acaaagaat agctcatctc accgtgtatc acaaattggc catgcggtcc gaacagttgc    70860
ccatggtaaa agaccggatt tcctatgtca tagctgccgc aacgccggag gtactgcgcg   70920
atgccgagcg ggtagcagaa gccagagggg aaaggaaatt ccgctttagc gaggtctctg   70980
tcccggaggt tccaggacg tttagcaaca gcgccaagac gcgggccgtc caaaaaccca    71040
aggtattgat ctctgacatg gcggaagacc cgacatatct aatcgaaaac aatattcccc   71100
tcaacacaga ttattatcta tcacatctat taggaactct atgtgtaatt ttcaaggctt   71160
tattcggcaa tgacaccaaa acaacggata ctgtattaaa gcgatttatt cccgaaactt   71220
atacagagga tcgcgcctac gcgacgcgag ttgcgcgcgc cgtctttgcg gagatacgca   71280
gcggggccgg tctaagttct agcgaggagg aagaaactct tcaaagactg aatagagctt   71340
tccgtattct aacagaagtt cgccgtcgat attaatgtcg catagcttac agtacacgtc   71400
```

| | |
|---|---|
| gtcggcgttg acggctggga catcactcga atctgtttga cgatcgtatt cttttctaat | 71460 |
| gactaataaa aagttaccgc gccacacgtg agcgattatg ctgtaattct tacaggccgt | 71520 |
| ttttaaacaa tcaatcaatt tgtagtggag gtggagagct ttcccgggga acacgacata | 71580 |
| catcatgtat tcaagggagc ctgcttcctg atccaagtaa aacaacacct tcacattttt | 71640 |
| cattccagaa tcgagtagca catagtatgc gaaaaaaagt tccgggattg ccaaaatacg | 71700 |
| agaaagggca atttcgctat cttttccccg ctcctctccg caccccattc tgccgcccaa | 71760 |
| ggccacgata gaagccatga aattcctata atgataaatg ttgtttatct gttggacata | 71820 |
| tgccaatatc aaagaggcac gatcgtttcg ccccaatcgc gggtctccgc tagccgtgca | 71880 |
| cgtagggcaa cagccaccaa ctccgagata ataccccatt cccgacaaag acaaacagtt | 71940 |
| atctgcgaca gcttccgaca tattgaacgg caacgagact ggcgttgtct tgatgatcgg | 72000 |
| cacagccaaa tccttgacta ccattagttc ctccgatggg gactcttcaa cgaaatcgaa | 72060 |
| gtaagcgcga tacaaatcga catctggttt tcgagacccg cgtttcgtac cgcatgccgg | 72120 |
| cgcttgtaga tctcgccatt gccgccgcga ccgtcttgct atccctccgc tacgccctac | 72180 |
| agatctgcgt cgtatgaaaa tgcaaccggt catgccggga attacgatgt cacacgtagg | 72240 |
| tttgtagcgt gtgctcgaga gatatcaggg atatagagtg tctttgaaga aatgcgccag | 72300 |
| cgtctttgac gaacgcggat aaagtagtcg gccggggagg gaaaacctga tatgtcttga | 72360 |
| acgtgtacgc caaggcccaa aacccggcgc atacgcgacc ttcgaaacgg ttatggcttg | 72420 |
| cgagccgagc tttatggagt gccaattctt cccggctcgc taggtccggg tggtcgaaca | 72480 |
| atgaccgtgg attggtctgc gctatccgcg cagcacacat cgggtcgcaa aagaagtgtt | 72540 |
| tgtagattgc ttccgttccc gtgcctttga gcagcgccac gaagtatccg tcatcttcaa | 72600 |
| aatcggcatt tctctcctgc gtcccccacg cctccaacac cggttctatg ctatggaaaa | 72660 |
| tgccgatgtt gttagctgaa taggcaatga tatcgcgctt aaattgccgc attgcaagcc | 72720 |
| agtacgtgcg gattagtagg aagttgcaca ataagcattc cgcggacgtt ccccctttgg | 72780 |
| ttatcgcgtg ctttaattgt gttaccatta agggtcctaa ctccaaatca ggttctgagt | 72840 |
| catcttcgta acagtgacta tatgcccgag tcgcccctct agcaagatct attctgttgt | 72900 |
| cttttccaaaa cttgctgacc gtctccttcc taaatttcgc tgccataaga gcgagttcgc | 72960 |
| tcgccccatc tggtgcagat cccgtgcccg aaagcaataa taggacgaga ttcgtataac | 73020 |
| ccatagtaga gtcctcgccg ctcgaccgtt ccgtatactg agaccgatta gtgcacggtg | 73080 |
| ctagtgcacc aagatcgttc tccccgtcag gcagtgcttt gctcaaacga agctgcaatt | 73140 |
| cgcgctcgta aatatcgtcg tccgacaatg cgcgtataat gcaactttcc gtttgagaaa | 73200 |
| aattacattc tacgcttctc gcgcagtcct tccagcctgc caaagcgacg gaaagcgagg | 73260 |
| tgggaattga gccgaccgtt tgaccgtttt gtgggacttt cctttactt tcgtgtccag | 73320 |
| ctgccgtgtc gcattggccc tcgtacgacg agtgacccat gtcggacacc gtcgtcaaca | 73380 |
| tggcccgcgt agcgctttgg gccaaatacg aatagttact gtacaacact ttagcgtcac | 73440 |
| ccgcgcacag cgaccgtcct cttttccccg ccgaacggcc ttgatttgca cggggcacga | 73500 |
| taacctcgtt atgccgtctt cccggtaccc ccccgtcagt tcgaaaacaa ccatgcagaa | 73560 |
| agaagtgtct ctggatatcc tcaaaagtta aatgctttct cccaaacgag cctaccaacg | 73620 |
| tgcaaccgtg atcgaccaga aaatgcttat ccattatata cacgaattcg aacgctgcta | 73680 |
| taaacattgt tgtagcgcat ggtggagaac caagacattt ggaacacaaa aatgcgtaat | 73740 |
| cggccatcca tatagccgat aatccgaatt tgtgcttata tatatctaaa acacggcaaa | 73800 |

```
cgagacattg tctatctaga gcaaaaacct cggctgccgt cccgataaac gtcgccagct   73860
cttgatgctc gattccgtct tcgcaatctt ctgcgctttc gctaccactg caactctgac   73920
cagcctgaag actgttggtc ttaatagcgt gggcggagag tagcaattcg ttaaagagcg   73980
tatcgttgta cgtcaatatt tcaggatcga acgctatgta agggcatttt aaggactcct   74040
cgacccatcc ttccgacgcg gatgctcccg gagatcgaat aaacggtagt tcgacagtac   74100
gatgggccat ggccgctgag acaaacactc ggcaagtaga tacgcctcgg ttagccgacg   74160
cgatcccaga cgtagagttg ctgtcggacg atgtcgataa attagctgaa cgctatattt   74220
gcgacgggat cgtatatcgc gtatggttcg aatacctaat acccgatgaa ttagatttga   74280
tttccccgac aaccgacggg aagtttaatt atctatcatt cactagaaga cttgcttctg   74340
ccatccgaca tggtcgtgcc ggagctggga gtgcgacccc tacgtcgttt atcagtgccg   74400
agcgtgtctg tgaccatggg gccgttttga gagggcggag cgagagattt gcatccgtaa   74460
ttaataggtt ccttgacttg catcaaattc tgaaggattg ttagaaacta gcaagccgaa   74520
cataattgct ccgccgtata tcttttttc ttttacgaag gcatacagcg aatgatgagc   74580
gcgcctcaga gtaagccctg tcgtcgtgca ggactaatag cacggatcag gctcatcgtc   74640
ggcggagatt taactatggg caattccgat cccggactcg cggagtcttt ttccggtcgc   74700
gttccggcac gttgcgtatt tcaattcagt ggggcagacg gcgtgagag cgcgtttccc   74760 gttgaatacg taatgagaat gatgaacgat tgggcggggg gtgagtgcga tccctacatt   74820
aaaatacaga ataccggcgt ctccgttcta atcgaagggt ttttcgctcc tccgacaaac   74880
gccgctagag cgccgctgtg cgccgacaaa gtgaacgtcc tgttaaacac taccgattct   74940
acgggcgtcg ttttatctga tatcaaaagg tttaaaaaat cagtgggtgt ggattgcagg   75000
cctttccagg cttgcctaaa cgttcattgc tttgtaaggc taccaaatgt tcagctggcc   75060
ttcagattcg tcggcccgac cgatccggcc agaacatcaa aactgctcga ctcggccgta   75120
gcgtcttaca attcgaaagc gaaacagcgg ttcaaaaaca gttcgagggc tatcgataac   75180
gaatcgagac cctgcgcact tcatgagtgt gttccgatcc cggtaagaga tgaaacgcag   75240
aaactgacta gccaatctga tataaggacc cctaggcgcg tgctgaccat actcaagaaa   75300
atttcgagcg gtgagtacgt aacgaccgta cgcgtctcga tccgcaaaat tatactgtgc   75360
ctggtcagtg tattcgtagt tataaccgcc tggtggtgct acccgctcta aaacctcgcg   75420
acgcggcgtc acgtttccag tcggaacacc gcaccacaga gtcatcatcg gcgccactac   75480
atcgcgcgag actgcaatgt ctcgcacgcc ctctccccag ctttcgcctg tttcacaagc   75540
gttcgatccc tccgacttga gcacttacaa gttggatgtg ctggttaact acccccctctc   75600 ggatttggtg catcacctta atgccatacc gcgaaacctg caagtttccg acaggcattc   75660
cgacctgaac gcagctaaaa tcaacgtttt acgggctctt tgtgtgggat tttctgacgt   75720
gcggcgcaaa aatgatactc gcactttaca acgcacgccc atgttcgcaa tcggcgacgc   75780
cgcatcgcgc ttgagaccgt ccattggatt gaaacggaca ttccccacgg gcatattctc   75840
aacaactatc ataaactctc ccgcagacga tgatgcatag cttttgtgag tcgacatgct   75900
ttaataaaaa attatccaaa tcgaacgagt ctacttccct atgtcagtta tccggtcagg   75960
agcattttga ttttaaatat ctctatcgtt aatgtatcga ttctggctct caattgttgt   76020
cgtgcgtgtg cgatttgcct ggccatcttt tcgcatgccc tagtgagtgc gtaaagcgcg   76080
ctgcgtccca cctgcctaaa atcgcgcctt gtcaataatc tatcggcaga gattactcgg   76140
```

```
gacgcgctcg attcgtccgt gctggagcga tcgctatcag gaacactaga ttgcgactcg   76200
ccatccgtgt tagaatccac ggacgataga gactccagcg caaacagata tcgctctggg   76260
tcgatattgg agtcctgttg cttattttgc cctgcttctg cttccgtgac cacgaaccct   76320
ctgtacatgt tgtgatggtc gtgctttgcc gttgtcgcct tgcatggcga acgtcggcac   76380
gtattaatgg gtttcgactg cgaactagac ggctgcgcgg gtctcgacag aatgtttccc   76440
agaaccgcac tactcggcga cgaaggctcc gctaatataa cgtccggggg cgcaaatgcg   76500
aagtggtcgt acagtccgtg ctgcgccgga ctcccgaccg ccgcctgctt tttgccacca   76560
ggtgccgtcg agatatcgac ggagcggtca accggttcca ggttaagatc cgcggtaata   76620
acggctggcg acgctcgttg taacaaggga gacgagtcgc ggcgcacgga agcgagtccc   76680
cctaaagtat cgcatcttgg ccttgacgca ttgttaggac gaaacgggc ggcgcccttg   76740 tccgagatcc gtccgattga atcaatcctc gttccggcac gcgacggctt cagcgctctt   76800
atccctattc ctccgtcttc gtcgtcggga atcagggatt ttgtcgaaga cgcgacaaca   76860
aatggtgttg aggtcgaatc ggagtcagat cgatgtggaa tgtttggagt tccatgcttt   76920
ttcctatcat cgcgtaccga gttatccgaa ataactacgg caggggactt ttggtcgaga   76980
gcgcagccgg gtgcgttaca cgcggctgcc gtatcggtaa attttagcct cccacgatag   77040
acaggctttg gcatatcgtg cgcccgttcg ctgacatcga tatgttttac ggggcgcccc   77100
ttctgcctct cctcgatccc gactgctgcg taggtagatt gctcgttatg tgttttttta   77160
gttacgacga gttttgagt ggctggagat aacagggacg ggctcaatgt ttcattattt   77220
gggggggcga gcttatagtg aaaggcgagt ttggaagagg cgccatcgga agcatcggtg   77280
ctaaccgtag aaggacactc gacattctcg ggaactaccc ggtcgctacg atcgttcaac   77340
tctttatgaa acaaaaaacc cgtttcagca ttgtcgtaga cgtccttctc tgcagccatc   77400
ccatcccaca tgctctctct atcccgacta aagtcattcc ctggtaattc ttcatcttcc   77460
gacgccgttc caatagatag tacatcctcg acatcgccgt ctcggctctt gttgtacacg   77520
gggatcggat attgtctaga ttcgtcggaa aaaaaattag ccgcgtcctg tcggtcgagc   77580
acggcgatgt catcatatga cgcgcccgtt tccacgcgaa tgccgcatc tatgtatggc   77640 agttccgaga gaacagcgtc atcgctggaa gttagccgta ttacggggat agggtcgaat   77700
accgtcttag gccatagaac tttcacggga accattcccg tgtccactat cactaaacac   77760
ggaggagcgg aagaaagggg cttggaggct atgagatggg acaagtgttc cagctgttgg   77820
ccgaggcatg cattttcgat tggattgctg tcgtctgcca acaatttccc cccccaggaa   77880
gtcgtgtcgg atgaaacggc ggcaggttcg agaaagcagc cctcggagcc gcttctcgag   77940
tcgaaaagac ggacacacag attcagtcca gagccgagg aatacgcttc tggacattct   78000
gcggcgatca cgatccgtgc cccgaataat gtagctgcgg ctgccagatc catagcgttt   78060
acttttaaga ctccgctagg gggtgtggac gtgacggtaa atgtcatcgc cactcctgtg   78120
ggttcatata aattgggacc gtctgaacct ttcgggatag ttttgtcggc gggacgtaac   78180
acggacgatg tggtcacgtc taaagtcgaa gcagcgtccc cgcgggctgt gacgacgtca   78240
tcgtagcttc tacagctttg ctctatctcc gcgggtagaa gcgaggacca catcaccgcc   78300
aatgcggttg gcggaatgca catacgagcc agcactgttg tcgttgtcaa aagattcgac   78360
ggcacgaccg cacgaatttt ggcaaggccc gtactcgtag ccccacctac accttcccag   78420
ggtttaaggg ggtctgtttc ggaaaggctg ccttgtttcc aatcagaata ccgcaaagca   78480
aaaagggatc cgcctgacgg gtcccacgct ccgcccgtta aactcatcgg tcggcaattc   78540
```

```
gagtccgacg gggcatctttt ggatagctgc gtagataaac agttgataaa cgccgtagtg   78600
gacagcgact cattgatagc gccatagagc gtcttatcca taaaatcgta ctggctaata   78660
agatcgagct gggaaaaggt caagacgtgc cccggcatgc acgtcataat agcaaccatc   78720
acgtcggcca actccagccg aacgggtcgt ccatttgcag ctattttttt aagccccttt   78780
ttgtcggcgg caggggcgac ttgccccgga agaaaaaaaa tatcagacaa gctagcaccc   78840
gttttacgcg tgagcgtaat ggccattaat gcgcaataaa tggacccgat cgcttttact   78900
gtgccatccg ccagccaatc gtagttttgc gtacgtacat acttggtgaa ggcgcggaaa   78960
ttatccgccg cggcttgaac gaaacccagc ctcaaggcca tgatgtcgcc tagcatgccc   79020
gcggcaacta ccatatctct agttgacata acttttgaag ggatcgcggg cctcaggctt   79080
aggccggagg gctcgcacaa acacgcggcc atttttcac caacagttcg atagcagaca     79140
gaatatctca ggggcgcgtc ggaggcgtct aaatatgtat ggatgcctgg gatatctatt   79200
tcagaaaacg cctcctgcag cgtgacaaca actgatggtc tgatccaagc agctactcgg   79260
tgtttaagat atcgatccac gaaccccgcg gccggtctgt tgttcgcgtc agcattcaat   79320
cctgtatcag aggggaggag cgatggacac ccggcaactc ccggcaaaat ggcggaatat   79380
gcagcataca gcgccaatct cagctttaca agccgcgagt atcgagttac gtgccgaacg   79440
taccacttgg ggagccgttt agagagaata tcgaattgcg aggctattgt actgagatcg   79500
tttaagacaa aggttggcgg gatctttgca cacagagtgt ccatctgttt ttgaatcgat   79560
tccgtttctt tgagggccgc cagaaaagca tccatgactc cggctctgtc tctgtatttc   79620
gcatcgataa gtccgatgat tttagccggc agcctagcat actctgcgtt atcgcgcaaa   79680
gcgttgatcg tattggaaga gactttagcg cgagcagcac tatctcgggc ggcggcaaac   79740
ccctctgagc tcttgtccat cctgtcctta tcgtgcataa acgtggacca tgtgtcatcc   79800
caagcgactt cggcaagcgc tagttcggat tttaactcgt ccaatcggct cgctaagtcc   79860
gcgagagcat cgatccgctc cgcgtatata gtcatcggac cgctttcgtc gatccgggaa   79920
gttagctcgt gcgaatctat gacagatcgg gcgtgtttta gccactctac cgtttgggta   79980
tccaattctt tagtttcttc gactttactc aaaagtattg ccgcttgagt gactatgtcg   80040
ttcgcagttt cagccttttc aatagctttc gctatatgcg gaggcatcgc gaccagccgc   80100
agcaggtttt ttaaattggc caattgctcc gccgtctctc tgtctgcggc ataagaaact   80160
tcggccaaac tcttcagaat aacttcagct ctcgatttcg cgccctcaat agctgtcgtt   80220
acccgcagct ttattgagga gacggcttct atatcgcgtt ggagagtatg agcgctatac   80280
tctgcatagg ctgtcccgtt gaacgccgta atgtcttcct tttccaaatc gttggttatt   80340
gtcagtatgg cgttcgccga aggaatcacg atagagaccc catattcaag agcgcgacgc   80400
gccccctcag ggctatacat tctagccaga ttctccaatg cctctctaat ttctatatct   80460
accctccccg ctgcgtgaag agcctctacc ctcatttgtt catgccgagc taaaagccc     80520 gtaaattcct catgcccgtt acgataaaaa tccacgtatt tggccaacgt tgggaccgct   80580
cttacgtctg gttcaatttc gcccaataac gtgtaatagt ccaagttccc gccgcgggca   80640
tccgcgtgcc ttaatatagc gagtactatc ttgattaact gtagcaaggc gtcgcagcta   80700
actccgaaaa gttttgtgta ataaggagcc gccgctataa acgcgtctag ccaggtcata   80760
tttttcaaaa atgctatagg aggcagaatt ccatgaattc tattcggggt ggaaaacggg   80820
ttgaacttca atacagtttc tatcgcatcg tgaatcgcac gaccatgcga cataacaatt   80880
```

```
ttctcggctc tggctctgaa acggatagtg tcgtagccgg ccaccacggc ccttttctcc    80940
aaatcactca tctccatagc atcaaattcg gatttcagct cggcattgga tagtagggaa    81000
tgaatcgagg aaacccaaac gtcttcgcta tgcgatctct gggcacttat cagatttctc    81060
tcgtaggttg taacggccgc ctccaattct acggtccgct gatttacaag ccctaccgat    81120
tttgccaggt cggcaatttt acgttggatg tgggggtccg taacatgcgc gtgactctcg    81180
agagctgcga tggctgtatt ggcgtctctc gcgctctgca gcgcgtgagc tatttcagtt    81240
ctggcgctca ttataacact ggcgtcgcta tcagcggctg ctgttttggg atctgaagtt    81300
ttgaccttgg ttattgacgc gatcacgcta ttgagtgccg cgcgcactgc ccgatgtaga    81360
ccatctaaac ggtccccgtg ctgcgccacg cccgcggcca cctcagcgtc ggataacagc    81420
accgttaaga acgaaaacgc gtcatcctgg cctgcgggta gatcggccat tattcccgta    81480
gagggagtgt ctgcagtcgc cctgtttaca tcggatacgg cgttctgcag cgccgtaaca    81540
gccgccgtag ttttttcgac cgacatcggt tcgaggcgcg cagcggcgac tgctgcagaa    81600
agcgtatcgg catgtttccc gaaaaaaacc gacgcggccg gataaccccc aattggaccc    81660
aatattacgc gtatggccag agagaaagga atgccgaggc cagataactc tgcggcagtg    81720
ctcgtactgg ggtgtgacaa aattgtccta tactgagaga acaacagcca caaatccgtt    81780
cgcaaagtcc caataacatc gggtggtgcg agagctagaa aggtctctag cggccccgta    81840
tctccaggga tggattgcgt tatggttttg actgtcgagt ccaatgcgcg caacccagca    81900
aacctttgta gaggacgcag catcagctta atcgaagaat ataaagttct gatctcctcg    81960
taacgatatt gaagtgccgc aattaaggtt tcggcatcca gccgcctacg ggcgatagcc    82020
gcgcggtcat ccgaacttag caaatttgca aatttgtcgc cccctaaagc atttgacaat    82080
tttactaact caaccacatc cttcataact tcctccagtt tttgaagatc ggccgttgtc    82140
tccaaatcag tgtatgacgc aactctagct tccaactcat gtaagcggtc caaatccgcc    82200
agggctgttt cacggcgggc ggcgttgttg ttaacggcat cgacttcttt gatcagtgtt    82260
tcaaactctt gtcgactaat ccacccgccc gcttgaacgg ctgccattgc cgttttccat    82320
accgccagat tttctggatt ttctaaatta gagtcatttt ccagcagatc cccgagcaat    82380
ttagattccg gtgcagttgt tacgggcggc ggggcctgcg cgccactacg cgccgctact    82440
agggcaataa catcatcgag cacagataat gatgcgaaca gcctggccat tttttcatgt    82500
tgctcgacaa cgaccatttt aaatctagat gtgctagcca cgttggctcg aagcgcattc    82560
gcgctataga gagcccccctt caagtaatat tcgtgtagtg cgttgccgac tgcatcaacg    82620
gctgccctct caatagcagt caagcgctgt gtaacgacag atggggagac tttagctatg    82680
ctctcgtcgt cgcgcgatcc agaagtaccc ccagatcctc ccattataaa tgcatcaaat    82740
gaggcgtgca tcaatcgaac gccggcgtcg agggcctcca attcagctag tatgagttcc    82800
gccttcctcc tggcaacagt ttccctatca cgtatgaacc tgcacagcga tgcgactctg    82860
tcggtcaagc tctgttcggc atgcaaagac gtcttctctg agtatatctt tcctggatta    82920
ctattaaacg cgcttactaa cgatgtcgcc atcctttcgt agattctatc tgcatccgca    82980
gtgctcgcct ctctctctat agagtccaaa gttttgtgaa gggcatctgt gagctcctcc    83040
acttccagag ccactaatac cagcttgctt agggccaatt tgcctatctt ggaattttca    83100
gaaagtacag attctatgag gtctgcagat tctccggctc gcgaaaccgc cattcccgta    83160
gaatcaatga acgcgctaaa gtgggcgggc ctcgtaaatg ctttaaataa tgatgccatc    83220
tcggcttcta cgacagatcc tatttccgtt gtggttcgag cgccgttttc gataacgtag    83280
```

```
ttgaacaatc tggtaaaagt atccagccca catatatcca gaagtccgtc atagtcaccc   83340
gaccgtgaca agtggatggt cattcccata cttaaagcta tagattgctc taaatcatcg   83400
atgttagcat tgatgtcgct cagaatagag ctagggacgt gttcgcttgt ccatagcccg   83460
tctcgtagcg actcgtcccc ttcccccgct accgtgtgag gattaaaagg tggccggtct   83520
cgcaacgatt ggccgtgcac gaagtgctca gcacgcgcct gagaacttat aaactcattg   83580
aaggagacat tgtccggccg ggtagcttct tcttgaccag gtatattatg tgtcgtgctc   83640
gatccactat ctgcttgttc agacaaactt atcgatggag ccaccggatt gtccgtatag   83700
gtcaaacatc gtttagtttt ccgggacggt tttctgctcg aagattgacc ttggccatcg   83760
acggataagt tctctgaact tgacggagga gtccatacag ggcgcctcct cttatgtctc   83820
tcaaaagact gtttgggcgg ggagctagat ttcgtgtcag tttcaagccg aactacattt   83880
tcccgcgttt tgggcaaatc aggccttgtt agcaccgaca gatcatcgcc gatgtccggg   83940
aatgcagtgg tccacgcatt tacgatggac tcatgattgg ttatatcaca tatggcatca   84000
actggagcct cctcgggagg caggacgtat gcgtcctcct ccgcatagcc catttcccgc   84060
ctaacatcca catcccctgc agcgacggga gaacgatcac ttctggaatc gacagcgact   84120
ttgatgtcct cgctacgtga cgtggaggtt ccaatgatga tcctagttgt tgtaggctgt   84180
ggcctgtaag ggggatcgag attggccagc actactttaa tgttctcttc ctcgttaacc   84240
ctgcctagat ccaaaacgat gtccgctgta ccgtacagcc gtgatacggc tgatattatt   84300
tcttcctttg gcggtgtact ggagatcata gatacaaagt aaacaaaggt cgcggaccac   84360
tctggcgccg tcgagggatc cgcataggac gtgagatatt gataaaaata accctcgctt   84420
actcgaacga tacacgcttg gcctatgtgg ccatgaccgt gtggatcgaa aatgtagatt   84480
ccgttatcgg atctgtacac ccctattcct atgacgccga tgacgatcag gcaataaata   84540
tcacctcgtt tctgcttcca tacttttttct atgaatgtcc gcgcagatat ttgggtttct   84600
aagatagtgg aggtgttttc atctacgtag aagtccaatt ctccatagga gctcgaaaac   84660
gcaacacaca agttgccgtc gggctcattt gataagatcc tgtttggtaa atcgtgaggg   84720
acgcaagtcg tataccttcc atcgcgagag gtttctattg tccattcctt tccctgcaat   84780
aacagtctat ctatggcctc ggtcgacaat accgcatcca acccatacgc aaaaactacg   84840
cgcagaaacg ccaatgacga ccgcaagcat gaaaccgatg accccggact caagtccggg   84900
gcaaattgat tcctgttgcc aacggcaact agtgtaaagt cggtggcatc aaccaccatt   84960
cttgcccatt catctaggat tacctccgaa tccatgtttg ttcccgaacg catggcgcgg   85020
ttttgcatgt tcgagacgga gctgtccctc gaattatccg atgtttccaa gcgccgcgtc   85080
gagggactcg gttgtaaccg cgtagatttc ttggatgggc gtgtagtgct ccctctactc   85140
tcactagcag ccatatagac gatggggcgg aatggcgcgt cttttcagat tgcgctttgt   85200
cattgagcga gttagacatt aaaagttgat taactccaaa attgtgatca atcagttgcg   85260
gccgcgtaag tggcgtggct gcaacatcca agtcggcacg aacgaacgat acgccaggcc   85320
gtaaaacgat agacgtgtgc gtcacgcatt gcgatctctc gcctgccttt cgttattaaa   85380
caccgtatcg acaatgtcga ccaaaccgtc tacagttact ctcggtttta tgaggaagtc   85440
cttcgcaaaa ttggcaaggt ccacatcatc gtgtgccacc gtatccaaat ccaatgtatc   85500
aaaattgagt tcgtcacgat gagttaaatt gtgcctcgat gtcagttcga ctactagggc   85560
ggggctatcg tcggttacta cgggcagacg gcccagcagg gtcgctacag ctgcgtcgat   85620
```

```
ttcgtcgttc gtgacacggt cttccatatc acgcggaacc tcgatccgat cagctatttt   85680
ttgccatact actcccacat tctctatagc actggccaag tcctgcgaac ttctgtcacg   85740
aaacgtagaa tttatttccg acaacgtttg ccatttgtcc agcagccaca cgatatcgcc   85800
ggtcccgggc ggcgtggaac acgatgtcaa ggctctgacg tgcaggtcca gcgaattctg   85860
caggcgagcc aatctggcat agtcggttcc gagggtagaa aaatagcttg ctgcctttac   85920
gctaaataaa attgcgcgct ccattaaatt atcgcatgta tgaacttgtt tcccagtttc   85980
ttctattaaa gtccgcaaca ccattgattt gagtcttaca ttcgccatta catcacccga   86040
ggagtcgtag aattccctga gagccgacag cacatcaacg attttccatg tgccaaaatt   86100
ggcacgcggc tcgccacggc ggtaaaccgt tacagtacct cctgctgtac cagctgcgaa   86160
tttacacgca aagaaatgct taaatatgta cgcaaattta accaactgcc tggatcgctc   86220
cgctaaatat gccgcacact tcaacgttct atccgctaag taattgaatt gaagtcctag   86280
ggccgttcca tgcatactaa tcaaaagcaa actattcgat atctctggac ggggggggcat   86340 aatcggtctg gtctctggcg gtaccatctg cacgccgca tagaccacgt cgtacaattc   86400
gcccatcagc atttccagat tatacgcatc gtccgtggta ggcttggccg tcagatctct   86460
agcaaacgga gcgagtgagg aaattagagc attgagcttg tttctatgat tcacgaaact   86520
gccaatgtac ggcgcgccgt aatccctggc ccaagtcaaa atttcgataa cagtgtttat   86580
cgggcgttca gaaagacag atgtcgtgat agccgacaat gcgtccacgc aaacggtagc   86640
tagaatatat cttagaaaat ggggagttgt gctttcaggt gtgatgggca tggattcagg   86700
atagcgaatt gtcatggcca gacgaatcat acggctctcc aggtctgggt ccactgcatt   86760
tggtccagag atactctcta aatccgaatg gtccacacta gctagatgtt ccgacggttc   86820
acctccaatt aactcttccg gtggcacgat tccccatata tgctcggctc tggagtcgaa   86880
ccatagcatg agtgactcct ttgcaaattg tattgctcga ttggcagtcc cggccccgct   86940
ctggcggatt gcgctatcca tttccgcggc gaggatcgct cgtgcagact ttacatagtc   87000
ctcgtgggga tttggcggta tacatcgccc taatatctga gctatgattg cgctatctaa   87060
cccaagtact tttatgaaat ctgaatcggc gtccggagga aggccattgt ccatataatt   87120
ggttaagtaa gtcatgccgg gaccataact ttccatgagt ccgaaaacga tgtttccgat   87180
gacagctatg catccgataa cctgttgtac gtcgtcaaat gtgtcgagtt cattaacagt   87240
accacgagtt tttcccaaat ttgcctttag cgccgattca taaacccggc atgcctgtct   87300
cacaaaacct cttctataa gcgcttccaa taactgtctc ggcgacgaac tgtgttgtac   87360 agcccccccat gcccgcctag ccgattcgga gagtttcgct ttagcagcat cgagagcgcc   87420
cccgccgtca tttaagtcgc catcggtaat aagccggacc acggcagaca tatggatcgc   87480
taaggcatct tctgttaatg cgtgatcagc taatataatg tctggtccgt tccgcaactt   87540
ttccgctacc ataccgggct gaactgcata tacatacggg tctccgtatg ctatggcggc   87600
agatgctcta acatcatatg ctgttctttt catattgttt gcctctacgg ccgagataag   87660
ttcgcgcgag cccaatgcgc tggcatcttc tgcgaataga tcctttaact gagaaggatg   87720
gggcgatcgc ggacttttaa aatattgatc gacaagggcc agcgtaaata gtattcgagt   87780
gagtggcgta aaggccctat ttgttgtaca tcgagacata ataacaaacg gggtgatcca   87840
cccgacggct atagaaatta atcgaattcc ttcctgaaca aacgggaaat cgtaaataag   87900
tttaaagcgc gtctgcgtca aggaagctgg tagttccaaa gcattaggag caggttgacg   87960
tccggataac aaccccttcgg aagtataatc aaacgcgtcc gtggcgatct cttcaaaaat   88020
```

```
tgtcagccac tcacttatta ggggccacaa aacactcggt ccaaaaggac atgatctgcg    88080
cagaccgttt cgggtaagcc acgcaatggc ttcttctccc gtcatttcgg ccgccaatct    88140
acgcaaccta cgagaatcgt cttttccagga cattttatcc caccttacgg aggtacgcca   88200
caagatgaat ccgacaaaat tttgggccag cattgccgct tctgggcttc ctgtttgttt    88260
gtagacctcg agcacagccg cgaatgcatc gcgccacgtc gattccactt gctgaatact    88320
cattgtttct agagcctgga aaaatgatcc gatagcagtt cttgcttccg cagctgtagc    88380
atttccccac ggttccagtg gcgccgttcc agccgataaa gaccttagtg tatccagtaa    88440
agttttcaac gggaatctcg cttcgccctg ggtttcagac atggcgcgcc aataggtagg    88500
gatggatcta cgtatgtcaa tggaggccgt ataaagcttc aataataata cgttccctaa    88560
aatgctgtgc tccgcaccgc agaaaaatat cgtgtgatcc gcagttacac cataccgtac    88620
tttatcatct ccatgacgca tcgagatccc gtataggccg gcccacgtaa gaggcacacg    88680
cgctacataa ctttgttgcg tttaactaca ccgccagtcc tgtattgcag tatactaggt    88740
gacatacagc gatttttatg tgcagtagtg cacacgcagt tgtcgcaaaa cgggcttgca    88800
aacgatcatc gccaatacag gatctcttta taactggttg ttgatagtgg acgtcatgaa    88860
aaccactttt cgaacaagcg acgtgcaggc atccaacacg cagtcaaatg cctcggacag    88920
gctgcatgac atcttacgga gcatcaataa ctcaatgcac tccggcattg ttcggcgcat    88980
caacataggc tatccgcatg cgggcaacag gcgcgggacg ttgaccgccg gattggaact    89040
gttgagcaat acgatcacaa cgaccccctcc cggggcaaac atacaccgct ccattgcaaa    89100
ttcggcaggc gaagctacgg caacgatcat acaatcttta cgaacatatt ccggaagtgg    89160
agatctgaac acgaatggtg ataataacgt cctttcccga cagatcagcc tgacagattt    89220
ctgtttcccc gatgcggaga tgccaggact aattgtctta tctatgcgac atccactgga    89280
tataaacagc gaagcattat acagcacacc tgccggacgg gacccacggg cattggagtc    89340
agcgtggtat gaattatctg aactggccgc ggtatcggta aacagattag acggaagtgg    89400
tgtccggccg tccctattat cgctctcatt tcttattgct tcccgcgcgg gagactatgc    89460
ggataaatgt ggtgctgagg ctgtaagagc tcacgtgatt agcaattacg gccgccggcg    89520
gatagaggac aggctcgaca ggttcggaag ctgccaagca gcaatgttga gatgtcacgt    89580
gttcccacac cgacatatgc aagtattagg gggaatggtg tcgtggatcg cacagcgcga    89640
aatcgccagt ataaccgccg tggtcaaggg ctctcaagag agcgccagga cagaacagac    89700
caacaatcca agatcgtcgg tatacgttcc cgcatgcgcc tatctcgatt tagataaaga    89760
gattcacatg ctccatgatg acagagcttc ttcgctacta tacctcgttt tcgtttatgc    89820
acaacacctc ggacgcgaga gcatccgtgt atatctcatg cggagtcgtt taggggaatc    89880
ggtgttcaga gaaggcctcg gttacctgta ctccgggcta agagccggta acgctattaa    89940
cggtctggcc ggtataatag cgccacatgg agtagacgcg aatacggaat tccattatc    90000 aaaagctttc gaggtacaca aacacgcctg tcgaaacacc ggaatcggac ctcgagactc    90060
cgagaaagtg gactggcgtt tagatctccg aggccgccct acaaagaatt cctgcatgta    90120
cgcagcatac tgtcgcgtag ggcacttgaa cgagtattcg atgccggcga agaagtctga    90180
acgttgtggc gggtctgtgg aggtccctgt tgtatgggtg ccgggagtag tgtgggatat    90240
cggagaatgg accgagtgtt atcagtagag agttggctac accgagatcc ggcatcatac    90300
cttacgtgaa ctgcttacgt ttggggatgt ttttgcgtcg gtgtttgggg aggagtcaat    90360
```

```
cttataaaaa gcctatttgt ggtacgcttc ggtctcgcgc tcactgagca acccgtattt    90420
tatccagtct gaaatcagaa tctaaaatgc agcgatccga tgaaaacgaa tccctcgaag    90480
cgaatagaaa tttggacacc gcctcgcgta actgtactga tgtgcaggta gccttgataa    90540
tggcaacgaa attgcatcgc atccagcagc aacttgcgag catgggatat ttatctggct    90600
acgattccgt gcccgatatt actacacccg tgaaagttct gcgcgagcgc attacccatc    90660
tagtaaatac attgaaaccc gtttgccgtt tcgatgagcg cgtgtactac gcctgcgggg    90720
agctggtgca tttacggatc aaatcacagg aagctacttt tgatgcgtgg ttgatgtcga    90780
aaaaattaag cctgaaaggc gagatcgtag ataacataca gcgccacaga ggtcacgtag    90840
agacggatat gctgcgcttt tacgagtaa cctatccctg gctgaaacga ctgggtttac     90900
agtcggcgtt gaaatacgaa gaatatctga ctgagttgga agacggcaaa aagaatctc     90960 tttgccagtt ttttgttcgg ctggccgcgg cggcagcaac cgaagcgtca acaaaaaag     91020 ctttcatgtc ggctttgggt accgaagtgt cgacctggga aacggctttc acggcttttt    91080
ttttcgctct cgctcgtcag atatttgtcc catcgactcc ctgtatgctt tttttgggc     91140 gcgaaggaac ctcaaccgcg agctgttatc tcatggaccc cagaactata aatacacacg    91200 atcccttaa agcgatcgcc gacgatatag ttccccatct cctagcgaga ggagggatag     91260
ggatatcgtt gcagcattta aaccaaaaaa caggccttat gcctgtgatg aaagtattgg    91320
attccttagt gatggccgcg aatgcggggg agcgtcgacc cacggggggta tgcgtttatc    91380 tcgaaccgtg gcacgcggac atcatgtctg cattaaatat gcgcggcatg atggcgacgg    91440
aagagtcccg taggtgcgat aacgtatta tcgccctttg gacttgcgat ttactgttta     91500
agcgctacga gagacacgca aacggggaga aaaatgtgac gtggaccta ttcgattccc     91560 gcgcgtcgat attggccacg cttcacggat cggaattcga aaaggagtat aaccgtttag    91620
aagcggaagg tttaggcgta gctagcctcc ctgtaaggga tttgatgttc gcaataatca    91680
aaagtgcggc gtccaccggt agcccctta ttctctttaa agacgcgtgc aacaagcact     91740
acattacaga tactcaagga gacgccattg caggctctaa tctgtgtacc gaaatcattc    91800
aaaaaaccga cggaaataca aacggggtgt gcagcttagt aagcgtcaac ctcgcccgat    91860
gtgttttcga cgagaacgga gagaaaaaat ttgatttttc cgcccttaga cgcgccgtgc    91920
ggctggctac ggtgttcgtt aactcgataa tgtctagcag cgatgttccg actgcgaaat    91980
ctcgttccgg taaagatcga cacagatcca tgggcatagg cgttcagggg cttcatacag    92040
ctctgttgtc aatgggtctc gatttgagcg atgaacgcgt caagcccctc aacaagcaga    92100
tttttgaatt gatgttgtta gaggccatga cggtcagttg tgaattttgc gaaggcgggt    92160
tgcccgcctt cgccgacttc tccaacagct attactcacg ggggcgcctg cattttgatg    92220
gctgggcaaa cgtaggctta agtatgcccg aagagtggaa tgcgctgcgg gagagaatac    92280
aggcgtccgg gttatacaat gcccagttcg tagcgttgat gccgacagcc gcatccgcac    92340
aagtaaccga agtgagtgag agttttttgc ccgtgttcag caacatgttt aacaaagtga    92400
cgacggcggg ggaactactg cggcccaata atcaattaat gggagagttg agggagatct    92460
atgcggataa tgaggatcgg cgattgaaag ccatagcagc gttggagtgc gcgaactggt    92520
gcgtggagac cgctctggga aataagcccg aatgctctca attacttaaa tacaaaacgg    92580
cgttcgagta cgaccaatcc ctcctaatag atttgtgtgc cgatagggcg ccttttgtgg    92640
atcaaagcca gtcgatgact ctgtttgtga cggaagcggc tgacgaacg ctgctggcgt     92700 ctcacgtcat gaacctactc ttacgcgcct ataaagccgg cctgaaaaca ggaatgtatt    92760
```

```
actgcaagat acgcaaggcg actaatgccg gagtattcag cggtaacggc gaattgacct   92820
gctcgtcctg catactataa tctccaagca tcccggcatt ttgaccatgg ccacgcaagc   92880
acgcgggaac gaatttgtca gcggccaaac cgcacctctg cacaaaaacc cgtgtcccga   92940
aaacgcggcg gccgtcctaa agatggaagg tatcgagatc gaaccttcga ctagttccgc   93000
tagagataat tacaaagtgt cacggtactt ctacgtcccc gaatgccag  atatagggca   93060 cctccgagct ttgagtatta tgaaccgatg gacggagacc gaatttgtcg tcgccgagga   93120
tctcggggac gtcgccaagc ttagcgaaga agaaaaaaat ttctaccgat tcctctttac   93180
gtttctctct gctgcagacg atttggttaa ccttaatata gacaatctgt taggtttatt   93240
cgaacaaaag gatattcacc actattactt cgagcaggaa tgtatagaag ctgtccactc   93300
tcgggcctat agcattattc agctgatgtt attcgacaac gactcctcgg cgcgcgcaaa   93360
atatgttcag tctgcgttag agtcccccgt catccaatct aaattggaat ggttagaccg   93420
acgtatacta gagtgcacgt ctataccaga aaaatatatc cttatgattt taacagaagg   93480
cattttcttt tcagcatcct tcgcggctat cgcttatttg cgcacgaata acctctttgt   93540
cgttacatgc cagattaaca acctgatcag cagagacgaa gcgatacacg tagaggcgtc   93600
gtgctgcatt ttcaagaatt atatcgctgg caacaagcca tccaccgctc gcatccaagc   93660
cttatttagc gaagccgtcg acttggaatg tgcatttctc cgcgcagccg caccacgcga   93720
ctctcgctta ttggatattg gctcaatctg tagctatgtt cgttacagcg ccgacagatt   93780
attgagaatg ttggacgtgc caccgattta cggcgaaccc agcccgctg ccgactttcc    93840 gctatctcta atgtccgctt caaataatac aaatttcttc gaaagaagaa gcaccgcgta   93900
ctccgggagt gtatcgaacg atctttaatt agcctgtgtg caactgtact ttctacccct   93960
acccacaaga attaataaat gaattcaaat tatcgctttt cgcaccgtgt agtttgtgat   94020
gcatcccttc cccagtacct tatcagcacg gagtcgaaag gccgtacctc cgggatacac   94080
cttagaaatg cggttgaaat aactgaagct tcggcctcat tgggtatact gcgaaacacc   94140
aattcttcaa ccgctacatc gtcacgtata tcctgcatta tggggaatcg ttttaaaata   94200
ctaattctgg gcgttctgcg ctcgggcatt atagtcgcaa tgacgtgctt tatgaacttg   94260
tattcgagaa cttcgcatct cgttttttggg gggtgcaaag atcttaacaa gctgtaattg   94320
gacgcgagat ccctgttcgc atcgggcata tcagccggtc tctcgtaatg atggccgccc   94380
gtgatctcag gattgcaaca attcatcaac gacgaccggc cacgctcgtt atcgctcgct   94440
ttaccgcaga tagtgcccga accctgcttc aatgtcccta gatctattat ctcttgcatg   94500
gatttcagtg tgtgttcgca atggaggtct gtttgacacc gaacgaagtt agacaaaaac   94560
gtgaaatagt ccatttttaa cgccgccaaa acatctctgc agtagatagt cggcggaaat   94620
attctagtaa ggtcgatgat tatatcacat cccatcaata gcatgtctgt atctgaagat   94680
aacacatacg caaccgtttt ggtgtgaaag aggttagcac agatatcgtc cgcttccatc   94740
atggccacat cgacataagg gtatcccata tagcgaatgg tatccatgca gagcctatgt   94800
agaattttgg gcgtatcaga cttatcgctc catctgcgtg gtcttttccg cttccgcgtt   94860
cttttgttcc gcgcttctcc ggtatccgca ttctcgcatt cgtcgcgcga acgtacttgc   94920
agcctcccag aacctcctcc cctcgcgatg cgagtagctg ctagcgcctt tgctccataa   94980
agcgttttcc catacttcga aaaccccccgg tccgatacaa acaccggata atacgaccgt   95040
tggtgtaaca aacgcagcag acagtataag caccgcagcg tggcgaccga gttgtcgact   95100
```

```
ccgtcgacct taccagggta aattttttcc agcagtccat acataacatt ccataaatcc   95160
acggcaatgg gcgtcatagc cccgccggat atcgaacccg aaatgtgact tctcactaat   95220
ccgttcgcat aggcgaagtg catgcaaccg tacacgccca tggcaacttt cggagtcgca   95280
gtgtaagaga cacggggtaa tacgaatttt gaattttggg agtatctgtc aagtatattc   95340
aactcttgaa taaccacgac caggcgtagc tatccaaatg ccgaaacgtt aagccgctcc   95400
ataaaacctt gattccacta ttcaattgtg caatagttgg attagggcag gtattcggct   95460
ctatctgttc accgtataca cgctataccg tcctttaaat tagacaaggt gcgcgtctct   95520
aaacctataa ttcccggtag cggtataagc gacacttatt acatgcctat ccaccacgtg   95580
atgcaaccca cacgattcac gttgaagaca tgtgacattt gctgtaaata tacgcaggta   95640
acaatgtgtg cggcgaatta gacttacagc caatagtaag cgcgacataa cactaaatgg   95700
gcggcgcgac attcgagtgc ctataggaga ccgatatacg taaccacgcg tggtgcgatt   95760
gcgacccagg ctccttcgat ataagctttc cccctcacat ccggagccat ccgttagatt   95820
gactctgcct cagcctatac aacgcgccaa agaacagtgt gctacggaca gaagtgacgc   95880
cgacttgagt tcacggcatc gagaccccag aaccggtctc ggcgatggcg cgataacta   95940 tgagcgatga acacatcata gacgatgcag gggccacttc taacgattcg cccaattcct   96000
ggaaagtcgt cttggccgga gagaaattta gaacggtatc ggctgcagta cgcgcaatag   96060
tagattctgt gaagaatccc ctaatcatat tcagcgacga cggattaatg atacagggca   96120
cgatttgcgg tcagcaaaca ttcgttccta tcgagtgcgc cgcctttagt gaatttgaat   96180
ggcgcgggtc cgcggccata ttcctggcgc taacagattc gaggcgtact ttattagacg   96240
cgtttaaatg cgacaagaaa aaagcaatcg aggtctcctt tacgttccga ggggaaccgc   96300
cgtcgcgaca tctaacccag acagtcacgt atgtaactga taacggatcg ttctcgagtg   96360
ctatcatcaa gtatgaactg tggtgcgcct cagttttatt cccgcaaaaa attcccgatg   96420
ttacgttctc agtaaacaaa cagcaattaa acaagatttt ggctatagcc gccaagagac   96480
ggcacgagca actaacattt gcgttgaaag cagaaggggg gttttatgcc ggaactgtgt   96540
gcgatgttat aagtttcgat gtagacggga gcgcaatgac tcagtatccg tataatgcca   96600
cgactgcggt ctcgtctgcc ctcgtcttag catgcgggaa gaaaagagcc gcccgtaatg   96660
cacccgtgac tgcatatggg agcggaaaac ctttctgcct cgcactgaaa gacacgaccg   96720
cgttccgaaa cgtcgtacag aaaattaaaa ccggctcggc aggggcagat ttgggatttt   96780
atacggcgtg caatccaccg atgctatgcg tgcgtccgca cgcgttcggc agcctgaccg   96840
cttttctatt ttgcaactcg gattgcatgt ctatatacga attggaggaa gcgagtgtag   96900
cggtcggcgc agtaacatcg aaacgcataa acgaatattt tcccagagta tcgaccatcg   96960
attcccggaa aaggcgcccg tcttcggtcc tctcggaggg ggatgggaaa ctccttaaac   97020
ccgacggcca ataggtctcg tgtccgcgcg cggaccacag tcatgacgcg gggaggtcaa   97080
actgatataa gatgtgataa gactgcttag atttcattcg acctggttat tcggacatac   97140
atggagcccg tcgacaacgc gtctccgtta cctccgactg gcgcgggaca ctgtcttcat   97200
aggattgttt gcatcgaccc tccatgtaca gcaaccattg gcagcgggag gagcggcaat   97260
aggtgcataa aatgtattat ggttacgacg ggctccctgt tatcgatggc cgcacacttg   97320
accgtcaccg tattttgcgt ttccgtgatt ccgtgtatag atcgaaccgc agcctatcca   97380
cgctgcacta tgggcgccat cttcgcattc ctattctttt ttaacatgcg gcttactgca   97440
cgatcatcgg aaatagtgct gctcattggc agaccgacac aattttatg cgctctgaca    97500
```

```
gcatcaatcg ccgacacggt cgccaaacat ctagcggcta cccataagga ttacctgacg    97560
acattgcgag caatagaagt aatgtctctg ttgactttg tcatgctcgg agctctgatc    97620
gcatcttatc attacgtctg catagcaacg tctggagacg tgacgtggaa gaccgggttt    97680
ttagttgtgg cggcagggac gattgccggc atcacggctc cgtatggaga catttctcct    97740
ctagccggct ttcttcggc gtatacggcg ttagctattc acgtggtcag agacgccagt    97800
cggtctctaa tgaacacgtg ctactaccgt gcacgtcggg aaattactgt gaacggtgca    97860
tatcgcctcg gtcgcgcgcg tctcccgccc agcacggacg ccgaggcgac gcgcgaagaa    97920
gacgtatcca gttacgatac gctgggggg aatattccta cgataattct gagcctcata    97980
gcggtcatct cgattccagc catagccagc tttcaaaagt acatgtcgaa cgcaactaag    98040
caccagtcaa cattgactga cacgttacgc agtatatgcg gtttcttggt gggtacaagt    98100
gtcgcgatat tccttccgtc gcgctaccac gaggttctgt tccgtccaat tcttgtatta    98160
ctgttaatat tcggggcaat ggctactacc ttagccggct tcggtttact tctcgggccg    98220
acattgtttt ccgcgacagc cgcggttctg tgctgctaca cttgtataaa tgtacgcaac    98280
gcgaatagcg gaataaagca attggcggcc gccgcagctg gtaaatgcat attaggaact    98340
gccatctcga gcatgttggt ttgcgtgtta atacaatatt cctgatcgcg gagcgattaa    98400 ttttatatc atgtgctcat agcgttcttt cgaactgcga ataaaacttt cgtggctact    98460 aaggggcct atcgtgggtt tatgcgctgt cgaaaacatg aaagggccga tttaaagcta    98520
agttgcgcag gcagaggcca ctccatatac gctctcggag acgcggctcg cacgccagct    98580
gaaatatttt ccccatgcac gcgtcacgcg cgttgcgagc tttggggtgg acgagactct    98640
tatttgtcgt tttattttcg ggccgcgtcc taagcgctag cattaacccc gatctagcta    98700
cacccccggt cattgctttc aacccgtcaa gtattccggc cgatgatggg cctttggcca    98760
aagttcctgc atccccgccg gcaggggaga aagaggagag ccacaagaat gcaagcgacg    98820
cgcgtaggat gcctagtata gtttgcgata aagaagaagt tttcgttttc ctgaacaaga    98880
ccgggcgttt cgtgtgcact cttaagatcc cccctccctc cgacaacgaa tggtcgaact    98940
ttgctctgga ccttatttc aatccgatcg aataccatgc taatgagaag aacgtggaag    99000
cagcgcgtat tgctggcctc tatggggtgc ccggatcaga ttacgcctac ccgcgtcctt    99060
ctgaattaat ctcttctatt cggcgagacc cccaaggac cttttggaca agcccatcgg    99120
cacatggaga caagtacttc atatggctaa acaaaacgac gaatacgatg ggcgtggaaa    99180
ttaggaacgt cgactacgca gacaacggtt acatccaagt tgccatgcgg gatcctttca    99240
atcggccttt actagataag cacgtgtaca tccgcgtgtg tcaacgaccc gcctcggtcg    99300
acgttctagc ccccccgtc ctcagtgcg ataagtacaa ggcttcatgc atcgttaggc    99360 attttatcc accgggctcc gtctatgtgt tctggaggca agatgggaat atcgttacac    99420
cacgtaagga cacggacgga agtttttggt ggtttgaatc agcccgggga gccaccctgg    99480
tatctacgat aacgctgggc aactcggcca tcgaccctcc tcccaagatt tcatgtctgg    99540
tagcctggaa gcagggaaat atgatgagta ctacgaacgc cactgcaatc ccgaccgtat    99600
atcatcatcc ccgatatcc ctggctttca aagatgggta tgcaatatgt actacgcaat    99660
gtgtgccgtt cggaattacc atacgatggt tagtacacga tgaacccaaa cctaatacaa    99720
cttatgatac tgtggttaca ggtctttgca ggaccctcaa gcggcataga aatatcatca    99780
gccgaatatt actccaagat gactggcaga aaacaaagta tacatgtcgt ctcatcggct    99840
```

```
atcctttcga cgaagacaaa tttcaagctt tcgattactt cgacgcgacg ccatcgacga   99900
gggggtcccc catggttctc gcgatagcgg ctgttgtggg actagctttg attttgggaa   99960
tgggtacact cctgacggct ctgtgtttct acgcctccgg gaaaaaatac atattacttt  100020
cgtccgtcta gtttgcggtg acattgatct ggctcattat atgccccgag ctcttgtaac  100080
atcgcggacg cgatttccgt agtaggcaca tctcaaatgc aaaagcggca tgtcaaccgt  100140
ataggtacat ccggccctgc ttacagtcgg tagggcatat atccaccgga aaacttcagc  100200
tttagactcc tcaggtgatg aggaatagta tgtaaccctc tagcagtacg gtatttctaa  100260
aaaaaggtag atccttttcc acacggcaca gactaaataa cgtacactac acaggttctc  100320
tcgaacttcg tttggaccgg aattattccc tcggcagcgc ctaaaaagca aacctctaga  100380
gtagataagt gtcagtgaac ctaggccttc tttgttccac ggctggaaag ctaagggacg  100440
aggtacacgc gaccccagcc acgcacgaac agagtttaac ggaagcgtcg tttgcgggat  100500
aaggttgtcg gaccccgcgg gtccgttgaa aagtggctgc gcgcctaccg acgaatacgt  100560
cggtaacaat tttagaaatc gaatatgact gcgagtaccg tacaatcgcg aaatacggtc  100620
tctatatagc tactcggtcc ttaaatatgt aagtatgatg tcccctactc ccgaagacga  100680
ccgcgacttg gtcgcagtac gtgggctgct ccggatgatg gacgagacca catctgagcg  100740
acacaaacgt tcgcgttcag gatgcccccg gttgttatgc ggttgtacga tcgggatcgc  100800
tcttactgtg ttcgtcatca cagctacggt cgtgctagct tcgctgtttg cattctctta  100860
catgtccctg gagtccggta catgtcctca cgaatggatc ggtttaggct atagttgtat  100920
gcgcgcgatg gggagcaacg ctaccgagct agaagcccta gatacgtgct cccgacataa  100980
cagcaagctt gtcgacttta ctcatgcgaa aattctaatc gaagctatcg cgccgttcgc  101040
ctccacggac gccaatagca gcaacgtctt ccgactacgc gatagtagaa caacgtgcgt  101100
acgccccact gccgcaggac cggtggccgt cgactgcccg aggacctgta ccgccatatg  101160
ccagcggccg cgcccattga gtatcgtcgc ttcgataatc agggacgccc gtacttctct  101220
tcgtctagaa cgtcgcgaat attacgaagt ttatacggcc attctctcaa atggcagcgt  101280
gaaataaacg cgagagaccg agcattagag tagcacttat ttattctatc gcagagaaac  101340
accgcgcgcg ttcaaaaaaa acacaggcgg ggtacgataa atttacgcgg ccgcgctatg  101400
tttactttat acatcagagg tcatcgtcaa cctgcgcaaa atttccgtta ccgtaaccgt  101460
gccgccacga tgcttgcgca cggcttttgg gcgtggaccg gtcggtgcct ccaaaaggcg  101520
ttcgggggc gtttcgggga ccgtactggg agatccgaca gccacggcgt tgcacatatc  101580
tgccggaatc gccaatcccg tcgtagaagc acaaccattc ctttcaatcg aaaaagtggc  101640
agggagggtt gcggctcggt ccgatgcggg cgaaggctcc gcatctgtgc gggtcccatt  101700
tgacgtagat gccgtagtcg gtgtcgggga gcggagataa gttagcgagc actgagcggg  101760
aggcggggag tcttgagtga agtgcatagt gaagatggac tgtccattag aggcaggcgc  101820
ttcactggtc tcgcccccgt cctctaccca cgcacgcttc gattgctggg gcgagtcttg  101880
caagcatcta acgactgagt cacctcccctt agccgcgggt tggtaggtga ccgtcgactt  101940
aactcgtgcg tgtttgaacc agagcgccac cgtggattcc gtgtcagccc acgtgcacga  102000
gttcatggtc ggaaatagct cccccaggaa gcactggaac cgtttctgtt gccggagagc  102060
acgtctcaat gttgagttag ccatgccgcc ctgcagccat accgcatacc cgttaaagac  102120
catgttgagg atatattgac agcggtaatt caaaagacca accaacgcca caatagcgac  102180
tacaggccgc gatacttcac tttctgggct gcttcgccac gcgcagcacg tccacaaagc  102240
```

```
gcccatgtga acaagagggg ctaaaacggt tccgataaaa tggcataaca tcgtagtgtc 102300
ggcccagctt tccgatggta gggaactcac ggcttcggca agggccaaaa atacggtatc 102360
aaagtcgctc ggggcccgag ggccgaagac gttagggcac gcgcgcagat ctaacacgtc 102420
cattagccac accgcccacg tatacaacgt ccttacataa ctcagcaata gttgcaagcg 102480
tatcgacgta tcggcactag gcgccgttac atcatcgggt ctcatgtagt aggcgtattt 102540
ttgaataagc tctgtcccgt cccgaatctc tcgccaacat ctgagataca gtgcattatc 102600
tttcgcgagt tggaacggtt tcttgaccaa ggcgttacga ttaatgatag ggtaaaagag 102660
caatgctgct tcacgtctag tcggatcgca ggtctcgggc gaaccggcac ggcatccatc 102720
gcgtctcatc tctaaataat tcatgtaaga ggcctgataa cacctcttga ccgacgcacg 102780
agtcagcttt ttttttttca tacggcgcgc aatgcgcgcg cggtagggcc tcgtatactc 102840
ttccgaggca tccctaacg cgaggtagac gacgatacat tccggaactt tgttagaagg 102900
agcgtcgcgc aacagcgttt gtcgcaaagc agagagaaat cctgagggga gcacttctac 102960
gagcgcgtct tcttgagctc ggatacccga aagagatgta cccgttgttt ccgatagctg 103020
acacgggtac tcctggacgc gcgtcggcga acctcgtgac cgggaattta acgccaacga 103080
atccgtctcc ggctcgggag aagttggcgt aaacaactcc ggcgacatgc tagcgcaagc 103140
atatcggtcc atcggaatct atacagatta ggcgcagtac ggaaaggccg acttttggga 103200
cgcgaagtgg ccagaagcat cgctttcctt agcacaacta ttcttaaatg cgatgcttac 103260
tcagggcgga ttgatagtcc cgcccatacg gcgcgtcacc acgatctgca cgccgctccg 103320
tgcgcttttt ttttaccggt ccgttttttt gaagatcgcc tccttcgcat cttctaacac 103380
atcctgcagc gaggctagcg tgccgagaag gttatacccg ctcggaggcg gtactagctt 103440
tagagcttcc aactctccat tcttctcctc tccacgaatc gctgtcgcaa tgccgtcggg 103500
cgggtctcct cgctcaaatt ccaattctaa atactccata gctcgtcgc ggtcggctat 103560 atattcatct acgctaacag gtcgatacaa gcctttacat acgtagcaca ggtggcggta 103620
tagcttaaac gtttccgacc aaacgtctac agcgaggtcg tggtacatgg cggcgatcgt 103680
gaggtgcgcg acgccgatat tcaaatgccc tagcagacgt tgcagaacaa tggtagtggc 103740
taccacggtt gcggttaagg tgtctcccga ctcgatatct ctctcattcg ccgaggtgct 103800
gcgcgatacg aactcgttca taagctccgt aagcgcagat ctagtagcga cataagcccc 103860
gacgaaagtc tcccctagcg gcgcgcccc ggtaccataa gaagctgatt ccaatctccc 103920
caggcacatt ccttccgcat aaagaacatc gaggctctcc attgggagct ttttatgacc 103980
acggcctagc agtcgcgccc acgcgcgaac acgattagct ttgaaacggt gaagcattcg 104040
acccgacgaa acatacagga actgcgcggc gatactagca gccacacatc ccacagtaac 104100
gcacgacgat agcatttcaa gttcttcttt cgtcacagac accgtgtcag acgacactct 104160
cgacaataaa aacacttctg cccgtagcat agcggcagcg gcatagcgca ctgcactttt 104220
acacttcgat cccaaaatgc aacggagttc tggccagtac gccagagagc cgtaggaagc 104280
acgtaaaatt gcagcagcgg ggcccttcgc cttacggata gcgccgcctt caaacatttt 104340
agcgtcaccc gtaggaacgc gtggcaaaga cgacaataat ttggcgcgac cgaatttgga 104400 aaagcccccct ttatgtatcc tcaccgctag ctccaaagcc gaggtaatta agaaaataat 104460
agcgtctttc tgattcagct cgccagacac tacggcactc ctcagggcat ctatcccgag 104520
gcagagaata agcgcgtgtg cttgcttcgc cgtccgtttc caggcgagag cgccttttgg 104580
```

```
tggcgcggac gtatacatat cccccttggc atagtctgat ctgctgtcag aatgccaaag   104640
tggaccgtcc ccgaaagtat tgccccgggt atgtagtaat ttgtcttctc gtatagcctc   104700
gactcgaggc acgggttcca acagccgccg caacggaatg aacgtgccaa ggctctcgat   104760
aaacgtcgga ctcgtgcctt cgaccttgat gctattgaga tcgggttcgg ccgataaagg   104820
ggaagggacc gtgtaagcag atacgacccg ctcgtaaggc cgtaaatcgt catcatctcc   104880
cgaaaagctg tcgcttccca gagattgact cttttctcta gacgatgcac ccgagccttt   104940
acttatccag ttctgtttta agtcagacgg cgcacgctcc aagctgctgt cgcgattaaa   105000
tgaggttcga tcctcatgac cgccggctct cggtcctcgc ctgcgtgacg atccgcggcg   105060
tcgtccgcgc acgcgcccag accgagccgc atgtgtgtat tcccccctc tagatgatct     105120 tcctctaaac tggacccatc ttctggatcg atggcgacct tcagagccat tcgagcctat   105180
cgaagaccgg ccagaacccc tagaataatg cgtgcgcacg ctagcgtttc gatgtcgccg   105240
tctagatgac gacctccgac gtctagacct aggtctcgac ctcgatgagg cgtctgtcat   105300
gtcgcgcgac gcatcccggc ctgaacgatc cgaagagcgt ccctcccgat ctctgcgata   105360
gtgcgtatga gcactagcgt tgcgatgacg acgcctagac gaagaccttc gccgtttaga   105420
ccgaggttta gatctcgacg atgcgtctat cgcatcacgc ggtacatccc gtcccgtatg   105480
ctccaaaggg cgtctatccc gaaaagtatc tcgaatgtag ccaataaacc cttgtccgtt   105540
gcgacgactc gtagatccgg cagagctcct atatccatca gtctctaggc gatcgtacgt   105600
atcgtcgtag ttcgtctctg atggtcccac gtgtatgctt gccatgttat agggacttcg   105660
cgataatcgg acacgcgttt tagttccgcg cgttacataa tctcggaccg aaccggttct   105720
ctgtcgctgc tcttgaccga catccccatg acggtgtaga gccagcattc gccttcccgt   105780
cacaactcac cggcaaagta cggcggccgt ccatcgccgt ctcatttat acggtgccta     105840 atcgaacggc ggaaccgtag ctatatcgac cgcgttccat tgagaagggg gcgcgaggaa   105900
cggtaacgaa gtaaatataa taaaatcatt tattagctgt cgcttttacg tacaacattg   105960
ttttaactac aaaatcgtac cgtcgcatca agtattacat caccgtttac cgttcgcggc   106020
ttacattgtg cgagcagcag cgatatcctc ggcaatcgcg ggcccgggat gtgtagaatc   106080
ccgcaacatc gctttcacga tagtcccatg gccacacgac gggccggcct tcccagcgcg   106140
gccgctctct ccccgcgctg atgatcgcgc tcttggaggg tgcatgagag agtcacttc    106200 cagctttgat ttgatgcact ggaatagata cgcggatgcc ctaggcgcgt ttgctaaaaa   106260
tgcaggcggg gctgtcaaag gcatacccg ctcttccact aactcgcatc gcatcaccgg     106320
cagtccgagt tcggaccgta cgtaattttg tgttcttaat tcggcggcgg ttaacgcacg   106380
cccttcaact atcacaacgc cgtggttaaa aataaccggt tgaaataaac actgaaagtg   106440
tcgtaattgg tgccaatcgc accgcaggtg tgcaaataag ttttgccttt tcctctgact   106500
ggcttcgagt cgccgcgata catctcttgt aaccgaaagg tataaatgca tatacagaag   106560
tcttgcgaac cttccgcctt cccggtaata cgccccggcg atagatcgcc ggggcgtctc   106620
tgacctgccg acgcacatat cgcatcgcga gggttcgttc gctccctgcc taagataaca   106680
tgccaaagca cgacaataac cgcaaagtag agtgacatag gattttttctc tagcttccaa  106740 ttccatcgaa aagaatttt gaatctccgt aacataaaca ggcaagccgt cctttgttaa    106800
tgggggccgc gggacttcca tcccgcaatg ttcgtttaga tttatcgccg tatatgccca   106860
tttctcttcg gacgccgcat ctaggacttc gctaggagag acggacagta gggttgcatg   106920
ttcgtataag tgcccattaa tcggaaagca cgagaacaag tctacgttta gtttttccag   106980
```

```
ccgagataac agggacgggc cctctgtaaa atccagttcg tgcaagagcc tgttgtacaa 107040
gcggttcgga ggattcggat ttggggacgg aagcgaaatt ttgatcgaaa atggagcact 107100
caaagagaac gaggcagatt gctccgcgca tctcgtttga gagcaaagag tttcgctaaa 107160
gctttcaatg ccgcggagga tgtccgaatc caaacagtcc gtcattccgt ttacgggcgc 107220
ttcgatctcg gcggataagt ccgtactgtc gcggcgagca tctcgactcc ccggtcccat 107280
tctccgcgtc gccatccatc tgcttagtag cgcccgcccc actaccgata ctttatgtga 107340
cgctattcac tctcgctact atagttacca cgggaacttg agtagtggcg acgtgaagtc 107400
gtcggagcgc gaccggggt ttttgagcga cgatctctct tatctaccgg agtgctctcg 107460
tcaccgtcgc gttttccata ttgggatctg gacttagggt ttcccatatc cggcgacagt 107520
ccggactcct ccgataattt tcgcgtacat gcctcagctt catccaatag gtttgcccct 107580
tcttgaatcg tgatcttgat tatagccctg gcgaggaatt cctcgagctc cgcattggtc 107640
ctcggggcgt tccgacgcca aagggaaagc gctcccctat atgcatggta ctgggccaca 107700
gcagctacgg ctccgcagaa tatacgctcg ttatagacga gcgtgtttga tcgccaggta 107760
ctagttgctg acgccggagt cgtactaaag gcaaatttcc cttttctat tgccctggct 107820 ccgggtttgg cacgaacttt ggaggacagc gactcccctc tttgggtttc cgatgaggaa 107880
tcttttcttt cgatctttac agatctgcgt ctttgtaatg aatgagacgg ggggagatc 107940 cggtccggcg actcgttctt ggacgaatct cgtcgagcgc gggtcgacga tatatgggca 108000
ctattatccg gtgacgtgcg catagttgag cgacgtcgac tcgacttacg tctatccgaa 108060
tctcccattg tatctcgtat taggcagccg attacagacg cgacgggccg ttacgtttca 108120
ccgtgttgcg tctccgacac tgatcaagct gttcacggca atgacattct tatacggaaa 108180
cagtagcgcc cacgcccaca cgatcttacc agccgtcatc gaacatactt gccgtgaata 108240
gtcggaagca tgcatggtac gacccggcca agagggcgga gattaccgcc accagaccta 108300
gataaaaaag gaccgagaag ccagaagaaa aggctataga cacgcctacg gcggaacacg 108360
tagattccca gaaatttcct gccacggcga tcggccttcc cgaatcgatc gaagtagctc 108420
gcgactccac gagggacgca attacgcaaa ttaacacttt acagaccaca tgatggatgt 108480
cggacaaacc catccctgcg gtaacgcttt ggaaaagatg tcctcgcacg cgtcggggc 108540 tccgtggcgc atgcagttct ccgtcgatga agcgatatat gcgaggaacc cagaaggttg 108600
gacctgttat atagaagaac gcgacccgcg ctgtcttcgc gttatcaacg actgtgcgat 108660
ctcgttgccc aaacgcgatg ttaagcgaa gtatgaaata tgtgcgttag atctaggtgt 108720
acgagtggca gttcctcgga attatgtcgt tgtgctggcg aaattgacgg acccggatcc 108780
aacgtctcgg ggcgtacccg taatccgcgt tgccaatgga ctaatagatt ctggatacag 108840
ggggaacgtt cgagtggtac tttttgtacga agcagcttgc accattccta aaaacgggct 108900
ggttatacgt ctggcgctcg tgcagttggc ctatccggat ttcaacagtc gcgtgctttt 108960
tgacctcgct gatatcacgc cccacttgga ttgcgggcct aactttctcga tgtcgattgc 109020 aaccgctgct aaatcgcaca gcgctcaggc tcgaccgcta ttgcccctg gcggcgagaa 109080 actatggccg gaaccgggt gtcgggcact cgtctgtttg tacagcgatc gcgtgtctcg 109140
ggcaactcat tataacactt tagacagcaa tgtcatattt gccgtaaggt acaatgattc 109200
tacgaccgtt atcggcttaa aagatgtccc gaagtatgtg cataaaacat ttgtacggtt 109260
ttatacatcc ggtcaatttg caacgttcgt tccttttac gagacattta atacaaagcg 109320
```

```
gcacgaagat gcggcttacg atatattcgc tccgagcgac attgtattgg aatcaatgtc 109380
ttctgtaact atcgcgatac agcagcgata tgcatgtgcg gataagtcaa tggttccttg 109440
gatcttcgga cggtcgtcca tgaatttgcg cgggttgatt atttccccat ctaggtggat 109500
gcccgattcg tggttaacgc tgactttatg caacttaacg gaagcaaaag cgaccattaa 109560
acgcggagat aggatcgccc agctgttgtt agtcaatcag gaagccgctg cgttgcttcc 109620
aacggaaggc ggcacggctg cgctgttccc tacagtaggt aaatgccgtc gtcccgcagc 109680
gtccgcggaa gctaagtgga gggaaacggc agcattcgat acggaatcgg gcaggagcga 109740
gagagagtgt gccggcttcg ggtcgagcgg gcaataatgt atagttgcgc acgattacat 109800
acaaaacaat aaacacgaac accacgctgc gttctggaca atcagtttat tcagttacac 109860
agtccggtaa catgccctcg ttgactccac atgtcttagc ccttctaccg cttcccttac 109920
ttacatcaca tgacgttgca catgccgctt gctcggcttc agagtgcggc ggcgaaggta 109980
gccctcccac ccgaccgtaa atatctgctc cactttcgtc cccgcagtta cggggggtcag 110040 tagcttccga tagctctaag ttttccgttt cgggacacgc ggccaacgct tcgagcgagc 110100
aatcatttgg ggaagatttt aagcctaacg ctctttccac tagagcgata tcattcatag 110160
cagtctctgt agcagcagtt attttgtatcg cgtgttctac gaaggcatcc gttcgtcccg 110220
tgccgacaga catgtagatc tgcaagaggg cggcggcaca cgtgtccacc attcgctgcg 110280 cattttttgcg atgggtctcg acgaccgcgt cgagcccagg ggttccttgt cccgaaacat 110340
gacgagatag gcaatcgaga ttacggagac acgcactgta cattctagcc aacgactggc 110400
cacgaaccag ttttcgcact ccgtcggcag acaatatcgc catttctaat gtgatgggcg 110460
tggggagcat aagattgacg gcttgtaccg cctccctgaa acgatgcata actctgtcgg 110520
aggaagacga ggtagacagt gctgtgtatt ccggctgaat ttttctagag cgccttctta 110580
acccggcgtg cattgtggcc aaatcttcta ttatgtccga tataccggag gatgccgacc 110640
ctgggatcaa agttttgttt gccgttgatg gttgcgccgt ctcgttctcc cttgcacttc 110700
ttacgggtca ggtcccatct atcaatcccg tctacgttat cagccactgg gatccgggca 110760
atcgtttgtt agatgtcctt tgccaccgcg cagacgatcg cgactgcgga agaataccga 110820
atgaacgagg agatttaaac gcggtctccg accctctaaa agtagagttt tgccttctca 110880
gtcaaatgac acgcggtttg gcggcgcgcc atttaaaatt gcggacgcga gcgatattcg 110940
tgtgccggtt tacttcgcat tccgagatta actccatcgt ggcttctata gcttccggag 111000
cgcctattca aacagactta ttaatagcca ccctctccga atatgacaca tttcgcctac 111060
atgatgactt caacatcgcc ctccacatct ctctcgcctg tttatcgcaa aagcgccgca 111120
atgggaaaga gccggcaaaa tcaccggatc gaaatctgct atcgattatg gcgggaacct 111180
tttctggagg tcggcgcggt ctagccgggc tgtatttaca atacgagcaa aaagtcaccg 111240
cggcctaccg acgtgtatat ggggggtcga cgacgacagc gttctggtac gtgtctaaat 111300
ttggaccgga agaaaagagc ctggtcttgg cgctacgtta ttaccttttg caagctcagg 111360
ccgaacctac tgggattgct acgggttacg atttacaggc cataaaagat atctgcgaca 111420
cgtacgctgt acccgtagag gccaatccta ccgggttttc gacggcagac ttgacatcgt 111480
ttgccagatt atcgcgtttc tgttgcgtga gcaattatgc caacggtccc gtagctaggg 111540
cgtttcccct atacgtggaa cacagaattg cagccgacgt gacagaagtg gatgcattga 111600
aagagtatat agaaagagac cggtccgggt taaagatttc ggatttggaa tttgtcaaat 111660
atatttactt ggcttacttc gagtgctaca atcgtgctca attaagacgt catttgcgag 111720
```

```
acgtgaccgt gcgttgtccc gaagaagatg tctacaaacg ctcgtctctg gggaaacacg   111780
cagtcgataa tttctttacg catgtgagat ccagactaaa cgtgaacgat cacatagcat   111840
gtaacgtatc tccggatcaa gtggaaatgg gaaacgtttt gacccgagca ttttgtaggg   111900
ccaggaccta tccaccgagt accatggaaa gcgatgcgcg tttcaccggg atttgcgaac   111960
cctcgtcggt gattataaag cgtctggatg ccctagaatc gacattacac aaatacggat   112020
ggccgcgcgc acggtctgaa acagttaaca tgatgtcaga gtgcgcgaat ttgcccatcg   112080
cttcatctgc cgatagtctt aggccacccg gcctgccgct agaacatcca ggcactcatt   112140
gccggggtgg tccaatgatc gtaaagcgcc tactagcgct agtatccgca gatgcacgtg   112200
tcggggacat aggaccgaca aacatgctca ccggcattcg ggaatcggcc gtcaagggcc   112260
ctcttccgat ttaccggata ggcatgtcca aaggcaaaca agcgtttgcc gtgatggtgg   112320
ccgattgttg ggacaaaatc atcccgtctc cgggaattgt gaaagcccat ctctctaaac   112380
tcggcagatc cggtagagcc cccgaagacg atgtgatcgc ccgagatatt ttttttacat   112440
cagaacttga gcgagtcacg ggccatgctg cggaactgcc gtactttacc tgcggccctg   112500
ccgaagaaca acagtacata aatcgcaacg aagtgttcaa tgacaatctt attgtgggga   112560
acataatcct ggatgtcgat gtgcacttac gaaccccgt acccgtcaaa cttttgcatg    112620
tggcaatgag aggttttagg accggtgcgc tcaaagcgtt gtctctatta cttccaaaag   112680
caaaaataga tcacggctcg tacccgtgct acttttacaa aacctcgtgc aagaaatctc   112740
gagtcgtgca cgtaaaacat tggatgtcgt ctactaccga cttcgctctc gactgcgacg   112800
gtcccgccgt cgaaagtgca gactgcgaac tagaaatggg cttcgatgac ccgttactta   112860
tggatcaaat tgatgattcc atcagtagat gtgagtcaga tgcatcaagt ttgccgtcgg   112920
acgccgatct gccttgtaac tgtcacgaaa aaataggatt gcgggtctgc attccggtgc   112980
cgcccccgta tctactcgta ggtagcagaa caatgagcgg tctggctagg gtactgcaac   113040
aatcggttct gttagaacgt agtttcgtag aacctatcgg ttcgtatctc aaaaactatg   113100
atatagttga tagcggagta tatggtcacg gtcgcagctt gcggcttcct ttttttggca   113160
agatagacga gaccgggctt atatcaggcc gcctgcttcc gttttgcgtg ataccggagc   113220
gctgcggtga cgcagaacag ttcgttctgt ctcatttaca gcctaaaacc tttcacttcc   113280
acagtcccat gcccgaagaa gatcacgcgt ctgtagttct gaagggccta ggcggagagt   113340
atgccggatt cttttgaaaaa aaaatcacga tcaatagaga tacgttttc ggaatcagat   113400 tatccttagc ggtagctctg aaagccaggg gggttgacat taacgactct gcggcaatcg   113460
tatcattcgt aacggagcac attttagatg acataattca gtacatgcat gaccacatac   113520
ccgatcacgc tgcggaatat aatcacgttt ctgtttcgtg ctgcgtcatt agaccagatt   113580
ggatcctctt gcagctaatg gccaataaaa cattgggacg cgctcacggg tttacgtgcg   113640
tgaggtttaa gcatacaaga acgactcgaa tgagttcgcg ttcgtatttg tctttaaaca   113700
tcgacgcaca tggtaggttg tgcgcgtgtg tgattcagca gtgttttgcg gccaagtgtg   113760
gaaacaataa actccgtact cttttttacg tggatgtcga ttcgaaatgc caggcagaac   113820
atcgatagcc ctttcgggaa ttatactctg catctcgaca tacgccatcg ctttggtgat   113880
ctacacgacg atgatagcta aacacggttc tgggtgcatc tatgccgtcc tggtagacag   113940
cgatcatcgc gatgccaaaa attttacatg ggagccatac aattctacac tggtatacac   114000
gccgctgggg aataaattac cattggacgg aggatttggc ggttttagcg atgtatgtaa   114060
```

```
cacatatctg atcaacgcga cggatttatt cggacgcgcg tctcacgcgt ccgccaagtc   114120
gaaaatccgt tcggtggtag gaacgcgcaa ttgcgcagcc tacttttgga agacgcatat   114180
acaagccttg accttttccc taagttcgta cattatgttt tgcgtcatta gagaatggag   114240
acgcatgttt ggggtggtgc gatctgaaaa cgacagaata ccgccgacga cgtacacgaa   114300
gaattatact gccagggtaa tcgctaacgg attgctaaaa acggtatata ctagaatgtc   114360
tgaatttatg tgcgagatta ctatatacaa aaattctatg tgcagaatat ttacagacga   114420
ccctatctcg tttatcttac gtcacccttt ggctgcgatt ctccttataa ccgagcggct   114480
cataaggctc ggcgcacagt gtctgtgtgt actaacggta tcgattttt ttgtaccgtg   114540 taaaatagtt ttatcgaaat ggttcttgtc tatcaccgga gttttcttag gaatcgttat   114600
ttgcaccgag atgggcctgc tgatagaccc gggaccggct gaaaaacctg tcatgtttgc   114660
agaagttgcc ccagccccca aacccagca gaacggcgtg gctgtcccgt tcggtgcaca   114720
cgctgtatgt tccaattgct gcgcctccat aatctccagc atagtcatca aagttctgta   114780
cgtgttattc atggttaccc tcatcgttac cctcgtgcga tatgaacgag cgctccagat   114840
tgccctgttc gggcgtgcgt acctacccta aacattagt ggccaagcct cctatttgca   114900
tcgcgcggat gtgacacgct aaccgcgaga ccttataaat ggttccaatg agtcattcgc   114960
ccctcgggtg tacgcggtat tctacagcag cgtattagat aaactacacg ggtttgccgt   115020
cgcgcctcaa ggaaaatgtc agtgggagct ttctctcgtg attgggacga tataatgagt   115080
ttgtcagact acgattttac agaggaagaa tccttagatg aaagcggcga actgaaagaa   115140
ttcaagaaca cgtccgcgtt gaatgctatt gagacagccc gcgacgcaat tgaaagatca   115200
gccaattcaa accccccat cgaagaaccg tcgttcatct ccaaatctca tgcaggcgag   115260
acctcggcct cgaaatatag aagcttgccc ctcgacatcg aaaaggcaga acggtgtgat   115320
gacactcgag gctacaacgt gagttcggga aaacgaatgc gtttggcagt ttcggccact   115380
gttgacctgt gcgagtctga gatcgaacgg caatgtctga atacgaaaac gcgggaccgt   115440
gcacggtccc ccaaacattt tgcatcccat tatgaaatcg ccgccaaaat acacgatctt   115500
cccagatcta cgggaaaaag gcaacggcat cgcacgttag attctcgctc acgacgccac   115560
ttagcgggag agcatcggcg gcggggagct catgacgagg aaagcagaca cttttccctc   115620
agaatgcgtg accctcattc agcacccggc aagagcccgc tgtcgaaaag gcgcagtccc   115680
gttaggctcc gtaacctctc tgtgcaggag gaacttaacg cgatgctaca acgagagaaa   115740
ctgaagctcg acatgatttc gagagagcgc aatttccgca cttctagcaa aaaccgctgg   115800
gcctcagtac tggcattctc ctgtaccgga aaaagtgggg catacgggtc tcagataacg   115860
tggcaatatt tgcttcaaga gggaccggag cttagaaaga cgttcgaaaa tagacctaga   115920
acctcattgc tggcgtctgc ggcgcgcgaa gctgtgttgc ggggcgaaaa cttagttgcg   115980
gcattggaga gcgccgagga aaccctggca tggctgaaat tacactctgt tctaaaactg   116040
cgtttaatga accatgaccc tattttcagg acggcgggtg ccgtcttaga taatctcaag   116100
ctgaaactcg cacccataat gatgtgtaga aatggtacag acaaacggtc gttaggagac   116160
atgctgagaa gatccgccac ggacgatatc gccgattcat tgaccttatg cttaattttg   116220
ctatcgcgta ttcatcgcat gatgatgtat cgcgtgtcgg gtagaaaaga tagttccatg   116280
atagatcctc ggggatacat gagagagtat actcctggtg aatgtatggc gggtatattg   116340
cattacgtag acgcgcatgc aaaaacgtgt tccgacagag cgtgcaattt atatattagc   116400
tgtacccttg tgcctgttta cgtacacggc aggtactttc gatgcaattc cgcgtttgat   116460
```

```
atgtaaccta ctacagacgg gcaattttgt attcttcaat agctttattt gatatccatt  116520
aaacttaaat aaagacaccg atattcaatt ggacatgaac agcgtgcgtt ttattttaca  116580
cttagcctgt gtgctttcga caccgagtag gaaaacgaag gacctgaaat tgcacgcacg  116640
accgaaggaa ataagccatc gcaatcgcat ttgaaatcca agtaggcaaa ttcaggagaa  116700
cctatcactt cattgaacaa gttctcgagt attcttatga atgataagca ctggagcccg  116760
ccagggcgat cgcagacaca actaattaac atgccgtgag tgctgaagtt ctctctcatg  116820
gcagattcgc ataagtaaat agtcttcctt cgagttccta tctccgtgaa tctgcggggg  116880
ttcatcagaa gcgcaggttt gatttccgac gtgtgattag aatgaaattg tcgaaagaca  116940
gtctttagag tcattggcat gtctgtcagt actatggaca cttccttgcg gcagcgatcg  117000
gtaaggaacc acagtagttc cttaggtagt atgtttctac ctaggaacca cggtgttccc  117060
acggccaaaa accaagcgtg gtcaaacgat ccggtgctcg gagaagaacg ctgcgtatcc  117120
gctacccaaa gcagtatcct ttcgcagata gacgacgttg ccgtgaccat tctcccttt c  117180
caacctcccg tcagtacact gtttattggg ccccggcgt gcgtgaggag taccggtcta  117240
gcgactattc cataaacgtt agtcggtgag agttctctcg gggtgagcca cattgggaag  117300
cccgtctggg ttggagcgtc cgatgtagag tcgtaattgg cgcagcgctg accctgcggt  117360
ctacaatgca tggtcatgct agacgggaca actagtcgcc cggtgcattt ttcattacgg  117420
ccatccctta cgtccacgta ccacgtgccg tgagtgtgta ggtaacacgt agtgggcgtg  117480
gaaaaactta tataacaccc ggcagaaacc acgtgcgccc agcggtggca gatcctcagt  117540
tctacagtgt ccaatggcgg aaagtacagc tgaaccgtca gcttcaccgg tacgaattcc  117600
gtacgtttgg caagtgatcg ctccgttagc aattgacgtg ccgtccgcct ctactcaact  117660
agctacgggc gaacatgtgt catgtgccgc atccgttatt cctcgttcgt acgtcatacg  117720
ggcagcgtgt aaatcgtcga cgactttcca cgcgttcttc tttggattgg cgacggatcc  117780
gtctgagaac atgtcccaat gcggtgcctc gtatatcgcg tatagaatga acaagaagtt  117840
acggactggt cgattgacag gcgaccaatg cgagtcgcct ttttctcatg cgacgatcat  117900
cgactcactg gatgaaaact acagcatggc tatagaggga ctgtgttttc attgccactg  117960
cgaaaataag ttttcgctcg agtgttggag atcggctttt agcgctgccg aaaaaatcgc  118020
atcgcagtgc agagctattc gcgagtacgg acactgaata aaaacgaatc atgatttgat  118080
ctaccatttc agcatttatt ggtttataca ttctcgggtt cgtatgtata caaaatctta  118140
tggcaacccg cgataacaat tcatttacgc ataccaattg cgagagctag gggcgcaccc  118200
tcaggttcgc ctacgccggt atagcgttga gatctaatac gggagtagtg attttgcagg  118260
aatgtaagtg gtagtaacac ctaaagaaaa ccacatacta acgctctact gttcactcgt  118320
atctacgtgc agtgaggttc ccgcatatgt ttgcgcgtca tcaatcgctc tcgccagtat  118380
cgccacaatg cgttttttcgc gcgcgggtat tgggacgcag tgtaagtgga atagcattcc  118440
gcaggcaaaa aagttgtttg tcatgcaagc atccatcaag tagcaatcac atagtgggac  118500
cagacgcctc aaagcgacgt agtggggga accctcttcc cattgcaacc actttcgaaa  118560
tctgtaggta tatgctgcca gccagcgcct tgttctgacg gttattaccc tgaacccctt  118620
aaatgggaag aagaatccaa ggtaccaatc gttggcgact ggcccgtgcg gacaacgggt  118680
taaggatgtg acaaactgtg tttgcgtggg tacgtttacg atgtatttcg aatcccgcac  118740
gacgcattcc tcccagtgag atagtagtat cccataattc atgcatctga ctaccttggg  118800
```

```
ggtgagacac gctgtaatat gaggcgtcgc ttgtaaaacg cacctgtatg gaaccgttcc    118860
gagttcgggg attgattcta tgatagcaag tctacttatt ccggaaaccg ccatgacatc    118920
gcacaaagga agcagttggt taattgcatg aatcagaatg tttgtttcca gcacggcacc    118980
tccaaaggaa aataatgttt cgatgcacgt tcgtgcccccg ttctctgtat tacagcttac   119040
tagcgcaagg ctgaggacaa aaacgagttc gggcttttgta tgttcgagcg gaacaccaat   119100
gcgacatacc gtatcgctta agttttttcat aaaagtggat cttgcacgtt tgccagatct   119160
gctccaatcg gccgaaaaaa atttgcgcac aatcggatgc atgtctgtgc ctacaaatac    119220
catgaaacat aattcttgtg ctggacccccc atccccgcta tctatatcta cattgtctga   119280
catgtgttgt gccgacaaca aacggtgtct tgtatcccca tcaatccagc gctttctgag    119340
gtttacgggc tttaggatgg acacatcacc gcatttcggc acgcataacg cgggcatgtc    119400
tgaacgggca acgattctct ctgtgagcag atcgagacgg ccgtgacgca caccacgtgc    119460
cggtacatta ggcacgactg tagcaaaagg atggtagcga tggagccagc ctaccgacag    119520
tcccgcaaaa aatcttatcg gcggaatgtc tcttttaagg ggtagtgtgt tacgaaccga    119580
tgaattcaat ttctctgtcc aaccacttat cgcttccgca acagaaaaat cgtttctaag    119640
ttgcgaatat gtttctacca cccacttgag atcgctgcga agggcttccg acatttttt     119700
agcgtattcc tcatctccat cacaatcaca gtcgtgtctt tcatttgcaa gtgtgggcgc    119760
gcagatgtct acgcgacgac ttaaccgaga cactgtttct ctagtgtacc ggtaacatgg    119820
actggcgccc gctctgaccg ttagcatgcg tttggatgca accgaggtta gataaacgtc    119880
tggagaactg cccaattctt tgctttcact ggcacatatc caaccgtatg tatcctctgt    119940
ctgtcctgcc gcctcaaagt taccggggag aggtccggga ctcgctagac agaagtcgat    120000
ttgggaaaat tctgtgtcat tgttgtaggg actgtgcggc ctatctacca tagttgcaga    120060
atcgtgcatt agaatttcag cgagcatgga atcgatacgt tcgtcggcac ccgcatatac    120120
ggcacctatt cctattcgcg tacaagagtc atcttctaca tcaagcttcc agaacgttgt    120180
caggtattcg ccataggctg caaagtctgc atctgtggtt cttcttacaa attcaatctc    120240
cgggttccaa cgtccacgtc ccatacatag gttgcgcaac gtgatcgagt acgccaacgt    120300
attgaaatca tttatgctag atgcttcgct attatcttcg aacaaaatta tcgtatacaa    120360
tttcgattga tgcatcgatc gaaggactga caaatctgtc gcatatgtct cctcggggag    120420
aggtgtgacg gtgataggct cgtccctacg ttcgaaccgg ataaggccta ctgtagcggt    120480
ggtttcagta gtcctgatgc atcgtaaaat tgtggcctcg gttctaattt tcccgagtaa    120540
ggcccacgga ggtccgcaat tactattaca cagggcctgg attacggagg aagtgccagt    120600
tggtgcacac cgaaactctg gaaaccattc cttggacgga ataggagggt ggaatttttg    120660
tcgtttagtc cactccatct gttcgtacat ggaaaatcgt gttaattcct gatcgtcgaa    120720
atgtgctaat ggagctatag tgctgcgttc ggctggtgcg gaacctatag acacgacata    120780
ttttggttgc acgtgcagtt ctctgagctg attaggaaat aatactgcgt ttgatgatag    120840
caaagacctt tcgggatcga gctccggagt gcagtgcgaa gcgtgaacaa ttctactttt    120900
cttccgagac ggtgtgaagc aaaacatctt gacgatgcta cgttctatgg cattctgcaa    120960
caataaagta tcaaattatt ttgacattat catctatagt atgagcggtg tgttatataa    121020
gaggacgaaa cacttgtgaa gtagacacgt tttattcagg aactcacatt ttcactacta    121080
cgctgttgtg agcagagaga taagcgcggc ggaaaaaaca gtcacaaata ctactgttaa    121140
tataatgatc gcagccgcat cctgtcgggc attaaacaac caatcctctt catcattagt    121200
```

```
ttccgaagag ctagtctcat aaggcggcgg aggagagtcg taggtaggag gtggtccatt  121260
tgaggcttca tacggaggca aatatgcagc gtcgcattga ccgtccccca gttgtaattc  121320
gaaatgttca tataccgatt ccccgggagc gtctaaaaat ggttgctcct catgtaacgc  121380
ttgcgcttcg ctcgtcagac cgcggtctag ctctgcgctc gtaagttcgg tttgcggtcg  121440
gtcgctatcc attttccctc gcccgcagta actgtgtcga tggttcacta ctctcgaagg  121500
agttaaattg cctactttct cctcgaatct cgaatgtggc tatgcagcat cagggtcatt  121560
agcgtcagta ttttcctctt tggagtctat ggctctaccc caaataccte ccgcgattgc  121620 tcctgtgcat aaggccataa acaggccggc cctctgccaa cccgttgaat ccaccttcac  121680
tgctctgcca attagtattc ctgcaaaaaa tgccatgcat gatcccatta ctaatgatct  121740
tgcggaccga ataagcgtga ttaccattaa ggagcgcatt gtagcattct cagattccac  121800
agataaaaca gtacgaggta ctgtaggagc aaggcgctga cctacgaggt tttgttgcac  121860 cttteccgct cctttttctg ctatcatcag taagttaatg gactgcacga tttcgctttc  121920 ggccccggagg aggcggcggg catcttgtac cgcgcgctcg gcgcgccgga gcaggcgcgc  121980
gtgcgcctcg tccgcgtccg cgcccgcgtc cgcgcccggg tcgtcgcccg ggtcgtcgcc  122040
cgggtcggcg cccgggtcgt cgcccgcgcc cgcgcccgcg tcgtcgcccg ggtcgtcgcc  122100
cgggtcgtcg cccgggtccg cgccggtcc gcgccctccg gcgtcgttct ctccggcgtc  122160
cgggtcgccc cctccgtccc cggctccgct ctcgcgctcc gcatccctct cggcgtccgg  122220
aggggcgcgc ggatcagcgg tcgggtcgcg atcgcgtccg tcggatcggc gccttttccc  122280
ccgccgcatc gcgttccgcc gggccggtcg gacgggagaa gaaggggggag ggggggaagg  122340 aggagagggg ggagggaggg tagccggccg gcctgcagtt cgggaagagc gggggaggcg  122400
ccgtccgagg ccgccgggga ggaggttgtg gggggcggga ggatgtgtgg gggaagggaa  122460
gggggagacg gccgaaacct acgcgttcgc cgcggcgtcc gatccgggat cgctcccgac  122520
ggggctctcg ttcggcgatc gcttatcctc tgccgccacc ttgcgtccgt tcgcgggaag  122580
cgccggaccg gcgctctaag cggagatccg gcgcctccgc ttcttatgac cgggccggtc  122640
gtgagggcgt aacgatcacg tgatgcaatg caaacgagcg gggcgaacgc gtcagcgttc  122700
gcaccgcgaa ccaatataag attatatata taatatatta ttggcgcaag gtgcgaacgc  122760
ccgtccgggc caatcgggaa gcgggatcct atgccacgtg ttcgtgtccg gccgcggccc  122820 gcgccgggg ctagaaacgc cgcccccctc ccacggggggc ggattcgggg acctccggcc  122880
tacaaatacg cgagcggagg tccggcgggg accgtcgttc cgctggccgg cccgccgtcc  122940
gaaagcgcgg gaccgcggta ataaagcgcc cgccgtcgcg gatcggattt tctggtcgtt  123000
cttttaccgc cgggcgaacc gcgcggcgaa cgaacccgtc ccgttgggat cgcaggcggc  123060
cgggaagcga tcgcgcgccg tcccgagaac gtcgtctacg gctcgcgttc gcggggggtcg  123120 ccgacgggtg gaaggggggat gggtaccgag ggcatcgaac tggccgagct cggcatctcc  123180
gccttcgggc cgcgaccctc gcggcgtccg gaaccgtcgg acgtcgaggg aggacgcccc  123240
atcgttctcg tccgcggatc gtcccgatcc ctcgcacgag aacgagatcc gaccccgcgt  123300
cggcgacgcg gccgaacgcc gctcgcgaaa cacggtcgcg ggtcgccccc cgactttccc  123360 cccggcccccg cacccgcggc gaggtcggaa cctcgggaat cgattgaaaa cgggccggtc  123420
gagataggac cgctctctcg ttcggaagcg gagcaataaa gccgttcggc gtgagctcgg  123480
gatgagtctc ggacgcgcgt cggtccgttt ctgcccttgc ggcgctctac gaaagaaccc  123540
```

```
gatgaggccg cgttctgttc gggagcggtc ccgagctgta gggatcggct cagtagtaac   123600
tcgtctcggg tttcgatcga gttctagcga accccgaaag gggggtacga ggaagcttgc   123660
ggcctgccgc aaaaagactc cgaggagaat agcttatccg cgatacgccg cccccctcaac  123720 cgttcagcac tcacttcggc gtcagttccg aagtgacttt gtctggccgg ctcggcgcga   123780
gccggcctcg gagagaacgc gtacatagcg atcgtgggct gggcaacgag ataggagtag   123840
agggatgggg aaaaagtgaa gtcccgcgct ggctctggac gaggcggaac gaaatggggg   123900
aggggacggc ctctcgaacg agagcggggg tggggcatgg tcggtggagg ggtgtgggaa   123960
acgccgcgac gccgcggccc gtccatgtgg taatgcgggg aatagagttc cctgacgggg   124020
aggagttgtc agctcaccgg tcccgtgatc aacgcatatg ccacatatat gcaacccgc    124080 gaccctctcc tcacgaacag ggtagagggt ctcgctttgt tgcacacaca agcacactca   124140
cttttgcggc gacaatgaaa atcgtgagcc cagaccaatt gccccatata gtgttaacgg   124200
cctccgacgg aacaacgag ttcagtattc gagattggtc gctatgggat cgggatccgg    124260
aatcccgtgc aggtacgcac cgcgggctcc gtcaaacgga acgctctctt ttggagcgat   124320
gtcgtttggg tccgggcccg agtagggttc ggccggctat ttccctcccc ccccccccc    124380 caagcccgtg cgggaccgag gttgagtggg aaggtctcgc ctgccggatc ggggggagg    124440 ggaaaagacg tttgcgttat ccggaatcga gccggaccgt tttacgtttc agagttcgaa   124500
cacgctctca cgagctgcag ccaccggctc aagccctcag accgcgtccg cgccccgggc   124560
cagcctagcg tcgcaaacgt ctggaagagt ctgtggagtt tggtttcgag ggccgtgcgg   124620
ggaaacgcag agggctccta cggacgaccg gaggagggag acgccgaaac tgccgtgtaa   124680
acgaatgctt agcggagccg cgcccgggac gcgtcgtttc ttgcgaaacg gggtggatcg   124740
ctcgcccgct cttagccctc gcgtacagtg cgtcgatcgt taaggtgtac gtgcgtgtac   124800
gagaccgcgt gcgagcggtc tcgtcgtagt gcgtatgaac gtgtttatta aaaagtcttt   124860
ctcgcttcgt tcccgtttcg gtgtctggcg atggcgcggg cggggagtc cgtcgcgtaa    124920 gtcggggaac gtactttgtc ctctcctctc ccccgaggcg ggatgtgcga ggggggggc    124980 gacgggcgac cgggaatgcg tgcgattagt gttgtggaga acgtaccgcg ccgaggcccg   125040
cggtgcgcgc gaagggttag ttgggggagg ggcacgcgca tcataagtcg ctcgcggatc   125100
gtccaggtgt ttgtgcgggg gatacagttt cgcgacgggg aggagccgtt agctcaccgg   125160
ccccgcggga gacgcagatg cgatataaac agcccgcgg tccacctcct tgttcgcgac    125220
ctgctactta gcctcgcttc gttcccacgt ataagcacca ctgacttacg cggcgaccgt   125280
ggaagtcgcg agttccgacc agtgtcgcgt atatgtgtta acgccccg tcggaaccga     125340 attccacatt cgagatgaag tgctacggaa tcaggaatcc cgtcccggcc gcgcgcacac   125400
ccacacacac ccccacacac accccacac acccccacac acaccgcggc tacagagcgg    125460
ctgtcgtagt acgtataggc gcgagcgcga acacttgcac ggactctcgt cgtagcacgt   125520
tcaaatcggt ttattaaagc cctcatgctc agactccgtg tcgatggcgg ggggggggg    125580 gtggtgagtg acacgaactt actttcctgc gacgctcccg agaggaggtg tgcaccgggc   125640
cgttttctcc gagactgaaa agagaaagaa aagctccgcc gttcgcccgg ccgagcgccc   125700
ggacgcaccg gtgtccgtac ggccttcgga cgcttagaga gcgcgggcgt ttcgcgccgc   125760
tgcggcgttt aggcgcgcag cggcgcgttt gcaaaaaaaa agaatgtacg gagagacccg   125820
cccgccagcc tctccgggcc ggagcggaaa cgccgcgtta tctctacgcc cccgaccgc    125880 acatccgaat gcgcggtcgg atcgcgaggt taactccctg cccgcgcccg cgctccgcgc   125940
```

```
tcccccctgcg ttgtttaccg gttcgcgatc gcgatcgcgg aagtcgcagg gccgacttcc   126000
ttgtttacat tgaatacgtc gacggaagcg caactgcgta tgtccgccgc gcagacgcag   126060
aagcgccggg gccgaatccg ggaagaagag taatacgggg cttctccagc gcgtaagtac   126120
cggcgttccg ggcggtcggc gagtcggcgg agaaaaggtg gatcgcgagc gcgatccgaa   126180
tccgcgggcc gagggaaat  tcttcctatc ccctgtgcgt tgagcgcccc gtgccgtgcc   126240 gccttttttcc gtttccggtc ggactcggag ccttcccgcc gcacggttcg gactcccccc   126300 ccccccgca  acggttttat tttcccgcgt tcgaccccgg cgtgatgtcc gcttttctgt   126360
taaaccgtgc gttcgtctta tagggaagcc atcttaattc tgacatgcgc gaatgcgtct   126420 ttccccttc  caaggcctaa ccccccccgc gctttctcgt ttccgccgtg ggccatttat   126480
cttccccccc gcgtaaacaa ttatccctcc cccgcgcgtc ctacttttct tctgagacct   126540
atcgcctttg gcgattctag tcagattgcc ttttatagtc aagtttcgag cagatcctaa   126600
gcaagcatgc cctgtacccc acccccccttc taaataaatt tccgatccct ggaggtttcc   126660
ggagtatttg tcccaggagc ggggtcctat gcagtaatcg taggtctttc atgtatgggg   126720
gggggggagg gggggggaga tgcgaacgcc cacactggtg ttggttcgtc cgccacggaa   126780
gctggaaccc catcggacgt ctcggcgccc tgtttgcaaa atgtcaggta cttgtagtgc   126840
attccacgta ggaaaatggt cgtgagggga gggggggctg agttttttctg ttatgggtat   126900 cctgaggggt ctacgtgaaa gtgactggcc ttccgttttc ccacagaaac gttgtgtggt   126960
acggtgcacc ctgagagatg atctatattc tcaggaagtt ccgtgcccga aacgctctga   127020
acgataagct tctagattgc atcggggatt cctctgagaa gagcgggtgg ggaaatacat   127080
agccgttaaa gtctcgcggt ccgatatccc cgtttggccg gtggatgagt cgcgatggcc   127140
ggacggggcc ggaaatgcga tccttctttt gcgggctatt tgcgatggaa gggaaaggca   127200
aaccggaaaa cttaaggccg tttggtgtgt ttttcccttc catcgcaggt cgtgccgcag   127260
tacttttgaa tcggagggag acgtcgggcg agtgggaatg ggcatcgcgg ggtcatcctt   127320
tattctggga cgaccgcgaa tctacgtgtc gtctcagtct ggacggccca tggaaaaaaa   127380
aaagagtcga gaggcgtggg ggggggggga ggcctgaacg gccggcgcga taaggggtac   127440
gtggtcaatc ttggcgatta agcctagata ttgcgcgggg agtggggcgg cggtccaatg   127500
cctagaaggg cattattcga aatttggagt cgggctgcgt agcgacgggt ggcgcgcatt   127560 aatacccccta tcttttttttt ttttgcttcg tttcttgtgg ccggcttggg aaatgtcagc   127620
ggaaaacatg cacccgctgt gtgaatgtaa accgcgtaag taaacccgtg ttagactaga   127680
tttcgcaagt tgcgaagggg ggcgattggg gaggaggaag tctgaacgga ggggggagaa   127740 gggaggggg  aggggaagg  ctgaacggag ggggagaag  ggagggggga ggggaaggc   127800 tgaacggagg tgggagaagg gggaagaagg gagggagtgg ggaggggggg gggagaagag   127860
gggaaggggg aaggggggaa gggaggggggg gaagggaggg ggggaaggga gggggggaag   127920 ggagggggggg aaggagggg  gggaagggag ggggaagggga ggaagagggg agggggggg   127980 aagggaggaa gaagggaggg gggaagaagg gagggggggaa gaagggaggg gggaagaagg   128040 gagggggggaa gaagggaggg gggaagaagg gagggggggaa gaagggaggg gggaagaagg   128100 gagggggggaa gaagggaggg gggagaaggg agggggggag aagggagggg ggaagaaggg   128160 agggggggaga aggggccctg gcgagatcgg ctctgaattc ttcgttgtag atagcagacg   128220
accgtaaacc tgaagtacct gtgacttgga cggtgatgag atgtttggcc tagttacagg   128280
```

```
gactggcctt tgttagacac gatggccttt ggaaacgcat ccagtctgtt ttggcatctg   128340
agtggcgcgt agccgttgtc agatgccaga gagactgaaa tgtttctcga ggactctaac   128400
cgtaatctga ataggcccgg accttaatcc caataggccg tgccgggata tcagaggaga   128460
gccgctcgga ccgctgcgat tccatccttc gactagcgac ttgttatggc gggtaatagc   128520
cggacgacgg agtctcggcg gttcgacctt agcgggcccc ggataggttt ctcggttggg   128580
gacaaagggg aggtagaggc gtcggatgcg gggcgatgag cgggtattta ggccacgaga   128640
tcaggtgttg tgaggaaggg gtaacgacgc cgtattgcgg tcggaccgca cgacggcgcg   128700
tcgtccagtc cttcccgggt cccctagagg tgtcacgttc taggacaacc gggacggaca   128760
gggcgacgcg cgcgaaatgc ctcgtatcgc ctgatatgct cggaacgagt cggggaaggg   128820
cgcgaaagcg agagttacta ctcggaactc gggactgttc gtatgttttc tctcaggctg   128880
gcattgcacg tgtcattgcc gttgtgcaat gcctgcggag agaaagacga attgattccc   128940
cgtgccgctc cccgtcgtgt gggacaaggt tgggagggct ctgggcgaag aaccggctga   129000
gcatcggcgc gcgcgccgtg tccccccctcg gcggtgtgca cggagtatc gggcgccgtc   129060
ctcatgcccc cctccgaggg tagcacgcgg tggtcgctgc ggtcttttca aaacaggttc   129120
tgcgaagcag agatgcgtcg gcgcgcgagc gaagcgaacc gagctctgct ccgtccttag   129180
cgtggtgcct gagattttaa cacgtatcgt ctcaagtact gcgcgcaagg accgaggcgg   129240
cgttccaaac gtcggacggg acggcgcggc gtcgtcgcgc gccgcggaaa tcgttacacg   129300
ctccgcttcc tccttcgcgg ggtgcttgag atcaccgaat gacgggatcg agcaccacgc   129360
cgatggacgg agatgcgcg cggtacgttc actgaatcgc aacgaggccg ggccgcgctg   129420
cagggatggc cgcgggtacg cgcgccgagt atgggggggc gcgtgctctc ctacggccga   129480
ctcttgggag cgtgcatcgt tcggggtcg gctgttgggt aagacgtggt ctctttcagg   129540
tcggtgctgt tattttcggc ggggcgcggg acttcgtcct gggccgtctt acacgcacgt   129600
cactctggtc gtatcggtag tcctagtggc ttgcttgtag gctgtccgtc ggaggaagac   129660
agcaccgccg cccagctgcc tgtgcgagcg caggactcgt gtccacgtcc tgcgtgactg   129720
ttcgcccgcc gttcggatgg tccgtggtac ggtgtcctgt gttgtgtgag aggtctccgt   129780
acaccggacc atcgaagggg ggtgggggg atatgcgacc gcagagcgac ttttaggctg   129840
ccgctgtgca gtgttcggtt gggtggggag ggaggaatgt ctgtaaatct tacggcgata   129900
tgctggatcg tgagaggtga gtacgtgtct gtgcgggtag gtgggagcat aaccacaaaa   129960
agactagaat tctgcccgcg gggaaatggc ggtgtgtgta atgcttctgt tccaaacgaa   130020
ggtgcggaat aggagcgaaa tggaccgacc ttcccccgcg acgacgtaag tggcttgtta   130080
cgacctggga ggcctagctg tgttctcgct cgttgccagt ggataggctc gcccttttt   130140
gtaacagatg gcgatggaac agaggttcct atgtgggggg ggggggcgg aaggataac   130200
gtctatcgat cccgaagtct tcgttgcgga tatgagacga tcagtactct caccgatctg   130260
catatcggac gcggagggc gagagagggc ccgtggttag gcgtctgtac tccgaactgc   130320
ttccattttt tcccttacgg tgcctgacgt cgtatttta cggttagatg ccgtcaggga   130380
aagatggag tttgtttgct cgagccctgc cggcggactg caggcgaaga agtagccggg   130440
cgcgaagcgg ctgggaatcg ggtcgcgtgg cgtgtcctcc ttcggacgag tgcttgccgg   130500
ggagtaaccg tcatgcacta ctccgggggt aggacgcgac gtgcgacgcg ctctccggat   130560
cggtgccgtc tgcctgaga tcgagagcat cggacggagc ccagcgccgt cctttgtgct   130620
gtgtgtgaga ggtcgtcatc ccttctcggg caccgcaccg aaggatggag tgggccctcg   130680
```

```
aaacgtcatc cggaacgccg cgggacgaag ccgccccggt aaagtccaga cgcgcgcagt   130740
tccctccttc gtccggtgtt cgaggcgtga gacttttgta ttgccgcgtc gagcaccgtg   130800
ctggaggaag gagatggcgc tctactccgg gacgaaggcg ctgcggagcg catcgcgtgg   130860
tgttagaggt ggatcctgtc atcaagcacc acgtcgatgg acggagactg ggcgcgaagc   130920
gttctgcggg atcgcgtgga acgagggcgc accctcggtc gcgattttct cgacgcctac   130980
cctcggcgtt gttcgtcggc cgagggtagg cgcagaggaa atcgcggtcg ctgtggactc   131040
cggtgtctgg tatcatgtcc ggctcgagtc gtacgtcctg aaatgttgct tctgattccg   131100
acgggtcttc ttcacgtacc tctctatggc tgcatcttta tggccatagt gaggtacgtg   131160
taggctacct gccggagaaa ggcggtcccg acgaatacgc gtcccgtgta gcggtcgccc   131220
gctctgcgat gggctggttc cggcatcaat attgcagggt ctattttgt ggtgggcgtg    131280
accgcgcatc gcatcgaaat aaatctttaa accggccgag ttcattgttg ggctatgctc   131340
ggttttcggg ggggggtgt ggaaggaggg tactaggtta gggttagggt cgggcccttt     131400
gggtcatggt cagggttagg cctttaaggt catgcttagg tctttagggg cagggtcggg   131460
cctttagggt gatggttggg cccttagggg caggggctcg gggtaagggt tagtgccagg   131520
gtcgggtgtc agggtcatgg acagggatat gccgttaagg ttagggttgg ggtccaaagt   131580
taggcgttta ggggtcgggt cgggttcggg gttaggcctt tagggttgt gtctggttta    131640
gggttaggcc tttaggggca gtctcggggt cgtggttagg cgtttagggg tcgggtcgag   131700
ttcggggtta gacctttagg ggtagtgtcg ggtttagggt taggccttta ggggtagtgt   131760
cgttgtcggg gttaggcctg tagggtagt gtcgttgtcg gggttaggcc tttaggggta    131820
gtgtcgggt cggggttagg cctttagggg caagctcagg tgcagggtcg gggttaggcc   131880
tttagggca gggttagggt cagggtcggg gttaggcttc tggatcgggt ctttaggggtc   131940
ggggttaggc ttctggatcg ggtctttagg gtcggggtga ttatgatcag agactaagag   132000
cgcgaaggcc tatcagtgtt aggttctctg ggtcagggtt aaggcctcgg ggttagggtc   132060
tcaagggcgg cgtttggctt aggggccccg ggttaggacc tgtcaaggtc agggttatgg   132120
cctatcagag ttcgtggtca caggtgtaag ggttattagg gcctattaat gtcaggccct   132180
attcgggtta ggctcccacc gagtactaag gttagggtct tgtaagggtt ggggcccgta   132240
agggtagggg ctgggtctg ttacgggcag ggccccccc acacggttcg acctgccacg     132300
cttaggttcc catcccccct cccccccccg agtagggtta gggcctggca ggggtagggt   132360
aggcgcgaag gttgggcccg ttagggctag gagcgaccct cctccccccc cccattattg   132420
ttagtctgtt aaggaggcgt tccccctccc cgtcagggtt agggcctgtt aggggtaggg   132480
taacagggtt aggttagggg ttaaggtctc tcggaattag ggcggggcgt gtaatggtta   132540
tagggtcagg gcgtgccgcg gattgagggt cggggccggc gagggtgtcg ttccggtgtt   132600
tacgaaacg gcggatgtgc gcgcatgcgc tcgcgcgcga ccagacgga cggacgacg     132660
gacgcgtctc gtagcagcat tccatgggcg ttttttattcg tactggccga cggcttcagc   132720
ccgggtcggg gctaggagcg cccgcgtgcg cgatgaagcc gccgtctccc ggcggcgacg   132780
caaaggctgc ggtccgcggt tcccaagcgt cctgcgtccc cgccattgct gcaccgctgc   132840
cggaaaaaga aaacatcct gtacgcactt cccgagcgcc gggacagagg cggtctccgc   132900
cagccccccg cgaaattcca aaagccggt gtggcggact cggccatgga atctacgggg   132960
ggggggttga gggggggatg cggcgctgta gtcgccggat gcagtcagga cacggaaatt   133020
```

```
aagcgcgtcc ggacgtgccg gacaatcgcg tacgcggaag tgcttgcacg ggaagtaaac   133080
agtggaccgc ggcttacctt cccagcagga gtacggtgtt cgcggagaaa actgtaaggc   133140
gggagcccat cgtcgtgcgc tcccggtcct ctcggaatcg gctgcgagtc tcaaaaaaac   133200
aggaaagggg atcggcctca caaaaccact tcctcattcg tgactgcgcg tagcctccgt   133260
tcttgaaagc ggttggcgtt cgcacagacc tgagtcgaca ccgcctacct gttgtttact   133320
ttcaatgtag tgcgttgcac agagacgctc ggggccgggt acaagttgcc cgggtccgcg   133380
ggtctgaagc acgcactctt ccgttgaagg acggggtggg aaagcggatt attggacccc   133440
gcgatagggt ctgttagggt cggggggttcg gcctgtcatc acggtcgggg ttagggcctg   133500
tcttattcgt tttagtgcct gttagggcca cattaagggc ttgggccagg gccgtttacg   133560
gtggcggtta gggcctctcg gggtcggcgt caggactgtt agggtcactg ttatggcctt   133620
tcagggttag ggtaatagtc catagtcggg gtcaggacat attaagggta gcggctttgg   133680
cggttacggc atgtagggct aggaccttt aatgtaacgg gcagcgttgg tgtcatgtat   133740
cacggtcggg gtgactgtta ggcctcgccg ggcctcattt cacggtcggg gctatggcag   133800
ggtcagagtc tgtggtggtg tgcttcggtc acccactgtg tccgcgcaat gctgcgcgtt   133860
cattctgcct gtagccgaca gttcgcgggg tgcggcagcc cgcgggctga gtgcacctgt   133920
ggcggcggga ggctgcggcc cagccgcgtt aattgttgtg ctatgttcct tttttggggg   133980
gggggtgaaa tgcaggggggg gatattaagt tggttagggt tagggttagg gttagggtta   134040
gggttagggt tagggttagg gttagggtta gggttagggt tagggttagg gttagggtta   134100
ggccgttagg gttagggtta ggcctttagg gttagggtta ggcctttagg gttagggtta   134160
gggtgaattt ttttattca gttcgccgcc gcgagagttt tggtatgacg tttggtggtg   134220
gccagggtcc gccgcgcgca tgctccctac ggtccgccgc gcgcatgctc cctacggtcc   134280
gccgcgcgca tgctcgctag ggtccgccgc gcgcatgctc gcaaatgtcg actgcgcgca   134340
tgcgcgcacg ggtccgctac gcatttccgg gcggcctagc gagcgcccgc gcggccggcg   134400
ggcatgtccg gcggggatgc agcgtgcggc tcggcctact ggccgcgcgg agccgccggc   134460
ggtcggcggt ctaacgcttg gagtcgcgcc cccccccccc ccccgatcag acgcaaggct   134520
ttttcaggcg cccgtctcgg tcacttagga cagccgcggt tcgtctcgaa aaggtctgc    134580 ggcgtgggtg gtgggggaaa gggggagggg cagaacagtc cagagaccgt cacgggcgaa   134640 cgattgggt ccgcgggggg cgcgaggtgg actcggtagc cgccgcggtc cgatccggaa    134700
accgtgtccc cctgcgcctt tcttcgggcc cgctcgccga cgcgaatggg gtgggggagg   134760
ggggtgcgcg ggcgaacaat tagggaccgc ggagtgcgac agcgggcctc ggtagccgcc   134820
gcggtccgat ccgaaacccc tgtcccgctg ccgctttcct cgggcccgct cgccgactcg   134880
atcagaaacc cgtctccccc gccatttta tgtctcccgt atgcgcgctc gttcccgcca   134940
ctttctggtg ccgctgcgga agaggatagc cgggcgggcg agcgggcgag cgcgccgcgg   135000
accgaaccgc tccgcgggct gcgcagggga ccgcagagat tgctccccgcg cgagggatcg   135060 atccgcgggg tagagggctc tccgcgaaca gcgtaagaac agaggtgtcc ccgcgcgccg   135120
ctgcctccgg acgcacccc cgccccccc ccccgccca cccagggcga ccgaaacccc    135180
ctgccgccgc cggcaagagt cggtcagaga gcgcgaatga tgtctgtcgc atctggtccc   135240
ttcattcatt cattcattca ttcattcatt cattcattca tttatttatt tatttattcg   135300
ccagcgctac atctcaatcc cagctaccgt taacccctacc accacccccc cccccccccc   135360
cgaccttgag cggttctatc cgttcgagat gaccttcacg gagcggagct cgttgcagga   135420
```

```
tccggaggag cggtttccgc agccctaggg atcgcgattc ttcggtacag ccgcgcaggc   135480
cttcggaaag gacgcggcga tctgagtcca gggggccacg gctccgcgcc cgcggtttcg   135540
gttcccgggc agaccgccgt cggggacccc cgggagcttt cggagaaggt agggcggagt   135600
tctgaggctt gagggacaat gagcggcggg tcggttcggt tcacgtcgcc gtcgggatcc   135660
ggtgcggccc cgtccgactt tgccgtggga ggctccattg tccgtcccct ccccccttg    135720 gcggagcgca gggcgaaagg accccgcttt cgccgccgct cctcctcgta caggccacgg   135780
gtcttctagg cgctgtcgcc gcgcggtctt cctttacga aactttctct accgcgtttg    135840
cgggagaaca ctacggcgaa cgcgcccgcg ggctcgccgg cgcttctgcg ctactgaatg   135900
gccgggcgaa ggtgcgcgcg gggcattcgt tctgggaaca ggtatagagg cgtggccacg   135960
gccgaccaat ggaccaggcg gtgacgcatc cgcacggcag accgcggccc gtacgactaa   136020
cagcgcggaa cgcaaccgag ccgcggggtt ccgctggccc cctaatttat ttgtccgtct   136080
ccccgctcgc ggatgatatg tcgtacccgc ggggctgctt gtccagatag cccttaaaag   136140
tccgccgagt gactccccc gcccccccc cccgaccct gacttagcct tcactcgccg     136200
aagacttcag agtcgctgag gccaagggc gaaggaggac cgggcagcgt cggaggatga     136260
attatcctct gtcgcgcgcc ctgttcctcc tggacggtgg tctccggcgg accgccgtcc     136320
ccttccagcc acactacaga cgagctacgt aggtgagcga gcatctcgcg ggccaataaa     136380
ctgcacgtcg cttcgggaac gtgaacgacg actggctggg cgtgcggatc ggggggagg     136440 actacggagc ggcaaacgtc gcagacggtc ctatttaaga aatcggggga aactatggcg     136500 ttcttttgg gctccaagac gtacacggga cgcagcgggg cgtacagtcc ccacttgaga      136560
gcggctcggt gggagtgcga ctctccagct aaaaagtcgg ggccgggcgg cctctggcgc     136620
ccggccacaa gggcgaggga ggctgcgagg taggagagag cggtcattgg gaccgtcgcg     136680
acgcggtcca gtcgcgtcgc gaccttgtat cggacgttgc ttccgcagca cagactgatg     136740
tcgccggccg cggggttttc gcggcgaaag tgcgtttcca gctcacgtag gaccacgggg     136800
cccagcacgt cccgcgaggt tatgaccgtc gtagctagat cggggtggcc aggccatcgg     136860
acggagcatt ggctgcgggg cgagacgtg cacctgacgt agcggacggc ttcttccacg       136920
aggcgcgggc cgttctccgg gcgatcttga tcctctagcg tgtccaggac cacgagcctt      136980
ttttctcgtt tcaaacagag gcgttgcagg tgttccagga cgcccgcaaa accgaggtcc     137040 tgagggaca ggaacatgac gccggccgcg gtcagcgccg aaacgtccgg cgccgctctc       137100
caccggcccg cccaggcggc gctctccggt aggcagaggc ggttggcgag tgcggcgagc     137160
aggaaagaga gtcctccccg gttcgggtcg aaccggggtc ccccgggggg cgagccgggc    137220
gccggtacgc aaaacaggtg ctcgcctggg ttggccgtgt acaggatgac gagagcgaca    137280
tcttcaggcg aagcctgctg atgccgcatc caagcggtgc gcgctctgag agagacgacg    137340
gccgtgcggc acaacactcc ctcggacgca gcagtgtctg ggcttctgct gacgtgcgag    137400
ggagtgctcg ccacgcgagc gatctccgcc atggcctccg gagaacgcgc caacggctga    137460
cgccacagag tcggtatttg gcgaagctg tcagctcgt cgactccttc gcctggacaa       137520
taggcgtcga ggtgcggggg gccggcatag ccagcaatcg gagttccaat gggggcttc     137580 ctaaaggcgg cgccacgatg ccgtcgatcg cctaacgaca gggaaccgtc cataatgcgc    137640
gcggggtcgc gccacggaaa gcaacgtggg cgcttgggcg ggaaaggccc ggcgtcgcgg    137700
cacgcttcag gggggtggg gggccttgtg cagctggcga caggcggagg tccggcgcct    137760
```

```
gtccgggacc ttcccaaacg cggacgcggg ttctcgacgg cgttgtccgc gccgtcgaga    137820
accgccgcgg gagctgattt tctcttcctt gactcggctg acgtttgggc gcaaagggcc    137880
cgcacgggct cgggagaact tgcggggccg gggtcgtaac aaggctccgc ggagcgcgac    137940
cggccctcgg acgttccgga agaggccgcg tcggcgtccg cgagaaggcg cgccacgcgt    138000
tgcagccgtc gggccttctc gcgggatcgt accggttcgc ccctcgaccc acattcgcgc    138060
aggagcacgg aagtaatgtc cctcgaccca gggcatcgcc aaggccgagc ggggtctttg    138120
ctaagcaacg ggccgatcgc ttccgttatc agggccaccg cattagccgc gagagttcgc    138180
tcctggcgcc cccgaggagc cgaaccgttc gcgtaggccg cgtacacggc gctcctgaga    138240
tcaagcaggt ctcggagcca cgacccgagc agagcccggc attttttccca ctgttcgtgg    138300
ccggcgggtc gagggaaggg cccgtcctcg caagacgaca gcatttccgc gaccgcgccc    138360
ggaccgtcgg gtccgcgcag aagcgccgcc acgaccccct cgcactccag cgcgcaagcg    138420
tccaccagct cgttcagcgg ccgggtagac gcgaaaccgt ccccggcagg gatgtccgga    138480
cgcgcgggcg cgaccaatcg gtattcgggg acgtccagca ggccctcctc tagcgcggaa    138540
ttgaaggccg cgacgccccg cgcacgcgg tcgtggatcg tggacacgtc tattaccggg    138600
atgagcccgg ccgccgtact ttgggcagtg acgggtgccc gatttgaaat aggcgatgcc    138660
gaggggcgtc gcatttcggc gctggctgca gacgccatag gcgcgtaggc tttcctgagg    138720
gagcggaaca tgaactcttt ctgatctttg cagtacctgc gagtcataga cacgctggcg    138780
gcgatgtgcg gtagcgccca aagcagattt cgcttcttca tggcgctggc tatgtggggt    138840
atgcatttgt tgaccgtccc cgtgacggcc gcgcccggcg aactgtgcga gctctgaaac    138900
ttcgtgacat agatgtgatt gagcgctgcg tcggtgggcg agagcttgcc gtggtgtgcc    138960
cagttcaggg ggttcgcctt cacgtctttg ttaagcatgg cgcttacgag cgcctcgtac    139020
tgtttggcgc agttccccat ttcctccacg tacaccggga ggggaccggg agtagagagg    139080
aatctaacgg cggcctgctc tacttcaggg atgccccgga gcgcctgtcg gtgtccgccg    139140
agaggcccga accagcaccg gccggccggc ggggagggaa tttgccacca cacctcttgg    139200
tcgaggtcat ccggcggtgg cggcgcagca gtttccgagg acggtgatgg cgcccgccgg    139260
ccgcggccgc gccgtcctcc gcggccgcgg ccgcggcctc tggcagcgca ttgaggcgct    139320
cctgcctcgc gggtcggcga cctggatgag gtgcgcgaag aagggcggc agacgactgt    139380
tccgatgaag agggcgcgga cgacgaagag gacgaggaag aggaagcgga cgaggaggag    139440
gaagatctgg agcgacaccc gagcgaaggg tacgaggccg gggaggccg gggtagggga    139500
tgggaagcgc gggtcgccgg cgtgccaacc tcctgttgta atgcctgttt tagaacagca    139560
ggtggagctg ttgtgtgcga accatcggag cccgatcccg gctggactct gcggtaacgt    139620
tcctgcgtac cggtggggct gctaacgagg cccggcctcg gagacggccc gttccagtct    139680
ggaacgggaa gggggggaaa catgggcgct ccgtcgtccc tcgcgccgga cggctgacgg    139740
aggtgtctga atcggcgtag cgccgcgcg gtgacgcgg cgcgccaatc aagtatggct    139800
ttgtacagag gtctgacccg ttttttcgatg gccggaccgc aggcggggaa ccccagttcg    139860
accatagcga cggcgagctg ctgcaccatg aatccgtagg cgcgtgcggg acgagagccg    139920
tggggcgtcc cgccgggttc cggatttccg ttccgcagcg ccaacttcga ttccctgacg    139980
gccgcggaaa gcgcgggagg gagcgcggtg gcgggcgggg ggggcatttc gaaaggcacc    140040
tcgaagccgg gccgcacgtc ggggccgacg atgtagtcgt ctgggccag cagtaacccc    140100
cgacgcactt tgaaaaaaag acacctgtaa tgtagcatct tgaaatcgtt ccaggtgagc    140160
```

```
ccggtccagg ggttcgggct gccttcccgg ccttccaccc accgaatctc ctcgagcaga   140220
ggacagaagt tggaggcata aagccgccg cggcgccggc tgcagtcgag accgcggggg   140280
gattcagagg gcggcgttcc gttccagtcc tcgtccaagg gagtacccgc gcccggcggc   140340
ggcgcgcacc ccgaaagca cggcagacca cgagccgctt gtaattgata ggaaaagtcg   140400
cgtgtcagaa cgtgggccat gtactggacg cgcctgacgc agcggagtcg gtccagccag   140460
cggtatgaaa ggcggggaac cttcgacacg aaatcggggg tgacttgaag gccgaggaag   140520
cgaaggagcg ccgacaaaat gtaagcgtac gtcggggtgc gcggagccgg tctcgggagc   140580
cgtgttaccg cttcccagat gcgcgttggc agcactatcg gggcggggag ggggagcggg   140640
cactcgttct gcgggcccca tccgcaaccc tgcgattcta acacgctttc cccgtcctcg   140700
gacggcgaca tatcgtccag ggtcgagaga acgaggcgcg cgcatcgaga aaacaaccac   140760
atcttgcagg ccgcccagtc attccccagc tcgttcggag ggcacgggaa gaccggctcc   140820
tggggcagcg ggcgacccct tcgcgcaacg cattcgaacg gccggtagtc gctgtcgagt   140880
aaaggggcct ctctcggcag ttcgatagac cccggtgagg tccgcagagg gctgccgcgc   140940
ggagtaggta agatttctct gagtaccgct tccctcgcca gccgatccca gtaggaaggg   141000
caccggcgag cgtccgacaa cgcgaggaga aaaaccttag ggttgtctcc ggaggacggc   141060
tccgtcgcgc cgtcgcgagc cccgcgcgc cacaacatag cgtggctccc cggctggcgg   141120
gccaccaact cgagctcttc tcgaggggg gatgggatcc tggcggatgc ggataggcgg   141180
cagacgtact ggaagcccgc gcccctggta cgggggcccc cgccctcgga aacgctcgat   141240
ttacggcggg ctgggactcg gtcgctccgg aggggagcgg gtgcgaggcg ggggctgaa   141300 ggggacaacg gaggggaagg acgctgacaa gaagcagaga gggctggggg gtccgggaa   141360 agaggcctgt cgtggagagg ggttggcgga ggtgggtag acgccggagg cgagtcaagc   141420
ggtagagacg cagacgggga ggatgtctgc gtagagggag gggagtaga cggcagaggc   141480 gtgggggag gggaaccgtg cggaggggg gtatgcggag gtggcgtagg aggagggggg   141540
ctaaggggag gtggcgtagg aggaggggg ctaaggggg gtggcgtagg aggaggggg   141600 ctaaggggag gtggtgtagg gggagtgggt gaatggtgtt gagcgaacgg tcccggcgtc   141660
agcggagaaa atgtccatgg gaagttcacg ataggttcgg ggggggtgg gggggcacg   141720 cccgagggag ggggagagt ttcgacacag acggcgagcg gcgtgcaggc gccggtgggc   141780
ttacagggcg cgtcagatac gcagcggacg gggtcgtttg atttgcgggg atccataggg   141840
ctcggttcgc cccgttccga acccgcgggg actagatcgc cgactgtctt ttgccaagaa   141900
caggaccgcg gggccgccgc ggccgttttcg tttccacaga cgtccacgat gtccgcggtg   141960
gaactgacga cctcgccagg agaccctga tgcgcgccgt cgggggttc ggcggaacgg   142020 agacccgtat ccgaacctc cgaaacggca ccctcaatgc cgaaaggggc tcgtgcgccg   142080
gcaaggctgc ccgcgacggg agccgcgcgg cagggatt tagaccgtgg cgggacggc   142140 tgccgaccgg gcgtcggggg cacggccacg ctcggtgtat tcaagcacac gtcctggtac   142200
ggatctcccg gggtggcggg tggctgcgga gaaaatccgc cgttgtcggc taacatctct   142260
aacaggctgt agaaatcggg cggttctcc atgtccgagc aatgggggaa acgcgcgccg   142320
gtccaaccgt ggcgacgccg gcagcactgg cgatccgctc cttacagggg cgtaaatgca   142380
gggtttaatc gggcggatgg ggaccagcgc agggagcgcg gaaggagtcc tgctctgaaa   142440
aaaatgaggg ggaaccgtga gaaagcgttc cccgcagttc gcatcgcttc ttgccccccg   142500
```

```
cccaacacca ccaccacccc gcccctacac acaccacagc cacggctccg gcagtgccgg   142560
cctggctact cctttaatca ttaactccca tcaacgcgat ttgatccccg ggctgctctc   142620
cgaatcagcc gagcccccata ggtaaacatt ccgccgccca caacgtttct tgtcaaacaa   142680
acgcttatcg gccggattgc gaaacgagca ggttttgcca ttagatatgc tgcggtcagc   142740
gctgctaggc tccccggggg caaacattct cctagcgacg ccgaggtaag gagacattaa   142800
ccctcgacac gctcctgcga gcgactgtgc ggttcgtgcg gtttgtttct ctcgctcccg   142860
acgttcctac cgccctcggg agagtgctcg cccgggggct agaacccgaa gcggaccggc   142920
ccttgagcat cgagacgctt aggctcgggc gaaccgcccg gctctaaaaa gtcaagcgcg   142980
cgcgtgtatt tcttttttttt ggggggggggg ggggggggtgg tggtggtggt tggagacaga   143040
agaggagaga aacggagggg gtggtggtgg ttggagacag aagaggagag aaacggaggg   143100
ggtggtggtg gttggagaca aagaggagag aaacggagg gggcggtggt ggttggagac   143160
agaagaggag agaaatggag ggggtggtgg tgggagagaa ataccgacgg ccggacagag   143220
cgaattatta agcacccaac gctcacgcca acacgtccca cctctttccc cgacccgcgc   143280
cgcccccccc cccccgata ttcgcgtcgg gggtcaggga caaagagagg cgacggggca   143340
ataggcgctg cgtgggggag ggggggccgg ccctacttgc ccctaacgca ccggcgtcca   143400
cgcgatcgcg cgacccgaca gcacctacca ggagcgcggt gccggcggca gcccccttctc   143460 gattcggctc ggagctagcc gggagagacg gccgcggtca cgtctcccctt tccgaacgcc   143520 tagcgatata gttacagacc gaagcgagcc gtgtcacacc aagtcactta gccgcaattc   143580
tgttcccctt cccccacaca cataacagga gacatagcgc atgggaggggg ctttccttat   143640 ctctcgagca gaggtcgccg acacgtcaac gaagggcggt acgtgtgtgg taagtagcag   143700
agatcggagt tggtcccgat ttactaacat ctaataccga tcgttcatag ccgcctggaa   143760
tttgcgggca taacccgcgg ataacggtac tggtcaggga agcaacgcag cgcagacacg   143820
acccgatata aaagactgca aacgaggttt tgtaggggta atgagatgat gtggaaaaga   143880
aatgggtcag ggggcgctgt ttgttgtgac acatttgcgc ctagtgtggg accggggcgt   143940
gcggcgagca cccagcgcgg aacgactcgc aagctgacgg tgcagggcta actcgcatta   144000
gaggaagtgt ttgctgattt cttcgtagac gctctgcgcc gagagcgtct cctcgtttaa   144060
cctttatgaa gaaggaagtc gctcccatct ggtgcggaac gatgggtac ttctctccgt   144120 aatgggaac cgaaaactga accaaataca gaaattagaa gaggaacatc ggcttttccc   144180
gttatgtaaa aggaccatgg ggtcgcgtcc gggaggaggg ggagagtttg gggaactcgg   144240
ggccctaaga gcgctacacc agactcttca taataccata tgtcaaggca gttgcggtaa   144300
atatagcgac gaccgcaacc gaacgggtat ttcttctaca ggttagaacc atcccatgac   144360
ccatgcgaaa agtgttacgg cacagagaag gccagaggga aactccgcgt ccggcaaagc   144420
gcacggtaag acactcgcga ggttgtgcaa cagcgcatcg ccccgggtag aaccgacagg   144480
tttatcttca gatggctatc gcggacaact cgtcgtcggg gctgggggag gggggggtat   144540
gtgtcagcca cttccatcct cgtcgctgtc gtcgctcgca aatgtgggct atcaacgctt   144600
ctcgattaaa aaagacaaaa ctagaggggc atccgcaata aacgacaatg tttcatcaca   144660
aaacaaatgg cgtggtctat tcttttttcgt ttgcctctga tcctgggcgg tccgtactgc   144720
ggggtgatag ataaaagaag acaacagcag ggaatcgagg tggcgagctc acaaattgcg   144780
aagctcagcc tatgccggcg atgatggccg atgagggaat gtaggaagag agggcgtatc   144840
cccgattgac gatggtgcga ccaccaaccg agtccgtgta ctcctatctt ccattctcac   144900
```

```
gacaccggac atgagaaacg atgcgcggag caagtcgggg ggggggggggg gaatgaatcc    144960 acggcacgcg cagcgcttcc tttacattgc accacgtgac catattccca taatgacggc    145020
aggcgttatc tatataatgc caggcagaag tcttacttcc gctcgcgatc actattgtcg    145080
tcacacgggg agtctgacta ggcggtatgg acggcgtacg agacagagta ttacctgata    145140
cgtcaacgga caacgagatc taccttgggt cggggtatcc ggtgcaatta catgatgaat    145200
atgggcaaat ttctctaggc tcgccggtcg aaagcagcaa tagcacagga aattttttgtg   145260 ctccgccatg gatgccggat atccctcgtt taagtaatga tacatgtaag atatttcggt    145320
gtctgactag ctgtcgtctc aattgcgcac cgttccacga tgctctcaga gagccttgc     145380 tcgatatgca catgttaggt cgaatgggat tccgtctacg acagcacgaa tgggaacgta    145440
tcatgcagtt gactccagat gagagcatta acctgcggag aactctcctg gaagccgacg    145500
agcggagcag tcattgtatg ccgaacgtgt acgcatctga cattagtaat tccctcgaag    145560
ctggtacaat gcaagttacc tccagctcca atatccgggg tatcagcaac aagtccgtaa    145620
atcactgatt acaaaactca ctgatgtaga cgaacaataa atgtcctatt gccagtaatc    145680
actttgcctg ttatttattg aatgagtatg tcgcgttaat taagtaacgc agtgtgggcg    145740
tgacttgtac catatagatt tctattgact acaacgttat ccgacctgac atttgggagc    145800
tgggtgtcta tagagacaga aggtgcacca ccgcgcaaga taatattgtg atatgtccag    145860
tgaggtatgt gaagtaccat caccgcaaaa gcaaatgggc ctgtggtcgg tgtgccgcaa    145920
acttcgcaga acatctcatc tgtggccgga tcctgcgaat gagaaagtat acggtatact    145980
ttctgctggt ggagtacata tatcatccct gccaaagtct gtacgcggtt tggcccgaac    146040
tgtattgacc gctgccatgg tctctttcgc ggcaatgaaa gctggtatgc cgccatccat    146100
tcacctgtgg cgtgagataa tggatttaac tgacgcaaca atccgccgcg aacaacggtc    146160
cacatcaaat ttctacgtag ccggttcgtt gaggaaaata gtaagtgttg cattgcgaaa    146220
ttataagcat gcacctgaaa cgcatggaga aatggatagc cgtctgactg ctattatgta    146280
ttggtgttgt cttgggcatc ctggctgctg tattgtttcc catttatatg aggaaaacag    146340
tgatctgatt aagttgttgg gaatggcaac aggctgtgga gaaagcccgc ttactgaagt    146400
agagtcttat tggaagcctt tatgccgggc tgtagcagcg aaggggaatg cattaattta    146460
cgacgacgtc gaagtggcac attacctgat caacgtgcga caatcgtctg aatcttcgcc    146520
tccagacgat ggggaagaca ttgagtaaat ttgcgcgaat gacagggctc ggaaacaatg    146580
tatagagttt tgcaaataaa cactttattg acttaccaga agttattgca tcttattgta    146640
atctgcgtca atattctcta acttcagtta aaacgtagca atcgcagagg ggcaaactag    146700
agaaaaatgg acccgcgacc taaatctcgt ctaaaacgct ccagtgcttt acagttcgat    146760
aatctggacc tggggacgcg tataggatcg ttcctccaca tgcgctgctg tcggtatctc    146820
gaatccccgg tattcagttg aatcgttggc ggagtgtcct cctggactct gcaatgttcc    146880
ctagccgtct tcactatctc gtgcaaggct ctataataca gttcctctgc agaccgtcg    146940 ttgctcttcc cttctgcgtc gttagttatt tctgtaggct ccagacgatt tgcctgcatt    147000
tgtgcgcaac ataatctgat tgcattccct atctcgtctt ccggtaatcc cataggtgtt    147060
cggtattcgc agataggtag agaaagcacc actgcaaatc gtgcaatttc cattgcccca    147120
accaatattt ttttttaagaa cggcatcgcc gttaatgtac ctcgggcatt gtgacgatcg    147180
aaacccttat ggatgcctaa agagagcatt gcggtccagt tctccaggtg aaaagagaat    147240
```

```
agcgcgggta gaaacgggcc gattagtttt atcttcgccg cgtccctaat atcccaagtt   147300
ctgcagtata acttccatcg tccgttttcg acaaggtccg gcgcgacata gtttgaaatg   147360
tcatctatca gaaacatctc gcccatcgta gaaaaaaacc tgtacgcaga ccataaaacc   147420
attcggtacc acatatcctt gtgtatatca acgatatgt tggttatgtc gttggcggat    147480
gttgtatgaa atagagctaa gcgttctctg gattccacgc actgaacgat tccgttagtc   147540
aattcatctg ctaacatagg ccaaaagttt attcgtgtta cttttctcgg cggtttggca   147600 aaacgcccc ttggcacatc catgtcatta aatacagcgg cataactcct actcatgtgt    147660
tccatagccc aggtttctgt tcggtctgct actacgatca gatcagtggc gcgatcagat   147720
gcgtgggatg aatgaagtgt atccgaaagc agttttgaga tatacgctaa actgtacgac   147780
gattgtggca ctaaacgaag ctttgcgcga ccccatccc acgcggagtc tgtgcaaggt    147840
taatgaccct cgcagttcat tcggaagtta taactgccgc cttcgcacat ttctttttgt   147900
cctgttttgt attgccataa cagataggaa ttgaaacctg atcctcctgt ttttgcagc    147960 atggccagca acagaatact ttgtcggatc gactacttgc gcgagatggt tccgttcttg   148020
gaggtttcgg cgggtcgggt ggagaaccta ttattttata cacacacgtc ataccgttgt   148080
cgcgaaaatg ttctttgtct tctgccgtct cgaacgtcgg ttcccacgta gacgttagga   148140
gcgttggaat ggtatcagga agagcccacg gcatgccgga ccaagtaccc gctactttga   148200
ccgcgagcag tctcttcggt aatgggatgt attccagagc agcgcggcag agatcagcgg   148260
cccccactat ccacagactg tatgaagtgt tttctgaaac atcggactcc aacatcaaat   148320
atccagacat aacatcttgc cattcggaag cacatccgcc gacatcttca aatagcctaa   148380
ctataaacga gtctctagtt cctgctaacc cagtacctcg aatgccagtc ccatccggtg   148440
ggttcgtcct gataatcggt ctctgacgcc gaggaagaac taaaggggg ctggaaaagc    148500 ggaacagatc tgcagaccga acgactacag acacgcccac atcatcatgt atctgttcca   148560
tgcattgctt tatgagaaaa atccataagg ccgaggcggc atctctagat ctcccgggga   148620
gtctctcgca ctcatctagg agagtgacga cagttatcat agacacgccc atttgtgcac   148680
caaacgaaaa gttcctgtac tggtggagcg tcggcgcggg aatcggtccg tgctctgaaa   148740
ccagtgtcta gacagaagac catccggtaa attctggtgt atgaactgac ggtctccaga   148800
cgaacgtcga agacattaac gatggaaact aacgagcttt cttcaaaagt gtctgattac   148860
aacgctaata gaccttacga aactatacgc agcgatacca gtgacacaga tccgtcggtg   148920
tcgtgtggga ctctctccga caaagacggg gacgacgaag aatctataga tttaagcaag   148980
gtcccgaatg caacgaatgt cggcgcaggt gaagattgca catcccccaa cgacgggcgc   149040
acagagttat gccgtacgac ttcggttacc ggaccggcct cggtcgtgag gatgcaatac   149100
aatattattt caccattacc gcccagctcg gagggccgcg tattcgtctg tacccgttgg   149160
gacgatgtca gcaataagaa ggtgattgtt aaagtcgtca ccggaggtag agacccaggg   149220
agagaaatcg agatcgtaaa gacactttcc cattgcgcga ttatacagct aattcatgca   149280
tatagttgga aatctacggt atgtatggta atgcctaagt ataaatgcga tctgtttacc   149340
tatgtggata gaaaggaatc aataccttg aaagacgtta ttgtcattga acgacgtttg    149400
ttggaagctc tggtttatct gcacggcaaa ggtgtaattc atcgcgatgt aaagacagaa   149460
aacatatttc tggactaccc cggaaacgct gttttgggag atttcggggc agcgtgcaaa   149520
ttagacatgc atgataatag tcccaagtgc tatggttggg ccggaactat ggaaacaaat   149580
tccccagagc tcctcgcgct agatccttat tgtgccaaaa cagatatctg gagtgccggg   149640
```

```
cttgtgttat tcgagatgtc tgccaaaaaa aggacactgt ttggaaaaca agtaaaaacc 149700
tccagttctc aactgagagc attgattaga tgtttgcaga tccacgcttt agaatttcca 149760
caggatgaat ccacgactct atgcaaacaa ttcaaacaat atgcaatccc actgcggcct 149820
cctttctcca ttccagaagt tgtaagaaga aatatcccgt caatggatgt tgagtataca 149880
attgcaaaaa tgctcacatt tgatcaagag tttagacctt cggctcaaga catcctggcg 149940
ttccccctct ttgtgaaaga agccccccaa aatctccagg ccctatttgt tccctgagtg 150000
ctaacagcac atgcaatcga atcccattag aagccgtgct atttaaattt taatgtcgca 150060
tagaaatata tggtatacgg cgccacgcag agctctatac ggcttccact ttagaagcca 150120
atgttttgtc atcagtgagt aatacgactt gggttacaag agacaaacat aatacgtcga 150180
acttaacaaa tgccggaatc tgtacccgtt ttctcatcgc cgctgctgca tattaacggc 150240
aggaagccct taggtatagc ctgagcgttt ttacgtccac tgcattgcca tattcgctac 150300
atcacgtatt tctacaagaa gatgagagtg tctattcaac gggcaatttt cctgatatac 150360
atatgtacag tctccatgtc cagctcggaa aaaactcgta atgaggacgc ctctcgtatt 150420
agttcttcgg acacctttcg cctaaaagaa ttccccgtat ctgcgatacc atcgcctcta 150480
ctcgacgtag tcgataactc gtacccgacg aaacacgtca tatacactga cacttgcggt 150540
ttcgctgttt tgaatcccac cggcgatccg aaatacacaa tcctcagctt acttttgatg 150600
ggacgacata gatacgatgc tactgttgca tggtacgtcc tgggtaagac atgtgctaga 150660
ccaatttatc tacgcgtatt ttcagattgt catacaaatg aacaatttgg gatgtgcact 150720
tcaaaatctc cgggatggtg ggatattggt tatgcaaaaa ctgcgtatat tgaccgtgat 150780
gagttgacgt tagtattagc tgctcctgct ccagagttgg gtgggctata cacacgttta 150840
atcataatta atggcgagcc aatatctagt gacatacttc taacgattga ggggacgtgt 150900 agttttcgc tcaaaggccc aatcgacgac cggctctgta aaccattcaa ctttttttgta 150960 aatgggacca cgcttgacat aggcatgttt cctgcacgaa ctccccgacc ccatgaagaa 151020
aacgtaaaac agtggcttac gcgccaaagc ggaaaactgg atacggttat tggtgaagcg 151080
tccatgcgtc atgcagcaga tttgccacgt gcttttagag attcgtatt gaaatcgcct 151140 aaagataacc tacctgacga ccctggaagg cctacagttt caattagcag tatccatgcc 151200
aatgatgcct atgtaggaag cacctctctg tatgaccaat cgctacgcgc aactgaagag 151260
ccagtattgc catctgtaga tgaggcccgt cctgcgcttt atacaaatgc agagaggaac 151320
cccaggatgc aactaataat ttctgccatt gttgttgcta gtactgtaat ggtcgcactg 151380
attgggataa gtgcatgtat tgttaggaaa tgctgtaaaa ggaaaatcaa aagagggata 151440
cctcaacgcc cgtccaggaa agtgtattcc cgcctatgat tacgtatgga cttgggcgtg 151500
tcgacacaga cacaaaaccc agtttgcggc cttcttgaaa ctatcgatgt aatgtctctg 151560
tcgaacgggc acatggcaca ttggagtgcg gcgtccaaaa aacatatact atgtttccta 151620
tttcttgtca cggggagcca ttctctaatc ttcaccggga cttcgttatc cgcatcgacg 151680
gatcaatcgg ccatcgttgc cttctgtgga ctcgacaaaa cggtgaatgt ttacggtaga 151740
cttttcttct tgggtgactc ggttggtgtt atttcttacg atggaacgac agaaattctg 151800
agatggaacg aaaaactaaa gtgtttctcg gtcatgtatg ccgcgttgta tacggactgc 151860 cccccttgcag ggtctgcttt atttagagga tgtagaagcg cggtggtgta tgctaccct 151920 catgacaggg tgaagccggt ttccgaaaaa ggattactgc tgtgcatttc agatcccaga 151980
```

```
atttctgaca ccggtacata ttacatccgc gtgtccctcg ccggcagaaa tgtcagtgat    152040
attttcagaa ttgacgtcgt tgtgacgagt agcagtattc atacatgcgg ccatgcggat    152100
aaaggtatac aggaatgtat taggtatgcc gaccgtgtgt cattcgagaa ctatctaatt    152160
ggacacgtgg gacaattgct gcctgtcgac tcagagctac acgccgtgta taatgtcact    152220
cccagatcgg tcgttgggac aaatactgat accatgtcag cttttactaa ttcgacaaca    152280
aaatctgctt cgacgaattt aatcgctatg aagactactc atccaccaag tacgcggcgc    152340
tgtaacttga ggcgtgccct tccaaaatta atatacatgt cttcattggc aggcctgtgc    152400
cttctcgtac tattaattgg tagagcggtt gtaaagtgca aaacgcccaa acccaaaatc    152460
tacaagggcg actccacctc tgacggcatc tcgcttatca attctgcagt aaacgacgca    152520
tttgggtgta atcctgcaaa agaggttgat ccctcgaata tttctgaagg cgagaagctg    152580
gaaaacatgc agaaaacgac cggaaatgta gaaaagtaac cgtgcgagtt atgagctgga    152640
atggacgtta catgcgggaa gaagtagggc gtaactaagt acatgttaga aggggagggg    152700
cgggttttga cttttaaaag cacaccgcgc gaccacggcg gaattatgct tgatataccc    152760
gggctacgtg gcataatgtc ttgtccgcga atgcccctttt tcctaatggc ggcgatgatg    152820
tgcagtgcaa ccaccgtaaa tcgtatacta attccccagg ggaattcggc aacacttaag    152880
atctccagat atccgccggt tgtagatggg actccatata cagagacgtg gacatggatc    152940
tctaatcgct gcaacgaaac ggcgactgga tacgtatgtt tggacagcgt taattgtttt    153000
catgacttaa tcgttaaaat ggcctgttgg cggtattcca agaggtaat actgcgcact    153060 gccagattcg tggtagagag gggcgtgtta aaaacgatag agaccgctaa gctgcgcaac    153120
gctccgcgtg tattgattgt ggacaacgtg gacactcaat ggactgtttt gaatgcgagc    153180
gagcaaaacg cgggcattta tattcgatat tcccgaaatg gaacgagaac cgctcacgta    153240
gatgccatag tccttgccgt ttctggtcga aagagaggca gggtgccacc gacagtttat    153300
cctgttggac catttttgca caaattccaa atctcccctta aaaatttttaa aacgttctta    153360 tatcaggtgg gggataccgt tacaatatcg ataactacac gcctggagac gacggttcgt    153420
gcgttcaagt tggagtttcg ggtaatgttt ctccccctaca gtccaaactg taagtcgttc    153480
actatttacg agccgtgtat tttccacccc aaagagccag agtgcatatc tccgtcggag    153540
ctatcggaat gtcggtttgc atcaaacgcg caggtcctgg aaattgccgc cgcacgctcg    153600
gtgaactgca gcgcgggccg cgcgtgccat tacgatgccg aggtcgacga atcgatgcag    153660
caaaggttcg cattccttta ttcggaaatc ccctcgttta caattggcaa tgccgggccg    153720
ggggacgcgg gtctgtacgt cgtcgtcgct ctgtgcgatg agcggccgac aacttggact    153780
cacgtctatc tatcgacctt ggacaagatc ctagatgtgc acgagatcgc tcacaagccg    153840
ggatttgatg acagagtctt atcgagcaat gacgacgccg ctcgcggtgt aagacccgga    153900
gcggccatcg agaaagaatc aggtaggctc cgtctaagcg gagccctaat tgcatcgatc    153960
gtgctggtgg ccgcggccgt cgtaactacg gtaagctttt gcggagcttg cgtcttccgg    154020
tggcgtcgca ggtgccaccg gaagacgcaa gctcccggca actcttgcaa gtacatgtcg    154080
ttgccccaaa atcattggga agagttttac gacgacgtta gggttggcag cgcccctcag    154140
tatgagcagt ttaaccaaag gttgcccgag agaacgagat caggctacac cgcttggctc    154200
tcgtctgata tagccgccgt aagaaagcgt ctcgattgaa atcgccgaga cgtgcgtgcc    154260
gattgttgtt tttattgtat cgcccgtact taacggtcct ttatcccgc gcgaaataaa    154320 actgtccgac tcagtctact ggtgctcgcg tttacctcca ctgcgtaccg cgcgccaatt    154380
```

```
ttcgtgtagg tgtgcgtatg gtggagtggt ttgggggacc ctgtctctaa gccggcacac   154440
tccacgctat ttccccccgc ccggtgggca caagcgcttg cgggaggaac cagttgtcgg   154500
tttttatgc gggctcctca gcaccttcgc cacccaccca cactccgcgc cccgactgcg    154560
cgaagctgcc ccgtttaggc aaacggggcc cggccggcgc gacgcagaag aataaagcag   154620
actccgtcgt ttcttctata atggagggta tactcgttta ttgcgacatc acaccccgtg   154680
ttgctatttt aaattgaagg ccgttgataa cccgcatcat ccactaacgt cgttagcgat   154740
aacgattgta tcttcccccc cccccccacc tacggtttgt cgacagctat gataagcgga   154800
ggaaaacctg cctgattcct tgggcgggga tccttgtgcg ctgtcttgct ctgtatgcgc   154860
cgacccaaag ccgcctcctc ctcaacgtaa atttaaccgc ccaggccgcg tagttgcgtg   154920
tcctgaacgg gaaagaagtt cgttcgctgt tattgtggtc attaccgtaa ctgtcccggc   154980
gtgcctccat ctgctgagtc ccgtgcagac tggcatgagg atggttgttc ggcggcaggc   155040
aactccccccc tcatccctac taatcccgaa tgcctttaat gatcacgcaa taaccctcc   155100
tcttaacaat atctctttt cgatgaagat ttcagttccc ccataacacg gcagaacgag    155160
tctgatccct gatcaattgg aacgacttcc ttcttcagaa aggttaaacg aggacacagt   155220
ctgcgacgag agggcttaac acttcctcct gtgcgagagc gcgtctctgc gatgtggctt   155280
cgccgcaaag tccttttccca tactaggcgt aaaccgcact ataacaactc ccctcccccc    155340
cagcacccaa ggggcccgtg aaaccgcgac tggtttcttc ttcactggct cagtactgca   155400
aatgtgctgc ttacctcgtg attgctgtcg tcggggctcg ttcgcacttt ccaggccacc   155460
aaagaaagcg agaccagagc caatcgggac catctccgaa ccttgttcgc taccacacac   155520
gtgccgccct ttgttgacgt ggccgcaaac agagctcgtg gccacgccaa cgaactgctc   155580
gtcctataaa accctccca tactcaatgc cccctgaaat gtttgcaggg gggaaagtga   155640
agccttctgc ttcattcagg tgttcgcaat cgttagggac tcaacggtct gtccatctac   155700
ccaggtgcac accaatgtgg tgaatggtaa aatggcgttt atttgatggt ggcaacagct   155760
tatataatcg tgcatagctt cgtctacgcc catatgtcct tgcgtcattc cttccttatc   155820
tagttgccac caatgagcat atggaatgtc ttgcttttc cttatttggt ctttagacta    155880
ttcaagttgc ctctggctct attgactac atttccccct ccctatcgtt agggactcaa    155940
cggtctgtcc atctacccag gtgcacacca atgtggtgaa tggtaaaatg cgtttatttt   156000
gatggtggca acagcttata taatcgtgca tagcttcgtc tacgcccata tgtccttgcg   156060
tcattccttc cttatctagt tgccaccaat gagcatatgg aatgtcttgc ttttccttaa   156120
tttggtcttt agactattca agttgcctct ggctctattt gactacattt cccctccct    156180
atcgttaggg actcaacggt ctgtccatct acccaggtgc acaccaatgt ggtgaatggt   156240
aaaatggcgt ttatttgatg gtggcaacag cttatataat cgtgcatagc ttcgtctacg   156300
cccatatgtc cttgcgtcat tccttcctta tctagttgcc accaatgagc atatggaatg   156360
tcttgctttt tccttatttg gtctttagac tattcaagtt gcctctggct ctatttgact   156420
acaggaaagg gagacgtgac cgcggccgtc tctcccggct agctccgagc cgaatcgaga   156480
aggggctgcc gccggcaccg cgctcctggt aggtgctgtc gggtcgcgcg atcgcgtgga   156540
cgccggtgcg ttaggggcaa gtagggccgg cccccctcc cccacgcagc gcctattgcc    156600
ccgtcgcctc tctttgtccc tgaccccgac gcgaatatcg gggggggggg gggcggcgcg   156660
ggtcggggaa agaggtggga cgtgttggcg tgagcgttgg gtgcttaata attcgctctg   156720
```

```
tccggccgtc ggtatttctc tcccaccacc accccctcca tttctctcct cttctgtctc   156780
caaccaccac cgcccctcc  gtttctctcc tcttctgtct ccaaccacca ccaccccctc   156840
cgtttctctc ctcttctgtc tccaaccacc accacccct  ccgtttctct cctcttctgt   156900
ctccaaccac caccaccacc ccccccccc  ccccaaaaa  aaagaaatac acgcgcgcgc   156960 ttgactttt  agagccgggc ggttcgcccg agcctaagcg tctcgatgct caagggccgg   157020
tccgcttcgg gttctagccc ccgggcgagc actctcccga gggcgtagg  aacgtcggga   157080 gcgagagaaa caaaccgcac gaaccgcaca gtcgctcgca ggagcgtgtc gagggttaat   157140
gtctccttac ctcggcgtcg ctaggagaat gtttgccccc ggggagccta gcagcgctga   157200
ccgcagcata tctaatggca aaacctgctc gtttcgcaat ccggccgata agcgtttgtt   157260
tgacaagaaa cgttgtgggc ggcggaatgt ttacctatgg ggctcggctg attcggagag   157320
cagcccgggg atcaaatcgc gttgatggga gttaatgatt aaaggagtag ccaggccggc   157380
actgccggag ccgtggctgt ggtgtgtgta ggggcggggt ggtggtggtg ttgggcgggg   157440
ggcaagaagc gatgcgaact gcgggaacg  ctttctcacg gttcccctc  attttttca    157500 gagcaggact ccttccgcgc tccctgcgct ggtcccatc  cgcccgatta accctgcat    157560 ttacgccct  gtaaggagcg gatcgccagt gctgccggcg tcgccacggt tggaccggcg   157620
cgcgtttccc ccattgctcg gacatggaga acccgcccga tttctacagc ctgttagaga   157680
tgttagccga caacgcgga  ttttctccgc agccaccgc  caccccggga gatccgtacc   157740
aggacgtgtg cttgaataca ccgagcgtgg ccgtgccccc gacgcccggt cggcagcccg   157800
tcccgccacg gtctaaatcc cctgcccgcg cggctcccgt cgcgggcagc cttgccggcc   157860
cacgagcccc tttcggcatt gagggtgccg tttcggaggg ttcggatacg ggtctccgtt   157920
ccgccgaacc ccccgacggc gcgcatcagg ggtctcctgg cgaggtcgtc agttccaccg   157980
cggacatcgt ggacgtctgt ggaaacgaaa cggccgcggc ggccccgcgg tcctgttctt   158040
ggcaaaagac agtcggcgat ctagtccccg cgggttcgga acggggcgaa ccgagcccta   158100
tggatccccg caaatcaaac gaccccgtcc gctgcgtatc tgacgcgccc tgtaagccca   158160
ccggcgcctg cacgccgctc gccgtctgtg tcgaaactct cccccctccc tcgggcgtgc   158220
cccccccacc cccccccgaa cctatcgtga acttcccatg gacatttctt ccgctgacgc   158280
cgggaccgtt cgctcaacac cattcaccca ctccccctac accacctccc cttagccccc   158340
ctcctcctac gccacccccc cttagccccc ctcctcctac gccacctccc cttagccccc   158400
ctcctcctac gccacctccg catacccccc ctccgcacgg ttcccctccc ccacgcctc    158460 tgccgtctac ctcccctccc tctacgcaga catcctcccc gtctgcgtct ctaccgcttg   158520
actcgcctcc ggcgtctacc ccacctccgc caaccctct  ccacgacagg cctctttccc   158580
cggacccccc agccctctct gcttcttgtc agcgtccttc ccctccgttg tccccttcag   158640 cccccgcct  cgcacccgct ccctccgga  gcgaccgagt cccagcccgc cgtaaatcga   158700
gcgtttccga gggcggggc  ccccgtacca ggggcgcggg cttccagtac gtctgccgcc   158760
tatccgcatc cgccaggatc ccatccccc  ctcgagaaga gctcgagttg gtggcccgcc   158820
agccggggag ccacgctatg ttgtggcgcg cgggggctcg cgacgcgcg  acggagccgt   158880 cctccggaga caaccctaag gttttctcc  tcgcgttgtc ggacgctcgc cggtgccctt   158940
cctactggga tcggctggcg agggaagcgg tactcagaga aatcttacct actccgcgcg   159000
gcagccctct gcggacctca ccggggtcta tcgaactgcc gagagaggcc cctttactcg   159060
acagcgacta ccggccgttc gaatggcgtt gcgcgaaggg tcgcccgctg ccccaggagc   159120
```

```
cggtcttccc gtgccctccg aacgagctgg ggaatgactg ggcggcctgc aagatgtggt  159180
tgttttctcg atgcgcgcgc ctcgttctct cgaccctgga cgatatgtcg ccgtccgagg  159240
acggggaaag cgtgttagaa tcgcagggtt gcggatgggg cccgcagaac gagtgcccgc  159300
tccccctccc cgccccgata gtgctgccaa cgcgcatctg ggaagcggta acacggctcc  159360
cgagaccggc tccgcgcacc ccgacgtacg cttacatttt gtcggcgctc cttcgcttcc  159420
tcggccttca agtcaccccc gatttcgtgt cgaaggttcc ccgcctttca taccgctggc  159480
tggaccgact ccgctgcgtc aggcgcgtcc agtacatggc ccacgttctg acacgcgact  159540
tttcctatca attacaagcg gctcgtggtc tgccgtgctt tccggcgtgc gcgccgccgc  159600
cgggcgcggg tactcccttg gacgaggact ggaacggaac gccgccctct gaatccccccc  159660 gcggtctcga ctgcagccgg cgccgcgcg gcttctatgc ctccaacttc tgtcctctgc  159720
tcgaggagat tcggtgggtg gaaggccggg aaggcagccc gaaccectgg accgggctca  159780 cctggaacga tttcaagatg ctacattaca ggtgtctttt tttcaaagtg cgtcgggggt  159840
tactgctggc cccagacgac tacatcgtcg gccccgacgt gcggcccggc ttcgaggtgc  159900 cttttcgaaat gccccccccg cccgccaccg cgctccctcc cgcgctttcc gcggccgtca  159960
gggaatcgaa gttggcgctg cggaacggaa atccggaacc cggcgggacg ccccacggct  160020
ctcgtcccgc acgcgcctac ggattcatgg tgcagcagct cgccgtcgct atggtcgaac  160080
tggggttccc cgcctgcggt ccggccatcg aaaaacgggt cagacctctg tacaaagcca  160140
tacttgattg gcgcgccgcc gtcaccgccg cggcgctacg ccgattcaga cacctccgtc  160200
agccgtccgg cgcgagggac gacggagcgc ccatgtttcc ccccccttccc gttccagact  160260 ggaacgggcc gtctccgagg ccgggcctcg ttagcagccc caccggtacg caggaacgtt  160320
accgcagagt ccagccggga tcgggctccg atggttcgca cacaacagct ccacctgctg  160380
ttctaaaaca ggcattacaa caggaggttg gcacgccggc gacccgcgct tcccatcccc  160440
taccccggcc tcccccggcc tcgtacccctt cgctcgggtg tcgctccaga tcttcctcct  160500
cctcgtccgc ttcctcttcc tcgtcctctt cgtcgtccgc gccctcttca tcggaacagt  160560
cgtctgccgc ccccttcttcg cgcacctcat ccaggtcgcc gacccgcgag caggagcgc  160620 ctcaatgcgc tgccagaggc cgcggccgcg gccgcggagg acggcgcggc cgcggccggc  160680
gggcgccatc accgtcctcg gaaactgctg cgccgccacc gccggatgac ctcgaccaag  160740
aggtgtggtg gcaaattccc tccccgccgg ccggccggtg ctggttcggg cctctcggcg  160800
gacaccgaca ggcgctccgg ggcatccctg aagtagagca ggccgccgtt agattcctct  160860
ctactcccgg tcccctcccg gtgtacgtgg aggaaatggg gaactgcgcc aaacagtacg  160920
aggcgctcgt aagcgccatg cttaacaaag acgtgaaggc gaaccccctg aactgggcac  160980
accacggcaa gctctcgccc accgacgcag cgctcaatca catctatgtc acgaagtttc  161040
agagctcgca cagttcgccg ggcgcggccg tcacggggac ggtcaacaaa tgcatacccc  161100
acatagccag cgccatgaag aagcgaaatc tgctttgggc gctaccgcac atcgccgcca  161160
gcgtgtctat gactcgcagg tactgcaaag atcagaaaga gttcatgttc cgctcccctca  161220 ggaaagccta cgcgcctatg gcgtctgcag ccagcgccga aatgcgacgc ccctcggcat  161280
cgcctatttc aaatcgggca cccgtcactg cccaaagtac ggcggccggg ctcatcccgg  161340
taatagacgt gtccacgatc cacgaccgcg tgcgccgggg cgtcgcggcc ttcaattccg  161400
cgctagagga gggcctgctg gacgtccccg aataccgatt ggtcgcgccc gcgcgtccgg  161460
```

```
acatccctgc cggggacggt ttcgcgtcta cccggccgct gaacgagctg gtggacgctt  161520
gcgcgctgga gtgcgagggg gtcgtggcgg cgcttctgcg cggacccgac ggtccgggcg  161580
cggtcgcgga aatgctgtcg tcttgcgagg acgggccctt ccctcgaccc gccggccacg  161640
aacagtggga aaaatgccgg gctctgctcg ggtcgtggct ccgagacctg cttgatctca  161700
ggagcgccgt gtacgcggcc tacgcgaacg gttcggctcc tcggggcgc caggagcgaa  161760
ctctcgcggc taatgcggtg gccctgataa cggaagcgat cggcccgttg cttagcaaag  161820
accccgctcg gccttggcga tgccctgggt cgagggacat tacttccgtg ctcctgcgcg  161880
aatgtgggtc gaggggcgaa ccggtacgat cccgcgagaa ggcccgacgg ctgcaacgcg  161940
tggcgcgcct tctcgcggac gccgacgcgg cctcttccgg aacgtccgag ggccggtcgc  162000
gctccgcgga gccttgttac gaccccggcc ccgcaagttc tcccgagccc gtgcgggccc  162060
tttgcgccca acgtcagcc gagtcaagga agagaaaatc agctcccgcg gcggttctcg  162120
acggcgcgga caacgccgtc gagaacccgc gtccgcgttt gggaaggtcc cggacaggcg  162180
ccggacctcc gcctgtcgcc agctgcacaa ggcccccac cccccctgaa gcgtgccgcg  162240
acgccgggcc tttcccgccc aagcgcccac gttgctttcc gtggcgcgac cccgcgcgca  162300
ttatggacgg ttccctgtcg ttaggcgatc gacggcatcg tggcgccgcc tttaggaagc  162360
cccccattgg aactccgatt gctggctatg ccggcccccc gcacctcgac gcctattgtc  162420
caggcgaagg agtcgacgag ctgaccagct tcgcccaaat accgactctg tggcgtcagc  162480
cgttggcgcg ttctccggag gccatggcgg agatcgctcg cgtggcgagc actccctcgc  162540
acgtcagcag aagcccagac actgctgcgt ccgagggagt gttgtgccgc acggccgtcg  162600
tctctctcag agcgcgcacc gcttggatgc ggcatcagca ggcttcgcct gaagatgtcg  162660
ctctcgtcat cctgtacacg gccaacccag gcgagcacct gttttgcgta ccggcgcccg  162720
gctcgccccc cggggaccc cggttcgacc cgaaccgggg aggactctct ttcctgctcg  162780
ccgcactcgc caaccgcctc tgcctaccgg agagcgccgc ctgggcgggc cggtggagag  162840
cggcgccgga cgtttcggcg ctgaccgcgg ccggcgtcat gttcctgtcc cctcaggacc  162900
tcggttttgc gggcgtcctg gaacacctgc aacgcctctg tttgaaacga gaaaaaaggc  162960
tcgtggtcct ggacacgcta gaggatcaag atcgcccgga gaacggcccg cgcctcgtgg  163020
aagaagccgt ccgctacgtc aggtgcaccg tctcgccccg cagccaatgc tccgtccgat  163080
ggcctggcca ccccgatcta gctacgacgg tcataacctc gcgggacgtg ctgggccccg  163140
tggtcctacg tgagctggaa acgcactttc gccgcgaaaa ccccgcggcc ggcgacatca  163200
gtctgtgctg cggaagcaac gtccgataca aggtcgcgac gcgactggac cgcgtcgcga  163260
cggtcccaat gaccgctctc tcctacctcg cagcctcctc ggcccttgtg gccgggcgcc  163320
agaggccgcc cggccccgac tttttagctg gagagtcgca ctcccaccga gccgctctca  163380
agtggggact gtacgccccg ctgcgtcccg tgtacgtctt ggagcccaaa agaacgcca  163440
tagtttcccc cgatttctta aataggaccg tctgcgacgt tgccgctcc gtagtcctcc  163500
ccccgatcc gcacgcccag ccagtcgtcg ttcacgttcc cgaagcgacg tgcagtttat  163560
tggcccgcga gatgctcgct cacctacgta gctcgtctgt agtgtggctg gaaggggacg  163620
gcggtccgcc ggagaccacc gtccaggagg aacagggcgc gcgacagagg ataattcatc  163680
ctccgacgct gccggtcct ccttcgccct tggccctcag cgactctgaa gtcttcggcg  163740
agtgaaggct aagtcagggt cggggggggg ggggcggggg gagtcactcg gcggactttt  163800
aagggctatc tggacaagca gccccgcggg tacgacatat catccgcgag cggggagacg  163860
```

```
gacaaataaa ttagggggcc agcggaaccc cgcggctcgg ttgcgttccg cgctgttagt    163920
cgtacgggcc gcggtctgcc gtgcggatgc gtcaccgcct ggtccattgg tcggccgtgg    163980
ccacgcctct atacctgttc ccagaacgaa tgccccgcgc gcaccttcgc ccggccattc    164040
agtagcgcag aagcgccggc gagcccgcgg gcgcgttcgc cgtagtgttc tcccgcaaac    164100
gcggtagaga aagtttcgta aaaggaagac cgcgcggcga cagcgcctag aagacccgtg    164160
gcctgtacga ggaggagcgg cggcgaaagc ggggtccttt cgccctgcgc tccgccaaag    164220
gggggagggg acggacaatg gagcctccca cggcaaagtc ggacggggcc gcaccggatc    164280
ccgacggcga cgtgaaccga accgacccgc cgctcattgt ccctcaagcc tcagaactcc    164340
gccctacctt ctccgaaagc tcccgggggt ccccgacggc ggtctgcccg ggaaccgaaa    164400
ccgcgggcgc ggagccgtgg cccctggac tcagatcgcc gcgtcctttc cgaaggcctg    164460
cgcggctgta ccgaagaatc gcgatcccta gggctgcgga aaccgctcct ccggatcctg    164520
caacgagctc cgctccgtga aggtcatctc gaacggatag aaccgctcaa ggtcgggggg    164580
gggggggggg gtggtggtag ggttaacggt agctgggatt gagatgtagc gctggcgaat    164640
aaataaataa ataaatgaat gaatgaatga atgaatgaat gaatgaatga atgaagggac    164700
cagatgcgac agacatcatt cgcgctctct gaccgactct tgccggcggc ggcaggggt    164760 ttcggtcgcc ctgggtggcc gggggggggg gggcggggg tgcgtccgga ggcagcggcg    164820
cgcggggaca cctctgttct tacgctgttc gcggagagcc ctctacccccg cggatcgatc    164880 cctcgcgcgg gagcaatctc tgcggtcccc tgcgcagccc gcggagcggt tcggtccgcg    164940
gcgcgctcgc ccgctcgccc gcccggctat cctcttccgc agcggcacca gaaagtggcg    165000
ggaacgagcg cgcatacggg agacataaaa atggcggggg agacgggttt ctgatcgagt    165060
cggcgagcgg gcccgaggaa agcggcagcg ggacagggtt tccggatcgg accgcggcgg    165120 ctaccgagc ccgctgtcgc actccgcggt ccctaattgt tcgcccgcgc accccctcc    165180 cccaccccat tcgcgtcggc gagcgggccc gaagaaagcg cagggggac acggtttccg    165240 gatcggaccg cggcggctac cgagtccacc tcgcgccccc cgcggacccc aatcgttcgc    165300
ccgtgacggt ctctggactg ttctgcccct ccccctttcc cccaccaccc acgccgcaga    165360 ccttttttcga gacgaaccgc ggctgtccta agtgaccgag acgggcgcct gaaaaagcct    165420
tgcgtctgat cggggggggg ggggggggcgc gactccaagc gttagaccgc cgaccgccgg    165480
cggctccgcg cggccagtag gccgagccgc acgctgcatc cccgccggac atgcccgccg    165540
gccgcgcggg cgctcgctag gccgcccgga aatgcgtagc ggaccgtgc gcgcatgcgc    165600 gcagtcgaca tttgcgagca tgcgcgcggc ggaccctagc gagcatgcgc gcggcggacc    165660
gtagggagca tgcgcgcggc ggaccgtagg gagcatgcgc gcggcggacc ctggccacca    165720
ccaaacgtca taccaaaact ctcgcggcgg cgaactgaat aaaaaaaatt caccctaacc    165780
ctaaccctaa aggcctaacc ctaaccctaa aggcctaacc ctaaccctaa cggcctaacc    165840
ctaaccctaa ccctaaccct aaccctaacc ctaaccctaa ccctaaccct aaccctaacc    165900
ctaaccctaa ccctaaccct aaccaactta atatccccccc ctgcatttca cccccccccc    165960
aaaaaaggaa catagcacaa caattaacgc ggct                                165994

<210> SEQ ID NO 15
<211> LENGTH: 22
<212> TYPE: DNA
<213> ORGANISM: artificial sequence
<220> FEATURE:
```

<223> OTHER INFORMATION: MB080 primer

<400> SEQUENCE: 15
cgaacaaact tcatcgctat gc                                          22

<210> SEQ ID NO 16
<211> LENGTH: 22
<212> TYPE: DNA
<213> ORGANISM: artificial sequence
<220> FEATURE:
<223> OTHER INFORMATION: MB081 primer

<400> SEQUENCE: 16
taactcaaat gcgaagcgtt gc                                          22

<210> SEQ ID NO 17
<211> LENGTH: 21
<212> TYPE: DNA
<213> ORGANISM: artificial sequence
<220> FEATURE:
<223> OTHER INFORMATION: SB-1 US10 primer

<400> SEQUENCE: 17
tcaacgtgcg acaatcgtct g                                           21

<210> SEQ ID NO 18
<211> LENGTH: 21
<212> TYPE: DNA
<213> ORGANISM: artificial sequence
<220> FEATURE:
<223> OTHER INFORMATION: SB-1 SORF4 primer

<400> SEQUENCE: 18
atgtggagga acgatcctat a                                           21

<210> SEQ ID NO 19
<211> LENGTH: 18
<212> TYPE: DNA
<213> ORGANISM: artificial sequence
<220> FEATURE:
<223> OTHER INFORMATION: ALLNDVFprimer

<400> SEQUENCE: 19
atggcttggg aataatac                                               18

<210> SEQ ID NO 20
<211> LENGTH: 18
<212> TYPE: DNA
<213> ORGANISM: artificial sequence
<220> FEATURE:
<223> OTHER INFORMATION: mCMVF primer

<400> SEQUENCE: 20
aactccgccc gttttatg                                               18

<210> SEQ ID NO 21
<211> LENGTH: 18
<212> TYPE: DNA
<213> ORGANISM: artificial sequence
<220> FEATURE:
<223> OTHER INFORMATION: SV40tailR primer

<400> SEQUENCE: 21
tcgactctag aggatccg                                               18

-continued

<210> SEQ ID NO 22
<211> LENGTH: 21
<212> TYPE: DNA
<213> ORGANISM: artificial sequence
<220> FEATURE:
<223> OTHER INFORMATION: newSB-1 UL55R primer

<400> SEQUENCE: 22
atggctatag agggactgtg t                                            21

<210> SEQ ID NO 23
<211> LENGTH: 21
<212> TYPE: DNA
<213> ORGANISM: artificial sequence
<220> FEATURE:
<223> OTHER INFORMATION: New SB-1 ORF5F primer

<400> SEQUENCE: 23
gatctcaacg ctataccggc g                                            21

<210> SEQ ID NO 24
<211> LENGTH: 21
<212> TYPE: DNA
<213> ORGANISM: artificial sequence
<220> FEATURE:
<223> OTHER INFORMATION: OptF primer

<400> SEQUENCE: 24
actgacaaca ccctacatgg c                                            21

<210> SEQ ID NO 25
<211> LENGTH: 19
<212> TYPE: DNA
<213> ORGANISM: artificial sequence
<220> FEATURE:
<223> OTHER INFORMATION: VIIoptF RP primer

<400> SEQUENCE: 25
gccagcacca ggctcaggg                                               19

<210> SEQ ID NO 26
<211> LENGTH: 18
<212> TYPE: DNA
<213> ORGANISM: artificial sequence
<220> FEATURE:
<223> OTHER INFORMATION: SV40promoterF primer

<400> SEQUENCE: 26
agcttggctg tggaatgt                                                18

<210> SEQ ID NO 27
<211> LENGTH: 21
<212> TYPE: DNA
<213> ORGANISM: artificial sequence
<220> FEATURE:
<223> OTHER INFORMATION: SB1 43.F primer

<400> SEQUENCE: 27
gctctcggag acgcggctcg c                                            21

<210> SEQ ID NO 28
<211> LENGTH: 21
<212> TYPE: DNA
<213> ORGANISM: artificial sequence
<220> FEATURE:
<223> OTHER INFORMATION: SB1 45.R primer

<400> SEQUENCE: 28
gctcttgtaa catcgcggac g                                        21

<210> SEQ ID NO 29
<211> LENGTH: 18
<212> TYPE: DNA
<213> ORGANISM: artificial sequence
<220> FEATURE:
<223> OTHER INFORMATION: SV40 promoter F primer

<400> SEQUENCE: 29
agcttggctg tggaatgt                                            18

<210> SEQ ID NO 30
<211> LENGTH: 20
<212> TYPE: DNA
<213> ORGANISM: artificial sequence
<220> FEATURE:
<223> OTHER INFORMATION: HVTUS10 FP primer

<400> SEQUENCE: 30
ccggcaacat acataatgtg                                          20

<210> SEQ ID NO 31
<211> LENGTH: 18
<212> TYPE: DNA
<213> ORGANISM: artificial sequence
<220> FEATURE:
<223> OTHER INFORMATION: HVTUS10 RP primer

<400> SEQUENCE: 31
ggcactatcc acagtacg                                            18

<210> SEQ ID NO 32
<211> LENGTH: 19
<212> TYPE: DNA
<213> ORGANISM: artificial sequence
<220> FEATURE:
<223> OTHER INFORMATION: CaoptF RP primer

<400> SEQUENCE: 32
gccagcacca ggctcatca                                           19

<210> SEQ ID NO 33
<211> LENGTH: 18
<212> TYPE: DNA
<213> ORGANISM: artificial sequence
<220> FEATURE:
<223> OTHER INFORMATION: SynTailR primer

<400> SEQUENCE: 33
atgttctggc acctgcac                                            18

<210> SEQ ID NO 34
<211> LENGTH: 1437
<212> TYPE: DNA
<213> ORGANISM: artificial sequence
<220> FEATURE:
<223> OTHER INFORMATION: DNA sequence encoding glycoprotein C of SB-1
      strain with GenBank accession No. HQ840738

<400> SEQUENCE: 34
atgcacgcgt cacgcgcgtt gcgagctttg gggtggacga gactcttatt tgtcgtttta    60
ttttcgggcc gcgtcctaag cgctagcatt aaccccgatc tagctacacc cccggtcatt   120

```
gctttcaacc cgtcaagtat tccggccgat gatgggcctt tggccaaagt tcctgcatcc    180
ccgccggcag gggagaaaga ggagagccac aagaatgcaa gcgacgcgcg taggatgcct    240
agtatagttt gcgataaaga agaagttttc gttttcctga caagaccgg  gcgtttcgtg    300
tgcactctta agatcgcccc tccctccgac aacgaatggt cgaactttgc tctggacctt    360
attttcaatc cgatcgaata ccatgctaat gagaagaacg tggaagcagc gcgtattgct    420
ggcctctatg gggtgcccgg atcagattac gcctacccgc gtccttctga attaatctct    480
tctattcggc gagaccccca agggaccttt tggacaagcc catcggcaca tggagacaag    540
tacttcatat ggctaaacaa aacgacgaat acgatgggcg tggaaattag gaacgtcgac    600
tacgcagaca acggttacat ccaagttgcc atgcgggatc ctttcaatcg gcctttacta    660
gataagcacg tgtacatccg cgtgtgtcaa cgacccgcct cggtcgacgt tctagccccc    720
cccgtcctca gtggcgataa gtacaaggct tcatgcatcg ttaggcattt ttatccaccg    780
ggctccgtct atgtgttctg gaggcaagat gggaatatcg ttacaccacg taaggacacg    840
gacggaagtt tttggtggtt tgaatcagcc cggggagcca ccctggtatc tacgataacg    900
ctgggcaact cggccatcga ccctcctccc aagatttcat gtctggtagc ctggaagcag    960
ggaaatatga tgagtactac gaacgccact gcaatcccga ccgtatatca tcatccccgg   1020
atatccctgg ctttcaaaga tgggtatgca atatgtacta cgcaatgtgt gccgttcgga   1080
attaccatac gatggttagt acacgatgaa cccaaaccta atacaactta tgatactgtg   1140
gttacaggtc tttgcaggac cctcaagcgg catagaaata tcatcagccg aatattactc   1200
caagatgact ggcagaaaac aaagtataca tgtcgtctca tcggctatcc tttcgacgaa   1260
gacaaatttc aagctttcga ttacttcgac gcgacgccat cgacgagggg gtcccccatg   1320
gttctcgcga tagcggctgt tgtgggacta gctttgattt tgggaatggg tacactcctg   1380
acggctctgt gtttctacgc ctccgggaaa aaatacatat tactttcgtc cgtctag      1437
```

<210> SEQ ID NO 35
<211> LENGTH: 478
<212> TYPE: PRT
<213> ORGANISM: artificial sequence
<220> FEATURE:
<223> OTHER INFORMATION: glycoportein C of SB-1 strain with GenBank
      accession No. AEI00252

<400> SEQUENCE: 35

Met His Ala Ser Arg Ala Leu Arg Ala Leu Gly Trp Thr Arg Leu Leu
1               5                   10                  15

Phe Val Val Leu Phe Ser Gly Arg Val Leu Ser Ala Ser Ile Asn Pro
            20                  25                  30

Asp Leu Ala Thr Pro Pro Val Ile Ala Phe Asn Pro Ser Ser Ile Pro
        35                  40                  45

Ala Asp Asp Gly Pro Leu Ala Lys Val Pro Ala Ser Pro Pro Ala Gly
    50                  55                  60

Glu Lys Glu Glu Ser His Lys Asn Ala Ser Asp Ala Arg Arg Met Pro
65                  70                  75                  80

Ser Ile Val Cys Asp Lys Glu Glu Val Phe Val Phe Leu Asn Lys Thr
                85                  90                  95

Gly Arg Phe Val Cys Thr Leu Lys Ile Ala Pro Pro Ser Asp Asn Glu
            100                 105                 110

Trp Ser Asn Phe Ala Leu Asp Leu Ile Phe Asn Pro Ile Glu Tyr His
        115                 120                 125

```
Ala Asn Glu Lys Asn Val Glu Ala Ala Arg Ile Ala Gly Leu Tyr Gly
    130                 135                 140

Val Pro Gly Ser Asp Tyr Ala Tyr Pro Arg Pro Ser Glu Leu Ile Ser
145                 150                 155                 160

Ser Ile Arg Arg Asp Pro Gln Gly Thr Phe Trp Thr Ser Pro Ser Ala
                165                 170                 175

His Gly Asp Lys Tyr Phe Ile Trp Leu Asn Lys Thr Thr Asn Thr Met
            180                 185                 190

Gly Val Glu Ile Arg Asn Val Asp Tyr Ala Asp Asn Gly Tyr Ile Gln
        195                 200                 205

Val Ala Met Arg Asp Pro Phe Asn Arg Pro Leu Leu Asp Lys His Val
210                 215                 220

Tyr Ile Arg Val Cys Gln Arg Pro Ala Ser Val Asp Val Leu Ala Pro
225                 230                 235                 240

Pro Val Leu Ser Gly Asp Lys Tyr Lys Ala Ser Cys Ile Val Arg His
                245                 250                 255

Phe Tyr Pro Pro Gly Ser Val Tyr Val Phe Trp Arg Gln Asp Gly Asn
            260                 265                 270

Ile Val Thr Pro Arg Lys Asp Thr Asp Gly Ser Phe Trp Trp Phe Glu
        275                 280                 285

Ser Ala Arg Gly Ala Thr Leu Val Ser Thr Ile Thr Leu Gly Asn Ser
290                 295                 300

Ala Ile Asp Pro Pro Lys Ile Ser Cys Leu Val Ala Trp Lys Gln
305                 310                 315                 320

Gly Asn Met Met Ser Thr Thr Asn Ala Thr Ala Ile Pro Thr Val Tyr
                325                 330                 335

His His Pro Arg Ile Ser Leu Ala Phe Lys Asp Gly Tyr Ala Ile Cys
            340                 345                 350

Thr Thr Gln Cys Val Pro Phe Gly Ile Thr Ile Arg Trp Leu Val His
        355                 360                 365

Asp Glu Pro Lys Pro Asn Thr Thr Tyr Asp Thr Val Val Thr Gly Leu
370                 375                 380

Cys Arg Thr Leu Lys Arg His Arg Asn Ile Ile Ser Arg Ile Leu Leu
385                 390                 395                 400

Gln Asp Asp Trp Gln Lys Thr Lys Tyr Thr Cys Arg Leu Ile Gly Tyr
                405                 410                 415

Pro Phe Asp Glu Asp Lys Phe Gln Ala Phe Asp Tyr Phe Asp Ala Thr
            420                 425                 430

Pro Ser Thr Arg Gly Ser Pro Met Val Leu Ala Ile Ala Ala Val Val
        435                 440                 445

Gly Leu Ala Leu Ile Leu Gly Met Gly Thr Leu Leu Thr Ala Leu Cys
450                 455                 460

Phe Tyr Ala Ser Gly Lys Lys Tyr Ile Leu Leu Ser Ser Val
465                 470                 475

<210> SEQ ID NO 36
<211> LENGTH: 4734
<212> TYPE: DNA
<213> ORGANISM: artificial sequence
<220> FEATURE:
<223> OTHER INFORMATION: plasmid pSB1 44cds for gC deletion

<400> SEQUENCE: 36
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
```

```
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt acctcgcgaa    420
tgcatctaga tgccaatgaa ttcgcgatag cttcgattag aattttcgca tgagtaaagt    480
cgacaagctt gctgttatgt cgggagcacg tatctagggc ttctagctcg gtagcgttgc    540
tccccatcgc gcgcatacaa ctatagccta aaccgatcca ttcgtgagga catgtaccgg    600
actccaggga catgtaagag aatgcaaaca gcgaagctag cacgaccgta gctgtgatga    660
cgaacacagt aagagcgatc ccgatcgtac aaccgcataa caaccggggg catcctgaac    720
gcgaacgttt gtgtcgctca gatgtggtct cgtccatcat ccggagcagc ccacgtactg    780
cgaccaagtc gcggtcgtct tcgggagtag gggacatcat acttacatat ttaaggaccg    840
agtagctata tagagaccgt atttcgcgat tgtacggtac tcgcagtcat attcgatttc    900
taaaattgtt accgacgtat tcgtcggtag gcgcgcagcc acttttcaac ggacccgcgg    960
ggtccgacaa ccttatcccg caaacgacgc ttccgttaaa ctctgttcgt gcgtggctgg   1020
ggtcgcgtgt acctcgtccc ttagcttttcc agccgtggaa caagaaggc ctaggttcac   1080 tgacacttat ctactctaga ggtttgcttt ttaggcgctg ccgagggaat aattccggtc   1140
caaacgaagt tcgagagaac ctgtgtagtg tacgttattt agtctgtgcc gtgtggaaaa   1200
ggatctacct tttttttagaa ataccgtact gctagagggt tacatactat tcctcatcac   1260
ctgaggagtc taaagctgaa gttttccggt ggatatatgc cctaccgact gtaagcaggg   1320
ccggatgtac ctatacggtt gacatgccgc ttttgcattt gagatgtgcc tactacggaa   1380
atcgcgtccg cgatgttaca agagctcggg gcatataatg agccagatca atgtcaccgc   1440
aaacctgcag ggatatcggg cccctgcag gggggaaaat atttcagctg gcgtgcgagc   1500
cgcgtctccg agagcgtata tggagtggcc tctgcctgcg caacttagct ttaaatcggc   1560
cctttcatgt tttcgacagc gcataaaccc acgataggcc cctttagtag ccacgaaagt   1620
tttattcgca gttcgaaaga acgctatgag cacatgatat aaaaattaat cgctccgcga   1680
tcaggaatat tgtattaaca cgcaaaccaa catgctcgag atggcagttc ctaatatgca   1740
tttaccagct gcggcggccg ccaattgctt tattccgcta ttcgcgttgc gtacatttat   1800
acaagtgtag cagcacagaa ccgcggctgt cgcggaaaac aatgtcggcc cgagaagtaa   1860
accgaagccg gctaaggtag tagccattgc cccgaatatt aacagtaata caagaattgg   1920
acggaacaga acctcgtggt agcgcgacgg aaggaatatc gcgacacttg tacccaccaa   1980
gaaaccgcat atactgcgta acgtgtcagt caatgttgac tggtgcttag ttgcgttcga   2040
catgtacttt tgaaagctgg ctatggctgg aatcagatg accgctatga ggctcagaat   2100
tatcgtagga atattccccc ccagcgtatc gtaactggat acgtcttctt cgcgcgtcgc   2160
ctcggcgtcc gtgctgggcg ggagacgcgc gcgaccgagg cgatatgcac cgttcacagt   2220
aatttcccga cgtgcacggt agtagcacgt gttcattaga gaccgactgg cgtctctgac   2280
cacgtgaata gctaacgccg tatacgccga agaaagccg gctagaggag aaatgtctcc   2340
atacggagcc gtgatgccgg caatcgtccc tgccgccaca actaaaaacc cggtcttcca   2400
cgtcacgtct ccagacgttg ctatgcagac gtaatgataa gatgcgatca gagctccgag   2460
```

```
catgacaaaa gcccgactgc agaggcctgc atgcaagctt ggcgtaatca tggtcatagc    2520
tgtttcctgt gtgaaattgt tatccgctca caattccaca caacatacga gccgaagca    2580
taaagtgtaa agcctggggt gcctaatgag tgagctaact cacattaatt gcgttgcgct    2640
cactgcccgc tttccagtcg ggaaacctgt cgtgccagct gcattaatga atcggccaac    2700
gcgcggggag aggcggtttg cgtattgggc gctcttccgc ttcctcgctc actgactcgc    2760
tgcgctcggt cgttcggctg cggcgagcgg tatcagctca ctcaaaggcg gtaatacggt    2820
tatccacaga atcaggggat aacgcaggaa agaacatgtg agcaaaaggc cagcaaaagg    2880
ccaggaaccg taaaaaggcc gcgttgctgg cgtttttcca taggctccgc cccccctgacg    2940
agcatcacaa aaatcgacgc tcaagtcaga ggtggcgaaa cccgacagga ctataaagat    3000
accaggcgtt tccccctgga agctccctcg tgcgctctcc tgttccgacc ctgccgctta    3060
ccggatacct gtccgccttt ctcccttcgg aagcgtggc gctttctcat agctcacgct    3120
gtaggtatct cagttcggtg taggtcgttc gctccaagct gggctgtgtg cacgaacccc    3180
ccgttcagcc cgaccgctgc gccttatccg gtaactatc tcttgagtcc aacccggtaa    3240
gacacgactt atcgccactg gcagcagcca ctggtaacag gattagcaga gcgaggtatg    3300
taggcggtgc tacagagttc ttgaagtggt ggcctaacta cggctacact agaagaacag    3360
tatttggtat ctgcgctctg ctgaagccag ttaccttcgg aaaaagagtt ggtagctctt    3420
gatccggcaa acaaaccacc gctggtagcg gtggtttttt tgtttgcaag cagcagatta    3480
cgcgcagaaa aaaaggatct caagaagatc ctttgatctt ttctacgggg tctgacgctc    3540
agtggaacga aaactcacgt taagggattt tggtcatgag attatcaaaa aggatcttca    3600
cctagatcct tttaaattaa aaatgaagtt ttaaatcaat ctaaagtata tatgagtaaa    3660
cttggtctga cagttaccaa tgcttaatca gtgaggcacc tatctcagcg atctgtctat    3720
ttcgttcatc catagttgcc tgactccccg tcgtgtagat aactacgata cgggagggct    3780
taccatctgg ccccagtgct gcaatgatac cgcgagaccc acgctcaccg gctccagatt    3840
tatcagcaat aaaccagcca gccggaaggg ccgagcgcag aagtggtcct gcaactttat    3900
ccgcctccat ccagtctatt aattgttgcc gggaagctag agtaagtagt tcgccagtta    3960
atagtttgcg caacgttgtt gccattgcta caggcatcgt ggtgtcacgc tcgtcgtttg    4020
gtatggcttc attcagctcc ggttcccaac gatcaaggcg agttacatga tcccccatgt    4080
tgtgcaaaaa agcggttagc tccttcggtc ctccgatcgt tgtcagaagt aagttggccg    4140
cagtgttatc actcatggtt atggcagcac tgcataattc tcttactgtc atgccatccg    4200
taagatgctt ttctgtgact ggtgagtact caaccaagtc attctgagaa tagtgtatgc    4260
ggcgaccgag ttgctcttgc ccggcgtcaa tacgggataa taccgcgcca catagcagaa    4320
ctttaaaagt gctcatcatt ggaaaacgtt cttcggggcg aaaactctca aggatcttac    4380
cgctgttgag atccagttcg atgtaaccca ctcgtgcacc caactgatct tcagcatctt    4440
ttactttcac cagcgtttct gggtgagcaa aacaggaag gcaaaatgcc gcaaaaaagg    4500
gaataagggc gacacggaaa tgttgaatac tcatactctt ccttttttcaa tattattgaa    4560
gcatttatca gggttattgt ctcatgagcg gatacatatt tgaatgtatt tagaaaaata    4620
aacaaatagg ggttccgcgc acatttcccc gaaaagtgcc acctgacgtc taagaaacca    4680
ttattatcat gacattaacc tataaaaata ggcgtatcac gaggccctt  cgtc    4734
```

<210> SEQ ID NO 37
<211> LENGTH: 4085

<212> TYPE: DNA
<213> ORGANISM: artificial sequence
<220> FEATURE:
<223> OTHER INFORMATION: partial plasmid sequence of pSB1 44cds SV
      FCAopt for vSB1-009

<400> SEQUENCE: 37

| | | | | | |
|---|---|---|---|---|---|
| cttttgtcat | gctcggagct | ctgatcgcat | cttatcatta | cgtctgcata | gcaacgtctg | 60 |
| gagacgtgac | gtggaagacc | gggtttttag | ttgtggcggc | agggacgatt | gccggcatca | 120 |
| cggctccgta | tggagacatt | tctcctctag | ccggcttttct | ttcggcgtat | acggcgttag | 180 |
| ctattcacgt | ggtcagagac | gccagtcggt | ctctaatgaa | cacgtgctac | taccgtgcac | 240 |
| gtcgggaaat | tactgtgaac | ggtgcatatc | gcctcggtcg | cgcgcgtctc | ccgcccagca | 300 |
| cggacgccga | ggcgacgcgc | gaagaagacg | tatccagtta | cgatacgctg | gggggaata | 360 |
| ttcctacgat | aattctgagc | ctcatagcgg | tcatctcgat | tccagccata | gccagctttc | 420 |
| aaaagtacat | gtcgaacgca | actaagcacc | agtcaacatt | gactgacacg | ttacgcagta | 480 |
| tatgcggttt | cttggtgggt | acaagtgtcg | cgatattcct | tccgtcgcgc | taccacgagg | 540 |
| ttctgttccg | tccaattctt | gtattactgt | taatattcgg | ggcaatggct | actaccttag | 600 |
| ccggcttcgg | tttacttctc | gggccgacat | tgttttccgc | gacagccgcg | gttctgtgct | 660 |
| gctacacttg | tataaatgta | cgcaacgcga | atagcggaat | aaagcaattg | gcggccgccg | 720 |
| cagctggtaa | atgcatatta | ggaactgcca | tctcgagcat | gttggtttgc | gtgttaatac | 780 |
| aatattcctg | atcgcggagc | gattaatttt | tatatcatgt | gctcatagcg | ttctttcgaa | 840 |
| ctgcgaataa | aactttcgtg | gctactaaag | gggcctatcg | tgggtttatg | cgctgtcgaa | 900 |
| aacatgaaag | ggccgattta | aagctaagtt | gcgcaggcag | aggccactcc | atatacgctc | 960 |
| tcggagacgc | ggctcgcacg | ccagctgaaa | tattttcccc | cctgcaggtc | gacccaattc | 1020 |
| gagctcggta | cagcttggct | gtggaatgtg | tgtcagttag | ggtgtggaaa | gtccccaggc | 1080 |
| tccccagcag | gcagaagtat | gcaaagcatg | catctcaatt | agtcagcaac | caggtgtgga | 1140 |
| aagtccccag | gctccccagc | aggcagaagt | atgcaaagca | tgcatctcaa | ttagtcagca | 1200 |
| accatagtcc | cgcccctaac | tccgcccatc | ccgcccctaa | ctccgcccag | ttccgcccat | 1260 |
| tctccgcccc | atggctgact | aatttttttt | atttatgcag | aggccgaggc | cgcctcggcc | 1320 |
| tctgagctat | tccagaagta | gtgaggaggc | ttttttggag | gcctaggctt | ttgcaaaaag | 1380 |
| ctcccggggc | ggccgccacc | atgggcagca | gcccagcac | ctggatcagc | gtgaccctga | 1440 |
| tgctgatcac | cagaaccatg | ctgatcctga | gctgcatctg | ccccacaagc | agcctggacg | 1500 |
| gcagacccct | ggccgctgcc | ggcatcgtgg | tgaccggcga | caaggccgtg | aacatctaca | 1560 |
| ccagcagcca | gaccggcagc | atcatcatca | agctgctgcc | caacatgccc | aaggacaaag | 1620 |
| aggcctgcgc | caaggccccc | tggaagcct | acaacagaac | cctgaccacc | ctgctgaccc | 1680 |
| ccctgggcga | cagcatcaga | gaatccagg | gcagcgccac | cacaagcggc | ggaggaaagc | 1740 |
| agggcagact | ggtgggcgct | atcatcggga | gcgtggccct | gggcgtggcc | acagctgccc | 1800 |
| agattaccgc | tgcagccgcc | ctgattcagg | ccaatcagaa | cgccgccaac | atcctgagac | 1860 |
| tgaaagagag | cattgccgcc | accaacgacg | ccgtgcacga | agtgacaaac | ggactgtccc | 1920 |
| agctggctgt | cgctgtcggc | aagatgcagc | agttcgtgaa | caaccagttc | aacaacaccg | 1980 |
| ccagagagct | ggactgcatc | aagatcgccc | agcaggtggg | cgtggagctg | aacctgtacc | 2040 |
| tgaccgagct | gaccacagtg | ttcggcccc | agatcacaag | cccccgctctg | acccagctga | 2100 |
| caatccaggc | cctgtacaac | ctggctggcg | gcaacatgga | ctatctgctg | actaagctgg | 2160 |

```
gagtgggcaa caaccagctg tccagcctga tcgggtccgg gctgatcaca ggcaacccca    2220
tcctgtacga cagccagaca cagctgctgg gcatccagat caacctgcca tccgtgggaa    2280
gcctgaacaa catgagagcc acctacctgg aaaccctgag cgtgtccacc accaagggct    2340
tcgccagcgc cctggtgccc aaggtggtga cacaggtggg cagcgtgatc gaggaactgg    2400
acaccagcta ctgcatcgag agcgacatcg acctgtactg caccagagtg gtgaccttcc    2460
caatgagccc cggcatctac agctgcctga gcggcaacac cagcgcctgc atgtacagca    2520
agaccgaagg agcactgaca acaccctaca tggccctgaa gggaagcgtg atcgccaact    2580
gcaagatgac cacctgcaga tgcgccgacc ccccaggcat catcagccag aactacggcg    2640
aggccgtgag cctgatcgac aaacattcct gtagcgtgct gtccctggat ggcatcacac    2700
tgagactgag cggcgagttc gacgccacct accagaagaa catcagcatc ctggacagcc    2760
aggtgatcgt gaccggcaac ctggacatca gcaccgagct gggcaacgtg aacaacagca    2820
tcagcagcac cctggacaag ctggccgagt ccaacaacaa gctgaacaaa gtgaacgtga    2880
acctgaccag cacaagcgcc ctgatcacct acatcgtgct ggccatcgtg tccctggcct    2940
tcggcgtgat cagcctggtg ctggcctgct acctgatgta caagcagaga gcccagcaga    3000
aaaccctgct gtggctgggc aataacaccc tggaccagat gagggccacc accagaacct    3060
gatgagcggc cgcgatacct gcaggtttgc ggtgacattg atctggctca ttatatgccc    3120
cgagctcttg taacatcgcg gacgcgattt ccgtagtagg cacatctcaa atgcaaaagc    3180
ggcatgtcaa ccgtataggt acatccggcc ctgcttacag tcggtagggc atatatccac    3240
cggaaaactt cagctttaga ctcctcaggt gatgaggaat agtatgtaac cctctagcag    3300
tacggtattt ctaaaaaaag gtagatcctt ttccacacgg cacagactaa ataacgtaca    3360
ctacacaggt tctctcgaac ttcgtttgga ccggaattat tccctcggca gcgcctaaaa    3420
agcaaacctc tagagtagat aagtgtcagt gaacctaggc cttctttgtt ccacggctgg    3480
aaagctaagg gacgaggtac acgcgacccc agccacgcac gaacagagtt taacggaagc    3540
gtcgtttgcg ggataaggtt gtcggacccc gcgggtccgt tgaaaagtgg ctgcgcgcct    3600
accgacgaat acgtcggtaa caatttaga aatcgaatat gactgcgagt accgtacaat    3660
cgcgaaatac ggtctctata tagctactcg gtccttaaat atgtaagtat gatgtcccct    3720
actcccgaag acgaccgcga cttggtcgca gtacgtgggc tgctccggat gatggacgag    3780
accacatctg agcgacacaa acgttcgcgt tcaggatgcc cccggttgtt atgcggttgt    3840
acgatcggga tcgctcttac tgtgttcgtc atcacagcta cggtcgtgct agcttcgctg    3900
tttgcattct cttacatgtc cctggagtcc ggtacatgtc ctcacgaatg atcggttta    3960 ggctatagtt gtatgcgcgc gatggggagc aacgctaccg agctagaagc cctagatacg    4020
tgctcccgac ataacagcaa gcttgtcgac tttactcatg cgaaaattct aatcgaagct    4080
atcgc                                                               4085
```

<210> SEQ ID NO 38
<211> LENGTH: 4344
<212> TYPE: DNA
<213> ORGANISM: artificial sequence
<220> FEATURE:
<223> OTHER INFORMATION: partial plasmid sequence of pHM103+Fopt for vHVT114

<400> SEQUENCE: 38

```
gagctcaggg tatgatactc agctgttatt gtggccgacc aggaggactc caatgcttag    60
```

```
cattcataag aacgctagag atgctattta acgatgtgct gtcgtctaaa gaatttgtgc      120
atttagcctt taaatgtaaa accaatgacg cattcactac gctcgtgcgt gcaatttctg      180
ggccagggta tgcatattcc ataacagaaa tcgacacttg agaagaggat ctgactgttt      240
gggataaagg tcgtttgggt ctgtcctagc gatataattt atatgacgat atacattaaa     300
catctgtgtg cagtacttag gtatttaatc atgtcgatga aatgttatgt gtaaatatcg      360
gacaatatag ataacgggca cgctgctatt gtaacgtgcg cccgcgcgct agtgctgact      420
aatagtgtgg atgatgtata cagtatatta caaacggaaa tgatacgtaa taaattatgt      480
actcttattg atttataaaa acatacatgc agtgttgcta tgtcacataa ttagcctcgc      540
ccgtctacgc tccactgaag ataatgggct cccgctgttc aaaaaaatca gcgtgcgtcg      600
ataagacttt ggtgcagtct cttcggggtc gcaatttaga tttgccgcat ggagggtatc      660
tggggatttt tgccaatgct ggagcgacga ctgtacgatt cgtcccatcg ggatctagca      720
gaccaatgat gttgacacac atcggccatg catgtacgga cggtctattg cgcgagtttg      780
ttattttcga aggacaagat ggaagtgtat atggaaccga caataatgtt agtttgcatt      840
tcttagggcg gaatctacat gatatcttat ccaagcgggg tatgagccag agagatgtga      900
tggtcataaa gggtaaattt tttagatctg aaataacgca gttgcccaaa caacgatcgc      960
gattaaaaga aaaatcggat ggttcaatta ggacatgcat ggattctgtg cgcataaacc     1020
ataaccgcag cactgttggg cacttcggta actcaaatgc gaagcgttgc acgtctgcga     1080
taactacgcc tactatgcac attgttactc ctgcatctta aaaatatatc ctgtagtaat     1140
tttcacagca atgtcataac atcatctcgc taaagaatga cctgggattg gagaagtaat     1200
gaatatttgc aaccaatgca ttgaataaac taacattaaa cgaattcgag ctcggtacag     1260
cttggctgtg gaatgtgtgt cagttagggt gtggaaagtc cccaggctcc ccagcaggca     1320
gaagtatgca aagcatgcat ctcaattagt cagcaaccag gtgtggaaag tccccaggct     1380
ccccagcagg cagaagtatg caaagcatgc atctcaatta gtcagcaacc atagtcccgc     1440
ccctaactcc gcccatcccg cccctaactc gcccagttc cgccattct ccgcccatg      1500 gctgactaat ttttttatt tatgcagagg ccgaggccgc ctcggcctct gagctattcc     1560
agaagtagtg aggaggcttt tttggaggcc taggcttttg caaaaagctg cggccgccac     1620
catgggcagc aagcccagca caagaatccc agccccctg atgctgatca cccgcatcat     1680
gctgatcctg ggctgcatca gacccacaag ctccctggat ggacgccccc tggccgctgc     1740
cggcatcgtg gtgaccggcg acaaggccgt gaacgtgtac accagcagcc agaccggcag     1800
catcatcgtg aagctgctgc ccaacatgcc cagagacaaa gaggcctgcg ccaaggcccc     1860
cctggaagcc tacaacagaa ccctgaccac cctgctgacc cccctgggcg acagcatcag     1920
aaagatccag ggctccgtga gcacaagcgg cggaggaaag cagggcagac tgatcggcgc     1980
cgtgatcggc agcgtggccc tgggagtggc tacagctgcc cagattaccg ctgcagccgc     2040
cctgatccag gccaaccaga acgccgccaa catcctgaga ctgaaagaga gcattgccgc     2100
caccaacgag gccgtgcacg aagtgaccga cggcctgagc cagctgtccg tggccgtggg     2160
caagatgcag cagttcgtga acgaccagtt caacaacacc gccagagagc tggactgcat     2220
caagatcacc cagcaggtgg gcgtggagct gaacctgtac ctgaccgagc tgaccacagt     2280
gttcggcccc cagatcacaa gcccagccct gacacagctg accatccagg ccctgtacaa     2340
cctggctggc ggcaacatgg actatctgct gacaaagctg ggaatcggca acaaccagct     2400
```

```
gtccagcctg atcggaagcg gcctgatcac cggctacccc atcctgtacg acagccagac    2460
acagctgctg ggcatccagg tgaacctgcc cagcgtgggc aacctgaaca acatgcgcgc    2520
cacctacctg gaaaccctga gcgtgtccac caccaagggc tacgccagcg ccctggtgcc    2580
caaggtggtg acacaggtgg gcagcgtgat cgaggaactg acaccagct actgcatcga    2640 gagcgacctg gacctgtact gcaccagaat cgtgaccttc ccaatgagcc ccggcatcta    2700
cagctgcctg agcggcaaca ccagcgcctg catgtacagc aagaccgaag gcgcactgac    2760
aacaccctac atggccctga agggaagcgt gatcgccaac tgcaagatca ccacctgcag    2820
atgcaccgac cccccaggca tcatcagcca gaactacggc gaggccgtga gcctgatcga    2880
tcgccattcc tgtaacgtgc tgtccctgga cggcatcaca ctgagactga gcggcgagtt    2940
cgatgccacc taccgaaaga acatcagcat cctggacagc caggtgatcg tgaccggcaa    3000
cctggacatc agcaccgagc tgggcaacgt gaataacagc atcagcaacg ccctggacag    3060
actggccgag agcaacagca agctggaaaa agtgaacgtg cgcctgacat ccacttccgc    3120
tctgatcacc tacatcgtgc tgaccgtgat cagcctggtg ttcggcgccc tgagcctggt    3180
gctggcctgc tacctgatgt acaagcagaa ggcccagcag aaaaccctgc tgtggctggg    3240
caacaacacc ctggaccaga tgagagccac caccagagcc tgatgagcgg ccgcggggat    3300
ccagacatga taagatacat tgatgagttt ggacaaacca aactagaat gcagtgaaaa    3360 aaatgcttta tttgtgaaat tgtgatgct attgctttat ttgtaaccat tataagctgc    3420
aataaacaag ttaacaacaa caattgcatt gattttatgt ttcaggttca gggggaggtg    3480
tgggaggttt tttcggatcc tctagagtcg acaattattt tatttaataa catatagccc    3540
aaagacctct atgaacattt agtttcccgt atactcaacg gcgcgtgtac acacgcatct    3600
ctttgcatag cgatgaagtt tgttcggcag cagaaaatgc agatatccaa caatctggag    3660
aaaacttatc atcacagtgg cagtggaaac atacccccct ctatattcatg gtataattat    3720 cgtctacagc gtccaggata gtggcgtgag aaaatggaga tctgcagccc tccttttccat    3780 ggcatgccgc tttattgttc attaaacgca caatggtctc aacgccagat atgggcatag    3840
attctgaaga acccgttgac aatccgaaga agaaggcgtg caggtctttg gaagactcgc    3900
acgttggtct tataatgtat gatcgagatg tcaccctaat gccacatggt acaggcttat    3960
cgcggtcatg cgatcggac ttgtaatttg caacgatggg caaggatcg acgacatgcc    4020 aaacattctg aacccgtaga gatgttaacg atgacgagga tgaatatccc atgctcgctg    4080
ccatagtatc aagtacaccg cgaataagga gcgcgtccaac atcgttatat gcacacaatg    4140
ggctacacgt gactaacacc cccgaatatt agtcatatgt gagtttcagt ctggctccca    4200
tatagcctgt agactatttg tggtttaagt gtgaacgagg cgctgtgaac gagactcggg    4260
ccgattgtaa gaacaagcaa atgcactttc catttaacaa gaagtgtaga gagaatactc    4320
aacctctttg gatgtatcct cgag                                          4344

<210> SEQ ID NO 39
<211> LENGTH: 1362
<212> TYPE: DNA
<213> ORGANISM: artificial sequence
<220> FEATURE:
<223> OTHER INFORMATION: IBDV DNA encoding VP2 protein

<400> SEQUENCE: 39 atgacaaaacc tgcaagatca aacccaacag attgttccgt tcatacggag ccttctgatg      60
ccaacaaccg gaccggcgtc cattccggac gacacccctg agaagcacac tctcaggtca     120
```

```
gagacctcga cctacaattt gactgtgggg gacacagggt cagggctaat tgtcttttc      180 cctggattcc ctggctcaat tgtgggtgct cactacacac tgcagagcaa tgggaactac      240
aagttcgatc agatgctcct gactgcccag aacctaccgg ccagctacaa ctactgcaga      300
ctagtgagtc ggagtctcac agtgaggtca agcacactcc ctggtggcgt ttatgcacta      360
aacggcacca taaacgccgt gaccttccaa ggaagcctga gtgaactgac agatgttagc      420
tacaatgggt tgatgtctgc aacagccaac atcaacgaca aaattgggaa tgtcctggta      480
ggggaagggg tcactgtcct cagcctaccc acatcatatg atcttgggta tgtgaggctt      540
ggtgacccca ttcccgctat agggcttgac ccaaaaatgg tagctacatg cgacagcagt      600
gacaggccca gagtctacac cataactgca gccgatgatt accaattctc atcacagtac      660
caaccaggtg gggtaacaat cacactgttc tcagccaaca ttgatgctat cacaagcctc      720
agcattgggg gagagctcgt gtttcaaaca agcgtccaag gccttgtact gggcgccacc      780
atctacctta taggctttga tgggactgcg gtaatcacca gagctgtagc cgcagataat      840
gggctgacgg ccggcaccga caatcttatg ccattcaatc ttgtcattcc aaccaatgag      900
ataacccagc caatcacatc catcaaactg agatagtga cctccaaaag tggtggtcag      960 gcagggatc agatgtcatg gtcggcaagt gggagcctag cagtgacgat ccatggtggc     1020
aactatccag gggccctccg tcccgtcaca ctagtagcct acgaaagagt ggcaacagga     1080
tccgtcgtta cggtcgctgg ggtgagtaac ttcgagctga ttccaaatcc tgaactagca     1140
aagaacctgg ttacagaata cggccgattt gacccaggag ccatgaacta cacaaaattg     1200
atactgagtg agagggaccg tcttggcatc aagaccgtct ggccaacaag ggagtacact     1260
gattttcgtg agtacttcat ggaggtggcc gacctcaact ctcccctgaa gattgcagga     1320
gcatttggct tcaaagacat aatccgggct ataaggaggt aa                        1362
```

<210> SEQ ID NO 40
<211> LENGTH: 453
<212> TYPE: PRT
<213> ORGANISM: artificial sequence
<220> FEATURE:
<223> OTHER INFORMATION: IBDV VP2 protein

<400> SEQUENCE: 40

```
Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140
```

```
Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Ile Gly Gly Glu Leu Val Phe Gln Thr Ser Val Gln Gly Leu Val
                245                 250                 255

Leu Gly Ala Thr Ile Tyr Leu Ile Gly Phe Asp Gly Thr Ala Val Ile
            260                 265                 270

Thr Arg Ala Val Ala Ala Asp Asn Gly Leu Thr Ala Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg
    450
```

<210> SEQ ID NO 41
<211> LENGTH: 5178
<212> TYPE: DNA
<213> ORGANISM: artificial sequence
<220> FEATURE:
<223> OTHER INFORMATION: partial plasmid sequence of SB-1 US10mFwt SbfI for vSB1-004

<400> SEQUENCE: 41

```
gacataacca acatatcgtt tgatatacac aaggatatgt ggtaccgaat ggttttatgg      60
tctgcgtaca ggttttttc tacgatgggc gagatgtttc tgatagatga catttcaaac     120
tatgtcgcgc cggaccttgt cgaaaacgga cgatggaagt tatactgcag aacttgggat     180
attagggacg cggcgaagat aaaactaatc ggcccgtttc tacccgcgct attctctttt     240
```

```
cacctggaga actggaccgc aatgctctct ttaggcatcc ataagggttt cgatcgtcac      300
aatgcccgag gtacattaac ggcgatgccg ttcttaaaaa aaatattggt tggggcaatg      360
gaaattgcac gatttgcagt ggtgctttct ctacctatct gcgaataccg aacacctatg      420
ggattaccgg aagacgagat agggaatgca atcagattat gttgcgcaca atgcaggca      480 aatcgtctgg agcctacaga aataactaac gacgcagaag ggaagagcaa cgacgggtct      540
gcagaggaac tgtattatag agccttgcac gagatagtga agacggctag ggaacattgc      600
agagtccagg aggacactcc gccaacgatt caactgaata ccggggattc gagataccga      660
cagcagcgca tgtggaggaa cgatcctata cgcgtcccca ggtccagatt atcgaactgt      720
aaagcactgg agcgttttag acgagattta ggtcgcgggt ccatttttct ctagtttgcc      780
cctctgcgat tgctacgttt taactgaagt tagagaatat tgacgcagat tacaataaga      840
tgcaataact tctggtaagt caataaagtg cctgcaggcc caattcaata gtggatcccc      900
caactccgcc cgtttatga ctagaaccaa tagttttaa tgccaaatgc actgaaatcc      960
cctaatttgc aaagccaaac gcccctatg tgagtaatac ggggactttt tacccaattt     1020
cccacgcgga aagccccta atacactcat atggcatatg aatcagcacg gtcatgcact     1080
ctaatggcgg cccataggga cttttccacat aggggggcgtt caccatttcc cagcataggg     1140
gtggtgactc aatggccttt acccaagtac attgggtcaa tgggaggtaa gccaatgggt     1200
ttttcccatt actggcaagc acactgagtc aaatgggact ttccactggg ttttgcccaa     1260
gtacattggg tcaatgggag gtgagccaat gggaaaaacc cattgctgcc aagtacactg     1320
actcaatagg gactttccaa tgggtttttc cattgttggc aagcatataa ggtcaatgtg     1380
ggtgagtcaa tagggacttt ccattgtatt ctgcccagta cataaggtca ataggggtg     1440 aatcaacagg aaagtcccat ggagccaag tacactgcgt caatagggac tttccattgg     1500
gttttgccca gtacataagg tcaataggg atgagtcaat gggaaaaacc cattggagcc     1560
aagtacactg actcaatagg gactttccat tgggttttgc ccagtacata aggtcaatag     1620
ggggtgagtc aacaggaaag ttccattgga gccaagtaca ttgagtcaat agggactttc     1680
caatgggttt tgcccagtac ataaggtcaa tgggaggtaa gccaatgggt ttttcccatt     1740
actggcacgt atactgagtc attagggact ttccaatggg ttttgcccag tacataaggt     1800
caataggggt gaatcaacag gaaagtccca ttggagccaa gtacactgag tcaataggga     1860
ctttccattg ggttttgccc agtacaaaag gtcaataggg ggtgagtcaa tgggttttc     1920 ccattattgg cacgtacata aggtcaatag gggtgagtca ttgggttttt ccagccaatt     1980
taattaaaac gccatgtact ttcccaccat tgacgtcaat gggctattga aactaatgca     2040
acgtgacctt taaacggtac tttcccatag ctgattaatg ggaaagtacc gttctcgagc     2100
caatacacgt caatgggaag tgaaagggca gccaaaacgt aacaccgccc cggttttccc     2160
ctggaaattc catattggca cgcattctat tggctgagct gcgttctacg tgggtataag     2220
aggcgcgacc agcgtcggta ccgtcgcagt cttcggtctg accaccgtag aacgcagagc     2280
tcctcgctgc aggcggccgc atgggctcca aaccttctac caggatccca gcacctctga     2340
tgctgatcac ccgattatg ctgatattgg gctgtatccg tccgacaagc tctcttgacg     2400
gcaggcctct tgcagctgca ggaattgtag taacaggaga taaggcagtc aatgtataca     2460
cttcgtctca gacagggtca atcatagtca agttgctccc gaatatgccc agggataagg     2520
aggcgtgtgc aaaagcccca ttagaggcat ataacagaac actgactact ttgctcactc     2580
```

```
ctcttggcga ctccatccgc aagatccaag ggtctgtgtc cacatctgga ggaggcaagc    2640
aaggccgcct gataggtgct gttattggca gtgtagctct tggggttgca acagcggcac    2700
agataacagc agctgcggcc ctaatacaag ccaaccagaa tgccgccaac atcctccggc    2760
ttaaggagag cattgctgca accaatgaag ctgtgcatga agtcaccgac ggattatcac    2820
aactatcagt ggcagttggg aagatgcagc agtttgtcaa tgaccagttt aataatacgg    2880
cgcgagaatt ggactgtata aaaatcacac aacaggttgg tgtagaactc aacctatacc    2940
taactgaatt gactacagta ttcgggccac agatcacctc ccctgcatta actcagctga    3000
ccatccaggc actttataat ttagctggtg gcaatatgga ttacttatta actaagttag    3060 gtataggaa caatcaactc agctcgttaa ttggtagcgg cctgatcact ggttacccta    3120
tactgtatga ctcacagact caactcttgg gcatacaagt gaatttaccc tcagtcggga    3180
acttaaataa tatgcgtgcc acctatttgg agaccttatc tgtaagtaca accaaaggat    3240
atgcctcagc acttgtcccg aaagtagtga cacaagtcgg ttccgtgata gaagagcttg    3300
acacctcata ctgtatagag tccgatctgg atttatattg tactagaata gtgacattcc    3360
ccatgtcccc aggtatttat tcctgtttga gcggcaacac atcagcttgc atgtattcaa    3420
agactgaagg cgcactcact acgccgtata tggcccttaa aggctcagtt attgccaatt    3480
gtaaaataac aacatgtaga tgtacagacc ctcctggtat catatcgcaa aattatggag    3540
aagctgtatc cctgatagat agacattcgt gcaatgtctt atcattagac gggataactc    3600
taaggctcag tggggaattt gatgcaactt atcaaaagaa catctcaata ctagattctc    3660
aagtcatcgt gacaggcaat cttgatatat caactgaact tggaaacgtc aacaattcaa    3720
tcagcaatgc cttggatagg ttggcagaaa gcaacagcaa gctagaaaaa gtcaatgtca    3780
gactaaccag cacatctgct ctcattacct atattgttct aactgtcatt tctctagttt    3840
tcggtgcact tagtctggtg ttagcgtgtt acctgatgta caaacagaag gcacaacaaa    3900
agaccttgct atggcttggg aataatcccc tcgatcagat gagagccact acaagagcat    3960
gagcggccgc ggggatccag acatgataag atacattgat gagtttggac aaaccacaac    4020
tagaatgcag tgaaaaaaat gctttatttg tgaaatttgt gatgctattg ctttatttgt    4080
aaccattata agctgcaata acaagttaaa caacaacaat tgcattgatt ttatgtttca    4140
ggttcagggg gaggtgtggg aggtttttc ggatcctcta gagtcgaggg tcgacgatat    4200
cctgcaggtt tatttgcaaa actctataca ttgtttccga gccctgtcat tcgcgcaaat    4260
ttactcaatg tcttccccat cgtctggagg cgaagattca gacgattgtc gcacgttgat    4320
caggtaatgt gccacttcga cgtcgtcgta aattaatgca ttcccttcg ctgctacagc    4380 ccggcataaa ggcttccaat aagactctac ttcagtaagc gggctttctc cacagcctgt    4440
tgccattccc aacaacttaa tcagatcact gttttcctca tataaatggg aaacaataca    4500
gcagccagga tgcccaagac aacaccaata cataatagca gtcagacggc tatccatttc    4560
tccatgcgtt tcaggtgcat gcttataatt tcgcaatgca acacttacta ttttcctcaa    4620
cgaaccggct acgtagaaat ttgatgtgga ccgttgttcg cggcggattg ttgcgtcagt    4680
taaatccatt atctcacgcc acaggtgaat ggatggcggc ataccagctt tcattgccgc    4740
gaaagagacc atggcagcgg tcaatacagt tcgggccaaa ccgcgtacag actttggcag    4800
ggatgatata tgtactccac cagcagaaag tataccgtat actttctcat tcgcaggatc    4860
cggccacaga tgagatgttc tgcgaagttt gcggcacacc gaccacaggc ccatttgctt    4920
ttgcggtgat ggtacttcac atacctcact ggacatatca caatattatc ttgcgcggtg    4980
```

```
gtgcaccttc tgtctctata gacacccagc tcccaaatgt caggtcggat aacgttgtag     5040
tcaatagaaa tctatatggt acaagtcacg cccacactgc gttacttaat taacgcgaca     5100
tactcattca ataaataaca ggcaaagtga ttactggcaa taggacattt attgttcgtc     5160
tacatcagtg agttttgt                                                   5178
```

<210> SEQ ID NO 42
<211> LENGTH: 4226
<212> TYPE: DNA
<213> ORGANISM: artificial sequence
<220> FEATURE:
<223> OTHER INFORMATION: partial plasmid sequence of SB1 UL55 SVFopt syn tail SbfI for vSB1-006

<400> SEQUENCE: 42

```
gtcctcagcc ttgcgctagt aagctgtaat acagagaacg gggcacgaac gtgcatcgaa       60
acattatttt cctttggagg tgccgtgctg gaaacaaaca ttctgattca tgcaattaac      120
caactgcttc ctttgtgcga tgtcatggcg gtttccggaa taagtagact tgctatcata      180
gaatcaatcc ccgaactcgg aacggttcca tacaggtgcg ttttacaagc gacgcctcat      240
attacagcgt gtctcacccc caaggtagtc agatgcatga attatgggat actactatct      300
cactgggagg aatgcgtcgt gcgggattcg aaatacatcg taaacgtacc cacgcaaaca      360
cagtttgtca catccttaac ccgttgtccg cacgggccag tcgccaacga ttggtacctt      420
ggattcttct tcccatttaa ggggttcagg gtaataaccg tcagaacaag gcgctggctg      480
gcagcatata cctacagatt tcgaaagtgg ttgcaatggg aagagggttc cccccactac      540
gtcgctttga ggcgtctggt cccactatgt gattgctact tgatggatgc ttgcatgaca      600
aacaactttt ttgcctgcgg aatgctattc cacttacact gcgtcccaat acccgcgcgc      660
gaaaaacgca ttgtggcgat actggcgaga gcgattgatg acgcgcaaac atatgcggga      720
acctcactgc acgtagatac gagtgaacag tagagcgtta gtatgtggtt ttctttaggt      780
gttactacca cttacattcc tacaaaatca ctactcccgt attagatctc aacgctatac      840
cggcgtaggc gaacctgagg gtgcgcccct agctctcgca attggtatgc gtaaatgaat      900
tgttatcgcg ggttgccata agattttgta tacatacgaa cccgagaatg tataaaccaa      960
taaatgctga aatggtagac ctgcaggtcg acccaattcg agctcggtac agcttggctg     1020
tggaatgtgt gtcagttagg gtgtggaaag tccccaggct ccccagcagg cagaagtatg     1080
caaagcatgc atctcaatta gtcagcaacc aggtgtggaa agtccccagg ctccccagca     1140
ggcagaagta tgcaaagcat gcatctcaat tagtcagcaa ccatagtccc gcccctaact     1200
ccgcccatcc cgcccctaac tccgcccagt tccgcccatt ctccgcccca tggctgacta     1260
atttttttta tttatgcaga ggccgaggcc gcctcggcct ctgagctatt ccagaagtag     1320
tgaggaggct ttttggagg cctaggcttt tgcaaaaagc tcccgggcg ccgccacca       1380 tgggcagcaa gcccagcaca agaatcccag ccccctgat gctgatcacc cgcatcatgc     1440
tgatcctggg ctgcatcaga cccacaagct ccctggatgg acgccccctg ccgctgccg     1500 gcatcgtggt gaccggcgac aaggccgtga acgtgtacac cagcagccag accgcagca     1560 tcatcgtgaa gctgctgccc aacatgccca gagacaaaga ggcctgcgcc aaggccccc     1620 tggaagccta caacgaaacc ctgaccaccc tgctgacccc cctgggcgac agcatcagaa     1680
agatccaggg ctccgtgagc acaagcggcg gaggaaagca gggcagactg atcggcgccg     1740
tgatcggcag cgtggcccct gggagtggcta cagctgccca gattaccgct gcagccgccc     1800
```

```
tgatccaggc caaccagaac gccgccaaca tcctgagact gaaagagagc attgccgcca    1860
ccaacgaggc cgtgcacgaa gtgaccacg gcctgagcca gctgtccgtg gccgtgggca     1920
agatgcagca gttcgtgaac gaccagttca acaacaccgc cagagagctg gactgcatca    1980
agatcaccca gcaggtgggc gtggagctga acctgtacct gaccgagctg accacagtgt    2040
tcggccccca gatcacaagc ccagccctga cacagctgac catccaggcc ctgtacaacc    2100
tggctggcgg caacatggac tatctgctga caaagctggg aatcggcaac aaccagctgt    2160
ccagcctgat cggaagcggc ctgatcaccg ctacccat cctgtacgac agccagacac      2220
agctgctggg catccaggtg aacctgccca gcgtgggcaa cctgaacaac atgcgcgcca    2280
cctacctgga aaccctgagc gtgtccacca ccaagggcta cgccagcgcc ctggtgccca    2340
aggtggtgac acaggtgggc agcgtgatcg aggaactgga caccagctac tgcatcgaga    2400
gcgacctgga cctgtactgc accagaatcg tgaccttccc aatgagcccc ggcatctaca    2460
gctgcctgag cggcaacacc agcgcctgca tgtacagcaa gaccgaaggc gcactgacaa    2520 cacccctacat ggccctgaag ggaagcgtga tcgccaactg caagatcacc acctgcagat    2580
gcaccgaccc cccaggcatc atcagccaga actacgcga ggccgtgagc ctgatcgatc      2640
gccattcctg taacgtgctg tccctggacg gcatcacact gagactgagc ggcgagttcg    2700
atgccaccta ccagaagaac atcagcatcc tggacgccca ggtgatcgtg accggcaacc    2760
tggacatcag caccgagctg ggcaacgtga ataacagcat cagcaacgcc ctggacagac    2820
tggccgagag caacagcaag ctggaaaaag tgaacgtgcg cctgacatcc acttccgctc    2880
tgatcaccta catcgtgctg accgtgatca gcctggtgtt cggcgccctg agcctggtgc    2940
tggcctgcta cctgatgtac aagcagaagg cccagcagaa aaccctgctg tggctgggca    3000
acaacaccct ggaccagatg agagccacca ccagagcctg atgagcggcc gcgatatcaa    3060
taaaatatct ttattttcat tacatctgtg tgttggtttt tgtgtgaat cgatagtact     3120 aacatacgct ctccatcaaa acaaaacgaa acaaaacaaa ctagcaaaat aggctgtccc    3180
cagtgcaagt gcaggtgcca gaacatttct cttctagacc tgcaggtcaa atcatgattc    3240 gttttttattc agtgtccgta ctcgcgaata gctctgcact gcgatgcgat tttttcggca   3300
gcgctaaaag ccgatctcca acactcgagc gaaaacttat tttcgcagtg caatgaaaa     3360 cacagtccct ctatagccat gctgtagttt tcatccagtg agtcgatgat cgtcgcatga    3420
gaaaaaggcg actcgcattg gtcgcctgtc aatcgaccag tccgtaactt cttgttcatt    3480
ctatacgcga tatacgaggc accgcattgg gacatgttct cagacggatc cgtcgccaat    3540
ccaaagaaga acgcgtggaa agtcgtcgac gatttacacg ctgcccgtat gacgtacgaa    3600
cgaggaataa cggatcggc acatgacaca tgttcgcccg tagctagttg agtagaggcg     3660
gacggcacgt caattgctaa cggagcgatc acttgccaaa cgtacggaat tcgtaccggt    3720
gaagctgacg gttcagctgt actttccgcc attggacact gtagaactga ggatctgcca    3780
ccgctgggcg cacgtggttt ctgccgggtg ttatataagt ttttccacgc ccactacgtg    3840
ttacctacac actcacggca cgtggtacgt ggacgtaagg gatggccgta atgaaaatg     3900 caccgggcga ctagttgtcc cgtctagcat gaccatgcat tgtagaccgc aggtccagcg    3960
ctgcgccaat tacgactcta catcggacgc tccaacccag acgggcttcc caatgtggct    4020 cacccccgaga gaactctcac cgactaacgt ttatggaata gtcgctagac cggtactcct   4080
cacgcacgcc gggggcccaa taaacagtgt actgacggga ggttggaaag ggagaatggt    4140
```

<210> SEQ ID NO 43
<211> LENGTH: 4085
<212> TYPE: DNA
<213> ORGANISM: artificial sequence
<220> FEATURE:
<223> OTHER INFORMATION: partial plasmid sequence of pSB1 44cds SVOptF for vSB1-007

<400> SEQUENCE: 43

```
cacggcaacg tcgtctatct gcgaaaggat actgctttgg gtagcggata cgcagcgttc     4200
ttctccgagc accggatcgt ttgacc                                          4226 gcgatagctt cgattagaat tttcgcatga gtaaagtcga caagcttgct gttatgtcgg      60
gagcacgtat ctagggcttc tagctcggta gcgttgctcc ccatcgcgcg catacaacta     120
tagcctaaac cgatccattc gtgaggacat gtaccggact ccagggacat gtaagagaat     180
gcaaacagcg aagctagcac gaccgtagct gtgatgacga acacagtaag agcgatcccg     240
atcgtacaac cgcataacaa ccgggggcat cctgaacgcg aacgtttgtg tcgctcagat     300
gtggtctcgt ccatcatccg gagcagccca cgtactgcga ccaagtcgcg gtcgtcttcg     360
ggagtagggg acatcatact tacatatttta aggaccgagt agctatatag agaccgtatt     420
tcgcgattgt acggtactcg cagtcatatt cgatttctaa aattgttacc gacgtattcg     480
tcggtaggcg cgcagccact tttcaacgga cccgcgggt ccgacaacct tatcccgcaa      540
acgacgcttc cgttaaactc tgttcgtgcg tggctggggt cgcgtgtacc tcgtccctta     600
gctttccagc cgtggaacaa agaaggccta ggttcactga cacttatcta ctctagaggt     660
ttgcttttta ggcgctgccg agggaataat tccggtccaa acgaagttcg agagaacctg     720
tgtagtgtac gttatttagt ctgtgccgtg tggaaaagga tctacctttt tttagaaata     780
ccgtactgct agagggttac atactattcc tcatcacctg aggagtctaa agctgaagtt     840
ttccggtgga tatatgccct accgactgta agcagggccg gatgtaccta tacggttgac     900
atgccgcttt tgcatttgag atgtgcctac tacggaaatc gcgtccgcga tgttacaaga     960
gctcggggca tataatgagc cagatcaatg tcaccgcaaa cctgcaggtc gacccaattc    1020
gagctcggta cagcttggct gtggaatgtg tgtcagttag ggtgtggaaa gtccccaggc    1080
tccccagcag gcagaagtat gcaaagcatg catctcaatt agtcagcaac caggtgtgga    1140
aagtccccag gctccccagc aggcagaagt atgcaaagca tgcatctcaa ttagtcagca    1200
accatagtcc cgcccctaac tccgcccatc ccgcccctaa ctccgcccag ttccgcccat    1260
tctccgcccc atggctgact aattttttt atttatgcag aggccgaggc cgcctcggcc    1320
tctgagctat tccagaagta gtgaggaggc ttttttggag gcctaggctt ttgcaaaaag    1380
ctcccggggc ggccgccacc atgggcagca agcccagcac aagaatccca gcccccctga    1440
tgctgatcac ccgcatcatg ctgatcctgg gctgcatcag acccacaagc tccctggatg    1500
gacgccccct ggccgctgcc ggcatcgtgg tgaccggcga caggccgtg aacgtgtaca    1560
ccagcagcca gaccggcagc atcatcgtga agctgctgcc caacatgccc agagacaaag    1620
aggcctgcgc caaggccccc ctggaagcct acaacagaac cctgaccacc ctgctgaccc    1680
ccctgggcga cagcatcaga aagatccagg gctccgtgag cacaagcggc ggaggaaagc    1740
agggcagact gatcggcgcc gtgatcggca gcgtggccct gggagtggct acagctgccc    1800
agattaccgc tgcagccgcc ctgatccagg ccaaccagaa cgccgccaac atcctgagac    1860
tgaaagagag cattgccgcc accaacgagg ccgtgcacga agtgaccgac ggcctgagcc    1920
```

```
agctgtccgt ggccgtgggc aagatgcagc agttcgtgaa cgaccagttc aacaacaccg    1980
ccagagagct ggactgcatc aagatcaccc agcaggtggg cgtggagctg aacctgtacc    2040
tgaccgagct gaccacagtg ttcggccccc agatcacaag cccagccctg acacagctga    2100
ccatccaggc cctgtacaac ctggctggcg caacatgga ctatctgctg acaaagctgg    2160
gaatcggcaa caaccagctg tccagcctga tcggaagcgg cctgatcacc ggctacccca    2220
tcctgtacga cagccagaca cagctgctgg gcatccaggt gaacctgccc agcgtgggca    2280
acctgaacaa catgcgcgcc acctacctgg aaaccctgag cgtgtccacc accaagggct    2340
acgccagcgc cctggtgccc aaggtggtga cacaggtggg cagcgtgatc gaggaactgg    2400
acaccagcta ctgcatcgag agcgacctgg acctgtactg caccagaatc gtgaccttcc    2460
caatgagccc cggcatctac agctgcctga gcggcaacac cagcgcctgc atgtacagca    2520
agaccgaagg cgcactgaca cacccctaca tggccctgaa gggaagcgtg atcgccaact    2580
gcaagatcac cacctgcaga tgcaccgacc ccccaggcat catcagccag aactacggcg    2640
aggccgtgag cctgatcgat cgccattcct gtaacgtgct gtccctggac ggcatcacac    2700
tgagactgag cggcgagttc gatgccacct accagaagaa catcagcatc ctggacagcc    2760
aggtgatcgt gaccggcaac ctggacatca gcaccgagct gggcaacgtg aataacagca    2820
tcagcaacgc cctggacaga ctggccgaga gcaacagcaa gctggaaaaa gtgaacgtgc    2880
gcctgacatc cacttccgct ctgatcacct acatcgtgct gaccgtgatc agcctggtgt    2940
tcggcgccct gagcctggtg ctggcctgct acctgatgta caagcagaag gcccagcaga    3000
aaaccctgct gtggctgggc aacaacaccc tggaccagat gagagccacc accagagcct    3060
gatgagcggc cgcgataccc tgcaggggga aaatatttca gctggcgtgc gagccgcgtc    3120
tccgagagcg tatatggagt ggcctctgcc tgcgcaactt agctttaaat cggcccttc    3180 atgttttcga cagcgcataa acccacgata ggcccctta gtagccacga agtttatt    3240 cgcagttcga agaacgcta tgagcacatg atataaaaat taatcgctcc gcgatcagga    3300
atattgtatt aacacgcaaa ccaacatgct cgagatggca gttcctaata tgcatttacc    3360
agctgcggcg gccgccaatt gctttattcc gctattcgcg ttgcgtacat ttatacaagt    3420
gtagcagcac agaaccgcgg ctgtcgcgga aaacaatgtc ggcccgagaa gtaaaccgaa    3480
gccggctaag gtagtagcca ttgccccgaa tattaacagt aatacaagaa ttggacggaa    3540
cagaacctcg tggtagcgcg acggaaggaa tatcgcgaca cttgtaccca ccaagaaacc    3600
gcatatactg cgtaacgtgt cagtcaatgt tgactggtgc ttagttgcgt tcgacatgta    3660
cttttgaaag ctggctatgg ctggaatcga gatgaccgct atgaggctca gaattatcgt    3720
aggaatattc cccccagcg tatcgtaact ggatacgtct tcttcgcgcg tcgcctcggc    3780
gtccgtgctg ggcgggagac gcgcgcgacc gaggcgatat gcaccgttca cagtaattc    3840 ccgacgtgca cggtagtagc acgtgttcat tagagaccga ctggcgtctc tgaccacgtg    3900
aatagctaac gccgtatacg ccgaaagaaa gccggctaga ggagaaatgt ctccatacgg    3960
agccgtgatg ccggcaatcg tccctgccgc cacaactaaa aacccggtct tccacgtcac    4020
gtctccagac gttgctatgc agacgtaatg ataagatgcg atcagagctc cgagcatgac    4080
aaaag                                                                4085
```

<210> SEQ ID NO 44
<211> LENGTH: 4226
<212> TYPE: DNA
<213> ORGANISM: artificial sequence
<220> FEATURE:
<223> OTHER INFORMATION: partial plasmid sequence of SB-1 UL55 CAFopt
syn tail SbfI for vSB1-008

<400> SEQUENCE: 44

```
gtcctcagcc ttgcgctagt aagctgtaat acagagaacg gggcacgaac gtgcatcgaa     60
acattatttt cctttggagg tgccgtgctg gaaacaaaca ttctgattca tgcaattaac    120
caactgcttc ctttgtgcga tgtcatggcg gtttccggaa taagtagact tgctatcata    180
gaatcaatcc ccgaactcgg aacggttcca tacaggtgcg ttttacaagc gacgcctcat    240
attacagcgt gtctcacccc caaggtagtc agatgcatga attatgggat actactatct    300
cactgggagg aatgcgtcgt gcgggattcg aaatacatcg taaacgtacc cacgcaaaca    360
cagtttgtca catccttaac ccgttgtccg cacgggccag tcgccaacga ttggtacctt    420
ggattcttct tcccatttaa ggggttcagg gtaataaccg tcagaacaag gcgctggctg    480
gcagcatata cctacagatt tcgaaagtgg ttgcaatggg aagagggttc cccccactac    540
gtcgctttga ggcgtctggt cccactatgt gattgctact tgatggatgc ttgcatgaca    600
aacaactttt ttgcctgcgg aatgctattc cacttacact gcgtcccaat acccgcgcgc    660
gaaaaacgca ttgtggcgat actggcgaga gcgattgatg acgcgcaaac atatgcggga    720
acctcactgc acgtagatac gagtgaacag tagagcgtta gtatgtggtt ttctttaggt    780
gttactacca cttacattcc tacaaaatca ctactcccgt attagatctc aacgctatac    840
cggcgtaggc gaacctgagg gtgcgcccct agctctcgca attggtatgc gtaaatgaat    900
tgttatcgcg ggttgccata agattttgta tacatacgaa cccgagaatg tataaaccaa    960
taaatgctga aatggtagac ctgcaggtcg acccaattcg agctcggtac agcttggctg   1020
tggaatgtgt gtcagttagg gtgtggaaag tccccaggct ccccagcagg cagaagtatg   1080
caaagcatgc atctcaatta gtcagcaacc aggtgtggaa agtccccagg ctccccagca   1140
ggcagaagta tgcaaagcat gcatctcaat tagtcagcaa ccatagtccc gcccctaact   1200
ccgcccatcc cgcccctaac tccgcccagt tccgcccatt ctccgcccca tggctgacta   1260
atttttttta tttatgcaga ggccgaggcc gcctcggcct ctgagctatt ccagaagtag   1320
tgaggaggct tttttggagg cctaggcttt tgcaaaaagc tcccggggcg gccgccacca   1380
tgggcagcaa gcccagcacc tggatcagcg tgaccctgat gctgatcacc agaaccatgc   1440
tgatcctgag ctgcatctgc cccacaagca gcctggacgg cagacccctg gccgctgccg   1500
gcatcgtggt gaccggcgac aaggccgtga acatctacac cagcagccag accggcagca   1560
tcatcatcaa gctgctgccc aacatgccca aggacaaaga ggcctgcgcc aaggcccccc   1620
tggaagccta caacagaacc ctgaccaccc tgctgacccc cctgggcgac agcatcagaa   1680
gaatccaggg cagcgccacc acaagcggcg gaggaaagca gggcagactg gtgggcgcta   1740
tcatcgggag cgtggccctg ggcgtggcca cagctgccca gattaccgct gcagccgccc   1800
tgattcaggc caatcagaac gccgccaaca tcctgagact gaaagagagc attgccgcca   1860
ccaacgacgc cgtgcacgaa gtgacaaacg gactgtccca gctggctgtc gctgtcggca   1920
agatgcagca gttcgtgaac aaccagttca acaacaccgc cagagagctg gactgcatca   1980
agatcgccca gcaggtgggc gtggagctga acctgtacct gaccgagctg accacagtgt   2040
tcggccccca gatcacaagc cccgctctga cccagctgac aatccaggcc ctgtacaacc   2100
tggctggcgg caacatggac tatctgctga ctaagctggg agtgggcaac aaccagctgt   2160
ccagcctgat cgggtccggg ctgatcacag gcaaccccat cctgtacgac agccagacac   2220
```

```
agctgctggg catccagatc aacctgccat ccgtgggaag cctgaacaac atgagagcca    2280
cctacctgga aaccctgagc gtgtccacca ccaagggctt cgccagcgcc ctggtgccca    2340
aggtggtgac acaggtgggc agcgtgatcg aggaactgga caccagctac tgcatcgaga    2400
gcgacatcga cctgtactgc accagagtgg tgaccttccc aatgagcccc ggcatctaca    2460
gctgcctgag cggcaacacc agcgcctgca tgtacagcaa gaccgaagga gcactgacaa    2520
caccctacat ggccctgaag ggaagcgtga tcgccaactg caagatgacc acctgcagat    2580
gcgccgaccc cccaggcatc atcagccaga actacggcga ggccgtgagc ctgatcgaca    2640
aacattcctg tagcgtgctg tccctggatg gcatcacact gagactgagc ggcgagttcg    2700
acgccaccta ccagaagaac atcagcatcc tggacagcca ggtgatcgtg accggcaacc    2760
tggacatcag caccgagctg ggcaacgtga acaacagcat cagcagcacc ctggacaagc    2820
tggccgagtc caacaacaag ctgaacaaag tgaacgtgaa cctgaccagc acaagcgccc    2880
tgatcaccta catcgtgctg gccatcgtgt ccctggcctt cggcgtgatc agcctggtgc    2940
tggcctgcta cctgatgtac aagcagagag cccagcagaa aaccctgctg tggctgggca    3000
ataacaccct ggaccagatg agggccacca ccagaacctg atgagcggcc gcgatatcaa    3060
taaaatatct ttattttcat tacatctgtg tgttggtttt ttgtgtgaat cgatagtact    3120
aacatacgct ctccatcaaa acaaaacgaa acaaaacaaa ctagcaaaat aggctgtccc    3180
cagtgcaagt gcaggtgcca gaacatttct cttctagacc tgcaggtcaa atcatgattc    3240 gttttattc agtgtccgta ctcgcgaata gctctgcact gcgatgcgat tttttcggca    3300
gcgctaaaag ccgatctcca acactcgagc gaaaacttat tttcgcagtg caatgaaaa    3360 cacagtccct ctatagccat gctgtagttt tcatccagtg agtcgatgat cgtcgcatga    3420
gaaaaaggcg actcgcattg gtcgcctgtc aatcgaccag tccgtaactt cttgttcatt    3480
ctatacgcga tatcgaggc accgcattgg acatgttct cagacggatc cgtcgccaat    3540
ccaaagaaga acgcgtggaa agtcgtcgac gatttacacg ctgcccgtat gacgtacgaa    3600
cgaggaataa cggatgcggc acatgacaca tgttcgcccg tagctagttg agtagaggcg    3660
gacggcacgt caattgctaa cggagcgatc acttgccaaa cgtacggaat tcgtaccggt    3720
gaagctgacg gttcagctgt actttccgcc attggacact gtagaactga ggatctgcca    3780
ccgctgggcg cacgtggttt ctgccgggtg ttatataagt ttttccacgc ccactacgtg    3840
ttacctacac actcacggca cgtggtacgt ggacgtaagg gatggccgta atgaaaaatg    3900
caccgggcga ctagttgtcc cgtctagcat gaccatgcat tgtagaccgc aggtccagcg    3960
ctgcgccaat tacgactcta catcggacgc tccaacccag acgggcttcc caatgtggct    4020
caccccgaga gaactctcac cgactaacgt ttatggaata gtcgctagac cggtactcct    4080
cacgcacgcc gggggcccaa taaacagtgt actgacggga ggttggaaag ggagaatggt    4140
cacggcaacg tcgtctatct gcgaaaggat actgctttgg gtagcggata cgcagcgttc    4200
ttctccgagc accggatcgt ttgacc                                         4226
```

<210> SEQ ID NO 45
<211> LENGTH: 4335
<212> TYPE: DNA
<213> ORGANISM: artificial sequence
<220> FEATURE:
<223> OTHER INFORMATION: partial plasmid sequence of pHVT US2
      SV-Fopt-synPA for vHVT306

<400> SEQUENCE: 45

```
taaaatggga tctatcatta cattcgttaa gagtctggat aatttttactg tttgccagct    60
tcgatcttgg aacgtactgt ggatagtgcc ttacttggaa tcgtgaaaat ttgaaacgtc   120
cattatttgg atatcttccg gttgtcccat atcccgccct ggtaccgctc ggataccttg   180
cccgtatgga ttcgtattga cagtcgcgca atcggggacc aacaacgcgt gggtccacac   240
tcattcggaa atttttccgat gattctgaat atttattgcc gctcgttacg agtcgttgga   300
catatctgta atacatttct tcttctgaag gatcgctgca catttgatct atacattggc   360
caggatgttc aagtctcaga tgttgcattc tggcacagca caactttatg gcatttccga   420
tgtaatcgtc cggcagccct gggggagttc tatattcgca tattgggatg gtaaggacaa   480
tagcagatct cgcaacctcc agggaggcta taataacgtt tttaaaggat ggatttctca   540
taaaaatctg tcgcaaatta cactgagaat atcctttact agcgccgatt gagagcatcg   600
tcgtccaatt ttctaaatgg aaagaaaaca aggcgggcaa gagtgttcca acatttttca   660
ttttcggcga atctctcaaa tcccatggcg tgcaattgat tgcaaaattg gcacttccgt   720
tcacgtttgt atctccaaac tctaagacac ttttaattga aaaactacgt tctagtgtgg   780
aaagaaacct ataggcagac catagaacta tttgacacca catatctttt tgtatgtcaa   840
actgaccatg atcgtatgtt gctgaatgca ctagggcaat tcgctcgcgc gactccatac   900
attgaataat tccacacgtc agctcatcgg ttagcaaggt ccagtagttg aagtcattta   960
ttttttcccg cggctggcca aatctacctc tgggaatatc caagttgtcg aatatgatcg  1020
caccggctct ggtcatggtg aaggaacttg tagcataaag acgcaggtat catagggta  1080
ataattttttt attcactcac atactaaaag taacgcatat tagcaccatg tatgggctat  1140
caattgacat ttgcgtagca ctacatcacg attatgtaca acataatggg acaacatatg  1200
cctgcaggtc gacccaattc gagctcggta cagcttggct gtggaatgtg tgtcagttag  1260
ggtgtggaaa gtccccaggc tccccagcag gcagaagtat gcaaagcatg catctcaatt  1320
agtcagcaac caggtgtgga agtccccag gctccccagc aggcagaagt atgcaaagca  1380
tgcatctcaa ttagtcagca accatagtcc cgcccctaac tccgcccatc cgcccctaa  1440
ctccgcccag ttccgcccat tctccgcccc atggctgact aatttttttt atttatgcag  1500
aggccgaggc cgcctcggcc tctgagctat tccagaagta gtgaggaggc ttttttggag  1560
gcctaggctt ttgcaaaaag ctcccggggc ggccgccacc atgggcagca gcccagcac  1620
aagaatccca gccccctga tgctgatcac ccgcatcatg ctgatcctgg gctgcatcag  1680
acccacaagc tccctggatg gacgccccct ggccgctgcc ggcatcgtgg tgaccggcga  1740
caaggccgtg aacgtgtaca ccagcagcca gaccggcagc atcatcgtga agctgctgcc  1800
caacatgccc agagacaaag aggcctgcgc caaggccccc ctggaagcct acaacagaac  1860
cctgaccacc ctgctgaccc cctgggcga cagcatcaga aagatccagg ctccgtgag  1920
cacaagcggc ggaggaaagc agggcagact gatcggcgcc gtgatcggca gcgtggccct  1980
gggagtggct acagctgccc agattaccgc tgcagccgcc ctgatccagg ccaaccagaa  2040
cgccgccaac atcctgagac tgaaagagag cattgccgcc accaacgagg ccgtgcacga  2100
agtgaccgac ggcctgagcc agctgtccgt ggccgtgggc aagatgcagc agttcgtgaa  2160
cgaccagttc aacaacaccg ccagagagct ggactgcatc aagatcaccc agcaggtggg  2220
cgtggagctg aacctgtacc tgaccgagct gaccacagtg ttcggccccc agatcacaag  2280
cccagccctg acacagctga ccatccaggc cctgtacaac ctggctggcg gcaacatgga  2340
```

```
ctatctgctg acaaagctgg gaatcggcaa caaccagctg tccagcctga tcggaagcgg    2400
cctgatcacc ggctacccca tcctgtacga cagccagaca cagctgctgg gcatccaggt    2460
gaacctgccc agcgtgggca acctgaacaa catgcgcgcc acctacctgg aaaccctgag    2520
cgtgtccacc accaagggct acgccagcgc cctggtgccc aaggtggtga cacaggtggg    2580
cagcgtgatc gaggaactgg acaccagcta ctgcatcgag agcgacctgg acctgtactg    2640
caccagaatc gtgaccttcc caatgagccc cggcatctac agctgcctga gcggcaacac    2700
cagcgcctgc atgtacagca agaccgaagg cgcactgaca cacccctaca tggccctgaa    2760
gggaagcgtg atcgccaact gcaagatcac cacctgcaga tgcaccgacc cccaggcat    2820 catcagccag aactacggcg aggccgtgag cctgatcgat cgccattcct gtaacgtgct    2880
gtccctggac ggcatcacac tgagactgag cggcgagttc gatgccacct accagaagaa    2940
catcagcatc ctggacagcc aggtgatcgt gaccggcaac ctggacatca gcaccgagct    3000
gggcaacgtg aataacagca tcagcaacgc cctggacaga ctggccgaga gcaacagcaa    3060
gctggaaaaa gtgaacgtgc gcctgacatc cacttccgct ctgatcacct acatcgtgct    3120
gaccgtgatc agcctggtgt cggcgcccct gagcctggtg ctggcctgct acctgatgta    3180
caagcagaag gcccagcaga aaaccctgct gtggctgggc aacaacaccc tggaccagat    3240
gagagccacc accagagcct gatgagcggc cgcgatatca ataaaatatc tttattttca    3300
ttacatctgt gtgttggttt tttgtgtgaa tcgatagtac taacatacgc tctccatcaa    3360
aacaaaacga acaaaacaa actagcaaaa taggctgtcc ccagtgcaag tgcaggtgcc    3420
agaacatttc tcttctagac ctgcaggccc gggcaagtag atgcaatttc ctcacactag    3480
ttgggtttat ctactattga attttcccct atctgtgata cacttgggag cctctacaag    3540
catattgcca tcatgtacgt ttttatctac tgtcttaacg cccatgggaa cggaggcgtc    3600
gtcgtcatgt attggacggc aacataggca gcaacacaaa ttgcgtttag gtggggtgca    3660
tgtggactcg ataccaagcc cctgcagctg ggaacgtct ggtggagagc cgataatttg    3720
atatacgcac gccatattac tgtcgttgaa gtacgcctta tcttctatgt tttcaaattt    3780
aggttcccaa gtggacgtga gaagtgtttg tatctcacat ggaatggccc aaggcattcc    3840
agcccaggtg cctggtactt taatggcaaa caaacgtttt ggtagaggta ttgattctat    3900
tgcagttctg cagatatctg cagccccgag tatccacagg ctatacgata cgttatcgga    3960
ggcctccgat tctagcatta catagccggt cagtagatcc tgccattcgg tagcgcaacc    4020
ggctacatct tcaaacagtc tcacaataaa tgcatctctc gttcctgcca atccggaacc    4080
gggcatacca ctcccgcctg ccgatttaat tctcacaatt gggcgatgcc ggcggggcaa    4140
aacgaatgtg gatttggcaa accgacacag gtctgctgta cggactaata tgggcacacc    4200
cacatcattc ttcagatgct ccatgcattg ttctatgaga aagatccata gggtggaggc    4260
agcgtcacga gatcgcccag gcaatcgatc gcattcgtct agtaaagtga cgagagttat    4320
catgcacaca cccat                                                    4335
```

<210> SEQ ID NO 46
<211> LENGTH: 5381
<212> TYPE: DNA
<213> ORGANISM: artificial sequence
<220> FEATURE:
<223> OTHER INFORMATION: Partial plasmid pCD046+NDV-F VII YZCQ sequence
      for vHVT112

<400> SEQUENCE: 46

```
gagctcaggg tatgatactc agctgttatt gtggccgacc aggaggactc caatgcttag      60
cattcataag aacgctagag atgctattta acgatgtgct gtcgtctaaa gaatttgtgc     120
atttagcctt taaatgtaaa accaatgacg cattcactac gctcgtgcgt gcaatttctg     180
ggccagggta tgcatattcc ataacagaaa tcgacacttg agaagaggat ctgactgttt     240
gggataaagg tcgtttgggt ctgtcctagc gatataattt atatgacgat atacattaaa     300
catctgtgtg cagtacttag gtatttaatc atgtcgatga aatgttatgt gtaaatatcg     360
gacaatatag ataacgggca cgctgctatt gtaacgtgcg cccgcgcgct agtgctgact     420
aatagtgtgg atgatgtata cagtatatta caaacggaaa tgatacgtaa taaattatgt     480
actcttattg atttataaaa acatacatgc agtgttgcta tgtcacataa ttagcctcgc     540
ccgtctacgc tccactgaag ataatgggct cccgctgttc aaaaaaatca gcgtgcgtcg     600
ataagacttt ggtgcagtct cttcggggtc gcaatttaga tttgccgcat ggagggtatc     660
tggggatttt tgccaatgct ggagcgacga ctgtacgatt cgtcccatcg ggatctagca     720
gaccaatgat gttgacacac atcggccatg catgtacgga cggtctattg cgcgagtttg     780
ttattttcga aggacaagat ggaagtgtat atggaaccga caataatgtt agtttgcatt     840
tcttagggcg gaatctacat gatatcttat ccaagcgggg tatgagccag agagatgtga     900
tggtcataaa gggtaaattt tttagatctg aaataacgca gttgcccaaa caacgatcgc     960
gattaaaaga aaaatcggat ggttcaatta ggacatgcat ggattctgtg cgcataaacc    1020
ataaccgcag cactgttggg cacttcggta actcaaatgc gaagcgttgc acgtctgcga    1080
taactacgcc tactatgcac attgttactc ctgcatctta aaaatatatc ctgtagtaat    1140
tttcacagca atgtcataac atcatctcgc taaagaatga cctgggattg gagaagtaat    1200
gaatatttgc aaccaatgca ttgaataaac taacattaaa cgaattcaat agtggatccc    1260
ccaactccgc ccgttttatg actagaacca atagttttta atgccaaatg cactgaaatc    1320
ccctaatttg caaagccaaa cgcccccctat gtgagtaata cggggacttt ttacccaatt    1380
tcccacgcgg aaagcccccct aatacactca tatggcatat gaatcagcac ggtcatgcac    1440
tctaatggcg gcccataggg actttccaca taggggcgt tcaccatttc ccagcatagg    1500
ggtggtgact caatggcctt tacccaagta cattgggtca atgggaggta agccaatggg    1560
tttttcccat tactgcaag cacactgagt caaatgggac tttccactgg gttttgccca    1620
agtacattgg gtcaatggga ggtgagccaa tgggaaaaac ccattgctgc caagtacact    1680
gactcaatag ggactttcca atgggttttt ccattgttgg caagcatata aggtcaatgt    1740
gggtgagtca atagggactt tccattgtat tctgcccagt acataaggtc aatagggggt    1800
gaatcaacag gaaagtccca ttggagccaa gtacactgcg tcaatagggg actttccattg    1860 ggttttgccc agtacataag gtcaataggg gatgagtcaa tgggaaaaac ccattggagc    1920
caagtacact gactcaatag ggactttcca ttgggttttg cccagtacat aaggtcaata    1980
gggggtgagt caacaggaaa gttccattgg agccaagtac attgagtcaa tagggacttt    2040
ccaatgggtt ttgcccagta cataaggtca atgggaggta agccaatggg ttttttcccat    2100 tactggcacg tatactgagt cattagggac tttccaatgg gttttgccca gtacataagg    2160
tcaatagggg tgaatcaaca ggaaagtccc attggagcca agtacactga gtcaataggg    2220
actttccatt gggttttgcc cagtacaaaa ggtcaatagg gggtgagtca atgggttttt    2280
cccattattg gcacgtacat aaggtcaata ggggtgagtc attgggtttt tccagccaat    2340
ttaattaaaa cgccatgtac tttcccacca ttgacgtcaa tgggctattg aaactaatgc    2400
```

```
aacgtgacct ttaaacggta cttccccata gctgattaat gggaaagtac cgttctcgag    2460
ccaatacacg tcaatgggaa gtgaaagggc agccaaaacg taacaccgcc ccggttttcc    2520
cctggaaatt ccatattggc acgcattcta ttggctgagc tgcgttctac gtgggtataa    2580
gaggcgcgac cagcgtcggt accgtcgcag tcttcggtct gaccaccgta gaacgcagag    2640
ctcctcgctg caggcggccg catgggctct aaaccttcta ccaggatccc agcacctctg    2700
atgctgatca cccggattat gctgatattg gactgtatcc gtccgacaag ctctcttgac    2760
ggcaggcctc ttgcagctgc aggaattgta gtaacaggag ataaggcagt caatgtatat    2820
acctcgtctc agacagggtc aatcatagtc aagttgctcc cgaatatgcc caaggataag    2880
gaggcgtgtg cgaaagaccc attagaggca tataacagaa cactgactac tttgctcact    2940
cctcttggcg aatccatccg caagatccaa gggtctgtgt ccacgtctgg aggaggcaag    3000
caaggccgcc tgataggtgc tgttattggt agtgtagctc ttggggttgc aacagcggca    3060
caaataacag cagctgcggc cctaatacaa gccaaccaga atgctgccaa catccttcgg    3120
cttaaggaga gcattgctgc aaccaatgaa gctgtgcatg aagtcaccga cggattatca    3180
caactatcag tggcagttgg gaagatgcag cagtttgtca atgaccagtt taataataca    3240
gcgcgagaat tggactgtat aaaaatcaca caacaggttg gtgtagaact caacctatac    3300
ctaactgaat tgactacagt attcgggcca cagatcacct cccctgcatt aactcagctg    3360
accatccagg cactttataa tttagctggt ggcaatatgg attacttatt aactaagtta    3420
ggtataggga acaatcaact cagctcatta attggcagcg gcctgatcac tggttaccct    3480
atattgtatg actcacagac tcaactcttg ggcatacaag tgaatttgcc ctcagtcggg    3540
aacttaaata atatgcgtgc cacctattta gagaccttat ctgtaagtac agccaaagga    3600
tatgcctcag cacttgttcc aaaagtagtg acacaagtcg gttctgtgat agaagagctt    3660
gacacctcat actgtatagt gtccgatctg gatttatatt gtactagaat agtgacattc    3720
cccatgtccc caggtatttta ttcctgttta gcggcaaca catcagcttg catgtattca    3780
aagactgaag gcgcactcac tacgccgtat atggccctta aaggctcagt tattgccaat    3840
tgtaagataa caacatgtag atgtacagac cctcctggta tcatatcgca aaattatgga    3900
gaagctgtat ccctgataga tagacattcg tgcaatgtct tatcattaga cgggataact    3960
ctgaggctca gtggagaatt tgatgcaact tatcaaaaga acatctcaat actagattct    4020
caagtcatcg tgacaggcaa tcttgatata tcaactgaac ttggaaacgt caacaattca    4080
atcagcaatg ccttggataa gttggcaaaa agcaacagca agctagaaaa agtcaatgtc    4140
agactaacca gcacatccgc tctcattacc tatattgttc tgactgtcat ttctctagtt    4200
ttcggtgcac taagtctggg tttaacatgt tacctgatgt acaaacaaaa ggcacaacaa    4260
aagaccttgc tatggcttgg gaataatacc ctcgatcaga tgagagccac tacaagagca    4320
tgagcggccg cggggatcca gacatgataa gatacattga tgagtttgga caaaccacaa    4380
ctagaatgca gtgaaaaaaa tgctttattt gtgaaatttg tgatgctatt gctttatttg    4440
taaccattat aagctgcaat aaacaagtta caacaacaa ttgcattgat tttatgtttc    4500
aggttcaggg ggaggtgtgg gaggtttttt cggatcctct agagtcgaca attatttat    4560 ttaataacat atagcccaaa gacctctatg aacatttagt ttcccgtata ctcaacggcg    4620
cgtgtacaca cgcatctctt tgcatagcga tgaagtttgt tcggcagcag aaaatgcaga    4680
tatccaacaa tctggagaaa acttatcatc acagtggcag tggaaacata cccctctat    4740
```

| | |
|---|---:|
| attcatggta taattatcgt ctacagcgtc caggatagtg gcgtgagaaa atggagatct | 4800 |
| gcagccctcc tttccatggc atgccgcttt attgttcatt aaacgcacaa tggtctcaac | 4860 |
| gccagatatg ggcatagatt ctgaagaacc cgttgacaat ccgaagaaga aggcgtgcag | 4920 |
| gtctttggaa gactcgcacg ttggtcttat aatgtatgat cgagatgtca ccctaatgcc | 4980 |
| acatggtaca ggcttatcgc ggtcatggcg atcggacttg taatttgcaa cgatgggcaa | 5040 |
| aggatcgacg acatgccaaa cattctgaac ccgtagagat gttaacgatg acgaggatga | 5100 |
| atatcccatg ctcgctgcca tagtatcaag tacaccgcga ataaggacgc gtccaacatc | 5160 |
| gttatatgca cacaatgggc tacacgtgac taacacccccc gaatattagt catatgtgag | 5220 |
| tttcagtctg gctcccatat agcctgtaga ctatttgtgg tttaagtgtg aacgaggcgc | 5280 |
| tgtgaacgag actcgggccg attgtaagaa caagcaaatg cactttccat ttaacaagaa | 5340 |
| gtgtagagag aatactcaac ctctttggat gtatcctcga g | 5381 |

<210> SEQ ID NO 47
<211> LENGTH: 5381
<212> TYPE: DNA
<213> ORGANISM: artificial sequence
<220> FEATURE:
<223> OTHER INFORMATION: Partial plasmid pCD046+NDV Texas F sequence for vHVT113

<400> SEQUENCE: 47

| | |
|---|---:|
| gagctcaggg tatgatactc agctgttatt gtggccgacc aggaggactc caatgcttag | 60 |
| cattcataag aacgctagag atgctattta acgatgtgct gtcgtctaaa gaatttgtgc | 120 |
| atttagcctt taaatgtaaa accaatgacg cattcactac gctcgtgcgt gcaatttctg | 180 |
| ggccagggta tgcatattcc ataacagaaa tcgacacttg agaagaggat ctgactgttt | 240 |
| gggataaagg tcgtttgggt ctgtcctagc gatataattt atatgacgat atacattaaa | 300 |
| catctgtgtg cagtacttag gtatttaatc atgtcgatga atgttatgt gtaaatatcg | 360 |
| gacaatatag ataacgggca cgctgctatt gtaacgtgcg cccgcgcgct agtgctgact | 420 |
| aatagtgtgg atgatgtata cagtatatta caaacggaaa tgatacgtaa taaattatgt | 480 |
| actcttattg atttataaaa acatacatgc agtgttgcta tgtcacataa ttagcctcgc | 540 |
| ccgtctacgc tccactgaag ataatggggct cccgctgttc aaaaaaatca gcgtgcgtcg | 600 |
| ataagacttt ggtgcagtct cttcggggtc gcaatttaga tttgccgcat ggagggtatc | 660 |
| tggggatttt tgccaatgct ggagcgacga ctgtacgatt cgtcccatcg ggatctagca | 720 |
| gaccaatgat gttgacacac atcggccatg catgtacgga cggtctattg cgcgagtttg | 780 |
| ttatttttcga aggacaagat ggaagtgtat atggaaccga caataatgtt agtttgcatt | 840 |
| tcttagggcg gaatctacat gatatcttat ccaagcgggg tatgagccag agagatgtga | 900 |
| tggtcataaa gggtaaattt tttagatctg aaataacgca gttgcccaaa caacgatcgc | 960 |
| gattaaaaga aaaatcggat ggttcaatta ggacatgcat ggattctgtg cgcataaacc | 1020 |
| ataaccgcag cactgttggg cacttcggta actcaaatgc gaagcgttgc acgtctgcga | 1080 |
| taactacgcc tactatgcac attgttactc ctgcatctta aaaatatatc ctgtagtaat | 1140 |
| tttcacagca atgtcataac atcatctcgc taaagaatga cctgggattg agaagtaat | 1200 |
| gaatatttgc aaccaatgca ttgaataaac taacattaaa cgaattcaat agtggatccc | 1260 |
| ccaactccgc ccgttttatg actagaacca atagtttta atgccaaatg cactgaaatc | 1320 |
| ccctaatttg caaagccaaa cgcccccctat gtgagtaata cggggacttt ttacccaatt | 1380 |

-continued

```
tcccacgcgg aaagccccct aatacactca tatggcatat gaatcagcac ggtcatgcac   1440
tctaatggcg gcccataggg actttccaca taggggcgt tcaccatttc ccagcatagg    1500
ggtggtgact caatggcctt tacccaagta cattgggtca atgggaggta agccaatggg   1560
tttttcccat tactgcaag cacactgagt caaatgggac tttccactgg gttttgccca    1620
agtacattgg gtcaatggga ggtgagccaa tgggaaaaac ccattgctgc caagtacact   1680
gactcaatag gactttcca atgggttttt ccattgttgg caagcatata aggtcaatgt    1740
gggtgagtca atagggactt tccattgtat tctgcccagt acataaggtc aatagggggt   1800
gaatcaacag gaaagtccca ttggagccaa gtacactgcg tcaatagggga ctttccattg  1860
ggttttgccc agtacataag gtcaataggg gatgagtcaa tgggaaaaac ccattggagc   1920
caagtacact gactcaatag gactttccca ttgggttttg cccagtacat aaggtcaata   1980
ggggtgagt caacaggaaa gttccattgg agccaagtac attgagtcaa tagggacttt    2040
ccaatggggtt tgcccagta cataaggtca atgggaggta agccaatggg ttttcccat    2100
tactggcacg tatactgagt cattagggac tttccaatgg gttttgccca gtacataagg   2160
tcaataggg tgaatcaaca ggaaagtccc attggagcca agtacactga gtcaataggg    2220
actttccatt gggttttgcc cagtacaaaa ggtcaatagg gggtgagtca atgggttttt   2280
cccattattg gcacgtacat aaggtcaata ggggtgagtc attgggtttt ccagccaat    2340
ttaattaaaa cgccatgtac tttcccacca ttgacgtcaa tgggctattg aaactaatgc   2400
aacgtgacct ttaaacggta ctttcccata gctgattaat gggaaagtac cgttctcgag   2460
ccaatacacg tcaatgggaa gtgaaagggc agccaaaacg taacaccgcc ccggtttttcc  2520
cctggaaatt ccatattggc acgcattcta ttggctgagc tgcgttctac gtgggtataa   2580
gaggcgcgac cagcgtcggt accgtcgcag tcttcggtct gaccaccgta gaacgcagag   2640
ctcctcgctg caggcggccg catgggctcc agatcttcta ccaggatccc ggtacctcta   2700
atgctgatca tccgaaccgc gctgacactg agctgtatcc gtctgacaag ctctcttgat   2760
ggcaggcctc ttgcggctgc agggatcgtg gtaacaggag ataaagcagt caacatatac   2820
acctcatccc agacagggtc aatcatagtt aagttactcc cgaatatgcc caaggacaaa   2880
gaggtgtgtg caaaagcccc attggaggca tacaacagga cactgactac tttactcacc   2940
cccttggtg attctatccg caggatacaa gagtctgtga ctacttccgg aggaggcaag    3000
caaggccgcc tgataggtgc cattatcggc agtgtagctc ttggggttgc gacagctgca   3060
cagataacag cagcttcggc cctgatacaa gccaaccaga atgctgccaa catcctccgg   3120
cttaaagaga gcattgctgc aaccaatgaa gctgtgcacg aggtcactga cggattatca   3180
caactagcag tggcagtagg gaagatgcaa cagtttgtca atgaccagtt caataataca   3240
gcgcaagaat tggactgtat aaaaattgca cagcaggtcg gtgtagaact caacttgtac   3300
ctaactgaat tgactacagt atttgggcca caaatcactt cccctgcctt aactcagctg   3360
actatccaag cgctttacaa tctagctggt ggtaatatgg attacttgct gactaagtta   3420
ggtgtaggga acaaccaact cagctcatta attggtagcg gcttgatcac cggcaaccct   3480
attctgtacg actcacagac tcagatcttg ggtatacagg taactttgcc ttcagttggg   3540
aacctgaata atatgcgtgc cacctacctg agaccttat ctgtaagcac aaccaaggga    3600
tttgcctcag cacttgtccc aaaagtggtg acacaggtcg gttccgtgat agaagaactt   3660
gacacctcat actgtatagg gaccgacttg gatttatact gtacaagaat agtgacattc   3720
cctatgtctc ctggtatttta ttcttgtctg agcggtaata catcggcttg catgtattca   3780
```

```
aagactgaag gcgcacttac tacgccatat atggctctca aaggctcagt tattgccaat    3840
tgcaagctga caacatgtag atgtgcagat cccccaggta tcatatcgca aaattatgga    3900
gaagctgtgt ccttaataga taggcactca tgcaacgtct tatccttaga cgggataact    3960
ctgaggctca gtggggaatt tgatgcaacc tatcaaaaga atatctctat actagattct    4020
caagttatag tgacaggcaa tcttgatata tcaactgagc ttgggaatgt caacaactca    4080
ataagtaatg ccctgaataa gttagaggaa agcaacagca actagacaa agtcaatgtc    4140 aaactgacca gcacatctgc tctcattacc tacatcgttt taactgtcat atctcttgtt    4200
tttggtgtac ttagcctggt tctagcatgc tacctgatgt acaagcaaaa ggcacaacaa    4260
aagaccttgt tatggcttgg gaataatacc cttgatcaga tgagagccac tacaaaaata    4320
tgagcggccg cggggatcca gacatgataa gatacattga tgagtttgga caaaccacaa    4380
ctagaatgca gtgaaaaaaa tgctttattt gtgaaatttg tgatgctatt gctttatttg    4440
taaccattat aagctgcaat aaacaagtta caacaacaa ttgcattgat tttatgtttc    4500
aggttcaggg ggaggtgtgg gaggttttt cggatcctct agagtcgaca attatttat    4560 ttaataacat atagcccaaa gacctctatg aacatttagt ttcccgtata ctcaacggcg    4620
cgtgtacaca cgcatctctt tgcatagcga tgaagtttgt tcggcagcag aaaatgcaga    4680
tatccaacaa tctggagaaa acttatcatc acagtggcag tggaaacata ccccctctat    4740
attcatggta taattatcgt ctacagcgtc caggatagtg gcgtgagaaa atggagatct    4800
gcagccctcc tttccatggc atgccgcttt attgttcatt aaacgcacaa tggtctcaac    4860
gccagatatg ggcatagatt ctgaagaacc cgttgacaat ccgaagaaga aggcgtgcag    4920
gtctttggaa gactcgcacg ttggtcttat aatgtatgat cgagatgtca ccctaatgcc    4980
acatggtaca ggcttatcgc ggtcatggcg atcggacttg taatttgcaa cgatgggcaa    5040
aggatcgacg acatgccaaa cattctgaac ccgtagagat gttaacgatg acgaggatga    5100
atatcccatg ctcgctgcca tagtatcaag tacaccgcga ataaggacgc gtccaacatc    5160
gttatatgca cacaatgggc tacacgtgac taacaccccc gaatattagt catatgtgag    5220
tttcagtctg gctcccatat agcctgtaga ctatttgtgg tttaagtgtg aacgaggcgc    5280
tgtgaacgag actcgggccg attgtaagaa caagcaaatg cactttccat ttaacaagaa    5340
gtgtagagag aatactcaac ctctttggat gtatcctcga g                       5381
```

<210> SEQ ID NO 48
<211> LENGTH: 4600
<212> TYPE: DNA
<213> ORGANISM: artificial sequence
<220> FEATURE:
<223> OTHER INFORMATION: Partial plasmid pHM119 sequence for vHVT039

<400> SEQUENCE: 48

```
gagctcaggg tatgatactc agctgttatt gtggccgacc aggaggactc caatgcttag      60
cattcataag aacgctagag atgctattta acgatgtgct gtcgtctaaa gaatttgtgc     120
atttagcctt taaatgtaaa accaatgacg cattcactac gctcgtgcgt gcaatttctg     180 ggccaggta tgcatattcc ataacagaaa tcgacacttg agaagaggat ctgactgttt      240
gggataaagg tcgtttgggt ctgtcctagc gatataattt atatgacgat atacattaaa     300
catctgtgtg cagtacttag gtatttaatc atgtcgatga aatgttatgt gtaaatatcg     360
gacaatatag ataacgggca cgctgctatt gtaacgtgcg cccgcgcgct agtgctgact     420
```

-continued

```
aatagtgtgg atgatgtata cagtatatta caaacggaaa tgatacgtaa taaattatgt    480
actcttattg atttataaaa acatacatgc agtgttgcta tgtcacataa ttagcctcgc    540
ccgtctacgc tccactgaag ataatgggct cccgctgttc aaaaaaatca gcgtgcgtcg    600
ataagacttt ggtgcagtct cttcggggtc gcaatttaga tttgccgcat ggagggtatc    660
tggggatttt tgccaatgct ggagcgacga ctgtacgatt cgtcccatcg ggatctagca    720
gaccaatgat gttgacacac atcggccatg catgtacgga cggtctattg cgcgagtttg    780
ttattttcga aggacaagat ggaagtgtat atggaaccga caataatgtt agtttgcatt    840
tcttagggcg gaatctacat gatatcttat ccaagcgggg tatgagccag agagatgtga    900
tggtcataaa gggtaaattt tttagatctg aaataacgca gttgcccaaa caacgatcgc    960
gattaaaaga aaaatcggat ggttcaatta ggacatgcat ggattctgtg cgcataaacc   1020
ataaccgcag cactgttggg cacttcggta actcaaatgc gaagcgttgc acgtctgcga   1080
taactacgcc tactatgcac attgttactc ctgcatctta aaaatatatc ctgtagtaat   1140
tttcacagca atgtcataac atcatctcgc taaagaatga cctgggattg gagaagtaat   1200
gaatatttgc aaccaatgca ttgaataaac taacattaaa cgaattccga tgtttagtca   1260
cgatagacat cggttcgccc agccgtcgaa tacagcatta tattttagtg ttgaaaatgt   1320
agggctgctt cctcacttaa aggaggaaat ggctcgattc atgtttcata gcagtagaaa   1380
aacagattgg accgtcagta agtttagagg gttttatgac tttagcacta tagataatgt   1440
aactgcggcc catcgcatgg cttggaaata tatcaaagaa ctgattttg caacagcttt    1500
attttcttct gtatttaaat gtggcgaatt gcacatctgt cgtgccgaca gtttgcagat   1560
caacagcaat ggagactatg tatggaaaaa tggaatatat ataacatatg aaaccgaata   1620
tccacttata atgattctgg ggtcagaatc aagcacttca gaaacgcaaa atatgactgc   1680
aattattgat acagatgttt tttcgttgct ttattctatt ttgcagtata tggccccgt   1740
tacggcagat caggtgcgag tagaacagat taccaacagc cacgccccca tctgacccgt   1800
ccaatattct tgtgtccctg cattttatct cacacaattt atgaacagca tcattaagat   1860
catctcactg cggccgcaag atgggctcca gatcttctac caggatcccg gtacctctaa   1920
tgctgatcat ccgaaccgcg ctgacactga gctgtatccg tctgacaagc tctcttgatg   1980
gcaggcctct tgcggctgca gggatcgtgg taacaggaga taaagcagtc aacatataca   2040
cctcatccca gacagggtca atcatagtta agttactccc gaatatgccc aaggacaaag   2100
aggtgtgtgc aaaagcccca ttggaggcat acaacaggac actgactact ttactcaccc   2160
ccccttggtga ttctatccgc aggatacaag agtctgtgac tacttccgga ggaaggagac   2220
agagacgctt tataggtgcc attatcggca gtgtagctct tggggttgcg acagctgcac   2280
agataacagc agcttcggcc ctgatacaag ccaaccagaa tgctgccaac atcctccggc   2340
ttaaagagag cattgctgca accaatgaag ctgtgcacga ggtcactgac ggattatcac   2400
aactagcagt ggcagtaggg aagatgcaac agtttgtcaa tgaccagttc aataatacag   2460
cgcaagaatt ggactgtata aaaattgcac agcaggtcgg tgtagaactc aacttgtacc   2520
taactgaatt gactacagta tttgggccac aaatcacttc ccctgcctta actcagctga   2580
ctatccaagc gctttacaat ctagctggtg gtaatatgga ttacttgctg actaagttag   2640
gtgtagggaa caaccaactc agctcattaa ttggtagcgg cttgatcacc ggcaacccta   2700
ttctgtacga ctcacagact cagatcttgg gtatacaggt aactttgcct tcagttggga   2760
acctgaataa tatgcgtgcc acctacctgg agaccttatc tgtaagcaca accaagggat   2820
```

```
ttgcctcagc acttgtccca aaagtggtga cacaggtcgg ttccgtgata agaaacttg      2880 acacctcata ctgtataggg accgacttgg atttatactg tacaagaata gtgacattcc      2940
ctatgtctcc tggtatttat tcttgtctga gcggtaatac atcggcttgc atgtattcaa      3000
agactgaagg cgcacttact acgccatata tggctctcaa aggctcagtt attgccaatt      3060
gcaagctgac aacatgtaga gtgcagatc ccccaggtat catatcgcaa aattatggag       3120
aagctgtgtc cttaatagat aggcactcat gcaacgtctt atccttagac gggataactc      3180
tgaggctcag tggggaattt gatgcaacct atcaaaagaa tatctctata ctagattctc      3240
aagttatagt gacaggcaat cttgatatat caactgagct tgggaatgtc aacaactcaa      3300
taagtaatgc cctgaataag ttagaggaaa gcaacagcaa actagacaaa gtcaatgtca      3360
aactgaccag cacatctgct ctcattacct acatcgtttt aactgtcata tctcttgttt      3420
ttggtgtact tagcctggtt ctagcatgct acctgatgta caagcaaaag gcacaacaaa      3480
agaccttgtt atggcttggg aataataccc ttgatcagat gagagccact acaaaaatat      3540
gagcggccgc ggggatccag acatgataag atacattgat gagtttggac aaaccacaac      3600
tagaatgcag tgaaaaaaat gctttatttg tgaaatttgt gatgctattg ctttatttgt      3660
aaccattata agctgcaata acaagttaa caacaacaat tgcattcatt ttatgtttca       3720
ggttcagggg gaggtgtggg aggttttttc ggatcctcta gagtcgacaa ttattttatt      3780
taataacata tagcccaaag acctctatga acatttagtt tcccgtatac tcaacggcgc      3840
gtgtacacac gcatctcttt gcatagcgat gaagtttgtt cggcagcaga aaatgcagat      3900
atccaacaat ctggagaaaa cttatcatca cagtggcagt ggaaacatac cccctctata      3960
ttcatggtat aattatcgtc tacagcgtcc aggatagtgg cgtgagaaaa tggagatctg      4020
cagccctcct ttccatggca tgccgcttta ttgttcatta aacgcacaat ggtctcaacg      4080
ccagatatgg gcatagattc tgaagaaccc gttgacaatc cgaagaagaa ggcgtgcagg      4140
tctttggaag actcgcacgt tggtcttata atgtatgatc gagatgtcac cctaatgcca      4200
catggtacag gcttatcgcg gtcatggcga tcggacttgt aatttgcaac gatgggcaaa      4260
ggatcgacga catgccaaac attctgaacc cgtagagatg ttaacgatga cgaggatgaa      4320
tatcccatgc tcgctgccat agtatcaagt acaccgcgaa taaggacgcg tccaacatcg      4380
ttatatgcac acaatgggct acacgtgact aacaccccg aatattagtc atatgtgagt       4440
ttcagtctgg ctcccatata gcctgtagac tatttgtggt ttaagtgtga acgaggcgct      4500
gtgaacgaga ctcgggccga ttgtaagaac aagcaaatgc actttccatt taacaagaag      4560
tgtagagaga atactcaacc tctttggatg tatcctcgag                            4600
```

<210> SEQ ID NO 49
<211> LENGTH: 1662
<212> TYPE: DNA
<213> ORGANISM: artificial sequence
<220> FEATURE:
<223> OTHER INFORMATION: NDV Texas F gene (wild type non-modified)

<400> SEQUENCE: 49

```
atgggctcca gatcttctac caggatcccg gtacctctaa tgctgatcat ccgaaccgcg        60
ctgacactga gctgtatccg tctgacaagc tctcttgatg caggcctct tgcggctgca       120 gggatcgtgg taacaggaga taagcagtc aacatataca cctcatccca gacagggtca       180
atcatagtta agttactccc gaatatgccc aaggacaaag aggtgtgtgc aaaagcccca      240
```

```
ttggaggcat acaacaggac actgactact ttactcaccc cccttggtga ttctatccgc    300
aggatacaag agtctgtgac tacttccgga ggaaggagac agagacgctt tataggtgcc    360
attatcggca gtgtagctct tggggttgcg acagctgcac agataacagc agcttcggcc    420
ctgatacaag ccaaccagaa tgctgccaac atcctccggc ttaaagagag cattgctgca    480
accaatgaag ctgtgcacga ggtcactgac ggattatcac aactagcagt ggcagtaggg    540
aagatgcaac agtttgtcaa tgaccagttc aataatacag cgcaagaatt ggactgtata    600
aaaattgcac agcaggtcgg tgtagaactc aacttgtacc taactgaatt gactacagta    660
tttgggccac aaatcacttc ccctgcctta actcagctga ctatccaagc gctttacaat    720
ctagctggtg gtaatatgga ttacttgctg actaagttag gtgtagggaa caaccaactc    780
agctcattaa ttggtagcgg cttgatcacc ggcaacccta ttctgtacga ctcacagact    840
cagatcttgg gtatacaggt aactttgcct tcagttggga acctgaataa tatgcgtgcc    900
acctacctgg agaccttatc tgtaagcaca accaagggat tgcctcagc acttgtccca    960 aaagtggtga cacaggtcgg ttccgtgata gaagaacttg cacctcata ctgtataggg   1020 accgacttgg atttatactg tacaagaata gtgacattcc ctatgtctcc tggtatttat   1080
tcttgtctga gcggtaatac atcggcttgc atgtattcaa agactgaagg cgcacttact   1140
acgccatata tggctctcaa aggctcagtt attgccaatt gcaagctgac aacatgtaga   1200
tgtgcagatc ccccaggtat catatcgcaa aattatggag aagctgtgtc cttaatagat   1260
aggcactcat gcaacgtctt atccttagac gggataactc tgaggctcag tgggggaattt   1320 gatgcaacct atcaaaagaa tatctctata ctagattctc aagttatagt gacaggcaat   1380
cttgatatat caactgagct tgggaatgtc aacaactcaa taagtaatgc cctgaataag    1440
ttagaggaaa gcaacagcaa actagacaaa gtcaatgtca aactgaccag cacatctgct   1500
ctcattacct acatcgtttt aactgtcata tctcttgttt ttggtgtact agcctggtt    1560 ctagcatgct acctgatgta caagcaaaag gcacaacaaa agaccttgtt atggcttggg   1620
aataataccc ttgatcagat gagagccact acaaaaatat ga                      1662
```

<210> SEQ ID NO 50
<211> LENGTH: 553
<212> TYPE: PRT
<213> ORGANISM: artificial sequence
<220> FEATURE:
<223> OTHER INFORMATION: NDV Texas F protein (wild type non-modified; cleavage site underlined)

<400> SEQUENCE: 50

Met Gly Ser Arg Ser Ser Thr Arg Ile Pro Val Pro Leu Met Leu Ile
1               5                   10                  15

Ile Arg Thr Ala Leu Thr Leu Ser Cys Ile Arg Leu Thr Ser Ser Leu
            20                  25                  30

Asp Gly Arg Pro Leu Ala Ala Ala Gly Ile Val Val Thr Gly Asp Lys
        35                  40                  45

Ala Val Asn Ile Tyr Thr Ser Ser Gln Thr Gly Ser Ile Ile Val Lys
    50                  55                  60

Leu Leu Pro Asn Met Pro Lys Asp Lys Glu Val Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Arg
            100                 105                 110

-continued

Arg Gln Arg Arg Phe Ile Gly Ala Ile Ile Gly Ser Val Ala Leu Gly
            115                 120                 125

Val Ala Thr Ala Ala Gln Ile Thr Ala Ala Ser Ala Leu Ile Gln Ala
        130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Asn
            180                 185                 190

Thr Ala Gln Glu Leu Asp Cys Ile Lys Ile Ala Gln Gln Val Gly Val
        195                 200                 205

Glu Leu Asn Leu Tyr Leu Thr Glu Leu Thr Thr Val Phe Gly Pro Gln
210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Ile Leu Gly Ile Gln Val Thr
        275                 280                 285

Leu Pro Ser Val Gly Asn Leu Asn Asn Met Arg Ala Thr Tyr Leu Glu
    290                 295                 300

Thr Leu Ser Val Ser Thr Thr Lys Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Gly Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Ala Leu Lys Gly Ser Val Ile Ala Asn Cys Lys Leu Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Arg His Ser Cys Asn Val Leu Ser Leu Asp Gly Ile
            420                 425                 430

Thr Leu Arg Leu Ser Gly Glu Phe Asp Ala Thr Tyr Gln Lys Asn Ile
        435                 440                 445

Ser Ile Leu Asp Ser Gln Val Ile Val Thr Gly Asn Leu Asp Ile Ser
    450                 455                 460

Thr Glu Leu Gly Asn Val Asn Asn Ser Ile Ser Asn Ala Leu Asn Lys
465                 470                 475                 480

Leu Glu Glu Ser Asn Ser Lys Leu Asp Lys Val Asn Val Lys Leu Thr
                485                 490                 495

Ser Thr Ser Ala Leu Ile Thr Tyr Ile Val Leu Thr Val Ile Ser Leu
            500                 505                 510

Val Phe Gly Val Leu Ser Leu Val Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Ile
545                 550

<210> SEQ ID NO 51
<211> LENGTH: 1662
<212> TYPE: DNA
<213> ORGANISM: artificial sequence
<220> FEATURE:
<223> OTHER INFORMATION: NDV-F YZCQ wildtype DNA

<400> SEQUENCE: 51

| | | |
|---|---|---|
| atgggctcca gatcttctac caggatcccg gtacctctaa tgctgatcat ccgaaccgcg | 60 |
| ctgacactga gctgtatccg tctgacaagc tctcttgatg gcaggcctct tgcggctgca | 120 |
| gggatcgtgg taacaggaga taaagcagtc aacatataca cctcatccca gacagggtca | 180 |
| atcatagtta agttactccc gaatatgccc aaggacaaag aggtgtgtgc aaaagcccca | 240 |
| ttggaggcat acaacaggac actgactact ttactcaccc cccttggtga ttctatccgc | 300 |
| aggatacaag agtctgtgac tacttccgga ggaggcaagc aaggccgcct gataggtgcc | 360 |
| attatcggca gtgtagctct ggggttgcg acagctgcac agataacagc agcttcggcc | 420 |
| ctgatacaag ccaaccagaa tgctgccaac atcctccggc ttaaagagag cattgctgca | 480 |
| accaatgaag ctgtgcacga ggtcactgac ggattatcac aactagcagt ggcagtaggg | 540 |
| aagatgcaac agtttgtcaa tgaccagttc aataatacag cgcaagaatt ggactgtata | 600 |
| aaaattgcac agcaggtcgg tgtagaactc aacttgtacc taactgaatt gactacagta | 660 |
| tttgggccac aaatcacttc ccctgcctta actcagctga ctatccaagc gctttacaat | 720 |
| ctagctggtg gtaatatgga ttacttgctg actaagttag gtgtagggaa caaccaactc | 780 |
| agctcattaa ttggtagcgg cttgatcacc ggcaacccta ttctgtacga ctcacagact | 840 |
| cagatcttgg gtatacaggt aactttgcct tcagttggga acctgaataa tatgcgtgcc | 900 |
| acctacctgg agaccttatc tgtaagcaca accaagggat tgcctcagc acttgtccca | 960 |
| aaagtggtga cacaggtcgg ttccgtgata gaagaacttg acacctcata ctgtatagg | 1020 |
| accgacttgg atttatactg tacaagaata gtgacattcc ctatgtctcc tggtatttat | 1080 |
| tcttgtctga gcggtaatac atcggcttgc atgtattcaa agactgaagg cgcacttact | 1140 |
| acgccatata tggctctcaa aggctcagtt attgccaatt gcaagctgac aacatgtaga | 1200 |
| tgtgcagatc ccccaggtat catatcgcaa aattatggag aagctgtgtc cttaatagat | 1260 |
| aggcactcat gcaacgtctt atccttagac gggataactc tgaggctcag tggggaattt | 1320 |
| gatgcaacct atcaaaagaa tatctctata ctagattctc aagttatagt gacaggcaat | 1380 |
| cttgatatat caactgagct tgggaatgtc aacaactcaa taagtaatgc cctgaataag | 1440 |
| ttagaggaaa gcaacagcaa actagacaaa gtcaatgtca aactgaccag cacatctgct | 1500 |
| ctcattacct acatcgtttt aactgtcata tctcttgttt ttggtgtact tagcctggtt | 1560 |
| ctagcatgct acctgatgta caagcaaaag gcacaacaaa agaccttgtt atggcttggg | 1620 |
| aataataccc ttgatcagat gagagccact acaaaaatat ga | 1662 |

<210> SEQ ID NO 52
<211> LENGTH: 553
<212> TYPE: PRT
<213> ORGANISM: artificial sequence
<220> FEATURE:
<223> OTHER INFORMATION: NDV-F protein from wildtype YZCQ strain (Amino Acid Sequence of NDV-F of Texas strain with lentogenic cleavage site sequence)

<400> SEQUENCE: 52

Met Gly Ser Arg Ser Ser Thr Arg Ile Pro Val Pro Leu Met Leu Ile
1               5                   10                  15

Ile Arg Thr Ala Leu Thr Leu Ser Cys Ile Arg Leu Thr Ser Ser Leu
            20                  25                  30

Asp Gly Arg Pro Leu Ala Ala Gly Ile Val Val Thr Gly Asp Lys
        35                  40                  45

Ala Val Asn Ile Tyr Thr Ser Ser Gln Thr Gly Ser Ile Ile Val Lys
    50                  55                  60

Leu Leu Pro Asn Met Pro Lys Asp Lys Glu Val Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Gly
            100                 105                 110

Lys Gln Gly Arg Leu Ile Gly Ala Ile Ile Gly Ser Val Ala Leu Gly
        115                 120                 125

Val Ala Thr Ala Ala Gln Ile Thr Ala Ala Ser Ala Leu Ile Gln Ala
130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Asn
            180                 185                 190

Thr Ala Gln Glu Leu Asp Cys Ile Lys Ile Ala Gln Gln Val Gly Val
        195                 200                 205

Glu Leu Asn Leu Tyr Leu Thr Glu Leu Thr Thr Val Phe Gly Pro Gln
210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Ile Leu Gly Ile Gln Val Thr
        275                 280                 285

Leu Pro Ser Val Gly Asn Leu Asn Asn Met Arg Ala Thr Tyr Leu Glu
290                 295                 300

Thr Leu Ser Val Ser Thr Thr Lys Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Gly Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
370                 375                 380

Ala Leu Lys Gly Ser Val Ile Ala Asn Cys Lys Leu Thr Thr Cys Arg
385                 390                 395                 400

```
Cys Ala Asp Pro Pro Gly Ile Ile Ser Gln Asn Tyr Gly Glu Ala Val
                405                 410                 415

Ser Leu Ile Asp Arg His Ser Cys Asn Val Leu Ser Leu Asp Gly Ile
            420                 425                 430

Thr Leu Arg Leu Ser Gly Glu Phe Asp Ala Thr Tyr Gln Lys Asn Ile
        435                 440                 445

Ser Ile Leu Asp Ser Gln Val Ile Val Thr Gly Asn Leu Asp Ile Ser
    450                 455                 460

Thr Glu Leu Gly Asn Val Asn Asn Ser Ile Ser Asn Ala Leu Asn Lys
465                 470                 475                 480
Leu Glu Glu Ser Asn Ser Lys Leu Asp Lys Val Asn Val Lys Leu Thr
                485                 490                 495
Ser Thr Ser Ala Leu Ile Thr Tyr Ile Val Leu Thr Val Ile Ser Leu
            500                 505                 510
Val Phe Gly Val Leu Ser Leu Val Leu Ala Cys Tyr Leu Met Tyr Lys
        515                 520                 525
Gln Lys Ala Gln Gln Lys Thr Leu Leu Trp Leu Gly Asn Asn Thr Leu
    530                 535                 540
Asp Gln Met Arg Ala Thr Thr Lys Ile
545                 550

<210> SEQ ID NO 53
<211> LENGTH: 1662
<212> TYPE: DNA
<213> ORGANISM: artificial sequence
<220> FEATURE:
<223> OTHER INFORMATION: NDV-F Texas wildtype DNA

<400> SEQUENCE: 53
atgggctcta aaccttctac caggatccca gcacctctga tgctgatcac ccggattatg      60
ctgatattgg actgtatccg tccgacaagc tctcttgacg gcaggcctct tgcagctgca     120
ggaattgtag taacaggaga taaggcagtc aatgtatata cctcgtctca gacagggtca     180
atcatagtca agttgctccc gaatatgccc aaggataagg aggcgtgtgc gaaagaccca     240
ttagaggcat ataacagaac actgactact ttgctcactc ctcttggcga atccatccgc     300
aagatccaag ggtctgtgtc cacgtctgga ggaggcaagc aaggccgcct gataggtgct     360
gttattggta gtgtagctct tggggttgca acagcggcac aaataacagc agctgcggcc     420
ctaatacaag ccaaccagaa tgctgccaac atccttcggc ttaaggagag cattgctgca     480
accaatgaag ctgtgcatga agtcaccgac ggattatcac aactatcagt ggcagttggg     540
aagatgcagc agtttgtcaa tgaccagttt aataatacag cgcgagaatt ggactgtata     600
aaaatcacac aacaggttgg tgtagaactc aacctatacc taactgaatt gactacagta     660
ttcgggccac agatcacctc ccctgcatta actcagctga ccatccaggc actttataat     720
ttagctggtg gcaatatgga ttacttatta actaagttag gtatagggaa caatcaactc     780
agctcattaa ttggcagcgg cctgatcact ggttacccta tattgtatga ctcacagact     840
caactcttgg gcatacaagt gaatttgccc tcagtcggga acttaaataa tatgcgtgcc     900
acctatttag agaccttatc tgtaagtaca gccaaaggat atgcctcagc acttgttcca     960
aaagtagtga cacaagtcgg ttctgtgata gaagagcttg acacctcata ctgtatagag    1020
tccgatctgg atttatattg tactagaata gtgacattcc ccatgtcccc aggtatttat    1080
tcctgtttaa gcggcaacac atcagcttgc atgtattcaa agactgaagg cgcactcact    1140
```

```
acgccgtata tggcccttaa aggctcagtt attgccaatt gtaagataac aacatgtaga    1200
tgtacagacc ctcctggtat catatcgcaa aattatggag aagctgtatc cctgatagat    1260
agacattcgt gcaatgtctt atcattagac gggataactc tgaggctcag tggagaattt    1320
gatgcaactt atcaaaagaa catctcaata ctagattctc aagtcatcgt gacaggcaat    1380
cttgatatat caactgaact tggaaacgtc aacaattcaa tcagcaatgc cttggataag    1440
ttggcaaaaa gcaacagcaa gctagaaaaa gtcaatgtca gactaaccag cacatccgct    1500
ctcattacct atattgttct gactgtcatt tctctagttt tcggtgcact aagtctgggt    1560
ttaacatgtt acctgatgta caaacaaaag gcacaacaaa agaccttgct atggcttggg    1620
aataataccc tcgatcagat gagagccact acaagagcat ga                       1662
```

<210> SEQ ID NO 54
<211> LENGTH: 553
<212> TYPE: PRT
<213> ORGANISM: artificial sequence
<220> FEATURE:
<223> OTHER INFORMATION: NDV-F protein from wildtype Texas strain (Amino
      Acid Sequence of NDV-F VIId wt YZCQ with lentogenic cleavage site
      sequence)

<400> SEQUENCE: 54

```
Met Gly Ser Lys Pro Ser Thr Arg Ile Pro Ala Pro Leu Met Leu Ile
1               5                   10                  15

Thr Arg Ile Met Leu Ile Leu Asp Cys Ile Arg Pro Thr Ser Ser Leu
            20                  25                  30

Asp Gly Arg Pro Leu Ala Ala Ala Gly Ile Val Val Thr Gly Asp Lys
        35                  40                  45

Ala Val Asn Val Tyr Thr Ser Ser Gln Thr Gly Ser Ile Ile Val Lys
    50                  55                  60

Leu Leu Pro Asn Met Pro Lys Asp Lys Glu Ala Cys Ala Lys Asp Pro
65                  70                  75                  80

Leu Glu Ala Tyr Asn Arg Thr Leu Thr Thr Leu Leu Thr Pro Leu Gly
                85                  90                  95

Glu Ser Ile Arg Lys Ile Gln Gly Ser Val Ser Thr Ser Gly Gly Gly
            100                 105                 110

Lys Gln Gly Arg Leu Ile Gly Ala Val Ile Gly Ser Val Ala Leu Gly
        115                 120                 125

Val Ala Thr Ala Ala Gln Ile Thr Ala Ala Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ser
                165                 170                 175

Val Ala Val Gly Lys Met Gln Gln Phe Val Asn Asp Gln Phe Asn Asn
            180                 185                 190

Thr Ala Arg Glu Leu Asp Cys Ile Lys Ile Thr Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Tyr
```

-continued

|   |   |   |   |   | 260 |   |   |   |   | 265 |   |   |   |   | 270 |   |   |
|---|---|---|---|---|---|---|---|---|---|---|---|---|---|---|---|---|---|

Pro Ile Leu Tyr Asp Ser Gln Thr Gln Leu Leu Gly Ile Gln Val Asn
            275              280              285

Leu Pro Ser Val Gly Asn Leu Asn Asn Met Arg Ala Thr Tyr Leu Glu
290                  295                300

Thr Leu Ser Val Ser Thr Ala Lys Gly Tyr Ala Ser Ala Leu Val Pro
305              310              315            320

Lys Val Val Thr Gln Val Gly Ser Val Ile Glu Glu Leu Asp Thr Ser
            325              330              335

Tyr Cys Ile Glu Ser Asp Leu Asp Leu Tyr Cys Thr Arg Ile Val Thr
            340              345              350

Phe Pro Met Ser Pro Gly Ile Tyr Ser Cys Leu Ser Gly Asn Thr Ser
            355              360              365

Ala Cys Met Tyr Ser Lys Thr Glu Gly Ala Leu Thr Thr Pro Tyr Met
        370              375              380

Ala Leu Lys Gly Ser Val Ile Ala Asn Cys Lys Ile Thr Thr Cys Arg
385                  390              395            400

Cys Thr Asp Pro Pro Gly Ile Ile Ser Gln Asn Tyr Gly Glu Ala Val
            405              410              415

Ser Leu Ile Asp Arg His Ser Cys Asn Val Leu Ser Leu Asp Gly Ile
            420              425              430

Thr Leu Arg Leu Ser Gly Glu Phe Asp Ala Thr Tyr Gln Lys Asn Ile
            435              440              445

Ser Ile Leu Asp Ser Gln Val Ile Val Thr Gly Asn Leu Asp Ile Ser
        450              455              460

Thr Glu Leu Gly Asn Val Asn Asn Ser Ile Ser Asn Ala Leu Asp Lys
465                  470              475            480

Leu Ala Lys Ser Asn Ser Lys Leu Glu Lys Val Asn Val Arg Leu Thr
            485              490              495

Ser Thr Ser Ala Leu Ile Thr Tyr Ile Val Leu Thr Val Ile Ser Leu
        500              505              510

Val Phe Gly Ala Leu Ser Leu Gly Leu Thr Cys Tyr Leu Met Tyr Lys
            515              520              525

Gln Lys Ala Gln Gln Lys Thr Leu Leu Trp Leu Gly Asn Asn Thr Leu
        530              535              540

Asp Gln Met Arg Ala Thr Thr Arg Ala
545                  550

<210> SEQ ID NO 55
<211> LENGTH: 622
<212> TYPE: DNA
<213> ORGANISM: artificial sequence
<220> FEATURE:
<223> OTHER INFORMATION: MDV gB promoter

<400> SEQUENCE: 55
cgatgtttag tcacgataga catcggttcg cccagccgtc gaatacagca ttatatttta      60
gtgttgaaaa tgtagggctg cttcctcact taaaggagga atggctcga ttcatgtttc      120 atagcagtag aaaaacagat tggaccgtca gtaagtttag agggttttat gactttagca      180
ctatagataa tgtaactgcg gcccatcgca tggcttggaa atatatcaaa gaactgattt      240
ttgcaacagc tttatttttct tctgtattta aatgtggcga attgcacatc tgtcgtgccg      300
acagtttgca gatcaacagc aatggagact atgtatggaa aaatggaata tatataacat      360
atgaaaccga atatccactt ataatgattc tggggtcaga atcaagcact tcagaaacgc      420

| | | | | |
|---|---|---|---|---|
| aaaatatgac | tgcaattatt | gatacagatg | ttttttcgtt | gctttattct | attttgcagt | 480 |
| atatggcccc | cgttacggca | gatcaggtgc | gagtagaaca | gattaccaac | agccacgccc | 540 |
| ccatctgacc | cgtccaatat | tcttgtgtcc | ctgcatttta | tctcacacaa | tttatgaaca | 600 |
| gcatcattaa | gatcatctca | ct | | | | 622 |

<210> SEQ ID NO 56
<211> LENGTH: 4850
<212> TYPE: DNA
<213> ORGANISM: artificial sequence
<220> FEATURE:
<223> OTHER INFORMATION: Partial plasmid HVT SORF3-US2 gpVar-Ewtsyn sequence for vHVT202

<400> SEQUENCE: 56

| | | | | | | |
|---|---|---|---|---|---|---|
| taaaatggga | tctatcatta | cattcgttaa | gagtctggat | aattttactg | tttgccagct | 60 |
| tcgatcttgg | aacgtactgt | ggatagtgcc | ttacttggaa | tcgtgaaaat | ttgaaacgtc | 120 |
| cattatttgg | atatcttccg | gttgtcccat | atcccgccct | ggtaccgctc | ggataccttg | 180 |
| cccgtatgga | ttcgtattga | cagtcgcgca | atcggggacc | aacaacgcgt | gggtccacac | 240 |
| tcattcggaa | attttccgat | gattctgaat | atttattgcc | gctcgttacg | agtcgttgga | 300 |
| catatctgta | atacatttct | tcttctgaag | gatcgctgca | catttgatct | atacattggc | 360 |
| caggatgttc | aagtctcaga | tgttgcattc | tggcacagca | caactttatg | gcatttccga | 420 |
| tgtaatcgtc | cggcagccct | gggggagttc | tatattcgca | tattgggatg | gtaaggacaa | 480 |
| tagcagatct | cgcaacctcc | agggaggcta | taataacgtt | tttaaaggat | ggatttctca | 540 |
| taaaaatctg | tcgcaaatta | cactgagaat | atcctttact | agcgccgatt | gagagcatcg | 600 |
| tcgtccaatt | ttctaaatgg | aaagaaaaca | aggcgggcaa | gagtgttcca | aacattttca | 660 |
| ttttcggcga | atctctcaaa | tcccatggcg | tgcaattgat | tgcaaaattg | gcacttccgt | 720 |
| tcacgtttgt | atctccaaac | tctaagacac | ttttaattga | aaaactacgt | tctagtgtgg | 780 |
| aaagaaaccct | ataggcagac | catagaacta | tttgacacca | catatctttt | tgtatgtcaa | 840 |
| actgaccatg | atcgtatgtt | gctgaatgca | ctagggcaat | tcgctcgcgc | gactccatac | 900 |
| attgaataat | tccacacgtc | agctcatcgg | ttagcaaggt | ccagtagttg | aagtcattta | 960 |
| tttttccccg | cggctggcca | aatctacctc | tgggaatatc | caagttgtcg | aatatgatcg | 1020 |
| caccggctct | ggtcatggtg | aaggaacttg | tagcataaag | acgcaggtat | catagggta | 1080 |
| atatttttt | attcactcac | atactaaaag | taacgcatat | tagcaccatg | tatgggctat | 1140 |
| caattgacat | ttgcgtagca | ctacatcacg | attatgtaca | acataatggg | acaacatatg | 1200 |
| cctgcaggtt | agtcatatgt | tacttggcag | aggccgcatg | gaaagtccct | ggacgtggga | 1260 |
| catctgatta | atacgtgagg | aggtcagcca | tgttcttttt | ggcaaaggac | tacggtcatt | 1320 |
| ggacgtttga | ttggcatggg | atagggtcag | ccagagttaa | cagtgttctt | ttggcaaagg | 1380 |
| gatacgtgga | aagtcccggg | ccatttacag | taaactgata | cggggacaaa | gcacagccat | 1440 |
| atttagtcat | gtattgcttg | gcagagggtc | tatggaaagt | ccctggacgt | gggacgtctg | 1500 |
| attaatatga | agaaggtca | gccagaggta | gctgtgtcct | ttttggcaaa | gggatacggt | 1560 |
| tatgggacgt | ttgattggac | tgggataggg | tcagccagag | ttaacagtgt | tcttttggca | 1620 |
| aaggaaacgt | ggaaagtccc | gggccattta | cagtaaactg | atactgggac | aaagtacacc | 1680 |
| catatttagt | catgttcttt | ttggcaaaga | gcatctggaa | agtcccgggc | agcattatag | 1740 |
| tcacttggca | gagggaaagg | gtcactcaga | gttaagtaca | tctttccagg | gccaatattc | 1800 |

```
cagtaaatta cacttagttt tatgcaaatc agccacaaag gggattttcc cggtcaatta    1860
tgactttttc cttagtcatg cggtatccaa ttactgccaa attggcagta catactaggt    1920
gattcactga catttggccg tcctctggaa agtccctgga aaccgctcaa gtactgtatc    1980
atggtgactt tgcattttg gagagcacgc cccactccac cattggtcca cgtaccctat     2040 ggggagtgg tttatgagta tataagggc tccggtttag aagccgggca gagcggccgc      2100
atgacaaacc tgcaagatca aacccaacag attgttccgt tcatacggag ccttctgatg    2160
ccaacaaccg gaccggcgtc cattccggac gacaccctgg agaagcacac tctcaggtca    2220
gagacctcga cctacaattt gactgtgggg acacagggt cagggctaat tgtcttttc      2280 cctggattcc ctggctcaat tgtgggtgct cactacacac tgcagagcaa tgggaactac    2340
aagttcgatc agatgctcct gactgccag aacctaccgg ccagctacaa ctactgcagg     2400
ctagtgagtc ggagtctcac agtaaggtca agcacactcc ctggtggcgt ttatgcacta    2460
aacggcacca taaacgccgt gaccttccaa ggaagcctga gtgaactgac agatgttagc    2520
tacaacgggt tgatgtctgc aacagccaac atcaacgaca aaattgggaa cgtcctagta    2580
ggggaagggg taaccgtcct cagcttaccc acatcatatg atcttgggta tgtgaggctt    2640
ggtgacccca tacccgctat agggcttgac ccaaaaatgg tagcaacatg tgacagcagt    2700
gacaggccca gagtctacac cataactgca gccgataatt accaattctc atcacagtac    2760
caaacaggtg gggtaacaat cacactgttc tcagccaaca ttgatgccat cacaagtctc    2820
agcgttgggg gagagctcgt gttcaaaaca agcgtccaaa gccttgtact gggcgccacc    2880
atctacctta taggctttga tgggactgcg gtaatcacca gagctgtggc cgcaaacaat    2940
gggctgacgg ccggcatcga caatcttatg ccattcaatc ttgtgattcc aaccaatgag    3000
ataacccagc caatcacatc catcaaactg gagatagtga cctccaaaag tgatggtcag    3060 gcagggaac agatgtcatg gtcggcaagt gggagcctag cagtgacgat ccatggtggc     3120
aactatccag gagccctccg tcccgtcaca ctagtggcct acgaaagagt ggcaacagga    3180
tctgtcgtta cggtcgctgg ggtgagcaac ttcgagctga tcccaaatcc tgaactagca    3240
aagaacctgg ttacagaata tggccgattt gacccaggag ccatgaacta cacgaaattg    3300
atactgagtg agagggaccg ccttggcatc aagaccgtct ggccaacaag ggagtacact    3360
gactttcgtg agtacttcat ggaggtggcc gacctcaact ctcccctgaa gattgcagga    3420
gcatttggct tcaaagacat aatccggggcc ataaggaggt gagcggccgc gatatcaata   3480
aaatatcttt attttcatta catctgtgtg ttggttttt gtgtgaatcg atagtactaa     3540
catacgctct ccatcaaaac aaaacgaaac aaaacaaact agcaaaatag gctgtcccca    3600
gtgcaagtgc aggtgccaga acatttctct tctagacctg caggcccggg gcaagtagat    3660
gcaatttcct cacactagtt gggtttatct actattgaat tttcccctat ctgtgataca    3720
cttgggagct ctacaagca tattgccatc atgtacgttt ttatctactg tcttaacgcc    3780
catgggaacg gaggcgtcgt cgtcatgtat tggacggcaa cataggcagc aacacaaatt    3840
gcgtttaggt ggggtgcatg tggactcgat accaagcccc tgcagctggg aacgtctgg    3900 tggagagccg ataatttgat atacgcacgc catattactg tcgttgaagt acgccttatc    3960
ttctatgttt tcaaatttag gttcccaagt ggacgtgaga agtgtttgta tctcacatgg    4020
aatggcccaa ggcattccag cccaggtgcc tggtacttta atggcaaaca aacgttttgg    4080
tagaggtatt gattctattg cagttctgca gatatctgca gccccgagta tccacaggct    4140
```

| | |
|---|---:|
| atacgatacg ttatcggagg cctccgattc tagcattaca tagccggtca gtagatcctg | 4200 |
| ccattcggta gcgcaaccgg ctacatcttc aaacagtctc acaataaatg catctctcgt | 4260 |
| tcctgccaat ccggaaccgg gcataccact cccgcctgcc gatttaattc tcacaattgg | 4320 |
| gcgatgccgg cggggcaaaa cgaatgtgga tttggcaaac cgacacaggt ctgctgtacg | 4380 |
| gactaatatg ggcacaccca catcattctt cagatgctcc atgcattgtt ctatgagaaa | 4440 |
| gatccatagg gtggaggcag cgtcacgaga tcgcccaggc aatcgatcgc attcgtctag | 4500 |
| taaagtgacg agagttatca tgcacacacc catgcccacg ccttccgaat aactggagct | 4560 |
| gtggaagatc ggaaacgtct ttttgactgc cggtctcgta ctactttcgc acaggtgtat | 4620 |
| acccggacgc gtactatata ttttatatca tccaacgtcc cgaaattaca tacgtggcgg | 4680 |
| cgatggaagt agatgttgag tcttcgaaag taagtgcctc gaatatgggt attgtctgtg | 4740 |
| aaaatatcga aagcggtacg acggttgcag aaccgtcgat gtcgccagat actagtaaca | 4800 |
| atagcttcga taacgaagac ttccgtgggc ctgaatacga tgtggagata | 4850 |

<210> SEQ ID NO 57
<211> LENGTH: 4943
<212> TYPE: DNA
<213> ORGANISM: artificial sequence
<220> FEATURE:
<223> OTHER INFORMATION: Partial plasmid SB1US2 gpVIIdwtsyn sequence for vSB1-010

<400> SEQUENCE: 57

| | |
|---|---:|
| tctcgtctaa aacgctccag tgctttacag ttcgataatc tggacctggg gacgcgtata | 60 |
| ggatcgttcc tccacatgcg ctgctgtcgg tatctcgaat ccccggtatt cagttgaatc | 120 |
| gttggcggag tgtcctcctg gactctgcaa tgttccctag ccgtcttcac tatctcgtgc | 180 |
| aaggctctat aatacagttc ctctgcagac ccgtcgttgc tcttcccttc tgcgtcgtta | 240 |
| gttatttctg taggctccag acgatttgcc tgcatttgtg cgcaacataa tctgattgca | 300 |
| ttccctatct cgtcttccgg taatcccata ggtgttcggt attcgcagat aggtagagaa | 360 |
| agcaccactg caaatcgtgc aatttccatt gccccaacca atattttttt taagaacggc | 420 |
| atcgccgtta atgtacctcg ggcattgtga cgatcgaaac ccttatggat gcctaaagag | 480 |
| agcattgcgg tccagttctc caggtgaaaa gagaatagcg cgggtagaaa cgggccgatt | 540 |
| agttttatct tcgccgcgtc cctaatatcc caagttctgc agtataactt ccatcgtccg | 600 |
| ttttcgacaa ggtccggcgc gacatagttt gaaatgtcat ctatcagaaa catctcgccc | 660 |
| atcgtagaaa aaaacctgta cgcagaccat aaaaccattc ggtaccacat atccttgtgt | 720 |
| atatcaaacg atatgttggt tatgtcgttg gcggatgttg tatgaaatag agctaagcgt | 780 |
| tctctggatt ccacgcactg aacgattccg ttagtcaatt catctgctaa cataggccaa | 840 |
| aagtttattc gtgttacttt tctcggcggt ttggcaaaac gccccttgg cacatccatg | 900 |
| tcattaaata cagcggcata actcctactc atgtgttcca tagcccaggt ttctgttcgg | 960 |
| tctgctacta cgatcagatc agtggcgcga tcagatgcgt gggatgaatg aagtgtatcc | 1020 |
| gaaagcagtt ttgagatata cgctaaactg tacgacgatt gtggcactaa acgaagcttt | 1080 |
| gcgcgacccc catcccacgc cctgcaggtt agtcatatgt tacttggcag aggccgcatg | 1140 |
| gaaagtccct ggacgtggga catctgatta atacgtgagg aggtcagcca tgttctttt | 1200 |
| ggcaaaggac tacggtcatt ggacgtttga ttggcatggg atagggtcag ccagagttaa | 1260 |
| cagtgttctt ttggcaaagg gatacgtgga aagtcccggg ccatttacag taaactgata | 1320 |

```
cggggacaaa gcacagccat atttagtcat gtattgcttg gcagagggtc tatggaaagt    1380
ccctggacgt gggacgtctg attaatatga agaaggtca gccagaggta gctgtgtcct    1440
ttttggcaaa gggatacggt tatgggacgt tgattggac tgggataggg tcagccagag    1500
ttaacagtgt tcttttggca aggaaacgt ggaaagtccc gggccattta cagtaaactg    1560
atactgggac aaagtacacc catatttagt catgttcttt ttggcaaaga gcatctggaa    1620
agtcccgggc agcattatag tcacttggca gagggaaagg gtcactcaga gttaagtaca    1680
tctttccagg gccaatattc cagtaaatta cacttagttt tatgcaaatc agccacaaag    1740
gggattttcc cggtcaatta tgacttttc cttagtcatg cggtatccaa ttactgccaa    1800
attggcagta catactaggt gattcactga catttggccg tcctctggaa agtccctgga    1860
aaccgctcaa gtactgtatc atggtgactt tgcattttg gagagcacgc cccactccac    1920
cattggtcca cgtaccctat gggggagtgg tttatgagta tataagggc tccggtttag    1980 aagccgggca gagcggccgc atgggctcca aaccttctac caggatccca gcacctctga    2040
tgctgatcac ccggattatg ctgatattgg gctgtatccg tccgacaagc tctcttgacg    2100
gcaggcctct tgcagctgca ggaattgtag taacaggaga taaggcagtc aatgtataca    2160
cttcgtctca gacagggtca atcatagtca agttgctccc gaatatgccc agggataagg    2220
aggcgtgtgc aaaagcccca ttagaggcat ataacagaac actgactact ttgctcactc    2280
ctcttggcga ctccatccgc aagatccaag gtctgtgtc cacatctgga ggaggcaagc    2340
aaggccgcct gataggtgct gttattggca gtgtagctct tggggttgca acagcggcac    2400
agataacagc agctgcggcc ctaatacaag ccaaccagaa tgccgccaac atcctccggc    2460
ttaaggagag cattgctgca accaatgaag ctgtgcatga agtcaccgac ggattatcac    2520
aactatcagt ggcagttggg aagatgcagc agtttgtcaa tgaccagttt aataatacgg    2580
cgcgagaatt ggactgtata aaaatcacac aacaggttgg tgtagaactc aacctatacc    2640
taactgaatt gactacagta ttcgggccac agatcacctc ccctgcatta actcagctga    2700
ccatccaggc actttataat ttagctggtg gcaatatgga ttacttatta actaagttag    2760
gtatagggaa caatcaactc agctcgttaa ttggtagcgg cctgatcact ggttacccta    2820
tactgtatga ctcacagact caactcttgg gcatacaagt gaatttaccc tcagtcggga    2880
acttaaataa tatgcgtgcc acctatttgg agaccttatc tgtaagtaca accaaaggat    2940
atgcctcagc acttgtcccg aaagtagtga cacaagtcgg ttccgtgata aagagcttg    3000 acacctcata ctgtatagag tccgatctgg atttatattg tactagaata gtgacattcc    3060
ccatgtcccc aggtatttat tcctgtttga gcggcaacac atcagcttgc atgtattcaa    3120
agactgaagg cgcactcact acgccgtata tggccctta aggctcagtt attgccaatt    3180
gtaaaataac aacatgtaga tgtacagacc ctcctggtat catatcgcaa aattatggag    3240
aagctgtatc cctgatagat agacattcgt gcaatgtctt atcattagac gggataactc    3300
taaggctcag tggggaattt gatgcaactt atcaaaagaa catctcaata ctagattctc    3360
aagtcatcgt gacaggcaat cttgatatat caactgaact tggaaacgtc aacaattcaa    3420
tcagcaatgc cttggataag ttggcagaaa gcaacagcaa gctagaaaaa gtcaatgtca    3480
gactaaccag cacatctgct ctcattacct atattgttct aactgtcatt tctctagttt    3540
tcggtgcact tagtctggtg ttagcgtgtt acctgatgta caacagaag gcacaacaaa    3600 agaccttgct atggcttggg aataatccc tcgatcagat gagagccact acaagagcat    3660
gagcggccgc gatatcaata aaatatcttt attttcatta catctgtgtg ttggttttt    3720
```

```
gtgtgaatcg atagtactaa catacgctct ccatcaaaac aaaacgaaac aaaacaaact    3780
agcaaaatag gctgtcccca gtgcaagtgc aggtgccaga acatttctct tctagacctg    3840
caggggagtc tgtgcaaggt taatgaccct cgcagttcat tcggaagtta taactgccgc    3900
cttcgcacat ttcttttgt cctgttttgt attgccataa cagataggaa ttgaaacctg    3960
atcctcctgt tttttgcagc atggccagca acagaatact tgtcggatc gactacttgc    4020 gcgagatggt tccgttcttg gaggtttcgg cgggtcgggt ggagaaccta ttattttata    4080
cacacacgtc ataccgttgt cgcgaaaatg ttctttgtct tctgccgtct cgaacgtcgg    4140
ttcccacgta gacgttagga gcgttggaat ggtatcagga agagcccacg gcatgccgga    4200
ccaagtaccc gctactttga ccgcgagcag tctcttcggt aatgggatgt attccagagc    4260
agcgcggcag agatcagcgg cccccactat ccacagactg tatgaagtgt tttctgaaac    4320
atcggactcc aacatcaaat atccagacat aacatcttgc cattcggaag cacatccgcc    4380
gacatcttca aatagcctaa ctataaacga gtctctagtt cctgctaacc cagtacctcg    4440
aatgccagtc ccatccggtg ggttcgtcct gataatcggt ctctgacgcc gaggaagaac    4500 taaaagggt ctggaaaagc ggaacagatc tgcagaccga acgactacag acacgcccac    4560
atcatcatgt atctgttcca tgcattgctt tatgagaaaa atccataagg ccgaggcggc    4620
atctctagat ctcccgggga gtctctcgca ctcatctagg agagtgacga cagttatcat    4680
agacacgccc atttgtgcac caaacgaaaa gttcctgtac tggtggagcg tcggcgcggg    4740
aatcggtccg tgctctgaaa ccagtgtcta gacagaagac catccggtaa attctggtgt    4800
atgaactgac ggtctccaga cgaacgtcga agacattaac gatggaaact aacgagcttt    4860
cttcaaaagt gtctgattac aacgctaata gaccttacga aactatacgc agcgatacca    4920
gtgacacaga tccgtcggtg tcg                                            4943
```

<210> SEQ ID NO 58
<211> LENGTH: 1362
<212> TYPE: DNA
<213> ORGANISM: artificial sequence
<220> FEATURE:
<223> OTHER INFORMATION: IBDV DNA encoding VP2 protein of IBDV E strain

<400> SEQUENCE: 58

```
atgacaaacc tgcaagatca aacccaacag attgttccgt tcatacggag ccttctgatg     60
ccaacaaccg gaccggcgtc cattccggac gacaccctgg agaagcacac tctcaggtca    120
gagacctcga cctacaattt gactgtgggg gacacagggt cagggctaat tgtcttttc    180 cctggattcc ctggctcaat tgtgggtgct cactacacac tgcagagcaa tgggaactac    240
aagttcgatc agatgctcct gactgcccag aacctaccgg ccagctacaa ctactgcagg    300
ctagtgagtc ggagtctcac agtaaggtca agcacactcc ctggtggcgt ttatgcacta    360
aacggcacca taaacgccgt gaccttccaa ggaagcctga gtgaactgac agatgttagc    420
tacaacgggt tgatgtctgc aacagccaac atcaacgaca aaattgggaa cgtcctagta    480
ggggaagggg taaccgtcct cagcttaccc acatcatatg atcttgggta tgtgaggctt    540
ggtgacccca tacccgctat agggcttgac ccaaaaatgg tagcaacatg tgacagcagt    600
gacaggccca gagtctacac cataactgca gccgataatt accaattctc atcacagtac    660
caaacaggtg gggtaacaat cacactgttc tcagccaaca ttgatgccat cacaagtctc    720
agcgttgggg gagagctcgt gttcaaaaca agcgtccaaa gccttgtact gggcgccacc    780
```

-continued

```
atctacctta taggctttga tgggactgcg gtaatcacca gagctgtggc cgcaaacaat    840
gggctgacgg ccggcatcga caatcttatg ccattcaatc ttgtgattcc aaccaatgag    900
ataacccagc caatcacatc catcaaactg gagatagtga cctccaaaag tgatggtcag    960 gcagggaac agatgtcatg gtcggcaagt gggagcctag cagtgacgat ccatggtggc    1020
aactatccag gagccctccg tcccgtcaca ctagtggcct acgaaagagt ggcaacagga    1080
tctgtcgtta cggtcgctgg ggtgagcaac ttcgagctga tcccaaatcc tgaactagca    1140
aagaacctgg ttacagaata tggccgattt gacccaggag ccatgaacta cacgaaattg    1200
atactgagtg agagggaccg ccttggcatc aagaccgtct ggccaacaag ggagtacact    1260
gactttcgtg agtacttcat ggaggtggcc gacctcaact ctcccctgaa gattgcagga    1320
gcatttggct tcaaagacat aatccgggcc ataaggaggt ga                      1362
```

<210> SEQ ID NO 59
<211> LENGTH: 453
<212> TYPE: PRT
<213> ORGANISM: artificial sequence
<220> FEATURE:
<223> OTHER INFORMATION: IBDV VP2 protein of IBDV E strain

<400> SEQUENCE: 59

```
Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asn Tyr Gln Phe Ser Ser Gln Tyr Gln Thr Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val Gln Ser Leu Val
                245                 250                 255

Leu Gly Ala Thr Ile Tyr Leu Ile Gly Phe Asp Gly Thr Ala Val Ile
```

|     |     |     |     | 260 |     |     |     | 265 |     |     |     | 270 |     |     |
| --- | --- | --- | --- | --- | --- | --- | --- | --- | --- | --- | --- | --- | --- | --- |
| Thr | Arg | Ala | Val | Ala | Asn | Asn | Gly | Leu | Thr | Ala | Gly | Ile | Asp | Asn |
|     |     |     | 275 |     |     |     |     | 280 |     |     |     |     | 285 |     |
| Leu | Met | Pro | Phe | Asn | Leu | Val | Ile | Pro | Thr | Asn | Glu | Ile | Thr | Gln | Pro |
|     | 290 |     |     |     |     | 295 |     |     |     |     | 300 |     |     |     |     |
| Ile | Thr | Ser | Ile | Lys | Leu | Glu | Ile | Val | Thr | Ser | Lys | Ser | Asp | Gly | Gln |
| 305 |     |     |     |     | 310 |     |     |     |     | 315 |     |     |     |     | 320 |
| Ala | Gly | Glu | Gln | Met | Ser | Trp | Ser | Ala | Ser | Gly | Ser | Leu | Ala | Val | Thr |
|     |     |     |     | 325 |     |     |     |     | 330 |     |     |     |     | 335 |     |
| Ile | His | Gly | Gly | Asn | Tyr | Pro | Gly | Ala | Leu | Arg | Pro | Val | Thr | Leu | Val |
|     |     |     | 340 |     |     |     |     | 345 |     |     |     |     | 350 |     |     |
| Ala | Tyr | Glu | Arg | Val | Ala | Thr | Gly | Ser | Val | Val | Thr | Val | Ala | Gly | Val |
|     |     | 355 |     |     |     |     | 360 |     |     |     |     | 365 |     |     |     |
| Ser | Asn | Phe | Glu | Leu | Ile | Pro | Asn | Pro | Glu | Leu | Ala | Lys | Asn | Leu | Val |
|     | 370 |     |     |     |     | 375 |     |     |     |     | 380 |     |     |     |     |
| Thr | Glu | Tyr | Gly | Arg | Phe | Asp | Pro | Gly | Ala | Met | Asn | Tyr | Thr | Lys | Leu |
| 385 |     |     |     |     | 390 |     |     |     |     | 395 |     |     |     |     | 400 |
| Ile | Leu | Ser | Glu | Arg | Asp | Arg | Leu | Gly | Ile | Lys | Thr | Val | Trp | Pro | Thr |
|     |     |     |     | 405 |     |     |     |     | 410 |     |     |     |     | 415 |     |
| Arg | Glu | Tyr | Thr | Asp | Phe | Arg | Glu | Tyr | Phe | Met | Glu | Val | Ala | Asp | Leu |
|     |     |     | 420 |     |     |     |     | 425 |     |     |     |     | 430 |     |     |
| Asn | Ser | Pro | Leu | Lys | Ile | Ala | Gly | Ala | Phe | Gly | Phe | Lys | Asp | Ile | Ile |
|     |     | 435 |     |     |     |     | 440 |     |     |     |     | 445 |     |     |     |
| Arg | Ala | Ile | Arg | Arg |
|     | 450 |     |     |     |

<210> SEQ ID NO 60
<211> LENGTH: 884
<212> TYPE: DNA
<213> ORGANISM: artificial sequence
<220> FEATURE:
<223> OTHER INFORMATION: Guinea pig CMV promoter

<400> SEQUENCE: 60

| ttagtcatat gttacttggc agaggccgca tggaaagtcc ctggacgtgg gacatctgat | 60 |
| taatacgtga ggaggtcagc catgttcttt ttggcaaagg actacggtca ttggacgttt | 120 |
| gattggcatg ggatagggtc agccagagtt aacagtgttc ttttggcaaa gggatacgtg | 180 |
| gaaagtcccg ggccatttac agtaaactga tacggggaca agcacagcc atatttagtc | 240 |
| atgtattgct tggcagaggg tctatggaaa gtccctggac gtgggacgtc tgattaatat | 300 |
| gaaagaaggt cagccagagg tagctgtgtc cttttttggca aagggatacg ttatgggac | 360 |
| gtttgattgg actgggatag ggtcagccag agttaacagt gttcttttgg caaaggaaac | 420 |
| gtggaaagtc ccgggccatt tacagtaaac tgatactggg acaaagtaca cccatattta | 480 |
| gtcatgttct ttttggcaaa gagcatctgg aaagtcccgg gcagcattat agtcacttgg | 540 |
| cagagggaaa gggtcactca gagttaagta catctttcca gggccaatat tccagtaaat | 600 |
| tacacttagt tttatgcaaa tcagccacaa aggggatttt cccggtcaat tatgactttt | 660 |
| tccttagtca tgcggtatcc aattactgcc aaattggcag tacatactag gtgattcact | 720 |
| gacatttggc cgtcctctgg aaagtccctg gaaaccgctc aagtactgta tcatggtgac | 780 |
| tttgcatttt tggagagcac gccccactcc accattggtc cacgtaccct atgggggagt | 840 |
| ggtttatgag tatataaggg gctccggttt agaagccggg caga | 884 |

```
<210> SEQ ID NO 61
<211> LENGTH: 30
<212> TYPE: DNA
<213> ORGANISM: artificial sequence
<220> FEATURE:
<223> OTHER INFORMATION: primer HM101

<400> SEQUENCE: 61
ccggaattcc gatgtttagt cacgatagac                                              30

<210> SEQ ID NO 62
<211> LENGTH: 35
<212> TYPE: DNA
<213> ORGANISM: artificial sequence
<220> FEATURE:
<223> OTHER INFORMATION: Primer HM102

<400> SEQUENCE: 62
ataagagcgg ccgcagtgag atgatcttaa tgatg                                        35

<210> SEQ ID NO 63
<211> LENGTH: 38
<212> TYPE: DNA
<213> ORGANISM: artificial sequence
<220> FEATURE:
<223> OTHER INFORMATION: primer F-ATG

<400> SEQUENCE: 63
tatagcggcc gcaagatggg ctccagatct tctaccag                                     38

<210> SEQ ID NO 64
<211> LENGTH: 34
<212> TYPE: DNA
<213> ORGANISM: artificial sequence
<220> FEATURE:
<223> OTHER INFORMATION: Primer F-STOP

<400> SEQUENCE: 64
cgaggcggcc gctcatattt ttgtagtggc tctc                                         34
```

What we claim is:

1. A composition or vaccine comprising a recombinant Gallid herpesvirus 3 (MDV-2) vector comprising one or two heterologous polynucleotides coding for and expressing at least one antigen of an avian pathogen, wherein the recombinant Gallid herpesvirus 3 vector is a recombinant SB-1 viral vector, and wherein one heterologous polynucleotide encodes a Newcastle Disease Virus fusion protein (NDV-F) having at least 99% sequence identity to a polypeptide having the sequence as set forth in SEQ ID NO:2 or wherein the NDV-F protein comprises SEQ ID NO:9, and wherein the composition or vaccine further comprises a pharmaceutically or veterinarily acceptable carrier, excipient, vehicle or adjuvant.

2. The composition or vaccine of claim 1, further comprising one or more compositions or vaccines selected from the group consisting of a recombinant HVT (Herpesvirus of Turkeys) vector (or MDV-3 or Meleagrid herpesvirus-1) comprising heterologous polynucleotides coding for and expressing at least one antigen of an avian pathogen, wild type HVT (MDV-3), recombinant MDV-1 vector (or Gallid herpesvirus-2) comprising heterologous polynucleotides coding for and expressing at least one antigen of an avian pathogen, wild type MDV-1, and a combination thereof.

3. The composition or vaccine of claim 1 or 2, wherein the one or two heterologous polynucleotides are inserted into the non-essential region of the Gallid herpesvirus 3 vector.

4. The composition or vaccine of claim 1 or 2, wherein the heterologous polynucleotide in any recombinant vector corresponds to the gene selected from the group consisting of Newcastle Disease Virus (NDV) F, Infectious Bursal Disease Virus (IBDV) VP2, infectious laryngotracheitis virus (ILTV) gB, ILTV gD, ILTV gI, and influenza hemaglutinnin (HA).

5. A recombinant Gallid herpesvirus 3 vector comprising one or two heterologous polynucleotides coding for and expressing at least one antigen of an avian pathogen, wherein the recombinant Gallid herpesvirus 3 vector is a recombinant SB-1 viral vector, and wherein one heterologous polynucleotide encodes a Newcastle Disease Virus fusion protein (NDV-F) having at least 99% sequence identity to a polypeptide having the sequence as set forth in SEQ ID NO:2 or wherein the NDV-F protein comprises SEQ ID NO:9.

6. The recombinant Gallid herpesvirus 3 vector of claim 5, wherein the heterologous polynucleotide corresponds to the gene selected from the group consisting of Newcastle Disease Virus (NDV) F, Infectious Bursal Disease Virus (IBDV) VP2, infectious laryngotracheitis virus (ILTV) gB, ILTV gD, ILTV gI, and influenza hemaglutinnin (HA).

7. The recombinant Gallid herpesvirus 3 vector of claim 5, wherein the one or two heterologous polynucleotides are inserted into the non-essential region of the Gallid herpesvirus 3 vector.

8. A method of vaccinating an animal comprising at least one administration of the composition or vector of claim 1 or 5.

9. The method of claim 8, wherein the method comprises a prime-boost administration regime.

10. A method for inducing an immunogenic or protective response in an animal against one or more avian pathogens comprising at least one administration of the composition or vector of claim 1 or 5.

11. The method of claim 10, wherein the avian pathogen is selected from the group consisting of Newcastle Disease Virus (NDV), Infectious Bursal Disease Virus (IBDV), infectious laryngotracheitis virus (ILTV), and influenza virus.

12. The method of claim 10, wherein the animal is avian.

13. The composition or vaccine of claim 3, wherein the heterologous polynucleotides are inserted in the region between SORF4 and US10, in the region between UL55 and LORF5, in the region coding for gC (UL44), in the region between SORF4 and US2, or a combination thereof.

14. The composition or vaccine of claim 1, wherein the recombinant MDV-2 vectors comprise a heterologous promoter selected from an immediate early CMV promoter, a mouse CMV promoter, a guinea pig CMV promoter, an SV40 promoter, a Pseudorabies Virus glycoprotein X promoter, a Herpes Simplex Virus-1 alpha 4 promoter, a Marek's Disease Virus glycoprotein C promoter, a Marek's Disease Virus glycoprotein B promoter, a Marek's Disease Virus glycoprotein E promoter, an Infectious Laryngotracheitis Virus glycoprotein B, an Infectious Laryngotracheitis Virus glycoprotein E promoter, an Infectious Laryngotracheitis Virus glycoprotein D promoter, an Infectious Laryngotracheitis Virus glycoprotein I promoter, or a Bovine Herpesvirus 1.1 VP8 promoter.

15. The composition or vaccine of claim 1, wherein the polynucleotide encoding NDV-F has at least 95% sequence identity to SEQ ID NO:1, 3, 4, 6, or 8.

16. The composition or vaccine of claim 1, wherein the two heterologous polynucleotides encode an NDV-F antigen and an IBDV VP2 antigen.

17. The composition or vaccine of claim 1, wherein the two heterologous polynucleotides encode an NDV-F antigen and an ILTV gD antigen.

18. The composition or vaccine of claim 1, wherein the two heterologous polynucleotides encode an NDV-F antigen and an influenza HA antigen.

19. The composition or vaccine of claim 1, wherein the two heterologous polynucleotides encode two NDV-F antigens.

20. The composition or vaccine of claim 1, wherein the composition further comprises a recombinant Herpesvirus of Turkeys (HVT) vector, wherein HVT is also known as MDV-3 or Meleagrid herpesvirus 1, and wherein the vector comprises a heterologous polynucleotide encoding IBDV VP2 antigen.

21. The recombinant Gallid herpesvirus 3 vector of claim 5, wherein the polynucleotide encoding NDV-F has at least 95% sequence identity to SEQ ID NO:1, 3, 4, 6, or 8.

22. The recombinant Gallid herpesvirus 3 vector of claim 5, wherein the two heterologous polynucleotides encode an NDV-F antigen and an IBDV VP2 antigen.

23. The recombinant Gallid herpesvirus 3 vector of claim 5, wherein the two heterologous polynucleotide encode an NDV-F antigen and an ILTV gD antigen.

24. The recombinant Gallid herpesvirus 3 vector of claim 5, wherein the two heterologous polynucleotides encode an NDV-F antigen and an influenza HA antigen.

25. The recombinant Gallid herpesvirus 3 vector of claim 5, wherein the two heterologous polynucleotides encode two NDV-F antigens.

* * * * *